United States Patent
Kastelein et al.

(10) Patent No.: US 12,139,545 B2
(45) Date of Patent: Nov. 12, 2024

(54) IL10 RECEPTOR BINDING MOLECULES AND METHODS OF USE

(71) Applicant: Synthekine, Inc., Menlo Park, CA (US)

(72) Inventors: Robert Kastelein, Menlo Park, CA (US); Mahalakshmi Ramadass, Menlo Park, CA (US); Deepti Rokkam, Menlo Park, CA (US); Patrick J. Lupardus, Menlo Park, CA (US); Sandro Vivona, Menlo Park, CA (US)

(73) Assignee: Synthekine, Inc., Menlo Park, CA (US)

( * ) Notice: Subject to any disclaimer, the term of this patent is extended or adjusted under 35 U.S.C. 154(b) by 0 days.

(21) Appl. No.: 18/164,351

(22) Filed: Feb. 3, 2023

(65) Prior Publication Data

US 2023/0322936 A1    Oct. 12, 2023

Related U.S. Application Data

(63) Continuation of application No. PCT/US2021/044834, filed on Aug. 5, 2021.

(60) Provisional application No. 63/136,098, filed on Jan. 11, 2021, provisional application No. 63/135,884, filed on Jan. 11, 2021, provisional application No. 63/078,745, filed on Sep. 15, 2020, provisional application No. 63/061,562, filed on Aug. 5, 2020.

(51) Int. Cl.
 *C07K 16/28* (2006.01)
 *A61K 45/06* (2006.01)
 *C12N 15/63* (2006.01)

(52) U.S. Cl.
 CPC .......... *C07K 16/2866* (2013.01); *A61K 45/06* (2013.01); *C12N 15/63* (2013.01); *C07K 2317/22* (2013.01); *C07K 2317/24* (2013.01); *C07K 2317/31* (2013.01); *C07K 2317/565* (2013.01); *C07K 2317/569* (2013.01); *C07K 2317/92* (2013.01)

(58) Field of Classification Search
None
See application file for complete search history.

(56) References Cited

U.S. PATENT DOCUMENTS

| | | |
|---|---|---|
| 8,258,268 B2 | 9/2012 | Wu et al. |
| 8,921,528 B2 | 12/2014 | Holt et al. |
| 8,975,382 B2 | 3/2015 | Revets et al. |
| 9,334,331 B2 | 5/2016 | Igawa et al. |
| 10,421,807 B2 | 9/2019 | Gonzales et al. |
| 10,927,186 B2 | 2/2021 | Roobrouck et al. |
| 2006/0002935 A1 | 1/2006 | Brewis et al. |
| 2006/0024295 A1 | 2/2006 | Brunetta |
| 2009/0220511 A1 | 9/2009 | Kotenko et al. |
| 2010/0297127 A1 | 11/2010 | Ghilardi et al. |
| 2011/0028695 A1 | 2/2011 | Revets et al. |
| 2011/0053865 A1 | 3/2011 | Saunders et al. |
| 2011/0142831 A1 | 6/2011 | Cua et al. |
| 2011/0177081 A1 | 7/2011 | Thiry et al. |
| 2011/0250213 A1 | 10/2011 | Tso et al. |
| 2012/0201746 A1 | 8/2012 | Liu et al. |
| 2012/0225081 A1 | 9/2012 | Gschwind et al. |
| 2012/0316324 A1 | 12/2012 | Adams et al. |
| 2013/0189262 A1 | 7/2013 | Wong et al. |
| 2014/0065142 A1 | 3/2014 | Roschke et al. |
| 2014/0099708 A1 | 4/2014 | Carballido Herrera et al. |
| 2014/0154256 A1 | 6/2014 | Wu et al. |
| 2014/0155581 A1 | 6/2014 | Gao et al. |
| 2014/0170154 A1 | 6/2014 | Presta |
| 2014/0302038 A1 | 10/2014 | Dimasi et al. |
| 2014/0363426 A1* | 12/2014 | Moore ................. C07K 16/22 435/69.6 |
| 2015/0079088 A1 | 3/2015 | Lowman et al. |
| 2016/0017387 A1 | 1/2016 | Hsieh et al. |
| 2016/0046730 A1 | 2/2016 | Ghayur et al. |
| 2016/0251440 A1 | 9/2016 | Roobrouck et al. |
| 2017/0106051 A1 | 4/2017 | Oh et al. |
| 2017/0298149 A1 | 10/2017 | Baeuerle et al. |
| 2018/0362655 A1 | 12/2018 | Wang et al. |
| 2018/0362668 A1 | 12/2018 | Xu |
| 2019/0185562 A1 | 6/2019 | Gromada et al. |
| 2019/0315864 A1 | 10/2019 | Xu et al. |
| 2019/0352404 A1 | 11/2019 | Xu et al. |
| 2019/0382500 A1 | 12/2019 | Abujoub et al. |
| 2020/0055912 A1 | 2/2020 | Kley et al. |
| 2020/0071716 A1 | 3/2020 | Raab et al. |
| 2020/0087624 A1 | 3/2020 | Wood et al. |
| 2020/0148772 A1 | 5/2020 | Ting et al. |
| 2020/0157237 A1 | 5/2020 | Regev et al. |
| 2020/0399382 A1 | 12/2020 | Blanchetot et al. |

(Continued)

FOREIGN PATENT DOCUMENTS

| | | |
|---|---|---|
| CN | 103396482 A | 11/2013 |
| CN | 111018985 A | 6/2019 |

(Continued)

OTHER PUBLICATIONS

Ikeuchi et al., Nature Portfolio, 11:20624, https://doi.org/10.1038/s41598-021-98977-8, Oct. 2021, downloaded Sep. 28, 2023.*

BioLegend, PE anti-mouse IL-23R Antibody, Catalog, Mar. 28, 2016, retrieved from the internet www.biolegend.com/en-us/global-elements/pdf-popup/pe-anti-mouse-il-23r-antibody-13084?filename=PE%20anti-mouse%20IL-23R%20Antibody.pdf&pdfgen=true.

Cairo, et al. "Control of multivalent interactions by binding epitope density." Journal of the American Chemical Society 124, No. 8 (2002): 1615-1619.

De Weerd, et al. "The interferons and their receptors-distribution and regulation." Immunology and cell biology 90, No. 5 (2012): 483-491.

Delgoffe et al., "Interpreting mixed signals: the cell's cytokine conundrum," Current Opinion in Immunology, vol. 23(5), pp. 632-638, Retrieved from the internet, URL: https://www.ncbi.nlm.nih.gov/pmc/articles/PMC3190023/pdf/nihms315192.pdf, (Oct. 2011 ).

(Continued)

*Primary Examiner* — Marianne P Allen
(74) *Attorney, Agent, or Firm* — Kilpatrick Townsend & Stockton LLP

(57) ABSTRACT

Provided herein are IL10R binding molecules that bind to IL10Ra and IL10Rb and comprise an IL10Rb sdAb and an IL10Rb VHH antibody.

15 Claims, 8 Drawing Sheets

Figure 1:
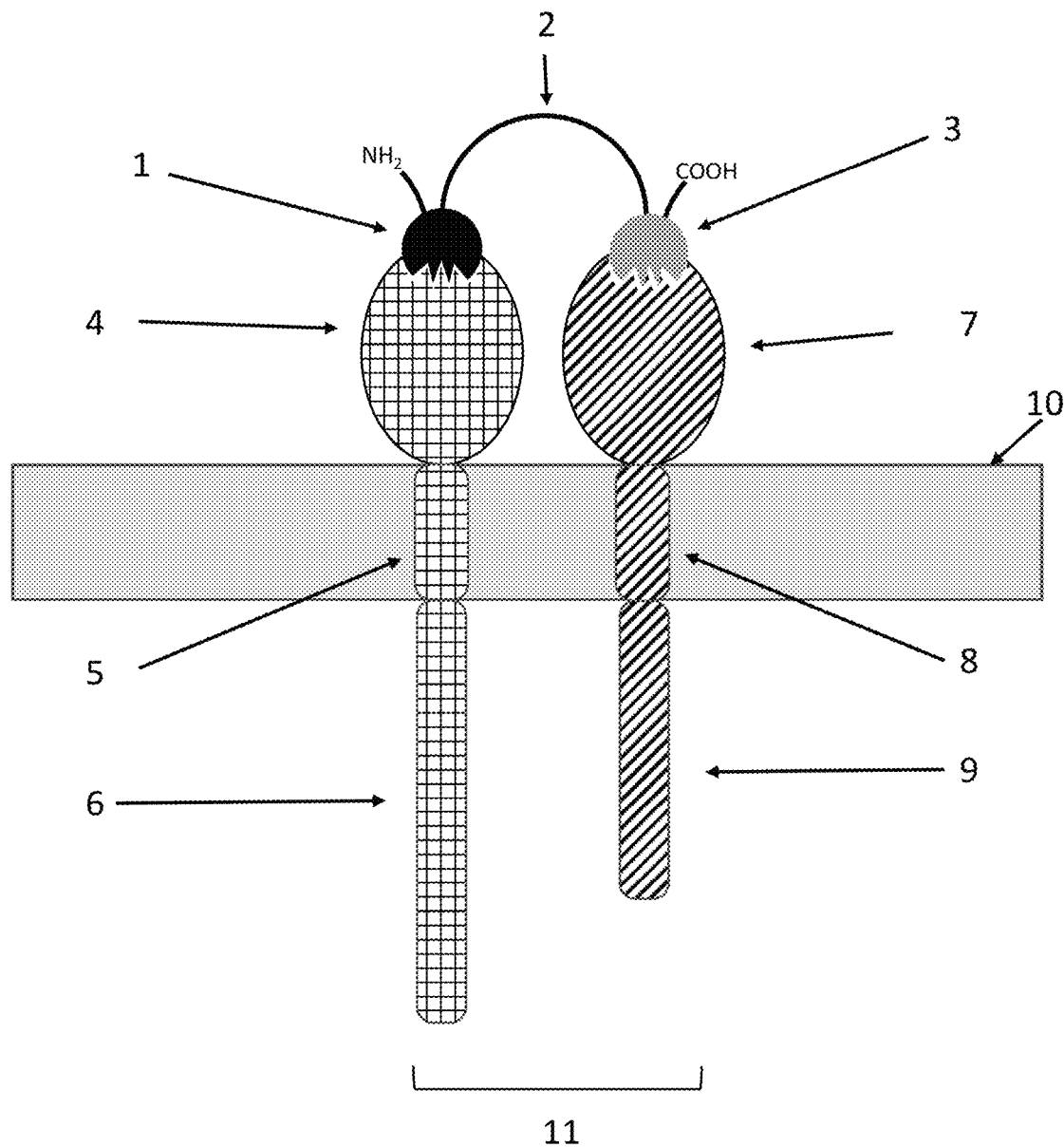

Specification includes a Sequence Listing.

(56) References Cited

U.S. PATENT DOCUMENTS

| | | |
|---|---|---|
| 2023/0272089 A1 | 8/2023 | Kastelein et al. |
| 2023/0272091 A1 | 8/2023 | Kastelein et al. |
| 2023/0322936 A1 | 10/2023 | Kastelein et al. |

FOREIGN PATENT DOCUMENTS

| | | |
|---|---|---|
| CN | 111040035 A | 4/2020 |
| WO | 2008/011081 A2 | 1/2008 |
| WO | 2009/068631 A1 | 6/2009 |
| WO | 2010/142551 A2 | 12/2010 |
| WO | 2011051327 A2 | 5/2011 |
| WO | 2011/095604 A1 | 8/2011 |
| WO | 2013/006544 A1 | 1/2013 |
| WO | 2013/059299 A1 | 4/2013 |
| WO | 2015142675 A2 | 9/2015 |
| WO | 2016/097313 A1 | 6/2016 |
| WO | 2017/198212 A1 | 11/2017 |
| WO | 2018233624 A1 | 12/2018 |
| WO | 2019/129221 A1 | 7/2019 |
| WO | 2019242632 A1 | 12/2019 |
| WO | 2020052543 A1 | 3/2020 |
| WO | 2020094834 A1 | 5/2020 |
| WO | 2020094836 A1 | 5/2020 |
| WO | 2020/113164 A1 | 6/2020 |
| WO | 2020/144164 A1 | 7/2020 |
| WO | 2020/187711 A1 | 9/2020 |
| WO | 2022031871 A1 | 2/2022 |
| WO | 2022031884 A2 | 2/2022 |
| WO | 2022031885 A2 | 2/2022 |
| WO | 2022032022 A2 | 2/2022 |
| WO | 2022055641 A1 | 3/2022 |
| WO | 2022055641 A2 | 3/2022 |
| WO | 2022150788 A2 | 7/2022 |

OTHER PUBLICATIONS

Fan, et al. "Bispecific antibodies and their applications." Journal of hematology & oncology 8 (2015): 1-14.

Franke et al. Human and murine interleukin 23 receptors are novel substrates for a disintegrin and metalloproteases ADAM10 and ADAM17. Journal of Biological Chemistry. May 13, 2016;291(20):10551-61.

Fu et al. Comparison of Camelus Bactrianus VHH Sequences From Conventional and Heavy Chain Antibodies. Genbank Entry (online) National Center for Biotechnology Information, Sep. 21, 2013. Retried www.ncbi.nlm.nih.gov/nucleotide/KF179376.1, 1 page from the Internet.

Goel, et al. "Plasticity within the antigen-combining site may manifest as molecular mimicry in the humoral immune response." The Journal of Immunology 173, No. 12 (2004): 7358-7367.

Heldin, Carl-Henrik. "Dimerization of cell surface receptors in signal transduction." Cell 80, No. 2 (1995): 213-223.

Holliger, et al. "" Diabodies": small bivalent and bispecific antibody fragments." Proceedings of the National Academy of Sciences 90, No. 14 (1993): 6444-6448.

https://www.ncbi.nlm.nih.gov/gene/163702 (accessed from the internet Sep. 1, 2023).

International Patent Application No. PCT/US2021/044698, "International Search Report and Written Opinion", Feb. 1, 2022, 13 pages.

International Search Report in PCT/US2021/044695, mailed Feb. 2, 2022, 14 pages.

International Search Report in PCT/US2021/044802, mailed Feb. 3, 2022, 16 pages.

International Search Report in PCT/US2021/044835, mailed Feb. 8, 2022, 17 pages.

International Search Report in PCT/US2021/044855, mailed Dec. 16, 2021, 11 pages.

International Search Report in PCT/US2021/044575, mailed Feb. 2, 2022.

International Search Report in PCT/US2021/044576, mailed Jan. 12, 2022, 12 pages.

International Search Report in PCT/US2021/044674, mailed Jan. 19, 2022, 12 pages.

International Search Report in PCT/US2021/044730, mailed Jun. 21, 2022, 26 pages.

International Search Report in PCT/US2021/044734, mailed Feb. 2, 2022, 13 pages.

International Search Report in PCT/US2021/044803, mailed Jan. 26, 2022, 11 pages.

International Search Report in PCT/US2021/044837, mailed Dec. 20, 2021, 11 pages.

International Search Report in PCT/US2021/044841 mailed Dec. 17, 2021, 10 pages.

International Search Report in PCT/US2021/044850, mailed Jan. 6, 2022, 9 pages.

International Search Report in PCT/US2021/044853, mailed Dec. 17, 2021, ten pages.

International Search Report and Written Opinion; PCT/US2021/44610, mailed Jan. 5, 2022; 11 pgs.

International Search Report and Written Opinion PCT/US2021/044602, dated Feb. 2, 2022, 13 pages.

Khan, et al. "Adjustable locks and flexible keys: plasticity of epitope-paratope interactions in germline antibodies." The Journal of Immunology 192, No. 11 (2014): 5398-5405.

Kontermann, Roland. "Dual targeting strategies with bispecific antibodies." In MAbs, vol. 4, No. 2, pp. 182-197. Taylor & Francis, 2012.

Lloyd, et al. "Modelling the human immune response: performance of a 1011 human antibody repertoire against a broad panel of therapeutically relevant antigens." Protein Engineering, Design & Selection 22, No. 3 (2009): 159-168.

Lo, et al. "Conformational epitope matching and prediction based on protein surface spiral features." BMC genomics 22, No. 2 (2021): 1-16.

Lundin, et al. "Production and partial characterization of mouse monoclonal antibodies recognizing common cytokine receptor gamma chain (ye) of human, mouse and primate origin Note." Apmis 109, No. 1 O (2001 ): 64 7-655.

Marks, et al. "How repertoire data are changing antibody science." Journal of Biological Chemistry 295, No. 29 (2020): 9823-9837.

Nie, et al. "Biology drives the discovery of bispecific antibodies as innovative therapeutics." Antibody therapeutics 3, No. 1 (2020): 18-62.

Saerens, et al. "Single-domain antibodies as building blocks for novel therapeutics." Current opinion in pharmacology 8, No. 5 (2008): 600-608.

Shahangain et al., VVH Against VEGF-RBD, Genbank entry (online) National Center for Biotechnology Information, May 2, 1215, retrieved from the internet www.ncbi.nlm.nih.gov/protein/BAR73350.1, 2 pages.

Shouval, et al. "Interleukin 1 O receptor signaling: master regulator of intestinal mucosal homeostasis in mice and humans." Advances in immunology 122 (2014): 177-210.

UniProtKB A0A066RQT8, UniProtKB Accession Numner: A0A066RQT8, Sep. 3, 2014, retrieved from internet www.uniprot.org/uniprot/A0A066RQT8.

Watzka, et al. "Guided selection of antibody fragments specific for human interferon γ receptor 1 from a human VH-and VL-gene repertoire." Immunotechnology 3, No. 4 (1998): 279-291.

Weidle et al., "The Intriguing Options of Multispecific Antibody Formats for treatment of Cancer," Cancer Genomics & Proteomics 10:1-18 (2013).

Wilton et al. sdAb-DB: the single domain antibody database. ACS Synthetic Biology. Nov. 16, 2018;7(11):2480-4.

Yoshinaga et al., J. Biochem 2008; 143:593-601 (Year: 2008).

Crepaldi et al. Up-regulation of IL-10R1 expression is required to render human neutrophils fully responsive to IL-10. The Journal of Immunology. Aug. 15, 2001;167(4):2312-22.

Donnelly et al.. The expanded family of class II cytokines that share the IL-10 receptor-2 (IL-10R2) chain. Journal of leukocyte biology. Aug. 2004;76(2):314-21.

(56) References Cited

OTHER PUBLICATIONS

Jiang et al. Regulation of interleukin-10 receptor ubiquitination and stability by beta-TrCP-containing ubiquitin E3 ligase. PloS one. Nov. 8, 2011;6(11):e27464.

International Search Report in PCT/US2021/044834, mailed Feb. 2, 2022, 15 pages.

Pingwara et al. IFN-λ Modulates the Migratory Capacity of Canine Mammary Tumor Cells via Regulation of the Expression of Matrix Metalloproteinases and Their Inhibitors. Cells. Apr. 23, 2021;10(5):999.

"Anti-IL28RA antibody (ab224395)", Available Online at: https://www.abcam.com/products/primary-antibodies/il28ra-antibody-ab224395.html, Retrieved from the internet Dec. 20, 2023, 4 pages.

"Human IL-28 R alpha /IFN-lambda R1 Antibody", Available Online at: https://www.rndsystems.com/products/human-il-28-ralpha-ifn-lambda-r1-antibody_af5260, Retrieved from the internet Dec. 20, 2023, 6 pages.

"IFNLR1 Interferon Lambda Receptor 1 [ *Homo sapiens* (Human) ]", National Library of Medicine, Gene ID: 163702, Accessed from Internet on Sep. 12, 2023, 9 pages.

Application No. PCT/US2021/044603 , International Preliminary Report on Patentability, Mailed On Feb. 16, 2023, 9 pages.

Application No. PCT/US2021/044603 , International Search Report and Written Opinion, Mailed On Feb. 2, 2022, 12 pages.

Application No. PCT/US2021/044695 , International Preliminary Report on Patentability, Mailed On Feb. 16, 2023, 10 pages.

Application No. PCT/US2021/044695 , International Search Report and Written Opinion, Mailed On Feb. 2, 2022, 14 pages.

Application No. PCT/US2021/044802 , International Preliminary Report on Patentability, Mailed On Feb. 16, 2023, 9 pages.

Application No. PCT/US2021/044802 , International Search Report and Written Opinion, Mailed On Feb. 3, 2022, 13 pages.

Application No. PCT/US2021/044841 , International Preliminary Report on Patentability, Mailed On Feb. 16, 2023, 7 pages.

Application No. PCT/US2021/044841 , International Search Report and Written Opinion, Mailed On Dec. 17, 2021, 10 pages.

Application No. PCT/US2021/044858 , International Preliminary Report on Patentability, Mailed On Feb. 16, 2023, 7 pages.

Application No. PCT/US2021/044858 , International Search Report and Written Opinion, Mailed On Dec. 20, 2021, 10 pages.

Application No. PCT/US2022/012049 , International Preliminary Report on Patentability, Mailed On Jul. 20, 2023, 10 pages.

Application No. PCT/US2022/012049 , International Search Report and Written Opinion, Mailed On Jun. 21, 2022, 14 pages.

Piche-Nicholas et al., "Changes in Complementarity-determining Regions Significantly Alter IgG Binding to the Neonatal Fc Receptor (FcRn) and Pharmacokinetics", MAbs, vol. 10, No. 1, Jan. 2018, pp. 81-94.

Santer et al., "Differential expression of interferon-lambda receptor 1 splice variants determines the magnitude of the antiviral response induced by interferon-lambda 3 in human immune cells", PLOS Pathogens, vol. 16, No. 4, Apr. 30, 2020, 26 pages.

Witte et al., "Monoclonal Antibodies Targeting the VEGF Receptor-2 (Flk1/KDR) as an Anti-angiogenic Therapeutic Strategy", Cancer and Metastasis Reviews, vol. 17, No. 2, Jun. 1998, pp. 155-161.

Wu et al., "Single-domain Antibodies as Therapeutics Against Human Viral Diseases", Frontiers in Immunology, vol. 8, Article 1802, Dec. 13, 2017, 13 pages.

Yu et al., "Interaction between Bevacizumab and Murine VEGF-A: A Reassessment", Investigative Ophthalmology & Visual Science, vol. 49, No. 2, Feb. 2008, pp. 522-527.

\* cited by examiner

FIG. 3A
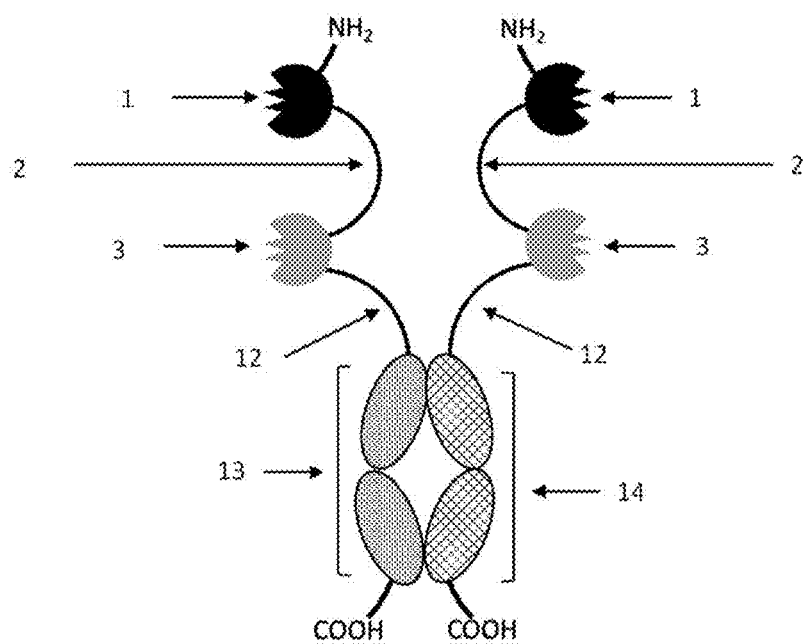
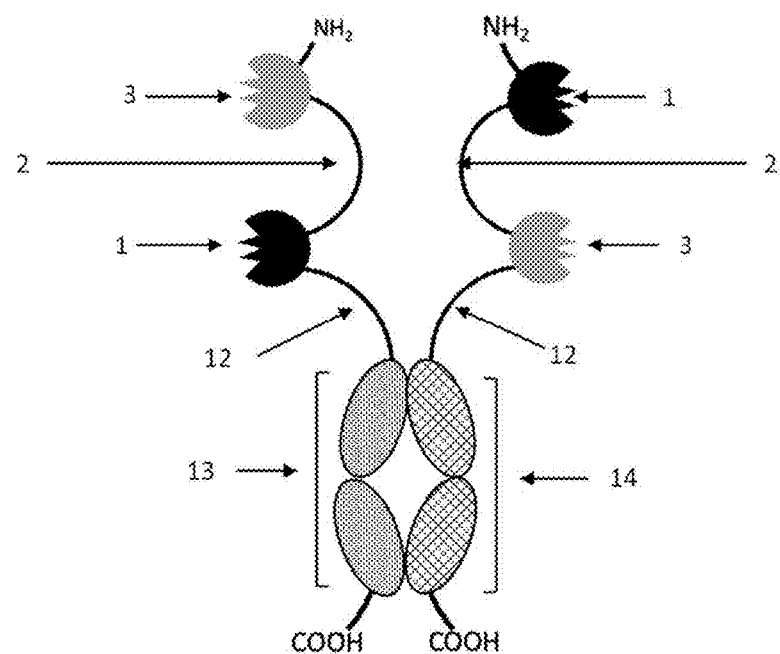
FIG. 3B

IL10 RECEPTOR BINDING MOLECULES AND METHODS OF USE

CROSS-REFERENCES TO RELATED APPLICATIONS

This application claims priority to U.S. Provisional Application No. 63/061,562, filed Aug. 5, 2020, U.S. Provisional Application No. 63/078,745, filed Sep. 15, 2020, U.S. Provisional Application No. 63/135,884, filed Jan. 11, 2021 and U.S. Provisional Application No. Ser. No. 63/136,098, filed on Jan. 11, 2021, the disclosures of which are hereby incorporated by reference in their entirety for all purposes.

SEQUENCE LISTING

The instant application contains a Sequence Listing which has been submitted electronically in XML format and is hereby incorporated by reference in its entirety. Said XML file, created on Feb. 2, 2023, is named 106249-1362149-001131US_SL.xml, and is 865 bytes in size.

BACKGROUND OF THE DISCLOSURE

Cytokine and growth-factor ligands typically signal through multimerization of cell surface receptors subunits. In some instance, cytokines act as multispecific (e.g., bispecific or trispecific) ligands which facilitate the association of such receptor subunits, bringing their intracellular domains into proximity such that intracellular signaling may occur. The nature of the cytokine determines which receptor subunits are associated to form the cytokine receptor complex. Cytokines thus act to bridge the individual receptor subunits into a receptor complex that results in intracellular signaling.

The intracellular domains of cytokine receptor subunits possess proline rich JAK binding domains which are typically located in the box1/box region of the intracellular domain of the cytokine receptor subunit near the interior surface of the cell membrane. Intracellular JAK kinases associate with JAK binding domains. When the intracellular domains receptor subunits are brought into proximity, typically by the binding of the cognate ligand for the receptor to the extracellular domains of the receptor subunits, the JAKs phosphorylate each other. Four Janus kinases have been identified in mammalian cells: JAK1, JAK2, JAK3 and TYK2. Ihle, et al. (1995) Nature 377(6550):591-4, 1995; O'Shea and Plenge (2012) *Immunity* 36(4):542-50. The phosphorylation of the JAK induces a conformational change in the JAK providing the ability to further phosphorylate other intracellular proteins which initiates a cascade that results in activation of multiple intracellular factors which transduce the intracellular signal associated with the receptor resulting intracellular responses such as gene transcription, frequently referred to as downstream signaling. In many instances, the proteins which are phosphorylated by the JAKs are members of the signal transducer and activator of transcription (STAT) protein family. Seven members of the mammalian STAT family have been identified to date: STAT1, STAT2, STAT3, STAT4, STAT5a STAT5b, and STAT6. Delgoffe, et al., (2011) Curr Opin Immunol. 23(5):632-8; Levy and Darnell (2002) Nat Rev Mol Cell Biol. 3(9):651-62 and Murray, (2007) J Immunol. 178(5):2623-9. The selective interplay of activated JAK and STAT proteins, collectively refer erred to as the JAK/STAT pathway, provide for a wide variety of intracellular responses observed in response to cytokine binding.

The human genome encodes for approximately forty different JAK/STAT cytokine receptors. In principle, approximately 1600 unique homodimeric and heterodimeric cytokine receptor pairs could be generated with the potential to signal through different JAK/TYK/STAT combinations (Bazan, *Proc Natl Acad Sci USA.* 87(18):6934-8, 1990; Huising et al., *J Endocrinol.* 189(1):1-25, 2006). However, as of the present knowledge, the human genome encodes for less than fifty different cytokine ligands (Bazan, *Proc Natl Acad Sci USA.* 87(18):6934-8, 1990; Huising et al., *J Endocrinol.* 189(1):1-25, 2006), limiting the scope of cytokine receptor complexes to those that can be assembled by the natural ligands. Given that interaction of the a cytokine ligand with the extracellular domains of the cytokine receptor subunits determines the composition of receptor subunits in a receptor complex and the intracellular JAK/TYK and RTK enzymes are degenerate, the number of cytokine and growth factor receptor dimer pairings that occur in nature represents only a fraction of the total number of signaling-competent receptor pairings theoretically allowed by the system.

Naturally occurring cytokine ligands mediate a wide variety of cellular response. In some instances, a heteromultimeric cytokine receptor is composed of one or more receptor subunits that is unique to the receptor complex, referred to as "proprietary" subunits, which interact with other receptor subunits that are shared by multiple cytokine receptors, frequently referred to as "common" receptor subunits. For example, the IL7 receptor is a heterodimeric receptor complex of the IL7Ra proprietary subunit and a CD132 subunit which is also referred to as the "common gamma" subunit as it is a shared receptor subunit of multiple cytokine receptor complexes including IL2, IL4, IL19, IL15 and IL21. The relative affinity and kinetic of the interaction of the cytokine for the ECDs of the receptor subunits and the stability of the complex formed in response to cytokine binding mediates the the nature and intensity of the intracellular signaling. In some instances, the binding of the cytokine to a the proprietary subunit enhances the formation of the complete receptor where the affinity of the cytokine for the common subunit may be significantly lower when not associated with the proprietary subunit.

The nuances of the interplay between the cytokine ligand and the receptor subunits is a matter of significant scientific investigation. For example, many properties of naturally occurring cytokines suggest their potential utility in the treatment of human disease but such naturally occurring cytokines may also trigger adverse and undesirable effects. In many instances, the disease is associated with a particular cell type which expresses the receptor for the potentially therapeutic cytokine. However, the cytokine receptor is also expressed on other cell types not desired to be targeted for therapeutic intervention. The administration of the native ligand activates both cell types resulting result in undesirable side effects.

Figure 6A:
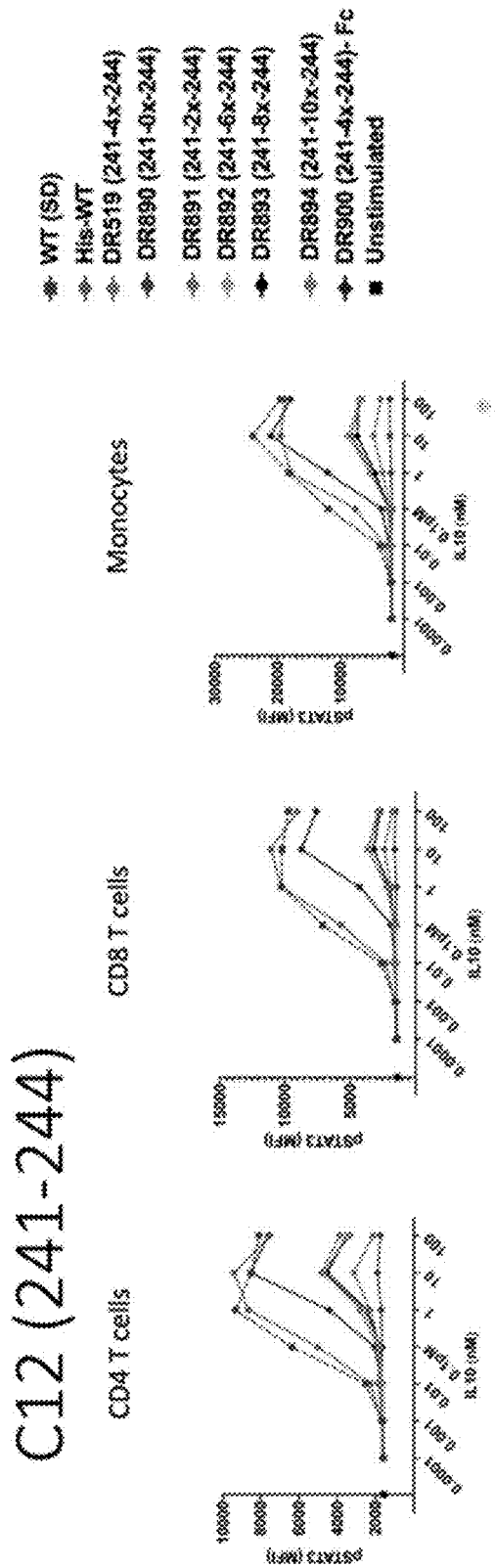
Figure 6B:
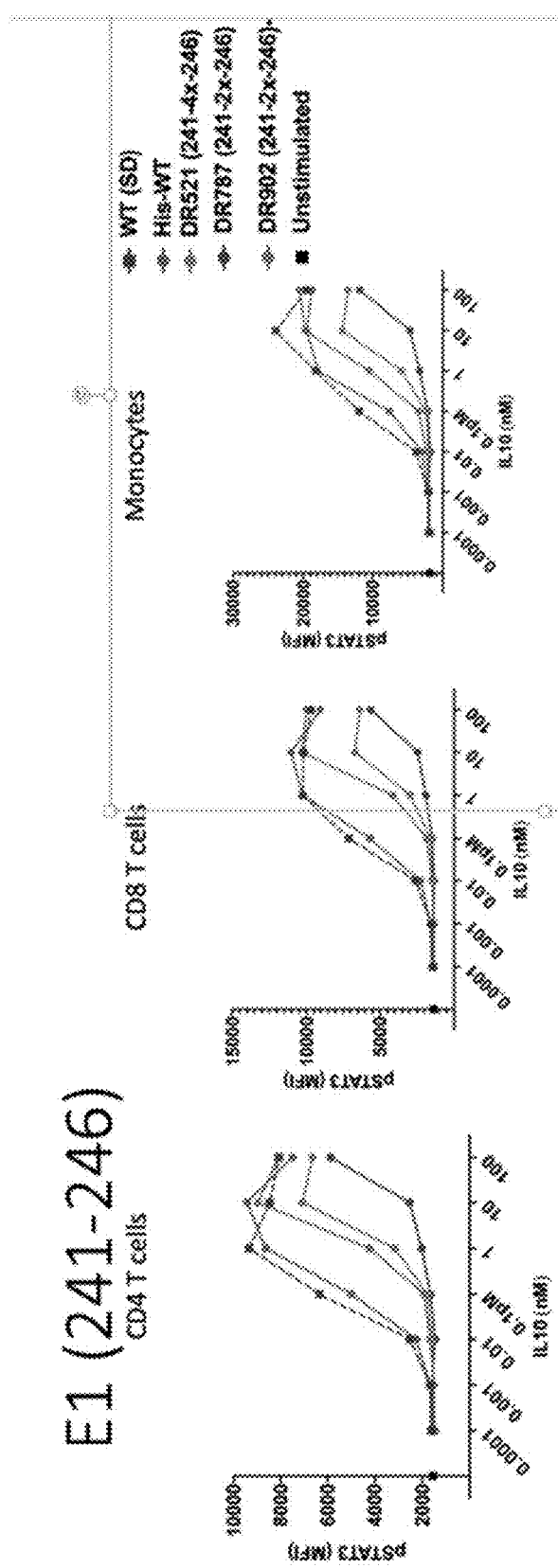
Figure 6C:
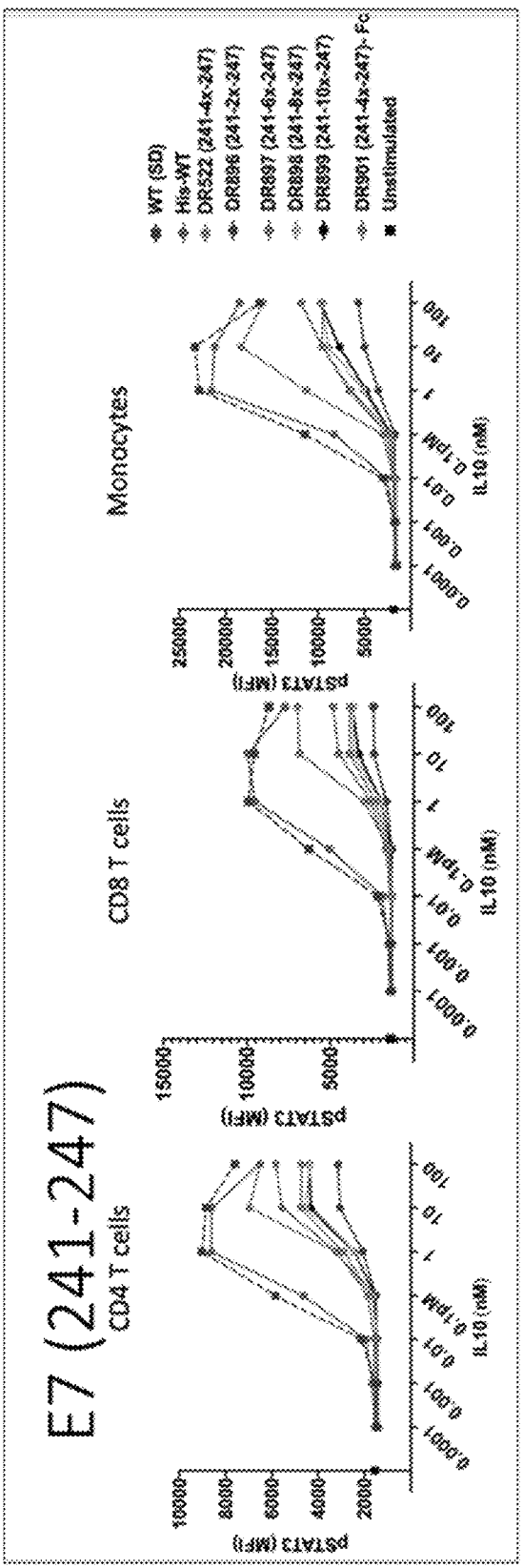

To attempt to generate cytokine analogs which provide selective activation of the desired cell types, a variety of engineered cytokine ligands (or components thereof) have been generated so as to selectively modulate their affinity for the extracellular domains of receptor subunits. These efforts have generated cytokine variants been shown to provide partial activity which results in uncoupling of the beneficial properties of the ligand from the undesired effects. See, e.g, Mendoza, et al. (2019) 567:56-60. However, the engineering of such selective cytokines ligand is based on selective modulation of individual amino acid residues at the interface of the ligand and the receptor. This protein engineering approach to modulation of cytokine receptor affinity requires a three dimensional, usually x-ray crystallographic, map of the interation of the receptor and the cytokine to identify the residues of the cytokine that interface with the receptor subunit. Additionally the effects of amino acid substitutions at these interface residues can be highly variable often requiring a significant amount of time consuming trial-and-error to identify the particular amino acid substitutions required to produce the desired activity profile. However, even once the engineered cytokine with the desired signaling profile is achieved, many proteins are highly sensitive to amino acid substitutions result in significant issues for recombinant expression, both in mammalian expression systems and procaryotic systems where such amino acid substitutions can affect protein refolding when expressed in inclusion bodies. The foregoing issues are particularly acute when the cytokine itself is heterodimeric. For example, IL12 exists a a heterodimer of the p35 and p40 subunits. The engineering of one residues of the interface of one subunit of the ligand engineering of the cytokine subunit at the interface with the receptor subunit (e.g. the p40/IL12Rb2 interface) may cause issues with the association of the cytokine ligand subunits (e.g. p35 and p40). Additionally, the p40 subunit of IL12 has functions as a monomer and homodimer whose activities may also be affected by such amino acid substitutions. Consequently, there is a need in the art for molecules which provide the activity of cytokines, that may be readily generated and engineered for receptor affinity and do not have independent off-target activity.

BRIEF DESCRIPTION OF THE FIGURES

FIG. 1 of the attached drawings provides a schematic representation of one embodiment of the binding molecule of the present disclosure comprising a first single domain antibody (1) and a second single domain antibody (3) and a linker (2) depicted as interacting with a cell membrane (10) associated heterodimeric receptor comprising a first receptor subunit comprising an extracellular domain (4), and transmembrane domain (5) and an intracellular domain (6) interaction of a binding molecule and a second first receptor subunit comprising an extracellular domain (7), and transmembrane domain (8) and an intracellular domain (9) wherein the intracellular domain of the first receptor (6) and the intracellular domain of the second receptor (9) on of a binding molecule are within a proximal distance (11).

FIGS. 2A-2B of the attached drawings provides a schematic representation of two illustrative configurations of binding molecules of the present disclosure. FIG. 2A provides a schematic representation of an illustrative single polypeptide chain binding molecule comprising, from amino to carboxy, a first single domain antibody (1) and a second single domain antibody (3) and a linker (2). FIG. 2B provides a schematic representation of a binding molecule comprising a first single domain antibody (1) and a second single domain antibody (3) and a linker (2) and a knob-into-hole Fc domain comprising a first subunit which is a Fc knob (13) and a second subunit which is a Fc hole (14) wherein the single domain antibody is stably associated with the Fc domain via a IgG hinge sequence (12).

FIGS. 2A-2B of the attached drawings provides a schematic representation of two illustrative configurations of binding molecules of the present disclosure. FIG. 2A provides a schematic representation of an illustrative binding molecule comprising a first single domain antibody (1) and a second single domain antibody (3) and a linker (2). FIG. 2B provides a schematic representation of a binding molecule comprising two polypeptide chains, the first polypeptide chain comprising (from amino to carboxy) a first single domain antibody (1), a linker sequence, a second single domain antibody (3), an IgG hinge sequence (12) and an Fc knob domain (13) and a second polypeptide comprising an Fc hole (14) wherein the first and second polypeptides are in stable association via the interaction of the knob-into-hole Fc domain.

FIGS. 3A-3B of the attached drawings provides a schematic representations of two illustrative configurations of binding molecules of the present disclosure. FIG. 3A provides a schematic representation of an illustrative binding molecule construct comprising two binding molecules each attached to a subunit of a knob-into-hole Fc domain, the construct comprising two polypeptide chains, the first polypeptide chain comprising, from amino to carboxy, a first single domain antibody (1), a linker (2) and a second single domain antibody (3), a IgG hinge sequence (12) and a Fc knob subunit (13) and a second polypeptide chain comprising, from amino to carboxy, a first single domain antibody (1), a linker (2) and a second single domain antibody (3), a IgG hinge sequence (12) and a Fc hole subunit (14) wherein the first and second polypeptides are in stable associate via the interaction of the knob-into-hole Fc domain. FIG. 3B provides schematic representation of a an alternative arrangement of a binding molecule construct comprising two polypeptides a first polypeptide chain comprising, from amino to carboxy, a first single domain antibody (1), a linker (2) and a second single domain antibody (3), an IgG hinge sequence (12) and a Fc knob subunit (13) and a second polypeptide chain comprising, from amino to carboxy, a first second domain antibody (3), a linker (2) and a first single domain antibody (1), a IgG hinge sequence (12) and a Fc hole subunit (14), wherein the first and second polypeptides are in stable association via the interaction of the knob-into-hole Fc domain.

FIG. 4A provides alternative schematic representations of configurations of the binding molecules of the present disclosure where one single domain antibody is attached to each subunit of a knob-into-hole Fc domain comprising two polypeptides, the first polypeptide comprising from amino to carboxy, a first single domain antibody (1), an IgG hinge sequence (12) and a Fc knob subunit (13), the second polypeptide comprising from amino to carboxy, a second single domain antibody (3), an IgG hinge sequence (12) and a Fc hole subunit (13), wherein the first and second single domain antibodies are in stable associate via the interaction of the knob-into-hole Fc domain.

FIG. 4B provides a schematic representations of a binding molecule the binding domains are single domain antibodies associated via transition metal coordinate covalent complex. As illustrated, the binding molecules comprises two polypeptide subunits: the first subunit comprising a first single domain antibody (1) is attached via a first linker (15) to a first chelating peptide (17) and second subunit comprising a second single domain antibody (3) is attached via a second linker (16) to a second chelating peptide (18), wherein the first chelating peptide (17) and second chelating peptide (18) form a coordinate covalent complex with a single transition metal ion ("M"). The transition metal ion may be in a kinetically labile or kinetically inert oxidation state.

FIG. 5 of the attached drawings provides the schematic representation of the protocol used to evaluate IL10R binding molecules for the effect of linker length on activity in CD4 T cells, CD8 T cells and monocytes isolated from PBMCs.

FIGS. 6A-6C of the attached drawings provides data from the evaluation of IL10R polypeptide binding molecules and the ability to induce IL10 activity as measured by phosphor STAT3 (y-axis) and varying concentrations of the IL10R binding molecule test articles on the x-axis as indicated to evaluate variations in distance between the IL10Ra and IL10Rb sdAbs on IL10 activity. In all experiments, the n-terminal IL10Ra sdAb of the polypeptide IL10R binding molecules was DR241. In FIG. 6A, the C-terminal IL2Rb sdAb was DR244. In FIG. 6B, the C-terminal IL2Rb sdAb was DR246. In FIG. 6C, the C-terminal IL2Rb sdAb was DR247. Various lines represent IL10R binding molecules wherein the distance between the IL10Ra and IL10Rb sdAbs was varied with linker length.

SUMMARY OF THE DISCLOSURE

The present disclosure provides compositions useful in the pairing of cellular receptors to generate desirable effects useful in treatment of disease in mammalian subjects.

The present disclosure provides compositions comprising at least a first domain that specifically binds to a first receptor subunit and a second domain that specifically binds to a second receptor subunit, such that upon contacting with a cell expressing the functional and second receptors, the composition causes the functional association of the first and second receptors, thereby triggering their interaction and resulting in downstream signaling. In some embodiments, the first and second receptors occur in proximity in response to the cognate ligand binding and are referred to herein as "natural" cytokine receptor pairs.

In one embodiment, present disclosure provides binding molecules that comprise a first domain that binds to IL10Ra of the IL10 receptor and a second domain that binds to IL10Rb of the IL10 receptor, such that upon contacting with a cell expressing IL10Ra receptor and IL10Rb receptor, the IL10R binding molecule causes the functional association of IL10Ra and IL10Rb, thereby resulting in functional dimerization of the receptors and downstream signaling.

The present disclosure provides disclosure provides cytokine receptor binding molecules that are ligands for a cytokine receptor, the cytokine receptor binding molecule comprising:

(a) a first single domain antibody (sdAb) that specifically binds to the extracellular domain a first subunit of a cytokine receptor; and (b) a second single domain antibody that specifically binds to extracellular domain of a second subunit of cytokine receptor subunit;

wherein:

the first sdAb and second sdAb are in stable association;

the first and second subunits of the cytokine receptor are dimerized in response to contact with the cognate ligand for the cytokine receptor; and contacting a cell expressing the first and the second subunist of the cytokine receptor with an effective amount of the cytokine receptor binding molecule results in the intracellular domains of the first and second subunits of the cytokine receptors being brought into proximity and results in intracellular signaling.

The IL10R binding molecules of the present disclosure comprise two or more single domain antibodies that selectively bind to the extracellular domain of the IL10Ra and IL10Rb receptor subunits. In one embodiment, the present disclosure provides an IL10 receptor (IL10R) binding molecule that is a ligand for the IL10R receptor, the IL10R receptor binding molecule comprising:

(c) a first single domain antibody (sdAb) that specifically binds to the extracellular domain the IL10Ra subunit of the IL10 receptor (an "IL10Ra sdAb"), and (d) a second single domain antibody that specifically binds to the extracellular domain of the IL10Rb subunit of the IL10 receptor (an "IL10Rb sdAb"), wherein:

the first sdAb and second sdAb are in stable association;

the IL10Ra and IL10Rb subunits of the IL10 receptor are dimerized in response to contact with the IL10R binding molecule; and contacting a cell expressing the IL10Ra and IL10Rb with an effective amount of the IL10R binding molecule results in the intracellular domains of IL10Ra and IL10Rb being brought into proximity and intracellular signaling.

In one embodiment, the cytokine receptor binding molecule is a ligand for the IL10 receptor and comprises a first sdAb that specifically binds to the extracellular domain of the IL10Ra receptor subunit and a second sdAb that specifically binds to the extracellular domain of the IL10Rb receptor subunit.

In some embodiments, the anti-IL10Rα sdAb is a VHH antibody (an anti IL10Rα VHH antibody) and/or the anti-IL10Rβ sdAb is a VHH antibody (an anti IL10Rβ VHH antibody). In some embodiments, the anti-IL10Rα sdAb and the anti-IL10Rβ sdAb are joined by a peptide linker. In some embodiments, the peptide linker comprises between 1 and 50 amino acids.

In another aspect, the disclosure provides a method for treating neoplastic diseases, such as cancer in a subject in need thereof, comprising administering to the subject the IL10R binding protein described herein, wherein the IL10R binding protein binds to and activates $CD8^+$ T cells, $CD4^+$ T cells, macrophages, and/or Treg cells. In some embodiments, the IL10R binding protein provides longer therapeutic efficacy than a pegylated IL10. In some embodiments, the cancer is a solid tumor cancer.

In other aspects, the IL10R binding proteins described herein can also be used to treat inflammatory diseases, such as Crohn's disease and ulcerative colitis, and autoimmune diseases, such as psoriasis, rheumatoid arthritis, and multiple sclerosis.

In some embodiments, one sdAb of the binding molecule is an scFv and the other sdAb is a VHH.

In some embodiments, the the first and second sdAbs are covalently bound via a chemical linkage.

In some some embodiments, the the first and second sdAbs are provided as single continuous polypeptide.

The present invention provides IL10R binding molecules that are synthetic ligands of the IL10 receptor.

In some embodiments, the IL10R binding molecule of the present invention is a polypeptide of the following formula [#1]:

$$H2N\text{-}(IL10\ VHH\ \#1)\text{-}(L1)_a\text{-}(IL10\ VHH\ \#2)\text{-}(L2)_b\text{-}(CP)_c\text{—}COOH \quad [\#1]$$

wherein: "-" represents a covalent bond; L1 and L2 are linkers; CP is a chelating peptide; a, b, and c are independently selected from the integers 0 or 1; "H2N" denotes the amino terminus; and "COOH" denotes the carboxy terminus of the polypeptide.

In some embodiments the present invention provides the IL10R binding molecule of the present invention is a polypeptide of the following formula [#1], wherein IL10 VHH #1 is an ILRa sdAb and IL10 VHH #2 is an IL10Rb sdAb, IL10 VHH #1 is an ILRb sdAb and IL10 VHH #2 is an IL10Ra sdAb.

In some embodiments, the invention provides and IL10R binding molecule comprising a IL10Ra sdAb comprising:
- a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 1, 4, 7, 10, 13, 16, 19, 22, 25, 28, 31, 34, 37, 40, 43, 46, 49, and 52;
- a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 2, 5, 8, 11, 14, 17, 20, 23, 26, 29, 32, 35, 38, 41, 44, 47, 50 and 53; and
- a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 3, 6, 9, 12, 15, 18, 21, 24, 27, 30, 33, 36, 39, 42, 45, 48, 51 and 54.

In some embodiments, the invention provides and IL10R binding molecule comprising a IL10Rb sdAb comprising:
- a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148 and 151;
- a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149 and 152; and
- a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150 and 153.

In some embodiments, the invention provides and IL10R binding molecule comprising a IL10Ra sdAb having least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative to any one of SEQ ID NOS: 154-171.

In some embodiments, the invention provides and IL10R binding molecule comprising a IL10Rb sdAb having least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative to any one of SEQ ID NOS: 172-198 or SEQ ID Nos:199-201.

In some embodiments, the invention provides and IL10R binding molecule comprising a having least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative to any one of SEQ ID NOS: 256-353.

In some embodiments, the invention provides and IL10R binding molecule comprising a IL10Rb sdAb having least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative to any one of SEQ ID NOS: 172-198 or SEQ ID Nos:199-201.

In some embodiments, the present invention provides IL10R binding molecules having at least 90% (e.g., 91%, 92%, 93%, 94%, 95%, 96%, 97%, 98%, 99%, or 100%) sequence identity to the sequence of any one of the IL10R binding molecules of Table 29 SEQ ID NOS: [DR1511-DR1525]. In some embodiments, the present invention provides IL10R binding molecules substantially identical of any one of the IL10R binding molecules of Table 29 SEQ ID NOS: [DR1511-DR1525]. In some embodiments, the present invention provides IL10R binding molecules identical to a sequence of any one of the IL10R binding molecules of Table 29 SEQ ID NOS: [DR1511-DR1525].

In one embodiment, the present disclosure provides an IL10Ra binding molecule that preferentially activates T cells, in particular CD8+ T cells, relative to monocytes. In one embodiment, the present disclosure provides an IL10Ra binding molecule of the formula #1 wherein the affinity of the IL10Ra sdAb has a higher affinity for the extracellular domain of IL10Ra than the affinity of the IL10Rb sdAb for the extracellular domain of IL10Rb.

In some embodiments, the present disclosure provides an IL10R binding molecule modified to provide prolonged duration of action in vivo in a mammalian subject and pharmaceutically acceptable formulations thereof. In some embodiments, the present invention provides a IL10R binding molecules of formula #1 that is PEGylated, wherein the PEG is conjugated to the IL10R binding molecule and the PEG is a linear or branched PEG molecule having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, or alternatively about 30,000 to about 40,000 daltons. In one embodiment of the disclosure, the PEG is a 40 kD branched PEG comprising two 20 kD arms.

The IL10R binding molecules of the present disclosure are useful in the treatment or prevention of disease in mammalian subjects. In some embodiments, the present disclosure provides for the treatment or prevention of autoimmune disease in a mammalian subject by the administration of a therapeutically effective amount of an IL10R binding molecule of the present disclosure. In some embodiments, the present disclosure provides for the treatment or prevention of infectious disease, including viral and chronic viral infections, in a mammalian subject by the administration of a therapeutically effective amount of an IL10R binding molecule of the present disclosure. In some embodiments, the present disclosure provides for the treatment or prevention of neoplastic disease in a mammalian subject by the administration of a therapeutically effective amount of an IL10R binding molecule of the present disclosure. In some embodiments, the present disclosure provides for the treatment or prevention of neoplastic, infectious or autoimmune in a mammalian subject by the administration of a therapeutically effective amount of an IL10R binding molecule of the present disclosure in combination with one or more supplementary therapeutic agents.

The present disclosure further provides a pharmaceutically acceptable formulation of an IL10R binding molecule for the administration to a mammalian subject. The present disclosure further provides a pharmaceutically acceptable composition for administration to a mammalian subject the composition comprising a nucleic acid sequence encoding a polypeptide IL10R binding molecule, a recombinant viral or non-viral vector encoding or polypeptide IL10R binding molecule, or a recombinantly modified mammalian cell comprising a nucleic acid sequence encoding a polypeptide IL10R binding molecule, in each case the nucleic acid sequence operably linked to one or more expression control elements functional in a mammalian cell.

The present disclosure provides nucleic acid sequences encoding polypeptide IL10R binding molecules. The present disclosure further provides a recombinant vector comprising a nucleic acid sequence encoding polypeptide IL10R binding molecules. The present disclosure further provides a recombinantly modified mammalian cell comprising a nucleic acid encoding a polypeptide IL10R binding molecule. The present disclosure further provides methods for the recombinant production, isolation, purification and characterization of a polypeptide IL10R binding molecule. of recombinant vectors comprising a provides nucleic acid sequences encoding polypeptide IL10R binding molecules.

The disclosure also provides an expression vector comprising a nucleic acid encoding the bispecific binding molecule operably linked to one or more expression control sequences. The disclosure also provides an isolated host cell comprising the expression vector expression vector comprising a nucleic acid encoding the bispecific binding molecule operably linked to one or more expression control sequences functional in the host cell.

In another aspect, the disclosure provides a pharmaceutical composition comprising the IL10R binding molecule described herein and a pharmaceutically acceptable carrier.

In another aspect, the disclosure provides a method of treating an autoimmune or inflammatory disease, disorder, or condition or a viral infection in a subject in need thereof, comprising administering to the subject a therapeutically effective amount of an IL10R binding molecule described herein or a pharmaceutical composition described herein.

Several advantages flow from the binding molecules described herein. The natural ligand of the IL10 receptor, IL10, causes IL10Ra and IL10Rb to come into proximity (i.e., by their simultaneous binding of IL10). However, when IL10 is used as a therapeutic in mammalian, particularly human, subjects, it may also trigger a number of adverse and undesirable effects by a variety of mechanisms including the presence of IL10Ra and IL10Rb on other cell types and the binding to IL10Ra and IL10Rb on the other cell types may result in undesirable effects and/or undesired signaling on cells expressing IL10Ra and IL10Rb. The present disclosure is directed to methods and compositions that modulate the multiple effects of IL10Ra and IL10Rb binding so that desired therapeutic signaling occurs, particularly in a desired cellular or tissue subtype, while minimizing undesired activity and/or intracellular signaling.

In some embodiments, the IL10R binding molecules described herein are partial agonists of the IL10 receptor. In some embodiments, the binding molecules described herein are designed such that the binding molecules are full agonists. In some embodiments, the binding molecules described herein are designed such that the binding molecules are super agonists.

In some embodiments, the binding molecules provide the maximal desired IL10 intracellular signaling from binding to IL10Ra and IL10Rb on the desired cell types, while providing significantly less IL10 signaling on other undesired cell types. This can be achieved, for example, by selection of binding molecules having differing affinities or causing different Emax for IL10Ra and IL10Rb as compared to the affinity of IL10 for IL10Ra and IL10Rb. Because different cell types respond to the binding of ligands to its cognate receptor with different sensitivity, by modulating the affinity of the dimeric ligand (or its individual binding moieties) for the IL10 receptor relative to wild-type IL10 binding facilitates the stimulation of desired activities while reducing undesired activities on non-target cells.

DETAILED DESCRIPTION OF THE INVENTION

To facilitate the understanding of present disclosure, certain terms and phrases are defined below as well as throughout the specification. The definitions provided herein are non-limiting and should be read in view of the knowledge of one of skill in the art would know.

Before the present methods and compositions are described, it is to be understood that this invention is not limited to a particular method or composition described, as such may, of course, vary. It is also to be understood that the terminology used herein is for the purpose of describing embodiments only and is not intended to be limiting.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited.

It should be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); AA or aa=amino acid(s); kb=kilobase(s); nt=nucleotide(s); pg=picogram; ng=nanogram; pg=microgram; mg=milligram; g=gram; kg=kilogram; dl or dL=deciliter; μl or pL=microliter; ml or mL=milliliter; l or L=liter; pM=micromolar; mM=millimolar; M=molar; kDa=kilodalton; i.m.=intramuscular(ly); i.p.=intraperitoneal (ly); SC or SQ=subcutaneous(ly); QD=daily; BID=twice daily; QW=once weekly; QM=once monthly; HPLC=high performance liquid chromatography; BW=body weight; U=unit; ns=not statistically significant; PBS=phosphate-buffered saline; PCR=polymerase chain reaction; HSA=human serum albumin; MSA=mouse serum albumin; DMEM=Dulbeco's Modification of Eagle's Medium; EDTA=ethylenediaminetetraacetic acid.

It will be appreciated that throughout this disclosure reference is made to amino acids according to the single letter or three letter codes. For the reader's convenience, the single and three letter amino acid codes are provided in Table 1.

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)). The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Definitions

Unless otherwise indicated, the following terms are intended to have the meaning set forth below. Other terms are defined elsewhere throughout the specification.

Activate: As used herein the term "activate" is used in reference to a receptor or receptor complex to reflect a biological effect, directly and/or by participation in a multicomponent signaling cascade, arising from the binding of an agonist ligand to a receptor responsive to the binding of the ligand.

Activity: As used herein, the term "activity" is used with respect to a molecule to describe a property of the molecule with respect to a test system (e.g. an assay) or biological or chemical property (e.g. the degree of binding of the molecule to another molecule) or of a physical property of a material or cell (e.g. modification of cell membrane potential). Examples of such biological functions include but are not limited to catalytic activity of a biological agent, the ability to stimulate intracellular signaling, gene expression, cell proliferation, the ability to modulate immunological activity such as inflammatory response. "Activity" is typically expressed as a level of a biological activity per unit of agent tested such as [catalytic activity]/[mg protein], [immunological activity]/[mg protein], international units (IU) of activity, [STAT5 phosphorylation]/[mg protein], [T-cell proliferation]/[mg protein], plaque forming units (pfu), etc. As used herein, the term "proliferative activity" refers to an activity that promotes cell proliferation and replication.

Administer/Administration: The terms "administration" and "administer" are used interchangeably herein to refer the act of contacting a subject, including contacting a cell, tissue, organ, or biological fluid of the subject in vitro, in vivo or ex vivo with an agent (e.g. an ortholog, an IL2 ortholog, an engineered cell expressing an orthogonal receptor, an engineered cell expressing an orthogonal IL2 receptor, a CAR-T cell expressing an orthogonal IL2 receptor, a chemotherapeutic agent, an antibody, or a pharmaceutical formulation comprising one or more of the foregoing). Administration of an agent may be achieved through any of a variety of art recognized methods including but not limited to the topical administration, intravascular injection (including intravenous or intraarterial infusion), intradermal injection, subcutaneous injection, intramuscular injection, intraperitoneal injection, inhalation and the like. The term "administration" includes contact of an agent to the cell, tissue or organ as well as the contact of an agent to a fluid, where the fluid is in contact with the cell, tissue or organ.

Affinity: As used herein the term "affinity" refers to the degree of specific binding of a first molecule (e.g., a ligand) to a second molecule (e.g., a receptor) and is measured by the equilibrium dissociation constant ($K_D$), a ratio of the dissociation rate constant between the molecule and its target ($K_{off}$) and the association rate constant between the molecule and its target ($K_{on}$).

Agonist: As used herein, the term "agonist" refers a first agent that specifically binds a second agent ("target") and interacts with the target to cause or promote an increase in the activation of the target. In some instances, agonists are activators of receptor proteins that modulate cell activation, enhance activation, sensitize cells to activation by a second agent, or up-regulate the expression of one or more genes, proteins, ligands, receptors, biological pathways, that may result in cell proliferation or pathways that result in cell cycle arrest or cell death such as by apoptosis. In some embodiments, an agonist is an agent that binds to a receptor and alters the receptor state, resulting in a biological response. The response mimics the effect of the endogenous activator of the receptor. The term "agonist" includes partial agonists, full agonists and superagonists. An agonist may be described as a "full agonist" when such agonist which leads to a substantially full biological response (i.e., the response associated with the naturally occurring ligand/receptor binding interaction) induced by receptor under study, or a partial agonist. In contrast to agonists, antagonists may specifically bind to a receptor but do not result the signal cascade typically initiated by the receptor and may to modify the actions of an agonist at that receptor. Inverse agonists are agents that produce a pharmacological response that is opposite in direction to that of an agonist. A "superagonist" is a type of agonist that is capable of producing a maximal response greater than the endogenous agonist for the target receptor, and thus has an activity of more than 100% of the native ligand. A super agonist is typically a synthetic molecule that exhibits greater than 110%, alternatively greater than 120%, alternatively greater than 130%, alternatively greater than 140%, alternatively greater than 150%, alternatively greater than 160%, or alternatively greater than 170% of the response in an evaluable quantitative or qualitative parameter of the naturally occurring form of the molecule when evaluated at similar concentrations in a comparable assay.

Antagonist: As used herein, the term "antagonist" or "inhibitor" refers a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist. Inhibitors are molecules that decrease, block, prevent, delay activation, inactivate, desensitize, or down-regulate, e.g., a gene, protein, ligand, receptor, biological pathway, or cell.

Antibody: As used herein, the term "antibody" refers collectively to: (a) glycosylated and non-glycosylated immunoglobulins (including but not limited to mammalian immunoglobulin classes IgG1, IgG2, IgG3 and IgG4) that specifically binds to target molecule and (b) immunoglobulin derivatives including but not limited to IgG(1-4)deltaCH2, F(ab')$_2$, Fab, ScFv, VH, VL, tetrabodies, triabodies, diabodies, dsFv, F(ab')$_3$, scFv-Fc and (scFv)$_2$ that competes with the immunoglobulin from which it was derived for binding to the target molecule. The term antibody is not restricted to immunoglobulins derived from any particular mammalian species and includes murine, human, equine, camelids, human antibodies. The term antibody includes so called "heavy chain antibodies" or "VHHs" or "Nanobodies®" as typically obtained from immunization of camelids (including camels, llamas and alpacas (see, e.g. Hamers-Casterman, et al. (1993) Nature 363:446-448). Antibodies having a given specificity may also be derived from non-mammalian sources such as VHHs obtained from immunization of cartilaginous fishes including, but not limited to, sharks. The term "antibody" encompasses antibodies isolatable from natural sources or from animals following immunization with an antigen and as well as engineered antibodies including monoclonal antibodies, bispecific antibodies, tri-specific, chimeric antibodies, humanized antibodies, human antibodies, CDR-grafted, veneered, or deimmunized (e.g., to remove T-cell epitopes) antibodies. The term ""human antibody" includes antibodies obtained from human beings as well as antibodies obtained from transgenic mammals comprising human immunoglobulin genes such that, upon stimulation with an antigen the transgenic animal produces antibodies comprising amino acid sequences characteristic of antibodies produced by human beings. The term antibody includes both the parent antibody and its derivatives such as affinity matured, veneered, CDR grafted (including CDR grafted VHHs), humanized, camelized (in the case of non-camel derived VHHs), or binding molecules comprising binding domains of antibodies (e.g., CDRs) in non-immunoglobulin scaffolds. The term "antibody" is not limited to any particular means of synthesis and includes naturally occurring antibodies isolatable from natural sources and as well as engineered antibodies molecules that are prepared by "recombinant" means including antibodies isolated from transgenic animals that are transgenic for human immunoglobulin genes or a hybridoma prepared therefrom, antibodies isolated from a host cell transformed with a nucleic acid construct that results in expression of an antibody, antibodies isolated from a combinatorial antibody library including phage display libraries or chemically synthesized (e.g., solid phase protein synthesis). In one embodiment, an "antibody" is a mammalian immunoglobulin. In some embodiments, the antibody is a "full length antibody" comprising variable and constant domains providing binding and effector functions. In most instances, a full-length antibody comprises two light chains and two heavy chains, each light chain comprising a variable region and a constant region. In some embodiments the term "full length antibody" is used to refer to conventional IgG immunoglobulin structures comprising two light chains and two heavy chains, each light chain comprising a variable region and a constant region providing binding and effector functions. The term antibody includes antibody conjugates comprising modifications to prolong duration of action such as fusion proteins or conjugation to polymers (e.g., PEGylated) as described in more detail below.

Binding molecule: As used herein, the term "binding molecule" refers to a bivalent molecule that can bind to the extracellular domain of two cell surface receptors. In some embodiments, a binding molecule specifically binds to two different receptors (or domains or subunits thereof) such that the receptors (or domains or subunits) are maintained in proximity to each other such that the receptors (or domains or subunits), including domains thereof (e.g., intracellular domains) interact with each other and result in downstream signaling.

CDR: As used herein, the term "CDR" or "complementarity determining region" is intended to mean the non-contiguous antigen combining sites found within the variable region of both heavy and light chain immunoglobulin polypeptides. CDRs have been described by Kabat et al., J. Biol. Chem. 252:6609-6616 (1977); Kabat, et al., U.S. Dept. of Health and Human Services publication entitled "Sequences of proteins of immunological interest" (1991) (also referred to herein as "Kabat 1991" or "Kabat"); by Chothia, et al. (1987) J. Mol. Biol. 196:901-917 (also referred to herein as "Chothia"); and MacCallum, et al. (1996) J. Mol. Biol. 262:732-745, where the definitions include overlapping or subsets of amino acid residues when compared against each other. Nevertheless, application of either definition to refer to a CDR of an antibody or grafted antibodies or variants thereof is intended to be within the scope of the term as defined and used herein. The term "Chothia Numbering" as used herein is recognized in the arts and refers to a system of numbering amino acid residues based on the location of the structural loop regions (Chothia et al. 1986, Science 233:755-758; Chothia & Lesk 1987, JMB 196:901-917; Chothia et al. 1992, JMB 227:799-817). For purposes of the present disclosure, unless otherwise specifically identified, the positioning of CDRs2 and 3 in the variable region of an antibody follows Kabat numbering or simply, "Kabat." The positioning of CDR1 in the variable region of an antibody follows a hybrid of Kabat and Chothia numbering schemes.

Clonotype: As used herein, a clonotype refers to a collection of binding molecules that originate from the same B-cell progenitor cell. The term "clonotype" is used to refer to a collection of antigen binding molecules that belong to the same germline family, have the same CDR3 lengths, and have 70% or greater homology in CDR3 sequence.

Comparable: As used herein, the term "comparable" is used to describe the degree of difference in two measurements of an evaluable quantitative or qualitative parameter. For example, where a first measurement of an evaluable quantitative parameter and a second measurement of the evaluable parameter do not deviate beyond a range that the skilled artisan would recognize as not producing a statistically significant difference in effect between the two results in the circumstances, the two measurements would be considered "comparable." In some instances, measurements may be considered "comparable" if one measurement deviates from another by less than 30%, alternatively by less than 25%, alternatively by less than 20%, alternatively by less than 15%, alternatively by less than 10%, alternatively by less than 7%, alternatively by less than 5%, alternatively by less than 4%, alternatively by less than 3%, alternatively by less than 2%, or by less than 1%. In particular embodiments, one measurement is comparable to a reference standard if it deviates by less than 15%, alternatively by less than 10%, or alternatively by less than 5% from the reference standard.

Conservative Amino Acid Substitution: As used herein, the term "conservative amino acid substitution" refers to an amino acid replacement that changes a given amino acid to a different amino acid with similar biochemical properties (e.g., charge, hydrophobicity, and size). For example, the amino acids in each of the following groups can be considered as conservative amino acids of each other: (1) hydrophobic amino acids: alanine, isoleucine, leucine, tryptophan, phenylalanine, valine, proline, and glycine; (2) polar amino acids: glutamine, asparagine, histidine, serine, threonine, tyrosine, methionine, and cysteine; (3) basic amino acids: lysine and arginine; and (4) acidic amino acids: aspartic acid and glutamic acid.

Derived From: As used herein in the term "derived from", in the context of an amino acid sequence or polynucleotide sequence (e.g., an amino acid sequence "derived from"), is meant to indicate that the polypeptide or nucleic acid has a sequence that is based on that of a reference polypeptide or nucleic acid (e.g., a naturally occurring polypeptide or an encoding nucleic acid), and is not meant to be limiting as to the source or method in which the protein or nucleic acid is made. By way of example, the term "derived from" includes homologs or variants of reference amino acid or DNA sequences.

Effective Concentration (EC): As used herein, the terms "effective concentration" or its abbreviation "EC" are used interchangeably to refer to the concentration of an agent (e.g., an hIL2 mutein) in an amount sufficient to effect a change in a given parameter in a test system. The abbreviation "E" refers to the magnitude of a given biological effect observed in a test system when that test system is exposed to a test agent. When the magnitude of the response is expressed as a factor of the concentration ("C") of the test agent, the abbreviation "EC" is used. In the context of biological systems, the term Emax refers to the maximal magnitude of a given biological effect observed in response to a saturating concentration of an activating test agent. When the abbreviation EC is provided with a subscript (e.g., $EC_{40}$, $EC_{50}$, etc.) the subscript refers to the percentage of the Emax of the biological observed at that concentration. For example, the concentration of a test agent sufficient to result in the induction of a measurable biological parameter in a test system that is 30% of the maximal level of such measurable biological parameter in response to such test agent, this is referred to as the "$EC_{30}$" of the test agent with respect to such biological parameter. Similarly, the term "$EC_{100}$" is used to denote the effective concentration of an agent that results the maximal (100%) response of a measurable parameter in response to such agent. Similarly, the term $EC_{50}$ (which is commonly used in the field of pharmacodynamics) refers to the concentration of an agent sufficient to results in the half-maximal (50%) change in the measurable parameter. The term "saturating concentration" refers to the maximum possible quantity of a test agent that can dissolve in a standard volume of a specific solvent (e.g., water) under standard conditions of temperature and pressure. In pharmacodynamics, a saturating concentration of a drug is typically used to denote the concentration sufficient of the drug such that all available receptors are occupied by the drug, and $EC_{50}$ is the drug concentration to give the half-maximal effect. The EC of a particular effective concentration of a test agent may be abbreviated with respect to the with respect to particular parameter and test system.

Enriched: As used herein in the term "enriched" refers to a sample that is non-naturally manipulated so that a species (e.g. a molecule or cell) of interest is present in: (a) a greater concentration (e.g., at least 3-fold greater, alternatively at least 5-fold greater, alternatively at least 10-fold greater, alternatively at least 50-fold greater, alternatively at least 100-fold greater, or alternatively at least 1000-fold greater) than the concentration of the species in the starting sample, such as a biological sample (e.g., a sample in which the molecule naturally occurs or in which it is present after administration); or (b) a concentration greater than the environment in which the molecule was made (e.g., a recombinantly modified bacterial or mammalian cell).

Extracellular Domain: As used herein the term "extracellular domain" or its abbreviation "ECD" refers to the portion of a cell surface protein (e.g. a cell surface receptor) which is outside of the plasma membrane of a cell. The term "ECD" may include the extra-cytoplasmic portion of a transmembrane protein or the extra-cytoplasmic portion of a cell surface (or membrane associated protein).

Identity: As used herein, the term "percent (%) sequence identity" or "substantially identical" used in the context of nucleic acids or polypeptides, refers to a sequence that has at least 50% sequence identity with a reference sequence. Alternatively, percent sequence identity can be any integer from 50% to 100%. In some embodiments, a sequence has at least 50%, 55%, 60%, 65%, 70%, 75%, 80%, 85%, 90%, 91%, 92%, 93%, 94%, 95%, 96%, 97%, 98%, or 99% sequence identity to the reference sequence as determined with BLAST using standard parameters, as described below. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. A comparison window includes reference to a segment of any one of the number of contiguous positions, e.g., a segment of at least 10 residues. In some embodiments, the comparison window has from 10 to 600 residues, e.g., about 10 to about 30 residues, about 10 to about 20 residues, about 50 to about 200 residues, or about 100 to about 150 residues, in which a sequence may be compared to a reference sequence of the same number of contiguous positions after the two sequences are optimally aligned. Algorithms that are suitable for determining percent sequence identity and sequence similarity are the BLAST and BLAST 2.0 algorithms, which are described in Altschul et al. (1990) *J Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)). The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a reference sequence if the smallest sum probability in a comparison of the test amino acid sequence to the reference amino acid sequence is less than about 0.01, more preferably less than about $10^{-5}$, and most preferably less than about $10^{-20}$.

Intracellular Signaling: As used herein, the terms "intracellular signaling" and "downstream signaling" are used interchangeably to refer to the to the cellular signaling process that is caused by the interaction of the intracellular domains (ICDs) of two or more cell surface receptors that are in proximity of each other. In receceptor complexes via the JAK/STAT pathway, the association of the ICDS of the receptor subunits brings the JAK domains of the ICDs into proximity which initiates a phosphorylation cascade in which STAT molecules are phosphorylated and translocate to the nucleus associating with particular nucleic acid sequences resulting in the activation and expression of particular genes in the cell. The binding molecules of the present disclosure provide intracelluar signaling characteristic of the IL10 receptor receptor when activated by its natural cognate IL10. To measure downstream signaling activity, a number of methods are available. For example, in some embodiments, one can measure JAK/STAT signaling by the presence of phosphorylated receptors and/or phosphorylated STATs. In other embodiments, the expression of one or more downstream genes, whose expression levels can be affected by the level of downstream signalinging caused by the binding molecule, can also be measured.

In An Amount Sufficient to Effect a Response: As used herein the phrase "in an amount sufficient to cause a response" is used in reference to the amount of a test agent sufficient to provide a detectable change in the level of an indicator measured before (e.g., a baseline level) and after the application of a test agent to a test system. In some embodiments, the test system is a cell, tissue or organism. In some embodiments, the test system is an in vitro test system such as a fluorescent assay. In some embodiments, the test system is an in vivo system which involves the measurement of a change in the level of a parameter of a cell, tissue, or organism reflective of a biological function before and after the application of the test agent to the cell, tissue, or organism. In some embodiments, the indicator is reflective of biological function or state of development of a cell evaluated in an assay in response to the administration of a quantity of the test agent. In some embodiments, the test system involves the measurement of a change in the level an indicator of a cell, tissue, or organism reflective of a biological condition before and after the application of one or more test agents to the cell, tissue, or organism. The term "in an amount sufficient to effect a response" may be sufficient to be a therapeutically effective amount but may also be more or less than a therapeutically effective amount.

In Need of Treatment: The term "in need of treatment" as used herein refers to a judgment made by a physician or other caregiver with respect to a subject that the subject requires or will potentially benefit from treatment. This judgment is made based on a variety of factors that are in the realm of the physician's or caregiver's expertise.

Isolated: As used herein the term "isolated" is used in reference to a polypeptide of interest that, if naturally occurring, is in an environment different from that in which it can naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was synthesized, for example isolated from a recombinant cell culture comprising cells engineered to express the polypeptide or by a solution resulting from solid phase synthetic means.

Kabat Numbering: The term "Kabat numbering" as used herein is recognized in the art and refers to a system of numbering amino acid residues which are more variable than other amino acid residues (e.g., hypervariable) in the heavy and light chain regions of immunoglobulins (Kabat, et al., (1971) *Ann. NY Acad. Sci.* 190:382-93; Kabat, et al., (1991) *Sequences of Proteins of Immunological Interest, Fifth Edition, U.S. Department of Health and Human Services, NIH Publication No.* 91-3242). The term "Chothia Numbering" as used herein is recognized in the arts and refers to a system of numbering amino acid residues based on the location of the structural loop regions (Chothia et al. 1986, *Science* 233:755-758; Chothia & Lesk 1987, JMB 196:901-917; Chothia et al. 1992, JMB 227:799-817). For purposes of the present disclosure, unless otherwise specifically identified, the positioning of CDRs 2 and 3 in the variable region of an antibody follows Kabat numbering or simply, "Kabat." The positioning of CDR1 in the variable region of an antibody follows a hybrid of Kabat and Chothia numbering schemes.

Ligand: As used herein, the term "ligand" refers to a molecule that exhibits specific binding to a receptor and results in a change in the biological activity of the receptor so as to effect a change in the activity of the receptor to which it binds. In one embodiment, the term "ligand" refers to a molecule, or complex thereof, that can act as an agonist or antagonist of a receptor. As used herein, the term "ligand" encompasses natural and synthetic ligands. "Ligand" also encompasses small molecules, e.g., peptide mimetics of cytokines and peptide mimetics of antibodies. The complex of a ligand and receptor is termed a "ligand-receptor complex."

As used herein, the term "linker" refers to a linkage between two elements, e.g., protein domains. A linker can be a covalent bond or a peptide linker. The term "bond" refers to a chemical bond, e.g., an amide bond or a disulfide bond, or any kind of bond created from a chemical reaction, e.g., chemical conjugation. The term "peptide linker" refers to an amino acid or polyeptide that may be employed to link two protein domains to provide space and/or flexibility between the two protein domains.

Modulate: As used herein, the terms "modulate", "modulation" and the like refer to the ability of a test agent to cause a response, either positive or negative or directly or indirectly, in a system, including a biological system, or biochemical pathway. The term modulator includes both agonists (including partial agonists, full agonists and superagonists) and antagonists.

Multimerization: As used herein, the term "multimerization" refers to two or more cell surface receptors, or domains or subunits thereof, being brought in close proximity to each other such that the receptors, or domains or subunits thereof, can interact with each other and cause intracellular signaling.

N-Terminus: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. The terms "immediately N-terminal" or "immediately C-terminal" are used to refers to a position of a first amino acid residue relative to a second amino acid residue where the first and second amino acid residues are covalently bound to provide a contiguous amino acid sequence.

Neoplastic Disease: As used herein and as discussed in more detail below, the term "neoplastic disease" refers to disorders or conditions in a subject arising from cellular hyper-proliferation or unregulated (or dysregulated) cell replication. The term neoplastic disease refers to disorders arising from the presence of neoplasms in the subject. Neoplasms may be classified as: (1) benign (2) pre-malignant (or "pre-cancerous"); and (3) malignant (or "cancerous"). The term "neoplastic disease" includes neoplastic-related diseases, disorders and conditions referring to conditions that are associated, directly or indirectly, with neoplastic disease, and includes, e.g., angiogenesis and precancerous conditions such as dysplasia or smoldering multiple myeloma. Examples of benign disorders arising from dysregulated cell replication include hypertrophic scars such as keloid scars.

Nucleic Acid: The terms "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the Operably Linked: The term "operably linked" is used herein to refer to the relationship between molecules, typically polypeptides or nucleic acids, which are arranged in a construct such that each of the functions of the component molecules is retained although the operable linkage may result in the modulation of the activity, either positively or negatively, of the individual components of the construct. For example, the operable linkage of a polyethylene glycol (PEG) molecule to a wild-type protein may result in a construct where the biological activity of the protein is diminished relative to the to the wild-type molecule, however the two are nevertheless considered operably linked. When the term "operably linked" is applied to the relationship of multiple nucleic acid sequences encoding differing functions, the multiple nucleic acid sequences when combined into a single nucleic acid molecule that, for example, when introduced into a cell using recombinant technology, provides a nucleic acid which is capable of effecting the transcription and/or translation of a particular nucleic acid sequence in a cell. For example, the nucleic acid sequence encoding a signal sequence may be considered operably linked to DNA encoding a polypeptide if it results in the expression of a preprotein whereby the signal sequence facilitates the secretion of the polypeptide; a promoter or enhancer is considered operably linked to a coding sequence if it affects the transcription of the sequence; or a ribosome binding site is considered operably linked to a coding sequence if it is positioned so as to facilitate translation. Generally in the context of nucleic acid molecules, the term "operably linked" means that the nucleic acid sequences being linked are contiguous, and, in the case of a secretory leader or associated subdomains of a molecule, contiguous and in reading phase. However, certain genetic elements such as enhancers may function at a distance and need not be contiguous with respect to the sequence to which they provide their effect but nevertheless may be considered operably linked.

Partial Agonist: As used herein, the term "partial agonist" refers to a molecule that specifically binds that bind to and activate a given receptor but possess only partial activation the receptor relative to a full agonist. Partial agonists may display both agonistic and antagonistic effects. For example, when both a full agonist and partial agonist are present, the partial agonist acts as a competitive antagonist by competing with the full agonist for the receptor binding resulting in net decrease in receptor activation relative to the contact of the receptor with the full agonist in the absence of the partial agonist. Clinically, partial agonists can be used to activate receptors to give a desired submaximal response when inadequate amounts of the endogenous ligand are present, or they can reduce the overstimulation of receptors when excess amounts of the endogenous ligand are present. The maximum response (Emax) produced by a partial agonist is called its intrinsic activity and may be expressed on a percentage scale where a full agonist produced a 100% response. A In some embodiments, the IL10R binding molecule has a reduced Emax compared to the Emax caused by IL10. Emax reflects the maximum response level in a cell type that can be obtained by a ligand (e.g., a binding molecule described herein or the native cytokine (e.g., IL10)). In some embodiments, the IL10R binding molecule described herein has at least 1% (e.g., between 1% and 100%, between 10% and 100%, between 20% and 100%, between 30% and 100%, between 40% and 100%, between 50% and 100%, between 60% and 100%, between 70% and 100%, between 80% and 100%, between 90% and 100%, between 1% and 90%, between 1% and 80%, between 1% and 70%, between 1% and 60%, between 1% and 50%, between 1% and 40%, between 1% and 30%, between 1% and 20%, or between 1% and 10%) of the $E_{max}$ caused by IL10. In other embodiments, the Emax of the IL10R binding molecule described herein is greater (e.g., at least 1%, 5%, 10%, 15%, 20%, 25%, 30%, 35%, 40%, 45%, or 50% greater) than the Emax of the natural ligand, IL10. In some embodiments, by varying the linker length of the IL10R binding molecules\, the $E_{max}$ of the IL10R binding molecule can be changed. The IL10R binding molecule can cause $E_{max}$ in the most desired cell types, and a reduced Emax in other cell types.

Polypeptide: As used herein the terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The term polypeptide include fusion proteins, including, but not limited to, fusion proteins with a heterologous amino acid sequence; fusion proteins with heterologous and homologous leader sequences; fusion proteins with or without N-terminal methionine residues; fusion proteins with amino acid sequences that facilitate purification such as chelating peptides; fusion proteins with immunologically tagged proteins; fusion proteins comprising a peptide with immunologically active polypeptide fragment (e.g. antigenic diphtheria or tetanus toxin or toxoid fragments) and the like.

Prevent: As used herein the terms "prevent", "preventing", "prevention" and the like refer to a course of action initiated with respect to a subject prior to the onset of a disease, disorder, condition or symptom thereof so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed due to genetic, experiential or environmental factors to having a particular disease, disorder or condition. In certain instances, the terms "prevent", "preventing", "prevention" are also used to refer to the slowing of the progression of a disease, disorder or condition from a present its state to a more deleterious state.

Proximity: As used herein, the term "proximity" refers to the spatial proximity or physical distance between two cell surface receptors, or domains or subunits thereof, after a binding molecule described herein binds to the two cell surface receptors, or domains or subunits thereof. In some embodiments, after the binding molecule binds to the cell surface receptors, or domains or subunits thereof, the spatial proximity between the cell surface receptors, or domains or subunits thereof, can be, e.g., less than about 500 angstroms, such as e.g., a distance of about 5 angstroms to about 500 angstroms. In some embodiments, the spatial proximity amounts to less than about 5 angstroms, less than about 20 angstroms, less than about 50 angstroms, less than about 75 angstroms, less than about 100 angstroms, less than about 150 angstroms, less than about 250 angstroms, less than about 300 angstroms, less than about 350 angstroms, less than about 400 angstroms, less than about 450 angstroms, or less than about 500 angstroms. In some embodiments, the spatial proximity amounts to less than about 100 angstroms. In some embodiments, the spatial proximity amounts to less than about 50 angstroms. In some embodiments, the spatial proximity amounts to less than about 20 angstroms. In some embodiments, the spatial proximity amounts to less than about 10 angstroms. In some embodiments, the spatial proximity ranges from about 10 to 100 angstroms, from about 50 to 150 angstroms, from about 100 to 200 angstroms, from about 150 to 250 angstroms, from about 200 to 300 angstroms, from about 250 to 350 angstroms, from about 300 to 400 angstroms, from about 350 to 450 angstroms, or about 400 to 500 angstroms. In some embodiments, the spatial proximity amounts to less than about 250 angstroms, alternatively less than about 200 angstroms, alternatively less than about 150 angstroms, alternatively less than about 120 angstroms, alternatively less than about 100 angstroms, alternatively less than about 80 angstroms, alternatively less than about 70 angstroms, or alternatively less than about 50 angstroms.

Receptor: As used herein, the term "receptor" refers to a polypeptide having a domain that specifically binds a ligand that binding of the ligand results in a change to at least one biological property of the polypeptide. In some embodiments, the receptor is a "soluble" receptor that is not associated with a cell surface. In some embodiments, the receptor is a cell surface receptor that comprises an extracellular domain (ECD) and a membrane associated domain which serves to anchor the ECD to the cell surface. In some embodiments of cell surface receptors, the receptor is a membrane spanning polypeptide comprising an intracellular domain (ICD) and extracellular domain (ECD) linked by a membrane spanning domain typically referred to as a transmembrane domain (TM). The binding of the ligand to the receptor results in a conformational change in the receptor resulting in a measurable biological effect. In some instances, where the receptor is a membrane spanning polypeptide comprising an ECD, TM and ICD, the binding of the ligand to the ECD results in a measurable intracellular biological effect mediated by one or more domains of the ICD in response to the binding of the ligand to the ECD. In some embodiments, a receptor is a component of a multicomponent complex to facilitate intracellular signaling. For example, the ligand may bind a cell surface molecule having not associated with any intracellular signaling alone but upon ligand binding facilitates the formation of a multimeric complex that results in intracellular signaling.

Recombinant: As used herein, the term "recombinant" is used as an adjective to refer to the method by a polypeptide, nucleic acid, or cell that was modified using recombinant DNA technology. A recombinant protein is a protein produced using recombinant DNA technology and may be designated as such using the abbreviation of a lower case "r" (e.g., rhIL2) to denote the method by which the protein was produced. Similarly, a cell is referred to as a "recombinant cell" if the cell has been modified by the incorporation (e.g., transfection, transduction, infection) of exogenous nucleic acids (e.g., ssDNA, dsDNA, ssRNA, dsRNA, mRNA, viral or non-viral vectors, plasmids, cosmids and the like) using recombinant DNA technology. The techniques and protocols for recombinant DNA technology are well known in the art such as those can be found in Sambrook, et al. (1989) Molecular Cloning: A Laboratory Manual (2d ed., Cold Spring Harbor Laboratory Press, Plainview, N.Y.) and other standard molecular biology laboratory manuals.

Response: The term "response," for example, of a cell, tissue, organ, or organism, encompasses a quantitative or qualitative change in a evaluable biochemical or physiological parameter, (e.g., concentration, density, adhesion, proliferation, activation, phosphorylation, migration, enzymatic activity, level of gene expression, rate of gene expression, rate of energy consumption, level of or state of differentiation) where the change is correlated with the activation, stimulation, or treatment, with or contact with exogenous agents or internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects. A "response" may be evaluated in vitro such as through the use of assay systems, surface plasmon resonance, enzymatic activity, mass spectroscopy, amino acid or protein sequencing technologies. A "response" may be evaluated in vivo quantitatively by evaluation of objective physiological parameters such as body temperature, bodyweight, tumor volume, blood pressure, results of X-ray or other imaging technology or qualitatively through changes in reported subjective feelings of well-being, depression, agitation, or pain. In some embodiments, the level of proliferation of CD3 activated primary human T-cells may be evaluated in a bioluminescent assay that generates a luminescent signal that is proportional to the amount of ATP present which is directly proportional to the number of viable cells present in culture as described in Crouch, et al. (1993) J. Immunol. Methods 160: 81-8 or using commercially available assays such as the CellTiter-Glo® 2.0 Cell Viability Assay or CellTiter-Glo® 3D Cell Viability kits commercially available from Promega Corporation, Madison WI 53711 as catalog numbers G9241 and G9681 in substantial accordance with the instructions provided by the manufacturer. In some embodiments, the level of activation of T cells in response to the administration of a test agent may be determined by flow cytometric methods as described as determined by the level of STAT (e.g., STAT1, STAT3, STAT5) phosphorylation in accordance with methods well known in the art.

Significantly Reduced Binding: As used herein, the term "exhibits significantly reduced binding" is used with respect to a variant of a first molecule (e.g. a ligand) which exhibits a significant reduction in the affinity for a second molecule (e.g. receptor) relative to the parent form of the first molecule. With respect to antibody variants, an antibody variant "exhibits significantly reduced binding" if the variant binds to the native form of the receptor with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent antibody from which the variant was derived. Similarly, with respect to variant ligands, a variant ligand "exhibits significantly reduced binding" if the variant ligand binds to a receptor with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent ligand from which the variant ligand was derived. Similarly, with respect to variant receptors, a variant ligand "exhibits significantly reduced binding" if the affinity of the variant receptors binds to a with an affinity of less than 20%, alternatively less than about 10%, alternatively less than about 8%, alternatively less than about 6%, alternatively less than about 4%, alternatively less than about 2%, alternatively less than about 1%, or alternatively less than about 0.5% of the parent receptor from which the variant receptor was derived.

Single Domain Antibody (sdAb): The term "single-domain antibody" or "sdAbs," refers to an antibody having a single (only one) monomeric variable antibody domain. A sdAb is able to bind selectively to a specific antigen. A VHH is an example of a sdAb.

Specifically Binds: As used herein the term "specifically binds" refers to the degree of affinity for which a first molecule exhibits with respect to a second molecule. In the context of binding pairs (e.g., ligand/receptor, antibody/antigen) a first molecule of a binding pair is said to specifically bind to a second molecule of a binding pair when the first molecule of the binding pair does not bind in a significant amount to other components present in the sample. A first molecule of a binding pair is said to specifically bind to a second molecule of a binding pair when the first molecule of the binding pair when the affinity of the first molecule for the second molecule is at least two-fold greater, alternatively at least five times greater, alternatively at least ten times greater, alternatively at least 20-times greater, or alternatively at least 100-times greater than the affinity of the first molecule for other components present in the sample. In a particular embodiment, where the first molecule of the binding pair is an antibody, the antibody specifically binds to the antigen (or antigenic determinant (epitope) of a protein, antigen, ligand, or receptor) if the equilibrium dissociation constant ($K_D$) between antibody and the antigen is lesser than about $10^{-6}$ M, alternatively lesser than about $10^{-8}$ M, alternatively lesser than about $10^{-10}$ M, alternatively lesser than about $10^{-11}$ M, lesser than about $10^{-12}$ M as determined by, e.g., Scatchard analysis (Munsen, et al. (1980) Analyt. Biochem. 107:220-239). In one embodiment, a ligand specifically binds to a receptor if the dissociation is greater than about $10^5$M, alternatively greater than about $10^6$ M, alternatively greater than about $10^7$M, alternatively greater than about $10^8$M, alternatively greater than about $10^9$ M, alternatively greater than about $10^{10}$ M, or alternatively greater than about $10^{11}$ M. Specific binding may be assessed using techniques known in the art including but not limited to competition ELISA assays, radioactive ligand binding assays (e.g., saturation binding, Scatchard plot, nonlinear curve fitting programs and competition binding assays); non-radioactive ligand binding assays (e.g., fluorescence polarization (FP), fluorescence resonance energy transfer (FRET); liquid phase ligand binding assays (e.g., real-time polymerase chain reaction (RT-qPCR), and immunoprecipitation); and solid phase ligand binding assays (e.g., multi-well plate assays, on-bead ligand binding assays, on-column ligand binding assays, and filter assays)) and surface plasmon resonance assays (see, e.g., Drescher et al., (2009) Methods Mol Biol 493:323-343 with commercially available instrumentation such as the Biacore 8+, Biacore S200, Biacore T200 (GE Healthcare Bio-Sciences, 100 Results Way, Marlborough MA 01752). In some embodiments, the present disclosure provides molecules (e.g., IL12RB1 binding sdAbs) that specifically bind to the hIL12RB1 isoform. As used herein, the binding affinity of an IL12RB1 binding molecule for the IL12RB1, the binding affinity may be determined and/or quantified by surface plasmon resonance ("SPR"). In evaluating binding affinity of an IL12RB1 binding molecule for the IL12RB1, either member of the binding pair may be immobilized, and the other element of the binding pair be provided in the mobile phase. In some embodiments, the sensor chip on which the protein of interest is to be immobilized is conjugated with a substance to facilitate binding of the protein of interest such as nitrilotriacetic acid (NTA) derivatized surface plasmon resonance sensor chips (e.g., Sensor Chip NTA available from Cytiva Global Life Science Solutions USA LLC, Marlborough MA as catalog number BR100407), as anti-His tag antibodies (e.g. anti-histidine CM5 chips commercially available from Cytiva, Marlborough MA), protein A or biotin. Consequently, to evaluate binding, it is frequently necessary to modify the protein to provide for binding to the substance conjugated to the surface of the chip. For example, the one member of the binding pair to be evaluated by incorporation of a chelating peptide comprising poly-histidine sequence (e.g., 6×His (SEQ ID NO: 532) or 8×His (SEQ ID NO: 534)) for retention on a chip conjugated with NTA. In some embodiments, the binding molecule may be immobilized on the chip and receptor subunit (or ECD fragment thereof) be provided in the mobile phase. Alternatively, the receptor subunit (or ECD fragment thereof) may be immobilized on the chip and the binding molecule be provided in the mobile phase. In either circumstance, it should be noted that modifications of some proteins for immobilization on a coated SPR chip may interfere with the binding properties of one or both components of the binding pair to be evaluated by SPR. In such cases, it may be necessary to switch the mobile and bound elements of the binding pair or use a chip with a binding agent that facilitates non-interfering conjugation of the protein to be evaluated. Alternatively, when evaluating the binding affinity of binding molecule for receptor subunit using SPR, the binding molecule may be derivatized by the C-terminal addition of a poly-His sequence (e.g., 6×His (SEQ ID NO: 532) or 8×His (SEQ ID NO: 534)) and immobilized on the NTA derivatized sensor chip and the receptor subunit for which the binding affinity is being evaluated is provided in the mobile phase. The means for incorporation of a poly-His sequence into the C-terminus of the binding molecule produced by recombinant DNA technology is well known to those of skill in the relevant art of biotechnology.

Subject: The terms "recipient", "individual", "subject", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is a human being.

Substantially Pure: As used herein, the term "substantially pure" indicates that a component of a composition makes up greater than about 50%, alternatively greater than about 60%, alternatively greater than about 70%, alternatively greater than about 80%, alternatively greater than about 90%, alternatively greater than about 95%, of the total content of the composition. A protein that is "substantially pure" comprises greater than about 50%, alternatively greater than about 60%, alternatively greater than about 70%, alternatively greater than about 80%, alternatively greater than about 90%, alternatively greater than about 95%, of the total content of the composition.

Suffering From: As used herein, the term "suffering from" refers to a determination made by a physician with respect to a subject based on the available information accepted in the field for the identification of a disease, disorder or condition including but not limited to X-ray, CT-scans, conventional laboratory diagnostic tests (e.g., blood count), genomic data, protein expression data, immunohistochemistry, that the subject requires or will benefit from treatment. The term suffering from is typically used in conjunction with a particular disease state such as "suffering from a neoplastic disease" refers to a subject which has been diagnosed with the presence of a neoplasm.

T-cell: As used herein the term "T-cell" or "T cell" is used in its conventional sense to refer to a lymphocyte that differentiates in the thymus, possess specific cell-surface antigen receptors, and include some that control the initiation or suppression of cell-mediated and humoral immunity and others that lyse antigen-bearing cells. In some embodiments the T cell includes without limitation naïve CD8$^+$ T cells, cytotoxic CD8$^+$ T cells, naïve CD4$^+$ T cells, helper T cells, e.g. T$_H$1, T$_H$2, T$_H$9, T$_H$11, T$_H$22, T$_{FH}$; regulatory T cells, e.g. T$_R$1, Tregs, inducible Tregs; memory T cells, e.g. central memory T cells, effector memory T cells, NKT cells, tumor infiltrating lymphocytes (TILs) and engineered variants of such T-cells including but not limited to CAR-T cells, recombinantly modified TILs and TCR engineered cells.

Terminus/Terminal: As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" refers to the position of a first amino acid residue relative to a second amino acid residue in a contiguous polypeptide sequence, the first amino acid being closer to the N-terminus of the polypeptide. "Immediately C-terminal" refers to the position of a first amino acid residue relative to a second amino acid residue in a contiguous polypeptide sequence, the first amino acid being closer to the C-terminus of the polypeptide.

Therapeutically Effective Amount: As used herein, the term The phrase "therapeutically effective amount" is used in reference to the administration of an agent to a subject, either alone or as part of a pharmaceutical composition or treatment regimen, in a single dose or as part of a series of doses in an amount capable of having any detectable, positive effect on any symptom, aspect, or characteristic of a disease, disorder or condition when administered to the subject. The therapeutically effective amount can be ascertained by measuring relevant physiological effects, and it may be adjusted in connection with a dosing regimen and in response to diagnostic analysis of the subject's condition, and the like. The parameters for evaluation to determine a therapeutically effective amount of an agent are determined by the physician using art accepted diagnostic criteria including but not limited to indicia such as age, weight, sex, general health, ECOG score, observable physiological parameters, blood levels, blood pressure, electrocardiogram, computerized tomography, X-ray, and the like. Alternatively, or in addition, other parameters commonly assessed in the clinical setting may be monitored to determine if a therapeutically effective amount of an agent has been administered to the subject such as body temperature, heart rate, normalization of blood chemistry, normalization of blood pressure, normalization of cholesterol levels, or any symptom, aspect, or characteristic of the disease, disorder or condition, modification of biomarker levels, increase in duration of survival, extended duration of progression free survival, extension of the time to progression, increased time to treatment failure, extended duration of event free survival, extension of time to next treatment, improvement objective response rate, improvement in the duration of response, and the like that that are relied upon by clinicians in the field for the assessment of an improvement in the condition of the subject in response to administration of an agent.

Treg Cell or Regulatory T Cell. The terms "regulatory T cell" or "Treg cell" as used herein refers to a type of CD4$^+$ T cell that can suppress the responses of other T cells including but not limited to effector T cells (Teff). Treg cells are characterized by expression of CD4, the a-subunit of the IL2 receptor (CD25), and the transcription factor forkhead box P3 (FOXP3) (Sakaguchi, Annu Rev Immunol 22, 531-

62 (2004). By "conventional CD4+ T cells" is meant CD4+ T cells other than regulatory T cells.

Transmembrane Domain: The term "transmembrane domain" or "TM" refers to the domain of a membrane spanning polypeptide which, when the membrane spanning polypeptide is associated with a cell membrane, is which is embedded in the cell membrane and is in peptidyl linkage with the extracellular domain (ECD) and the intracellular domain (ICD) of a membrane spanning polypeptide. A transmembrane domain may be homologous (naturally associated with) or heterologous (not naturally associated with) with either or both of the extracellular and/or intracellular domains. A transmembrane domain may be homologous (naturally associated with) or heterologous (not naturally associated with) with either or both of the extracellular and/or intracellular domains. In some embodiments, where the receptor is chimeric receptor comprising the intracellular domain derived from a first parental receptor and a second extracellular domains are derived from a second different parental receptor, the transmembrane domain of the chimeric receptor is the transmembrane domain normally associated with either the ICD or the ECD of the parent receptor from which the chimeric receptor is derived. Alternatively, the transmembrane domain of the receptor may be an artificial amino acid sequence which spans the plasma membrane. In some embodiments, where the receptor is chimeric receptor comprising the intracellular domain derived from a first parental receptor and a second extracellular domains are derived from a second different parental receptor, the transmembrane domain of the chimeric receptor is the transmembrane domain normally associated with either the ICD or the ECD of the parent receptor from which the chimeric receptor is derived.

Treat: The terms "treat", "treating", treatment" and the like refer to a course of action (such as administering a binding molecule described herein, or a pharmaceutical composition comprising same) initiated with respect to a subject after a disease, disorder or condition, or a symptom thereof, has been diagnosed, observed, or the like in the subject so as to eliminate, reduce, suppress, mitigate, or ameliorate, either temporarily or permanently, at least one of the underlying causes of such disease, disorder, or condition afflicting a subject, or at least one of the symptoms associated with such disease, disorder, or condition. The treatment includes a course of action taken with respect to a subject suffering from a disease where the course of action results in the inhibition (e.g., arrests the development of the disease, disorder or condition or ameliorates one or more symptoms associated therewith) of the disease in the subject.

VHH: As used herein, the term "VHH" is a type of sdAb that has a single monomeric heavy chain variable antibody domain. Such antibodies can be found in or produced from Camelid mammals (e.g., camels, llamas) which are naturally devoid of light chainsVHHs can be obtained from immunization of camelids (including camels, llamas, and alpacas (see, e.g., Hamers-Casterman, et al. (1993) Nature 363:446-448) or by screening libraries (e.g., phage libraries) constructed in VHH frameworks. Antibodies having a given specificity may also be derived from non-mammalian sources such as VHHs obtained from immunization of cartilaginous fishes including, but not limited to, sharks. In a particular embodiment, a VHH in a bispecific VHH$^2$ binding molecule described herein binds to a receptor (e.g., the first receptor or the second receptor of the natural or non-natural receptor pairs) if the equilibrium dissociation constant between the VHH and the receptor is greater than about $10^{-6}$ M, alternatively lesser than about $10^{-8}$ M, alternatively lesser than about $10^{-10}$ M, alternatively lesser than about $10^{-11}$ M, alternatively lesser than about $10^{-10}$ M, lesser than about $10^{-12}$ M as determined by, e.g., Scatchard analysis (Munsen, et al. 1980 Analyt. Biochem. 107:220-239). Standardized protocols for the generation of single domain antibodies from camelids are well known in the scientific literature. See, e.g., Vincke, et al (2012) Chapter 8 in *Methods in Molecular Biology*, Walker, J. editor (Humana Press, Totowa NJ). Specific binding may be assessed using techniques known in the art including but not limited to competition ELISA, BIACORE® assays and/or KINEXA® assays. In some embodiments, a VHH described herein can be humanized to contain human framework regions. Examples of human germlines that could be used to create humanized VHHs include, but are not limited to, VH3-23 (e.g., UniProt ID: P01764), VH3-74 (e.g., UniProt ID: A0A0B4J1X5), VH3-66 (e.g., UniProt ID: A0A0C4DH42), VH3-30 (e.g., UniProt ID: P01768), VH3-11 (e.g., UniProt ID: P01762), and VH3-9 (e.g., UniProt ID: P01782).

VHH$^2$: As used herein, the term "VHH$^2$" and "bispecific VHH$^2$" and "VHH dimer" refers to are used interchangeably to refer to a subtype of the binding molecules of the present disclosure wherein the first and second sdAbs are both VHHs and first VHH binding to a first receptor, or domain or subunit thereof, and a second VHH binding to a second receptor, or domain or subunit thereof.

Wild Type: As used herein, the term "wild type" or "WT" or "native" is used to refer to an amino acid sequence or a nucleotide sequence that is found in nature and that has not been altered by the hand of man.

Interleukin 10 Receptor Binding Molecules

The present invention provides IL10R binding molecules that are synthetic ligands of the IL10 receptor.

The IL10R binding molecules of the present disclosure comprise two or more single domain antibodies that selectively bind to the extracellular domain of the IL10Ra and IL10Rb receptor subunits. In one embodiment, the present disclosure provides an IL10 receptor (IL10R) binding molecule that is a ligand for the IL10R receptor, the IL10R receptor binding molecule comprising:

(e) a first single domain antibody (sdAb) that specifically binds to the extracellular domain the IL10Ra subunit of the IL10 receptor (an "IL10Ra sdAb"), and (f) a second single domain antibody that specifically binds to the extracellular domain of the IL10Rb subunit of the IL10 receptor (an "IL10Rb sdAb"), wherein:
the first sdAb and second sdAb are in stable association;
the IL10Ra and IL10Rb subunits of the IL10 receptor are dimerized in response to contact with the IL10R binding molecule; and
contacting a cell expressing the IL10Ra and IL10Rb with an effective amount of the IL10R binding molecule results in the intracellular domains of IL10Ra and IL10Rb being brought into proximity and intracellular signaling.

The IL10R binding molecules of the present disclosure are useful in the treatment or prevention of disease in mammalian subjects, In some embodiments, the present disclosure provides for the treatment or prevention of autoimmune disease in a mammalian subject by the administration of a therapeutically effective amount of an IL10R binding molecule of the present disclosure. In some embodiments, the present disclosure provides for the treatment or prevention of infectious disease, including viral and chronic viral infections, in a mammalian subject by the administration of a therapeutically effective amount of an IL10R binding molecule of the present disclosure. In some embodiments, the present disclosure provides for the treatment or prevention of neoplastic disease in a mammalian subject by the administration of a therapeutically effective amount of an IL10R binding molecule of the present disclosure. In some embodiments, the present disclosure provides for the treatment or prevention of neoplastic, infectious or autoimmune in a mammalian subject by the administration of a therapeutically effective amount of an IL10R binding molecule of the present disclosure in combination with one or more supplementary therapeutic agents.

In some embodiments, the present disclosure provides an IL10R binding molecule modified to provide prolonged duration of action in vivo in a mammalian subject and pharmaceutically acceptable formulations thereof.

The present disclosure further provides a pharmaceutically acceptable formulation of an IL10R binding molecule for the administration to a mammalian subject. The present disclosure further provides a pharmaceutically acceptable composition for administration to a mammalian subject the composition comprising a nucleic acid sequence encoding a polypeptide IL10R binding molecule, a recombinant viral or non-viral vector encoding or polypeptide IL10R binding molecule, or a recombinantly modified mammalian cell comprising a nucleic acid sequence encoding a polypeptide IL10R binding molecule, in each case the nucleic acid sequence operably linked to one or more expression control elements functional in a mammalian cell.

In some embodiments, the IL10R binding molecules of the present disclosure are polypeptides The present disclosure provides nucleic acid sequences enboding polypeptide IL10R binding molecules. The present disclosure further provides a recombinant vector comprising a nucleic acid sequences enboding polypeptide IL10R binding molecules. The present disclosure further provides a recombinantly modified mammalian cell comprising a nucleic acid enboding a polypeptide IL10R binding molecule. The present disclosure further provides methods for the recombinant production, isolation, purification and characterization of a polypeptide IL10R binding molecule. of recombinant vectors comprising a provides nucleic acid sequences enboding polypeptide IL10R binding molecules.

IL10:

The cognate ligand of the IL10 receptor (IL10R) is the cytokine IL10. The term IL10 includes human and murine (or mouse) IL10. Human IL10 (hIL10) is non-covalently linked homodimeric protein comprising two identical subunits. Each human IL10 monomer is expressed as a 178 amino acid pre-protein comprising 18 amino acid signal sequence which is post-translationally removed to render a 160 amino acid mature protein. The canonical amino acid sequence of the mature IL-10 protein (UniProt Reference No. P22301) without the signal sequence (corresponding to amino acids 19-178 of the pre-protein) is:

```
                                    (SEQ ID NO: 460)
SPGQGTQSENSCTHFPGNLPNMLRDLRDAFSRVKTFFQMKDQLDNLLL

KESLLEDFKGYLGCQALSEMIQFYLEEVMPQAENQDPDIKAHVNSLGE

NLKTLRLRLRRCHRFLPCENKSKAVEQVKNAFNKLQEKGIYKAMSEFD

IFINYIEAYMTMKIRN
```

Mouse (or murine) IL10 (mIL10) is a non-covalently linked homodimeric protein comprising two identical subunits. Each murine IL10 monomer is expressed as a 178 amino acid pre-protein comprising 18 amino acid signal sequence which is post-translationally removed to render a 160 amino acid mature protein. The canonical amino acid sequence of the mature IL-10 protein (UniProt Reference No. P18893) without the signal sequence (corresponding to amino acids 19-178 of the pre-protein) is:

```
                                    (SEQ ID NO: 461)
SRGQYSREDNNCTHFPVGQSHMLLELRTAFSQVKTFFQTKDQLDNILL

TDSLMQDFKGYLGCQALSEMIQFYLVEVMPQAEKHGPEIKEHLNSLGE

KLKTLRMRLRRCHRFLPCENKSKAVEQVKSDFNKLQDQGVYKAMNEFD

IFINCIEAYMMIKMKS.
```

IL10R binding molecules activate IL10 signaling in a cell expressing the IL10 receptor. The present disclosure provides IL10R binding molecules engineered to provide selective levels of intracellular signalling in cells expressing the IL10 receptor. The present invention provides IL10R binding molecules engineered to generate intracellular signalling in particular cell types.

IL10 Receptor

The IL10 receptor is a heterodimeric protein complex comprising the IL10Ra and IL10Rb subunits. The interaction of the IL10 on the surface of a mammalian cell expressing the IL10Ra and IL10Rb subunits results in dimerization of IL10Ra and IL10Rb and intracellular signaling. The intracellular signaling characteristic of IL10 mediated dimerization of the IL10Ra and IL10Rb is the activation of the JAK/STAT pathway, in particular the phosphorylation of STAT3 molecule which is a component of the intracellular signaling pathway that, in combination with other components of the signaling pathway results in modulation of gene expression. In some embodiments, the IL10 receptor the human IL10 receptor and the IL10 is the human IL10. In some embodiments the IL10 receptor is the murine IL10 receptor and the IL10 is the murine IL10. As used herein, the terms "IL10 receptor receptor" and "IL10 receptor" and "IL10R" are used interchangeably to refer to a heterodimeric complex comprising IL10Ra and IL10Rb. The term IL10R includes IL10 receptors of any mammal including but not limited to human beings, dogs, cats, mice, monkeys, cows, and pigs.

The IL10Ra component of the human IL10 receptor is the human IL10Ra (hIL10Ra) protein. The canonical full length hIL10Ra protein is a polypeptide possessing the amino acid sequence:

```
                                    (SEQ ID NO: 452)
MLPCLVVLLAALLSLRLGSDAHGTELPSPPSVWFEAEFFHHILHWTPI

PNQSESTCYEVALLRYGIESWNSISNCSQTLSYDLTAVTLDLYHSNGY

RARVRAVDGSRHSNWTVTNTRFSVDEVTLTVGSVNLEIHNGFILGKIQ

LPRPKMAPANDTYESIFSHFREYEIAIRKVPGNFTFTHKKVKHENFSL

LTSGEVGEFCVQVKPSVASRSNKGMWSKEECISLTRQYFTVTNVIIFF

AFVLLLSGALAYCLALQLYVRRRKKLPSVLLFKKPSPFIFISQRPSPE

TQDTIHPLDEEAFLKVSPELKNLDLHGSTDSGFGSTKPSLQTEEPQFL

LPDPHPQADRTLGNREPPVLGDSCSSGSSNSTDSGICLQEPSLSPSTG

PTWEQQVGSNSRGQDDSGIDLVQNSEGRAGDTQGGSALGHHSPPEPEV

PGEEDPAAVAFQGYLRQTRCAEEKATKTGCLEEESPLTDGLGPKFGRC
```

-continued
LVDEAGLHPPALAKGYLKQDPLEMTLASSGAPTGQWNQPTEEWSLLAL

SSCSDLGISDWSFAHDLAPLGCVAAPGGLLGSFNSDLVTLPLISSLQS

SE

For purposes of the present disclosure, the numbering of amino acid residues of the hIL10Ra polypeptides as described herein is made in accordance with the numbering of this canonical sequence UniProg Database Reference No. Q13651. Amino acids 1-21 of SEQ ID NO:452 are identified as the signal peptide of the IL10Ra, amino acids 22-235 of SEQ ID NO:452 are identified as the extracellular domain, amino acids 236-256 of SEQ ID NO:452 are identified as the transmembrane domain, and amino acids 257-578 of SEQ ID NO: 452 are identified as the intracellular domain.

The IL10Ra component of the mouse IL10 receptor is the mouse IL10Ra (mIL10Ra) protein. mIL10Ra is expressed as 575 amino acid pre-protein containing a 16 amino acid signal sequence which is post-translationally cleaved to render a 569 amino acid mature protein The canonical full length mIL10Ra is a polypeptide having the amino acid sequence:

(SEQ ID NO: 454)
MLSRLLPFLVTISSLSLEFIAYGTELPSPSYVWFEARFFQHILHWKPI

PNQSESTYYEVALKQYGNSTWNDIHICRKAQALSCDLTTFTLDLYHRS

YGYRARVRAVDNSQYSNWTTTETRFTVDEVILTVDSVTLKAMDGIIYG

TIHPPRPTITPAGDEYEQVFKDLRVYKISIRKFSELKNATKRVKQETF

TLTVPIGVRKFCVKVLPRLESRINKAEWSEEQCLLITTEQYFTVTNLS

ILVISMLLFCGILVCLVLQWYIRHPGKLPTVLVFKKPHDFFPANPLCP

ETPDAIHIVDLEVFPKVSLELRDSVLHGSTDSGFGSGKPSLQTEESQF

LLPGSHPQIQGTLGKEESPGLQATCGDNTDSGICLQEPGLHSSMGPAW

KQQLGYTHQDQDDSDVNLVQNSPGQPKYTQDASALGHVCLLEPKAPEE

KDQVMVTFQGYQKQTRWKAEAAGPAECLDEEIPLTDAFDPELGVHLQD

DLAWPPPALAAGYLKQESQGMASAPPGTPSRQWNQLTEEWSLLGVVSC

EDLSIESWRFAHKLDPLDCGAAPGGLLDSLGSNLVTLPLISSLQVEE

For purposes of the present disclosure, the numbering of amino acid residues of the mouse IL10Ra polypeptides as described herein is made in accordance with the numbering of this canonical sequence UniProt Database Reference No. Q61727. Amino acids 1-16 of SEQ ID NO: 454 are identified as the signal peptide of the mIL10Ra, amino acids 17-241 of SEQ ID NO: 454 are identified as the extracellular domain, amino acids 242-262 of SEQ ID NO: 454 are identified as the transmembrane domain, and amino acids 263-575 of SEQ ID NO: 454 are identified as the intracellular domain.

hIL10Rb is expressed as a 325 amino acid pre-protein, the first 19 amino acids comprising a signal sequence which is post-translationally cleaved in the mature 306 amino acid protein. Amino acids 20-220 (amino acids 1-201 of the mature protein) correspond to the extracellular domain, amino acids 221-242 (amino acids 202-223 of the mature protein) correspond to the 22 amino acid transmembrane domain, and amino acids 243-325 (amino acids 224-306 of the mature protein) correspond to the intracellular domain The canonical full length hIL10Rb precursor is a polypeptide having the amino acid sequence:

(SEQ ID NO: 456)
MAWSLGSWLGGCLLVSALGMVPPPENVRMNSVNFKNILQWESPAFAKGN

LTFTAQYLSYRIFQDKCMNTTLTECDFSSLSKYGDHTLRVRAEFADEHS

DWVNITFCPVDDTIIGPPGMQVEVLADSLHMRFLAPKIENEYETWTMKN

VYNSWTYNVQYWKNGTDEKFQITPQYDFEVLRNLEPWTTYCVQVRGFLP

DRNKAGEWSEPVCEQTTHDETVPSWMVAVILMASVFMVCLALLGCFALL

WCVYKKTKYAFSPRNSLPQHLKEFLGHPHHNTLLFFSFPLSDENDVFDK

LSVIAEDSESGKQNPGDSCSLGTPPGQGPQS

For purposes of the present disclosure, the numbering of amino acid residues of the human IL10Rb polypeptides as described herein is made in accordance with the numbering of the canonical sequence (UniProt ID: Q08334, SEQ ID NO:456).

Murine IL10Rb (mIL10Rb) is expressed as a 349 amino acid pre-protein comprising a 19 amino acid N-terminal signal sequence. Amino acids 20-220 (amino acids 1-201 of the mature protein) correspond to the extracellular domain, amino acids 221-241 (amino acids 202-222 of the mature protein) correspond to the 21 amino acid transmembrane domain, and amino acids 242-349 (amino acids 223-330 of the mature protein) correspond to the intracellular domain. The canonical full length mIL10Rb precursor protein including the signal sequence is a polypeptide of is referenced at UniProtKB database as entry Q61190. The canonical full length mIL10Rb precursor protein including the signal sequence is a polypeptide of the amino acid sequence:

(SEQ ID NO: 458)
MAPCVAGWLGGFLLVPALGIPPPEKVRMNSVNFKNILQWEVPAFPKTNL

TFTAQYESYRSFQDHCKRTASTQCDFSHLSKYGDYTVRVRAELADEHSE

WVNVTFCPVEDTIIGPPEMQIESLAESLHLRFSAPQIENEPETWTLKNI

YDSWAYRVQYWKNGTNEKFQVVSPYDSEVLRNLEPWTTYCIQVQGFLLD

QNRTGEWSEPICERTGNDEITPSWIVAIILIVSVLVVFLFLLGCFVVLW

LIYKKTKHTFRSGTSLPQHLKEFLGHPHHSTFLLFSFPPPEEAEVFDKL

SIISEESEGSKQSPEDNCASEPPSDPGPRELESKDEAPSPPHDDPKLLT

STSEV

For purposes of the present disclosure, the numbering of amino acid residues of the murine IL10Rb polypeptides as described herein is made in accordance with the numbering of this canonical sequence (UniProt ID: Q61190, SEQ ID NO 458.

Single Domain Antibody

The IL10R binding molecules of the present invention comprise two or more single domain antibodies. The term "single domain antibody" (sdAb) as used herein refers an antibody fragment consisting of a monomeric variable antibody domain that is able to bind specifically to an antigen and compete for binding with the parent antibody from which it is derived. The term "single domain antibody" includes scFv and VHH molecules. In some embodiments, one or both of the sdAbs of the cytokine receptor binding molecule is a an scFv. In some embodiments, one or both of the sdAbs is a VHH. In some embodiments, one or both of the sdAbs is a scFv.

The term single domain antibody includes engineered sdAbs including but not limited to chimeric sdAbs, CDR grafted sdAbs and humanized sdAbs. In some embodiments, the one or more of the sdAbs for incorporation into the IL10R binding molecules of the present disclosure are CDR grafted. CDRs obtained from antibodies, heavy chain antibodies, and sdAbs derived therefrom may be grafted onto alternative frameworks as described in Saerens, et al. (2005) J. Mol Biol 352:597-607 to generate CDR-grafted sdAbs. Any framework region can be used with the CDRs as described herein.

In some embodiments, one or more of the sdAbs for incorporation into the IL10R binding molecules is a chimeric sdAb, in which the CDRs are derived from one species (e.g., camel) and the framework and/or constant regions are derived from another species (e.g., human or mouse). In specific embodiments, the framework regions are human or humanized sequences. Thus, IL10R binding molecules comprising one or more humanized sdAbs are considered within the scope of the present disclosure.

In some embodiments, one or more of the sdAb of the cytokine receptor binding molecules of the present disclosure is a VHH. As used herein, the term "VHH" refers to a single domain antibody derived from camelid antibody typically obtained from immunization of camelids (including camels, llamas and alpacas (see, e.g., Hamers-Casterman, et al. (1993) Nature 363:446-448). VHHs are also referred to as heavy chain antibodies or Nanobodies® as Single domain antibodies may also be derived from non-mammalian sources such as VHHs obtained from IgNAR antibodies immunization of cartilaginous fishes including, but not limited to, sharks. A VHH is a type of single-domain antibody (sdAb) containing a single monomeric variable antibody domain. Like a full-length antibody, it is able to bind selectively to a specific antigen.

The complementary determining regions (CDRs) of VHHs are within a single-domain polypeptide. VHHs can be engineered from heavy-chain antibodies found in camelids. An exemplary VHH has a molecular weight of approximately 12-15 kDa which is much smaller than traditional mammalian antibodies (150-160 kDa) composed of two heavy chains and two light chains. VHHs can be found in or produced from Camelidae mammals (e.g., camels, llamas, dromedary, alpaca, and guanaco) which are naturally devoid of light chains. Descriptions of sdAbs and VHHS can be found in, e.g., De Greve et al., *Curr Opin Biotechnol.* 61:96-101, 2019; Ciccarese, et al., *Front Genet.* 10:997, 2019; Chanier and Chames, *Antibodies (Basel)* 8(1), 2019; and De Vlieger et al., *Antibodies (Basel)* 8(1), 2018. The CDRs derived from camelid VHHs may be used to prepare CDR-grafted VHHs which may be incorporated in the IL10R binding molecules.

In some embodiments, the VHH for incorporation into the IL10R binding molecule of the present disclosure is a humanized VHH containing human framework regions. The techniques for humanization of camelid single domain antibodies are well known in the art. See, e.g., Vincke, et al. (2009) *General Strategy to Humanize a Camelid Single-domain Antibody and Identification of a Universal Humanized Nanobody Scaffold* J. Biol. Chem. 284(5)3273-3284. Human framework regions useful in the preparation of humanized VHHs include, but are not limited to, VH3-23 (e.g., UniProt ID: P01764), VH3-74 (e.g., UniProt ID: A0A0B4J1X5), VH3-66 (e.g., UniProt ID: A0A0C4DH42), VH3-30 (e.g., UniProt ID: P01768), VH3-11 (e.g., UniProt ID: P01762), and VH3-9 (e.g., UniProt ID: P01782).

Stably Associated:

The IL10R binding molecules of the present disclosure comprise a single domain antibody that selectively binds to the extracellular domain of IL10Ra (an "IL10Ra sdAb") in stable association with a single domain antibody that selectively binds to the extracellular domain of IL10Rb (an "IL10Rb sdAb"). As used herein, the term "stably associated" or "in stable association with" are used to refer to the various means by which one molecule (e.g., a polypeptide) may be thermodynamically and/or kinetically associated with another molecule. The stable association of one molecule to another may be achieved by a variety of means, including covalent bonding and non-covalent interactions.

In some embodiments, stable association of the IL10Ra sdAb and IL10Rb sdAb may be achieved by a covalent bond such as peptide bond. In some embodiments, the covalent linkage between the first and second binding domains is a covalent bond between the C-terminus of the first binding domain and the N-terminus of the second binding domain.

In some embodiments, the covalent linkage of the the IL10Ra sdAb and IL10Rb sdAb of the IL10R binding protein is effected by a coordinate covalent linkage. The present disclosure provides examples of single domain antibodies comprising a chelating peptide. The chelating peptide results in a coordinate covalent linkage to a transition metal ion. In some embodiments, a transition metal ion is capable of forming a coordinate covalent linkage with two or more chelating peptides. Consequently, the first and second binding domains may each comprise a chelating peptide and a stable association of the binding domains by each subunit forming a coordinate covalent complex with a transition metal ion. In some embodiments, the transition metal ion is selected from vanadium, manganese, iron, iridium, osmium, rhenium platinum, palladium, cobalt, chromium or ruthenium. A schematic illustration of this configuration is provided in FIG. 4B, of the attached drawings. It should be noted that in each of the configurations illustrated in FIGS. 4A-4B, the N-terminal domain of the single domain antibody is presented to the environment enabling facilitating enhanced exposure of the CDRs of the sdAb to the target cytokine receptor ECD. The formation of the coordinate covalent linkage between the is favored when the transition metal ion is in a kinetically labile oxidation state, for example Co(II), Cr(II), or Ru(III). Following complexation, the oxidation state of the transition metal may be changed (oxidized or reduced) to a kinetically inert oxidation state, for example Co(III), Cr(III), or Ru(II), provide a kinetically inert coordinate covalent complex. The the formation of kinetically inert and kinetically labile coordinate covalent complexes between proteins comprising chelating peptides via a transition metal are described in more detail in Anderson, et al. U.S. Pat. No. 5,439,928 issued Aug. 8, 1995.

In some embodiments, the covalent linkage of the IL10Ra sdAb and IL10Rb sdAb of the IL-10R binding molecule may further comprise a linker. Linkers are molecules selected from selected from the group including, but not limited to, peptide linkers and chemical linkers. In some embodiments, the linker a joins the C-terminus of the IL10Ra sdAb to the N-terminus of the IL10Rb sdAb. In some embodiments, the linker joins the C-terminus of the IL10Rb sdAb to the N-terminus of the IL10Ra sdAb.

In some embodiments, the linker is a peptide linker. A peptide linker can include between 1 and 50 amino acids (e.g., between 2 and 50, between 5 and 50, between 10 and 50, between 15 and 50, between 20 and 50, between 25 and 50, between 30 and 50, between 35 and 50, between 40 and 50, between 45 and 50, between 2 and 45, between 2 and 40, between 2 and 35, between 2 and 30, between 2 and 25, between 2 and 20, between 2 and 15, between 2 and 10, between 2 and 5 amino acids). Glycine and glycine-serine polymers are relatively unstructured, and therefore may serve as a neutral tether between components. Examples of glycine polymers include (G)n, glycine-alanine polymers, alanine-serine polymers, glycine-serine polymers (for example, (GmSo)n (SEQ ID NO: 562), (GSGGS)n (SEQ ID NO: 563), (GmSoGm)n (SEQ ID NO: 564), (GmSoGm-SoGm)n (SEQ ID NO: 565), (GSGGSm)n (SEQ ID NO: 566), (GSGSmG)n (SEQ ID NO: 567) and (GGGSm)n (SEQ ID NO: 568), and combinations thereof, where m, n, and o are each independently selected from an integer of at least 1 to 20, e.g., 1-18, 216, 3-14, 4-12, 5-10, 1, 2, 3, 4, 5, 6, 7, 8, 9, or 10), and other flexible linkers. Exemplary flexible peptide linkers useful in the preparation of the IL10R binding molecules of the present disclosure include, but are note limited to, to the linkers provided in Table 16.

In some embodiments, the covalent linkage of the first and second domains may be achieved by a chemical linker. Examples of chemical linkers include aryl acetylene, ethylene glycol oligomers containing 2-10 monomer units, diamines, diacids, amino acids, or combinations thereof.

In some embodiments, stable association the IL10Ra sdAb and IL10Rb sdAb of the IL10R binding protein is be effected by non-covalent interaction. Examples of non-covalent interactions that provide a stable association between two molecules include electrostatic interactions (e.g., hydrogen bonding, ionic bonding, halogen binding, dipole-dipole interactions, Van der Waals forces and p-effects including cation-p interactions, anion-p interactions and p-p interactions) and hydrophobilic/hydrophilic interactions. In some embodiments, the stable association of sdAbs of the binding molecules of the present disclosure may be effected by non-covalent interactions.

Figure 4A:
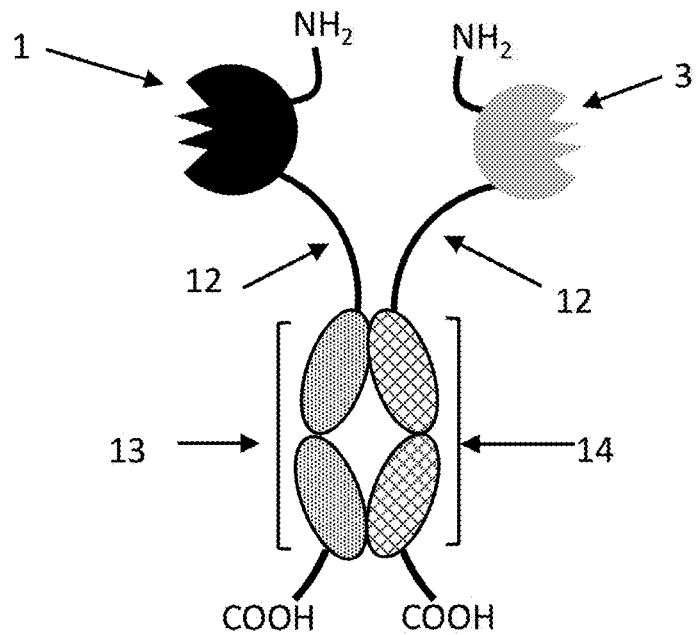
Figure 4B:
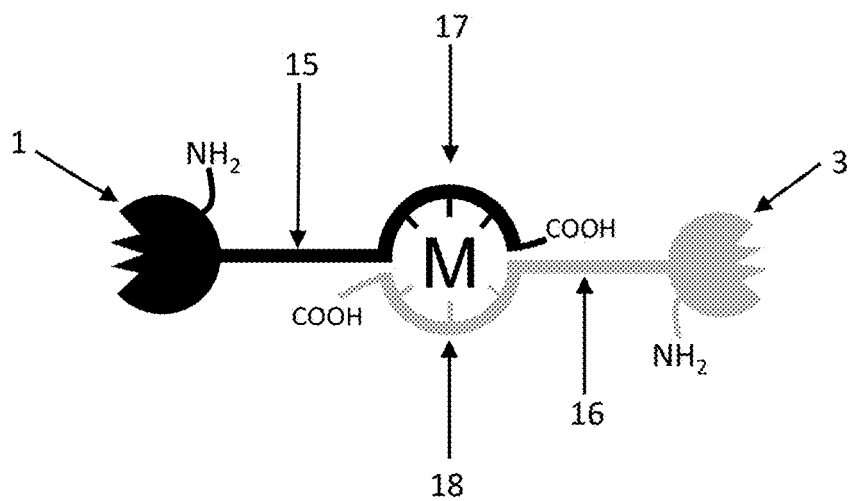

In one embodiment, the non-covalent stable association of the 110Ra sdAb and IL10Rb sdAb of the IL10R binding molecule may be achieved by conjugation a sdAb each monomer of a "knob-into-hole" engineered Fe dimer. The knob-into-hole modification refers to a modification at the interface between two immunoglobulin heavy chains in the CH3 domain, wherein: i) in a CH3 domain of a first heavy chain, an amino acid residue is replaced with an amino acid residue having a larger side chain (e.g., tyrosine or tryptophan) creating a projection from the surface ("knob") and ii) in the CH3 domain of a second heavy chain, an amino acid residue is replaced with an amino acid residue having a smaller side chain (e.g., alanine or threonine), thereby generating a cavity ("hole") within at interface in the second CH3 domain within which the protruding side chain of the first CH3 domain ("knob") is received by the cavity in the second CH3 domain. The knob-into-hole modification is more fully described in Ridgway, et al. (1996) Protein Engineering 9(7):617-621 and U.S. Pat. No. 5,731,168, issued Mar. 24, 1998, U.S. Pat. No. 7,642,228, issued Jan. 5, 2010, U.S. Pat. No. 7,695,936, issued Apr. 13, 2010, and U.S. Pat. No. 8,216,805, issued Jul. 10, 2012. In one embodiment, the "knob-into-hole modification" comprises the amino acid substitution T366W and optionally the amino acid substitution S354C in one of the antibody heavy chains, and the amino acid substitutions T366S, L368A, Y407V and optionally Y349C in the other one of the antibody heavy chains. Furthermore, the Fc domains may be modified by the introduction of cysteine residues at positions S354 and Y349 which results in a stabilizing disulfide bridge between the two antibody heavy chains in the Fe region (Carter, et al. (2001) Immunol Methods 248, 7-15). The knob-into-hole format is used to facilitate the expression of a first polypeptide (e.g., an IL10Rb binding sdAb) on a first Fc monomer with a "knob" modification and a second polypeptide on the second Fc monomer possessing a "hole" modification to facilitate the expression of heterodimeric polypeptide conjugates. The knob-into-hole format is used to facilitate the expression of a first polypeptide on a first Fc monomer with a "knob" modification and a second polypeptide on the second Fc monomer possessing a "hole" modification to facilitate the expression of heterodimeric polypeptide conjugates. One embodiment of an IL10R binding molecule wherein the IL10Ra sdAb and IL10Rb sdAb are in stable, non-covalent association is wherein the each sdAb of the IL10R binding molecule covalently bonded, optionally including a linker, to each subunit of the knob-into-hole Fc dimer as illustrated in FIG. 4A, of the attached drawings.

Generation and Evaluation of IL10Ra sdAbs

To generate sdAbs against the hIL2Ra, the extracellular domain of the hIL2Ra protein may be used an immunogen. The extracellular domain of the mature (lacking the signal sequence) hIL2Ra possesses the amino acid sequence (amino acids 22-235 of SEQ ID NO:452) has the amino acid sequence (SEQ ID NO: 453)
HGTELPSPPSVWFEAEFFHHILHWTPIPNQSESTCYEVALLRYGIESWN

SISNCSQTLSYDLTAVTLDLYHSNGYRARVRAVDGSRHSNWTVTNTRFS

VDEVTLTVGSVNLEIHNGFILGKIQLPRPKMAPANDTYESIFSHFREYE

IAIRKVPGNFTFTHKKVKHENFSLLTSGEVGEFCVQVKPSVASRSNKGM

WSKEECISLTRQYFTVTN

In some embodiments, when employed as an immunogen or a immunogenic composition, the hIL2Ra ECD may be provided as a domain of a fusion protein with an immunomodulatory protein.

To generate sdAbs against the mIL10Ra, the extracellular domain of the mIL10Ra protein may be used an immunogen. The extracellular domain of the extracellular domain of mIL10Ra possesses the amino acid sequence (amino acids 17-241 of SEQ ID NO:454) has the amino acid sequence (SEQ ID NO: 455)
LEFIAYGTELPSPSYVWFEARFFQHILHWKPIPNQSESTYYEVALKQYG

NSTWNDIHICRKAQALSCDLTTFTLDLYHRSYGYRARVRAVDNSQYSNW

TTTETRFTVDEVILTVDSVTLKAMDGIIYGTIHPPRPTITPAGDEYEQV

FKDLRVYKISIRKFSELKNATKRVKQETFTLTVPIGVRKFCVKVLPRLE

SRINKAEWSEEQCLLITTEQYFTVTNLSI

In some embodiments, when employed as an immunogen or a immunogenic composition, the mIL2Ra ECD may be provided as a domain of a fusion protein with an immumnomodulatory protein.

A series of hIL10Ra sdAbs were generated in substantial accordance with the teaching of Examples 1-4 herein. Briefly, a camel was sequentially immunized with the ECD of the human IL10Ra over a period several weeks of by the subcutaneous an adjuvated composition containing a recombinantly produced fusion proteins comprising the extracellular domain of the IL10Ra, the human IgG1 hinge domain and the human(IgG1 heavy chain Fe. Following immunization. RNAs extracted from a blood sample of appropriate size VHH-hinge-CH2-CH3 species were transcribed to generate DNA sequences, digested to identify the approximately 400 bp fragment comprising the nucleic acid sequence encoding the VHH domain was isolated. The isolated sequence was digested with restriction endonucleases to facilitate insertion into a phagemid vector for in frame with a sequence encoding a his-tag and transformed into E. coli to generate a phage library. Multiple rounds of bio-panning of the phage library were conducted to identify VHHs that bound to the ECD of IL10Ra (human or mouse as appropriate). Individual phage clones were isolated for periplasmic extract ELISA (PE-ELISA) in a 96-well plate format and selective binding confirmed by colormetric determination. The IL10Ra binding molecules that demonstrated specific binding to the IL10Ra antigen were isolated and sequenced and sequences analyzed to identify VHH sequences, CDRs and identify unique V-H- clonotypes. As used herein, the term "clonotypes" refers a collection of binding molecules that originate from the same B-cell progenitor cell, in particular collection of antigen binding molecules that belong to the same germline family, have the same CDR3 lengths, and have 70% or greater homology in CDR3 sequence.

The amino acid sequences of VHH molecules demonstrating specific binding to the hIL10Ra ECD antigen (hIL10Ra VHHs) are provided in Table 5 and the CDRs isolated from such VHHs are provided in Table 2. Nucleic acid sequences encoding the VHHs of Table 5 are provided in Table 8.

To confirm and evaluate binding affinities of the binding of the IL10Ra sdAbs, a representative example from each clonotype generated was selected for evaluation of binding via SPR. Evaluation of binding affinity of the hIL10Ra VHHs for ECD corresponding to SEQ ID NOS 159, 161, 162, 163, 165, 167 and 170 was conducted using surface plasmon resonance (SPR) in substantial accordance with the teaching of Example 5. Buffer-subtracted sensograms were processed with Biacore T200 Evaluation Software and globally fit with a 1:1 Langmuir binding model (bulk shift set to zero) to extract kinetics and affinity constants ($k_a$, $k_d$, $K_D$). $R_{MAX}$<100 RU indicates surface density compatible with kinetics analysis. Calculated $R_{max}$ values were generated using the equation: Rmax=Load (RU)×valency of ligand× (Molecular weight of analyte/Molecular weight of ligand). Surface activity was defined as the ratio of experimental/calculated Rmax. The results of these binding affinity experiments are provided in Table 22 below. The data provided in Table 22 demonstrats that the IL10Ra single domain antibodies generated possessed specific binding to the ECD of hIL10Ra.

and specifically bind to the ECD of hIL10Ra. In some embodiments, the IL10Ra sdAb is a single domain antibody comprising: a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 1, 4, 7, 10, 13, 16, 19, 22, 25, 28, 31, 34, 37, 40, 43, 46, 49 and 52; a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 2; 5, 8, 11, 14, 17, 20, 23, 26 29, 32, 35, 38, 41, 44, 47, 50 and 53; and a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 3, 6, 9, 12, 15, 21, 24, 27, 30, 33, 36, 39, 42, 45, 48, 51 and 54.

In some embodiments, the IL10Ra sdAb comprises a sequence having at least 90% (e.g., 91%, 92%, 93%, 94%, 95%, 96%, 97%, 98%, 99%, or 100%) sequence identity to a sequence of any one the of amino acid sequences of hIL10Ra sdAbs provided in Table 5 (SEQ ID NOS: 154-171) In certain embodiments, the IL10Ra sdAb comprises sequence that is substantially identical to a sequence of any one of the amino acid sequences of hIL10Ra sdAbs provided in Table 5 (SEQ ID NOS: 154-171). In certain embodiments, the IL10Ra sdAb comprises sequence that is identical to a sequence of any one the of amino acid sequences of hIL10Ra sdAbs provided in Table 5 (SEQ ID NOS: 154-171).

In another aspect, the disclosure provides an isolated nucleic acid encoding IL10Ra sdAb described herein. Table 8 provides DNA sequences (SEQ ID NOS: 205-222 encoding the IL10Ra sdAbs of Table 5 (SEQ ID NOS: 154-171). In certain embodiments, the present disclosure provides an isolated nucleic acid comprising a sequence having at least 90% (e.g., 91%, 92%, 93%, 94%, 95%, 96%, 97%, 98%, 99%, or 100%) sequence identity to a DNA sequence of Table 8 (SEQ ID NOS: 205-222). In certain embodiments, the present disclosure provides an isolated nucleic acid comprising a DNA sequence that is substantially identical to a DNA sequence of Table 8 (SEQ ID NOS: 205-222). In

TABLE 22 anti-hIL10Ra Mono-Fc VHHs binding to hIL10Ra-his (Antigen: Sino Biological, Catalog#10419)

| Ligand | SEQ ID NO | $k_{ON}$ (1/Ms) | $k_{OFF}$ (1/s) | Affinity (nM) | Rmax (RU) | Load (RU) | Calc. Rmax (RU) | Surface Activity |
|---|---|---|---|---|---|---|---|---|
| hIL-10Ra_VHH6 | 159 | 1.06E+05 | 1.90E−04 | 1.8 | 31.8 | 50.2 | 38 | 83% |
| hIL-10Ra_VHH8 | 161 | 1.68E+05 | 1.07E−03 | 6.4 | 17.7 | 40.6 | 31 | 57% |
| hIL-10Ra_VHH9 | 162 | 9.97E+04 | 1.15E−03 | 11.6 | 42.2 | 83.2 | 64 | 66% |
| hIL-10Ra_VHH10 | 163 | 1.04E+05 | 1.39E−03 | 13.4 | 106 | 242 | 185 | 57% |
| hIL-10Ra_VHH12 | 165 | 1.54E+05 | 1.19E−03 | 7.7 | 18.3 | 32.9 | 25 | 73% |
| hIL-10Ra_VHH14 | 167 | 9.84E+04 | 1.36E−04 | 1.4 | 17.1 | 44.1 | 34 | 51% |
| hIL-10Ra_VHH17 | 170 | 3.27E+05 | 1.97E−03 | 6 | 48.4 | 180 | 137 | 35% |

Table 2 provides CDRs useful in the preparation of IL10Ra sdAbs for incorporation into the binding molecules of the present disclosure. In some embodiments, the IL10Ra sdAbs are generated in response to immunization with the certain embodiments, the present disclosure provides an isolated nucleic acid comprising a DNA sequence that is identical to a DNA sequence of Table 8 (SEQ ID NOS: 205-222).

Generation and Evaluation of of IL10Rb VHHs

The present disclosure further provides provides IL10Rb sdAbs that specifically bind to the extracellular domain of the mouse and human IL10Rb (hIL10Rb) and mouse IL10Rb (mIL10Rb). The procedure employed for the generation of IL10Rb VHHs was substantially the same as provided above and in substantial accordance with the teaching of Example 5 with the exception of the antigen used for immunization as discussed in more detail below.

To generate sdAbs against the hIL10Rb, the extracellular domain of the hIL10Rb protein was used as the immunogen. The extracellular domain of mature (lacking the signal sequence) hIL10Rb possesses the amino acid sequence:

(SEQ ID NO: 457)
MVPPPENVRMNSVNFKNILQWESPAFAKGNLTFTAQYLSYRIFQDKCMN

TTLTECDFSSLSKYGDHTLRVRAEFADEHSDWVNITFCPVDDTIIGPPG

MQVEVLADSLHMRFLAPKIENEYETWTMKNVYNSWTYNVQYWKNGTDEK

FQITPQYDFEVLRNLEPWTTYCVQVRGFLPDRNKAGEWSEPVCEQTTHD

ETVPS

To generate sdAbs against mIL10Rb, the extracellular domain of the mIL10Rb protein was used as an immunogen. The extracellular domain of the mature (lacking the signal sequence) mIL10Rb possesses the amino acid sequence the extracellular domain of the hIL10Rb protein was used as the immunogen. The extracellular domain of mature (lacking the signal sequence) mIL10Rb possesses the amino acid sequence:

(SEQ ID NO: 459)
MIPPPEKVRMNSVNFKNILQWEVPAFPKTNLTFTAQYESYRSFQDHCK

RTASTQCDFSHLSKYGDYTVRVRAELADEHSEWVNVTFCPVEDTIIGP

PEMQIESLAESLHLRFSAPQIENEPETWTLKNIYDSWAYRVQYWKNGT

NEKFQVVSPYDSEVLRNLEPWTTYCIQVQGFLLDQNRTGEWSEPICER

TGNDEITPS

The amino acid sequences of VHH molecules generated in accordance with the foregoing and demonstrating specific binding to the hIL10Rb ECD antigen (hIL10Rb VHHs) are provided in Table 6 (SEQ ID NOS: 172-198) and the CDRs isolated from such VHHs are provided in Table 3 (SEQ ID NOS: 55-135). Nucleic acid sequences encoding the VHHs of Table 6 are provided in Table 9 (SEQ ID NOS: 223-249).

The amino acid sequences of VHH molecules generated in accordance with the foregoing and demonstrating specific binding to the mIL10Rb ECD antigen (mIL10Rb VHHs) are provided in Table 7 (SEQ ID NOS: 199-204) and the CDRs isolated from such VHHs are provided in Table 4 (SEQ ID NOS: 136-153). Nucleic acid sequences encoding the VHHs of Table 7 are provided in Table 10 (SEQ ID NOS: 250-255).

To confirm and evaluate binding affinities of the binding of the hIL10Rb sdAbs, a representative example from each clonotype generated was selected for evaluation of binding via SPR. Evaluation of binding affinity of the hIL10Rb binding molecules for hIL10Rb corresponding to SEQ ID NOS: 172, 174, 183, 186 187, 197 and 198 was conducted using surface plasmon resonance (SPR) in substantial accordance with the teaching of Example 5 Buffer-subtracted sensograms were processed with Biacore T200 Evaluation Software and globally fit with a 1:1 Langmuir binding model (bulk shift set to zero) to extract kinetics and affinity constants (ka, kd, KD). RMAX<100 RU indicates surface density compatible with kinetics analysis. Calculated Rmax values were generated using the equation: Rmax=Load (RU)×valency of ligand×(Molecular weight of analyte/Molecular weight of ligand). Surface activity was defined as the ratio of experimental/calculated Rmax. The results of these binding affinity experiments are provided in Table 23 below.

TABLE 23

| hIL10Rb Mono-Fc VHHs binding to hIL10Rb-his (Antigen: Sino Biological, Catalog#10945) | | | | | | | | |
|---|---|---|---|---|---|---|---|---|
| Ligand | SEQ ID | $k_{ON}$ (1/Ms) | $k_{OFF}$ (1/s) | Affinity (nM) | Rmax (RU) | Load (RU) | Calc. Rmax (RU) | Surface Activity |
| hIL-10Rb__VHH1 | 172 | 1.75E+05 | 1.44E−03 | 8.3 | 45.6 | 72.9 | 56 | 82% |
| hIL-10Rb__VHH12 | 183 | 1.11E+05 | 1.43E−03 | 12.9 | 28.1 | 54.6 | 42 | 67% |
| hIL-10Rb__VHH3 | 174 | 9.29E+04 | 2.14E−02 | 231 | 22.4 | 56.7 | 43 | 52% |
| hIL-10Rb__VHH15 | 186 | 7.18E+04 | 8.66E−03 | 121 | 28.9 | 210 | 160 | 18% |
| hIL-10Rb__VHH16 | 187 | 2.93E+03 | 2.21E−02 | 7540 | 227* | 54.4 | 42 | 545%* |
| hIL-10Rb__VHH26 | 197 | 6.78E+04 | 2.13E−02 | 314 | 25.6 | 62.2 | 47 | 54% |
| hIL-10Rb__VHH27 | 198 | 1.07E+07 | 2.54E−02 | 2.4 | 36.3 | 198 | 151 | 24% |

*Inaccurate fit

The data provided demonstrates that the hIL10Rb single domain antibodies generated possessed specific binding to the ECD of hIL10Rb and a range of binding affinities useful in the modulation of the activity of IL10R binding molecules as discussed below.

*Inaccurate fit

Tables 3 and 4 provides CDRs useful in the preparation of IL10Ra sdAbs for incorporation into the binding molecules of the present disclosure. In some embodiments, the IL10Ra sdAbs are generated in response to immunization with the and specifically bind to the ECD of hIL10Ra. In some embodiments, the IL10Ra sdAb is a single domain antibody comprising: a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to a CDR1 sequence of Table 3; a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to a CDR1 sequence of Table 3; and a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to a CDR1 sequence of Table 3. In some embodiments, the IL10Ra sdAbs are generated in response to immunization with the and specifically bind to the ECD of mIL10Ra. In some embodiments, the IL10Ra sdAb is a single domain antibody comprising: a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to a CDR1 sequence of Table 4; a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to a CDR1 sequence of Table 4; and a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to a CDR1 sequence of Table 4.

In some embodiments, the IL10Rb sdAb comprises a sequence having at least 90% (e.g., 91%, 92%, 93%, 94%, 95%, 96%, 97%, 98%, 99%, or 100%) sequence identity to a sequence of any one the of amino acid sequences of an hIL10Rb sdAb of Table 6 (SEQ ID NOS: 172-198). In certain embodiments, the IL10Rb sdAb comprises sequence that is substantially identical to a sequence of any one the of amino acid sequences of an hIL10ba sdAb of Table 6 (SEQ ID NOS: 172-198). In certain embodiments, the IL10Rb sdAb comprises sequence that is identical to a sequence of any one the of amino acid sequences of an hIL10ba sdAb of Table 6 (SEQ ID NOS: 172-198).

In some embodiments, the IL10Rb sdAb comprises a sequence having at least 90% (e.g., 91%, 92%, 93%, 94%, 95%, 96%, 97%, 98%, 99%, or 100%) sequence identity to a sequence of any one the of amino acid sequences of an mIL10Rb sdAb of Table 7 (SEQ ID NOS: 199-204). In certain embodiments, the IL10Rb sdAb comprises sequence that is substantially identical to a sequence of any one the of amino acid sequences of an mIL10Rb sdAb of Table 7 (SEQ ID NOS: 199-204). In certain embodiments, the IL10Rb sdAb comprises sequence that is identical to a sequence of any one the of amino acid sequences of mIL10Rb sdAb of Table 7 (SEQ ID NOS: 199-204).

In another aspect, the disclosure provides an isolated nucleic acid encoding IL10Rb sdAb described herein. In certain embodiments, the present disclosure provides an isolated nucleic acid comprising a sequence having at least 90% (e.g., 91%, 92%, 93%, 94%, 95%, 96%, 97%, 98%, 99%, or 100%) sequence identity to a DNA sequence of Table 9 (SEQ ID NOS: 223-249). In certain embodiments, the present disclosure provides an isolated nucleic acid comprising a DNA sequence that is substantially identical to a DNA sequence of Table 9 (SEQ ID NOS: 223-249). In certain embodiments, the present disclosure provides an isolated nucleic acid comprising a DNA sequence that is identical to a DNA sequence of Table 9 (SEQ ID NOS: 223-249).

In another aspect, the disclosure provides an isolated nucleic acid encoding IL10Rb sdAb described herein. In certain embodiments, the present disclosure provides an isolated nucleic acid comprising a sequence having at least 90% (e.g., 91%, 92%, 93%, 94%, 95%, 96%, 97%, 98%, 99%, or 100%) sequence identity to a DNA sequence of Table 10 (SEQ ID NOS: 250-255). In certain embodiments, the present disclosure provides an isolated nucleic acid comprising a DNA sequence that is substantially identical to a DNA sequence of Table 10 (SEQ ID NOS: 250-255). In certain embodiments, the present disclosure provides an isolated nucleic acid comprising a DNA sequence that is identical to a DNA sequence of Table 10 (SEQ ID NOS: 250-255).

Generation of IL10R Polypeptide Binding Molecules

In some embodiments, the IL10R binding molecule of the present invention is a polypeptide of the following formula [#1]:

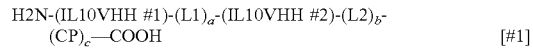

$$\text{H2N-(IL10VHH \#1)-(L1)}_a\text{-(IL10VHH \#2)-(L2)}_b\text{-(CP)}_c\text{—COOH} \qquad [\#1]$$

wherein: "-" represents a covalent bond; L1 and L2 are linkers; CP is a chelating peptide; a, b, and c are independently selected from the integers 0 or 1; "H2N" denotes the amino terminus; and "COOH" denotes the carboxy terminus of the polypeptide.

Using the hIL10Ra VHHs and hIL10Rb VHHs prepared above, a series of ninety-eight polypeptide IL10R binding molecules of formula [#1] were prepared as SEQ ID NOS: 256-353 and with respect to each of SEQ ID NOS 256-353: a=1 and L1=G3S (SEQ ID NO: 484); b=1 and L2=Ala-Ser; c=1 and CP=hexa-histidine (SEQ ID NO: 532). The IL10Ra VHH, linkers and IL10Ra VHH, chelating peptide elements of these ninety-eight IL-10 receptor binding proteins of SEQ ID NOS 256-353 is provided in Table 11. The amino acid sequences of SEQ ID NOS: 256-353 are provided in Table 12 and the DNA sequence encoding each of the foregoing used for expression of the IL10R binding molecules is provided in Table 14 (SEQ ID NOS: 353-402).

The IL10R binding proteins of Tables 11 and 12 were prepared and evaluated for IL10 activity. Details regarding the expression and purification of these 98 IL10R binding proteins is provided in the Examples. Briefly, nucleic acid sequences encoding SEQ ID Nos: 256-353 were synthesized as SEQ ID Nos: 354-451, respectively, and were inserted into a recombinant expression vector and expressed in HEK293 cells in 24 well plate format and purified in substantial accordance with Example 4. The supernatants containing the IL-10 receptor binding proteins of SEQ ID NOS: 192-298 were evaluated for activity with unstimulated and wild-type human IL-10 as controls in substantial accordance with Examples 5 and 6 herein. The results of these experiments are provided in Table 13.

As can be seen from the data provided in Table 13, IL-10 receptor binding proteins of the formula [#1] demonstrated IL-10 activity in the IL-10 activity assay. The level of IL-10 activity was categorized as low (above unstimulated and $A_{630}<1$), medium ($A_{630}$ 1-1.5) and high ($A_{630}>1.5$) based on absorbance readings. From the above data, 11 IL10 receptor binding proteins demonstrated high activity (SEQ ID NOs: 258, 273, 274, 275, 276, 282, 290, 297, 298, 308 and 314), 4 with medium activity (SEQ ID NOs: 267, 269, 271, and 333) and 8 VHHs with low activity (SEQ ID NOs: 276, 281, 283, 288, 291, 301, 303, and 313).

To further investigate and characterize the binding of the IL10R binding molecules prepared above, a selection of the foregoing molecules was evaluated for binding to the hIL10Ra and hIL10Rb receptor subunits by SPR in substantial accordance with the teaching of the Examples and the data presented in Table 24 and 25 below. The first column represents the VHHs used in the IL10R binding molecule (as provided in Table 5 and 6 above) and their orientation from amino to carboxy, and each molecule was expressed with a four amino acid G3S linker (SEQ ID NO: 484) between the VHHs conjugated to biotin. As illustrated by the data provided in Tables 24 and 25 below, the IL10R polypeptide binding molecules of the formula [#1] demonstrate single-digit nanomolar binding affinity to each of the hIL10Ra and hIL10Rb VHH subunits as determined by SPR. This data demonstrates that each of the hIL10Ra and hIL10Rb VHH subunits retains their respective binding affinity to their respective IL10 receptor subunits and that, as discussed in more detail below, retained activity whether provided in the "forward" or "reverse" configurations.

TABLE 24

Anti-hIL10Ra/hIL10Rb dual VHH binding to hIL10Ra-his
(Analyte = hIL10Ra his, Sino Biological cat#10419-H08H)

| Ligand (IL10R VHHs) | $k_{ON}$ (1/Ms) | $k_{OFF}$ (1/s) | Affinity (nM) | Rmax (RU) | Load (RU) | Calc. Rmax (RU) | Activity |
|---|---|---|---|---|---|---|---|
| hIL10Rb_VHH1 - hIL10Ra_VHH9 - biotin | 2.5E+05 | 2.7E−04 | 1.1 | 67.8 | 93 | 130.2 | 52% |
| hIL10Rb_VHH12 - hIL10Ra_VHH8 biotin | 1.8E+05 | 6.5E−05 | 0.35 | 41.6 | 53 | 74.2 | 56% |
| IL10 VHH DR509 biotin | 4.9E+05 | 1.3E−04 | 0.2 | 51.5 | 85 | 119 | 43% |
| hIL10Ra_VHH17 - hIL10Rb_VHH16 biotin | N/A | N/A | <5 | N/A | 53 | N/A | N/A |

TABLE 25 hIL10Ra/hIL10Rb dual VHH binding to hIL10Rb-his
(Analyte = Sino Biological cat#10945-H08H)

| Ligand (IL10R VHHs) | $k_{ON}$ (1/Ms) | $k_{OFF}$ (1/s) | Affinity (nM) | Rmax (RU) | Load (RU) | Calc. Rmax (RU) | Activity |
|---|---|---|---|---|---|---|---|
| hIL10Ra_VHH17 - hIL10Rb_VHH16 biotin | 1.6E+05 | 4.5E−04 | 2.9 | 30 | 62 | 86.8 | 34% |
| hIL10Rb_VHH12 - hIL10Ra_VHH8 biotin | 4.4E+05 | 6.8E−04 | 1.5 | 32 | 53 | 74.2 | 42% |
| hIL10Rb_VHH1 - hIL10Ra_VHH9 biotin | 6.6E+05 | 1.8E−03 | 2.7 | 31 | 90 | 126 | 25% |
| hIL10Ra_VHH12 - hIL10Rb_VHH27 biotin | 1.6E+06 | 3.0E−03 | 1.9 | 100 | 84 | 117.6 | 85% |

Modulation of Activity of Receptor Binding Molecules

In some embodiments, such as to achieve partial agonism or selective activation of particular cell types, the design of the IL10R binding molecules of the present disclosure may be modulated by structural variations in the design of the receptor binding molecule. This variation in activity may be employed to modulate the binding and activity of the IL10R receptor binding molecule, for to optimize the activity of the IL10R binding molecule to achieve partial agonism, selective cell type activation or to provide molecules having increased or decreased binding relative to the cognate ligand for each of the IL10Ra sdAb and IL10Rb sdAb for their respective receptor subunits.

The ability to modulate activity of the IL10R binding molecules of the present disclosure provides substantial benefits in multiple therapeutic applications. IL10 is a pleiotropic cytokine that regulates multiple immune responses through actions on T cells, B cells, macrophages, and antigen presenting cells (APC) and seemingly paradoxical activity which has limited its clinical development. IL10 is reported to suppress immune responses and inhibits the expression of IL-1α, IL-1β, IL-6, IL-8, TNF-α, GM-CSF and G-CSF in activated monocytes and macrophages. IL10 is associated with suppression of IFN-γ production by NK cells. In contrast, IL10 exhibits immuno-stimulatory properties, including enhancing the stimulation IL-2- and IL-4-treated thymocytes, enhancing the viability of B cells, and stimulating the presentation of MHC class II antigens. As a result, the use of IL-10 has been identified as useful in the treatment of a broad range of diseases, disorders and conditions, including inflammatory conditions, immune-related disorders, fibrotic disorders, metabolic disorders and cancer.

The IL10R molecules of the present disclosure enable modulation of activity provide significant benefits in the treatment of human disease. IL10R binding proteins described herein are useful in the treatment of neoplastic diseases, such as cancer (e.g., a solid tumor cancer; e.g., non-small-cell lung carcinoma (NSCLC), renal cell carcinoma (RCC), or melanoma) in a subject in need thereof. In some embodiments, the IL10R binding protein described herein can provide a longer therapeutic efficacy (e.g., lower effective dose, reduced toxicity) than IL10. The IL10R binding molecules of the present disclosure can trigger different levels of downstream signaling in different cell types. For example, by varying the length of the linker between the IL10Ra sdAb antibody and the IL10Rb sdAb antibody in the IL10R binding molecule, the IL10R binding molecules provides a higher level of downstream signaling in desired cell types compared to undesired cell types. In some embodiments the IL10R binding molecules is a partial IL10 agonist that selectively activates T cells (e.g., CD8$^+$ T cells) over macrophages. In some embodiments, activated T cells have an up-regulation of IFNgamma. In some embodiments, an IL10R binding protein that is a partial agonist can suppress autoimmune inflammatory diseases such as ulcerative colitis and Crohn's disease.

In one embodiment, the present disclosure provides an IL10Ra binding molecule that preferentially activates T cells, in particular CD8+ T cells, relative to monocytes. In one embodiment, the present disclosure provides an IL10Ra binding molecule of the formula #1 wherein the affinity of the IL10Ra sdAb has a higher affinity for the extracellular domain of IL10Ra than the affinity of the IL10Rb sdAb for the extracellular domain of IL10Rb. In some embodiments, the present disclosure provides a IL10Ra molecule of formula #1, wherein the affinity of the IL10Ra sdAb has an affinity for the extracellular domain of IL10Ra of from about $10^{-8}$ to about $10^{-10}$ M, alternatively from about $10^{-9}$ to about $10^{-10}$M, or alternatively about $10^{-10}$ M and the IL10Rb sdAb an affinity for the extracellular domain of IL10Rb of from about $10^{-6}$ to about $10^{-9}$ M, alternatively from about $10^{-7}$ to about $10^{-9}$M, alternatively from about 10-7 to about $10^{-8}$M, alternatively about $10^{-9}$M, alternatively about $10^{-8}$M. In some embodiments, the present disclosure provides a IL10Ra molecule of formula #1, wherein the affinity of the IL10Ra sdAb has an affinity for the extracellular domain of IL10Ra of from about $10^{-8}$ to about $10^{-10}$ M, alternatively from about $10^{-9}$ to about $10^{-10}$M, or alternatively about $10^{-10}$ M and the IL10Rb sdAb an affinity for the extracellular domain of IL10Rb of from about $10^{-6}$ to about $10^{-9}$ M, alternatively from about $10^{-7}$ to about $10^{-9}$M, alternatively from about $10^{-7}$ to about $10^{-8}$M, alternatively about $10^{-9}$M, alternatively about $10^{-8}$M, and the affinity of the IL10Ra sdAb for ECD of IL10Ra is more than 2 fold higher, alternatively more than 5 fold higher, alternatively more than 10 fold higher, alternatively more than 20 fold higher, alternatively more than 40 fold higher, alternatively more than 50 fold higher, alternatively more than 60 fold higher, alternatively more than 70 fold higher, alternatively more than 80 fold higher, alternatively more than 90 fold higher, alternatively more than 100 fold higher, alternatively more than 150 fold higher, alternatively more than 200 fold higher or alternatively more than 500 fold higher than the affinity of the IL10Rb sdAb for ECD of IL10Rb In some embodiments, for example by varying the linker length, an IL10R binding molecule can cause a higher level of downstream signaling in T cells (e.g., CD8+ T cells) compared to the level of downstream signaling in macrophages, a cell type that expresses both IL10Ra and IL10Rb receptors but when activated too potently can cause anemia. When the downstream signaling in macrophages is activated to a high level, these activated macrophages can then eliminate aging red blood cells, causing anemia. The ability to modulate the activity of the IL10R binding molecule provides a molecule with a higher level of downstream signaling in T cells (e.g., CD8+ T cells) compared to the level of downstream signaling in macrophages, such that anemia is avoided. In some embodiments, the IL10R binding molecules of the present disclosure result in level of downstream signaling in T cells (e.g., CD8+ T cells) that is at least 1.1, 1.5, 2, 3, 5, or 10 times of the level of downstream signaling in macrophages. In other embodiments, different IL10Ra sdAb antibodies with different binding affinities and different IL10Rb sdAb antibodies with different binding affinities can be used to tune the activity of IL10R binding molecule. Further, when the IL10R binding molecule is provided as a single a polypeptide, the orientation of the two antibodies in the polypeptide can also be changed to make change the properties of the molecule. In some embodiments, it is desired to provide an the IL10R binding protein has a reduced Emax compared to the Emax caused by IL10, the cognate ligand for the IL10 receptor (i.e. an IL10R binding molecule that is a IL10 partial agonist). Emax reflects the maximum response level in a cell type that can be obtained by a ligand (e.g., a binding protein described herein or the cognate ligand (e.g., IL10)). In some embodiments, the IL10R binding protein described herein has at least 1% (e.g., between 1% and 100%, between 10% and 100%, between 20% and 100%, between 30% and 100%, between 40% and 100%, between 50% and 100%, between 60% and 100%, between 70% and 100%, between 80% and 100%, between 90% and 100%, between 1% and 90%, between 1% and 80%, between 1% and 70%, between 1% and 60%, between 1% and 50%, between 1% and 40%, between 1% and 30%, between 1% and 20%, or between 1% and 10%) of the Emax caused by hIL10.

Figure 2A:
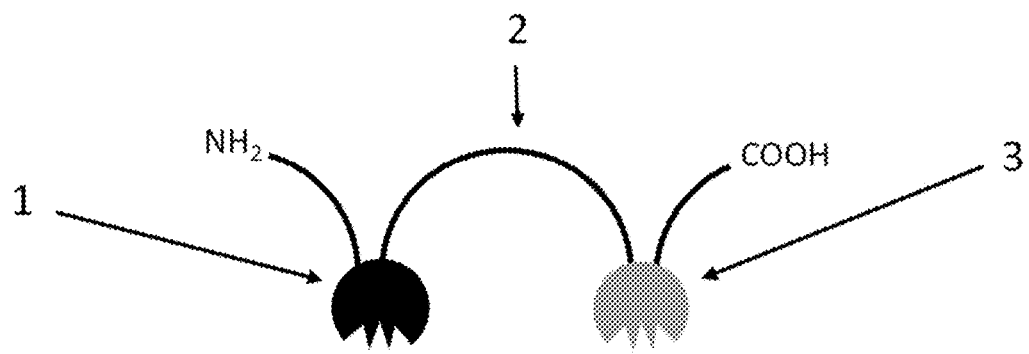

As previously discussed, the orientation of the sdAbs of the IL10R binding molecule may be used to optimize desired characteristics of the molecules. The orientation of the sdAbs of the IL10R my probided in a variety of different structures as illustrated in FIGS. 2, 3 and 4 of the attached drawings as expressed formulaically below:

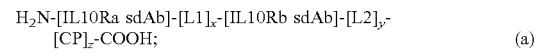  (a)

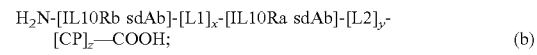  (b)

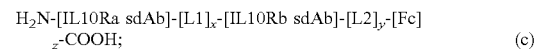  (c)

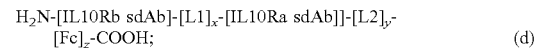  (d)

wherein and L1 and L2 are independently selected polypeptide linkers of 1-50 amino acids and x=0 or 1, y=0 or 1; and CP is a chelating peptide; "Fc" is a monomeric Fc domain and y=0 or 1; non-covalent complexes of the structure:

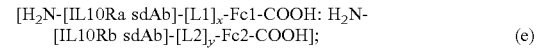  (e)

wherein and L1 and L2 are independently selected polypeptide linkers of 1-50 amino acids and x=0 or 1, y=0 or 1; and CP is a chelating peptide; "Fc1" is a monomeric Fc domain "Fc2" is a monomeric Fc domain wherein Fc1 and Fc2 form a stable non-covalent association, and y=0 or 1; and coordinate covalent complexes of the structure

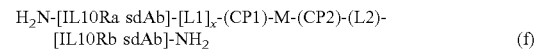  (f)

wherein and L1 and L2 are independently selected polypeptide linkers of 1-50 amino acids and x and y are independently selected from 0 or 1; and CP1 is a first chelating peptide; CP2 is a second chelating peptide; and M is a transition metal ion.

Examples of the means by which the modulation of the activity and/or specificity of the receptor binding molecule of the present disclosure include, but are not limited to, altering the sequential orientation of the IL10Ra sdAb and IL10Rb sdAb in polypeptide IL10R binding molecules, independently varying the of the binding affinity of each IL10Ra sdAb and IL10Rb sdAbs with respect to their respective IL10Ra and/or each target, and modulating the distance between the IL10Ra sdAb and IL10Rb sdAbs, such as by employing linkers or varying lengths, which will affect the proximity of the intracellular signaling domains of the IL10 receptor subunits and thereby achieve modulation, of the intracellular signaling characteristic of the binding of the cognate ligand to the receptor, for example the level of phosphor-STAT3 induced in the cell. As illustrated by the data provided below, each of these variations may be used to tune the properties of IL10R binding molecules.

Sequential Orientations of IL10Ra and IL10Rb sdAbs in Single Polypeptide IL10R Binding Molecules When the IL10R binding molecule comprises and IL10Ra sdAb and IL10Rb sdAb sequences in a single polypeptide, the IL10Ra sdAb and IL10Rb sdAb sequences may be arranged wherein the IL10Ra sdAb is N-terminal relative to the IL10Rb sdAb (termed herein as the "forward configuration") or IL10Rb sdAb is N-terminal relative to the IL10Ra sdAb (termed herein as the "reverse configuration"). The two orientations can be illustrated as examples of the compound of formula [#1] represented by the following formulas;

$H_2N$-[IL10Ra sdAb]-$[L1]_x$-[IL10Rb sdAb]-$[L2]_y$-$[CP]_z$-COOH; (a)

$H_2N$-[IL10Rb sdAb]-$[L1]_x$-[IL10Ra sdAb]-$[L2]_y$-$[CP]_z$-COOH; (b)

wherein: "-" represents a covalent bond; L1 and L2 are linkers; CP is a chelating peptide; a, b, and c are independently selected from the integers 0 or 1; "H2N" denotes the amino terminus; and "COOH" denotes the carboxy terminus of the polypeptide.

"Forward" Configuration:

In some embodiments, the IL10R binding molecule comprises a polypeptide of the structure of the formula [#1] wherein the N-terminal VHH of formula [#1] (i.e., IL10 VHH #1) is an IL10Ra VHH and the C-terminal VHH (i.e., IL10 VHH #2) is an IL10Rb VHH, and wherein: "-" represents a covalent bond; L1 and L2 are independently selected polypeptide linkers of Table 16, linkers; CP is a chelating peptide; a, b, and c are independently selected from the integers 0 or 1; "H2N" denotes the amino terminus; and "COOH" denotes the carboxy terminus of the polypeptide.

"Reverse" Configuration

In some embodiments, the IL10R binding molecule comprises a polypeptide of the structure of the formula [#1] wherein the N-terminal VHH of the above formula [#1] (i.e., IL10 VHH #1) is an anti-IL10Rb VHH and the C-terminal VHH (i.e., IL10 VHH #2) is an anti-IL10Ra VHH ("forward orientation") and wherein: "-" represents a covalent bond; L1 and L2 are independently selected polypeptide linkers of Table 16, linkers; CP is a chelating peptide; a, b, and c are independently selected from the integers 0 or 1; "H2N" denotes the amino terminus; and "COOH" denotes the carboxy terminus of the polypeptide.

Evaluation of Activity of Exemplary IL10R Molecules of Forward and Revserse Orientations IL10R binding molecules of forward and reverse orientation of the IL10Ra and IL10Rb sdAbs were generated in substantial accordance with the teaching of the Examples. IL10R binding molecules corresponding to sequence ID NOS: 256-304 are examples of the "forward configuration" or "forward orientation.". IL10R binding molecules corresponding to sequence ID NOS: 305-353 are examples of compounds of the "reverse orientation" or "reverse configuration". These "forward orientation" and "reverse orientation" molecules were evaluated for activity in accordance with the Examples and the data provided in Table 13. Referring to the binding data presented in Table 13, it can be seen that the orientation of IL10Ra and IL10Rb sdAb binding domains provides for substantial modulation of the IL10 activity in response to the sequential (forward v. reverse) orientation of the IL10Ra sdAb and an IL10Rb sdAbs of the IL10R binding molecules The CDRs isolated from the VHH molecules prepared above sequences may be used to prepare IL10R binding molecules of both the forward and reverse configurations. In some embodiments, the disclosure provides an IL10R binding molecule of the "forward" configuration wherein the IL10R binding molecule comprises a polypeptide from amino to carboxy terminus:

(a) an IL10Ra sdAb comprising:
  - a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 1, 4, 7, 10, 13, 16, 19, 22, 25, 28, 31, 34, 37, 40, 43, 46, 49, and 52;
  - a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 2, 5, 8, 11, 14, 17, 20, 23, 26, 29, 32, 35, 38, 41, 44, 47, 50 and 53; and
  - a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 3, 6, 9, 12, 15, 18, 21, 24, 27, 30, 33, 36, 39, 42, 45, 48, 51 and 54.

(b) polypeptide linker from 1-50 amino acids, alternatively 1-40 amino acids, alternatively 1-30 amino acids, alternatively 1-20 amino acids, alternatively 1-15 amino acids, alternatively 1-10 amino acids, alternatively 1-8 amino acids, alternatively 1-6 amino acids, alternatively 1-4 amino acids; and (c) an IL10Rb sdAb comprising:
  - a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148 and 151;
  - a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149 and 152; and
  - a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150 and 153.

In some embodiments, IL10R binding molecule of the "forward" configuration wherein the IL10R binding molecule comprises a polypeptide from amino to carboxy terminus:

(a) an IL10Ra sdAb of comprising an amino acid sequence having at least 90% (e.g., 91%, 92%, 93%, 94%, 95%, 96%, 97%, 98%, 99%, or 100%) sequence identity to a sequence of any one the of SEQ ID NOS: 154-171;
(b) polypeptide linker from 1-50 amino acids, alternatively 1-40 amino acids, alternatively 1-30 amino acids, alternatively 1-20 amino acids, alternatively 1-15 amino acids, alternatively 1-10 amino acids, alternatively 1-8 amino acids, alternatively 1-6 amino acids, alternatively 1-4 amino acids; and
(c) and IL10Rb sdAb comprises a sequence having at least 90% (e.g., 91%, 92%, 93%, 94%, 95%, 96%, 97%, 98%, 99%, or 100%) sequence identity to a sequence of any one of SEQ ID NOS:172-204.

In some embodiments, and IL10R molecule of the "forward" configuration wherein the IL10R binding molecule comprises a polypeptide having at 90% (e.g., 91%, 92%, 93%, 94%, 95%, 96%, 97%, 98%, 99%, or 100%) sequence identity to a sequence of any one the of SEQ ID NOS: 256-304.

In some embodiments, the disclosure provides an IL10R binding molecule of the "reverse" configuration wherein the IL10R binding molecule comprises a polypeptide from amino to carboxy terminus:
(a) an IL10Rb sdAb comprising:
  a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 55, 58, 61, 64, 67, 70, 73, 76, 79, 82, 85, 88, 91, 94, 97, 100, 103, 106, 109, 112, 115, 118, 121, 124, 127, 130, 133, 136, 139, 142, 145, 148 and 151;
  a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 56, 59, 62, 65, 68, 71, 74, 77, 80, 83, 86, 89, 92, 95, 98, 101, 104, 107, 110, 113, 116, 119, 122, 125, 128, 131, 134, 137, 140, 143, 146, 149 and 152; and
  a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 57, 60, 63, 66, 69, 72, 75, 78, 81, 84, 87, 90, 93, 96, 99, 102, 105, 108, 111, 114, 117, 120, 123, 126, 129, 132, 135, 138, 141, 144, 147, 150 and 153.
(b) polypeptide linker from 1-50 amino acids, alternatively 1-40 amino acids, alternatively 1-30 amino acids, alternatively 1-20 amino acids, alternatively 1-15 amino acids, alternatively 1-10 amino acids, alternatively 1-8 amino acids, alternatively 1-6 amino acids, alternatively 1-4 amino acids; and
(c) an IL10Ra sdAb comprising:
(d) a CDR1 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 1, 4, 7, 10, 13, 16, 19, 22, 25, 28, 31, 34, 37, 40, 43, 46, 49, and 52;
(e) a CDR2 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 2, 5, 8, 11, 14, 17, 20, 23, 26, 29, 32, 35, 38, 41, 44, 47, 50 and 53; and
(f) a CDR3 having at least 90% (e.g., 91%, 92%, 93%, 94%, 95%, 96%, 97%, 98%, 99%, or 100%) sequence identity, or having 0, 1, 2, or 3 amino acid changes, optionally conservative amino acid changes relative, to the sequence of any one of SEQ ID NOS: 3, 6, 9, 12, 15, 18, 21, 24, 27, 30, 33, 36, 39, 42, 45, 48, 51 and 54.

In some embodiments, the disclosure provides an IL10R binding molecule of the "reverse" configuration wherein the IL10R binding molecule comprises a polypeptide from amino to carboxy terminus:
(a) and IL10Rb sdAb comprising a sequence having at least 90% (e.g., 91%, 92%, 93%, 94%, 95%, 96%, 97%, 98%, 99%, or 100%) sequence identity to a sequence of any one of SEQ ID NOS:172-204;
(b) a polypeptide linker from 1-50 amino acids, alternatively 1-40 amino acids, alternatively 1-30 amino acids, alternatively 1-20 amino acids, alternatively 1-15 amino acids, alternatively 1-10 amino acids, alternatively 1-8 amino acids, alternatively 1-6 amino acids, alternatively 1-4 amino acids; and
(c) an IL10Ra sdAb of comprising an amino acid sequence having at least 90% (e.g., 91%, 92%, 93%, 94%, 95%, 96%, 97%, 98%, 99%, or 100%) sequence identity to a sequence of any one the of SEQ ID NOS: 154-171.

In some embodiments, the IL10R binding molecules is a polypeptide having at least 90% (e.g., 91%, 92%, 93%, 94%, 95%, 96%, 97%, 98%, 99%, or 100%) sequence identity to an IL10R binding molecule of formula #1 wherein IL10VHH #1 and IL10VHH #2 are correspond the SEQ ID of a row (e.g. IL10VHH #1 is SEQ ID NO: 165 and IL10VHH #2 is is SEQ ID NO: 198, etc.) of Table 20:

TABLE 20

| IL10R binding molecule of formula #1 comprising IL10VHH#1 and IL10VHH#2 | |
|---|---|
| IL10VHH#1 SEQ ID | IL10VHH#2 SEQ ID |
| 165 | 198 |
| 167 | 197 |
| 170 | 187 |
| 183 | 161 |
| 162 | 172 |
| 172 | 162 |
| 161 | 187 |
| 161 | 197 |
| 162 | 197 |
| 161 | 186 |
| 163 | 174 |
| 187 | 163 |
| 161 | 183 |
| 159 | 198 |
| 159 | 187 |
| 162 | 187 |
| 170 | 186 |
| 165 | 187 |
| 161 | 198 |
| 162 | 198 |
| 170 | 197 |
| 167 | 172 |
| 183 | 159 |
| 174 | 163 |
| 186 | 162 |

Evaluation of the Effects of Linker Length on IL10R Binding Molecule Activity

As discussed in the present disclosure, the activity of the IL10R dimeric VHH IL10R binding molecules of the present disclosure may be modulated by varying the length of the linker between the first and second IL10 VHH monomers. To illustrate the effects of variations of variations in linker length, a series of IL10R binding polypeptides of the formula [#1], in each case b=1 and L2=Ala-Ser; c=1; and CP=his×6 (SEQ ID NO: 532), were prepared containing variations in IL10VHH #2 while holding IL10VHH #1 sequence constant as DR241 (SEQ ID NO 170), the in accordance with the following Table 26:

TABLE 26

IL10Ra/IL10Rb Binding Molecules With Varying Linker Length

| Dimer Name | SEQ ID | IL10VHH#1 VHH Name | SEQ ID | a= | L1 | L1$_a$ | IL10VHH#2 VHH Name | SEQ ID |
|---|---|---|---|---|---|---|---|---|
| DR890 | 489 | DR241 | 170 | 0 | — | n/a | DR244 | 174 |
| DR891 | 490 | DR241 | 170 | 1 | GS | n/a | DR244 | 174 |
| DR519 | 300 | DR241 | 170 | 1 | 4x | 484 | DR244 | 174 |
| DR892 | 491 | DR241 | 170 | 1 | 6x | 470 | DR244 | 174 |
| DR893 | 492 | DR241 | 170 | 1 | 8x | 478 | DR244 | 174 |
| DR894 | 493 | DR241 | 170 | 1 | 10x | 472 | DR244 | 174 |
| DR787 | 494 | DR241 | 170 | 1 | 2x | n/a | DR246 | 187 |
| DR521 | 302 | DR241 | 170 | 1 | 4x | 484 | DR246 | 187 |
| DR896 | 494 | DR241 | 170 | 1 | GS | n/a | DR247 | 197 |
| DR522 | 303 | DR241 | 170 | 1 | 4x | 484 | DR247 | 197 |
| DR897 | 495 | DR241 | 170 | 1 | 6x | 470 | DR247 | 197 |
| DR898 | 496 | DR241 | 170 | 1 | 8x | 478 | DR247 | 197 |
| DR899 | 497 | DR241 | 170 | 1 | 10x | 472 | DR247 | 197 |

Figure 5:
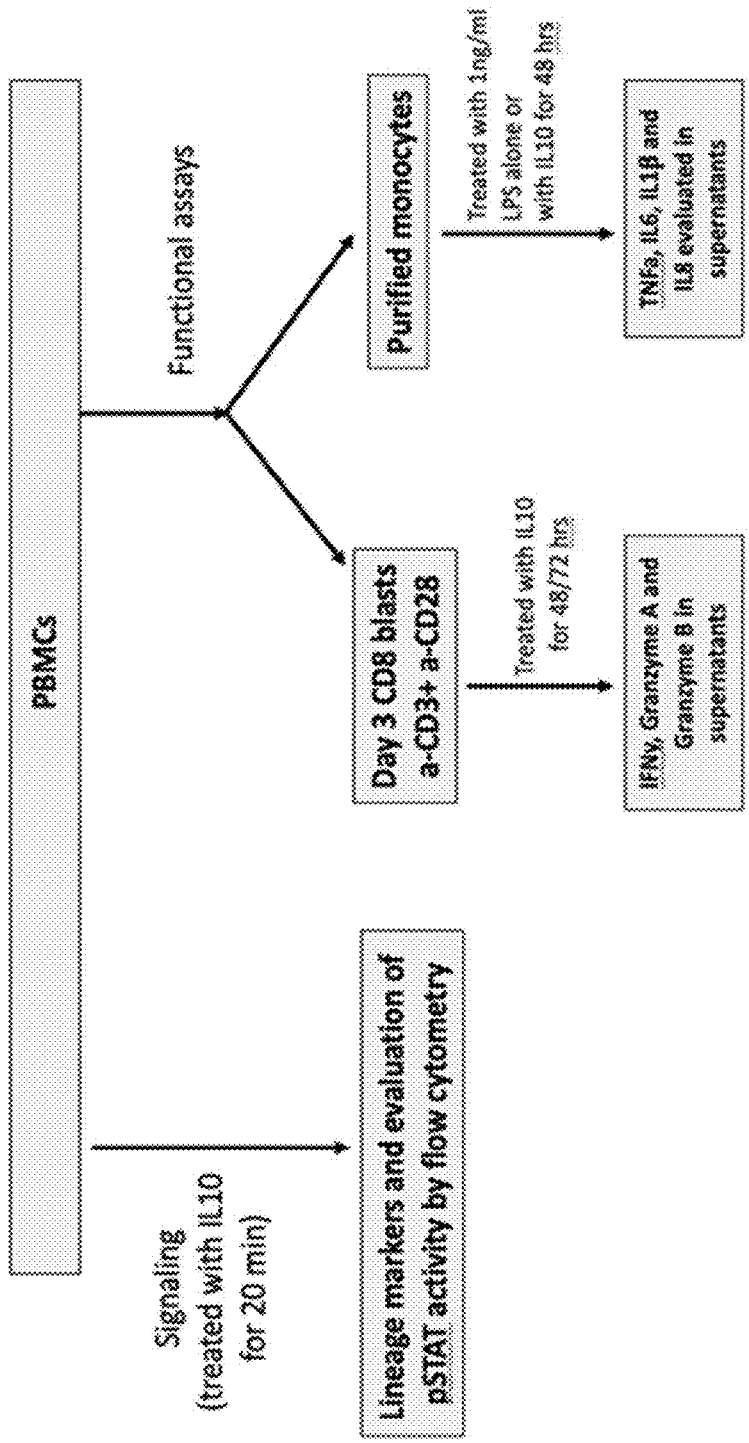

The level of pSTAT3 induced in response to the IL10R binding molecules corresponding to SEQ ID NOS: 489, 490, 300, 491, 492, 493, 494, 302, 494, 303, 495, 496 and 497 were evaluated for activity on CD4+ T cells, CD8+ T cells and monocytes using wild-type human IL10, a wild-type IL10 comprising a C-terminal His6 (SEQ ID NO: 532) chelating peptide and unstimulated as controls. The protocol for the assay and methodology involved is presented in FIG. 5 of the attached drawings. The results of these tests is provided in FIG. 6 of the attached drawings. To clarify the effect of linker length alone, in FIG. 6A-6C represent the condition where the IL10Ra sdAb and IL10Rb sdAb were held constant and only the length of the linker is varied the term 2X, 4X, etc. refers to the number of amino acids in the linker and the sequence of the linker is provided in Table 16. As illustrated by the data presented in FIG. 6, the variation of the linker length alone (maintain the sdAbs and other components constant as is reflected in FIGS. 6A-6C) may be used to modulate not only the level of activity of the IL10R binding molecule with respect to a given cell type (e.g. CD4+, CD8+, or monocyte), the variation in linker length may be used to reflect the modulating the activity of one cell type to another. As illustrated by the data provided variation of the distance between the IL10Ra and IL10Rb sdAbs, in some instances varying the length of the linker molecules, can provide modulation of the level of IL10 activity in a cell as measured by the levels of pSTAT3 activity.

Fc Conjugates

Figure 2B:
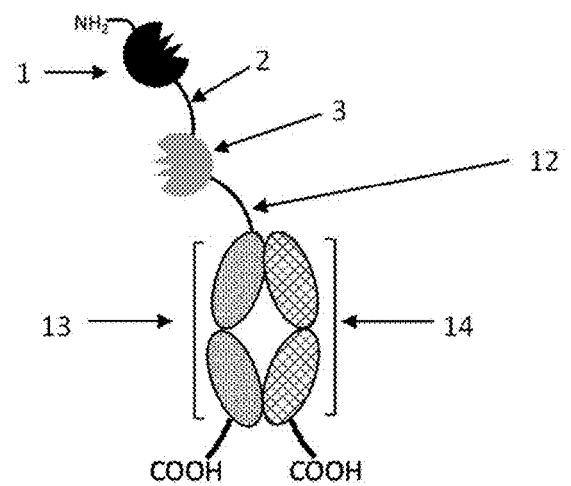

As discussed in the present disclosure, in some embodiments, the IL10R binding molecule may be conjugated to a subunit of an Fc domain as illustrated in FIG. 2B, and represented by the formula #2:

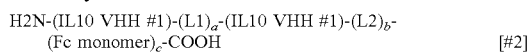

[#2]

A representative series of IL10R binding polypeptides of the formula [#1], in each case a=1, L1=G3S (SEQ ID NO: 484), b=1 and L2=Ala-Ser; c=1; and Fc monomer is a polypeptide of SEQ ID NO:502, were prepared containing variations in IL10VHH #2 while holding IL10VHH #1 sequence constant as DR241 (SEQ ID NO 170), the in accordance with the following Table 27. These features and details of the IL10Ra and IL10Rb sdAbs used in their construction are summarized in the following Table 27:

TABLE 27

IL10Ra/IL10Rb Binding Molecules With Varying Linker Length

| Dimer Name | SEQ ID | IL10VHH#1 VHH Name | SEQ ID | IL10VHH#2 VHH Name | SEQ ID | L2 | Fc Monomer |
|---|---|---|---|---|---|---|---|
| DR900 | 499 | DR241 | 170 | DR244 | 174 | AS | SEQ ID NO: 502 |
| DR902 | 500 | DR241 | 170 | DR246 | 187 | AS | SEQ ID NO: 502 |
| DR901 | 501 | DR241 | 170 | DR247 | 197 | AS | SEQ ID NO: 502 |

Data relating to the activity of each of these molecules at varying concentrations in CD4+, CD8+ and monocytes is also provided in FIG. 6. It should be noted that each of these Fc fusions was included relative to the non-Fc fused molecules having the same IL10Ra and IL10Rb sdAbs in the same orientation. Thus the data provided in FIG. 6 also may be used to evaluate the effect on IL10 activity of the IL10R binding molecule by the addition of the Fc domain. From the data provided, the Fc fusion fusion molecule contain the same IL10Ra and Il10Rb sdAbs in the same orientation (forward or reverse) and compared with the molecules having the same linker (4x als referred to as G3S (SEQ ID NO: 484), see Table 16) linker, the Fc fusions demonstrated comparable, in some instances enhanced activity relative to the non-Fc variant. This data demonstrates that the IL10R binding molecules of the present disclosure may be conjugated to an Fc domain to provide extended lifetime in vivo without and providing a level of IL10 activity in various cell types comparable to the non-Fc fused molecule.

Construction of IL10R Binding Molecules for Further Evaluation

Based on the foregoing experiments, a selected subset of IL10R binding molecules variants based on DR521 (SEQ ID NO: 304) were selected for further evaluation. The molecules used in these experiments may be represented by the formula [#1], wherein in each case a=1, L1=G3S (SEQ ID NO: 484) (SEQ ID NOr, b=1 and L2=Ala-Ser; CP=Hisx6 (SEQ ID NO: 532), the IL10 VHH #1 is the IL10Ra VHH DR241 (SEQ ID NO 170) and the IL10 VHH #2 is the IL10Rb VHH DR 246 (SEQ ID NO:187). The polypeptide of SEQ ID NO:170 is also referred to herein as DR241 and the polypeptide of SEQ ID NO:187 is also referred to herein as DR246.

DR521 (DR241-G3S-DR246-ASH6):

In one embodiment, exemplary polypeptide prepared for evaluation is a polypeptide of formula [#1], wherein in each case a=1, L1=G3S (SEQ ID NO: 484)-Ser, b=1 and L2=Ala-Ser; CP=Hisx6 (SEQ ID NO: 532), the IL10 VHH #1 is the IL10Ra VHH DR241 (SEQ ID NO 170) and the IL10 VHH #2 is the IL10Rb VHH DR 246 (SEQ ID NO:187): a=1 and L1 is a G3S linker (SEQ ID NO: 484); b=1 and L2 has the sequence Ala-Ser; and c=1 wherein CP is a histidine polypeptide hexamer (SEQ ID NO: 532), which polypeptide has the amino acid sequence:

(SEQ ID NO: 302)
QVQLQESGGGSVQAGGSLRLSCAASGYSNCSYDMTWYRQAPGKEREFV

SAIHSDGSTRYADSVKGRFFISQDNAKNTVYLQMNSLKPEDTAMYYCK

TDPLHCRAHGGSWYSVRANYWGQGTQVTVSSGGGSQVQLQESGGGSVE

AGGSLRLSCAASGYTHSSYCMGWFRQAPGKEREGVAAIDVDGSTTYAD

SVKGRFTISKDNAKNTLYLQMNSLKPEDTGMYYCAAEFADCSSNYFLP

PGAVRYWGQGTQVTVSSASHHHHHH

The polypeptide of SEQ ID NO:302 is also referred to herein as DR521. DR838 (Q1E N29Q DR521):

A polypeptide variant of DR521 (SEQ ID NO:302) SEQ ID NO:302 which incorporates amino acid substitutions 1QE and N29Q was prepared was has the amino acid sequence:

(SEQ ID NO: 486)
EVQLQESGGGSVQAGGSLRLSCAASGYSQCSYDMTWYRQAPGKEREFVS

AIHSDGSTRYADSVKGRFFISQDNAKNTVYLQMNSLKPEDTAMYYCKTD

PLHCRAHGGSWYSVRANYWGQGTQVTVSGGGSQVQLQESGGGSVEAGGS

LRLSCAASGYTHSSYCMGWFRQAPGKEREGVAAIDVDGSTTYADSVKGR

FTISKDNAKNTLYLQMNSLKPEDTGMYYCAAEFADCSSNYFLPPGAVRY

WGQGTQVTVSSASHHHHHH.

The polypeptide of SEQ ID NO: 486 is also referred to herein as DR838.

As discussed elsewhere, to avoid pyroglutamate formation at the N-terminus which complicates PEGylation by aldehyde chemistry, in the preparation of the DR838 (SEQ ID NO:486) a Q1E amino acid substation was incorporated to facilitate N-terminal PEGylation. Additionally, an examination of the sequence of the CDRs of DR521 (SEQ ID NO:302) indicates the presence of an N-linked glycosylation motif N-X-S in the sequence at Asn29-Cys30-Ser31. To eliminate such N-linked glycosylation motifs by modifying the sequence of the N-linked glycosylation motif to prevent glycosylation. In the preparation of the DR838 (SEQ ID NO:486) derivative of DR521 (SEQ ID NO:302), this N-linked glycosylation motif was eliminated by substituting the asparagine at position 29 of DR521 with a glutamine residue referred to as an N29Q substitution.

DR839 Q1E N29D DR521-Ala-Ser-HIS6

An additional polypeptide variant of SEQ ID NO:302 was prepared having an Q1E and N29D amino acid substitutions and has the amino acid sequence:

(SEQ ID NO: 487)
EVQLQESGGGSVQAGGSLRLSCAASGYSDCSYDMTWYRQAPGKEREFVS

AIHSDGSTRYADSVKGRFFISQDNAKNTVYLQMNSLKPEDTAMYYCKTD

PLHCRAHGGSWYSVRANYWGQGTQVTVSSGGGSQVQLQESGGGSVEAGG

SLRLSCAASGYTHSSYCMGWFRQAPGKEREGVAAIDVDGSTTYADSVKG

RFTISKDNAKNTLYLQMNSLKPEDTGMYYCAAEFADCSSNYFLPPGAVR

YWGQGTQVTVSSASHHHHHH.

The polypeptide of SEQ ID NO: 487 is also referred to herein as DR839.

DR841 (QIE S31A DR521)

An additional polypeptide variant of SEQ ID NO:302 was prepared having an Q1E and S31A amino acid substitution (to eliminate the Asn29-Cys30-Ser31 N-linked glycosylation motif of DR521) and has the amino acid sequence:

(SEQ ID NO: 488)
EVQLQESGGGSVQAGGSLRLSCAASGYSNCAYDMTWYRQAPGKEREFVS

AIHSDGSTRYADSVKGRFFISQDNAKNTVYLQMNSLKPEDTAMYYCKTD

PLHCRAHGGSWYSVRANYWGQGTQVTVSSGGGSQVQLQESGGGSVEAGG

SLRLSCAASGYTHSSYCMGWFRQAPGKEREGVAAIDVDGSTTYADSVKG

RFTISKDNAKNTLYLQMNSLKPEDTGMYYCAAEFADCSSNYFLPPGAVR

YWGQGTQVTVSSASHHHHHH.

The polypeptide of SEQ ID NO: 488 is also referred to herein as DR841.

Humanization of sdAbs

As previously discussed, the IL10Ra and IL10Rb VHH sdAbs which are useful in the preparation of IL10R binding molecules of the present disclosure may be humanized. To demonstrate the utility of humanized versions of the VHH components of the IL10R binding molecules, humanized versions of DR241 and DR246 were prepared and evaluated for binding to the ECDs of IL10Ra and IL10Rb, respectively by surface plasmon resonance spectroscopy (BiacoreR).

When humanizing VHHs with respect to a target, a consideration for the design of the humanized VHH is the distribution of amino acids at each position of the non-human framework which suggest amino acid residues the modification of which may introduce substantial modifications in the secondary and tertiary structure of the protein. The literature suggests that certain framework residues of the canonical llama VHH sequence VH3-66 (INSERT REF/SEQ) include positions V37, G44, L45 and W47 and vernier zone residues R94 and W103 may also be residues which are not readily susceptible to modification. To identify amino acids of the camel VHH framework regions which are highly conserved, approximately 1023 VHH sdAb sequences were obtained and a "R Script" to evaluate distributions of amino acids at each position. An amino acid distribution chart was used to identify rare residues at each position. It was determined that certain residues of the camel VHH framework regions are highly conserved.

Based this information, a best-fit human germline sequence VH3-was identified. A sequence alignment of DR241 suggests a 72% identity to best fit human germline sequence VH3-23. Humanized versions of the IL10Ra VHH DR241 (See Table 19). Humanized DR241 constructs show 88% identity to human. Humanized versions of the IL10Rb VHH DR246 (Table 19) were also prepared. A sequence alignment of DR241 suggests that DR246 possess 73% identity to best fit human germline VH3-23. The humanized DR246 (DR1228) construct shows 89% identity to human.

The following Table 19 provides examples of humanized IL10R binding molecules of the present disclosure

TABLE 19

Humanized IL10Ra/Rb VHH Binding Molecules

| Name | Description | Amino Acid Sequence (CDRs Underlined) | SEQ ID NO |
|---|---|---|---|
| DR1223 | Humanized DR241 IL10Ra | EVQLLESGGGLVQPGGSLRLSCAASGYTQCSYDMTWVRQAPGKGLEWVSAIHSDGSTRYADSVKGRFTISRDNSKNTLYLQMNSLRAEDTAVYYCKTDPLHCRAHGGSWYSVRANYWGQGTLVTVSS | 503 |
| DR1224 | Humanized DR241 IL10Ra | EVQLLESGGGLVQPGGSLRLSCAASGYTQCSYDMTWVRQAPGKGLEFVSAIHSDGSTRYADSVKGRFTISRDNSKNTLYLQMNSLRAEDTAVYYCKTDPLHCRAHGGSWYSVRANYWGQGTLVTVSS | 504 |
| DR1225 | Humanized DR241 IL10Ra | EVQLVESGGGLVQPGGSLRLSCAASGYTQCSYDMTWVRQAPGKGLEWVSAIHSDGSTRYADSVKGRFFISRDNSKNTLYLQMNSLRAEDTAVYYCKTDPLHCRAHGGSWYSVRANYWGQGTLVTVSS | 505 |
| DR1226 | Humanized DR241 IL10Ra | EVQLVESGGGLVQPGGSLRLSCAASGYTQCSYDMTWVRQAPGKGLEFVSAIHSDGSTRYADSVKGRFFISRDNSKNTLYLQMNSLRAEDTAVYYCKTDPLHCRAHGGSWYSVRANYWGQGTLVTVSS | 506 |
| DR1227 | Humanized DR246 IL10Rb | EVQLLESGGGLVQPGGSLRLSCAASGYTHSSYCMGWVRQAPGKGLEWVSAIDVDGSTTYADSVKGRFTISRDNSKNTLYLQMNSLRAEDTAVYYCAAEFADCSSNYFLPPGAVRYWGQGTLVTVSS | 507 |
| DR1228 | Humanized DR246 IL10Rb | EVQLLESGGGLVQPGGSLRLSCAASGYTHSSYCMGWVRQAPGKGLEGVSAIDVDGSTTYADSVKGRFTISRDNSKNTLYLQMNSLRAEDTAVYYCAAEFADCSSNYFLPPGAVRYWGQGTLVTVSS | 508 |
| DR1229 | Humanized DR246 IL10Rb | EVQLVESGGGLVQPGGSLRLSCAASGYTHSSYCMGWVRQAPGKGLEWVSAIDVDGSTTYADSVKGRFTISRDNSKNTLYLQMNSLRAEDTAVYYCAAEFADCSSNYFLPPGAVRYWGQGTLVTVSS | 509 |
| DR1230 | Humanized DR246 IL10Rb | EVQLVESGGGLVQPGGSLRLSCAASGYTHSSYCMGWVRQAPGKGLEGVSAIDVDGSTTYADSVKGRFTISRDNSKNTLYLQMNSLRAEDTAVYYCAAEFADCSSNYFLPPGAVRYWGQGTLVTVSS | 510 |
| DR1308 | Humanized DR241 IL10Ra | EVQLVESGGGLVQPGGSLRLSCAASGYTQCSYDMTWVRQAPGKGREFVSAIHSDGSTRYADSVKGRFFISRDNSKNTLYLQMNSLRAEDTAVYYCKTDPLHCRAHGGSWYSVRANYWGQGTLVTVSS | 511 |
| DR1309 | Humanized DR241 IL10Ra | EVQLQESGGGSVQAGGSLRLSCAASGYSQCSYDMTWYRQAPGKEREFVSAIHSDGSTRYADSVKGRFFISQDNAKNTVYLQMNSLKPEDTAMYYCKTDPLHCRAHGGSWYSVRANYWGQGTQVTVSS | 512 |

Nucleic acid sequences encoding the foregoing humanized sdAb are provided in Table 30.

In some embodiments, the present invention provides sdAbs having at least 90% (e.g., 91%, 92%, 93%, 94%, 95%, 96%, 97%, 98%, 99%, or 100%) sequence identity to the sequence of any one of the IL10Ra and IL10Rb sdAbs of Table 19. In some embodiments, the present invention provides sdAbs having substantially identical of any one of the sdAbs Table 19. In some embodiments, the present invention provides sdAbs having identical of any one of the sdAbs Table 19.

In the following series of experiments, the above referenced polypeptides were expressed recombinantly by transfection of a host cell with a vector comprising a synthetic nucleic acid sequences encoding DR521 and DR838, the synthetic nucleic acid sequence incorporating a 5' nucleic acid sequence encoding IgH signal peptide of the amino acid sequence.

Synthetic nucleic acid sequences encoding the DR1223, DR1224; DR1225, DR1226; DR1227; DR1228; DR1229 and DR1230 are provided in Table 31 urther comprising N-terminal signal peptide and carboxy terminal IgG4 hinge (SEQ ID NO: 485) and monomeric Fc domain (SEQ ID NO: 504) were prepared and cloned in pExSyn and transfected into expi293 cells. As provided in more detail in the Examples, the molecules were evaluated for binding to their respective targets (IL10Ra or IL10Rb) by SPR (Biacore). The supernatants from the cell culture were evaluated for binding to the ECDs of IL10Ra and IL10Rb respectively. In short, the Fc conjugated humanized VHHs were immobilized on a Protein A chip and the ECDs of the respective IL10 receptor subunits flowed in the mobile phase. The results of this study indicated that the humanized VHH sequences effectively retained binding to their respective targets. The foregoing humanized IL10Ra and IL10Rb VHHs may be used in the construction of humanized dimeric IL10R binding molecules of the present disclosure.

TABLE 28

Humanized versions of DR246 binding to IL10Rb-his (Sino Biological, Catalog#10945)

| Analyte | $k_{ON}$ (1/Ms) | $k_{OFF}$ (1/s) | Affinity (nM) | Rmax (RU) | Load (RU) | Calc. Rmax (RU) | Surface Activity |
|---|---|---|---|---|---|---|---|
| DR1227 | 4.6E+05 | 5.6E−03 | 12.3 | 68.3 | 327 | 497 | 14% |
| DR1228 | 1.3E+05 | 9.2E−04 | 7.0 | 112.4 | 328 | 499 | 23% |
| DR1229 | 7.0E+05 | 9.6E−03 | 13.8 | 68.6 | 330 | 502 | 14% |
| DR1230 | 1.4E+05 | 9.8E−04 | 7.1 | 121.8 | 331 | 504 | 24% |

Humanized IL10R Binding Molecules:

The present disclosure further provides IL10R binding molecules comprising humanized IL10Ra and/or IL10Rb sdAbs. The term "humanized IL10R binding molecule" refers to an IL10R binding molecule comprising a humanized IL10Ra and/or IL10Rb sdAbs.

The following Table 29 provides amino acid sequences of humanized IL10R binding molecules comprising IL10Ra and IL10Rb sdAbs and indicating the CDRs as underlined.

TABLE 29

Humanized IL10R Binding Molecules

| Name | Amino Acid Sequence | SEQ ID NO |
|---|---|---|
| DR1511 | EVQLVESGGGLVKPGGSLRLSCAASGYSNCAYDMTW YRQAPGKGLEWVSAIHSDGSTRYADSVKGRFFISRDN AKNSLYLQMNSLRAEDTAVYYCKTDPLHCRAHGGS WYSVRANYWGQGTLVTVSSGGGSEVQLVESGGGLV QPGGSLRLSCAASGYTHSSYCMGWVRQAPGKGLEGV SAIDVDGSTTYADSVKGRFTISRDNSKNTLYLQMNSL RAEDTAVYYCAAEFADCSSNYFLPPGAVRYWGQGTL VTVSSASHHHHHH | 513 |
| DR1512 | EVQLVESGGGLVQPGGSLRLSCAASGYSNCAYDMTW YRQAPGKGLEWVSAIHSDGSTRYADSVKGRFFISRDN SKNTLYLQMNSLRAEDTAVYYCKTDPLHCRAHGGS WYSVRANYWGQGTLVTVSSGGGSEVQLVESGGGLV QPGGSLRLSCAASGYTHSSYCMGWVRQAPGKGLEGV SAIDVDGSTTYADSVKGRFTISRDNSKNTLYLQMNSL RAEDTAVYYCAAEFADCSSNYFLPPGAVRYWGQGTL VTVSSASHHHHHH | 514 |
| DR1513 | EVQLLESGGGLVQPGGSLRLSCAASGYSNCAYDMTW YRQAPGKGLEWVSAIHSDGSTRYADSVKGRFFISRDN SKNTLYLQMNSLRAEDTAVYYCKTDPLHCRAHGGS WYSVRANYWGQGTLVTVSSGGGSEVQLVESGGGLV QPGGSLRLSCAASGYTHSSYCMGWVRQAPGKGLEGV SAIDVDGSTTYADSVKGRFTISRDNSKNTLYLQMNSL RAEDTAVYYCAAEFADCSSNYFLPPGAVRYWGQGTL VTVSSASHHHHHH | 515 |
| DR1514 | EVQLVESGGGLVKPGGSLRLSCAASGYSNCAYDMTW YRQAPGKGLEFVSAIHSDGSTRYADSVKGRFFISRDN AKNSLYLQMNSLRAEDTAVYYCKTDPLHCRAHGGS WYSVRANYWGQGTLVTVSSGGGSEVQLVESGGGLV QPGGSLRLSCAASGYTHSSYCMGWVRQAPGKGLEGV SAIDVDGSTTYADSVKGRFTISRDNSKNTLYLQMNSL RAEDTAVYYCAAEFADCSSNYFLPPGAVRYWGQGTL VTVSSASHHHHHH | 516 |
| DR1515 | EVQLVESGGGLVQPGGSLRLSCAASGYSNCAYDMTW YRQAPGKGLEFVSAIHSDGSTRYADSVKGRFFISRDNS KNTLYLQMNSLRAEDTAVYYCKTDPLHCRAHGGSW YSVRANYWGQGTLVTVSSGGGSEVQLVESGGGLVQP GGSLRLSCAASGYTHSSYCMGWVRQAPGKGLEGVSA IDVDGSTTYADSVKGRFTISRDNSKNTLYLQMNSLRA EDTAVYYCAAEFADCSSNYFLPPGAVRYWGQGTLVT VSSASHHHHHH | 517 |
| DR1516 | EVQLLESGGGLVQPGGSLRLSCAASGYSNCAYDMTW YRQAPGKGLEFVSAIHSDGSTRYADSVKGRFFISRDNS KNTLYLQMNSLRAEDTAVYYCKTDPLHCRAHGGSW YSVRANYWGQGTLVTVSSGGGSEVQLVESGGGLVQP GGSLRLSCAASGYTHSSYCMGWVRQAPGKGLEGVSA IDVDGSTTYADSVKGRFTISRDNSKNTLYLQMNSLRA EDTAVYYCAAEFADCSSNYFLPPGAVRYWGQGTLVT VSSASHHHHHH | 518 |
| DR1517 | EVQLVESGGGLVKPGGSLRLSCAASGYSNCAYDMTW YRQAPGKGREWVSAIHSDGSTRYADSVKGRFFISRDN AKNSLYLQMNSLRAEDTAVYYCKTDPLHCRAHGGS WYSVRANYWGQGTLVTVSSGGGSEVQLVESGGGLV QPGGSLRLSCAASGYTHSSYCMGWVRQAPGKGLEGV SAIDVDGSTTYADSVKGRFTISRDNSKNTLYLQMNSL RAEDTAVYYCAAEFADCSSNYFLPPGAVRYWGQGTL VTVSSASHHHHHH | 519 |
| DR1518 | EVQLVESGGGLVQPGGSLRLSCAASGYSNCAYDMTW YRQAPGKGREWVSAIHSDGSTRYADSVKGRFFISRDN SKNTLYLQMNSLRAEDTAVYYCKTDPLHCRAHGGS WYSVRANYWGQGTLVTVSSGGGSEVQLVESGGGLV QPGGSLRLSCAASGYTHSSYCMGWVRQAPGKGLEGV SAIDVDGSTTYADSVKGRFTISRDNSKNTLYLQMNSL RAEDTAVYYCAAEFADCSSNYFLPPGAVRYWGQGTL VTVSSASHHHHHH | 520 |
| DR1519 | EVQLLESGGGLVQPGGSLRLSCAASGYSNCAYDMTW YRQAPGKGREWVSAIHSDGSTRYADSVKGRFFISRDN SKNTLYLQMNSLRAEDTAVYYCKTDPLHCRAHGGS WYSVRANYWGQGTLVTVSSGGGSEVQLVESGGGLV QPGGSLRLSCAASGYTHSSYCMGWVRQAPGKGLEGV SAIDVDGSTTYADSVKGRFTISRDNSKNTLYLQMNSL RAEDTAVYYCAAEFADCSSNYFLPPGAVRYWGQGTL VTVSSASHHHHHH | 521 |
| DR1520 | EVQLVESGGGLVKPGGSLRLSCAASGYSNCAYDMTW YRQAPGKELEWVSAIHSDGSTRYADSVKGRFFISRDN AKNSLYLQMNSLRAEDTAVYYCKTDPLHCRAHGGS WYSVRANYWGQGTLVTVSSGGGSEVQLVESGGGLV QPGGSLRLSCAASGYTHSSYCMGWVRQAPGKGLEGV SAIDVDGSTTYADSVKGRFTISRDNSKNTLYLQMNSL RAEDTAVYYCAAEFADCSSNYFLPPGAVRYWGQGTL VTVSSASHHHHHH | 522 |
| DR1521 | EVQLVESGGGLVQPGGSLRLSCAASGYSNCAYDMTW YRQAPGKELEWVSAIHSDGSTRYADSVKGRFFISRDN SKNTLYLQMNSLRAEDTAVYYCKTDPLHCRAHGGS WYSVRANYWGQGTLVTVSSGGGSEVQLVESGGGLV QPGGSLRLSCAASGYTHSSYCMGWVRQAPGKGLEGV SAIDVDGSTTYADSVKGRFTISRDNSKNTLYLQMNSL RAEDTAVYYCAAEFADCSSNYFLPPGAVRYWGQGTL VTVSSASHHHHHH | 523 |
| DR1522 | EVQLLESGGGLVQPGGSLRLSCAASGYSNCAYDMTW YRQAPGKELEWVSAIHSDGSTRYADSVKGRFFISRDN SKNTLYLQMNSLRAEDTAVYYCKTDPLHCRAHGGS WYSVRANYWGQGTLVTVSSGGGSEVQLVESGGGLV QPGGSLRLSCAASGYTHSSYCMGWVRQAPGKGLEGV SAIDVDGSTTYADSVKGRFTISRDNSKNTLYLQMNSL RAEDTAVYYCAAEFADCSSNYFLPPGAVRYWGQGTL VTVSSASHHHHHH | 561 |
| DR1523 | EVQLVESGGGLVKPGGSLRLSCAASGYSNCAYDMTW YRQAPGKEREFVSAIHSDGSTRYADSVKGRFFISRDNA KNSLYLQMNSLRAEDTAVYYCKTDPLHCRAHGGSW YSVRANYWGQGTLVTVSSGGGSEVQLVESGGGLVQP GGSLRLSCAASGYTHSSYCMGWVRQAPGKGLEGVSA IDVDGSTTYADSVKGRFTISRDNSKNTLYLQMNSLRA EDTAVYYCAAEFADCSSNYFLPPGAVRYWGQGTLVT VSSASHHHHHH | 524 |
| DR1524 | EVQLVESGGGLVQPGGSLRLSCAASGYSNCAYDMTW YRQAPGKEREFVSAIHSDGSTRYADSVKGRFFISRDNS KNTLYLQMNSLRAEDTAVYYCKTDPLHCRAHGGSW YSVRANYWGQGTLVTVSSGGGSEVQLVESGGGLVQP GGSLRLSCAASGYTHSSYCMGWVRQAPGKGLEGVSA IDVDGSTTYADSVKGRFTISRDNSKNTLYLQMNSLRA | 525 |

TABLE 29-continued

Humanized IL10R Binding Molecules

| Name | Amino Acid Sequence | SEQ ID NO |
|---|---|---|
|  | EDTAVYYCAAEFADCSSNYFLPPGAVRYWGQGTLVT VSSASHHHHHH |  |
| DR1525 | EVQLLESGGGLVQPGGSLRLSCAASGYSNCAYDMTW YRQAPGKEREFVSAIHSDGSTRYADSVKGRFFISRDNS KNTLYLQMNSLRAEDTAVYYCKTDPLHCRAHGGSW YSVRANYWGQGTLVTVSSGGGSEVQLVESGGGLVQP GGSLRLSCAASGYTHSSYCMGWVRQAPGKGLEGVSA IDVDGSTTYADSVKGRFTISRDNSKNTLYLQMNSLRA EDTAVYYCAAEFADCSSNYFLPPGAVRYWGQGTLVT VSSASHHHHHH | 526 |
| DR1328 | EVQLVESGGGLVQPGGSLRLSCAASGYTQCSYDMTW VRQAPGKGLEFVSAIHSDGSTRYADSVKGRFFISRDNS KNTLYLQMNSLRAEDTAVYYCKTDPLHCRAHGGSW YSVRANYWGQGTLVTVSSGGGSEVQLVESGGGLVQP GGSLRLSCAASGYTHSSYCMGWVRQAPGKGLEWVS AIDVDGSTTYADSVKGRFTISRDNSKNTLYLQMNSLR AEDTAVYYCAAEFADCSSNYFLPPGAVRYWGQGTLV TVSSASHHHHHH | 527 |
| DR1329 | EVQLVESGGGLVQPGGSLRLSCAASGYTQCSYDMTW VRQAPGKGLEFVSAIHSDGSTRYADSVKGRFFISRDNS KNTLYLQMNSLRAEDTAVYYCKTDPLHCRAHGGSW YSVRANYWGQGTLVTVSSGGGSEVQLVESGGGLVQP GGSLRLSCAASGYTHSSYCMGWVRQAPGKGLEGVSA IDVDGSTTYADSVKGRFTISRDNSKNTLYLQMNSLRA EDTAVYYCAAEFADCSSNYFLPPGAVRYWGQGTLVT VSSASHHHHHH | 528 |
| DR1330 | EVQLVESGGGLVQPGGSLRLSCAASGYTQCSYDMTW YRQAPGKGLEFVSAIHSDGSTRYADSVKGRFFISRDNS KNTLYLQMNSLRAEDTAVYYCKTDPLHCRAHGGSW YSVRANYWGQGTLVTVSSGGGSEVQLVESGGGLVQP GGSLRLSCAASGYTHSSYCMGWVRQAPGKGLEWVS AIDVDGSTTYADSVKGRFTISRDNSKNTLYLQMNSLR AEDTAVYYCAAEFADCSSNYFLPPGAVRYWGQGTLV TVSSASHHHHHH | 529 |
| DR1331 | EVQLVESGGGLVQPGGSLRLSCAASGYTQCSYDMTW YRQAPGKGLEFVSAIHSDGSTRYADSVKGRFFISRDNS KNTLYLQMNSLRAEDTAVYYCKTDPLHCRAHGGSW YSVRANYWGQGTLVTVSSGGGSEVQLVESGGGLVQP GGSLRLSCAASGYTHSSYCMGWVRQAPGKGLEGVSA IDVDGSTTYADSVKGRFTISRDNSKNTLYLQMNSLRA EDTAVYYCAAEFADCSSNYFLPPGAVRYWGQGTLVT VSSASHHHHHH | 530 |

In some embodiments, the present invention provides IL10R binding molecules having at least 90% (e.g., 91%, 92%, 93%, 94%, 95%, 96%, 97%, 98%, 99%, or 100%) sequence identity to the sequence of any one of the IL10R binding molecules of Table 29. In some embodiments, the present invention provides IL10R binding molecules substantially identical of any one of the IL10R binding molecules of Table 29. In some embodiments, the present invention provides IL10R binding molecules identical to a sequence of any one of the IL10R binding molecules of Table 29.

Modifications to the Binding Molecule and sdAb Components

Chelating Peptides

In one embodiment, the present disclosure provides a IL10Rb1 binding molecule comprising one or more transition metal chelating polypeptide sequences known as chelating peptides. A chelating peptide is a polypeptide of the formula:

$(His)_a\text{-}(AA)_b\text{-}(His)_c$ wherein "His" is the amino acid histidine; "AA" is an amino acid other than proline; is a histidine residue a=an integer from 0 to 10; b=an integer from 0 to 4; c=an integer from 0-10; and random, block and alternating copolymers thereof. In some embodiments, the chelating peptide has and amino acid sequence selected from the group consisting of: SEQ ID NOS: 507-521. The incorporation of such a transition metal chelating domain facilitates purification immobilized metal affinity chromatography (IMAC) as described in Smith, et al. U.S. Pat. No. 4,569,794 issued Feb. 11, 1986. Examples of transition metal chelating polypeptides useful in the practice of the present IL12RB1 binding molecule are described in Smith, et al. supra and Dobeli, et al. U.S. Pat. No. 5,320,663 issued May 10, 1995, the entire teachings of which are hereby incorporated by reference. Particular transition metal chelating polypeptides useful in the practice of the present IL12RB1 binding molecule are polypeptides comprising 3-6 contiguous histidine residues (SEQ ID NO: 569) such as a six-histidine $(His)_6$ peptide (SEQ ID NO: 532) and are frequently referred to in the art as "His-tags." In addition to providing a purification "handle" for the recombinant proteins or to facilitate immobilization on SPR sensor chips, such the conjugation of the hIL12RB1 binding molecule to a chelating peptide facilitates the targeted delivery to IL12RB1 expressing cells of transition metal ions as kinetically inert or kinetically labile complexes in substantial accordance with the teaching of Anderson, et al., (U.S. Pat. No. 5,439,829 issued Aug. 8, 1995 and Hale, J. E (1996) Analytical Biochemistry 231(1):46-49. Regarding the "kinetically inert complex", the term "inert" refers to the degree of lability which to the ability of a particular complexed ion to engage in reactions that result in replacing one or more ligands in its coordination sphere by others. In an aqueous environment, the unoccupied coordination positions of the transition metal are occupied by water molecules. These water molecules must be displaced by the chelating peptide or organic chelating agent in order to form [transition metal:chelating peptide] complex. When such reactions occur rapidly, the reaction is termed "labile". However, where such reactions occur very slowly, the complex is said to be kinetically "inert". Kinetic lability or inertness is related to the reaction rate and are not to be confused with thermodynamic stability or instability. Cotton and Wilkinson illustrate this distinction:

A simple example of this [labile vs. stable] distinction is provided by the [Co(NH3)6]3+ ion which will persist for days in an acid medium because of its kinetic inertness or lack of lability despite the fact that it is thermodynamically unstable, as the following equilibrium constant shows:

$$[Co(NH_3)_6]^{3+} + 6H_3O^+ = [Co(H_2O)_6]^{3+} + 6NH_4 \quad K=10^{25}$$

In contrast, the stability of $[Ni(CN)4]^2$ is extremely high:

$$[Ni(CN)_4]^{2-} = Ni^{2+} + 4CN^- \quad K=10^{-22}$$

but the rate of exchange of $CN^-$ ions with isotopically labelled cyanide ion added to the solution is immeasurably fast by ordinary techniques.

Advanced Inorganic Chemistry. Cotton, FA and Wilkinson., G (1972) 3rd ed. Interscience Publishers, p. 652. In some embodiments, the transition metal ion is a reporter molecule such as a fluorescent compound or radioactive agent, including as radiological imaging or therapeutic agents.

In some embodiments, the chelating peptide is a chelating peptide provided in Table 21

TABLE 21

Chelating Peptides

| Abbreviation (if applicable | Amino Acid Sequence | SEQ ID NO |
|---|---|---|
| HIS5 | His-His-His-His-His | 531. |
| HIS6 | His-His-His-His-His-His | 532. |
| HIS7 | His-His-His-His-His-His-His | 533. |
| HIS8 | His-His-His-His-His-His-His-His | 534. |
| HIS9 | His-His-His-His-His-His-His-His-His | 535. |
| n/a | His-Trp-His-Met-Tyr | 536. |
| n/a | His-His-His-Met-Tyr | 537. |
| n/a | His-His-His-His-Tyr | 538. |
| n/a | His-Trp-His-Trp-His | 539. |
| n/a | His-Trp-His-His-His | 540. |
| n/a | His-His-His-His-Tyr-Met-His-His-His- | 541. |
| n/a | His-His-His-His-His | 542. |
| n/a | His-Trp-His-His-His- | 543. |
| n/a | His-Gly-His-Gly-Gly-Gly-His-Gly-His | 544. |
| n/a | His-Gly-His-Gly-Gly-Gly-Gly-Gly-Gly-His-Gly-His | 545. |

Elimination of N-Linked Glycosylation Sites

In some embodiments, it is possible that an amino acid sequence (particularly a CDR sequence) of the IL10Ra or IL10Rb sdAb may contain a glycosylation motif, particularly an N-linked glycosylation motif of the sequence Asn-X-Ser (N-X-S) or Asn-X-Thr (N-X-T), wherein X is any amino acid except for proline. In such instances, it is desirable to eliminate such N-linked glycosylation motifs by modifying the sequence of the N-linked glycosylation motif to prevent glycosylation. In some embodiments, the elimination of the Asn-X-Ser (N-X-S)N-linked glycosylation motif may be achieved by the incorporation of conservative amino acid substitution of the Asn (N) residue and/or Ser (S) residue of the Asn-X-Ser (N-X-S)N-linked glycosylation motif. In some embodiments, the elimination of the Asn-X-Thr (N-X-T) N-linked glycosylation motif may be achieved by the incorporation of conservative amino acid substitution of the Asn (N) residue and/or Thr (T) residue of the Asn-X-Thr (N-X-T)N-linked glycosylation motif. In some embodiments, elimination of the glycosylation site is not required when the IL10R binding molecule comprising the IL10Ra or IL10Rb sdAb is expressed in procaryotic host cells. Since procaryotic cells do not provide a mechanism for glycosylation of recombinant proteins, when employing a procaryotic expression system to produce a recombinant IL10R binding molecule comprising the IL10Ra or IL10Rb sdAb the modification of the sequence to eliminate the N-linked glycosylation sites may be obviated.

Association with Carrier Molecules to Increase Duration of Action

The IL10R binding molecule described herein can be modified to provide for an extended lifetime in vivo and/or extended duration of action in a subject. In some embodiments, the binding molecule can be conjugated to carrier molecules to provide desired pharmacological properties such as an extended half-life. In some embodiments, the binding molecule can be covalently linked to the Fc domain of IgG, albumin, or other molecules to extend its half-life, e.g., by pegylation, glycosylation, and the like as known in the art. In some embodiments, the IL10R binding molecule modified to provide an extended duration of action in a mammalian subject has a half-life in a mammalian of greater than 4 hours, alternatively greater than 5 hours, alternatively greater than 6 hours, alternatively greater than 7 hours, alternatively greater than 8 hours, alternatively greater than 9 hours, alternatively greater than 10 hours, alternatively greater than 12 hours, alternatively greater than 18 hours, alternatively greater than 24 hours, alternatively greater than 2 days, alternatively greater than 3 days, alternatively greater than 4 days, alternatively greater than 5 days, alternatively greater than 6 days, alternatively greater than 7 days, alternatively greater than 10 days, alternatively greater than 14 days, alternatively greater than 21 days, or alternatively greater than 30 days.

Modifications of the IL10R binding molecule to provide an extended duration of action in a mammalian subject include (but are not limited to);

- conjugation of the IL10R binding molecule to one or more carrier molecules,
- conjugation IL10R binding molecule to protein carriers molecules, optionally in the form of a fusion protein with additional polypeptide sequences (e.g, IL10R binding molecule -Fc fusions) and
- conjugation to polymers, (e.g. water soluble polymers to provide a PEGylated IL10R binding molecule).

It should be noted that the more than one type of modification that provides for an extended duration of action in a mammalian subject may be employed with respect to a given IL10R binding molecule. For example, IL10R binding molecule of the present disclosure may comprise both amino acid substitutions that provide for an extended duration of action as well as conjugation to a carrier molecule such as a polyethylene glycol (PEG) molecule.

Protein Carrier Molecules.

Examples of protein carrier molecules which may be covalently attached to the IL10R binding molecule to provide an extended duration of action in vivo include, but are not limited to albumins, antibodies and antibody fragments such and Fc domains of IgG molecules Fc Fusions:

In some embodiments, the IL10R binding molecule is conjugated to a functional domain of an Fc-fusion chimeric polypeptide molecule. Fc fusion conjugates have been shown to increase the systemic half-life of biopharmaceuticals, and thus the biopharmaceutical product can require less frequent administration. Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates. The "Fc region" useful in the preparation of Fc fusions can be a naturally occurring or synthetic polypeptide that is homologous to an IgG C-terminal domain produced by digestion of IgG with papain. IgG Fc has a molecular weight of approximately 50 kDa. The binding molecule described herein can be conjugated to the entire Fc region, or a smaller portion that retains the ability to extend the circulating half-life of a chimeric polypeptide of which it is a part. In addition, full-length or fragmented Fc regions can be variants of the wild-type molecule. In a typical presentation, each monomer of the dimeric Fc can carry a heterologous polypeptide, the heterologous polypeptides being the same or different.

Illustrative examples of Fc formats useful for IL10R binding molecules of the present disclosure are provided schematically in FIGS. 1-4 of the attached drawings.

Linkage of Binding Molecule to Fc Monomer

As indicated, the linkage of the IL10R binding molecule to the Fc subunit may incorporate a linker molecule as described below between the IL10R binding molecule and Fc subunit. In some embodiments, the IL10R binding molecule is expressed as a fusion protein with the Fc domain incorporating an amino acid sequence of a hinge region of an IgG antibody. The Fc domains engineered in accordance with the foregoing may be derived from IgG1, IgG2, IgG3 and IgG4 mammalian IgG species. In some embodiments, the Fc domains may be derived from human IgG1, IgG2, IgG3 and IgG4 IgG species. In some embodiments, the hinge region is the hinge region of an IgG1. In one particular embodiment, the IL10R binding molecule is linked to an Fc domain using an human IgG1 hinge domain.

Knob-Into-Hole Fc Format

In some embodiments, the dimeric Fc molecule may be engineered to possess a "knob-into-hole modification."

Albumin Carrier Molecules

In some embodiments, the IL10R binding molecule conjugated to an is albumin molecule (e.g., human serum albumin) which is known in the art to facilitate extended exposure in vivo. In one embodiment of the invention, the IL10R binding molecule is conjugated to albumin via chemical linkage or expressed as a fusion protein with an albumin molecule referred to herein as an IL10R binding molecule albumin fusion." The term "albumin" as used in the context αβhIL2 mutein albumin fusions include albumins such as human serum albumin (HSA), cyno serum albumin, and bovine serum albumin (BSA). In some embodiments, the HSA the HSA comprises a C34S or K573P amino acid substitution relative to the wild-type HSA sequence According to the present disclosure, albumin can be conjugated to a IL10R binding molecule at the carboxyl terminus, the amino terminus, both the carboxyl and amino termini, and internally (see, e.g., U.S. Pat. Nos. 5,876,969 and 7,056,701). In the HAS IL10R binding molecule contemplated by the present disclosure, various forms of albumin can be used, such as albumin secretion pre-sequences and variants thereof, fragments and variants thereof, and HSA variants. Such forms generally possess one or more desired albumin activities. In additional embodiments, the present disclosure involves fusion proteins comprising a IL10R binding molecule fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. As an alternative to chemical linkage between the IL10R binding molecule and the albumin molecule the IL10R binding molecule—albumin complex may be provided as a fusion protein comprising an albumin polypeptide sequence and an IL10R binding molecule recombinantly expressed in a host cell as a single polypeptide chain, optionally comprising a linker molecule between the albumin and IL10R binding molecules. Such fusion proteins may be readily prepared through recombinant technology to those of ordinary skill in the art. Nucleic acid sequences encoding such fusion proteins may be ordered from any of a variety of commercial sources. The nucleic acid sequence encoding the fusion protein is incorporated into an expression vector operably linked to one or more expression control elements, the vector introduced into a suitable host cell and the fusion protein solated from the host cell culture by techniques well known in the art.

Polymeric Carriers

In some embodiments, extended in vivo duration of action of the IL10R binding molecule may be achieved by conjugation to one or more polymeric carrier molecules such as XTEN polymers or water soluble polymers.

XTEN Conjugates

The IL10R binding molecule may further comprise an XTEN polymer. The XTEN polymer may be is conjugated (either chemically or as a fusion protein) the αβhIL2 mutein provides extended duration of akin to PEGylation and may be produced as a recombinant fusion protein in *E. coli*. XTEN polymers suitable for use in conjunction with the IL10R binding molecule of the present disclosure are provided in Podust, et al. (2016) "Extension of in vivo half-life of biologically active molecules by XTEN protein polymers", J Controlled Release 240:52-66 and Haeckel et al. (2016) "XTEN as Biological Alternative to PEGylation Allows Complete Expression of a Protease-Activatable Killin-Based Cytostatic" PLOS ONE DOI:10.1371/journal.pone.0157193 Jun. 13, 2016. The XTEN polymer may fusion protein may incorporate a protease sensitive cleavage site between the XTEN polypeptide and the hIL2 mutein such as an MMP-2 cleavage site.

Water Soluble Polymers

In some embodiments, the IL10R binding molecule can be conjugated to one or more water-soluble polymers. Examples of water soluble polymers useful in the practice of the present disclosure include polyethylene glycol (PEG), poly-propylene glycol (PPG), polysaccharides (polyvinylpyrrolidone, copolymers of ethylene glycol and propylene glycol, poly(oxyethylated polyol), polyolefinic alcohol,), polysaccharides), poly-alpha-hydroxy acid), polyvinyl alcohol (PVA), polyphosphazene, polyoxazolines (POZ), poly(N-acryloylmorpholine), or a combination thereof.

In some embodiments, IL10R binding molecule can be conjugated to one or more polyethylene glycol molecules or "PEGylated." Although the method or site of PEG attachment to the binding molecule may vary, in certain embodiments the PEGylation does not alter, or only minimally alters, the activity of the binding molecule.

PEGs suitable for conjugation to a polypeptide sequence are generally soluble in water at room temperature, and have the general formula $$R(O—CH_2—CH_2)_nO—R,$$

where R is hydrogen or a protective group such as an alkyl or an alkanol group, and where n is an integer from 1 to 1000. When R is a protective group, it generally has from 1 to 8 carbons. The PEG can be linear or branched. Branched PEG derivatives, "star-PEGs" and multi-armed PEGs are contemplated by the present disclosure.

In some instances, the sequences of IL10R binding molecules of the present disclosure provided in Tables 9 and 10 possess an N-terminal glutamine ("1Q") residue. N-terminal glutamine residues have been observed to spontaneously cyclyize to form pyroglutamate (pE) at or near physiological conditions. (See e.g., Liu, et al (2011) J. Biol. Chem.

286(13): 11211-11217). In some embodiments, the formation of pyroglutamate complicates N-terminal PEG conjugation particularly when aldehyde chemistry is used for N-terminal PEGylation. Consequently, when PEGylating the IL10R binding molecules of the present disclosure, particularly when aldehyde chemistry is to be employed, the IL10R binding molecules possessing an amino acid at position 1 (e.g., 1Q) are substituted at position 1 with an alternative amino acid or are deleted at position 1 (e.g., des-1Q). In some embodiments, the IL10R binding molecules of the present disclosure comprise an amino acid substitution selected from the group Q1E and Q1D.

In some embodiments, selective PEGylation of the IL10R binding molecules, for example, by the incorporation of non-natural amino acids having side chains to facilitate selective PEG conjugation, may be employed. Specific PEGylation sites can be chosen such that PEGylation of the binding molecule does not affect its binding to the target receptors.

In certain embodiments, the increase in half-life is greater than any decrease in biological activity. PEGs suitable for conjugation to a polypeptide sequence are generally soluble in water at room temperature, and have the general formula R(O-CH2-CH2)nO-R, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure.

A molecular weight of the PEG used in the present disclosure is not restricted to any particular range. The PEG component of the binding molecule can have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa, or from about 10 kDa to about 30 kDa. Linear or branched PEG molecules having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, or alternatively about 30,000 to about 40,000 daltons. In one embodiment of the disclosure, the PEG is a 40 kD branched PEG comprising two 20 kD arms.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods known in the art. Chromatography may be used to resolve conjugate fractions, and a fraction is then identified which contains the conjugate having, for example, the desired number of PEGs attached, purified free from unmodified protein sequences and from conjugates having other numbers of PEGs attached.

PEGs suitable for conjugation to a polypeptide sequence are generally soluble in water at room temperature, and have the general formula $R(O—CH_2—CH_2)_nO—R$, where R is hydrogen or a protective group such as an alkyl or an alkanol group, and where n is an integer from 1 to 1000. When R is a protective group, it generally has from 1 to 8 carbons.

Two widely used first generation activated monomethoxy PEGs (mPEGs) are succinimdyl carbonate PEG (SC-PEG; see, e.g., Zalipsky, et al. (1992) *Biotehnol. Appl. Biochem* 15:100-114) and benzotriazole carbonate PEG (BTC-PEG; see, e.g., Dolence, et al. U.S. Pat. No. 5,650,234), which react preferentially with lysine residues to form a carbamate linkage but are also known to react with histidine and tyrosine residues. Use of a PEG-aldehyde linker targets a single site on the N-terminus of a polypeptide through reductive amination.

Pegylation most frequently occurs at the α-amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General PEGylation strategies known in the art can be applied herein.

The PEG can be bound to a binding molecule of the present disclosure via a terminal reactive group (a "spacer") which mediates a bond between the free amino or carboxyl groups of one or more of the polypeptide sequences and polyethylene glycol. The PEG having the spacer which can be bound to the free amino group includes N-hydroxysuccinylimide polyethylene glycol, which can be prepared by activating succinic acid ester of polyethylene glycol with N-hydroxysuccinylimide.

In some embodiments, the PEGylation of the binding molecules is facilitated by the incorporation of non-natural amino acids bearing unique side chains to facilitate site specific PEGylation. The incorporation of non-natural amino acids into polypeptides to provide functional moieties to achieve site specific PEGylation of such polypeptides is known in the art. See e.g., Ptacin et al., PCT International Application No. PCT/US2018/045257 filed Aug. 3, 2018 and published Feb. 7, 2019 as International Publication Number WO 2019/028419A1.

The PEG conjugated to the polypeptide sequence can be linear or branched. Branched PEG derivatives, "star-PEGs" and multi-armed PEGs are contemplated by the present disclosure. Specific embodiments PEGs useful in the practice of the present disclosure include a 10 kDa linear PEG-aldehyde (e.g., Sunbright® ME-100AL, NOF America Corporation, One North Broadway, White Plains, NY 10601 USA), 10 kDa linear PEG-NHS ester (e.g., Sunbright® ME-100CS, Sunbright® ME-100AS, Sunbright® ME-100GS, Sunbright® ME-100HS, NOF), a 20 kDa linear PEG-aldehyde (e.g., Sunbright® ME-200AL, NOF), a 20 kDa linear PEG-NHS ester (e.g., Sunbright® ME-200CS, Sunbright® ME-200AS, Sunbright® ME-200GS, Sunbright® ME-200HS, NOF), a 20 kDa 2-arm branched PEG-aldehyde the 20 kDA PEG-aldehyde comprising two 10 kDA linear PEG molecules (e.g., Sunbright® GL2-200AL3, NOF), a 20 kDa 2-arm branched PEG-NHS ester the 20 kDA PEG-NHS ester comprising two 10 kDA linear PEG molecules (e.g., Sunbright® GL2-200TS, Sunbright® GL200GS2, NOF), a 40 kDa 2-arm branched PEG-aldehyde the 40 kDA PEG-aldehyde comprising two 20 kDA linear PEG molecules (e.g., Sunbright® GL2-400AL3), a 40 kDa 2-arm branched PEG-NHS ester the 40 kDA PEG-NHS ester comprising two 20 kDA linear PEG molecules (e.g., Sunbright® GL2-400AL3, Sunbright® GL2-400GS2, NOF), a linear 30 kDa PEG-aldehyde (e.g., Sunbright® ME-300AL) and a linear 30 kDa PEG-NHS ester.

In some embodiments, a linker can used to join the IL10R binding molecule and the PEG molecule. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids. Examples of flexible linkers are described in Section IV. Further, a multimer (e.g., 1, 2, 3, 4, 5, 6, 7, 8, 9, 10, 10-20, 20-30, or 30-50) of these linker sequences may be linked together to provide flexible linkers that may be used to conjugate two molecules. Alternative to a polypeptide linker, the linker can be a chemical linker, e.g., a PEG-aldehyde linker. In some embodiments, the binding molecule is acetylated at the N-terminus by enzymatic reaction with N-terminal acetyltransferase and, for example, acetyl CoA. Alternatively, or in addition to N-terminal acetylation, the binding molecule can be acetylated at one or more lysine residues, e.g., by enzymatic reaction with a lysine acetyltransferase. See, for example Choudhary et al. (2009) Science 325 (5942):834-840.

In some embodiments, the present invention provides a IL10R binding molecules of formula #1 that is PEGylated, wherein the PEG is conjugated to the IL10R binding molecule and the PEG is a linear or branched PEG molecule having molecular weights from about 2,000 to about 80,000 daltons, alternatively about 2,000 to about 70,000 daltons, alternatively about 5,000 to about 50,000 daltons, alternatively about 10,000 to about 50,000 daltons, alternatively about 20,000 to about 50,000 daltons, alternatively about 30,000 to about 50,000 daltons, alternatively about 20,000 to about 40,000 daltons, or alternatively about 30,000 to about 40,000 daltons. In one embodiment of the disclosure, the PEG is a 40 kD branched PEG comprising two 20 kD arms.

Fatty Acid Carriers

In some embodiments an IL10R binding molecule having an extended duration of action in a mammalian subject and useful in the practice of the present disclosure is achieved by covalent attachment of the IL10R binding molecule to a fatty acid molecule as described in Resh (2016) Progress in Lipid Research 63: 120-131. Examples of fatty acids that may be conjugated include myristate, palmitate and palmitoleic acid. Myristoylate is typically linked to an N-terminal glycine but lysines may also be myristoylated. Palmitoylation is typically achieved by enzymatic modification of free cysteine —SH groups such as DHHC proteins catalyze S-palmitoylation. Palmitoleylation of serine and threonine residues is typically achieved enzymatically using PORCN enzymes. In some embodiments, the IL10R binding molecule is acetylated at the N-terminus by enzymatic reaction with N-terminal acetyltransferase and, for example, acetyl CoA. Alternatively, or in addition to N-terminal acetylation, the IL10R binding molecule is acetylated at one or more lysine residues, e.g., by enzymatic reaction with a lysine acetyltransferase. See, for example Choudhary et al. (2009) Science 325 (5942):834L2 ortho840.

Modifications to Provide Additional Functions

In some embodiments, embodiment, the IL10R binding molecule may comprise a functional domain of a chimeric polypeptide. IL10R binding molecule fusion proteins of the present disclosure may be readily produced by recombinant DNA methodology by techniques known in the art by constructing a recombinant vector comprising a nucleic acid sequence comprising a nucleic acid sequence encoding the IL10R binding molecule in frame with a nucleic acid sequence encoding the fusion partner either at the N-terminus or C-terminus of the IL10R binding molecules\, the sequence optionally further comprising a nucleic acid sequence in frame encoding a linker or spacer polypeptide.

FLAG Tags

In other embodiments, the IL10R binding molecule can be modified to include an additional polypeptide sequence that functions as an antigenic tag, such as a FLAG sequence. FLAG sequences are recognized by biotinylated, highly specific, anti-FLAG antibodies, as described herein (see e.g., Blanar et al. (1992) Science 256:1014 and LeClair, et al. (1992) PNAS-USA 89:8145). In some embodiments, the binding molecule further comprises a C-terminal c-myc epitope tag.

Targeting Moieties:

In some embodiments, IL10R binding molecule is conjugated to molecule which provides ("targeting domain") to facilitate selective binding to particular cell type or tissue expressing a cell surface molecule that specifically binds to such targeting domain, optionally incorporating a linker molecule of from 1-40 (alternatively 2-20, alternatively 5-20, alternatively 10-20) amino acids between IL10R binding molecule sequence and the sequence of the targeting domain of the fusion protein.

In other embodiments, a chimeric polypeptide including a IL10R binding molecule and an antibody or antigen-binding portion thereof can be generated. The antibody or antigen-binding component of the chimeric protein can serve as a targeting moiety. For example, it can be used to localize the chimeric protein to a particular subset of cells or target molecule. Methods of generating cytokine-antibody chimeric polypeptides are described, for example, in U.S. Pat. No. 6,617,135.

In some embodiments, the targeting moiety is an antibody that specifically binds to at least one cell surface molecule associated with a tumor cell (i.e. at least one tumor antigen) wherein the cell surface molecule associated with a tumor cell is selected from the group consisting of GD2, BCMA, CD19, CD33, CD38, CD70, GD2, IL3R 2, CD19, mesothelin, Her2, EpCam, Mucd, RORI, CD133, CEA, EGRFRVIII, PSCA, GPC3, Pan-ErbB and FAP.

Recombinant Production

Alternatively, the IL10R binding molecules of the present disclosure are produced by recombinant DNA technology. In the typical practice of recombinant production of polypeptides, a nucleic acid sequence encoding the desired polypeptide is incorporated into an expression vector suitable for the host cell in which expression will be accomplish, the nucleic acid sequence being operably linked to one or more expression control sequences encoding by the vector and functional in the target host cell. The recombinant protein may be recovered through disruption of the host cell or from the cell medium if a secretion leader sequence (signal peptide) is incorporated into the polypeptide.

Nucleic Acid Sequences Encoding the IL10R binding molecules In some embodiments, the IL10R binding molecule is produced by recombinant methods using a nucleic acid sequence encoding the IL10R binding molecule (or fusion protein comprising the IL10R binding molecules). The nucleic acid sequence encoding the desired αβhIL10R binding molecule can be synthesized by chemical means using an oligonucleotide synthesizer.

The nucleic acid molecules are not limited to sequences that encode polypeptides; some or all of the non-coding sequences that lie upstream or downstream from a coding sequence (e.g., the coding sequence of IL-2) can also be included. Those of ordinary skill in the art of molecular biology are familiar with routine procedures for isolating nucleic acid molecules. They can, for example, be generated by treatment of genomic DNA with restriction endonucleases, or by performance of the polymerase chain reaction (PCR). In the event the nucleic acid molecule is a ribonucleic acid (RNA), molecules can be produced, for example, by in vitro transcription.

The nucleic acid molecules encoding the IL10R binding molecule (and fusions thereof) may contain naturally occurring sequences or sequences that differ from those that occur naturally, but, due to the degeneracy of the genetic code, encode the same polypeptide. These nucleic acid molecules can consist of RNA or DNA (for example, genomic DNA, cDNA, or synthetic DNA, such as that produced by phosphoramidite-based synthesis), or combinations or modifications of the nucleotides within these types of nucleic acids. In addition, the nucleic acid molecules can be double-stranded or single-stranded (i.e., either a sense or an antisense strand).

Nucleic acid sequences encoding the IL10R binding molecule may be obtained from various commercial sources that provide custom made nucleic acid sequences. Amino acid sequence variants of the IL10R binding molecules of the present disclosure are prepared by introducing appropriate nucleotide changes into the coding sequence based on the genetic code which is well known in the art. Such variants represent insertions, substitutions, and/or specified deletions of, residues as noted. Any combination of insertion, substitution, and/or specified deletion is made to arrive at the final construct, provided that the final construct possesses the desired biological activity as defined herein.

Methods for constructing a DNA sequence encoding a IL10R binding molecule and expressing those sequences in a suitably transformed host include, but are not limited to, using a PCR-assisted mutagenesis technique. Mutations that consist of deletions or additions of amino acid residues to a IL10R binding molecule can also be made with standard recombinant techniques. In the event of a deletion or addition, the nucleic acid molecule encoding a IL10R binding molecule is optionally digested with an appropriate restriction endonuclease. The resulting fragment can either be expressed directly or manipulated further by, for example, ligating it to a second fragment. The ligation may be facilitated if the two ends of the nucleic acid molecules contain complementary nucleotides that overlap one another, but blunt-ended fragments can also be ligated. PCR-generated nucleic acids can also be used to generate various mutant sequences.

A IL10R binding molecule of the present disclosure may be produced recombinantly not only directly, but also as a fusion polypeptide with a heterologous polypeptide, e.g. a signal sequence or other polypeptide having a specific cleavage site at the N-terminus or C-terminus of the mature IL10R binding molecules. In general, the signal sequence may be a component of the vector, or it may be a part of the coding sequence that is inserted into the vector. The heterologous signal sequence selected preferably is one that is recognized and processed (i.e., cleaved by a signal peptidase) by the host cell. The inclusion of a signal sequence depends on whether it is desired to secrete the IL10R binding molecule from the recombinant cells in which it is made. If the chosen cells are prokaryotic, it generally is preferred that the DNA sequence not encode a signal sequence. When the recombinant host cell is a yeast cell such as *Saccharomyces cerevisiae*, the alpha mating factor secretion signal sequence may be employed to achieve extracellular secretion of the IL10R binding molecule into the culture medium as described in Singh, U.S. Pat. No. 7,198,919 B1 issued Apr. 3, 2007.

In the event the IL10R binding molecule to be expressed is to be expressed as a chimera (e.g., a fusion protein comprising a IL10R binding molecule and a heterologous polypeptide sequence), the chimeric protein can be encoded by a hybrid nucleic acid molecule comprising a first sequence that encodes all or part of the IL10R binding molecule and a second sequence that encodes all or part of the heterologous polypeptide. For example, subject IL10R binding molecules described herein may be fused to a hexa-/octa-histidine tag (SEQ ID NOS 532 and 534, respectively) to facilitate purification of bacterially expressed protein, or to a hemagglutinin tag to facilitate purification of protein expressed in eukaryotic cells. By first and second, it should not be understood as limiting to the orientation of the elements of the fusion protein and a heterologous polypeptide can be linked at either the N-terminus and/or C-terminus of the IL10R binding molecules. For example, the N-terminus may be linked to a targeting domain and the C-terminus linked to a hexa-histidine tag (SEQ ID NO: 532) purification handle.

The complete amino acid sequence of the polypeptide (or fusion/chimera) to be expressed can be used to construct a back-translated gene. A DNA oligomer containing a nucleotide sequence coding a IL10R binding molecule can be synthesized. For example, several small oligonucleotides coding for portions of the desired polypeptide can be synthesized and then ligated. The individual oligonucleotides typically contain 5' or 3' overhangs for complementary assembly.

Codon Optimization:

In some embodiments, the nucleic acid sequence encoding the IL10R binding molecule may be "codon optimized" to facilitate expression in a particular host cell type. Techniques for codon optimization in a wide variety of expression systems, including mammalian, yeast and bacterial host cells, are well known in the and there are online tools to provide for a codon optimized sequences for expression in a variety of host cell types. See e.g. Hawash, et al., (2017) 9:46-53 and Mauro and Chappell in Recombinant Protein Expression in Mammalian Cells: Methods and Protocols, edited by David Hacker (Human Press New York). Additionally, there are a variety of web based on-line software packages that are freely available to assist in the preparation of codon optimized nucleic acid sequences.

Expression Vectors:

Once assembled (by synthesis, site-directed mutagenesis or another method), the nucleic acid sequence encoding an a IL10R binding molecule will be inserted into an expression vector. A variety of expression vectors for uses in various host cells are available and are typically selected based on the host cell for expression. An expression vector typically includes, but is not limited to, one or more of the following: an origin of replication, one or more marker genes, an enhancer element, a promoter, and a transcription termination sequence. Vectors include viral vectors, plasmid vectors, integrating vectors, and the like. Plasmids are examples of non-viral vectors.

To facilitate efficient expression of the recombinant polypeptide, the nucleic acid sequence encoding the polypeptide sequence to be expressed is operably linked to transcriptional and translational regulatory control sequences that are functional in the chosen expression host.

Selectable Marker:

Expression vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Regulatory Control Sequences:

Expression vectors for a IL10R binding molecules of the present disclosure contain a regulatory sequence that is recognized by the host organism and is operably linked to nucleic acid sequence encoding the IL10R binding molecules\. The terms "regulatory control sequence," "regulatory sequence" or "expression control sequence" are used interchangeably herein to refer to promoters, enhancers, and other expression control elements (e.g., polyadenylation signals). See, for example, Goeddel (1990) in Gene Expression Technology: Methods in Enzymology 185 (Academic Press, San Diego CA USA Regulatory sequences include those that direct constitute expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. In selecting an expression control sequence, a variety of factors understood by one of skill in the art are to be considered. These include, for example, the relative strength of the sequence, its controllability, and its compatibility with the actual DNA sequence encoding the subject a IL10R binding molecules\, particularly as regards potential secondary structures.

Promoters:

In some embodiments, the regulatory sequence is a promoter, which is selected based on, for example, the cell type in which expression is sought. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

A T7 promoter can be used in bacteria, a polyhedrin promoter can be used in insect cells, and a cytomegalovirus or metallothionein promoter can be used in mammalian cells. Also, in the case of higher eukaryotes, tissue-specific and cell type-specific promoters are widely available. These promoters are so named for their ability to direct expression of a nucleic acid molecule in a given tissue or cell type within the body. Skilled artisans are well aware of numerous promoters and other regulatory elements which can be used to direct expression of nucleic acids.

Transcription from vectors in mammalian host cells may be controlled, for example, by promoters obtained from the genomes of viruses such as polyoma virus, fowlpox virus, adenovirus (such as human adenovirus serotype 5), bovine papilloma virus, avian sarcoma virus, cytomegalovirus, a retrovirus (such as murine stem cell virus), hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication.

Enhancers:

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, alpha-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence but is preferably located at a site 5' from the promoter. Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. Construction of suitable vectors containing one or more of the above-listed components employs standard techniques.

In addition to sequences that facilitate transcription of the inserted nucleic acid molecule, vectors can contain origins of replication, and other genes that encode a selectable marker. For example, the neomycin-resistance (neoR) gene imparts G418 resistance to cells in which it is expressed, and thus permits phenotypic selection of the transfected cells. Additional examples of marker or reporter genes include beta-lactamase, chloramphenicol acetyltransferase (CAT), adenosine deaminase (ADA), dihydrofolate reductase (DHFR), hygromycin-B-phosphotransferase (HPH), thymidine kinase (TK), lacZ (encoding beta-galactosidase), and xanthine guanine phosphoribosyltransferase (XGPRT). Those of skill in the art can readily determine whether a given regulatory element or selectable marker is suitable for use in a particular experimental context.

Proper assembly of the expression vector can be confirmed by nucleotide sequencing, restriction mapping, and expression of a biologically active polypeptide in a suitable host.

Host Cells:

The present disclosure further provides prokaryotic or eukaryotic cells that contain and express a nucleic acid molecule that encodes a a IL10R binding molecules. A cell of the present disclosure is a transfected cell, i.e., a cell into which a nucleic acid molecule, for example a nucleic acid molecule encoding a mutant IL-2 polypeptide, has been introduced by means of recombinant DNA techniques. The progeny of such a cell are also considered within the scope of the present disclosure.

Host cells are typically selected in accordance with their compatibility with the chosen expression vector, the toxicity of the product coded for by the DNA sequences of this invention, their secretion characteristics, their ability to fold the polypeptides correctly, their fermentation or culture requirements, and the ease of purification of the products coded for by the DNA sequences. Suitable host cells for cloning or expressing the DNA in the vectors herein are the prokaryote, yeast, or higher eukaryote cells.

In some embodiments the recombinant IL10R binding molecule can also be made in eukaryotes, such as yeast or human cells. Suitable eukaryotic host cells include insect cells (examples of Baculovirus vectors available for expression of proteins in cultured insect cells (e.g., Sf9 cells) include the pAc series (Smith et al. (1983) Mol. Cell Biol. 3:2156-2165) and the pVL series (Lucklow and Summers (1989) Virology 170:31-39)); yeast cells (examples of vectors for expression in yeast $S.$ $cerevisiae$ include pYepSec1 (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif), and pPicZ (Invitrogen Corporation, San Diego, Calif)); or mammalian cells (mammalian expression vectors include pCDM8 (Seed (1987) Nature 329:840) and pMT2PC (Kaufman et al. (1987) EMBO J. 6:187:195)).

Examples of useful mammalian host cell lines are mouse L cells (L-M[TK-], ATCC #CRL-2648), monkey kidney CV1 line transformed by SV40 (COS-7, ATCC CRL 1651); human embryonic kidney line (HEK293 or HEK293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and a human hepatoma line (Hep G2). In mammalian cells, the expression vector's control functions are often provided by viral regulatory elements. For example, commonly used promoters are derived from polyoma, Adenovirus 2, cytomegalovirus, and Simian Virus 40.

The IL10R binding molecule may be produced in a prokaryotic host, such as the bacterium $E.$ $coli$, or in a eukaryotic host, such as an insect cell (e.g., an Sf21 cell), or mammalian cells (e.g., COS cells, NIH 3T3 cells, or HeLa cells). These cells are available from many sources, including the American Type Culture Collection (Manassas, Va.). In selecting an expression system, it matters only that the components are compatible with one another. Artisans or ordinary skill are able to make such a determination. Furthermore, if guidance is required in selecting an expression system, skilled artisans may consult Ausubel et al. (Current Protocols in Molecular Biology, John Wiley and Sons, New York, N.Y., 1993) and Pouwels et al. (Cloning Vectors: A Laboratory Manual, 1985 Suppl. 1987).

In some embodiments, a IL10R binding molecule obtained will be glycosylated or unglycosylated depending on the host organism used to produce the mutein. If bacteria are chosen as the host then the a IL10R binding molecule produced will be unglycosylated. Eukaryotic cells, on the other hand, will typically result in glycosylation of the IL10R binding molecules.

In some embodiments, it is possible that an amino acid sequence (particularly a CDR sequence) of an sdAb to be incorporated into a IL10R binding molecule may contain a glycosylation motif, particularly an N-linked glycosylation motif of the sequence Asn-X-Ser (N-X-S) or Asn-X-Thr (N-X-T), wherein X is any amino acid except for proline. In such instances, it is desirable to eliminate such N-linked glycosylation motifs by modifying the sequence of the N-linked glycosylation motif to prevent glycosylation. In some embodiments, the N-linked glycosylation motif is disrupted by the incorporation of conservative amino acid substitution of the Asn (N) residue of the N-linked glycosylation motif.

For other additional expression systems for both prokaryotic and eukaryotic cells, see Chapters 16 and 17 of Sambrook et al. (1989) Molecular Cloning: A Laboratory Manual (2nd ed., Cold Spring Harbor Laboratory Press, Plainview, N.Y.). See, Goeddel (1990) in Gene Expression Technology: Methods in Enzymology 185 (Academic Press, San Diego, Calif.).

Transfection:

The expression constructs of the can be introduced into host cells to thereby produce a IL10R binding molecule disclosed herein. The expression vector comprising a nucleic acid sequence encoding IL10R binding molecule is introduced into the prokaryotic or eukaryotic host cells via conventional transformation or transfection techniques. Suitable methods for transforming or transfecting host cells can be found in Sambrook et al. (1989) Molecular Cloning: A Laboratory Manual (2d ed., Cold Spring Harbor Laboratory Press, Plainview, N.Y.) and other standard molecular biology laboratory manuals. To facilitate transfection of the target cells, the target cell may be exposed directly with the non-viral vector may under conditions that facilitate uptake of the non-viral vector. Examples of conditions which facilitate uptake of foreign nucleic acid by mammalian cells are well known in the art and include but are not limited to chemical means (such as Lipofectamine®, Thermo-Fisher Scientific), high salt, and magnetic fields (electroporation).

Cell Culture:

Cells may be cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression and will be apparent to the ordinarily skilled artisan.

Recovery of Recombinant Proteins:

Recombinantly produced IL10R binding molecule polypeptides can be recovered from the culture medium as a secreted polypeptide if a secretion leader sequence is employed. Alternatively, the IL10R binding molecule polypeptides can also be recovered from host cell lysates. A protease inhibitor, such as phenyl methyl sulfonyl fluoride (PMSF) may be employed during the recovery phase from cell lysates to inhibit proteolytic degradation during purification, and antibiotics may be included to prevent the growth of adventitious contaminants.

Various purification steps are known in the art and find use, e.g. affinity chromatography. Affinity chromatography makes use of the highly specific binding sites usually present in biological macromolecules, separating molecules on their ability to bind a particular ligand. Covalent bonds attach the ligand to an insoluble, porous support medium in a manner that overtly presents the ligand to the protein sample, thereby using natural specific binding of one molecular species to separate and purify a second species from a mixture. Antibodies are commonly used in affinity chromatography. Size selection steps may also be used, e.g. gel filtration chromatography (also known as size-exclusion chromatography or molecular sieve chromatography) is used to separate proteins according to their size. In gel filtration, a protein solution is passed through a column that is packed with semipermeable porous resin. The semipermeable resin has a range of pore sizes that determines the size of proteins that can be separated with the column.

A recombinantly IL10R binding molecule by the transformed host can be purified according to any suitable method. Recombinant IL10R binding molecules can be isolated from inclusion bodies generated in *E. coli*, or from conditioned medium from either mammalian or yeast cultures producing a given mutein using cation exchange, gel filtration, and or reverse phase liquid chromatography. The substantially purified forms of the recombinant a IL10R binding molecule can be purified from the expression system using routine biochemical procedures, and can be used, e.g., as therapeutic agents, as described herein.

In some embodiments, where the IL10R binding molecule is expressed with a purification tag as discussed above, this purification handle may be used for isolation of the IL10R binding molecule from the cell lysate or cell medium. Where the purification tag is a chelating peptide, methods for the isolation of such molecules using immobilized metal affinity chromatography are well known in the art. See, e.g., Smith, et al. U.S. Pat. No. 4,569,794.

The biological activity of the IL10R binding molecules recovered can be assayed for activating by any suitable method known in the art and may be evaluated as substantially purified forms or as part of the cell lysate or cell medium when secretion leader sequences are employed for expression.

Pharmaceutical Formulations

In some embodiments, the subject IL10R binding molecule (and/or nucleic acids encoding the IL10R binding molecule or recombinant cells incorporating a nucleic acid sequence and modified to express the IL10R binding molecules) can be incorporated into compositions, including pharmaceutical compositions. Such compositions typically include the polypeptide or nucleic acid molecule and a pharmaceutically acceptable carrier. A pharmaceutical composition is formulated to be compatible with its intended route of administration and is compatible with the therapeutic use for which the IL10R binding molecule is to be administered to the subject in need of treatment or prophyaxis.

Carriers:

Carriers include a sterile diluent such as water for injection, saline solution, fixed oils, polyethylene glycols, glycerine, propylene glycol or other synthetic solvents. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants, e.g., sodium dodecyl sulfate. For intravenous administration, suitable carriers include physiological saline, bacteriostatic water, Cremophor EL™ (BASF, Parsippany, N.J.) or phosphate buffered saline (PBS).

Buffers:

The term buffers includes buffers such as acetates, citrates or phosphates and agents for the adjustment of tonicity such as sodium chloride or dextrose. pH can be adjusted with acids or bases, such as mono- and/or di-basic sodium phosphate, hydrochloric acid or sodium hydroxide (e.g., to a pH of about 7.2-7.8, e.g., 7.5).

Dispersions:

Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Preservatives:

The pharmaceutical formulations for parenteral administration to a subject should be sterile and should be fluid to facilitate easy syringability. It should be stable under the conditions of manufacture and storage and are preserved against the contamination. Prevention of the action of microorganisms can be achieved by various antibacterial and antifungal agents, for example, agents such as benzyl alcohol or methyl parabens; antioxidants such as ascorbic acid or sodium bisulfite; chelating agents such as ethylenediaminetetraacetic acid, parabens, chlorobutanol, phenol, ascorbic acid, thimerosal, and the like. Sterile solutions can be prepared by incorporating the active compound in the required amount in an appropriate solvent with one or a combination of ingredients enumerated above, as required, followed by filtered sterilization.

Tonicity Agents:

In many cases, it will be preferable to include isotonic agents, for example, sugars, polyalcohols such as mannitol, sorbitol, sodium chloride in the composition.

Routes of Administration:

In some embodiments of the therapeutic methods of the present disclosure involve the administration of a pharmaceutical formulation comprising a IL10R binding molecule (and/or nucleic acids encoding the IL10R binding molecule or recombinantly modified host cells expressing the IL10R binding molecules) to a subject in need of treatment. The pharmaceutical formulation comprising a IL10R binding molecules of the present disclosure may be administered to a subject in need of treatment or prophyaxis by a variety of routes of administration, including parenteral administration, oral, topical, or inhalation routes.

Parenteral Administration:

In some embodiments, the methods of the present disclosure involve the parenteral administration of a pharmaceutical formulation comprising a IL10R binding molecule (and/or nucleic acids encoding the IL10R binding molecule or recombinantly modified host cells expressing the IL10R binding molecules) to a subject in need of treatment. Examples of parenteral routes of administration include, for example, intravenous, intradermal, subcutaneous, transdermal (topical), transmucosal, and rectal administration. Parenteral formulations comprise solutions or suspensions used for parenteral application can include vehicles the carriers and buffers. Pharmaceutical formulations for parenteral administration include sterile aqueous solutions (where water soluble) or dispersions and sterile powders for the extemporaneous preparation of sterile injectable solutions or dispersion. The parenteral preparation can be enclosed in ampoules, disposable syringes or multiple dose vials made of glass or plastic. In one embodiment, the formulation is provided in a prefilled syringe for Oral Administration:

In some embodiments, the methods of the present disclosure involve the oral administration of a pharmaceutical formulation comprising a IL10R binding molecule (and/or nucleic acids encoding the IL10R binding molecule or recombinantly modified host cells expressing the IL10R binding molecules) to a subject in need of treatment. Oral compositions, if used, generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel™, or corn starch; a lubricant such as magnesium stearate or Sterotes™; a glidant such as colloidal silicon dioxide; a sweetening agent such as sucrose or saccharin; or a flavoring agent such as peppermint, methyl salicylate, or orange flavoring.

Inhalation Formulations:

In some embodiments, the methods of the present disclosure involve the inhaled administration of a pharmaceutical formulation comprising a IL10R binding molecule (and/or nucleic acids encoding the IL10R binding molecule or recombinantly modified host cells expressing the IL10R binding molecules) to a subject in need of treatment. In the event of administration by inhalation, subject IL10R binding molecules, or the nucleic acids encoding them, are delivered in the form of an aerosol spray from pressured container or dispenser which contains a suitable propellant, e.g., a gas such as carbon dioxide, or a nebulizer. Such methods include those described in U.S. Pat. No. 6,468,798.

Mucosal and Transdermal Formulations:

In some embodiments, the methods of the present disclosure involve the mucosal or transdermal administration of a pharmaceutical formulation comprising a IL10R binding molecule (and/or nucleic acids encoding the IL10R binding molecule or recombinantly modified host cells expressing the IL10R binding molecules) to a subject in need of treatment. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories suppositories (e.g., with conventional suppository bases such as cocoa butter and other glycerides) or retention enemas for rectal delivery. For transdermal administration, the active compounds are formulated into ointments, salves, gels, or creams as generally known in the art and may incorporate permeation enhancers such as ethanol or lanolin.

Extended Release and Depot Formulations:

In some embodiments of the method of the present disclosure, the IL10R binding molecule is administered to a subject in need of treatment in a formulation to provide extended release of the IL10R binding molecule agent. Examples of extended release formulations of the injectable compositions can be brought about by including in the composition an agent which delays absorption, for example, aluminum monostearate and gelatin. In one embodiment, the subject IL10R binding molecules or nucleic acids are prepared with carriers that will protect the IL10R binding molecules against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Administration of Nucleic Acids Encoding the IL10R Binding Molecules:

In some embodiments of the method of the present disclosure, delivery of the the IL10R binding molecule to a subject in need of treatment is achieved by the administration of a nucleic acid encoding the IL10R binding molecules. Methods for the adminstration nucleic acid encoding the IL10R binding molecule to a subject is achieved by transfection or infection using methods known in the art, including but not limited to the methods described in McCaffrey et al. (Nature (2002) 418:6893), Xia et al. (Nature Biotechnol. (2002) 20:1006-1010), or Putnam (Am. J. Health Syst. Pharm. (1996) 53: 151-160 erratum at Am. J. Health Syst. Pharm. (1996) 53:325). In some embodiments, the IL10R binding molecule is administered to a subject by the administration of a pharmaceutically acceptable formulation of recombinant expression vector comprising a nucleic acid sequence encoding the IL10R binding molecule operably linked to one or more expression control sequences operable in a mammalian subject. In some embodiments, the expression control sequence may be selected that is operable in a limited range of cell types (or single cell type) to facilitate the selective expression of the IL10R binding molecule in a particular target cell type. In one embodiment, the recombinant expression vector is a viral vector. In some embodiments, the recombinant vector is a recombinant viral vector. In some embodiments the recombinant viral vector is a recombinant adenoassociated virus (rAAV) or recombinant adenovirus (rAd), in particular a replication deficient adenovirus derived from human adenovirus serotypes 3 and/or 5. In some embodiments, the replication deficient adenovirus has one or more modifications to the E1 region which interfere with the ability of the virus to initiate the cell cycle and/or apoptotic pathways in a human cell. The replication deficient adenoviral vector may optionally comprise deletions in the E3 domain. In some embodiments the adenovirus is a replication competent adenovirus. In some embodiments the adenovirus is a replication competent recombinant virus engineered to selectively replicate in the target cell type.

In some embodiments, particularly for administration of IL10R binding molecules to the subject, particular for treatment of diseases of the intestinal tract or bacterial infections in a subject, the nucleic acid encoding the IL10R binding molecule may be delivered to the subject by the administration of a recombinantly modified bacteriophage vector encoding the IL10R binding molecules\. As used herein, the terms 'procaryotic virus," "bacteriophage" and "phage" are used interchangeably hereinto describe any of a variety of bacterial viruses that infect and replicate within a bacterium. Bacteriophage selectively infect procaryotic cells, restricting the expression of the IL10R binding molecule to procaryotic cells in the subject while avoiding expression in mammalian cells. A wide variety of bacteriophages capable of selection a broad range of bacterial cells have been identified and characterized extensively in the scientific literature. In some embodiments, the phage is modified to remove adjacent motifs (PAM). Elimination of the of Cas9 sequences from the phage genome reduces ability of the Cas9 endonuclease of the target procaryotic cell to neutralize the invading phage encoding the IL10R binding molecules.

Administration of Recombinantly Modified Cells Expressing the IL10R Binding Molecule In some embodiments of the method of the present disclosure, delivery of the the IL10R binding molecule to a subject in need of treatment is achieved by the administration of recombinant host cells modified to express the IL10R binding molecule may be administered in the therapeutic and prophylactic applications described herein. In some embodiments, the recombinant host cells are mammalian cells, e.g., human cells.

In some embodiments, the nucleic acid sequence encoding the IL10R binding molecule (or vectors comprising same) may be maintained extrachromosomally in the recombinantly modified host cell for administration. In other embodiments, the nucleic acid sequence encoding the IL10R binding molecule may be incorporated into the genome of the host cell to be administered using at least one endonuclease to facilitate incorporate insertion of a nucleic acid sequence into the genomic sequence of the cell. As used herein, the term “endonuclease” is used to refer to a wild-type or variant enzyme capable of catalyzing the cleavage of bonds between nucleic acids within a DNA or RNA molecule, preferably a DNA molecule. Endonucleases are referred to as “rare-cutting” endonucleases when such endonucleases have a polynucleotide recognition site greater than about 12 base pairs (bp) in length, more preferably of 14-55 bp. Rare-cutting endonucleases can be used for inactivating genes at a locus or to integrate transgenes by homologous recombination (HR) i.e. by inducing DNA double-strand breaks (DSBs) at a locus and insertion of exogenous DNA at this locus by gene repair mechanism. Examples of rare-cutting endonucleases include homing endonucleases (Grizot, et al (2009) Nucleic Acids Research 37(16):5405-5419), chimeric Zinc-Finger nucleases (ZFN) resulting from the fusion of engineered zinc-finger domains (Porteus M and Carroll D., Gene targeting using zinc finger nucleases (2005) Nature Biotechnology 23(3):967-973, a TALEN-nuclease, a Cas9 endonuclease from CRISPR system as or a modified restriction endonuclease to extended sequence specificity (Eisenschmidt, et al. 2005; 33(22): 7039-7047).

In some embodiments, particularly for administration of IL10R binding molecules to the intestinal tract, the IL10R binding molecule may be delivered to the subject by a recombinantly modified procaryotic cell (e.g., *Lactobacillus* lacti). The use of engineered procaryotic cells for the delivery of recombinant proteins to the intestinal tract are known in the art. See, e.g. Lin, et al. (2017) Microb Cell Fact 16:148. In some embodiments, the engineered bacterial cell expressing the IL10R binding molecule may be administered orally, typically in aqueous suspension, or rectally (e.g. enema).

Methods of Use

The present disclosure further provides methods of treating a subject suffering from a disease disorder or condition by the administration of a therapeutically effective amount of an IL10R binding molecule (or nucleic acid encoding an IL10R binding molecule including recombinant viruses encoding the IL10R binding molecules) of the present disclosure.

Inflammatory and Autoimmune Disorders

Disorders amenable to treatment with an IL10R binding molecule (including pharmaceutically acceptable formulations comprising an IL10R binding molecules and/or the nucleic acid molecules that encode them including recombinant viruses encoding such an IL10R binding molecules) of the present disclosure include inflammatory or autoimmune diseases including but not limited to, organ rejection, graft versus host disease, autoimmune thyroid disease, multiple sclerosis, allergy, asthma, neurodegenerative diseases including Alzheimer’s disease, systemic lupus erythramatosis (SLE), autoinflammatory diseases, inflammatory bowel disease (IBD), Crohn’s disease, diabetes including Type 1 or type 2 diabetes, inflammation, autoimmune disease, atopic diseases, paraneoplastic autoimmune diseases, cartilage inflammation, arthritis, rheumatoid arthritis, juvenile arthritis, juvenile rheumatoid arthritis, juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter’s Syndrome, SEA Syndrome (Seronegativity Enthesopathy Arthropathy Syndrome), juvenile dermatomyositis, juvenile psoriatic arthritis, juvenile scleroderma, juvenile systemic lupus erythematosus, juvenile vasculitis, pauciarticular rheumatoidarthritis, polyarticular rheumatoidarthritis, systemic onset rheumatoidarthritis, ankylosing spondylitis, enteropathic arthritis, reactive arthritis, Reiter’s syndrome,SEA Syndrome(Seronegativity, Enthesopathy, Arthropathy Syndrome).

Other examples of proliferative and/or differentiative disorders amenable to treatment with IL10R binding molecules (including pharmaceutically acceptable formulations comprising IL10R binding molecules and/or the nucleic acid molecules that encode them including recombinant viruses encoding such IL10R binding molecules) of the present disclosure include, but are not limited to, skin disorders. The skin disorder may involve the aberrant activity of a cell or a group of cells or layers in the dermal, epidermal, or hypodermal layer, or an abnormality in the dermal-epidermal junction. For example, the skin disorder may involve aberrant activity of keratinocytes (e.g., hyperproliferative basal and immediately suprabasal keratinocytes), melanocytes, Langerhans cells, Merkel cells, immune cell, and other cells found in one or more of the epidermal layers, e.g., the stratum basale (stratum germinativum), stratum *spinosum*, stratum *granulosum*, stratum lucidum or stratum corneum. In other embodiments, the disorder may involve aberrant activity of a dermal cell, for example, a dermal endothelial, fibroblast, immune cell (e.g., mast cell or macrophage) found in a dermal layer, for example, the papillary layer or the reticular layer.

Examples of inflammatory or autoimmune skin disorders include psoriasis, psoriatic arthritis, dermatitis (eczema), for example, exfoliative dermatitis or atopic dermatitis, *pityriasis rubra* pilaris, *pityriasis* rosacea, parapsoriasis, *pityriasis* lichenoiders, lichen planus, lichen *nitidus*, ichthyosiform dermatosis, keratodermas, dermatosis, alopecia areata, pyoderma gangrenosum, vitiligo, pemphigoid (e.g., ocular cicatricial pemphigoid or bullous pemphigoid), urticaria, prokeratosis, rheumatoid arthritis that involves hyperproliferation and inflammation of epithelial-related cells lining the joint capsule; dermatitises such as seborrheic dermatitis and solar dermatitis; keratoses such as seborrheic keratosis, senile keratosis, actinic keratosis, photo-induced keratosis, and keratosis follicularis; acne vulgaris; keloids and prophylaxis against keloid formation; nevi; warts including verruca, condyloma or condyloma *acuminatum*, and human papilloma viral (HPV) infections such as venereal warts; leukoplakia; lichen planus; and keratitis. The skin disorder can be dermatitis, e.g., atopic dermatitis or allergic dermatitis, or psoriasis.

The compositions of the present disclosure (including pharmaceutically acceptable formulations comprising IL10R binding molecules and/or the nucleic acid molecules that encode them including recombinant viruses encoding such IL10R binding molecules) can also be administered to a patient who is suffering from (or may suffer from) psoriasis or psoriatic disorders. The term "psoriasis" is intended to have its medical meaning, namely, a disease which afflicts primarily the skin and produces raised, thickened, scaling, nonscarring lesions. The lesions are usually sharply demarcated erythematous papules covered with overlapping shiny scales. The scales are typically silvery or slightly opalescent. Involvement of the nails frequently occurs resulting in pitting, separation of the nail, thickening and discoloration. Psoriasis is sometimes associated with arthritis, and it may be crippling. Hyperproliferation of keratinocytes is a key feature of psoriatic epidermal hyperplasia along with epidermal inflammation and reduced differentiation of keratinocytes. Multiple mechanisms have been invoked to explain the keratinocyte hyperproliferation that characterizes psoriasis. Disordered cellular immunity has also been implicated in the pathogenesis of psoriasis. Examples of psoriatic disorders include chronic stationary psoriasis, plaque psoriasis, moderate to severe plaque psoriasis, psoriasis vulgaris, eruptive psoriasis, psoriatic erythroderma, generalized pustular psoriasis, annular pustular psoriasis, or localized pustular psoriasis.

Treatment of Neoplastic Disease

The present disclosure provides methods of use of IL10R binding molecules in the treatment of a subject suffering from a neoplastic disease disorder or condition by the administration of a therapeutically effective amount of an IL10R binding molecule (or nucleic acid encoding an IL10R binding molecule including recombinant vectors encoding IL10R binding molecules) as described herein.

The compositions and methods of the present disclosure are useful in the treatment of subject suffering from a neoplastic disease characterized by the presence neoplasms, including benign and malignant neoplasms, and neoplastic disease.

Examples of benign neoplasms amenable to treatment using the compositions and methods of the present disclosure include but are not limited to adenomas, fibromas, hemangiomas, and lipomas. Examples of pre-malignant neoplasms amenable to treatment using the compositions and methods of the present disclosure include but are not limited to hyperplasia, atypia, metaplasia, and dysplasia. Examples of malignant neoplasms amenable to treatment using the compositions and methods of the present disclosure include but are not limited to carcinomas (cancers arising from epithelial tissues such as the skin or tissues that line internal organs), leukemias, lymphomas, and sarcomas typically derived from bone fat, muscle, blood vessels or connective tissues). Also included in the term neoplasms are viral induced neoplasms such as warts and EBV induced disease (i.e., infectious mononucleosis), scar formation, hyperproliferative vascular disease including intimal smooth muscle cell hyperplasia, restenosis, and vascular occlusion and the like.

The term "neoplastic disease" includes cancers characterized by solid tumors and non-solid tumors including but not limited to breast cancers; sarcomas (including but not limited to osteosarcomas and angiosarcomas and fibrosarcomas), leukemias, lymphomas, genitourinary cancers (including but not limited to ovarian, urethral, bladder, and prostate cancers); gastrointestinal cancers (including but not limited to colon esophageal and stomach cancers); lung cancers; myelomas; pancreatic cancers; liver cancers; kidney cancers; endocrine cancers; skin cancers; and brain or central and peripheral nervous (CNS) system tumors, malignant or benign, including gliomas and neuroblastomas, astrocytomas, myelodysplastic disorders; cervical carcinoma-in-situ; intestinal polyposes; oral leukoplakias; histiocytoses, hyperprofroliferative scars including keloid scars, hemangiomas; hyperproliferative arterial stenosis, psoriasis, inflammatory arthritis; hyperkeratoses and papulosquamous eruptions including arthritis.

The term neoplastic disease includes carcinomas. The term "carcinoma" refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. The term neoplastic disease includes adenocarcinomas. An "adenocarcinoma" refers to a carcinoma derived from glandular tissue or in which the tumor cells form recognizable glandular structures.

As used herein, the term "hematopoietic neoplastic disorders" refers to neoplastic diseases involving hyperplastic/neoplastic cells of hematopoietic origin, e.g., arising from myeloid, lymphoid or erythroid lineages, or precursor cells thereof.

Myeloid neoplasms include, but are not limited to, myeloproliferative neoplasms, myeloid and lymphoid disorders with eosinophilia, myeloproliferative/myelodysplastic neoplasms, myelodysplastic syndromes, acute myeloid leukemia and related precursor neoplasms, and acute leukemia of ambiguous lineage. Exemplary myeloid disorders amenable to treatment in accordance with the present disclosure include, but are not limited to, acute promyeloid leukemia (APML), acute myelogenous leukemia (AML) and chronic myelogenous leukemia (CML).

Lymphoid neoplasms include, but are not limited to, precursor lymphoid neoplasms, mature B-cell neoplasms, mature T-cell neoplasms, Hodgkin's Lymphoma, and immunodeficiency-associated lymphoproliferative disorders. Exemplary lymphic disorders amenable to treatment in accordance with the present disclosure include, but are not limited to, acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM).

In some instances, the hematopoietic neoplastic disorder arises from poorly differentiated acute leukemias (e.g., erythroblastic leukemia and acute megakaryoblastic leukemia). As used herein, the term "hematopoietic neoplastic disorders" refers malignant lymphomas including, but are not limited to, non-Hodgkins lymphoma and variants thereof, peripheral T cell lymphomas, adult T-cell leukemia/lymphoma (ATL), cutaneous T cell lymphoma (CTCL), large granular lymphocytic leukemia (LGF), Hodgkin's disease and Reed-Steinberg disease.

The determination of whether a subject is "suffering from a neoplastic disease" refers to a determination made by a physician with respect to a subject based on the available information accepted in the field for the identification of a disease, disorder or condition including but not limited to X-ray, CT-scans, conventional laboratory diagnostic tests (e.g. blood count, etc.), genomic data, protein expression data, immunohistochemistry, that the subject requires or will benefit from treatment.

The adaptive immune system recognizes the display of certain cell surface proteins in response to tumor mutations facilitating the recognition and elimination of neoplastic cells. Tumors that possess a higher tumor mutation burden (TMB) are more likely to exhibit such "tumor antigens." Indeed, clinical experience shows that tumors comprised of neoplastic cells exhibiting a high tumor mutation burden are more likely to respond to immune therapies, including immune checkpoint blockade (Rizvi, et al. (2015) Science 348(6230): 124-128; Marabelle, et al. (2020) Lancet Oncol 21(10):1353-1365). Tumor mutation burden is useful as a biomarker to identify tumors with an increased sensitivity to immune therapies such as those provided in the present disclosure.

In some embodiments, the compositions and methods of the present disclosure are useful in the treatment of neoplastic disease associated with the formation of solid tumors exhibiting an intermediate or high tumor mutational burden (TMB). In some embodiments, the compositions and compositions and methods of the present disclosure are useful in the treatment of immune sensitive solid tumors exhibiting an intermediate or high tumor mutational burden (TMB). Examples of neoplastic diseases associated with the formation of solid tumors having an intermediate or high tumor mutational burden amenable to treatment with the compositions and methods of the present disclosure include, but are not limited to, non-small cell lung cancer and renal cell cancer. In one embodiment, the compositions and methods are useful in the treatment of non-small cell lung cancer (NSCLC) exhibiting an intermediate or high TMB. NSCLC cells typically harbor a significant number of mutations and are therefore more sensitive to immune therapies. The current standard of care for NSCLC is stratified by the cancer initiating mechanisms and generally follows the recommendations of NCCN or ASCO. A large proportion of NSCLC has increased TMB and is therefore initially more sensitive to immune therapies. However, most tumors eventually relapse on immune checkpoint inhibition. Patients with relapsed tumors typically show reduced T cell infiltration in the tumor, systemic T cell exhaustion and a suppressed immune response compared to the lesions prior to immune checkpoint inhibition. Therefore, improved immune therapies are required, re-activating and expanding the exhausted, rare tumor infiltrating T cells.

Combination of IL10R binding molecules with Supplemental Therapeutic Agents:

The present disclosure provides for the use of the IL10R binding molecules of the present disclosure in combination with one or more additional active agents ("supplemental agents"). Such further combinations are referred to interchangeably as "supplemental combinations" or "supplemental combination therapy" and those therapeutic agents that are used in combination with IL10R binding molecules of the present disclosure are referred to as "supplemental agents." As used herein, the term "supplemental agents" includes agents that can be administered or introduced separately, for example, formulated separately for separate administration (e.g., as may be provided in a kit) and/or therapies that can be administered or introduced in combination with the hIL10R binding molecules.

As used herein, the term "in combination with" when used in reference to the administration of multiple agents to a subject refers to the administration of a first agent at least one additional (i.e. second, third, fourth, fifth, etc.) agent to a subject. For purposes of the present invention, one agent (e.g. hIL10R binding molecule) is considered to be administered in combination with a second agent (e.g. a modulator of an immune checkpoint pathway) if the biological effect resulting from the administration of the first agent persists in the subject at the time of administration of the second agent such that the therapeutic effects of the first agent and second agent overlap. For example, the PD1 immune checkpoint inhibitors (e.g. nivolumab or pembrolizumab) are typically administered by IV infusion every two weeks or every three weeks while the hIL10R binding molecules of the present disclosure are typically administered more frequently, e.g. daily, BID, or weekly. However, the administration of the first agent (e.g. pembrolizumab) provides a therapeutic effect over an extended time and the administration of the second agent (e.g. an hIL10R binding molecule) provides its therapeutic effect while the therapeutic effect of the first agent remains ongoing such that the second agent is considered to be administered in combination with the first agent, even though the first agent may have been administered at a point in time significantly distant (e.g. days or weeks) from the time of administration of the second agent. In one embodiment, one agent is considered to be administered in combination with a second agent if the first and second agents are administered simultaneously (within 30 minutes of each other), contemporaneously or sequentially. In some embodiments, a first agent is deemed to be administered "contemporaneously" with a second agent if first and second agents are administered within about 24 hours of each another, preferably within about 12 hours of each other, preferably within about 6 hours of each other, preferably within about 2 hours of each other, or preferably within about 30 minutes of each other. The term "in combination with" shall also understood to apply to the situation where a first agent and a second agent are co-formulated in single pharmaceutically acceptable formulation and the co-formulation is administered to a subject. In certain embodiments, the hIL10R binding molecule and the supplemental agent(s) are administered or applied sequentially, e.g., where one agent is administered prior to one or more other agents. In other embodiments, the hIL10R binding molecule and the supplemental agent(s) are administered simultaneously, e.g., where two or more agents are administered at or about the same time; the two or more agents may be present in two or more separate formulations or combined into a single formulation (i.e., a co-formulation). Regardless of whether the agents are administered sequentially or simultaneously, they are considered to be administered in combination for purposes of the present disclosure.

Establishing Optimum Combinatorial Therapies:

Further embodiments comprise a method or model for determining the optimum amount of an agent(s) in a combination. An optimum amount can be, for example, an amount that achieves an optimal effect in a subject or subject population, or an amount that achieves a therapeutic effect while minimizing or eliminating the adverse effects associated with one or more of the agents. In some embodiments, the methods involving the combination of an hIL10R binding molecule and a supplemental agent which is known to be, or has been determined to be, effective in treating or preventing a disease, disorder or condition described herein (e.g., a cancerous condition) in a subject (e.g., a human) or a subject population, and an amount of one agent is titrated while the amount of the other agent(s) is held constant. By manipulating the amounts of the agent(s) in this manner, a clinician is able to determine the ratio of agents most effective for, for example, treating a particular disease, disorder or condition, or eliminating the adverse effects or reducing the adverse effects such that are acceptable under the circumstances.

Supplemental Agents Useful in the Treatment of Inflammatory or Autoimmune Disorders In some embodiments, the method further comprises administering of the IL10R binding molecule of the present disclosure in combination with one or more supplemental agents selected from the group consisting of a corticosteroid, a Janus kinase inhibitor, a calcineurin inhibitor, a mTor inhibitor, an IMDH inhibitor, a biologic, a vaccine, and a therapeutic antibody. In certain embodiments, the therapeutic antibody is an antibody that binds a protein selected from the group consisting of BLyS, CD11a, CD20, CD25, CD3, CD52, IgEIL12/IL23, IL17a, IL1B, IL4Ra, IL5, IL6R, integrin-α4β7, RANKL, TNFα, VEGF-A, and VLA-4.

In some embodiments, the supplemental agent is one or more agents selected from the group consisting of corticosteroids (including but not limited to prednisone, budesonide, prednilisone), Janus kinase inhibitors (including but not limited to tofacitinib (Xeljanz®), calcineurin inhibitors (including but not limited to cyclosporine and tacrolimus), mTor inhibitors (including but not limited to sirolimus and everolimus), IMDH inhibitors (including but not limited to azathioprine, leflunomide and mycophenolate), biologics such as abatcept (Orencia®) or etanercept (Enbrel®), and therapeutic antibodies.

Examples of therapeutic antibodies that may be administered as supplemental agents in combination with the IL10R binding molecules of the present disclosure in the treatment of autoimmune disease include but are not limited to anti-CD25 antibodies (e.g. daclizumab and basiliximab), anti-VLA-4 antibodies (e.g. natalizumab), anti-CD52 antibodies (e.g. alemtuzumab), anti-CD20 antibodies (e.g. rituximab, ocrelizumab), anti-TNF antibodies (e.g. infliximab, and adalimumab), anti-IL6R antibodies (e.g. tocilizumab), anti-TNFα antibodies (e.g. adalimumab (Humira®), golimumab, and infliximab), anti-integrin-α4β7 antibodies (e.g. vedolizumab), anti-IL17a antibodies (e.g. brodalumab or secukinumab), anti-IL4Rα antibodies (e.g. dupilumab), anti-RANKL antibodies, IL6R antibodies, anti-IL1ßantibodies (e.g. canakinumab), anti-CD11a antibodies (e.g. efalizumab), anti-CD3 antibodies (e.g. muramonab), anti-IL5 antibodies (e.g. mepolizumab, reslizumab), anti-BLyS antibodies (e.g. belimumab); and anti-IL12/IL23 antibodies (e.g ustekinumab). Many therapeutic antibodies have been approved for clinical use against autoimmune disease.

Examples of antibodies approved by the United States Food and Drug Administration (FDA) for use in the treatment of autoimmune diseases in a subject suffering therefrom that may be administered as supplemental agents in combination with the IL10R binding molecules of the present disclosure (and optionally additional supplemental agents) for the treatment of the indicated autoimmune disease include but are not limited toatezolizumab, olaratumab, ixekizumab, trastuzumab, infliximab, rituximab, edrecolomab, daratumumab, elotuzumab, necitumumab, dinutuximab, nivolumab, blinatumomab, pembrolizumab, pertuzumab, brentuximab vedotin, ipilimumab, ofatumumab, certolizumab pegol, catumaxomab, panitumumab, bevacizumab, ramucirumab, siltuximab, enfortumab vedotin, polatuzumab vedotin, [fam]-trastuzumab deruxtecan, cemiplimab, moxetumomab pasudotox, mogamuizumab, tildrakizumab, ibalizumab, durvalumab, inotuzumab, ozogamicin, avelumab, obinutuzumab, ado-trastuzumab emtansine, cetuximab, tositumomab-I131, ibritumomab tiuxetan, gemtuzumab, and ozogamicin.

The foregoing antibodies useful as supplemental agents in the practice of the methods of the present disclosure may be administered alone or in the form of any antibody drug conjugate (ADC) comprising the antibody, linker, and one or more drugs (e.g. 1, 2, 3, 4, 5, 6, 7, or 8 drugs) or in modified form (e.g. PEGylated).

Supplemental Agents Useful in The Treatment of Neoplastic Disease:

In some embodiments, the supplemental agent is a chemotherapeutic agent. In some embodiments the supplemental agent is a "cocktail" of multiple chemotherapeutic agents. IN some embodiments the chemotherapeutic agent or cocktail is administered in combination with one or more physical methods (e.g. radiation therapy). The term "chemotherapeutic agents" includes but is not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins such as bleomycin A2, cactinomycin, calicheamicin, carabicin, caminomycin, carzinophilin, chromomycins, dactinomycin, daunorubicin and derivaties such as demethoxy-daunomycin, 11-deoxydaunorubicin, 13-deoxydaunorubicin, detorubicin, 6-diazo-5-oxo-L-norleucine, doxorubicin, epirubicin, esorubicin, idarubicin, marcellomycin, mitomycins such as mitomycin C, N-methyl mitomycin C; mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate, dideazatetrahydrofolic acid, and folinic acid; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel, nab-paclitaxel and doxetaxel; chlorambucil; gemcitabine; 6-thioguanine; mercaptopurine; methotrexate; platinum and platinum coordination complexes such as cisplatin, oxaplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylomithine (DMFO); retinoic acid; esperamicins; capecitabine; taxanes such as paclitaxel, docetaxel, cabazitaxel; carminomycin, adriamycins such as 4'-epiadriamycin, 4-adriamycin-14-benzoate, adriamycin-14-octanoate, adriamycin-14-naphthaleneacetate; cholchicine and pharmaceutically acceptable salts, acids or derivatives of any of the above.

The term "chemotherapeutic agents" also includes anti-hormonal agents that act to regulate or inhibit hormone action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above.

In some embodiments, a supplemental agent isone or more chemical or biological agents identified in the art as useful in the treatment of neoplastic disease, including, but not limited to, a cytokines or cytokine antagonists such as IL-12, INFα, or anti-epidermal growth factor receptor, irinotecan; tetrahydrofolate antimetabolites such as pemetrexed; antibodies against tumor antigens, a complex of a monoclonal antibody and toxin, a T-cell adjuvant, bone marrow transplant, or antigen presenting cells (e.g., dendritic cell therapy), anti-tumor vaccines, replication competent viruses, signal transduction inhibitors (e.g., Gleevec® or Herceptin®) or an immunomodulator to achieve additive or synergistic suppression of tumor growth, non-steroidal anti-inflammatory drugs (NSAIDs), cyclooxygenase-2 (COX-2) inhibitors, steroids, TNF antagonists (e.g., Remicade® and Enbrel®), interferon-β1a (Avonex®), and interferon-β1b (Betaseron®) as well as combinations of one or more of the foreoing as practied in known chemotherapeutic treatment regimens including but not limited to TAC, FOLFOX, TPC, FEC, ADE, FOLFOX-6, EPOCH, CHOP, CMF, CVP, BEP, OFF, FLOX, CVD, TC, FOLFIRI, PCV, FOLFOXIRI, ICE-V, XELOX, and others that are readily appreciated by the skilled clinician in the art.

In some embodiments, the hIL10R binding molecule is administered in combination with BRAF/MEK inhibitors, kinase inhibitors such as sunitinib, PARP inhibitors such as olaparib, EGFR inhibitors such as osimertinib (Ahn, et al. (2016) J Thorac Oncol 11:S115), IDO inhibitors such as epacadostat, and oncolytic viruses such as talimogene laherparepvec (T-VEC).

In some embodiments, a "supplemental agent" is a therapeutic antibody (including bi-specific and tri-specific antibodies which bind to one or more tumor associated antigens including but not limited to bispecific T cell engagers (BITEs), dual affinity retargeting (DART) constructs, and trispecific killer engager (TriKE) constructs).

In some embodiments, the therapeutic antibody is an antibody that binds to at least one tumor antigen selected from the group consisting of HER2 (e.g. trastuzumab, pertuzumab, ado-trastuzumab emtansine), nectin-4 (e.g. enfortumab), CD79 (e.g. polatuzumab vedotin), CTLA4 (e.g. ipilumumab), CD22 (e.g. moxetumomab pasudotox), CCR4 (e.g. magamuizumab), IL23p19 (e.g. tildrakizumab), PDL1 (e.g. durvalumab, avelumab, atezolizumab), IL17a (e.g. ixekizumab), CD38 (e.g. daratumumab), SLAMF7 (e.g. elotuzumab), CD20 (e.g. rituximab, tositumomab, ibritumomab and ofatumumab), CD30 (e.g. brentuximab vedotin), CD33 (e.g. gemtuzumab ozogamicin), CD52 (e.g. alemtuzumab), EpCam, CEA, fpA33, TAG-72, CAIX, PSMA, PSA, folate binding protein, GD2 (e.g. dinuntuximab), GD3, IL6 (e.g. silutxumab) GM2, Ley, VEGF (e.g. bevacizumab), VEGFR, VEGFR2 (e.g. ramucirumab), PDGFR (e.g. olartumumab), EGFR (e.g. cetuximab, panitumumab and necitumumab), ERBB2 (e.g. trastuzumab), ERBB3, MET, IGF1R, EPHA3, TRAIL R1, TRAIL R2, RANKL RAP, tenascin, integrin aVP3, and integrin a4s1.

Examples of antibody therapeutics which are FDA approved and may be used as supplemental agents for use in the treatment of neoplastic disease include those provided in the table below.

| Name | Tradename(s) | Target; format | Indication |
|---|---|---|---|
| [fam]-trastuzumab deruxtecan | Enhertu | HER2; Humanized IgG1 ADC | HER2+ breast cancer |
| Enfortumab vedotin | Padcev | Nectin-4; Human IgG1 ADC | Urothelial cancer |
| Polatuzumab vedotin | Polivy | CD79b; Humanized IgG1 ADC | Diffuse large B-cell lymphoma |
| Cemiplimab | Libtayo | PD-1; Human mAb | Cutaneous squamous cell carcinoma |
| Moxetumomab pasudotox | Lumoxiti | CD22; Murine IgG1 dsFv immunotoxin | Hairy cell leukemia |
| Mogamuizumab | Poteligeo | CCR4; Humanized IgG1 | Cutaneous T cell lymphoma |
| Tildrakizumab | Ilumya | IL23p19; Humanized IgG1 | Plaque psoriasis |
| Ibalizumab | Trogarzo | CD4; Humanized IgG4 | HIV infection |
| Durvalumab | IMFINZI | PD-L1; Human IgG1 | Bladder cancer |
| Inotuzumab ozogamicin | BESPONSA | CD22; Humanized IgG4, ADC | Hematological malignancy |

-continued

| Name | Tradename(s) | Target; format | Indication |
|---|---|---|---|
| Avelumab | Bavencio | PD-L1; Human IgG1 | Merkel cell carcinoma |
| Atezolizumab | Tecentriq | PD-L1; Humanized IgG1 | Bladder cancer |
| Olaratumab | Lartruvo | PDGRFα; Human IgG1 | Soft tissue sarcoma |
| Ixekizumab | Taltz | IL-17a; Humanized IgG4 | Psoriasis |
| Daratumumab | Darzalex | CD38; Human IgG1 | Multiple myeloma |
| Elotuzumab | Empliciti | SLAMF7; Humanized IgG1 | Multiple myeloma |
| Necitumumab | Portrazza | EGFR; Human IgG1 | Non-small cell lung cancer |
| Dinutuximab | Unituxin | GD2; Chimeric IgG1 | Neuroblastoma |
| Nivolumab | Opdivo | PD1; Human IgG4 | Melanoma, non-small cell lung cancer |
| Blinatumomab | Blincyto | CD19, CD3; Murine bispecific tandem scFv | Acute lymphoblastic leukemia |
| Pembrolizumab | Keytruda | PD1; Humanized IgG4 | Melanoma |
| Ramucirumab | Cyramza | VEGFR2; Human IgG1 | Gastric cancer |
| Siltuximab | Sylvant | IL-6; Chimeric IgG1 | Castleman disease |
| Obinutuzumab | Gazyva | CD20; Humanized IgG1; Glycoengineered | Chronic lymphocytic leukemia |
| Ado-trastuzumab emtansine | Kadcyla | HER2; Humanized IgG1, ADC | Breast cancer |
| Pertuzumab | Perjeta | HER2; Humanized IgG1 | Breast Cancer |
| Brentuximab vedotin | Adcetris | CD30; Chimeric IgG1, ADC | Hodgkin lymphoma, systemic anaplastic large cell lymphoma |
| Ipilimumab | Yervoy | CTLA-4; Human IgG1 | Metastatic melanoma |
| Ofatumumab | Arzerra | CD20; Human IgG1 | Chronic lymphocytic leukemia |
| Certolizumab pegol | Cimzia | TNF; Humanized Fab, pegylated | Crohn disease |
| Catumaxomab | Removab | EPCAM/CD3;Rat/mouse bispecific mAb | Malignant ascites |
| Panitumumab | Vectibix | EGFR; Human IgG2 | Colorectal cancer |
| Bevacizumab | Avastin | VEGF; Humanized IgG1 | Colorectal cancer |
| Cetuximab | Erbitux | EGFR; Chimeric IgG1 | Colorectal cancer |
| Tositumomab-I131 | Bexxar | CD20; Murine IgG2a | Non-Hodgkin lymphoma |
| Ibritumomab tiuxetan | Zevalin | CD20; Murine IgG1 | Non-Hodgkin lymphoma |
| Gemtuzumab ozogamicin | Mylotarg | CD33; Humanized IgG4, ADC | Acute myeloid leukemia |
| Trastuzumab | Herceptin | HER2; Humanized IgG1 | Breast cancer |
| Infliximab | Remicade | TNF; Chimeric IgG1 | Crohn disease |
| Rituximab | MabThera, Rituxan | CD20; Chimeric IgG1 | Non-Hodgkin lymphoma |
| Edrecolomab | Panorex | EpCAM; Murine IgG2a | Colorectal cancer |

In some embodiments, where the antibody is a bispecific antibody targeting a first and second tumor antigen such as HER2 and HER3 (abbreviated HER2×HER3), FAP×DR-5 bispecific antibodies, CEA×CD3 bispecific antibodies, CD20×CD3 bispecific antibodies, EGFR-EDV-miR16 trispecific antibodies, gp100×CD3 bispecific antibodies, Ny-eso×CD3 bispecific antibodies, EGFR×cMet bispecific antibodies, BCMA×CD3 bispecific antibodies, EGFR-EDV bispecific antibodies, CLEC12A×CD3 bispecific antibodies, HER2×HER3 bispecific antibodies, Lgr5×EGFR bispecific antibodies, PD1×CTLA-4 bispecific antibodies, CD123×CD3 bispecific antibodies, gpA33×CD3 bispecific antibodies, B7-H3×CD3 bispecific antibodies, LAG-3×PD1 bispecific antibodies, DLL4×VEGF bispecific antibodies, Cadherin-P×CD3 bispecific antibodies, BCMA×CD3 bispecific antibodies, DLL4×VEGF bispecific antibodies, CD20×CD3 bispecific antibodies, Ang-2×VEGF-A bispecific antibodies, CD20×CD3 bispecific antibodies, CD123×CD3 bispecific antibodies, SSTR2×CD3 bispecific antibodies, PD1×CTLA-4 bispecific antibodies, HER2×HER2 bispecific antibodies, GPC3×CD3 bispecific antibodies, PSMA×CD3 bispecific antibodies, LAG-3×PD-L1 bispecific antibodies, CD38×CD3 bispecific antibodies, HER2×CD3 bispecific antibodies, GD2×CD3 bispecific antibodies, and CD33× CD3 bispecific antibodies. Such therapeutic antibodies may be further conjugated to one or more chemotherapeutic agents (e.g antibody drug conjugates or ADCs) directly or through a linker, especially acid, base or enzymatically labile linkers.

In some embodiments, a supplemental agent is one or more non-pharmacological modalities (e.g., localized radiation therapy or total body radiation therapy or surgery). By way of example, the present disclosure contemplates treatment regimens wherein a radiation phase is preceded or followed by treatment with a treatment regimen comprising an IL10R binding molecule and one or more supplemental agents. In some embodiments, the present disclosure further contemplates the use of an IL10R binding molecule in combination with surgery (e.g. tumor resection). In some embodiments, the present disclosure further contemplates the use of an IL10R binding molecule in combination with bone marrow transplantation, peripheral blood stem cell transplantation or other types of transplantation therapy.

some embodiments, a "supplemental agent" is an immune checkpoint modulator for the treatment and/or prevention neoplastic disease in a subject as well as diseases, disorders or conditions associated with neoplastic disease. The term "immune checkpoint pathway" refers to biological response that is triggered by the binding of a first molecule (e.g. a protein such as PD1) that is expressed on an antigen presenting cell (APC) to a second molecule (e.g. a protein such as PDL1) that is expressed on an immune cell (e.g. a T-cell) which modulates the immune response, either through stimulation (e.g. upregulation of T-cell activity) or inhibition (e.g. downregulation of T-cell activity) of the immune response. The molecules that are involved in the formation of the binding pair that modulate the immune response are commonly referred to as "immune checkpoints." The biological responses modulated by such immune checkpoint pathways are mediated by intracellular signaling pathways that lead to downstream immune effector pathways, such as cell activation, cytokine production, cell migration, cytotoxic factor secretion, and antibody production. Immune checkpoint pathways are commonly triggered by the binding of a first cell surface expressed molecule to a second cell surface molecule associated with the immune checkpoint pathway (e.g. binding of PD1 to PDL1, CTLA4 to CD28, etc.). The activation of immune checkpoint pathways can lead to stimulation or inhibition of the immune response.

In one embodiment, the immune checkpoint pathway modulator is an antagonist of a negative immune checkpoint pathway that inhibits the binding of PD1 to PDL1 and/or PDL2 ("PD1 pathway inhibitor"). PD1 pathway inhibitors result in the stimulation of a range of favorable immune response such as reversal of T-cell exhaustion, restoration cytokine production, and expansion of antigen-dependent T-cells. PD1 pathway inhibitors have been recognized as effective variety of cancers receiving approval from the USFDA for the treatment of variety of cancers including melanoma, lung cancer, kidney cancer, Hodgkins lymphoma, head and neck cancer, bladder cancer and urothelial cancer.

The term PD1 pathway inhibitors includes monoclonal antibodies that interfere with the binding of PD1 to PDL1 and/or PDL2. Antibody PD1 pathway inhibitors are well known in the art. Examples of commercially available PD1 pathway inhibitors that monoclonal antibodies that interfere with the binding of PD1 to PDL1 and/or PDL2 include nivolumab (Opdivo®, BMS-936558, MDX1106, commercially available from BristolMyers Squibb, Princeton NJ), pembrolizumab (Keytruda®MK-3475, lambrolizumab, commercially available from Merck and Company, Kenilworth NJ), and atezolizumab (Tecentriq®, Genentech/Roche, South San Francisco CA). Additional PD1 pathway inhibitors antibodies are in clinical development including but not limited to durvalumab (MEDI4736, Medimmune/AstraZeneca), pidilizumab (CT-011, CureTech), PDR001 (Novartis), BMS-936559 (MDX1105, BristolMyers Squibb), and avelumab (MSB0010718C, Merck Serono/Pfizer) and SHR-1210 (Incyte). Additional antibody PD1 pathway inhibitors are described in U.S. Pat. No. 8,217,149 (Genentech, Inc) issued Jul. 10, 2012; U.S. Pat. No. 8,168,757 (Merck Sharp and Dohme Corp.) issued May 1, 2012, U.S. Pat. No. 8,008,449 (Medarex) issued Aug. 30, 2011, U.S. Pat. No. 7,943,743 (Medarex, Inc) issued May 17, 2011.

In some embodiments, the methods of the disclosure may include the combination of the administration of an IL10R binding molecules with supplemental agents in the form of cell therapies for the treatment of neoplastic, autoimmune or inflammatory diseases. Examples of cell therapies that are amenable to use in combination with the methods of the present disclosure include but are not limited to engineered T cell products comprising one or more activated CAR-T cells, engineered TCR cells, tumor infiltrating lymphocytes (TILs), engineered Treg cells. As engineered T-cell products are commonly activated ex vivo prior to their administration to the subject and therefore provide upregulated levels of CD25, cell products comprising such activated engineered T cells types are amenable to further support via the administration of an CD25 biased IL10R binding molecule as described herein. Examples of commercially available CAR-T cell products that may be modified to incorporate an orthogonal receptor of the present invention include axicabtagene ciloleucel (marketed as Yescarta® commercially available from Gilead Pharmaceuticals) and tisagenlecleucel (marketed as Kymriah® commercially available from Novartis).

Prophylactic Applications

In some embodiments where the IL10R binding molecule is used in prophylaxis of disease, the supplementary agent may be a vaccine. The IL10R binding molecule of the present invention may be administered to a subject in combination with vaccines as an adjuvant to enhance the immune response to the vaccine in accordance with the teaching of Doyle, et al U.S. Pat. No. 5,800,819 issued Sep. 1, 1998. Examples of vaccines that may be combined with the IL10R binding molecule of the present invention include are HSV vaccines, *Bordetella pertussis, Escherichia coli* vaccines, pneumococcal vaccines including multivalent pneumococcal vaccines such as Prevnar® 13, diptheria, tetanus and pertussis vaccines (including combination vaccines such as Pediatrix®) and Pentacel®), varicella vaccines, *Haemophilus influenzae* type B vaccines, human papilloma virus vaccines such as Garasil®, polio vaccines, Leptospirosis vaccines, combination respiratory vaccine, *Moraxella* vaccines, and attenuated live or killed virus vaccine products such as bovine respiratory disease vaccine (RSV), multivalent human influenza vaccines such as Fluzone® and Quadravlent Fluzone®), feline leukemia vaccine, transmissible gastroenteritis vaccine, COVID-19 vaccine, and rabies vaccine.

TABLES

TABLE 1

| Amino Acid Abbreviations | | |
|---|---|---|
| G | Glycine | Gly |
| P | Proline | Pro |
| A | Alanine | Ala |
| V | Valine | Val |
| L | Leucine | Leu |
| I | Isoleucine | Ile |
| M | Methionine | Met |
| C | Cysteine | Cys |
| F | Phenylalanine | Phe |
| Y | Tyrosine | Tyr |
| W | Tryptophan | Trp |
| H | Histidine | His |
| K | Lysine | Lys |
| R | Arginine | Arg |
| Q | Glutamine | Gln |
| N | Asparagine | Asn |
| E | Glutamic Acid | Glu |
| D | Aspartic Acid | Asp |
| S | Serine | Ser |
| T | Threonine | Thr |

TABLE 2 hIL10Ra VHH CDR Amino Acid Sequences

| CDR1 AA Seq | CDR1 SEQ ID | CDR2 AA Seq | CDR2 SEQ ID | CDR3 AA Seq | CDR1 SEQ ID |
|---|---|---|---|---|---|
| YLYSIDYMA | 1 | VIYTASGATFYPDSVKG | 2 | VRKTDSYLFDAQSFTY | 3 |
| YLYSTNYMA | 4 | VIYTASGATLYTDSVKG | 5 | VRKTDSYLFDAQSFTY | 6 |
| YLYSTNYMA | 7 | VIYTASGATLYTDSVKG | 8 | VRKTDSYLFDAQSFTY | 9 |
| YLYSIDYMA | 10 | VIYTASGATFYPDSVKG | 11 | VRKTDSYLFDAQSFTY | 12 |
| YLYSTNYMA | 13 | AIYTASGATLYSDSNKG | 14 | VRKTGSYLFDAQSFTY | 15 |
| FTYSSYCMG | 16 | SIDSDGSTSYTDSVKG | 17 | DLMSTVVPGFCGFLLSAGMDY | 18 |
| YTENSNCMG | 19 | TIYTGVGSTYYADSVKG | 20 | EPLSRVYGGSCPTPTFGY | 21 |
| YTYSMYCMG | 22 | QINSDGSTSYADSVKG | 23 | DSRVYGGSWYERLCGPYTYEYNY | 24 |
| YAYSTYCMG | 25 | AIDSGGSTSYADSVKG | 26 | VPPPPDGGSCLFLGPEIKVSKADFRY | 27 |
| YLYSIDYMA | 28 | VIYTASGATFYPDSVKG | 29 | VRKTDSYLFDAQSFTY | 30 |
| YTYSSYCMG | 31 | VIDSDGSTSYADSVKG | 32 | DLGHYRPPCGVLYLGMDY | 33 |
| YTYSSNCMG | 34 | TIYTGGGNTYYADSVKG | 35 | EPLSRVYGGSCPTPTFDY | 36 |
| YSYSSNCMG | 37 | TIHTGGGSTYYADSVKG | 38 | EPLSRLYGGSCPTPTFGY | 39 |
| YTYSSYCMG | 40 | VIDSDGSTSYADSVKG | 41 | DLGHYRPPCGVLYLGMDY | 42 |
| YTYSGYCMG | 43 | VIDSDGSTSYADSVKG | 44 | DLGHYRPPCGVLYLGMDY | 45 |
| YTYSNYCMG | 46 | TIDSDGNTSYADSVKG | 47 | DLGHYRPPCGAYYYGMDY | 48 |
| YSNCSYDMT | 49 | AIHSDGSTRYADSVKG | 50 | DPLHCRAHGGSWYSVRANY | 51 |
| YTYNSNCMG | 52 | TIYTGVGSTYYADSVKG | 53 | EPLSRVYGGSCPTPTFGY | 54 |

TABLE 3 hIL10Rb VHH CDR Amino Acid Sequences

| CDR1 AA Seq | CDR1 SEQ ID | CDR2 AA Seq | CDR2 SEQ ID | CDR3 AA Seq | CDR3 SEQ ID |
|---|---|---|---|---|---|
| YTYSSGCMG | 55 | AINSDGSTSYADSVKG | 56 | EPYCSGGYPRWSVAEFGY | 57 |
| YTYSSYCMG | 58 | AIDSDGSTRYADSVKG | 59 | EPYCSGGYKRTMVAEFGY | 60 |
| YTYNSYCMG | 61 | TIDSDGMTRYADSVKG | 62 | DADCTIAAMTTNP | 63 |
| YLYSIDYMA | 64 | VIYTASGATFYPDSVKG | 65 | VRKTDSYLFDAQSFTY | 66 |
| YTYSSYCMG | 67 | HIDSDGSTTYADSVKG | 68 | DPIPGPGYCDGGPNKY | 69 |
| DLYSTNYVA | 70 | VIYTASGATLYSDSVKG | 71 | VRKTGHYLFDAQSFTY | 72 |
| YTYSSGCMG | 73 | TINSDGSTNYADSVKG | 74 | EPYCSGGYPRWSVAEFGY | 75 |
| YSYSSYCMG | 76 | AIASDGSTSYADSVKG | 77 | EPWCTGGYSRLTPAEYGY | 78 |
| YTYSSGCMG | 79 | TINSDGSTNYADSVKG | 80 | EPYCSGGYPRWSVAEFGY | 8 |
| YTYSSYCMG | 82 | HIDSDGSTTYADSVKG | 83 | DPIPGPGYCDGGPNKY | 84 |
| YTYSSYCMG | 85 | AIDSDGSTRYADSVKG | 86 | EPYCSGGYKRTMVAEFGY | 87 |
| YTYSSYCMG | 88 | HIDSDGSTTYADSVKG | 89 | DPIPGPGYCDGGPNKY | 90 |
| YTYSSYCMG | 91 | HIDSDGSTTYADSVKG | 92 | DPIPGPGYCDGGPNNY | 93 |
| YTYSSGCMG | 94 | TINSDGSTNYADSVKG | 95 | EPYCSGGYPRWSVAEFGY | 96 |
| YTASVNYMG | 97 | TIFTGAGTTYYANSVKG | 98 | DERGGLLYRPAYEYTY | 99 |

TABLE 3-continued hIL10Rb VHH CDR Amino Acid Sequences

| CDR1 AA Seq | CDR1 SEQ ID | CDR2 AA Seq | CDR2 SEQ ID | CDR3 AA Seq | CDR3 SEQ ID |
|---|---|---|---|---|---|
| YTHSSYCMG | 100 | AIDVDGSTTYADSVKG | 101 | EFADCSSNYFLPPGAVRY | 102 |
| YTASVNYMG | 103 | TIFTGAGTTYYANSVKG | 104 | DERGGLLYRPAYEYTY | 105 |
| DTYSSYCMG | 106 | FIDSDGSTRYADSVEG | 107 | EPYCSGGYHRKEMAEFGY | 108 |
| YTYSSYCMG | 109 | HIDSDGSTSYADSVKG | 110 | DPIPGPGYCDGGPNKY | 111 |
| YTYSSYCMG | 112 | HIDSDGSTTYADSVKG | 113 | DPIPGPGYCDGGPNKY | 114 |
| YTASNNCMG | 115 | VIFTGAGTSYYDSSVG | 116 | EDDCTLLLMTPNPDDQ | 117 |
| YTDSRYCMG | 118 | HIDSDGSTSYADSVKG | 119 | DPIPGPGYCDGGPNKY | 120 |
| YTYSSYCMG | 121 | AIDSDGSTRYADSVKG | 122 | EPYCSGGYKRTMVAEFGF | 123 |
| YTYSSYCMG | 124 | HIDSDGSTTYADSVKG | 125 | DPIPGPGYCDGGPNNY | 126 |
| YTYSSYCMG | 127 | HIDSDGSTTYADSVKG | 128 | DPIPGPGYCDGGPNNY | 129 |
| YSYSSYCMG | 130 | TIDSDGMTRYADSVKG | 131 | PLYDCDSGAVGRNPPY | 132 |
| YTYLRGCMG | 133 | VMDVVGDRRSYIDSVKG | 134 | GPNCVGWRSGLDY | 135 |

TABLE 4

ANTI MOUSE mIL10RB VHHs and CDRs Amino Acid (AA)

| CDR1 AA Seq | CDR1 SEQ ID | CDR2 AA Seq | CDR2 SEQ ID | CDR3 AA Seq | CDR3 SEQ ID |
|---|---|---|---|---|---|
| YTASSICMG | 136 | VITTAASGTYYADSVNG | 137 | TRRGGDCLDPLQTPAVNT | 138 |
| DTYSRKYIA | 139 | VMYTPGSATYYTDTVMG | 140 | KASGSMFNFRDYTY | 141 |
| YASCSRAMR | 142 | YIDGVGSTGYADSV | 143 | GCRADGSNSLDNY | 144 |
| YTYNRRFMG | 145 | IIYTPNSSTFYADSVTG | 146 | ARIASMTELSVRDMDY | 147 |
| YIALNACMA | 148 | TIVTDGSRTYYADSVKG | 149 | DRRCPVSRAPYEYELRY | 150 |
| YTYNGKCMA | 151 | GIYTGGSSTYYADSVKG | 152 | SRSCSDLRRRSIAY | 153 |

TABLE 5 hIL10Ra VHH Amino Acid Sequences

| Name | VHH Amino Acid Sequence | SEQ ID |
|---|---|---|
| hIL10Ra VHH1 | QVQLQESGGGSIQAGGSLRLSCAASRYLYSIDYMAWFRQSPGKERE PVAVIYTASGATFYPDSVKGRFTISQDNAKMTVYLQMNSLKSEDTA MYYCAAVRKTDSYLFDAQSFTYWGQGTQVTVSS ( | 154 |
| hIL10Ra VHH2 | QVQLQESGGGSVQAGGSLRLSCVASRYLYSTNYMAWFRQSPGKERE AVAVIYTASGATLYTDSVKGRFTISQDNAKMTVYLQMNRLKSEDTA MYYCAAVRKTDSYLFDAQSFTYWGQGTQVTVSS | 155 |
| hIL10Ra VHH3 | QVQLQESGGGSIQAGGSLRLSCVASRYLYSTNYMAWFRQSPGKERE AVAVIYTASGATLYTDSVKGRFTISQDNAKMTVYLQMNRLKSEDTA MYYCAAVRKTDSYLFDAQSFTYWGQGTQVTVSS | 156 |
| hIL10Ra VHH4 | QVQLQESGGGSIQAGGSLRLSCAASRYLYSIDYMAWFRQSPGKERE PAAVIYTASGATFYPDSVKGRFTISQDNAKMTVYLQMNSLKSEDTA MYYCAAVRKTDSYLFDAQSFTYWGQGTQVTVSS | 157 |

TABLE 5-continued hIL10Ra VHH Amino Acid Sequences

| Name | VHH Amino Acid Sequence | SEQ ID |
|---|---|---|
| hIL10Ra VHH5 | QVQLQESGGGSIQAGGSLRLSCVASKYLYSTNYMAWFRQSPGERE AVAAIYTASGATLYSDSNKGRFTISQDNAKMTVYLQMNSLKSEDTA MYYCAAVRKTGSYLFDAQSFTYWGQGTQVTVSS | 158 |
| hIL10Ra VHH6 | QVQLQESGGGSVQAGGSLRLSCAASRFTYSSYCMGWFRQAPGERE GVASIDSDGSTSYTDSVKGRFTISKDNAKNTLYLQMNSLKPEDTAM YYCALDLMSTVVPGFCGFLLSAGMDYWGKGTQVTVSS | 159 |
| hIL10Ra VHH7 | QVQLQESGGGSVQAGGSLRLSCAVSGYTFNSNCMGWFRQAPGERE GVATIYTGVGSTYYADSVKGRFTISQDNAKNTVYLQMNSLKPEDTA MYYCAAEPLSRVYGGSCPTPTFGYWGQGTQVTVSS | 160 |
| hIL10Ra VHH8 | QVQLQESGGGSVQAGGSLRLSCAASGYTYSMYCMGWFRQAPGERE GVAQINSDGSTSYADSVKGRFTISKDNAKNTLYLQMNSLKPEDTAM YYCAADSRVYGGSWYERLCGPYTYEYNYWGQGTQVTVSS | 161 |
| hIL10Ra VHH9 | QVQLQESGGGSVQAGGSLRLSCAVSGYAYSTYCMGWFRQAPGERE GVAAIDSGGSTSYADSVKGRFTISKDNAKNTLYLRMNSLKPEDTAM YYCAAVPPPPDGGSCLFLGPEIKVSKADFRYWGQGTQVTVSS | 162 |
| hIL10Ra VHH10 | QVQLQESGGGSVQAGGSLRLSCAASRYLYSIDYMAWFRQSPGERE PVAVIYTASGATFYPDSVKGRFTISQDNAKMTVYLQMNSLKSEDTA MYYCAAVRKTDSYLFDAQSFTYWGQGTQVTVSS | 163 |
| hIL10Ra VHH11 | QVQLQESGGGSVQAGGSLRLSCGASRYTYSSYCMGWFRQAPGERE GVAVIDSDGSTSYADSVKGRFTISKDNGKNTLYLQMNSLKPEDTAM YYCAADLGHYRPPCGVLYLGMDYWGKGTQVTVSS | 164 |
| hIL10Ra VHH12 | QVQLQESGGGSVQAGGSLRLSCTVSGYTYSSNCMGWFRQAPGERE GVATIYTGGGNTYYADSVKGRFTISQDNAKNTVYLQMNNLKPEDTA MYYCAAEPLSRVYGGSCPTPTFDYWGQGTQVTVSS | 165 |
| hIL10Ra VHH13 | QVQLQESGGGSVQAGGSLRLSCAVSGYSYSSNCMGWFRQAPGERE GVATIHTGGGSTYYADSVKGRFTISQDNAKNTVYLQMNSLKPEDTA MYYCAAEPLSRLYGGSCPTPTFGYWGQGTQVTVSS | 166 |
| hIL10Ra VHH14 | QVQLQESGGGSVQAGGSLRLSCGASGYTYSSYCMGWFRQVPGKERE GVAVIDSDGSTSYADSVKGRFTISKDNGKNTLYLQMNSLKPEDTAM YYCAADLGHYRPPCGVLYLGMDYWGKGTQVTVSS | 167 |
| hIL10Ra VHH15 | QVQLQESGGGSVQAGGSLRLSCGASGYTYSGYCMGWFRQAPGKERE GVAVIDSDGSTSYADSVKGRFTISKDNGKNTLYLQMNSLKPEDTAM YYCAADLGHYRPPCGVLYLGMDYWGKGTQVTVSS | 168 |
| hIL10Ra VHH16 | QVQLQESGGGSVQAGGSLRLACAASRYTYSNYCMGWFRQAPGKERE GVATIDSDGNTSYADSVKGRFTISRDNAKNTLYLQMNSLKPGDTAM YYCAADLGHYRPPCGAYYYGMDYWGKGTQVTVSS | 169 |
| hIL10Ra VHH17 | QVQLQESGGGSVQAGGSLRLSCAASGYSNCSYDMTWYRQAPGKERE FVSAIHSDGSTRYADSVKGRFFISQDNAKNTVYLQMNSLKPEDTAM YYCKTDPLHCRAHGGSWYSVRANYWGQGTQVTVSS | 170 |
| hIL10Ra VHH18 | QVQLQESGGGSVQAGGSLRLSCAVSGYTYNSNCMGWFRQAPGKERE GVATIYTGVGSTYYADSVKGRFTISQDNAKNTVYLQMNSLKPEDTA MYYCAAEPLSRVYGGSCPTPTFGYWGQGTQVTVSS | 171 |

TABLE 6

ANTI HUMAN hIL10Rb VHH Sequences

| Name | VHH AA Sequence (CDRs Underlined) | SEQ ID |
|---|---|---|
| IL10Rb VHH-1 | QVQLQESGGGSVQAGGSLRLSCAASG<u>YTYSSGCM</u>GWFRQAPGKEREAVA AI<u>NSDGSTSYADSVK</u>GRFTISKDNAKNTLYLQMNSLKPEDTAMYYCAAE <u>PYCSGGYPRWSVAEFGY</u>WGQGTQVTVSS | 172 |
| hIL10Rb VHH-2 | QVQLQESGGGSVQAGGSLRLSCAASG<u>YTYSSYCM</u>GWFRQAPGKEREGVA AI<u>DSDGSTRYADSVK</u>GRFTISKDNAKNTLYLQMNSLKPEDTAMYYCAAE <u>PYCSGGYKRTMVAEFGY</u>WGQGTQVTVSS | 173 |
| hIL10Rb VHH-3 | QVQLQESGGGSVQAGGSLRLSCAASR<u>YTYNSYCM</u>GWFRQAPGKEREGVA <u>TIDSDGMTRYADSVK</u>GRFTISKDNAKNTLYLQMNSLKPEDTAMYYCAAD <u>ADCTIAAMTTNPLG</u>QGTQVTVSS | 174 |

TABLE 6-continued

ANTI HUMAN hIL10Rb VHH Sequences

| Name | VHH AA Sequence (CDRs Underlined) | SEQ ID |
|---|---|---|
| hIL10Rb VHH-4 | QVQLQESGGGSIQAGGSLRLSCAAS<u>RYLYSIDYMA</u>WFRQSPGKEREPVA<br>VI<u>YTASGATFYPDS</u>VKGRFTISQDNAKMTVYLQMNSLKSEDTAMYYCAA<br><u>VRKTDSYLFDAQSFTY</u>WGQGTQVTVSS | 175 |
| hIL10Rb VHH-5 | QVQLQESGGGLVQPGGSLRLSCAASG<u>YTYSSYCMG</u>WFRQAPGKEREGVA<br>HI<u>DSDGSTTYADS</u>VKGRFTISKDNAKNTLYLQMNSLKPEDTAMYYCAAD<br><u>PIPGPGYCDGGPNKY</u>WGQGTQVTVSS | 176 |
| hIL10Rb VHH-6 | QVQLQESGGGSIQAGGSLTLSCAAS<u>RDLYSTNYVA</u>WFRQSPGKEREAVA<br>VI<u>YTASGATLYSDS</u>VKGRFTISQDNAKMTVYLQMNSLKSEDTAMYYCAA<br><u>VRKTGHYLFDAQSFTY</u>WGQGTQVTVSS | 177 |
| hIL10Rb VHH-7 | QVQLQESGGGSVQAGGSLRLSCAASG<u>YTYSSGCMG</u>WFRQAPGKEREGVA<br>TI<u>NSDGSTNYADS</u>VKGRFTISKDNAKNTLYLQMNSLKPEDTAMYYCAAE<br><u>PYCSGGYPRWSVAEFGY</u>WGQGTQVTVSS | 178 |
| hIL10Rb VHH-8 | QVQLQESGGGSVQAGGSLRLSCAASG<u>YSYSSYCMG</u>WFRQAPGKEREGVA<br>AI<u>ASDGSTSYADS</u>VKGRFAISKDNAKNTLYLQMASLKPEDTAMYYCAAE<br><u>PWCTGGYSRLTPAEYGY</u>WGQGTQVTVSS | 179 |
| hIL10Rb VHH-9 | QVQLQESGGGLVQPGGSLRLSCAASG<u>YTYSSGCMG</u>WFRQAPGKEREGVA<br>TI<u>NSDGSTNYADS</u>VKGRFTISKDNAKNTLYLQMNSLKPEDTAMYYCAAE<br><u>PYCSGGYPRWSVAEFGY</u>WGQGTQVTVSS | 180 |
| hIL10Rb VHH-10 | QVQLQESGGGLVQPGGSLRLSCAASG<u>YTYSSYCMG</u>WFRQAPGKEREGVA<br>HI<u>DSDGSTTYADS</u>VKGRFAISKDNAKNTLYLQMNSLKPEDTAMYYCAAD<br><u>PIPGPGYCDGGPNKY</u>WGQGTQVTVSS | 181 |
| hIL10Rb VHH-11 | QVQLQESGGGSVQAGGSLRLSCAASG<u>YTYSSYCMG</u>WFRQAPGKGREGVA<br>AI<u>DSDGSTRYADS</u>VKGRFTISKDNAKNTLYLQMNSLKPEDTAMYYCAAE<br><u>PYCSGGYKRTMVAEFGY</u>WGQGTQVTVSS | 182 |
| hIL10Rb VHH-12 | QVQLQESGGGSVQAGGSLRLSCAASG<u>YTYSSYCMG</u>WFRQAPGKEREGVA<br>HI<u>DSDGSTSYADS</u>VKGRFTISKDNAKNTLYLQMNSLKPEDTAMYYCAAD<br><u>PIPGPGYCDGGPNKY</u>WGQGTQVTVSS | 183 |
| hIL10Rb VHH-13 | QVQLQESGGGSVQAGGSLRLSCAASG<u>YTYSSYCMG</u>WFRQAPGKEREGVA<br>HI<u>DSDGSTSYADS</u>VKGRFTISKDNAKNTLYLQMNSLKPEDTAMYYCAAD<br><u>PIPGPGYCDGGPNNY</u>WGQGTQVTVSS | 184 |
| hIL10Rb VHH-14 | QVQLQESGGGSVQAGGSLRLSCAASG<u>YTYSSGCMG</u>WFRQAPGKEREGVA<br>TI<u>NSDGSTNYADS</u>VKGRFTISKDNAKNTLYLQMNSLKPEDTGMYYCAAE<br><u>PYCSGGYPRWSVAEFGY</u>WGQGTQVTVSS | 185 |
| hIL10Rb VHH-15 | QVQLQESGGGSVQAGGSLRLSCTVS<u>RYTASVNYMG</u>WFRQAPGKEREGVA<br>TI<u>FTGAGTTYYANS</u>VKGRFTISRDNAKNTAYLQMNSLKPEDTAIYYCAV<br><u>DFRGGLLYRPAYEYTY</u>RGQGTQVTVSS | 186 |
| hIL10Rb VHH-16 | QVQLQESGGGSVEAGGSLRLSCAASG<u>YTHSSYCMG</u>WFRQAPGKEREGVA<br>AI<u>DVDGSTTYADS</u>VKGRFTISKDNAKNTLYLQMNSLKPEDTGMYYCAAE<br><u>FADCSSNYFLPPGAVRY</u>WGQGTQVTVSS | 187 |
| hIL10Rb VHH-17 | QVQLQESGGGSVQAGGSLRLSCTVS<u>RYTASVNYMG</u>WFRQAPGKEREGVA<br>TI<u>FTGAGTTYYANS</u>VKGRFTISRDNAKNTAYLQMNSLKPEDTAMYYCAV<br><u>DFRGGLLYRPAYEYTY</u>RGQGTQVTVSS | 188 |
| hIL10Rb VHH-18 | QVQLQESGGGSVQAGGSLRLSCAASG<u>DTYSSYCMG</u>WFRQAPGKEREGVA<br>FI<u>DSDGSTRYADS</u>VEGRFTISKDNAKNTLYLQMNSLKPEDTAMYYCAAE<br><u>PYCSGGYHRKEMAEFGY</u>WGQGTQVTVSS | 189 |
| hIL10Rb VHH-19 | QVQLQESGGGSVQAGGSLRLSCAASG<u>YTYSSYCMG</u>WFRQAPGKEREGVA<br>HI<u>DSDGSTSYADS</u>VKGRFTISKDNAKNTLYLQMNSLKPEDTAMYYCAAD<br><u>PIPGPGYCDGGPNKY</u>RGQGTQVTVSS | 190 |
| hIL10Rb VHH-20 | QVQLQESGGGSVQAGGSLRLSCAASG<u>YTYSSYCMG</u>WFRQAPGKEREGVA<br>HI<u>DSDGSTTYADS</u>VKGRFAISKDNAKNTLYLQMNSLKPEDTAMYYCAAD<br><u>PIPGPGYCDGGPNKY</u>WGQGTQVTVSS | 191 |
| hIL10Rb VHH-21 | QVQLQESGGGSVQAGGSLRLSCTGS<u>GYTASNNCMG</u>WFRQAPGKEREGVA<br>VI<u>FTGAGTSYYDSS</u>VGRLFISSQDAASTLDQLLMSLLPDDTAVMYCAE<br><u>DDCTLLLMTPNPDDQ</u>WSRLSVSS | 192 |
| hIL10Rb VHH-22 | QVQLQESGGGSVQAGGSLRLSCAASG<u>YTDSRYCMG</u>WFRKAPGKEREGVA<br>HI<u>DSDGSTSYADS</u>VKGRFTISKDNAKNTLYLQMNSLKPEDTAMYYCAAD<br><u>PIPGPGYCDGGPNKY</u>WGQGTQVTVSS | 193 |

TABLE 6-continued

ANTI HUMAN hIL10Rb VHH Sequences

| Name | VHH AA Sequence (CDRs Underlined) | SEQ ID |
|---|---|---|
| hIL10Rb VHH-23 | QVQLQESGGGSVQAGGSLRLSCAASGYTYSSYCMGWFRQAPGKEREGVA AIDSDGSTRYADSVKGRFTISKDNAKKILYLQMNSLKVEDTAMYYCAAE PYCSGGYKRTMVAEFGFWGQGTQVTVSS | 194 |
| hIL10Rb VHH-24 | QVQLQESGGGSVQAGGSLKLSCAASGYTYSSYCMGWFRQAPGKEREGVA HIDSDGSTTYADSVKGRFTISKDNAKNTLYLQMNSLKPEDTAMYYCAAD PIPGPGYCDGGPNNYWGQGTQVTVSS | 195 |
| hIL10Rb VHH-25 | QVQLQESGGGSVQAGGSLRLSCAASGYTYSSYCMGWFRQAPGKEREGIA HIDSDGSTTYADSVKGRFTISKDNAKNTLYLQMNSLKPEDTAMYYCAAD PIPGPGYCDGGPNNYWGQGTQVTVSS | 196 |
| hIL10Rb VHH-26 | QVQLQESGGGSVQAGGSLRLSCAASGYSYSSYCMGWFRQAPGKEREGVA TIDSDGMTRYADSVKGRFTISKDNAKNTLYLQMNSLKPEDTAMYYCAAP LYDCDSGAVGRNPPYWGQGTQVTVSS | 197 |
| hIL10Rb VHH-27 | QVQLQESGGGSVQTGGSLRLSCAASGYTYLRGCMGWFRQAPGKEREGVA VMDVVGDRRSYIDSVKGRFTISRDNAANSVYLQMDNLKPEDTAMYYCTA GPNCVGWRSGLDYWGQGTQVTVSS | 198 |

TABLE 7

ANTI MOUSE mIL10RB VHHs and CDRs Amino Acid (AA) Sequences

| Name | VHH AA Sequence | SEQ ID |
|---|---|---|
| DR1322 | QVQLQESGGGSVQAGGALRLSCTASGYTASSICMGWFRQAPGKERERVAVITTAASGTYYADSVNGRFSISQNNAKNTVYLQMNSLKPDDTAMYYCAATRRGGDCLDPLQTPAYNTWGQGTQVTVSS | 199 |
| DR1323 | QVQLQESGGGSVQAGGSLRLSCVASGDTYSRKYIAWVRQVPGKEREGVAVMYTPGSATYYDTVMGRFTISQDNAKNTVYLQMNSLKPEDTAMYFCAAKASGSMFNFRDYTYWGQGTQVTVSS | 200 |
| DR1324 | QVQLQESGGGSVQAGGSLRLSCATSGYASCSRAMRWYRQAPGKEREFVAYIDGVSTGYADSVKGRFTISQDNAKYTAYLQMNSLKPEDTAMYYCNRGCRADGSNSLDNYWGQGTQVTVSS | 201 |
| DR1325 | QVQLQESGGGSVQAGGSLRLSCAASGYTYNRRFMGWFRQAPGKEREGLAIIYTPNSSTFYADSVTGRFTISQDSARNTVYLQMNSLKPEDTAMYYCAAARIASMTELSVRDMDYWGKGTQVTVSS | 202 |
| DR1326 | QVQLQESGGGSVQAGGSLRLSCTASRYIALNACMAWIRQAPGSEREVVATIVTDGSRTYYADSVKGRFTISQDNAKNTMYLQMNGLKPEDTAMYYCAADRRCPVSRAPYEYELRYWGQGTQVTVSS | 203 |
| DR1327 | QVQLQESGGGSVQAGGSLRLSCAASGYTYNGKCMAWFRQAPGKEREVVAGIYTGGSSTYYADSVKGRFTISQDNAKNTVYLQMDSLKPEDTAMYYCATSRSCSDLRRRSIAYWGQGTQVTVSS | 204 |

TABLE 8 hIL10Ra VHH DNA Sequences

| VHH Name | Sequence | SEQ ID |
|---|---|---|
| hIL10Ra VHH1 | CAGGTTCAGCTTCAGGAGTCCGGTGGAGGCTCCATCCAGGCCGGGGCTCTCTCCGCCTGTCTTGCGCCGCTTCCAGATACCTCTACAGTATCGACTACATGGCTTGGTTTCGTCAGAGCCCAGGAAAAGAGCGGGAACCCGTGGCAGTAATCTACACTGCCTCAGGTGCCACATTTTACCCCGACTCTGTCAAGGGCAGGTTCACCATCTCTCAGGATAATGCCAAGATGACAGTGTACTTGCAGATGAACTCCCTGAAATCTGAGGATACCGCTATGTATTACTGTGCCGCAGTGCGCAAGACCGATTCTTACCTGTTCGACGCTCAGAGTTTTACCTACTGGGGCCAGGGCACTCAGGTCACCGTCAGCAGC | 205 |
| hIL10Ra VHH2 | CAGGTGCAGTTGCAGGAGTCCGGCGGGGGTTCCGTGCAAGCAGGCGGATCTCTGCGCCTGTCCTGCGCTGGCCTCTCGTTATTTGTATAGCACCAACTACATGGCTTGGTTCCGTCAGTCCCCAGGCAAAGAGCGCGAAGCCGTAGCCGTAATCTATACGGCCTCTGGGCAACACTCTATACCGACTCAGTGAAGGGACGCTTCACGATTTCCCAAGACAATGCAAAGATGACCGTGTACTTGCAGATGAACGCCCTGAAGAGCGAGGACACGGCTATGTATTACTGCGCAGCCGTGCGCAAGACCGACTCCTACTTGTTTGACGCTCAGTCCTTCACTTATTGGGGCCAGGGTACACAGGTCACCGTGAGCAGT | 206 |
| hIL10Ra VHH3 | CAAGTACAGCTCCAGGAGAGCGGCGGTGGATCTATCCAAGCAGGGGGTAGCCTTAGGTTGTCCTGTGTGGCGTCCAGATACCTGTATAGCACGAACTACATGGCATGGTTCAGACAGTCCCCAGGCAAGGAACGCGAGGCAGTCGCC | 207 |

TABLE 8-continued hIL10Ra VHH DNA Sequences

| VHH Name | Sequence | SEQ ID |
|---|---|---|
| | GTTATTTACACTGCATCTGGGGCCACCCTCTATACGGACAGCGTGAAGG<br>GAAGGTTTACAATCTCCCAGGACAACGCGAAGATGACCGTGTACCTTCA<br>GATGAACCGCCTGAAGTCCGAGGACACCGCCATGTATTACTGTGCAGCG<br>GTGCGCAAGACCGACAGCTATCTGTTCGACGCGCAGTCATTCACTTATT<br>GGGGCCAAGGAACCCAAGTGACCGTCAGCTCA | |
| hIL10Ra<br>VHH4 | CAGGTGCAGCTCCAAGAGTCCGGGGGAGGCTCTATCCAGGCGGGAGGCA<br>GTCTGCGCTTGTCCTGCGCCGCAAGTCGTTATCTGTACTCCATTGATTA<br>CATGGCATGGTTCCGCCAGTCCCCAGGTAAGGAACGTGAACCTGCCGCT<br>GTGATCTACACCGCTTCTGGAGCAACCTTTTATCCTGATAGCGTTAAGG<br>GTCGCTTCACCATCTCTCAGGATAACGCCAAAATGACAGTGTACCTCCA<br>GATGAACAGCCTGAAGTCTGAGGACACTGCCATGTACTATTGTGCGGCT<br>GTGCGCAAGACCGACTCCTATCTGTTTGATGCACAGAGCTTTACCTATT<br>GGGGTCAGGGCACCCAGGTGACTGTGTCTAGC | 208 |
| hIL10Ra<br>VHH5 | CAGGTCCAGTTGCAGGAGTCCGGTGGAGGTTCCATCCAGGCGGGTGGGT<br>CCCTTCGTCTCTCCTGCGTGGCCTCTAAGTACCTGTATTCAACCAACTA<br>CATGGCATGGTTCAGACAGTCTCCCGGCAAAGAGCGTGAGGCAGTGGCC<br>GCGATCTATACAGCTTCTGGGGCACCCTGTACTCTGATTCCAATAAGG<br>GAAGGTTCACTATCTCACAGGATAACGCCAAAATGACCGTCTACCTTCA<br>GATGAACAGCCTCAAGTCTGAAGACACGGCAATGTATTACTGTGCAGCG<br>GTGCGCAAAACTGGGAGCTACCTGTTTGACGCTCAGTCTTTCACTTATT<br>GGGGCCAGGGTACGCAGGTGACAGTCTCTTCT | 209 |
| hIL10Ra<br>VHH6 | CAGGTGCAACTCCAGGAGAGCGGAGGCGGTTCTGTTCAGGCAGGAGGTT<br>CCCTGAGACTGTCCTGTGCCGCGTCTCGCTTTACGTATTCATCCTACTG<br>CATGGGATGGTTCAGACAAGCGCCGGGGAAAGAAAGGGAAGGCGTGGCC<br>TCCATTGACTCCGACGGCTCAACTTCATACACTGATAGCGTGAAAGGCC<br>GGTTCACCATCTCTAAGGACAACGCGAAGAACACCCTGTATCTCCAGAT<br>GAACAGCCTCAAGCCTGAGGATACTGCCATGTACTATTGCGCACTCGAC<br>CTGATGTCTACTGTGGTCCCAGGCTTCTGCGGGTTCCTGCTCTCTGCTG<br>GCATGGACTACTGGGGGAAGGGCACTCAGGTAACGGTTAGCTCC | 210 |
| hIL10Ra<br>VHH7 | CAGGTGCAGCTTCAGGAATCTGGCGGGGGCTCCGTGCAGGCCGGGGGCT<br>CCCTCAGACTTTCCTGTGCCGTCTCCGGTTACACATTTAACAGTAACTG<br>TATGGGCTGGTTCCGCCAGGCACCAGGCAAGGAGAGGGAAGGTGTGGCC<br>ACAATCTATACTGGTGTTGGGAGTACGTACTATGCTGATTCCGTGAAAG<br>GTCGCTTCACAATTTCCCAGGACAACGCGAAGAACACTGTGTACTTGCA<br>GATGAATAGCCTGAAGCCTGAAGATACCGCAATGTATTACTGCGCTGCC<br>GAGCCACTCTCCCGCGTATATGGTGGAAGTTGCCCCACCCCCACTTTCG<br>GTTACTGGGGCCAGGGCACTCAAGTGACCGTGTCCTCT | 211 |
| hIL10Ra<br>VHH8 | CAGGTTCAGCTTCAGGAGTCTGGGGGCGGTTCAGTGCAGGCTGGCGGTT<br>CTCTCCGCCTGTCCTGCGCTGCCAGCGGCTATACTTACAGCATGTACTG<br>CATGGGCTGGTTCCGGCAAGCCCCCGGCAAAGAGCGTGAGGGCGTCGCT<br>CAAATCAACAGCGACGGGTCAACCAGCTACGCCGATTCTGTCAAGGGCA<br>GATTTACTATCAGCAAGGACAACGCCAAAAACACACTGTACCTCCAGAT<br>GAACTCTTTGAAGCCTGAGGACACCGCGATGTATTACTGCGCCGCTGAC<br>AGCCGCGTGTACGGTGGCAGCTGGTATGAGAGGCTGTGCGGCCCGTACA<br>CCTACGAGTACAACTATTGGGACAGGGCACGCAGGTGACAGTTAGCTC<br>C | 212 |
| hIL10Ra<br>VHH9 | CAGGTGCAACTGCAAGAGAGTGGCGGAGGCTCCGTCCAGGCTGGAGGTT<br>CCCTGCGGCTGTCTTGCGCCGTCAGCGGCTACGCATATTCCACTTACTG<br>TATGGGTTGGTTCCGCCAGGCCCCTGGAAAGGAACGCGAGGGTGTTGCC<br>GCTATTGATAGCGGAGGCTCCACATCCTATGCGGACTCCGTGAAAGGTC<br>GTTTCACCATCTCCAAGGATAACGCCAAGAACACTCTGTACCTGCGCAT<br>GAACTCTCTGAAGCCTGAAGACACTGCCATGTATTACTGCGCCGCTGTG<br>CCCCCTCCACCCGACGGGGGCTCTTGTCTGTTTCTTGGCCCGGAGATCA<br>AGGTGTCCAAGGCTGATTTCCGTTATTGGGGCCAGGGAACTCAAGTCAC<br>CGTGTCTTCC | 213 |
| hIL10Ra<br>VHH10 | CAGGTCCAGCTCCAGGAGTCCGGTGGAGGCTCCGTTCAGGCCGGTGGCA<br>GCTTGCGTCTGAGCTGCGCGGCTTCAAGATACCTGTACTCCATTGATTA<br>CATGGCATGGTTCCGTCAGTCTCCTGGCAAGGAGCGCGAGCCCGTCGCT<br>GTGATCTATACCGCCAGCGGAGCCACGTTCTACCCTGATTCCGTCAAGG<br>GCCGCTTCACCATTAGCCAAGACAACGCTAAGATGACGGTGTACCTCCA<br>AATGAATAGCCTGAAAAGCGAGGACACAGCGATGTATTACTGCGCCGCT<br>GTTAGGAAAACTGATAGTTACCTGTTCGATGCACAGTCTTTCACTTACT<br>GGGGGCAGGGCACCCAAGTTACCGTCTCCTCT | 214 |
| hIL10Ra<br>VHH11 | CAGGTGCAGCTCCAGGAATCTGGAGGGGGCAGTGTGCAGGCCGGGGGCT<br>CCCTGCGCTTGAGCTGTGGAGCCAGCCGCTACACGTATTCCAGTTACTG<br>TATGGGCTGGTTCAGACAAGCTCCGGGTAAGGAGAGAGAGGGAGTTGCC<br>GTAATTGATTCTGACGGGTCCACTAGCTATGCGGATTCAGTCAAGGGCC<br>GGTTCACCATCAGCAAGGACAATGGTAAGAACACACTGTACCTGCAAAT | 215 |

TABLE 8-continued hIL10Ra VHH DNA Sequences

| VHH Name | Sequence | SEQ ID |
|---|---|---|
| | GAACAGCCTGAAGCCCGAGGACACCGCCATGTACTATTGTGCCGCTGAT<br>CTCGGACATTACCGCCCTCCCTGCGGTGTGCTCTATCTCGGGATGGACT<br>ATTGGGGTAAGGGCACCCAGGTGACCGTGTCCTCT | |
| hIL10Ra<br>VHH12 | CAGGTGCAGCTCCAGGAAAGCGGCGGGGGTAGCGTTCAAGCAGGTGGGT<br>CCCTGCGCTTGAGCTGTACTGTGTCCGGCTACACCTACTCAAGCAACTG<br>CATGGGATGGTTCCGTCAGGCCCCTGGCAAGGAACGCGAAGGCGTGGCT<br>ACTATCTACACCGGCGGTGGCAACACTTATTACGCCGACTCCGTTAAGG<br>GGCGTTTCACTATCAGCCAAGACAACGCCAAGAACACCGTGTATCTGCA<br>AATGAATAACCTGAAGCCTGAAGACACCGCCATGTATTACTGTGCTGCC<br>GAGCCCCTTTCCCGCGTTTACGGCGGTTCTTGTCCTACCCCTACCTTTG<br>ACTACTGGGGTCAGGGAACACAGGTGACAGTGTCCAGT | 216 |
| hIL10Ra<br>VHH13 | CAAGTCCAACTCCAGGAATCTGGGGGAGGCTCCGTACAGGCTGGCGGTT<br>CCCTTCGTCTGTCCTGTGCTGTGTCAGGGTACTCCTACTCCAGTAACTG<br>TATGGGCTGGTTCCGGCAAGCCCCCGGAAAGGAGCGCGAGGGCGTGGCT<br>ACCATCCACACAGGGGGCGGTTCCACATATTACGCCGATAGTGTCAAGG<br>GCCGCTTCACCATTAGTCAGGACAACGCCAAGAATACCGTTTACCTTCA<br>AATGAACTCTTTGAAACCTGAGGACACTGCGATGTATTACTGTGCGGCA<br>GAGCCTTTGTCCCGCCTGTACGGGGATCTTGTCCGACCCCGACTTTCG<br>GGTACTGGGGACAGGGCACCCAGGTGACAGTGTCCTCC | 217 |
| hIL10Ra<br>VHH14 | CAGGTGCAGTTGCAGGAAAGCGGGGGTGGCAGCGTCCAAGCCGGTGGCA<br>GCCTGCGTCTGTCCTGCGGTGCCTCCGGCTATACTTACTCCAGCTATTG<br>CATGGGTTGGTTCCGCCAAGTGCCAGGAAAGGAGCGTGAGGGGTGGCT<br>GTAATTGATTCAGATGGGTCAACAAGCTACGCTGACAGCGTTAAAGGTC<br>GCTTCACCATCAGTAAGGACAACGGCAAGAACACCCTCTACCTGCAAAT<br>GAACTCCCTGAAGCCGGAGGATACCGCAATGTATTACTGTGCCGCTGAC<br>TTGGGACACTACCGCCCTCCGTGCGGTGTGCTTTATCTGGGCATGGATT<br>ACTGGGGTAAGGGAACCCAAGTGACGGTGTCTTCT | 218 |
| hIL10Ra<br>VHH15 | CAGGTACAACTCCAGGAGTCTGGCGGTGGGTCCGTGCAGGCAGGTGGCA<br>GCCTTCGCCTCTCCTGCGGGGCCTCCGGGTACACCTATAGTGGCTACTG<br>CATGGGGTGGTTCAGGCAAGCCCCCGGTAAGGAACGTGAGGGAGTTGCT<br>GTGATTGATTCAGATGGGTCCACGAGTTACGCTGACTCCGTGAAAGGTA<br>GGTTCACAATCTCCAAAGATAATGGCAAGAACACCCTCTACCTTCAGAT<br>GAATAGCCTGAAGCCAGAAGACACCGCCATGTATTACTGTGCTGCCGAC<br>CTGGGACACTATCGCCCTCCGTGCGGGTCCTGTACTTGGGCATGGACT<br>ATTGGGGCAAGGGGACCCAGGTGACTGTGTCCTCT | 219 |
| hIL10Ra<br>VHH16 | CAGGTGCAGTTGCAGGAATCCGGTGGAGGCTCTGTTCAGGCCGGGGGCT<br>CTCTCCGCCTGGCCTGCGCAGCCTCCAGGTATACTTACAGCAACTACTG<br>CATGGGGTGGTTTCGCCAGGCTCCGGGCAAAGAGCGTGAGGGAGTGGCT<br>ACTATTGATTCCGATGGAAACACCAGCTACGCCGATAGCGTGAAGGGCA<br>GATTTACTATCAGCAGAGATAACGCTAAAAACGTTGTACCTCCAGAT<br>GAACTCACTCAAGCCGGGGACACAGCTATGTATTACTGCGCAGCCGAT<br>CTGGGTCACTACCGCCCGCCCTGCGCGCATATTACTATGGCATGGACT<br>ACTGGGGCAAGGGCACCCAGGTGACCGTGTCCAGT | 220 |
| hIL10Ra<br>VHH17 | CAGGTGCAGCTCCAAGAGTCTGGCGGGGGTTCCGTGCAAGCCGGTGGCT<br>CACTCAGGTTGAGTTGCGCAGCCAGCGGCTATAGCAACTGTTCCTATGA<br>CATGACTTGGTATCGCCAGGCCCCTGGCAAAGAGCGTGAGTTCGTGTCA<br>GCTATTCACTCCGACGGCTCCACTCGTTATGCGGACTCTGTGAAGGGCC<br>GGTTTTTCATCTCCCAGGACAACGCTAAAAACACTGTCTATTTGCAGAT<br>GAACTCTCTGAAACCCGAAGATACCGCCATGTACTATTGCAAAACCGAT<br>CCTCTGCATTGTCGCGCCCACGGCGGGAGTTGGTACTCTGTGCGGGCCA<br>ACTATTGGGGCCAGGGCACCCAGGTCACCGTGTCCTCA | 221 |
| hIL10Ra<br>VHH18 | CAGGTACAACTCCAGGAGTCTGGCGGTGGCAGCGTGCAGGCAGGCGGAA<br>GCCTGAGGCTGTCCTGCGCTGTATCTGGCTACACTTATAATTCCAACTG<br>CATGGGTTGGTTTCGGCAGGCTCCAGGTAAGGAGCGCGAGGGCGTCGCC<br>ACCATTTATACAGGTGTTGGCAGCACATATTACGCCGACAGCGTGAAGG<br>GAAGGTTCACCATCTCCCAAGACAATGCGAAAAACACAGTGTATCTCCA<br>GATGAATAGCCTGAAGCCCGAGGACACGGCTATGTATTACTGCGCTGCC<br>GAGCCACTGAGCAGAGTGTATGGGGGCAGCTGTCCTACACCCACTTTCG<br>GCTATTGGGGTCAAGGCACCCAGGTTACAGTCAGCTCC | 222 |

TABLE 9

Nucleic Acid Sequences Encoding hIL10Rb VHHS

| Name of VHH | DNA Sequence | SEQ ID NO. |
|---|---|---|
| IL10Rb VHH-1 | CAGGTGCAGCTTCAGGAATCAGGCGGAGGCAGCGTGCAGGCAGGGGGTA GCCTGCGTCTGTCTTGCGCAGCCAGCGGGTACACCTACAGCTCTGGCTG TATGGGCTGGTTTCGCCAAGCCCCAGGAAAAGAACGGGAAGCCGTGGCG GCTATCAATAGCGACGGCTCCACCTCCTATGCTGACTCCGTCAAAGGAC GCTTCACCATTAGTAAAGATAACGCCAAGAACACCTTGTACCTTCAGAT GAACTCCTTGAAACCGGAGGACACCGCAATGTATTACTGTGCGGCTGAG CCCTACTGCTCAGGAGGCTACCCACGGTGGTCAGTGGCCGAGTTTGGTT ATTGGGGCCAGGGCACCCAAGTGACTGTGTCCTCC | 223 |
| hIL10Rb VHH-2 | CAGGTGCAACTCCAGGAGTCAGGGGGAGGTTCCGTGCAGGCTGGCGGTT CTCTCAGGTTGTCTTGCGCGGCCAGCGGCTATACGTACAGTAGCTACTG CATGGGCTGGTTCCGGCAAGCCCCCGGCAAGGAGCGCGAAGGCGTGGCT GCCATTGATTCCGATGGATCTACTAGGTATGCTGATAGTGTAAAGGGCC GCTTCACAATCTCCAAGGACAATGCCAAGAACACACTGTATTTGCAAAT GAACTCCCTCAAGCCCGAGGATACCGCTATGTACTATTGCGCTGCCGAA CCATACTGTTCCGGTGGCTATAAGCGCACTATGGTGGCCGAGTTCGGAT ACTGGGGTCAAGGCACACAGGTCACAGTGTCCTCT | 224 |
| hIL10Rb VHH-3 | CAGGTGCAGTTGCAGGAGTCCGGGGGCGGTAGCGTTCAGGCTGGAGGGT CCCTGCGTCTGAGTTGTGCGGCATCTCGGTATACTTATAACAGTTACTG TATGGGTTGGTTCCGCCAGGCACCTGGAAAGGAGCGGGAGGGGGTGGCG ACTATTGATAGCGACGGAATGACCAGATATGCCGACTCTGTGAAGGGAA GATTTACTATCTCAAAAGATAATGCCAAGAACACACTCTATTTGCAGAT GAACAGCCTCAAGCCAGAGGATACCGCTATGTATTACTGTGCTGCCGAC GCTGATTGCACCATCGCTGCCATGACGACCAACCCCTTGGGCCAGGGAA CCCAAGTAACCGTCTCTAGC | 225 |
| hIL10Rb VHH-4 | CAGGTCCAGCTCCAGGAATCTGGTGGCGGGTCTATCCAGGCGGGTGGCA GCCTGCGGCTGAGTTGCGCCGCTTCCCGCTACCTGTATAGTATTGATTA TATGGCCTGGTTCAGGCAGTCACCGGGCAAGAGCGCGAACCCGTCGCT GTGATTTACACAGCCTCTGGTGCCACCTTCTATCCCGATAGTGTGAAGG GCCGGTTCACTATCTCTCAAGACAACGCGAAGATGACTGTCTATCTTCA GATGAACTCTCTGAAGTCCGAGGACACTGCCATGTATTACTGTGCCGCT GTGCGCAAGACGGACTCTTATCTGTTCGATGCCCAGAGTTTCACTTACT GGGGTCAGGGTACTCAGGTGACCGTATCCTCC | 226 |
| hIL10Rb VHH-5 | CAGGTGCAGCTCCAGGAGTCTGGTGGCGGGCTGGTTCAGCCTGGGGGTT CACTCCGGTTGTCCTGCGCTGCGTCTGGTTATACCTACTCCAGCTACTG TATGGGTTGGTTCCGCCAGGCACCGGGGAAGGAGAGGGAGGCGTGGCT CACATTGATTCTGATGGCTCTACGACCTACGCTGATAGCGTTAAGGGGC GCTTCACTATCTCCAAGGATAACGCCAAGAACACCCTGTATCTGCAAAT GAACAGCCTGAAGCCAGAAGACACTGCCATGTACTATTGCGCTGCCGAT CCTATTCCCGGTCCTGGCTATTGTGACGGCGGTCCTAACAAGTACTGGG GCCAAGGCACACAGGTGACTGTCAGTTCC | 227 |
| hIL10Rb VHH-6 | CAGGTTCAACTCCAGGAATCCGGCGGTGGAAGCATTCAGGCGGGCGGTT CTTTGACTCTGAGCTGTGCGGCATCTCGGGACCTTTACAGCACTAACTA TGTTGCCTGGTTCCGGCAGTCCCCCGGCAAGGAACGCGAAGCTGTGGCC GTGATTTATACAGCCAGCGGCGCAACCCTGTATAGCGATTCAGTCAAAG GCCGGTTCACCATCTCCCAGGACAACGCGAAGATGACCGTGTACCTGCA AATGAACAGCCTGAAGTCTGAGGACACTGCCATGTATTACTGCGCAGCT GTGAGAAAGACCGGACATTACCTCTTCGACGCCCAATCTTTCACCTACT GGGGCCAGGGAACCCAGGTCACCGTCTCCTCT | 228 |
| hIL10Rb VHH-7 | CAGGTGCAACTCCAGGAGTCAGGCGGTGGGTCCGTCCAGGCCGGTGGCT CCCTGAGGCTGAGTTGCGCCGCTTCCGGCTATACTTACTCCAGCGGTTG CATGGGGTGGTTCCGCCAAGCCCCCGGTAAAGAACGCGAGGGAGTGGCT ACAATTAACTCCGATGAAGCACTAACTACGCCGACTCTGTGAAGGGAC GCTTCACCATTAGCAAAGACAATGCTAAGAACACCCTTTACCTTCAAAT GAACAGCCTGAAGCCTGAGGATACCGCTATGTATTACTGTGCCGCAGAA CCGTATTGTAGCGGTGGCTACCCTCGCTGGTCCGTCGCCGAGTTCGGTT ATTGGGGCCAGGGGACCCAAGTGACTGTTTCTAGC | 229 |
| hIL10Rb VHH-8 | CAGGTGCAACTTCAGGAGAGCGGCGGGGCTCTGTGCAAGCTGGTGGCT CCCTGCGGCTCAGCTGTGCTGCCTCTGGGTATTCTTACAGTAGCTACTG TATGGGCTGGTTCAGACAGGCACCAGGCAAGGAGCGCGAGGGTGTGGCG GCCATCGCTTCCGACGGAGTACCAGCTACGCCGACAGCGTTAAAGGTA GGTTTGCCATCTCTAAGGATAATGCGAAGAATACACTCTACCTTCAGAT GGCTAGTCTGAAGCCAGAGGATACCGCCATGTATTACTGCGCGGCAGAG CCCTGGTGCACGGGAGGGTATTCACGCCTGACCCCGGCTGAGTATGGAT ACTGGGGGCAGGGCACCCAGGTGACCGTTAGCTCC | 230 |
| hIL10Rb VHH-9 | CAGGTCCAGTTGCAGGAAAGCGGAGGGGGCCTGGTGCAGCCAGGAGGTT CTCTGAGACTGAGCTGTGCCGCTTCTGGTTACACATATTCTAGCGGGTG CATGGGCTGGTTCCGCCAGGCTCCCGGCAAGGAACGTGAGGGTGTGGCA ACTATCAATTCCGACGGCTCTACAAACTACGCAGATTCTGTTAAAGGCC | 231 |

TABLE 9-continued

Nucleic Acid Sequences Encoding hIL10Rb VHHS

| Name of VHH | DNA Sequence | SEQ ID NO. |
|---|---|---|
| | GCTTCACAATCTCTAAGGACAACGCCAAAAACACTCTGTACTTGCAGAT<br>GAATAGCCTGAAGCCTGAAGACACTGCCATGTACTATTGCGCAGCTGAG<br>CCCTACTGTTCTGGAGGCTACCCCCGCTGGTCTGTGGCCGAGTTCGGTT<br>ACTGGGGACAAGGAACCCAGGTCACAGTGTCCAGT | |
| hIL10Rb VHH-10 | CAGGTTCAGCTCCAGGAGTCAGGCGGGGGTCTTGTCCAGCCTGGTGGCT<br>CCCTGCGCCTGTCCTGTGCTGCCTCCGGTTACACCTACTCCAGCTATTG<br>CATGGGATGGTTCAGACAAGCGCCAGGCAAGGAACGTGAGGGGGTCGCC<br>CACATTGACTCCGACGGTTCCACTACCTACGCCGACAGCGTCAAAGGCC<br>GCTTCGCGATTTCTAAGGATAACGCTAAGAATACTCTGTACTTGCAGAT<br>GAACTCACTGAAGCCAGAGGACACGGCCATGTATTACTGCGCAGCCGAT<br>CCGATCCCCGGCCCCGGCTATTGTGACGGTGGCCCGAACAAGTACTGGG<br>GACAGGGCACCCAAGTGACGGTGTCCTCT | 232 |
| hIL10Rb VHH-11 | CAGGTACAGTTGCAGGAGAGCGGAGGCGGTTCCGTGCAGGCAGGTGGCT<br>CTCTTAGACTGTCCTGCGCCGCGAGCGGGTACACCTACAGTAGCTATTG<br>TATGGGCTGGTTCCGCCAGGCTCCTGGTAAGGGTCGCGAGGGCGTCGCT<br>GCCATCGACTCCGATGGCTCTACTCGCTACGCAGATTCTGTCAAGGGGC<br>GCTTCACAATTTCCAAGGACAACGCCAAGAACACGCTTTACTTGCAGAT<br>GAACTCACTGAAGCCGGAGGACACCGCTATGTATTACTGCGCTGCCGAG<br>CCCTACTGTTCTGGGGGCTACAAGCGCACTATGGTGGCCGAGTTCGGAT<br>ATTGGGGCCAGGGTACACAGGTGACCGTCAGTTCT | 233 |
| hIL10Rb VHH-12 | CAGGTGCAGTTGCAGGAGTCTGGCGGTGGCTCTGTGCAGGCTGGGGGCT<br>CTCTGCGCCTGAGTTGCGCTGCCAGCGGTTACACCTACTCCAGCTATTG<br>TATGGGATGGTTCCGCCAGGCTCCGGGGAAGGAGAGGGAGGGCGTGGCC<br>CATATCGACTCTGATGGCTCCACATCCTACGCCGACAGCGTGAAGGGAC<br>GTTTCACCATTAGCAAGGACAATGCGAAGAATACCCTCTACTTGCAGAT<br>GAACTCCCTGAAGCCGGAGGATACTGCCATGTATTACTGCGCCGCTGAT<br>CCCATCCCCAGGGCCTGGGTACTGTGACGGAGGCCCGAACAAGTATTGGG<br>GACAAGGAACGCAGGTCACAGTGTCATCT | 234 |
| hIL10Rb VHH-13 | CAGGTACAACTCCAGGAGAGTGGTGGAGGCTCCGTTCAAGCCGGGGGCT<br>CCCTGCGGCTGTCCTGTGCGGCCAGCGGTTACACCTATTCATCTTACTG<br>TATGGGCTGGTTCCGGCAGGCCCCTGGTAAGGAAAGAGAGGGTGTCGCT<br>CACATTGATTCCGACGGTAGTACCTCTTACGCAGACTCTGTCAAGGGCA<br>GGTTCACCATCTCTAAGGACAATGCCAAGAACACCTTGTACCTCCAGAT<br>GAACTCTCTGAAGCCCGAGGACACTGCAATGTACTATTGTGCGGCTGAC<br>CCTATTCCCGGCCCTGGATATTGCGACGGCGGACCTAACAATTACTGGG<br>GACAGGGCACCCAGGTCACCGTCAGCTCC | 235 |
| hIL10Rb VHH-14 | CAGGTTCAGCTCCAAGAATCCGGCGGGGGCTCTGTGCAGGCGGGCGGAA<br>GTCTGCGTCTGTCATGCGCTGCCAGCGGGTACACTTACTCTTCCGGTTG<br>TATGGGCTGGTTTAGGCAGGCTCCGGGAAAGGAAAGGGAGGGCGTCGCA<br>ACTATCAACAGCGACGGCTCTACGAACTACGCTGACTCTGTGAAAGGCC<br>GCTTCACCATCAGCAAAGACAACGCCAAAAATACACTGTATCTCCAGAT<br>GAATAGCTTGAAACCCGAGGACACCGGAATGTATTACTGCGCGGCAGAG<br>CCATACTGTTCAGGCGGTTACCCAAGATGGTCCGTGGCTGAGTTCGGTT<br>ATTGGGGGCAGGGCACTCAGGTTACTGTGTCTTCC | 236 |
| hIL10Rb VHH-15 | CAGGTGCAGCTCCAGGAATCCGGGGGCGGTTCTGTGCAGGCTGGTGGCT<br>CTCTGCGCCTGTCTTGCACTGTTTCCAGGTACACTGCCTCTGTAAACTA<br>TATGGGCTGGTTTAGACAAGCTCCGGGCAAGGAACGCGAAGGCGTCGCT<br>ACCATCTTTACAGGTGCAGGTACGACCTATTACGCCAATAGCGTTAAAG<br>GGAGGTTCACCATCTCCAGGGACAATGCCAAAAACACAGCCTATCTCCA<br>GATGAACTCCCTCAAACCTGAAGACACAGCCATCTACTATTGCGCGGTT<br>GACTTCCGTGGTGGCCTGCTCTATAGACCGGCGTATGAGTACACCTACC<br>GTGGACAAGGCACCCAAGTCACAGTGAGCAGC | 237 |
| hIL10Rb VHH-16 | CAGGTGCAGCTCCAAGAGTCCGGCGGAGGGAGTGTAGAGGCTGGCGGGT<br>CCCTGCGCCTTAGCTGCGCGGCCAGCGGCTATACACACAGTTCTTATTG<br>TATGGGTTGGTTCCGCCAAGCTCCGGGAAAGGAGCGTGAGGGCGTGGCT<br>GCCATCGACTGGATGGCTCCACAACCTACGCCGACAGCGTGAAGGGCA<br>GGTTTACGATCTCTAAGGATAACGCTAAGAATACTCTCTATTTGCAGAT<br>GAACTCCCTCAAACCCGAGGATACAGGAATGTACTATTGCGCTGCCGAG<br>TTCGCCGACTGCTCAAGCAATTATTTCCTGCCTCCAGGAGCCGTTAGGT<br>ACTGGGGCCAGGGGACTCAGGTCACAGTAAGCAGC | 238 |
| hIL10Rb VHH-17 | CAGGTGCAGCTCCAGGAGAGCGGTGGCGGATCAGTGCAGGCTGGAGGCT<br>CCCTCAGACTGTCCTGCACCGTGAGCCGCTATACCGCCTCCGTCAACTA<br>TATGGATGGTTTAGGCAGGCTCCGGGCAAGGAGCGCGAGGGGGTCGCG<br>ACTATCTTCACCGGAGCCGGTACTACCTATTACGCTAATTCTGTTAAAG<br>GCCGCTTTACCATTAGTCGCGACAACGCTAAGAACACAGCTTACCTCCA<br>GATGAACTCTCTGAAGCCAGAGGATACCGCCATGTATTACTGCGCCGTG<br>GACTTCCGGGGCGGTTTGCTCTACCGCCCGGCCTACGAATACACCTATC<br>GCGGCCAGGGCACGCAGGTCACGGTGTCCTCA | 239 |

TABLE 9-continued

Nucleic Acid Sequences Encoding hIL10Rb VHHS

| Name of VHH | DNA Sequence | SEQ ID NO. |
|---|---|---|
| hIL10Rb VHH-18 | CAGGTGCAGCTCCAAGAGTCCGGTGGAGGCAGCGTCCAGGCCGGGGGTA GTCTTAGGCTCAGCTGTGCTGCCAGTGGAGACACCTACTCTTCCTATTG CATGGGATGGTTCAGACAGGCCCCCGGCAAAGAGCGCGAGGGCGTTGCA TTCATCGACTCCGACGGCTCCACTCGCTACGCCGATAGCGTGGAGGGCC GTTTTACCATCTCCAAGGACAACGCGAAGAACACTCTGTATCTGCAAAT GAACTCCCTGAAGCCCGAAGACACCGCCATGTACTATTGCGCGGCTGAG CCATACTGTAGTGGCGGATATCATCGTAAGGAAATGGCAGAGTTCGGCT ATTGGGGCCAGGGCACCCAGGTCACTGTGAGTTCC | 240 |
| hIL10Rb VHH-19 | CAGGTGCAGTTGCAGGAATCCGGCGGAGGCTCTGTGCAGGCGGGCGGTT CCCTCCGCCTGAGTTGTGCCGCGTCTGGCTATACTTACTCTTCCTATTG TATGGGATGGTTCCGGCAAGCGCCCGGCAAAGAGCGGGAGGGCGTTGCG CATATCGACAGTGATGGTAGCACCAGTTACGCTGATAGCGTGAAAGGCA GATTCACTATCTCAAAGGATAACGCGAAGAACACTCTTTACCTCCAGAT GAACTCCCTTAAACCTGAGGATACCGCGATGTATTACTGTGCTGCCGAC CCCATTCCCGGCCCTGGATACTGTGACGGAGGCCCTAACAAGTACCGTG GGCAAGGAACACAGGTCACAGTGTCCAGC | 241 |
| hIL10Rb VHH-20 | CAGGTGCAACTCCAGGAGTCTGGCGGGGGCAGCGTCCAGGCAGGTGGAA GTCTCCGTCTCTCATGTGCTGCCAGCGGCTATACATACTCCAGCTACTG TATGGGATGGTTTAGACAGGCACCCGGCAAGGAGCGCGAAGGGGTGGCC CATATCGACTCCGATGGCAGCACAACCTATGCCGACTCTGTGAAAGGGC GGTTCGCCATCTCCAAGGACAACGCTAAGAATACCCTGTACCTCCAGAT GAACTCTCTGAAGCCTGAGGACACCGCCATGTATTACTGCGCTGCCGAC CCAATCCCTGGCCCAGGTTACTGCGATGGGGGACCAAACAAATATTGGG GACAGGGCACGCAGGTTACAGTCTCCAGC | 242 |
| hIL10Rb VHH-21 | CAGGTCCAACTCCAGGAAAGTGGAGGTGGCTCTGTTCAGGCCGGGGGCA GCCTGAGGCTGAGCTGCACCGGCTCAGGCTATACAGCCAGTAATAACTG CATGGGCTGGTTCCGTCAAGCGCCCGGCAAAGAGCGTGAAGGTGTGGCC GTAATTTTTACCGGCGCTGGCACCAGCTATTACGACAGTTCCGTGGGCC GTCTGTTCATCAGCTCACAGGACGCCGCTTCCACCCTCGATCAGTTGCT GATGAGCCTTCTGCCCGATGACACCGCAGTAATGTACTGTGGAGCCGAA GATGACTGCACACTGCTCCTGATGACGCCAAACCCCGATGACCAATGGT CCCGCCTGAGTGTGTCCTCC | 243 |
| hIL10Rb VHH-22 | CAGGTGCAGCTCCAGGAGAGCGGGGCGGTTCTGTTCAGGCGGGAGGCA GCCTGCGTCTGTCCTGTGCAGCCTCTGGTTACACAGACAGTCGTTACTG CATGGGCTGGTTCCGCAAGGCACCTGGAAAGGAGCGCGAGGGTGTTGCG CACATCGACTCCGACGGGAGCACTAGCTATGCTGACAGCGTGAAGGGGC GCTTCACTATCAGCAAGGATAACGCGAAAAACACCTTGTACCTTCAGAT GAACTCCCTCAAACCCGAAGACACAGCGATGTACTATTGTGCCGCTGAT CCGATCCCAGGGCCTGGCTACTGTGATGGTGGACCTAATAAGTACTGGG GGCAGGGAACTCAGGTGACCGTGTCATCA | 244 |
| hIL10Rb VHH-23 | CAGGTCCAGTTGCAGGAATCTGGAGGCGGTTCCGTGCAAGCAGGGGGCT CACTCAGACTGTCCTGCGCTGCCAGCGGCTACACTTACTCTTCATATTG CATGGGCTGGTTCCGCCAGGCACCGGGCAAGGAGCGGGAAGGCGTGGCC GCTATTGATAGCGATGGCTCTACGCGCTACGCAGATAGCGTGAAAGGGA GGTTCACGATCTCCAAAGATAATGCCAAGAAAATTCTGTATCTCCAGAT GAACTCTCTGAAGGTCGAGGACACCGCCATGTACTATTGTGCAGCCGAA CCCTACTGTTCTGGTGGCTACAAGAGGACTATGGTGGCCGAGTTCGGCT TCTGGGGCCAGGGGACCCAAGTGACTGTCAGTAGC | 245 |
| hIL10Rb VHH-24 | CAGGTGCAACTTCAGGAGAGCGGTGGCGGATCTGTGCAGGCTGGAGGGT CTCTGAAGCTGTCCTGCGCGGCCAGCGGTTACACATACAGTAGCTACTG CATGGGATGGTTTCGTCAGGCCCCAGGCAAGGAGCGCGAAGGAGTGGCG CACATCGACTCCGATGGGTCCACCACATACGCCGACTCCGTGAAGGGCC GTTTCACAATCAGCAAGGATAACGCGAAGAACACGCTGTACTTGCAGAT GAACTCTCTCAAACCAGAGGACACTGCAATGTACTATTGCGCGGCTGAC CCCATCCCTGGCCCTGGTTACTGTGACGGTGGCCCAACAATTACTGGG GGCAAGGGACCCAAGTCACCGTGTCCTCC | 246 |
| hIL10Rb VHH-25 | CAGGTCCAGCTCCAGGAGTCCGGCGGGGCTCCGTCCAGGCAGGGGGCT CCCTGCGTCTGTCATGCGCCGCTTCTGGGTATACCTACAGTTCCTATTG TATGGGTTGGTTTCGCCAAGCACCCGGTAAGGAGCGCGAAGGTATTGCG CACATTGATAGCGATGGCTCCACAACCTATGCTGACAGTGTGAAAGGAC GCTTCACTATTTCCAAGGATAACGCTAAGAACACACTCTACCTTCAGAT GAACAGCCTGAAGCCGGAAGACACCGCAATGTACTATTGTGCAGCTGAC CCCATTCCTGGACCCGGTTACTGTGATGGAGGTCCTAATAACTATTGGG GACAGGGCACTCAAGTGACCGTCTCAAGC | 247 |
| hIL10Rb VHH-26 | CAGGTGCAGTTGCAGGAGAGCGGGGGTGGCTCTGTGCAGGCCGGGGGCT CCCTGAGGCTGAGCTGCGCGGCCAGCGGGTACAGCTACTCTAGCTATTG CATGGGTTGGTTCCGCCAGGCCCCTGGCAAGGAGCGCGAGGGAGTGGCC | 248 |

TABLE 9-continued

Nucleic Acid Sequences Encoding hIL10Rb VHHS

| Name of VHH DNA Sequence | | SEQ ID NO. |
|---|---|---|
| | ACGATTGACTCAGATGGCATGACCCGTTATGCGGATTCCGTCAAGGGGC GCTTCACCATCAGCAAAGATAACGCCAAAAATACCCTGTACTTGCAGAT GAACTCACTGAAACCTGAGGATACAGCCATGTATTACTGCGCAGCTCCG CTCTATGACTGTGACTCTGGTGCCGTGGGTAGAAACCCACCTTACTGGG GGCAGGGAACCCAGGTGACCGTGTCCTCA | |
| hIL10Rb VHH-27 | CAGGTCCAGCTCCAGGAAAGCGGTGGGGGCAGCGTCCAAACAGGGGGTA GCCTGCGCCTCTCTTGCGCAGCCAGCGGCTACACATATCTGCGCGGATG TATGGGCTGGTTCCGCCAGGCCCCTGGTAAGGAAAGAGAGGGGGTGGCC GTGATGGACGTGGTTGGAGACAGACGTTCCTACATTGATTCCGTGAAGG GCCGCTTTACTATCTCACGCGATAACGGGCTAACTCTGTGTATTTGCA GATGGATAACCTGAAGCCCGAGGACACCGCTATGTACTATTGCACAGCT GGTCCCAACTGTGTCGGTTGGCGCTCCGGCCTGGACTATTGGGGTCAGG GAACCCAGGTTACAGTTAGCAGT | 249 |

TABLE 10

Nucleic Acid Sequences Encoding mIL10Rb VHHS

| Name | DNA Sequence | SEQ ID NO |
|---|---|---|
| DR1322 DNA | CAGGTGCAGCTCCAGGAGAGTGGTGGCGGTTCTGTCCAAGCTGGCG GAGCCCTGCGCCTGTCCTGCACAGCAAGCGGCTACACCGCCTCTAG CATTTGCATGGGATGGTTCCGTCAGGCCCCAGGCAAGGAGAGGGAG AGAGTGGCTGTGATTACCACGGCAGCCTCCGGTACTTACTATGCCG ACTCTGTGAATGGCCGCTTCTCAATCTCTCAGAATAACGCCAAAAA TACTGTGTACCTCCAGATGAACTCCCTGAAACCTGACGATACCGCG ATGTATTACTGCGCAGCCACCCGGCGCGGCGGTGACTGCCTGGACC CATTGCAGACCCCAGCCTATAATACCTGGGGCCAGGGAACCCAGGT CACCGTCTCTTCT | 250 |
| DR1323 DNA | CAGGTGCAGCTCCAGGAAAGCGGCGGTGGCTCCGTCCAGGCCGGTG GCTCCCTGAGGCTGAGCTGTGTGGCTTCCGGCGATACTTATTCTCG CAAGTACATCGCATGGGTGCGTCAGGTGCCCGGTAAAGAACGTGAG GGAGTGGCAGTGATGTATACCCCAGGCTCCGCTACTTACTATACAG ACACAGTGATGGGTCGTTTCACCATCTCCCAGGACAACGCCAAGAA CACTGTGTACCTTCAAATGAACAGCCTCAAACCTGAAGACACCGCC ATGTACTTTTGCGCGGCCAAGGCCAGCGGCTCCATGTTTAACTTCC GCGATTACACTTATTGGGACAGGGCACTCAGGTGACCGTAAGCTC T | 251 |
| DR1324 DNA | CAGGTGCAGCTGCAAGAAAGCGGAGGTGGCTCTGTCCAGGCAGGAG GCTCCCTCCGGCTTAGCTGCGCTACCAGCGGGTATGCTTCCTGTTC CCGCGCCATGAGGTGGTACAGGCAGGCACCGGGCAAGGAGCGCGAA TTTGTGGCGTACATCGACGGGGTGGGCAGTACTGGTTATGCGGACA GCGTTAAAGGCCGGTTTACCATCTCCCAAGATAATGCAAAGTACAC GGCTTACTTGCAGATGAACTCCCTCAAGCCTGAGGATACCGCGATG TATTACTGTAATCGGGGCTGTAGAGCCGATGGTAGCAATAGTCTGG ACAACTACTGGGGCCAGGGCACACAGGTGACTGTCTCTTCA | 252 |
| DR1325 DNA | CAGGTGCAGTTGCAGGAGTCCGGCGGTGGCAGCGTTCAGGCGGGCG GTAGCCTGCGTCTGAGCTGCGCCGCGTCCGGCTACACCTATAACCG TCGCTTCATGGGTTGGTTCCGTCAAGCGCCCGGCAAGGAGAGAGAG GGCCTCGCCATTATCTACACCCCCAACAGCTCCACCTTCTACGCCG ACTCTGTGACGGGCCGCTTTACAATCTCACAGGATTCTGCCCGCAA CACCGTCTATTTGCAGATGAACTCCCTGAAACCTGAGGACACCGCT ATGTACTATTGTGCAGCCGCTCGCATCGCTTCTATGACTGAGCTTT CAGTGAGAGATATGGACTATTGGGGCAAGGGCACCCAGGTGACCGT TTCCTCC | 253 |
| DR1326 DNA | CAGGTACAACTCCAGGAGAGCGGGGGAGGTAGCGTACAGGCTGGCG GTCCTTGCGTCTGAGCTGCACTGCATCTCGTTACATCGCTCTTAA TGCGTGTATGGCTTGGATTCGGCAGGCCCCCGGCTCCGAAAGGGAG GTCGTGGCCACAATCGTGACTGATGGCTCCAGAACCTATTACGCAG ACTCTGTCAAGGGCCGGTTTACTATCTCTCAAGACAACGCCAAGAA CACCATGTACCTCCAGATGAACGGTTTGAAACCCGAAGACACCGCC ATGTATTACTGTCAGCCGACAGGCGCTGCCCCGTGTCCAGAGCCC CATACGAATACGAACTGCGCTACTGGGGTCAGGGCACCCAGGTGAC TGTCAGCAGC | 254 |

TABLE 10-continued

Nucleic Acid Sequences Encoding mIL10Rb VHHS

| Name | DNA Sequence | SEQ ID NO |
|---|---|---|
| DR1327 DNA | CAAGTCCAGCTTCAAGAAAGCGGAGGGGGCTCTGTTCAGGCAGGCG GGTCCCTCCGGCTGTCCTGCGCTGCCTCCGGCTACACATACAACGG AAAGTGCATGGCTTGGTTCCGCCAGGCTCCCGGCAAGGAGCGCGAA GTCGTGGCTGGCATTTACACCGGGGGCTCCAGCACATATTACGCCG ATAGTGTGAAGGGACGCTTTACGATTTCCCAAGACAATGCTAAAAA TACAGTCTATCTCCAGATGGACAGCCTGAAGCCCGAAGACACTGCC ATGTATTACTGCGCCACCAGCAGAAGCTGTAGCGACCTGCGCAGAC GCTCCATCGCCTACTGGGGACAGGGGACTCAGGTCACCGTCAGCTC T | 255 |

TABLE 11

Description of IL10R Receptor Binding Proteins Evaluated

| IL10 Binding Protein (SEQ ID NO: ) | N-terminal sdAb (SEQ ID NO:) | Linker | C-terminal sdAb (SEQ ID NO:) | C-terminal purification handle |
|---|---|---|---|---|
| 256 | 163 | G3S (SEQ ID NO: 484) | 172 | ASH6 (SEQ ID NO: 560) |
| 257 | 163 | G3S (SEQ ID NO: 484) | 183 | ASH6 (SEQ ID NO: 560) |
| 258 | 163 | G3S (SEQ ID NO: 484) | 174 | ASH6 (SEQ ID NO: 560) |
| 259 | 163 | G3S (SEQ ID NO: 484) | 186 | ASH6 (SEQ ID NO: 560) |
| 260 | 163 | G3S (SEQ ID NO: 484) | 187 | ASH6 (SEQ ID NO: 560) |
| 261 | 163 | G3S (SEQ ID NO: 484) | 197 | ASH6 (SEQ ID NO: 560) |
| 262 | 163 | G3S (SEQ ID NO: 484) | 198 | ASH6 (SEQ ID NO: 560) |
| 263 | 159 | G3S (SEQ ID NO: 484) | 172 | ASH6 (SEQ ID NO: 560) |
| 264 | 159 | G3S (SEQ ID NO: 484) | 183 | ASH6 (SEQ ID NO: 560) |
| 265 | 159 | G3S (SEQ ID NO: 484) | 174 | ASH6 (SEQ ID NO: 560) |
| 266 | 159 | G3S (SEQ ID NO: 484) | 186 | ASH6 (SEQ ID NO: 560) |
| 267 | 159 | G3S (SEQ ID NO: 484) | 187 | ASH6 (SEQ ID NO: 560) |
| 268 | 159 | G3S (SEQ ID NO: 484) | 197 | ASH6 (SEQ ID NO: 560) |
| 269 | 159 | G3S (SEQ ID NO: 484) | 198 | ASH6 (SEQ ID NO: 560) |
| 270 | 161 | G3S (SEQ ID NO: 484) | 172 | ASH6 (SEQ ID NO: 560) |
| 271 | 161 | G3S (SEQ ID NO: 484) | 183 | ASH6 (SEQ ID NO: 560) |
| 272 | 161 | G3S (SEQ ID NO: 484) | 174 | ASH6 (SEQ ID NO: 560) |
| 273 | 161 | G3S (SEQ ID NO: 484) | 186 | ASH6 (SEQ ID NO: 560) |
| 274 | 161 | G3S (SEQ ID NO: 484) | 187 | ASH6 (SEQ ID NO: 560) |
| 275 | 161 | G3S (SEQ ID NO: 484) | 197 | ASH6 (SEQ ID NO: 560) |
| 276 | 161 | G3S (SEQ ID NO: 484) | 198 | ASH6 (SEQ ID NO: 560) |
| 277 | 162 | G3S (SEQ ID NO: 484) | 172 | ASH6 (SEQ ID NO: 560) |
| 278 | 162 | G3S (SEQ ID NO: 484) | 183 | ASH6 (SEQ ID NO: 560) |
| 279 | 162 | G3S (SEQ ID NO: 484) | 174 | ASH6 (SEQ ID NO: 560) |
| 280 | 162 | G3S (SEQ ID NO: 484) | 186 | ASH6 (SEQ ID NO: 560) |
| 281 | 162 | G3S (SEQ ID NO: 484) | 187 | ASH6 (SEQ ID NO: 560) |
| 282 | 162 | G3S (SEQ ID NO: 484) | 197 | ASH6 (SEQ ID NO: 560) |
| 283 | 162 | G3S (SEQ ID NO: 484) | 198 | ASH6 (SEQ ID NO: 560) |
| 284 | 165 | G3S (SEQ ID NO: 484) | 172 | ASH6 (SEQ ID NO: 560) |
| 285 | 165 | G3S (SEQ ID NO: 484) | 183 | ASH6 (SEQ ID NO: 560) |
| 286 | 165 | G3S (SEQ ID NO: 484) | 174 | ASH6 (SEQ ID NO: 560) |
| 287 | 165 | G3S (SEQ ID NO: 484) | 186 | ASH6 (SEQ ID NO: 560) |
| 288 | 165 | G3S (SEQ ID NO: 484) | 187 | ASH6 (SEQ ID NO: 560) |
| 289 | 165 | G3S (SEQ ID NO: 484) | 197 | ASH6 (SEQ ID NO: 560) |
| 290 | 165 | G3S (SEQ ID NO: 484) | 198 | ASH6 (SEQ ID NO: 560) |
| 291 | 167 | G3S (SEQ ID NO: 484) | 172 | ASH6 (SEQ ID NO: 560) |
| 292 | 167 | G3S (SEQ ID NO: 484) | 183 | ASH6 (SEQ ID NO: 560) |
| 293 | 167 | G3S (SEQ ID NO: 484) | 174 | ASH6 (SEQ ID NO: 560) |
| 294 | 167 | G3S (SEQ ID NO: 484) | 186 | ASH6 (SEQ ID NO: 560) |
| 295 | 167 | G3S (SEQ ID NO: 484) | 187 | ASH6 (SEQ ID NO: 560) |
| 296 | 167 | G3S (SEQ ID NO: 484) | 197 | ASH6 (SEQ ID NO: 560) |
| 297 | 167 | G3S (SEQ ID NO: 484) | 198 | ASH6 (SEQ ID NO: 560) |
| 298 | 170 | G3S (SEQ ID NO: 484) | 172 | ASH6 (SEQ ID NO: 560) |
| 299 | 170 | G3S (SEQ ID NO: 484) | 183 | ASH6 (SEQ ID NO: 560) |
| 300 | 170 | G3S (SEQ ID NO: 484) | 174 | ASH6 (SEQ ID NO: 560) |
| 301 | 170 | G3S (SEQ ID NO: 484) | 186 | ASH6 (SEQ ID NO: 560) |
| 302 | 170 | G3S (SEQ ID NO: 484) | 187 | ASH6 (SEQ ID NO: 560) |
| 303 | 170 | G3S (SEQ ID NO: 484) | 197 | ASH6 (SEQ ID NO: 560) |
| 304 | 170 | G3S (SEQ ID NO: 484) | 198 | ASH6 (SEQ ID NO: 560) |
| 305 | 172 | G3S (SEQ ID NO: 484) | 163 | ASH6 (SEQ ID NO: 560) |

TABLE 11-continued

Description of IL10R Receptor Binding Proteins Evaluated

| IL10 Binding Protein (SEQ ID NO: ) | N-terminal sdAb (SEQ ID NO:) | Linker | C-terminal sdAb (SEQ ID NO:) | C-terminal purification handle |
|---|---|---|---|---|
| 306 | 172 | G3S (SEQ ID NO: 484) | 159 | ASH6 (SEQ ID NO: 560) |
| 307 | 172 | G3S (SEQ ID NO: 484) | 161 | ASH6 (SEQ ID NO: 560) |
| 308 | 172 | G3S (SEQ ID NO: 484) | 162 | ASH6 (SEQ ID NO: 560) |
| 309 | 172 | G3S (SEQ ID NO: 484) | 165 | ASH6 (SEQ ID NO: 560) |
| 310 | 172 | G3S (SEQ ID NO: 484) | 167 | ASH6 (SEQ ID NO: 560) |
| 311 | 172 | G3S (SEQ ID NO: 484) | 170 | ASH6 (SEQ ID NO: 560) |
| 312 | 183 | G3S (SEQ ID NO: 484) | 163 | ASH6 (SEQ ID NO: 560) |
| 313 | 183 | G3S (SEQ ID NO: 484) | 159 | ASH6 (SEQ ID NO: 560) |
| 314 | 183 | G3S (SEQ ID NO: 484) | 161 | ASH6 (SEQ ID NO: 560) |
| 315 | 183 | G3S (SEQ ID NO: 484) | 162 | ASH6 (SEQ ID NO: 560) |
| 316 | 183 | G3S (SEQ ID NO: 484) | 165 | ASH6 (SEQ ID NO: 560) |
| 317 | 183 | G3S (SEQ ID NO: 484) | 167 | ASH6 (SEQ ID NO: 560) |
| 318 | 183 | G3S (SEQ ID NO: 484) | 170 | ASH6 (SEQ ID NO: 560) |
| 319 | 174 | G3S (SEQ ID NO: 484) | 163 | ASH6 (SEQ ID NO: 560) |
| 320 | 174 | G3S (SEQ ID NO: 484) | 159 | ASH6 (SEQ ID NO: 560) |
| 321 | 174 | G3S (SEQ ID NO: 484) | 161 | ASH6 (SEQ ID NO: 560) |
| 322 | 174 | G3S (SEQ ID NO: 484) | 162 | ASH6 (SEQ ID NO: 560) |
| 323 | 174 | G3S (SEQ ID NO: 484) | 165 | ASH6 (SEQ ID NO: 560) |
| 324 | 174 | G3S (SEQ ID NO: 484) | 167 | ASH6 (SEQ ID NO: 560) |
| 325 | 174 | G3S (SEQ ID NO: 484) | 170 | ASH6 (SEQ ID NO: 560) |
| 326 | 186 | G3S (SEQ ID NO: 484) | 163 | ASH6 (SEQ ID NO: 560) |
| 327 | 186 | G3S (SEQ ID NO: 484) | 159 | ASH6 (SEQ ID NO: 560) |
| 328 | 186 | G3S (SEQ ID NO: 484) | 161 | ASH6 (SEQ ID NO: 560) |
| 329 | 186 | G3S (SEQ ID NO: 484) | 162 | ASH6 (SEQ ID NO: 560) |
| 330 | 186 | G3S (SEQ ID NO: 484) | 165 | ASH6 (SEQ ID NO: 560) |
| 331 | 186 | G3S (SEQ ID NO: 484) | 167 | ASH6 (SEQ ID NO: 560) |
| 332 | 186 | G3S (SEQ ID NO: 484) | 170 | ASH6 (SEQ ID NO: 560) |
| 333 | 187 | G3S (SEQ ID NO: 484) | 163 | ASH6 (SEQ ID NO: 560) |
| 334 | 187 | G3S (SEQ ID NO: 484) | 159 | ASH6 (SEQ ID NO: 560) |
| 335 | 187 | G3S (SEQ ID NO: 484) | 161 | ASH6 (SEQ ID NO: 560) |
| 336 | 187 | G3S (SEQ ID NO: 484) | 162 | ASH6 (SEQ ID NO: 560) |
| 337 | 187 | G3S (SEQ ID NO: 484) | 165 | ASH6 (SEQ ID NO: 560) |
| 338 | 187 | G3S (SEQ ID NO: 484) | 167 | ASH6 (SEQ ID NO: 560) |
| 339 | 187 | G3S (SEQ ID NO: 484) | 170 | ASH6 (SEQ ID NO: 560) |
| 340 | 197 | G3S (SEQ ID NO: 484) | 163 | ASH6 (SEQ ID NO: 560) |
| 341 | 197 | G3S (SEQ ID NO: 484) | 159 | ASH6 (SEQ ID NO: 560) |
| 342 | 197 | G3S (SEQ ID NO: 484) | 161 | ASH6 (SEQ ID NO: 560) |
| 343 | 197 | G3S (SEQ ID NO: 484) | 162 | ASH6 (SEQ ID NO: 560) |
| 344 | 197 | G3S (SEQ ID NO: 484) | 165 | ASH6 (SEQ ID NO: 560) |
| 345 | 197 | G3S (SEQ ID NO: 484) | 167 | ASH6 (SEQ ID NO: 560) |
| 346 | 197 | G3S (SEQ ID NO: 484) | 170 | ASH6 (SEQ ID NO: 560) |
| 347 | 198 | G3S (SEQ ID NO: 484) | 163 | ASH6 (SEQ ID NO: 560) |
| 348 | 198 | G3S (SEQ ID NO: 484) | 159 | ASH6 (SEQ ID NO: 560) |
| 349 | 198 | G3S (SEQ ID NO: 484) | 161 | ASH6 (SEQ ID NO: 560) |
| 350 | 198 | G3S (SEQ ID NO: 484) | 162 | ASH6 (SEQ ID NO: 560) |
| 351 | 198 | G3S (SEQ ID NO: 484) | 165 | ASH6 (SEQ ID NO: 560) |
| 352 | 198 | G3S (SEQ ID NO: 484) | 167 | ASH6 (SEQ ID NO: 560) |
| 353 | 198 | G3S (SEQ ID NO: 484) | 170 | ASH6 (SEQ ID NO: 560) |

TABLE 12

Amino Acid Sequences of IL10R Binding Molecules

| NAME | Amino Acid Sequence | SEQ ID NO |
|---|---|---|
| 163-172 | QVQLQESGGGSVQAGGSLRLSCAASRYLYSIDYMAWFRQSPGKEREP VAVIYTASGATFYPDSVKGRFTISQDNAKMTVYLQMNSLKSEDTAMY YCAAVRKTDSYLFDAQSFTYWGQGTQVTVSSGGGSQVQLQESGGGSV QAGGSLRLSCAASGYTYSSGCMGWFRQAPGKEREAVAAINSDGSTSY ADSVKGRFTISKDNAKNTLYLQMNSLKPEDTAMYYCAAEPYCSGGYP RWSVAEFGYWGQGTQVTVSSASHHHHHH | 256 |
| 163-183 | QVQLQESGGGSVQAGGSLRLSCAASRYLYSIDYMAWFRQSPGKEREP VAVIYTASGATFYPDSVKGRFTISQDNAKMTVYLQMNSLKSEDTAMY YCAAVRKTDSYLFDAQSFTYWGQGTQVTVSSGGGSQVQLQESGGGSV QAGGSLRLSCAASGYTYSSYCMGWFRQAPGKEREGVAHIDSDGSTSY ADSVKGRFTISKDNAKNTLYLQMNSLKPEDTAMYYCAADPIPGPGYC DGGPNKYWGQGTQVTVSSASHHHHHH | 257 |

TABLE 12-continued

Amino Acid Sequences of IL10R Binding Molecules

| NAME | Amino Acid Sequence | SEQ ID NO |
|---|---|---|
| 163-174 | QVQLQESGGGSVQAGGSLRLSCAASRYLYSIDYMAWFRQSPGKEREP VAVIYTASGATFYPDSVKGRFTISQDNAKMTVYLQMNSLKSEDTAMY YCAAVRKTDSYLFDAQSFTYWGQGTQVTVSSGGGSQVQLQESGGGSV QAGGSLRLSCAASRYTYNSYCMGWFRQAPGKEREGVATIDSDGMTRY ADSVKGRFTISKDNAKNTLYLQMNSLKPEDTAMYYCAADADCTIAAM TTNPLGQGTQVTVSSASHHHHHH | 258 |
| 163-186 | QVQLQESGGGSVQAGGSLRLSCAASRYLYSIDYMAWFRQSPGKEREP VAVIYTASGATFYPDSVKGRFTISQDNAKMTVYLQMNSLKSEDTAMY YCAAVRKTDSYLFDAQSFTYWGQGTQVTVSSGGGSQVQLQESGGGSV QAGGSLRLSCTVSRYTASVNYMGWFRQAPGKEREGVATIFTGAGTTY YANSVKGRFTISRDNAKNTAYLQMNSLKPEDTAIYYCAVDFRGGLLY RPAYEYTYRGQGTQVTVSSASHHHHHH | 259 |
| 163-187 | QVQLQESGGGSVQAGGSLRLSCAASRYLYSIDYMAWFRQSPGKEREP VAVIYTASGATFYPDSVKGRFTISQDNAKMTVYLQMNSLKSEDTAMY YCAAVRKTDSYLFDAQSFTYWGQGTQVTVSSGGGSQVQLQESGGGSV EAGGSLRLSCAASGYTHSSYCMGWFRQAPGKEREGVAAIDVDGSTTY ADSVKGRFTISKDNAKNTLYLQMNSLKPEDTGMYYCAAEFADCSSNY FLPPGAVRYWGQGTQVTVSSASHHHHHH | 260 |
| 163-197 | QVQLQESGGGSVQAGGSLRLSCAASRYLYSIDYMAWFRQSPGKEREP VAVIYTASGATFYPDSVKGRFTISQDNAKMTVYLQMNSLKSEDTAMY YCAAVRKTDSYLFDAQSFTYWGQGTQVTVSSGGGSQVQLQESGGGSV QAGGSLRLSCAASGYSYSSYCMGWFRQAPGKEREGVATIDSDGMTRY ADSVKGRFTISKDNAKNTLYLQMNSLKPEDTAMYYCAAPLYDCDSGA VGRNPPYWGQGTQVTVSSASHHHHHH | 261 |
| 163-198 | QVQLQESGGGSVQAGGSLRLSCAASRYLYSIDYMAWFRQSPGKEREP VAVIYTASGATFYPDSVKGRFTISQDNAKMTVYLQMNSLKSEDTAMY YCAAVRKTDSYLFDAQSFTYWGQGTQVTVSSGGGSQVQLQESGGGSV QTGGSLRLSCAASGYTYLRGCMGWFRQAPGKEREGVAVMDVVGDRRS YIDSVKGRFTISRDNAANSVYLQMDNLKPEDTAMYYCTAGPNCGWR SGLDYWGQGTQVTVSSASHHHHHH | 262 |
| 159-172 | QVQLQESGGGSVQAGGSLRLSCAASRFTYSSYCMGWFRQAPGKEREG VASIDSDGSTSYTDSVKGRFTISKDNAKNTLYLQMNSLKPEDTAMYY CALDLMSTVVPGFCGFLLSAGMDYWGKGTQVTVSSGGGSQVQLQESG GGSVQAGGSLRLSCAASGYTYSSGCMGWFRQAPGKEREAVAAINSDG STSYADSVKGRFTISKDNAKNTLYLQMNSLKPEDTAMYYCAAEPYCS GGYPRWSVAEFGYWGQGTQVTVSSASHHHHHH | 263 |
| 159-183 | QVQLQESGGGSVQAGGSLRLSCAASRFTYSSYCMGWFRQAPGKEREG VASIDSDGSTSYTDSVKGRFTISKDNAKNTLYLQMNSLKPEDTAMYY CALDLMSTVVPGFCGFLLSAGMDYWGKGTQVTVSSGGGSQVQLQESG GGSVQAGGSLRLSCAASGYTYSSYCMGWFRQAPGKEREGVAHIDSDG STSYADSVKGRFTISKDNAKNTLYLQMNSLKPEDTAMYYCAADPIPG PGYCDGGPNKYWGQGTQVTVSSASHHHHHH | 264 |
| 159-174 | QVQLQESGGGSVQAGGSLRLSCAASRFTYSSYCMGWFRQAPGKEREG VASIDSDGSTSYTDSVKGRFTISKDNAKNTLYLQMNSLKPEDTAMYY CALDLMSTVVPGFCGFLLSAGMDYWGKGTQVTVSSGGGSQVQLQESG GGSVQAGGSLRLSCAASRYTYNSYCMGWFRQAPGKEREGVATIDSDG MTRYADSVKGRFTISKDNAKNTLYLQMNSLKPEDTAMYYCAADADCT IAAMTTNPLGQGTQVTVSSASHHHHHH | 265 |
| 159-186 | QVQLQESGGGSVQAGGSLRLSCAASRFTYSSYCMGWFRQAPGKEREG VASIDSDGSTSYTDSVKGRFTISKDNAKNTLYLQMNSLKPEDTAMYY CALDLMSTVVPGFCGFLLSAGMDYWGKGTQVTVSSGGGSQVQLQESG GGSVQAGGSLRLSCTVSRYTASVNYMGWFRQAPGKEREGVATIFTGA GTTYYANSVKGRFTISRDNAKNTAYLQMNSLKPEDTAIYYCAVDFRG GLLYRPAYEYTYRGQGTQVTVSSASHHHHHH | 266 |
| 159-187 | QVQLQESGGGSVQAGGSLRLSCAASRFTYSSYCMGWFRQAPGKEREG VASIDSDGSTSYTDSVKGRFTISKDNAKNTLYLQMNSLKPEDTAMYY CALDLMSTVVPGFCGFLLSAGMDYWGKGTQVTVSSGGGSQVQLQESG GGSVEAGGSLRLSCAASGYTHSSYCMGWFRQAPGKEREGVAAIDVDG STTYADSVKGRFTISKDNAKNTLYLQMNSLKPEDTGMYYCAAEFADC SSNYFLPPGAVRYWGQGTQVTVSSASHHHHHH | 267 |
| 159-197 | QVQLQESGGGSVQAGGSLRLSCAASRFTYSSYCMGWFRQAPGKEREG VASIDSDGSTSYTDSVKGRFTISKDNAKNTLYLQMNSLKPEDTAMYY CALDLMSTVVPGFCGFLLSAGMDYWGKGTQVTVSSGGGSQVQLQESG GGSVQAGGSLRLSCAASGYSYSSYCMGWFRQAPGKEREGVATIDSDG | 268 |

TABLE 12-continued

Amino Acid Sequences of IL10R Binding Molecules

| NAME | Amino Acid Sequence | SEQ ID NO |
|---|---|---|
| | MTRYADSVKGRFTISKDNAKNTLYLQMNSLKPEDTAMYYCAAPLYDC<br>DSGAVGRNPPYWGQGTQVTVSSASHHHHHH | |
| 159-198 | QVQLQESGGGSVQAGGSLRLSCAASRFTYSSYCMGWFRQAPGKEREG<br>VASIDSDGSTSYTDSVKGRFTISKDNAKNTLYLQMNSLKPEDTAMYY<br>CALDLMSTVVPGFCGFLLSAGMDYWGKGTQVTVSSGGGSQVQLQESG<br>GGSVQTGGSLRLSCAASGYTYLRGCMGWFRQAPGKEREGVAVMDVVG<br>DRRSYIDSVKGRFTISRDNAANSVYLQMDNLKPEDTAMYYCTAGPNC<br>VGWRSGLDYWGQGTQVTVSSASHHHHHH | 269 |
| 161-172 | QVQLQESGGGSVQAGGSLRLSCAASGYTYSMYCMGWFRQAPGKEREG<br>VAQINSDGSTSYADSVKGRFTISKDNAKNTLYLQMNSLKPEDTAMYY<br>CAADSRVYGGSWYERLCGPYTYEYNYWGQGTQVTVSSGGGSQVQLQE<br>SGGGSVQAGGSLRLSCAASGYTYSSGCMGWFRQAPGKEREAVAAINS<br>DGSTSYADSVKGRFTISKDNAKNTLYLQMNSLKPEDTAMYYCAAEPY<br>CSGGYPRWSVAEFGYWGQGTQVTVSSASHHHHHH | 270 |
| 161-183 | QVQLQESGGGSVQAGGSLRLSCAASGYTYSMYCMGWFRQAPGKEREG<br>VAQINSDGSTSYADSVKGRFTISKDNAKNTLYLQMNSLKPEDTAMYY<br>CAADSRVYGGSWYERLCGPYTYEYNYWGQGTQVTVSSGGGSQVQLQE<br>SGGGSVQAGGSLRLSCAASGYTYSSYCMGWFRQAPGKEREGVAHIDS<br>DGSTSYADSVKGRFTISKDNAKNTLYLQMNSLKPEDTAMYYCAADPI<br>PGPGYCDGGPNKYWGQGTQVTVSSASHHHHHH | 271 |
| 161-174 | QVQLQESGGGSVQAGGSLRLSCAASGYTYSMYCMGWFRQAPGKEREG<br>VAQINSDGSTSYADSVKGRFTISKDNAKNTLYLQMNSLKPEDTAMYY<br>CAADSRVYGGSWYERLCGPYTYEYNYWGQGTQVTVSSGGGSQVQLQE<br>SGGGSVQAGGSLRLSCAASRYTYNSYCMGWFRQAPGKEREGVATIDS<br>DGMTRYADSVKGRFTISKDNAKNTLYLQMNSLKPEDTAMYYCAADAD<br>CTIAAMTTNPLGQGTQVTVSSASHHHHHH | 272 |
| 161-186 | QVQLQESGGGSVQAGGSLRLSCAASGYTYSMYCMGWFRQAPGKEREG<br>VAQINSDGSTSYADSVKGRFTISKDNAKNTLYLQMNSLKPEDTAMYY<br>CAADSRVYGGSWYERLCGPYTYEYNYWGQGTQVTVSSGGGSQVQLQE<br>SGGGSVQAGGSLRLSCTVSRYTASVNYMGWFRQAPGKEREGVATIFT<br>GAGTTYYANSVKGRFTISRDNAKNTAYLQMNSLKPEDTAIYYCAVDF<br>RGGLLYRPAYEYTYRGQGTQVTVSSASHHHHHH | 273 |
| 161-187 | QVQLQESGGGSVQAGGSLRLSCAASGYTYSMYCMGWFRQAPGKEREG<br>VAQINSDGSTSYADSVKGRFTISKDNAKNTLYLQMNSLKPEDTAMYY<br>CAADSRVYGGSWYERLCGPYTYEYNYWGQGTQVTVSSGGGSQVQLQE<br>SGGGSVEAGGSLRLSCAASGYTHSSYCMGWFRQAPGKEREGVAAIDV<br>DGSTTYADSVKGRFTISKDNAKNTLYLQMNSLKPEDTGMYYCAAEFA<br>DCSSNYFLPPGAVRYWGQGTQVTVSSASHHHHHH | 274 |
| 161-197 | QVQLQESGGGSVQAGGSLRLSCAASGYTYSMYCMGWFRQAPGKEREG<br>VAQINSDGSTSYADSVKGRFTISKDNAKNTLYLQMNSLKPEDTAMYY<br>CAADSRVYGGSWYERLCGPYTYEYNYWGQGTQVTVSSGGGSQVQLQE<br>SGGGSVQAGGSLRLSCAASGYSYSSYCMGWFRQAPGKEREGVATIDS<br>DGMTRYADSVKGRFTISKDNAKNTLYLQMNSLKPEDTAMYYCAAPLY<br>DCDSGAVGRNPPYWGQGTQVTVSSASHHHHHH | 275 |
| 161-198 | QVQLQESGGGSVQAGGSLRLSCAASGYTYSMYCMGWFRQAPGKEREG<br>VAQINSDGSTSYADSVKGRFTISKDNAKNTLYLQMNSLKPEDTAMYY<br>CAADSRVYGGSWYERLCGPYTYEYNYWGQGTQVTVSSGGGSQVQLQE<br>SGGGSVQTGGSLRLSCAASGYTYLRGCMGWFRQAPGKEREGVAVMDV<br>VGDRRSYIDSVKGRFTISRDNAANSVYLQMDNLKPEDTAMYYCTAGP<br>NCVGWRSGLDYWGQGTQVTVSSASHHHHHH | 276 |
| 162-172 | QVQLQESGGGSVQAGGSLRLSCAVSGYAYSTYCMGWFRQAPGKEREG<br>VAAIDSGGSTSYADSVKGRFTISKDNAKNTLYLRMNSLKPEDTAMYY<br>CAAVPPPPDGGSCLFLGPEIKVSKADFRYWGQGTQVTVSSGGGSQVQ<br>LQESGGGSVQAGGSLRLSCAASGYTYSSGCMGWFRQAPGKEREAVAA<br>INSDGSTSYADSVKGRFTISKDNAKNTLYLQMNSLKPEDTAMYYCAA<br>EPYCSGGYPRWSVAEFGYWGQGTQVTVSSASHHHHHH | 277 |
| 162-183 | QVQLQESGGGSVQAGGSLRLSCAVSGYAYSTYCMGWFRQAPGKEREG<br>VAAIDSGGSTSYADSVKGRFTISKDNAKNTLYLRMNSLKPEDTAMYY<br>CAAVPPPPDGGSCLFLGPEIKVSKADFRYWGQGTQVTVSSGGGSQVQ<br>LQESGGGSVQAGGSLRLSCAASGYTYSSYCMGWFRQAPGKEREGVAH<br>IDSDGSTSYADSVKGRFTISKDNAKNTLYLQMNSLKPEDTAMYYCAA<br>DPIPGPGYCDGGPNKYWGQGTQVTVSSASHHHHHH | 278 |
| 162-174 | QVQLQESGGGSVQAGGSLRLSCAVSGYAYSTYCMGWFRQAPGKEREG<br>VAAIDSGGSTSYADSVKGRFTISKDNAKNTLYLRMNSLKPEDTAMYY | 279 |

TABLE 12-continued

Amino Acid Sequences of IL10R Binding Molecules

| NAME | Amino Acid Sequence | SEQ ID NO |
|---|---|---|
| | CAAVPPPPDGGSCLFLGPEIKVSKADFRYWGQGTQVTVSSGGGSQVQ<br>LQESGGGSVQAGGSLRLSCAASRYTNSYCMGWFRQAPGKEREGVAT<br>IDSDGMTRYADSVKGRFTISKDNAKNTLYLQMNSLKPEDTAMYYCAA<br>DADCTIAAMTTNPLGQGTQVTVSSASHHHHHH | |
| 162-186 | QVQLQESGGGSVQAGGSLRLSCAVSGYAYSTYCMGWFRQAPGKEREG<br>VAAIDSGGSTSYADSVKGRFTISKDNAKNTLYLRMNSLKPEDTAMYY<br>CAAVPPPPDGGSCLFLGPEIKVSKADFRYWGQGTQVTVSSGGGSQVQ<br>LQESGGGSVQAGGSLRLSCTVSRYTASVNYMGWFRQAPGKEREGVAT<br>IFTGAGTTYYANSVKGRFTISRDNAKNTAYLQMNSLKPEDTAIYYCA<br>VDFRGGLLYRPAYEYTYRGQGTQVTVSSASHHHHHH | 280 |
| 162-187 | QVQLQESGGGSVQAGGSLRLSCAVSGYAYSTYCMGWFRQAPGKEREG<br>VAAIDSGGSTSYADSVKGRFTISKDNAKNTLYLRMNSLKPEDTAMYY<br>CAAVPPPPDGGSCLFLGPEIKVSKADFRYWGQGTQVTVSSGGGSQVQ<br>LQESGGGSVEAGGSLRLSCAASGYTHSSYCMGWFRQAPGKEREGVAA<br>IDVDGSTTYADSVKGRFTISKDNAKNTLYLQMNSLKPEDTGMYYCAA<br>EFADCSSNYFLPPGAVRYWGQGTQVTVSSASHHHHHH | 281 |
| 162-197 | QVQLQESGGGSVQAGGSLRLSCAVSGYAYSTYCMGWFRQAPGKEREG<br>VAAIDSGGSTSYADSVKGRFTISKDNAKNTLYLRMNSLKPEDTAMYY<br>CAAVPPPPDGGSCLFLGPEIKVSKADFRYWGQGTQVTVSSGGGSQVQ<br>LQESGGGSVQAGGSLRLSCAASGYSYSSYCMGWFRQAPGKEREGVAT<br>IDSDGMTRYADSVKGRFTISKDNAKNTLYLQMNSLKPEDTAMYYCAA<br>PLYDCDSGAVGRNPPYWGQGTQVTVSSASHHHHHH | 282 |
| 162-198 | QVQLQESGGGSVQAGGSLRLSCAVSGYAYSTYCMGWFRQAPGKEREG<br>VAAIDSGGSTSYADSVKGRFTISKDNAKNTLYLRMNSLKPEDTAMYY<br>CAAVPPPPDGGSCLFLGPEIKVSKADFRYWGQGTQVTVSSGGGSQVQ<br>LQESGGGSVQTGGSLRLSCAASGYTYLRGCMGWFRQAPGKEREGVAV<br>MDVVGDRRSYIDSVKGRFTISRDNAANSVYLQMDNLKPEDTAMYYCT<br>AGPNCVGWRSGLDYWGQGTQVTVSSASHHHHHH | 283 |
| 165-172 | QVQLQESGGGSVQAGGSLRLSCTVSGYTYSSNCMGWFRQAPGKEREG<br>VATIYTGGGNTYYADSVKGRFTISQDNAKNTVYLQMNNLKPEDTAMY<br>YCAAEPLSRVYGGSCPTPTFDYWGQGTQVTVSSGGGSQVQLQESGGG<br>SVQAGGSLRLSCAASGYTYSSGCMGWFRQAPGKEREAVAAINSDGST<br>SYADSVKGRFTISKDNAKNTLYLQMNSLKPEDTAMYYCAAEPYCSGG<br>YPRWSVAEFGYWGQGTQVTVSSASHHHHHH | 284 |
| 165-183 | QVQLQESGGGSVQAGGSLRLSCTVSGYTYSSNCMGWFRQAPGKEREG<br>VATIYTGGGNTYYADSVKGRFTISQDNAKNTVYLQMNNLKPEDTAMY<br>YCAAEPLSRVYGGSCPTPTFDYWGQGTQVTVSSGGGSQVQLQESGGG<br>SVQAGGSLRLSCAASGYTYSSYCMGWFRQAPGKEREGVAHIDSDGST<br>SYADSVKGRFTISKDNAKNTLYLQMNSLKPEDTAMYYCAADPIPGPG<br>YCDGGPNKYWGQGTQVTVSSASHHHHHH | 285 |
| 165-174 | QVQLQESGGGSVQAGGSLRLSCTVSGYTYSSNCMGWFRQAPGKEREG<br>VATIYTGGGNTYYADSVKGRFTISQDNAKNTVYLQMNNLKPEDTAMY<br>YCAAEPLSRVYGGSCPTPTFDYWGQGTQVTVSSGGGSQVQLQESGGG<br>SVQAGGSLRLSCAASRYTNSYCMGWFRQAPGKEREGVATIDSDGMT<br>RYADSVKGRFTISKDNAKNTLYLQMNSLKPEDTAMYYCAADADCTIA<br>AMTTNPLGQGTQVTVSSASHHHHHH | 286 |
| 165-186 | QVQLQESGGGSVQAGGSLRLSCTVSGYTYSSNCMGWFRQAPGKEREG<br>VATIYTGGGNTYYADSVKGRFTISQDNAKNTVYLQMNNLKPEDTAMY<br>YCAAEPLSRVYGGSCPTPTFDYWGQGTQVTVSSGGGSQVQLQESGGG<br>SVQAGGSLRLSCTVSRYTASVNYMGWFRQAPGKEREGVATIFTGAGT<br>TYYANSVKGRFTISRDNAKNTAYLQMNSLKPEDTAIYYCAVDFRGGL<br>LYRPAYEYTYRGQGTQVTVSSASHHHHHH | 287 |
| 165-187 | QVQLQESGGGSVQAGGSLRLSCTVSGYTYSSNCMGWFRQAPGKEREG<br>VATIYTGGGNTYYADSVKGRFTISQDNAKNTVYLQMNNLKPEDTAMY<br>YCAAEPLSRVYGGSCPTPTFDYWGQGTQVTVSSGGGSQVQLQESGGG<br>SVEAGGSLRLSCAASGYTHSSYCMGWFRQAPGKEREGVAAIDVDGST<br>TYADSVKGRFTISKDNAKNTLYLQMNSLKPEDTGMYYCAAEFADCSS<br>NYFLPPGAVRYWGQGTQVTVSSASHHHHHH | 288 |
| 165-197 | QVQLQESGGGSVQAGGSLRLSCTVSGYTYSSNCMGWFRQAPGKEREG<br>VATIYTGGGNTYYADSVKGRFTISQDNAKNTVYLQMNNLKPEDTAMY<br>YCAAEPLSRVYGGSCPTPTFDYWGQGTQVTVSSGGGSQVQLQESGGG<br>SVQAGGSLRLSCAASGYSYSSYCMGWFRQAPGKEREGVATIDSDGMT<br>RYADSVKGRFTISKDNAKNTLYLQMNSLKPEDTAMYYCAAPLYDCDS<br>GAVGRNPPYWGQGTQVTVSSASHHHHHH | 289 |

TABLE 12-continued

Amino Acid Sequences of IL10R Binding Molecules

| NAME | Amino Acid Sequence | SEQ ID NO |
|---|---|---|
| 165-198 DR509 | QVQLQESGGGSVQAGGSLRLSCTVSGYTYSSNCMGWFRQAPGKEREG VATIYTGGGNTYYADSVKGRFTISQDNAKNTVYLQMNNLKPEDTAMY YCAAEPLSRVYGGSCPTPTFDYWGQGTQVTVSSGGGSQVQLQESGGG SVQTGGSLRLSCAASGYTYLRGCMGWFRQAPGKEREGVAVMDVVGDR RSYIDSVKGRFTISRDNAANSVYLQMDNLKPEDTAMYYCTAGPNCVG WRSGLDYWGQGTQVTVSSASHHHHHH | 290 |
| 167-172 | QVQLQESGGGSVQAGGSLRLSCGASGYTYSSYCMGWFRQVPGKEREG VAVIDSDGSTSYADSVKGRFTISKDNGKNTLYLQMNSLKPEDTAMYY CAADLGHYRPPCGVLYLGMDYWGKGTQVTVSSGGGSQVQLQESGGGS VQAGGSLRLSCAASGYTYSSGCMGWFRQAPGKEREAVAAINSDGSTS YADSVKGRFTISKDNAKNTLYLQMNSLKPEDTAMYYCAAEPYCSGGY PRWSVAEFGYWGQGTQVTVSSASHHHHHH | 291 |
| 167-183 | QVQLQESGGGSVQAGGSLRLSCGASGYTYSSYCMGWFRQVPGKEREG VAVIDSDGSTSYADSVKGRFTISKDNGKNTLYLQMNSLKPEDTAMYY CAADLGHYRPPCGVLYLGMDYWGKGTQVTVSSGGGSQVQLQESGGGS VQAGGSLRLSCAASGYTYSSYCMGWFRQAPGKEREGVAHIDSDGSTS YADSVKGRFTISKDNAKNTLYLQMNSLKPEDTAMYYCAADPIPGPGY CDGGPNKYWGQGTQVTVSSASHHHHHH | 292 |
| 167-174 | QVQLQESGGGSVQAGGSLRLSCGASGYTYSSYCMGWFRQVPGKEREG VAVIDSDGSTSYADSVKGRFTISKDNGKNTLYLQMNSLKPEDTAMYY CAADLGHYRPPCGVLYLGMDYWGKGTQVTVSSGGGSQVQLQESGGGS VQAGGSLRLSCAASRYTYNSYCMGWFRQAPGKEREGVATIDSDGMTR YADSVKGRFTISKDNAKNTLYLQMNSLKPEDTAMYYCAADADCTIAA MTTNPLGQGTQVTVSSASHHHHHH | 293 |
| 167-186 | QVQLQESGGGSVQAGGSLRLSCGASGYTYSSYCMGWFRQVPGKEREG VAVIDSDGSTSYADSVKGRFTISKDNGKNTLYLQMNSLKPEDTAMYY CAADLGHYRPPCGVLYLGMDYWGKGTQVTVSSGGGSQVQLQESGGGS VQAGGSLRLSCTVSRYTASVNYMGWFRQAPGKEREGVATIFTGAGTT YYANSVKGRFTISRDNAKNTAYLQMNSLKPEDTAIYYCAVDFRGGLL YRPAYEYTYRGQGTQVTVSSASHHHHHH | 294 |
| 167-187 | QVQLQESGGGSVQAGGSLRLSCGASGYTYSSYCMGWFRQVPGKEREG VAVIDSDGSTSYADSVKGRFTISKDNGKNTLYLQMNSLKPEDTAMYY CAADLGHYRPPCGVLYLGMDYWGKGTQVTVSSGGGSQVQLQESGGGS VEAGGSLRLSCAASGYTHSSYCMGWFRQAPGKEREGVAAIDVDGSTT YADSVKGRFTISKDNAKNTLYLQMNSLKPEDTGMYYCAAEFADCSSN YFLPPGAVRYWGQGTQVTVSSASHHHHHH | 295 |
| 167-197 | QVQLQESGGGSVQAGGSLRLSCGASGYTYSSYCMGWFRQVPGKEREG VAVIDSDGSTSYADSVKGRFTISKDNGKNTLYLQMNSLKPEDTAMYY CAADLGHYRPPCGVLYLGMDYWGKGTQVTVSSGGGSQVQLQESGGGS VQAGGSLRLSCAASGYSYSSYCMGWFRQAPGKEREGVATIDSDGMTR YADSVKGRFTISKDNAKNTLYLQMNSLKPEDTAMYYCAAPLYDCDSG AVGRNPPYWGQGTQVTVSSASHHHHHH | 296 |
| 167-198 | QVQLQESGGGSVQAGGSLRLSCGASGYTYSSYCMGWFRQVPGKEREG VAVIDSDGSTSYADSVKGRFTISKDNGKNTLYLQMNSLKPEDTAMYY CAADLGHYRPPCGVLYLGMDYWGKGTQVTVSSGGGSQVQLQESGGGS VQTGGSLRLSCAASGYTYLRGCMGWFRQAPGKEREGVAVMDVVGDRR SYIDSVKGRFTISRDNAANSVYLQMDNLKPEDTAMYYCTAGPNCVGW RSGLDYWGQGTQVTVSSASHHHHHH | 297 |
| 170-172 | QVQLQESGGGSVQAGGSLRLSCAASGYSNCSYDMTWYRQAPGKEREF VSAIHSDGSTRYADSVKGRFFISQDNAKNTVYLQMNSLKPEDTAMYY CKTDPLHCRAHGGSWYSVRANYWGQGTQVTVSSGGGSQVQLQESGGG SVQAGGSLRLSCAASGYTYSSGCMGWFRQAPGKEREAVAAINSDGST SYADSVKGRFTISKDNAKNTLYLQMNSLKPEDTAMYYCAAEPYCSGG YPRWSVAEFGYWGQGTQVTVSSASHHHHHH | 298 |
| 170-183 | QVQLQESGGGSVQAGGSLRLSCAASGYSNCSYDMTWYRQAPGKEREF VSAIHSDGSTRYADSVKGRFFISQDNAKNTVYLQMNSLKPEDTAMYY CKTDPLHCRAHGGSWYSVRANYWGQGTQVTVSSGGGSQVQLQESGGG SVQAGGSLRLSCAASGYTYSSYCMGWFRQAPGKEREGVAHIDSDGST SYADSVKGRFTISKDNAKNTLYLQMNSLKPEDTAMYYCAADPIPGPG YCDGGPNKYWGQGTQVTVSSASHHHHHH | 299 |
| 170-174 | QVQLQESGGGSVQAGGSLRLSCAASGYSNCSYDMTWYRQAPGKEREF VSAIHSDGSTRYADSVKGRFFISQDNAKNTVYLQMNSLKPEDTAMYY CKTDPLHCRAHGGSWYSVRANYWGQGTQVTVSSGGGSQVQLQESGGG SVQAGGSLRLSCAASRYTYNSYCMGWFRQAPGKEREGVATIDSDGMT | 300 |

TABLE 12-continued

Amino Acid Sequences of IL10R Binding Molecules

| NAME | Amino Acid Sequence | SEQ ID NO |
|------|---------------------|-----------|
| | RYADSVKGRFTISKDNAKNTLYLQMNSLKPEDTAMYYCAADADCTIA<br>AMTTNPLGQGTQVTVSSASHHHHHH | |
| 170-186 | QVQLQESGGGSVQAGGSLRLSCAASGYSNCSYDMTWYRQAPGKEREF<br>VSAIHSDGSTRYADSVKGRFFISQDNAKNTVYLQMNSLKPEDTAMYY<br>CKTDPLHCRAHGGSWYSVRANYWGQGTQVTVSSGGGSQVQLQESGGG<br>SVQAGGSLRLSCTVSRYTASVNYMGWFRQAPGKEREGVATIFTGAGT<br>TYYANSVKGRFTISRDNAKNTAYLQMNSLKPEDTAIYYCAVDFRGGL<br>LYRPAYEYTYRGQGTQVTVSSASHHHHHH | 301 |
| 170-187<br>DR521 | QVQLQESGGGSVQAGGSLRLSCAASGYSNCSYDMTWYRQAPGKEREF<br>VSAIHSDGSTRYADSVKGRFFISQDNAKNTVYLQMNSLKPEDTAMYY<br>CKTDPLHCRAHGGSWYSVRANYWGQGTQVTVSSGGGSQVQLQESGGG<br>SVEAGGSLRLSCAASGYTHSSYCMGWFRQAPGKEREGVAAIDVDGST<br>TYADSVKGRFTISKDNAKNTLYLQMNSLKPEDTGMYYCAAEFADCSS<br>NYFLPPGAVRYWGQGTQVTVSSASHHHHHH | 302 |
| 170-197 | QVQLQESGGGSVQAGGSLRLSCAASGYSNCSYDMTWYRQAPGKEREF<br>VSAIHSDGSTRYADSVKGRFFISQDNAKNTVYLQMNSLKPEDTAMYY<br>CKTDPLHCRAHGGSWYSVRANYWGQGTQVTVSSGGGSQVQLQESGGG<br>SVQAGGSLRLSCAASGYSYSSYCMGWFRQAPGKEREGVATIDSDGMT<br>RYADSVKGRFTISKDNAKNTLYLQMNSLKPEDTAMYYCAAPLYDCDS<br>GAVGRNPPYWGQGTQVTVSSASHHHHHH | 303 |
| 170-198 | QVQLQESGGGSVQAGGSLRLSCAASGYSNCSYDMTWYRQAPGKEREF<br>VSAIHSDGSTRYADSVKGRFFISQDNAKNTVYLQMNSLKPEDTAMYY<br>CKTDPLHCRAHGGSWYSVRANYWGQGTQVTVSSGGGSQVQLQESGGG<br>SVQTGGSLRLSCAASGYTYLRGCMGWFRQAPGKEREGVAVMDVVGDR<br>RSYIDSVKGRFTISRDNAANSVYLQMDNLKPEDTAMYYCTAGPNCVG<br>WRSGLDYWGQGTQVTVSSASHHHHHH | 304 |
| 172-163 | QVQLQESGGGSVQAGGSLRLSCAASGYTYSSGCMGWFRQAPGKEREA<br>VAAINSDGSTSYADSVKGRFTISKDNAKNTLYLQMNSLKPEDTAMYY<br>CAAEPYCSGGYPRWSVAEFGYWGQGTQVTVSSGGGSQVQLQESGGGS<br>VQAGGSLRLSCAASRYLYSIDYMAWFRQSPGKEREPVAVIYTASGAT<br>FYPDSVKGRFTISQDNAKMTVYLQMNSLSEDTAMYYCAAVRKTDSY<br>LFDAQSFTYWGQGTQVTVSSASHHHHHH | 305 |
| 172-159 | QVQLQESGGGSVQAGGSLRLSCAASGYTYSSGCMGWFRQAPGKEREA<br>VAAINSDGSTSYADSVKGRFTISKDNAKNTLYLQMNSLKPEDTAMYY<br>CAAEPYCSGGYPRWSVAEFGYWGQGTQVTVSSGGGSQVQLQESGGGS<br>VQAGGSLRLSCAASRFTYSSYCMGWFRQAPGKEREGVASIDSDGSTS<br>YTDSVKGRFTISKDNAKNTLYLQMNSLKPEDTAMYYCALDLMSTVVP<br>GFCGFLLSAGMDYWGKGTQVTVSSASHHHHHH | 306 |
| 172-161 | QVQLQESGGGSVQAGGSLRLSCAASGYTYSSGCMGWFRQAPGKEREA<br>VAAINSDGSTSYADSVKGRFTISKDNAKNTLYLQMNSLKPEDTAMYY<br>CAAEPYCSGGYPRWSVAEFGYWGQGTQVTVSSGGGSQVQLQESGGGS<br>VQAGGSLRLSCAASGYTYSMYCMGWFRQAPGKEREGVAQINSDGSTS<br>YADSVKGRFTISKDNAKNTLYLQMNSLKPEDTAMYYCAADSRVYGGS<br>WYERLCGPYTYEYNYWGQGTQVTVSSASHHHHHH | 307 |
| 172-162<br>DR527 | QVQLQESGGGSVQAGGSLRLSCAASGYTYSSGCMGWFRQAPGKEREA<br>VAAINSDGSTSYADSVKGRFTISKDNAKNTLYLQMNSLKPEDTAMYY<br>CAAEPYCSGGYPRWSVAEFGYWGQGTQVTVSSGGGSQVQLQESGGGS<br>VQAGGSLRLSCAVSGYAYSTYCMGWFRQAPGKEREGVAAIDSGGSTS<br>YADSVKGRFTISKDNAKNTLYLRMNSLKPEDTAMYYCAAVPPPPDGG<br>SCLFLGPEIKVSKADFRYWGQGTQVTVSSASHHHHHH | 308 |
| 172-165 | QVQLQESGGGSVQAGGSLRLSCAASGYTYSSGCMGWFRQAPGKEREA<br>VAAINSDGSTSYADSVKGRFTISKDNAKNTLYLQMNSLKPEDTAMYY<br>CAAEPYCSGGYPRWSVAEFGYWGQGTQVTVSSGGGSQVQLQESGGGS<br>VQAGGSLRLSCTVSGYTYSSNCMGWFRQAPGKEREGVATIYTGGGNT<br>YYADSVKGRFTISQDNAKNTVYLQMNNLKPEDTAMYYCAAEPLSRVY<br>GGSCPTPTFDYWGQGTQVTVSSASHHHHHH | 309 |
| 172-167 | QVQLQESGGGSVQAGGSLRLSCAASGYTYSSGCMGWFRQAPGKEREA<br>VAAINSDGSTSYADSVKGRFTISKDNAKNTLYLQMNSLKPEDTAMYY<br>CAAEPYCSGGYPRWSVAEFGYWGQGTQVTVSSGGGSQVQLQESGGGS<br>VQAGGSLRLSCGASGYTYSSYCMGWFRQVPGKEREGVAVIDSDGSTS<br>YADSVKGRFTISKDNGKNTLYLQMNSLKPEDTAMYYCAADLGHYRPP<br>CGVLYLGMDYWGKGTQVTVSSASHHHHHH | 310 |
| 172-170 | QVQLQESGGGSVQAGGSLRLSCAASGYTYSSGCMGWFRQAPGKEREA<br>VAAINSDGSTSYADSVKGRFTISKDNAKNTLYLQMNSLKPEDTAMYY | 311 |

TABLE 12-continued

Amino Acid Sequences of IL10R Binding Molecules

| NAME | Amino Acid Sequence | SEQ ID NO |
|---|---|---|
|  | CAAEPYCSGGYPRWSVAEFGYWGQGTQVTVSSGGGSVQLQESGGGS VQAGGSLRLSCAASGYSNCSYDMTWYRQAPGKEREFVSAIHSDGSTR YADSVKGRFFISQDNAKNTVYLQMNSLKPEDTAMYYCKTDPLHCRAH GGSWYSVRANYWGQGTQVTVSSASHHHHHH |  |
| 183-163 | QVQLQESGGGSVQAGGSLRLSCAASGYTYSSYCMGWFRQAPGKEREG VAHIDSDGSTSYADSVKGRFTISKDNAKNTLYLQMNSLKPEDTAMYY CAADPIPGPGYCDGGPNKYWGQGTQVTVSSGGGSQVQLQESGGGSVQ AGGSLRLSCAASRYLYSIDYMAWFRQSPGKEREPVAVIYTASGATFY PDSVKGRFTISQDNAKMTVYLQMNSLKSEDTAMYYCAAVRKTDSYLF DAQSFTYWGQGTQVTVSSASHHHHHH | 312 |
| 183-159 | QVQLQESGGGSVQAGGSLRLSCAASGYTYSSYCMGWFRQAPGKEREG VAHIDSDGSTSYADSVKGRFTISKDNAKNTLYLQMNSLKPEDTAMYY CAADPIPGPGYCDGGPNKYWGQGTQVTVSSGGGSQVQLQESGGGSVQ AGGSLRLSCAASRFTYSSYCMGWFRQAPGKEREGVASIDSDGSTSYT DSVKGRFTISKDNAKNTLYLQMNSLKPEDTAMYYCALDLMSTVVPGF CGFLLSAGMDYWGKGTQVTVSSASHHHHHH | 313 |
| 183-161 | QVQLQESGGGSVQAGGSLRLSCAASGYTYSSYCMGWFRQAPGKEREG VAHIDSDGSTSYADSVKGRFTISKDNAKNTLYLQMNSLKPEDTAMYY CAADPIPGPGYCDGGPNKYWGQGTQVTVSSGGGSQVQLQESGGGSVQ AGGSLRLSCAASGYTYSMYCMGWFRQAPGKEREGVAQINSDGSTSYA DSVKGRFTISKDNAKNTLYLQMNSLKPEDTAMYYCAADSRVYGGSWY ERLCGPYTYEYNYWGQGTQVTVSSASHHHHHH | 314 |
| 183-162 | QVQLQESGGGSVQAGGSLRLSCAASGYTYSSYCMGWFRQAPGKEREG VAHIDSDGSTSYADSVKGRFTISKDNAKNTLYLQMNSLKPEDTAMYY CAADPIPGPGYCDGGPNKYWGQGTQVTVSSGGGSQVQLQESGGGSVQ AGGSLRLSCAVSGYAYSTYCMGWFRQAPGKEREGVAAIDSGGSTSYA DSVKGRFTISKDNAKNTLYLRMNSLKPEDTAMYYCAAVPPPPDGGSC LFLGPEIKVSKADFRYWGQGTQVTVSSASHHHHHH | 315 |
| 183-165 | QVQLQESGGGSVQAGGSLRLSCAASGYTYSSYCMGWFRQAPGKEREG VAHIDSDGSTSYADSVKGRFTISKDNAKNTLYLQMNSLKPEDTAMYY CAADPIPGPGYCDGGPNKYWGQGTQVTVSSGGGSQVQLQESGGGSVQ AGGSLRLSCTVSGYTYSSNCMGWFRQAPGKEREGVATIYTGGGNTYY ADSVKGRFTISQDNAKNTVYLQMNNLKPEDTAMYYCAAEPLSRVYGG SCPTPTFDYWGQGTQVTVSSASHHHHHH | 316 |
| 183-167 | QVQLQESGGGSVQAGGSLRLSCAASGYTYSSYCMGWFRQAPGKEREG VAHIDSDGSTSYADSVKGRFTISKDNAKNTLYLQMNSLKPEDTAMYY CAADPIPGPGYCDGGPNKYWGQGTQVTVSSGGGSQVQLQESGGGSVQ AGGSLRLSCGASGYTYSSYCMGWFRQVPGKEREGVAVIDSDGSTSYA DSVKGRFTISKDNGKNTLYLQMNSLKPEDTAMYYCAADLGHYRPPCG VLYLGMDYWGKGTQVTVSSASHHHHHH | 317 |
| 183-170 | QVQLQESGGGSVQAGGSLRLSCAASGYTYSSYCMGWFRQAPGKEREG VAHIDSDGSTSYADSVKGRFTISKDNAKNTLYLQMNSLKPEDTAMYY CAADPIPGPGYCDGGPNKYWGQGTQVTVSSGGGSQVQLQESGGGSVQ AGGSLRLSCAASGYSNCSYDMTWYRQAPGKEREFVSAIHSDGSTRYA DSVKGRFFISQDNAKNTVYLQMNSLKPEDTAMYYCKTDPLHCRAHGG SWYSVRANYWGQGTQVTVSSASHHHHHH | 318 |
| 174-163 | QVQLQESGGGSVQAGGSLRLSCAASRYTYNSYCMGWFRQAPGKEREG VATIDSDGMTRYADSVKGRFTISKDNAKNTLYLQMNSLKPEDTAMYY CAADADCTIAAMTTNPLGQGTQVTVSSGGGSQVQLQESGGGSVQAGG SLRLSCAASRYLYSIDYMAWFRQSPGKEREPVAVIYTASGATFYPDS VKGRFTISQDNAKMTVYLQMNSLKSEDTAMYYCAAVRKTDSYLFDAQ SFTYWGQGTQVTVSSASHHHHHH | 319 |
| 174-159 | QVQLQESGGGSVQAGGSLRLSCAASRYTYNSYCMGWFRQAPGKEREG VATIDSDGMTRYADSVKGRFTISKDNAKNTLYLQMNSLKPEDTAMYY CAADADCTIAAMTTNPLGQGTQVTVSSGGGSQVQLQESGGGSVQAGG SLRLSCAASRFTYSSYCMGWFRQAPGKEREGVASIDSDGSTSYTDSV KGRFTISKDNAKNTLYLQMNSLKPEDTAMYYCALDLMSTVVPGFCGF LLSAGMDYWGKGTQVTVSSASHHHHHH | 320 |
| 174-161 | QVQLQESGGGSVQAGGSLRLSCAASRYTYNSYCMGWFRQAPGKEREG VATIDSDGMTRYADSVKGRFTISKDNAKNTLYLQMNSLKPEDTAMYY CAADADCTIAAMTTNPLGQGTQVTVSSGGGSQVQLQESGGGSVQAGG SLRLSCAASGYTYSMYCMGWFRQAPGKEREGVAQINSDGSTSYADSV KGRFTISKDNAKNTLYLQMNSLKPEDTAMYYCAADSRVYGGSWYERL CGPYTYEYNYWGQGTQVTVSSASHHHHHH | 321 |

TABLE 12-continued

Amino Acid Sequences of IL10R Binding Molecules

| NAME | Amino Acid Sequence | SEQ ID NO |
|---|---|---|
| 174-162 | QVQLQESGGGSVQAGGSLRLSCAASRYTYNSYCMGWFRQAPGKEREG VATIDSDGMTRYADSVKGRFTISKDNAKNTLYLQMNSLKPEDTAMYY CAADADCTIAAMTTNPLGQGTQVTVSSGGGSQVQLQESGGGSVQAGG SLRLSCAVSGYAYSTYCMGWFRQAPGKEREGVAAIDSGGSTSYADSV KGRFTISKDNAKNTLYLRMNSLKPEDTAMYYCAAVPPPPDGGSCLFL GPEIKVSKADFRYWGQGTQVTVSSASHHHHHH | 322 |
| 174-165 | QVQLQESGGGSVQAGGSLRLSCAASRYTYNSYCMGWFRQAPGKEREG VATIDSDGMTRYADSVKGRFTISKDNAKNTLYLQMNSLKPEDTAMYY CAADADCTIAAMTTNPLGQGTQVTVSSGGGSQVQLQESGGGSVQAGG SLRLSCTVSGYTYSSNCMGWFRQAPGKEREGVATIYTGGGNTYYADS VKGRFTISQDNAKNTVYLQMNNLKPEDTAMYYCAAEPLSRVYGGSCP TPTFDYWGQGTQVTVSSASHHHHHH | 323 |
| 174-167 | QVQLQESGGGSVQAGGSLRLSCAASRYTYNSYCMGWFRQAPGKEREG VATIDSDGMTRYADSVKGRFTISKDNAKNTLYLQMNSLKPEDTAMYY CAADADCTIAAMTTNPLGQGTQVTVSSGGGSQVQLQESGGGSVQAGG SLRLSCGASGYTYSSYCMGWFRQVPGKEREGVAVIDSDGSTSYADSV KGRFTISKDNGKNTLYLQMNSLKPEDTAMYYCAADLGHYRPPCGVLY LGMDYWGKGTQVTVSSASHHHHHH | 324 |
| 174-170 | QVQLQESGGGSVQAGGSLRLSCAASRYTYNSYCMGWFRQAPGKEREG VATIDSDGMTRYADSVKGRFTISKDNAKNTLYLQMNSLKPEDTAMYY CAADADCTIAAMTTNPLGQGTQVTVSSGGGSQVQLQESGGGSVQAGG SLRLSCAASGYSNCSYDMTWYRQAPGKEREFVSAIHSDGSTRYADSV KGRFFISQDNAKNTVYLQMNSLKPEDTAMYYCKTDPLHCRAHGGSWY SVRANYWGQGTQVTVSSASHHHHHH | 325 |
| 186-163 | QVQLQESGGGSVQAGGSLRLSCTVSRYTASVNYMGWFRQAPGKEREG VATIFTGAGTTYYANSVKGRFTISRDNAKNTAYLQMNSLKPEDTAIY YCAVDFRGGLLYRPAYEYTYRGQGTQVTVSSGGGSQVQLQESGGGSV QAGGSLRLSCAASRYLYSIDYMAWFRQSPGKEREPVAVIYTASGATF YPDSVKGRFTISQDNAKMTVYLQMNSLKSEDTAMYYCAAVRKTDSYL FDAQSFTYWGQGTQVTVSSASHHHHHH | 326 |
| 186-159 | QVQLQESGGGSVQAGGSLRLSCTVSRYTASVNYMGWFRQAPGKEREG VATIFTGAGTTYYANSVKGRFTISRDNAKNTAYLQMNSLKPEDTAIY YCAVDFRGGLLYRPAYEYTYRGQGTQVTVSSGGGSQVQLQESGGGSV QAGGSLRLSCAASRFTYSSYCMGWFRQAPGKEREGVASIDSDGSTSY TDSVKGRFTISKDNAKNTLYLQMNSLKPEDTAMYYCALDLMSTVVPG FCGFLLSAGMDYWGKGTQVTVSSASHHHHHH | 327 |
| 186-161 | QVQLQESGGGSVQAGGSLRLSCTVSRYTASVNYMGWFRQAPGKEREG VATIFTGAGTTYYANSVKGRFTISRDNAKNTAYLQMNSLKPEDTAIY YCAVDFRGGLLYRPAYEYTYRGQGTQVTVSSGGGSQVQLQESGGGSV QAGGSLRLSCAASGYTYSMYCMGWFRQAPGKEREGVAQINSDGSTSY ADSVKGRFTISKDNAKNTLYLQMNSLKPEDTAMYYCAADSRVYGGSW YERLCGPYTYEYNYWGQGTQVTVSSASHHHHHH | 328 |
| 186-162 | QVQLQESGGGSVQAGGSLRLSCTVSRYTASVNYMGWFRQAPGKEREG VATIFTGAGTTYYANSVKGRFTISRDNAKNTAYLQMNSLKPEDTAIY YCAVDFRGGLLYRPAYEYTYRGQGTQVTVSSGGGSQVQLQESGGGSV QAGGSLRLSCAVSGYAYSTYCMGWFRQAPGKEREGVAAIDSGGSTSY ADSVKGRFTISKDNAKNTLYLRMNSLKPEDTAMYYCAAVPPPPDGGS CLFLGPEIKVSKADFRYWGQGTQVTVSSASHHHHHH | 329 |
| 186-165 | QVQLQESGGGSVQAGGSLRLSCTVSRYTASVNYMGWFRQAPGKEREG VATIFTGAGTTYYANSVKGRFTISRDNAKNTAYLQMNSLKPEDTAIY YCAVDFRGGLLYRPAYEYTYRGQGTQVTVSSGGGSQVQLQESGGGSV QAGGSLRLSCTVSGYTYSSNCMGWFRQAPGKEREGVATIYTGGGNTY YADSVKGRFTISQDNAKNTVYLQMNNLKPEDTAMYYCAAEPLSRVYG GSCPTPTFDYWGQGTQVTVSSASHHHHHH | 330 |
| 186-167 | QVQLQESGGGSVQAGGSLRLSCTVSRYTASVNYMGWFRQAPGKEREG VATIFTGAGTTYYANSVKGRFTISRDNAKNTAYLQMNSLKPEDTAIY YCAVDFRGGLLYRPAYEYTYRGQGTQVTVSSGGGSQVQLQESGGGSV QAGGSLRLSCGASGYTYSSYCMGWFRQVPGKEREGVAVIDSDGSTSY ADSVKGRFTISKDNGKNTLYLQMNSLKPEDTAMYYCAADLGHYRPPC GVLYLGMDYWGKGTQVTVSSASHHHHHH | 331 |
| 186-170 | QVQLQESGGGSVQAGGSLRLSCTVSRYTASVNYMGWFRQAPGKEREG VATIFTGAGTTYYANSVKGRFTISRDNAKNTAYLQMNSLKPEDTAIY YCAVDFRGGLLYRPAYEYTYRGQGTQVTVSSGGGSQVQLQESGGGSV QAGGSLRLSCAASGYSNCSYDMTWYRQAPGKEREFVSAIHSDGSTRY | 332 |

TABLE 12-continued

Amino Acid Sequences of IL10R Binding Molecules

| NAME | Amino Acid Sequence | SEQ ID NO |
|---|---|---|
| | ADSVKGRFFISQDNAKNTVYLQMNSLKPEDTAMYYCKTDPLHCRAHG GSWYSVRANYWGQGTQVTVSSASHHHHHH | |
| 187-163 | QVQLQESGGGSVEAGGSLRLSCAASGYTHSSYCMGWFRQAPGKEREG VAAIDVDGSTTYADSVKGRFTISKDNAKNTLYLQMNSLKPEDTGMYY CAAEFADCSSNYFLPPGAVRYWGQGTQVTVSSGGGSQVQLQESGGGS VQAGGSLRLSCAASRYLYSIDYMAWFRQSPGKEREPVAVIYTASGAT FYPDSVKGRFTISQDNAKMTVYLQMNSLKSEDTAMYYCAAVRKTDSY LFDAQSFTYWGQGTQVTVSSASHHHHHH | 333 |
| 187-159 | QVQLQESGGGSVEAGGSLRLSCAASGYTHSSYCMGWFRQAPGKEREG VAAIDVDGSTTYADSVKGRFTISKDNAKNTLYLQMNSLKPEDTGMYY CAAEFADCSSNYFLPPGAVRYWGQGTQVTVSSGGGSQVQLQESGGGS VQAGGSLRLSCAASRFTYSSYCMGWFRQAPGKEREGVASIDSDGSTS YTDSVKGRFTISKDNAKNTLYLQMNSLKPEDTAMYYCALDLMSTVVP GFCGFLLSAGMDYWGKGTQVTVSSASHHHHHH | 334 |
| 187-161 | QVQLQESGGGSVEAGGSLRLSCAASGYTHSSYCMGWFRQAPGKEREG VAAIDVDGSTTYADSVKGRFTISKDNAKNTLYLQMNSLKPEDTGMYY CAAEFADCSSNYFLPPGAVRYWGQGTQVTVSSGGGSQVQLQESGGGS VQAGGSLRLSCAASGYTYSMYCMGWFRQAPGKEREGVAQINSDGSTS YADSVKGRFTISKDNAKNTLYLQMNSLKPEDTAMYYCAADSRVYGGS WYERLCGPYTYEYNYWGQGTQVTVSSASHHHHHH | 335 |
| 187-162 | QVQLQESGGGSVEAGGSLRLSCAASGYTHSSYCMGWFRQAPGKEREG VAAIDVDGSTTYADSVKGRFTISKDNAKNTLYLQMNSLKPEDTGMYY CAAEFADCSSNYFLPPGAVRYWGQGTQVTVSSGGGSQVQLQESGGGS VQAGGSLRLSCAVSGYAYSTYCMGWFRQAPGKEREGVAAIDSGGSTS YADSVKGRFTISKDNAKNTLYLRMNSLKPEDTAMYYCAAVPPPPDGG SCLFLGPEIKVSKADFRYWGQGTQVTVSSASHHHHHH | 336 |
| 187-165 | QVQLQESGGGSVEAGGSLRLSCAASGYTHSSYCMGWFRQAPGKEREG VAAIDVDGSTTYADSVKGRFTISKDNAKNTLYLQMNSLKPEDTGMYY CAAEFADCSSNYFLPPGAVRYWGQGTQVTVSSGGGSQVQLQESGGGS VQAGGSLRLSCTVSGYTYSSNCMGWFRQAPGKEREGVATIYTGGGNT YYADSVKGRFTISQDNAKNTVYLQMNNLKPEDTAMYYCAAEPLSRVY GGSCPTPTFDYWGQGTQVTVSSASHHHHHH | 337 |
| 187-167 | QVQLQESGGGSVEAGGSLRLSCAASGYTHSSYCMGWFRQAPGKEREG VAAIDVDGSTTYADSVKGRFTISKDNAKNTLYLQMNSLKPEDTGMYY CAAEFADCSSNYFLPPGAVRYWGQGTQVTVSSGGGSQVQLQESGGGS VQAGGSLRLSCGASGYTYSSYCMGWFRQVPGKEREGVAVIDSDGSTS YADSVKGRFTISKDNGKNTLYLQMNSLKPEDTAMYYCAADLGHYRPP CGVLYLGMDYWGKGTQVTVSSASHHHHHH | 338 |
| 187-170 | QVQLQESGGGSVEAGGSLRLSCAASGYTHSSYCMGWFRQAPGKEREG VAAIDVDGSTTYADSVKGRFTISKDNAKNTLYLQMNSLKPEDTGMYY CAAEFADCSSNYFLPPGAVRYWGQGTQVTVSSGGGSQVQLQESGGGS VQAGGSLRLSCAASGYSNCSYDMTWYRQAPGKEREFVSAIHSDGSTR YADSVKGRFFISQDNAKNTVYLQMNSLKPEDTAMYYCKTDPLHCRAH GGSWYSVRANYWGQGTQVTVSSASHHHHHH | 339 |
| 197-163 | QVQLQESGGGSVQAGGSLRLSCAASGYSYSSYCMGWFRQAPGKEREG VATIDSDGMTRYADSVKGRFTISKDNAKNTLYLQMNSLKPEDTAMYY CAAPLYDCDSGAVGRNPPYWGQGTQVTVSSGGGSQVQLQESGGGSVQ AGGSLRLSCAASRYLYSIDYMAWFRQSPGKEREPVAVIYTASGATFY PDSVKGRFTISQDNAKMTVYLQMNSLKSEDTAMYYCAAVRKTDSYLF DAQSFTYWGQGTQVTVSSASHHHHHH | 340 |
| 197-159 | QVQLQESGGGSVQAGGSLRLSCAASGYSYSSYCMGWFRQAPGKEREG VATIDSDGMTRYADSVKGRFTISKDNAKNTLYLQMNSLKPEDTAMYY CAAPLYDCDSGAVGRNPPYWGQGTQVTVSSGGGSQVQLQESGGGSVQ AGGSLRLSCAASRFTYSSYCMGWFRQAPGKEREGVASIDSDGSTSYT DSVKGRFTISKDNAKNTLYLQMNSLKPEDTAMYYCALDLMSTVVPGF CGFLLSAGMDYWGKGTQVTVSSASHHHHHH | 341 |
| 197-161 | QVQLQESGGGSVQAGGSLRLSCAASGYSYSSYCMGWFRQAPGKEREG VATIDSDGMTRYADSVKGRFTISKDNAKNTLYLQMNSLKPEDTAMYY CAAPLYDCDSGAVGRNPPYWGQGTQVTVSSGGGSQVQLQESGGGSVQ AGGSLRLSCAASGYTYSMYCMGWFRQAPGKEREGVAQINSDGSTSYA DSVKGRFTISKDNAKNTLYLQMNSLKPEDTAMYYCAADSRVYGGSWY ERLCGPYTYEYNYWGQGTQVTVSSASHHHHHH | 342 |
| 197-162 | QVQLQESGGGSVQAGGSLRLSCAASGYSYSSYCMGWFRQAPGKEREG VATIDSDGMTRYADSVKGRFTISKDNAKNTLYLQMNSLKPEDTAMYY | 343 |

TABLE 12-continued

Amino Acid Sequences of IL10R Binding Molecules

| NAME | Amino Acid Sequence | SEQ ID NO |
|---|---|---|
| | CAAPLYDCDSGAVGRNPPYWGQGTQVTVSSGGGSQVQLQESGGGSVQ<br>AGGSLRLSCAVSGYAYSTYCMGWFRQAPGKEREGVAAIDSGGSTSYA<br>DSVKGRFTISKDNAKNTLYLRMNSLKPEDTAMYYCAAVPPPPDGGSC<br>LFLGPEIKVSKADFRYWGQGTQVTVSSASHHHHHH | |
| 197-165 | QVQLQESGGGSVQAGGSLRLSCAASGYSYSSYCMGWFRQAPGKEREG<br>VATIDSDGMTRYADSVKGRFTISKDNAKNTLYLQMNSLKPEDTAMYY<br>CAAPLYDCDSGAVGRNPPYWGQGTQVTVSSGGGSQVQLQESGGGSVQ<br>AGGSLRLSCTVSGYTYSSNCMGWFRQAPGKEREGVATIYTGGGNTYY<br>ADSVKGRFTISQDNAKNTVYLQMNNLKPEDTAMYYCAAEPLSRVYGG<br>SCPTPTFDYWGQGTQVTVSSASHHHHHH | 344 |
| 197-167 | QVQLQESGGGSVQAGGSLRLSCAASGYSYSSYCMGWFRQAPGKEREG<br>VATIDSDGMTRYADSVKGRFTISKDNAKNTLYLQMNSLKPEDTAMYY<br>CAAPLYDCDSGAVGRNPPYWGQGTQVTVSSGGGSQVQLQESGGGSVQ<br>AGGSLRLSCGASGYTYSSYCMGWFRQVPGKEREGVAVIDSDGSTSYA<br>DSVKGRFTISKDNGKNTLYLQMNSLKPEDTAMYYCAADLGHYRPPCG<br>VLYLGMDYWGKGTQVTVSSASHHHHHH | 345 |
| 197-170 | QVQLQESGGGSVQAGGSLRLSCAASGYSYSSYCMGWFRQAPGKEREG<br>VATIDSDGMTRYADSVKGRFTISKDNAKNTLYLQMNSLKPEDTAMYY<br>CAAPLYDCDSGAVGRNPPYWGQGTQVTVSSGGGSQVQLQESGGGSVQ<br>AGGSLRLSCAASGYSNCSYDMTWYRQAPGKEREFVSAIHSDGSTRYA<br>DSVKGRFFISQDNAKNTVYLQMNSLKPEDTAMYYCKTDPLHCRAHGG<br>SWYSVRANYWGQGTQVTVSSASHHHHHH | 346 |
| 198-163 | QVQLQESGGGSVQTGGSLRLSCAASGYTYLRGCMGWFRQAPGKEREG<br>VAVMDVVGDRRSYIDSVKGRFTISRDNAANSVYLQMDNLKPEDTAMY<br>YCTAGPNCVGWRSGLDYWGQGTQVTVSSGGGSQVQLQESGGGSVQAG<br>GSLRLSCAASRYLYSIDYMAWFRQSPGKEREPVAVIYTASGATFYPD<br>SVKGRFTISQDNAKMTVYLQMNSLKSEDTAMYYCAAVRKTDSYLFDA<br>QSFTYWGQGTQVTVSSASHHHHHH | 347 |
| 198-159 | QVQLQESGGGSVQTGGSLRLSCAASGYTYLRGCMGWFRQAPGKEREG<br>VAVMDVVGDRRSYIDSVKGRFTISRDNAANSVYLQMDNLKPEDTAMY<br>YCTAGPNCVGWRSGLDYWGQGTQVTVSSGGGSQVQLQESGGGSVQAG<br>GSLRLSCAASRFTYSSYCMGWFRQAPGKEREGVASIDSDGSTSYTDS<br>VKGRFTISKDNAKNTLYLQMNSLKPEDTAMYYCALDLMSTVVPGFCG<br>FLLSAGMDYWGKGTQVTVSSASHHHHHH | 348 |
| 198-161 | QVQLQESGGGSVQTGGSLRLSCAASGYTYLRGCMGWFRQAPGKEREG<br>VAVMDVVGDRRSYIDSVKGRFTISRDNAANSVYLQMDNLKPEDTAMY<br>YCTAGPNCVGWRSGLDYWGQGTQVTVSSGGGSQVQLQESGGGSVQAG<br>GSLRLSCAASGYTYSMYCMGWFRQAPGKEREGVAQINSDGSTSYADS<br>VKGRFTISKDNAKNTLYLQMNSLKPEDTAMYYCAADSRVYGGSWYER<br>LCGPYTYEYNYWGQGTQVTVSSASHHHHHH | 349 |
| 198-162 | QVQLQESGGGSVQTGGSLRLSCAASGYTYLRGCMGWFRQAPGKEREG<br>VAVMDVVGDRRSYIDSVKGRFTISRDNAANSVYLQMDNLKPEDTAMY<br>YCTAGPNCVGWRSGLDYWGQGTQVTVSSGGGSQVQLQESGGGSVQAG<br>GSLRLSCAVSGYAYSTYCMGWFRQAPGKEREGVAAIDSGGSTSYADS<br>VKGRFTISKDNAKNTLYLRMNSLKPEDTAMYYCAAVPPPPDGGSCLF<br>LGPEIKVSKADFRYWGQGTQVTVSSASHHHHHH | 350 |
| 198-165 | QVQLQESGGGSVQTGGSLRLSCAASGYTYLRGCMGWFRQAPGKEREG<br>VAVMDVVGDRRSYIDSVKGRFTISRDNAANSVYLQMDNLKPEDTAMY<br>YCTAGPNCVGWRSGLDYWGQGTQVTVSSGGGSQVQLQESGGGSVQAG<br>GSLRLSCTVSGYTYSSNCMGWFRQAPGKEREGVATIYTGGGNTYYAD<br>SVKGRFTISQDNAKNTVYLQMNNLKPEDTAMYYCAAEPLSRVYGGSC<br>PTPTFDYWGQGTQVTVSSASHHHHHH | 351 |
| 198-167 | QVQLQESGGGSVQTGGSLRLSCAASGYTYLRGCMGWFRQAPGKEREG<br>VAVMDVVGDRRSYIDSVKGRFTISRDNAANSVYLQMDNLKPEDTAMY<br>YCTAGPNCVGWRSGLDYWGQGTQVTVSSGGGSQVQLQESGGGSVQAG<br>GSLRLSCGASGYTYSSYCMGWFRQVPGKEREGVAVIDSDGSTSYADS<br>VKGRFTISKDNGKNTLYLQMNSLKPEDTAMYYCAADLGHYRPPCGVL<br>YLGMDYWGKGTQVTVSSASHHHHHH | 352 |
| 198-170 | QVQLQESGGGSVQTGGSLRLSCAASGYTYLRGCMGWFRQAPGKEREG<br>VAVMDVVGDRRSYIDSVKGRFTISRDNAANSVYLQMDNLKPEDTAMY<br>YCTAGPNCVGWRSGLDYWGQGTQVTVSSGGGSQVQLQESGGGSVQAG<br>GSLRLSCAASGYSNCSYDMTWYRQAPGKEREFVSAIHSDGSTRYADS<br>VKGRFFISQDNAKNTVYLQMNSLKPEDTAMYYCKTDPLHCRAHGGSW<br>YSVRANYWGQGTQVTVSSASHHHHHH | 353 |

TABLE 13

IL10R Binding Protein Activity

| TestArticle (SEQ ID NO:) | Abs 630 (25 nM) | Abs 630 (100 nM) |
|---|---|---|
| Unstimulated | 0.58 | 0.59 |
| WildType hIL10 | 2.08 | 2.04 |
| 256 | 0.49 | 0.39 |
| 257 | 0.45 | 0.36 |
| 258 | 0.49 | 0.38 |
| 259 | 1.85 | 1.13 |
| 260 | 0.49 | 0.39 |
| 261 | 0.44 | 0.34 |
| 262 | 1.38 | 0.40 |
| 263 | 1.77 | 1.02 |
| 264 | 1.52 | 0.67 |
| 265 | 0.54 | 0.46 |
| 266 | 0.49 | 0.39 |
| 267 | 0.75 | 0.53 |
| 268 | 0.53 | 0.41 |
| 269 | 0.46 | 0.37 |
| 270 | 1.41 | 0.73 |
| 271 | 1.93 | 1.65 |
| 272 | 0.47 | 0.38 |
| 273 | 0.52 | 0.41 |
| 274 | 0.46 | 0.37 |
| 275 | 0.51 | 0.36 |
| 276 | 0.46 | 0.36 |
| 277 | 1.19 | 1.00 |
| 278 | 1.61 | 1.18 |
| 279 | 0.49 | 0.39 |
| 280 | 0.49 | 0.37 |
| 281 | 0.66 | 0.69 |
| 282 | 0.44 | 0.36 |
| 283 | 0.48 | 0.39 |
| 284 | 0.45 | 0.34 |
| 285 | 0.48 | 0.39 |
| 286 | 0.46 | 0.39 |
| 287 | 0.90 | 0.51 |
| 288 | 0.50 | 0.44 |
| 289 | 0.48 | 0.39 |
| 290 | 0.49 | 0.37 |
| 291 | 1.73 | 0.59 |
| 292 | 0.78 | 0.47 |
| 293 | 0.54 | 0.43 |
| 294 | 0.49 | 0.39 |
| 295 | 0.72 | 0.46 |
| 296 | 0.54 | 0.38 |
| 297 | 0.46 | 0.36 |
| 298 | 0.84 | 0.38 |
| 299 | 0.47 | 0.37 |
| 300 | 2.08 | 2.11 |
| 301 | 2.05 | 1.91 |
| 302 | 1.98 | 2.09 |
| 303 | 1.92 | 1.93 |
| 304 | 1.96 | 2.06 |
| 305 | 0.59 | 0.35 |
| 306 | 0.69 | 0.49 |
| 307 | 0.44 | 0.34 |
| 308 | 0.48 | 0.39 |
| 309 | 0.45 | 0.37 |
| 310 | 0.51 | 0.44 |
| 311 | 0.48 | 0.40 |
| 312 | 0.48 | 0.39 |
| 313 | 0.47 | 0.39 |
| 314 | 0.49 | 0.42 |
| 315 | 0.51 | 0.41 |
| 316 | 0.48 | 0.39 |
| 317 | 0.45 | 0.38 |
| 318 | 0.50 | 0.45 |
| 319 | 0.47 | 0.36 |
| 320 | 0.54 | 0.41 |
| 321 | 0.46 | 0.40 |
| 322 | 0.46 | 0.41 |
| 323 | 0.64 | 0.38 |
| 324 | 0.61 | 0.44 |
| 325 | 0.49 | 0.42 |
| 326 | 0.47 | 0.56 |
| 327 | 0.52 | 0.54 |
| 328 | 0.44 | 0.34 |
| 329 | 0.48 | 0.39 |
| 330 | 0.45 | 0.36 |
| 331 | 0.50 | 0.41 |
| 332 | 0.47 | 0.36 |
| 333 | 0.49 | 0.54 |
| 334 | 1.43 | 1.14 |
| 335 | 0.50 | 0.44 |
| 336 | 0.54 | 0.45 |
| 337 | 0.49 | 0.40 |
| 338 | 0.51 | 0.41 |
| 339 | 0.49 | 0.42 |
| 340 | 0.46 | 0.51 |
| 341 | 0.60 | 0.48 |
| 342 | 0.45 | 0.36 |
| 343 | 0.46 | 0.37 |
| 344 | 0.50 | 0.43 |
| 345 | 0.52 | 0.44 |
| 346 | 0.43 | 0.35 |
| 347 | 0.45 | 0.35 |
| 348 | 0.46 | 0.36 |
| 349 | 0.46 | 0.38 |
| 350 | 0.43 | 0.35 |
| 351 | 0.43 | 0.34 |
| 352 | 0.54 | 0.65 |
| 353 | 0.56 | 0.61 |

TABLE 14

IL10 Receptor Binding Molecules Nucleic Acids

| DNA ENCODING SEQ ID NO. | DNA Sequence | SEQ ID NO |
|---|---|---|
| 256 | CAAGTGCAGCTGCAAGAGAGCGGAGGAGGAAGCGTGCAAGCCGGAGGCTCTCTGAGACTGAGCTGTGCCGCCTCTAGGTATCTGTACAGCATCGACTACATGGCTTGGTTCAGACAGAGCCCCGGCAAGGAGAGGGAGCCAGTGGCTGTCATCTACACTGCCTCCGGCGCCACATTCTATCCAGATAGCGTGAAGGGAAGGTTCACTATCAGCCAAGATAACGCCAAGATGACAGTGTATCTGCAGATGAACTCTCTGAAGAGCGAGGACACTGCCATGTACTACTGTGCCGCCGTGAGGAAGACAGATAGCTACCTCTTCGACGCCCAGAGCTTCACATACTGGGGCCAAGGCACACAAGTGACAGTCTCGAGCGGCGGAGGATCCCAAGTGCAGCTGCAAGAGAGCGGCGGAGGAAGCGTGCAAGCTGGAGGCTCTCTGAGGCTGAGCTGTGCTGCCAGCGGCTACACTTATAGCAGCGGCTGTATGGGCTGGTTCAGACAAGCCCCCGGCAAGGAAAGGGAAGCCGTGGCCGCCATCAATTCCGATGGCAGCACAAGCTACGCCGACAGCGTG | 354 |

TABLE 14-continued

IL10 Receptor Binding Molecules Nucleic Acids

| DNA ENCODING SEQ ID NO. | DNA Sequence | SEQ ID NO |
|---|---|---|
| | AAGGGAAGGTTCACAATCAGCAAGGACAACGCCAAGAACACACTCTAT CTGCAGATGAACTCTCTGAAGCCAGAGGACACAGCCATGTACTACTGC GCCGCTGAGCCTTACTGTAGCGGCGGCTACCCAAGATGGAGCGTCGCT GAGTTCGGCTACTGGGGCCAAGGCACACAAGTGACTGTCTCGTCTGCT AGCCACCATCACCATCACCAC | |
| 257 | CAAGTGCAGCTGCAAGAGAGCGGAGGAGGAAGCGTGCAAGCCGGAGGC TCTCTGAGACTGAGCTGTGCCGCCTCTAGGTATCTGTACAGCATCGAC TACATGGCTTGGTTCAGACAGAGCCCCGGCAAGGAGAGGGAGCCAGTG GCTGTCATCTACACTGCCTCCGGCGCCACATTCTATCCAGATAGCGTG AAGGGAAGGTTCACTATCAGCCAAGATAACGCCAAGATGACAGTGTAT CTGCAGATGAACTCTCTGAAGAGCGAGGACACTGCCATGTACTACTGT GCCGCCGTGAGGAAGACAGATAGCTACCTCTTCGACGCCCAGAGCTTC ACATACTGGGGCCAAGGCACACAAGTGACAGTCTCGAGCGGCGGAGGA TCCCAAGTGCAGCTGCAAGAGAGCGGAGGAGGCAGCGTCCAAGCCGGA GGCTCTCTGAGGCTGAGCTGTGCTGCCAGCGGCTACACTTACAGCAGC TACTGCATGGGCTGGTTCAGACAAGCCCCCGGCAAGGAGAGAGAGGGC GTGGCTCACATCGACAGCGACGGCTCCACAAGCTACGCCGATAGCGTG AAGGGAAGGTTCACAATCTCCAAGGACAACGCCAAGAACACTCTGTAC CTCCAGATGAACTCTCTGAAGCCAGAGGACACTGCCATGTACTACTGT GCCGCCGATCCAATTCCCGGCCCCGGCTACTGCGATGGCGGCCCTAAC AAGTACTGGGGCCAAGGCACACAAGTGACTGTCTCGTCTGCTAGCCAC CATCACCATCACCAC | 355 |
| 258 | CAAGTGCAGCTGCAAGAGAGCGGAGGAGGAAGCGTGCAAGCCGGAGGC TCTCTGAGACTGAGCTGTGCCGCCTCTAGGTATCTGTACAGCATCGAC TACATGGCTTGGTTCAGACAGAGCCCCGGCAAGGAGAGGGAGCCAGTG GCTGTCATCTACACTGCCTCCGGCGCCACATTCTATCCAGATAGCGTG AAGGGAAGGTTCACTATCAGCCAAGATAACGCCAAGATGACAGTGTAT CTGCAGATGAACTCTCTGAAGAGCGAGGACACTGCCATGTACTACTGT GCCGCCGTGAGGAAGACAGATAGCTACCTCTTCGACGCCCAGAGCTTC ACATACTGGGGCCAAGGCACACAAGTGACAGTCTCGAGCGGCGGAGGA TCCCAAGTGCAGCTGCAAGAGTCCGGAGGAGGAAGCGTGCAAGCCGGC GGATCTCTGAGACTGAGCTGTGCCGCCTCTAGGTACACTTACAACAGC TACTGCATGGGCTGGTTCAGACAAGCCCCCGGCAAGGAAAGAGAGGGC GTGGCCACTATCGATAGCGACGGCATGACTAGGTACGCTGATAGCGTC AAGGGAAGGTTCACAATCTCCAAGGACAATGCTAAGAACACTCTGTAC CTCCAGATGAACTCTCTGAAGCCAGAGGACACAGCCATGTACTACTGC GCTGCCGATGCCGACTGCACTATCGCCGCCATGACTACTAATCCTCTG GGCCAAGGCACACAAGTGACTGTCTCGTCTGCTAGCCACCATCACCAT CACCAC | 356 |
| 259 | CAAGTGCAGCTGCAAGAGAGCGGAGGAGGAAGCGTGCAAGCCGGAGGC TCTCTGAGACTGAGCTGTGCCGCCTCTAGGTATCTGTACAGCATCGAC TACATGGCTTGGTTCAGACAGAGCCCCGGCAAGGAGAGGGAGCCAGTG GCTGTCATCTACACTGCCTCCGGCGCCACATTCTATCCAGATAGCGTG AAGGGAAGGTTCACTATCAGCCAAGATAACGCCAAGATGACAGTGTAT CTGCAGATGAACTCTCTGAAGAGCGAGGACACTGCCATGTACTACTGT GCCGCCGTGAGGAAGACAGATAGCTACCTCTTCGACGCCCAGAGCTTC ACATACTGGGGCCAAGGCACACAAGTGACAGTCTCGAGCGGCGGAGGA TCCCAAGTGCAGCTGCAAGAGTCCGGCGGAGGCAGCGTCCAAGCCGGA GGATCTCTGAGGCTGAGCTGTACAGTGAGCAGATACACTGCCAGCGTG AACTACATGGGCTGGTTCAGACAAGCCCCCGGCAAAGAGAGAGAGGGC GTGGCCACAATCTTCACTGGCGCCGGCACAACATACTACGCCAACTCC GTCAAGGGAAGGTTCACAATCTCTAGGGACAACGCCAAGAACACTGCC TATCTGCAGATGAACTCCCTCAAGCCAGAGGACACTGCCATCTACTAC TGCGCCGTGGATTTCAGAGGCGGACTGCTGTATAGGCCAGCCTACGAG TACACTTATAGGGGCCAAGGCACACAAGTGACAGTCTCGTCTGCTAGC CACCATCACCATCACCAC | 357 |
| 260 | CAAGTGCAGCTGCAAGAGAGCGGAGGAGGAAGCGTGCAAGCCGGAGGC TCTCTGAGACTGAGCTGTGCCGCCTCTAGGTATCTGTACAGCATCGAC TACATGGCTTGGTTCAGACAGAGCCCCGGCAAGGAGAGGGAGCCAGTG GCTGTCATCTACACTGCCTCCGGCGCCACATTCTATCCAGATAGCGTG AAGGGAAGGTTCACTATCAGCCAAGATAACGCCAAGATGACAGTGTAT CTGCAGATGAACTCTCTGAAGAGCGAGGACACTGCCATGTACTACTGT GCCGCCGTGAGGAAGACAGATAGCTACCTCTTCGACGCCCAGAGCTTC ACATACTGGGGCCAAGGCACACAAGTGACAGTCTCGAGCGGCGGAGGA TCCCAAGTGCAGCTGCAAGAGAGCGGAGGAGGCAGCGTCGAAGCTGGA GGATCTCTGAGGCTGAGCTGTGCTGCCAGCGGCTACACTCACAGCAGC TACTGTATGGGCTGGTTCAGACAAGCCCCCGGCAAGGAGAGGGAAGGC GTGGCTGCCATCGACGTGGATGGCAGCACTACTTACGCCGACAGCGTG AAGGGAAGGTTCACTATCAGCCAAGGACAACGCCAAGAACACACTCTAT | 358 |

TABLE 14-continued

IL10 Receptor Binding Molecules Nucleic Acids

| DNA ENCODING SEQ ID NO. | DNA Sequence | SEQ ID NO |
|---|---|---|
|  | CTGCAGATGAACAGCCTCAAGCCAGAGGACACTGGCATGTACTACTGC GCCGCCGAGTTCGCCGATTGCAGCAGCAACTACTTTCTGCCTCCCGGC GCCGTCAGATATTGGGGCCAAGGCACTCAAGTGACAGTCTCGTCTGCT AGCCACCATCACCATCACCAC |  |
| 261 | CAAGTGCAGCTGCAAGAGAGCGGAGGAGGAAGCGTGCAAGCCGGAGGC TCTCTGAGACTGAGCTGTGCCGCCTCTAGGTATCTGTACAGCATCGAC TACATGGCTTGGTTCAGACAGAGCCCCGGCAAGGAGAGGGAGCCAGTG GCTGTCATCTACACTGCCTCCGGCGCCACATTCTATCCAGATAGCGTG AAGGGAAGGTTCACTATCAGCCAAGATAACGCCAAGATGACAGTGTAT CTGCAGATGAACTCTCTGAAGAGCGAGGACACTGCCATGTACTACTGT GCCGCCGTGAGGAAGACAGATAGCTACCTCTTCGACGCCCAGAGCTTC ACATACTGGGGCCAAGGCACACAAGTGACAGTCTCGAGCGGCGGAGGA TCCCAAGTGCAGCTGCAAGAGAGCGGAGGAGGAAGCGTCAAGCCGGA GGATCTCTGAGACTGAGCTGCGCCGCTAGTGGCTACTCCTACAGCAGC TACTGCATGGGCTGGTTTAGGCAAGCCCCCGGCAAGGAGAGAGAAGGC GTGGCCACTATCGACAGCGACGGCATGACAAGGTACGCCGACAGCGTG AAGGGAAGGTTCACAATCAGCAAGGACAACGCCAAGAACACTGTAT CTGCAGATGAACTCTCTGAAGCCAGAGGACACTGCCATGTACTACTGT GCCGCTCCTCTGTACGACTGTGATAGCGGCGCTGTGGGCAGAAATCCA CCTTATTGGGGCCAAGGCACTCAAGTGACAGTCTCGTCTGCTAGCCAC CATCACCATCACCAC | 359 |
| 262 | CAAGTGCAGCTGCAAGAGAGCGGAGGAGGAAGCGTGCAAGCCGGAGGC TCTCTGAGACTGAGCTGTGCCGCCTCTAGGTATCTGTACAGCATCGAC TACATGGCTTGGTTCAGACAGAGCCCCGGCAAGGAGAGGGAGCCAGTG GCTGTCATCTACACTGCCTCCGGCGCCACATTCTATCCAGATAGCGTG AAGGGAAGGTTCACTATCAGCCAAGATAACGCCAAGATGACAGTGTAT CTGCAGATGAACTCTCTGAAGAGCGAGGACACTGCCATGTACTACTGT GCCGCCGTGAGGAAGACAGATAGCTACCTCTTCGACGCCCAGAGCTTC ACATACTGGGGCCAAGGCACACAAGTGACAGTCTCGAGCGGCGGAGGA TCCCAAGTGCAGCTGCAAGAGAGCGGAGGCGGCAGCGTGCAGACTGGA GGCTCTCTGAGACTGAGCTGTGCTGCCAGCGGCTACACTTATCTGAGG GGCTGTATGGGCTGGTTTAGGCAAGCCCCCGGCAAGGAGAGAGAGGGC GTGGCCGTCATGGATGTGGTGGGCGATAGGAGAAGCTACATCGACAGC GTGAAGGGAAGGTTCACAATCTCTAGGGACAATGCCGCCAACAGCGTC TATCTGCAGATGGACAATCTGAAGCCAGAGGACACAGCCATGTACTAC TGCACTGCCGGCCCTAACTGTGTGGGCTGGAGAAGCGGACTGGATTAC TGGGGCCAAGGCACACAAGTGACAGTCTCGTCTGCTAGCCACCATCAC CATCACCAC | 360 |
| 263 | CAAGTGCAGCTGCAAGAGAGCGGAGGAGGAAGCGTGCAAGCCGGAGGC TCTCTGAGGCTGAGCTGTGCCGCCTCTAGGTTCACATACAGCAGCTAC TGCATGGGCTGGTTCAGACAAGCCCCCGGCAAAGAGAGAGAAGGCGTG GCCAGCATCGATAGCGATGGCTCCACTAGCTACACTGACAGCGTGAAG GGAAGGTTCACTATCAGCAAGGACAACGCCAAGAACACTCTGTATCTG CAGATGAACTCTCTGAAGCCAGAGGACACAGCCATGTACTACTGTGCC CTCGATCTGATGAGCACAGTGGTGCCCGGCTTCTGTGGCTTTCTGCTG AGCGCTGGCATGGATTACTGGGGCAAGGGCACTCAAGTGACTGTCTCG AGCGGCGGAGGATCCCAAGTGCAGCTGCAAGAGAGCGGCGGAGGAAGC GTGCAAGCTGGAGGCTCTCTGAGGCTGAGCTGTGCTGCCAGCGGCTAC ACTTATAGCAGCGGCTGTATGGGCTGGTTCAGACAAGCCCCCGGCAAG GAAAGGGAAGCCGTGGCCGCCATCAATTCCGATGGCAGCACAAGCTAC GCCGACAGCGTGAAGGGAAGGTTCACAATCAGCAAGGACAACGCCAAG AACACACTCTATCTGCAGATGAACTCTCTGAAGCCAGAGGACACAGCC ATGTACTACTGCGCCGCTGAGCCTTACTGTAGCGGCGGCTACCCAAGA TGGAGCGTCGCTGAGTTCGGCTACTGGGGCCAAGGCACACAAGTGACT GTCTCGTCTGCTAGCCACCATCACCATCACCAC | 361 |
| 264 | CAAGTGCAGCTGCAAGAGAGCGGAGGAGGAAGCGTGCAAGCCGGAGGC TCTCTGAGGCTGAGCTGTGCCGCCTCTAGGTTCACATACAGCAGCTAC TGCATGGGCTGGTTCAGACAAGCCCCCGGCAAAGAGAGAGAAGGCGTG GCCAGCATCGATAGCGATGGCTCCACTAGCTACACTGACAGCGTGAAG GGAAGGTTCACTATCAGCAAGGACAACGCCAAGAACACTCTGTATCTG CAGATGAACTCTCTGAAGCCAGAGGACACAGCCATGTACTACTGTGCC CTCGATCTGATGAGCACAGTGGTGCCCGGCTTCTGTGGCTTTCTGCTG AGCGCTGGCATGGATTACTGGGGCAAGGGCACTCAAGTGACTGTCTCG AGCGGCGGAGGATCCCAAGTGCAGCTGCAAGAGAGCGGAGGAGGCAGC GTCCAAGCCGGAGGCTCTCTGAGGCTGAGCTGTGCTGCCAGCGGCTAC ACTTACAGCAGCTACTGCATGGGCTGGTTCAGACAAGCCCCCGGCAAG GAGAGAGAGGGCGTGGCTCACATCGACAGCGACGGCTCCACAAGCTAC GCCGATAGCGTGAAGGGAAGGTTCACAATCTCCAAGGACAACGCCAAG AACACTCTGTACCTCCAGATGAACTCTCTGAAGCCAGAGGACACTGCC | 362 |

TABLE 14-continued

IL10 Receptor Binding Molecules Nucleic Acids

| DNA ENCODING SEQ ID NO. | DNA Sequence | SEQ ID NO |
|---|---|---|
|  | ATGTACTACTGTGCCGCCGATCCAATTCCCGGCCCCGGCTACTGCGAT GGCGGCCCTAACAAGTACTGGGGCCAAGGCACACAAGTGACTGTCTCG TCTGCTAGCCACCATCACCATCACCAC | |
| 265 | CAAGTGCAGCTGCAAGAGAGCGGAGGAGGAAGCGTGCAAGCCGGAGGC TCTCTGAGGCTGAGCTGTGCCGCCTCTAGGTTCACATACAGCAGCTAC TGCATGGGCTGGTTCAGACAAGCCCCCGGCAAAGAGAGAGAAGGCGTG GCCAGCATCGATAGCGATGGCTCCACTAGCTACACTGACAGCGTGAAG GGAAGGTTCACTATCAGCAAGGACAACGCCAAGAACACTCTGTATCTG CAGATGAACTCTCTGAAGCCAGAGGACACAGCCATGTACTACTGTGCC CTCGATCTGATGAGCACAGTGGTGCCCGGCTTCTGTGGCTTTCTGCTG AGCGCTGGCATGGATTACTGGGGCAAGGGCACTCAAGTGACTGTCTCG AGCGGCGGAGGATCCCAAGTGCAGCTGCAAGAGTCCGGAGGAGGAAGC GTGCAAGCCGGCGGATCTCTGAGACTGAGCTGTGCCGCCTCTAGGTAC ACTTACAACAGCTACTGCATGGGCTGGTTCAGACAAGCCCCCGGCAAG GAAAGAGAGGGCGTGGCCACTATCGATAGCGACGGCATGACTAGGTAC GCTGATAGCGTCAAGGGAAGGTTCACAATCTCCAAGGACAATGCTAAG AACACTCTGTACCTCCAGATGAACTCTCTGAAGCCAGAGGACACAGCC ATGTACTACTGCGCTGCCGATGCCGACTGCACTATCGCCGCCATGACT ACTAATCCTCTGGGCCAAGGCACACAAGTGACTGTCTCGTCTGCTAGC CACCATCACCATCACCAC | 363 |
| 266 | CAAGTGCAGCTGCAAGAGAGCGGAGGAGGAAGCGTGCAAGCCGGAGGC TCTCTGAGGCTGAGCTGTGCCGCCTCTAGGTTCACATACAGCAGCTAC TGCATGGGCTGGTTCAGACAAGCCCCCGGCAAAGAGAGAGAAGGCGTG GCCAGCATCGATAGCGATGGCTCCACTAGCTACACTGACAGCGTGAAG GGAAGGTTCACTATCAGCAAGGACAACGCCAAGAACACTCTGTATCTG CAGATGAACTCTCTGAAGCCAGAGGACACAGCCATGTACTACTGTGCC CTCGATCTGATGAGCACAGTGGTGCCCGGCTTCTGTGGCTTTCTGCTG AGCGCTGGCATGGATTACTGGGGCAAGGGCACTCAAGTGACTGTCTCG AGCGGCGGAGGATCCCAAGTGCAGCTGCAAGAGTCCGGCGGAGGCAGC GTCCAAGCCGGAGGATCTCTGAGGCTGAGCTGTACAGTGAGCAGATAC ACTGCCAGCGTGAACTACATGGGCTGGTTCAGACAAGCCCCCGGCAAA GAGAGAGAGGGCGTGGCCACAATCTTCACTGGCGCCGGCACAACATAC TACGCCAACTCCGTCAAGGGAAGGTTCACAATCTCTAGGGACAACGCC AAGAACACTGCCTATCTGCAGATGAACTCCCTCAAGCCAGAGGACACT GCCATCTACTACTGCGCCGTGGATTTCAGAGGCGGACTGCTGTATAGG CCAGCCTACGAGTACACTTATAGGGGCCAAGGCACACAAGTGACAGTC TCGTCTGCTAGCCACCATCACCATCACCAC | 364 |
| 267 | CAAGTGCAGCTGCAAGAGAGCGGAGGAGGAAGCGTGCAAGCCGGAGGC TCTCTGAGGCTGAGCTGTGCCGCCTCTAGGTTCACATACAGCAGCTAC TGCATGGGCTGGTTCAGACAAGCCCCCGGCAAAGAGAGAGAAGGCGTG GCCAGCATCGATAGCGATGGCTCCACTAGCTACACTGACAGCGTGAAG GGAAGGTTCACTATCAGCAAGGACAACGCCAAGAACACTCTGTATCTG CAGATGAACTCTCTGAAGCCAGAGGACACAGCCATGTACTACTGTGCC CTCGATCTGATGAGCACAGTGGTGCCCGGCTTCTGTGGCTTTCTGCTG AGCGCTGGCATGGATTACTGGGGCAAGGGCACTCAAGTGACTGTCTCG AGCGGCGGAGGATCCCAAGTGCAGCTGCAAGAGAGCGGAGGAGGCAGC GTCGAAGCTGGAGGATCTCTGAGGCTGAGCTGTGCTGCCAGCGGCTAC ACTCACAGCAGCTACTGTATGGGCTGGTTCAGACAAGCCCCCGGCAAG GAGAGGGAAGGCGTGGCTGCCATCGACGTGGATGGCAGCACTACTTAC GCCGACAGCGTGAAGGGAAGGTTCACTATCAGCAAGGACAACGCCAAG AACACACTCTATCTGCAGATGAACAGCCTCAAGCCAGAGGACACTGGC ATGTACTACTGCGCCGCCGAGTTCGCCGATTGCAGCAGCAACTACTTT CTGCCTCCCGGCCGCCGTCAGATATTGGGGCCAAGGCACTCAAGTGACA GTCTCGTCTGCTAGCCACCATCACCATCACCAC | 365 |
| 268 | CAAGTGCAGCTGCAAGAGAGCGGAGGAGGAAGCGTGCAAGCCGGAGGC TCTCTGAGGCTGAGCTGTGCCGCCTCTAGGTTCACATACAGCAGCTAC TGCATGGGCTGGTTCAGACAAGCCCCCGGCAAAGAGAGAGAAGGCGTG GCCAGCATCGATAGCGATGGCTCCACTAGCTACACTGACAGCGTGAAG GGAAGGTTCACTATCAGCAAGGACAACGCCAAGAACACTCTGTATCTG CAGATGAACTCTCTGAAGCCAGAGGACACAGCCATGTACTACTGTGCC CTCGATCTGATGAGCACAGTGGTGCCCGGCTTCTGTGGCTTTCTGCTG AGCGCTGGCATGGATTACTGGGGCAAGGGCACTCAAGTGACTGTCTCG AGCGGCGGAGGATCCCAAGTGCAGCTGCAAGAGAGCGGAGGAGGAAGC GTCCAAGCCGGAGGATCTCTGAGACTGAGCTGCGCCGCTAGTGCCTAC TCCTACAGCAGCTACTGCATGGGCTGGTTTAGGCAAGCCCCCGGCAAG GAGAGAGAAGGCGTGGCCACTATCGACAGCGACGGCATGACAAGGTAC GCCGACAGCGTGAAGGGAAGGTTCACAATCAGCAAGGACAACGCCAAG AACACACTGTATCTGCAGATGAACTCTCTGAAGCCAGAGGACACTGCC ATGTACTACTGTGCCGCTCCTCTGTACGACTGTGATAGCGGCGCTGTG | 366 |

TABLE 14-continued

IL10 Receptor Binding Molecules Nucleic Acids

| DNA ENCODING SEQ ID NO. | DNA Sequence | SEQ ID NO |
|---|---|---|
|  | GGCAGAAATCCACCTTATTGGGGCCAAGGCACTCAAGTGACAGTCTCG<br>TCTGCTAGCCACCATCACCATCACCAC |  |
| 269 | CAAGTGCAGCTGCAAGAGAGCGGAGGAGGAAGCGTGCAAGCCGGAGGC<br>TCTCTGAGGCTGAGCTGTGCCGCCTCTAGGTTCACATACAGCAGCTAC<br>TGCATGGGCTGGTTCAGACAAGCCCCCGGCAAAGAGAGAGAAGGCGTG<br>GCCAGCATCGATAGCGATGGCTCCACTAGCTACACTGACAGCGTGAAG<br>GGAAGGTTCACTATCAGCAAGGACAACGCCAAGAACACTCTGTATCTG<br>CAGATGAACTCTCTGAAGCCAGAGGACACAGCCATGTACTACTGTGCC<br>CTCGATCTGATGAGCACAGTGGTGCCCGGCTTCTGTGGCTTTCTGCTG<br>AGCGCTGGCATGGATTACTGGGGCAAGGGCACTCAAGTGACTGTCTCG<br>AGCGGCGGAGGATCCCAAGTGCAGCTGCAAGAGAGCGGAGGCGGCAGC<br>GTGCAGACTGGAGGCTCTCTGAGACTGAGCTGTGCTGCCAGCGGCTAC<br>ACTTATCTGAGGGGCTGTATGGGCTGGTTTAGGCAAGCCCCCGGCAAG<br>GAGAGAGAGGGCGTGGCCGTCATGGATGTGGTGGGCGATAGGAGAAGC<br>TACATCGACAGCGTGAAGGGAAGGTTCACAATCTCTAGGGACAATGCC<br>GCCAACAGCGTCTATCTGCAGATGGACAATCTGAAGCAGAGGACACA<br>GCCATGTACTACTGCACTGCCGGCCCTAACTGTGTGGGCTGGAGAAGC<br>GGACTGGATTACTGGGGCCAAGGCACACAAGTGACAGTCTCGTCTGCT<br>AGCCACCATCACCATCACCAC | 367 |
| 270 | CAAGTGCAGCTGCAAGAGTCCGGAGGAGGCAGCGTCCAAGCCGGAGGC<br>TCTCTGAGGCTGAGCTGTGCTGCCAGCGGCTACACTTACAGCATGTAC<br>TGCATGGGCTGGTTCAGACAAGCCCCCGGCAAGGAAAGAGAGGGCGTG<br>GCCCAGATCAATAGCGATGGCAGCACAAGCTACGCCGACAGCGTGAAG<br>GGAAGGTTCACTATCTCCAAGGACAACGCCAAGAACACTCTGTATCTG<br>CAGATGAACTCTCTGAAGCCAGAGGACACTGCCATGTACTACTGCGCT<br>GCCGATTCTAGGGTGTACGGCGGCAGCTGGTATGAGAGGCTCTGCGGC<br>CCTTACACATACGAGTACAACTACTGGGGCCAAGGCACACAAGTGACT<br>GTCTCGAGCGGCGGAGGATCCCAAGTGCAGCTGCAAGAGAGCGGCGGA<br>GGAAGCGTGCAAGCTGGAGGCTCTCTGAGGCTGAGCTGTGCTGCCAGC<br>GGCTACACTTATAGCAGCGGCTGTATGGGCTGGTTCAGACAAGCCCCC<br>GGCAAGGAAAGGGAAGCCGTGGCCGCCATCAATTCCGATGGCAGCACA<br>AGCTACGCCGACAGCGTGAAGGGAAGGTTCACAATCAGCAAGGACAAC<br>GCCAAGAACACACTCTATCTGCAGATGAACTCTCTGAAGCCAAGAGGAC<br>ACAGCCATGTACTACTGCGCCGCTGAGCCTTACTGTAGCGGCGGCTAC<br>CCAAGATGGAGCGTCGCTGAGTTCGGCTACTGGGGCAAGGCACACAA<br>GTGACTGTCTCGTCTGCTAGCCACCATCACCATCACCAC | 368 |
| 271 | CAAGTGCAGCTGCAAGAGTCCGGAGGAGGCAGCGTCCAAGCCGGAGGC<br>TCTCTGAGGCTGAGCTGTGCTGCCAGCGGCTACACTTACAGCATGTAC<br>TGCATGGGCTGGTTCAGACAAGCCCCCGGCAAGGAAAGAGAGGGCGTG<br>GCCCAGATCAATAGCGATGGCAGCACAAGCTACGCCGACAGCGTGAAG<br>GGAAGGTTCACTATCTCCAAGGACAACGCCAAGAACACTCTGTATCTG<br>CAGATGAACTCTCTGAAGCCAGAGGACACTGCCATGTACTACTGCGCT<br>GCCGATTCTAGGGTGTACGGCGGCAGCTGGTATGAGAGGCTCTGCGGC<br>CCTTACACATACGAGTACAACTACTGGGGCCAAGGCACACAAGTGACT<br>GTCTCGAGCGGCGGAGGATCCCAAGTGCAGCTGCAAGAGAGCGGAGGA<br>GGCAGCGTCCAAGCCGGAGGCTCTCTGAGGCTGAGCTGTGCTGCCAGC<br>GGCTACACTTACAGCAGCTACTGCATGGGCTGGTTCAGACAAGCCCCC<br>GGCAAGGAGAGAGAGGGCGTGGCTCACATCGACAGCGACGGCTCCACA<br>AGCTACGCCGATAGCGTGAAGGGAAGGTTCACAATCTCCAAGGACAAC<br>GCCAAGAACACTCTGTACCTCCAGATGAACTCTCTGAAGCCAGAGGAC<br>ACTGCCATGTACTACTGTGCCGCCGATCCAATTCCCGGCCCCGGCTAC<br>TGCGATGGCGGCCCTAACAAGTACTGGGGCCAAGGCACACAAGTGACT<br>GTCTCGTCTGCTAGCCACCATCACCATCACCAC | 369 |
| 272 | CAAGTGCAGCTGCAAGAGTCCGGAGGAGGCAGCGTCCAAGCCGGAGGC<br>TCTCTGAGGCTGAGCTGTGCTGCCAGCGGCTACACTTACAGCATGTAC<br>TGCATGGGCTGGTTCAGACAAGCCCCCGGCAAGGAAAGAGAGGGCGTG<br>GCCCAGATCAATAGCGATGGCAGCACAAGCTACGCCGACAGCGTGAAG<br>GGAAGGTTCACTATCTCCAAGGACAACGCCAAGAACACTCTGTATCTG<br>CAGATGAACTCTCTGAAGCCAGAGGACACTGCCATGTACTACTGCGCT<br>GCCGATTCTAGGGTGTACGGCGGCAGCTGGTATGAGAGGCTCTGCGGC<br>CCTTACACATACGAGTACAACTACTGGGGCCAAGGCACACAAGTGACT<br>GTCTCGAGCGGCGGAGGATCCCAAGTGCAGCTGCAAGAGTCCGGAGGA<br>GGAAGCGTGCAAGCCGGCGGATCTCTGAGACTGAGCTGTGCCGCCTCT<br>AGGTACACTTACAACAGCTACTGCATGGGCTGGTTCAGACAAGCCCCC<br>GGCAAGGAAAGAGAGGGCGTGGCCACTATCGATAGCGACGGCATGACT<br>AGGTACGCTGATAGCGTCAAGGGAAGGTTCACAATCTCCAAGGACAAT<br>GCTAAGAACACTCTGTACCTCCAGATGAACTCTCTGAAGCCAGAGGAC | 370 |

TABLE 14-continued

IL10 Receptor Binding Molecules Nucleic Acids

| DNA ENCODING SEQ ID NO. | DNA Sequence | SEQ ID NO |
|---|---|---|
| | ACAGCCATGTACTACTGCGCTGCCGATGCCGACTGCACTATCGCCGCC<br>ATGACTACTAATCCTCTGGGCCAAGGCACACAAGTGACTGTCTCGTCT<br>GCTAGCCACCATCACCATCACCAC | |
| 273 | CAAGTGCAGCTGCAAGAGTCCGGAGGAGGCAGCGTCCAAGCCGGAGGC<br>TCTCTGAGGCTGAGCTGTGCTGCCAGCGGCTACACTTACAGCATGTAC<br>TGCATGGGCTGGTTCAGACAAGCCCCCGGCAAGGAAAGAGAGGGCGTG<br>GCCCAGATCAATAGCGATGGCAGCACAAGCTACGCCGACAGCGTGAAG<br>GGAAGGTTCACTATCTCCAAGGACAACGCCAAGAACACTCTGTATCTG<br>CAGATGAACTCTCTGAAGCAGAGGACACTGCCATGTACTACTGCGCT<br>GCCGATTCTAGGGTGTACGGCGGCAGCTGGTATGAGAGGCTCTGCGGC<br>CCTTACACATACGAGTACAACTACTGGGGCCAAGGCACACAAGTGACT<br>GTCTCGAGCGGCGGAGGATCCCAAGTGCAGCTGCAAGAGTCCGGCGGA<br>GGCAGCGTCCAAGCCGGAGGATCTCTGAGGCTGAGCTGTACAGTGAGC<br>AGATACACTGCCAGCGTGAACTACATGGGCTGGTTCAGACAAGCCCCC<br>GGCAAAGAGAGAGAGGGCGTGGCCACAATCTTCACTGGCGCCGGCACA<br>ACATACTACGCCAACTCCGTCAAGGGAAGGTTCACAATCTCTAGGGAC<br>AACGCCAAGAACACTGCCTATCTGCAGATGAACTCCCTCAAGCCAGAG<br>GACACTGCCATCTACTACTGCGCCGTGGATTTCAGAGGCGGACTGCTG<br>TATAGGCCAGCCTACGAGTACACTTATAGGGGCCAAGGCACACAAGTG<br>ACAGTCTCGTCTGCTAGCCACCATCACCATCACCAC | 371 |
| 274 | CAAGTGCAGCTGCAAGAGTCCGGAGGAGGCAGCGTCCAAGCCGGAGGC<br>TCTCTGAGGCTGAGCTGTGCTGCCAGCGGCTACACTTACAGCATGTAC<br>TGCATGGGCTGGTTCAGACAAGCCCCCGGCAAGGAAAGAGAGGGCGTG<br>GCCCAGATCAATAGCGATGGCAGCACAAGCTACGCCGACAGCGTGAAG<br>GGAAGGTTCACTATCTCCAAGGACAACGCCAAGAACACTCTGTATCTG<br>CAGATGAACTCTCTGAAGCCAGAGGACACTGCCATGTACTACTGCGCT<br>GCCGATTCTAGGGTGTACGGCGGCAGCTGGTATGAGAGGCTCTGCGGC<br>CCTTACACATACGAGTACAACTACTGGGGCCAAGGCACACAAGTGACT<br>GTCTCGAGCGGCGGAGGATCCCAAGTGCAGCTGCAAGAGAGCGGAGGA<br>GGCAGCGTCGAAGCTGGAGGATCTCTGAGGCTGAGCTGTGCTGCCAGC<br>GGCTACACTCACAGCAGCTACTGTATGGGCTGGTTCAGACAAGCCCCC<br>GGCAAGGAGAGGGAAGGCGTGGCTGCCATCGACGTGGATGGCAGCACT<br>ACTTACGCCGACAGCGTGAAGGGAAGGTTCACTATCAGCAAGGACAAC<br>GCCAAGAACACACTCTATCTGCAGATGAACAGCCTCAAGCCAGAGGAC<br>ACTGGCATGTACTACTGCGCCGCCGAGTTCGCCGATTGCAGCAGCAAC<br>TACTTTCTGCCTCCCGGCGCCGTCAGATATTGGGGCAAGGCACTCAA<br>GTGACAGTCTCGTCTGCTAGCCACCATCACCATCACCAC | 372 |
| 275 | CAAGTGCAGCTGCAAGAGTCCGGAGGAGGCAGCGTCCAAGCCGGAGGC<br>TCTCTGAGGCTGAGCTGTGCTGCCAGCGGCTACACTTACAGCATGTAC<br>TGCATGGGCTGGTTCAGACAAGCCCCCGGCAAGGAAAGAGAGGGCGTG<br>GCCCAGATCAATAGCGATGGCAGCACAAGCTACGCCGACAGCGTGAAG<br>GGAAGGTTCACTATCTCCAAGGACAACGCCAAGAACACTCTGTATCTG<br>CAGATGAACTCTCTGAAGCCAGAGGACACTGCCATGTACTACTGCGCT<br>GCCGATTCTAGGGTGTACGGCGGCAGCTGGTATGAGAGGCTCTGCGGC<br>CCTTACACATACGAGTACAACTACTGGGGCCAAGGCACACAAGTGACT<br>GTCTCGAGCGGCGGAGGATCCCAAGTGCAGCTGCAAGAGAGCGGAGGA<br>GGAAGCGTCCAAGCCGGAGGATCTCTGAGACTGAGCTGCGCCGCTAGT<br>GGCTACTCCTACAGCAGCTACTGCATGGGCTGGTTTAGGCAAGCCCCC<br>GGCAAGGAGAGAGAAGGCGTGGCCACTATCGACAGCGACGGCATGACA<br>AGGTACGCCGACAGCGTGAAGGGAAGGTTCACAATCAGCAAGGACAAC<br>GCCAAGAACACACTGTATCTGCAGATGAACTCTCTGAAGCCAGAGGAC<br>ACTGCCATGTACTACTGTGCCGCTCCTCTGTACGACTGTGATAGCGGC<br>GCTGTGGGCAGAAATCCACCTTATTGGGGCCAAGGCACTCAAGTGACA<br>GTCTCGTCTGCTAGCCACCATCACCATCACCAC | 373 |
| 276 | CAAGTGCAGCTGCAAGAGTCCGGAGGAGGCAGCGTCCAAGCCGGAGGC<br>TCTCTGAGGCTGAGCTGTGCTGCCAGCGGCTACACTTACAGCATGTAC<br>TGCATGGGCTGGTTCAGACAAGCCCCCGGCAAGGAAAGAGAGGGCGTG<br>GCCCAGATCAATAGCGATGGCAGCACAAGCTACGCCGACAGCGTGAAG<br>GGAAGGTTCACTATCTCCAAGGACAACGCCAAGAACACTCTGTATCTG<br>CAGATGAACTCTCTGAAGCCAGAGGACACTGCCATGTACTACTGCGCT<br>GCCGATTCTAGGGTGTACGGCGGCAGCTGGTATGAGAGGCTCTGCGGC<br>CCTTACACATACGAGTACAACTACTGGGGCCAAGGCACACAAGTGACT<br>GTCTCGAGCGGCGGAGGATCCCAAGTGCAGCTGCAAGAGAGCGGAGGC<br>GGCAGCGTGCAGACTGGAGGCTCTCTGAGACTGAGCTGTGCTGCCAGC<br>GGCTACACTTATCTGAGGGGCTGTATGGGCTGGTTTAGGCAAGCCCCC<br>GGCAAGGAGAGAGAGGGCGTGGCCGTCATGGATGTGGTGGGCGATAGG<br>AGAAGCTACATCGACAGCGTGAAGGGAAGGTTCACAATCTCTAGGGAC<br>AATGCCGCCAACAGCGTCTATCTGCAGATGGACAATCTGAAGCCAGAG<br>GACACAGCCATGTACTACTGCACTGCCGGCCCTAACTGTGTGGGCTGG | 374 |

TABLE 14-continued

IL10 Receptor Binding Molecules Nucleic Acids

| DNA ENCODING SEQ ID NO. | DNA Sequence | SEQ ID NO |
|---|---|---|
|  | AGAAGCGGACTGGATTACTGGGGCCAAGGCACACAAGTGACAGTCTCG TCTGCTAGCCACCATCACCATCACCAC |  |
| 277 | CAAGTGCAGCTGCAAGAGAGCGGCGGAGGAAGCGTGCAAGCCGGAGGA TCTCTGAGACTGAGCTGCGCTGTGAGCGGCTACGCCTACTCCACATAC TGCATGGGCTGGTTTAGGCAAGCCCCCGGCAAAGAGAGAGAGGGCGTG GCTGCTATCGATAGCGGCGGCAGCACAAGCTACGCCGATAGCGTGAAG GGAAGGTTCACAATCAGCAAGGACAACGCCAAGAACACACTGTATCTG AGGATGAACTCTCTGAAGCCAGAGGACACAGCCATGTACTACTGTGCT GCTGTGCCTCCTCCTCCAGATGGCGGCAGCTGTCTGTTTCTGGGACCA GAGATCAAGGTCAGCAAGGCCGATTTTAGGTACTGGGGCCAAGGCACA CAAGTGACAGTCTCGAGCGGCGGAGGATCCCAAGTGCAGCTGCAAGAG AGCGGCGGAGGAAGCGTGCAAGCTGGAGGCTCTCTGAGGCTGAGCTGT GCTGCCAGCGGCTACACTTATAGCAGCGGCTGTATGGGCTGGTTCAGA CAAGCCCCCGGCAAGGAAAGGGAAGCCGTGGCCGCCATCAATTCCGAT GGCAGCACAAGCTACGCCGACAGCGTGAAGGGAAGGTTCACAATCAGC AAGGACAACGCCAAGAACACACTCTATCTGCAGATGAACTCTCTGAAG CCAGAGGACACAGCCATGTACTACTGCCGCTGAGCCTTACTGTAGC GGCGGCTACCCAAGATGGAGCGTCGCTGAGTTCGGCTACTGGGGCCAA GGCACACAAGTGACTGTCTCGTCTGCTAGCCACCATCACCATCACCAC | 375 |
| 278 | CAAGTGCAGCTGCAAGAGAGCGGCGGAGGAAGCGTGCAAGCCGGAGGA TCTCTGAGACTGAGCTGCGCTGTGAGCGGCTACGCCTACTCCACATAC TGCATGGGCTGGTTTAGGCAAGCCCCCGGCAAAGAGAGAGAGGGCGTG GCTGCTATCGATAGCGGCGGCAGCACAAGCTACGCCGATAGCGTGAAG GGAAGGTTCACAATCAGCAAGGACAACGCCAAGAACACACTGTATCTG AGGATGAACTCTCTGAAGCCAGAGGACACAGCCATGTACTACTGTGCT GCTGTGCCTCCTCCTCCAGATGGCGGCAGCTGTCTGTTTCTGGGACCA GAGATCAAGGTCAGCAAGGCCGATTTTAGGTACTGGGGCCAAGGCACA CAAGTGACAGTCTCGAGCGGCGGAGGATCCCAAGTGCAGCTGCAAGAG AGCGGAGGAGGCAGCGTCCAAGCCGGAGGCTCTCTGAGGCTGAGCTGT GCTGCCAGCGGCTACACTTACAGCAGCTACTGCATGGGCTGGTTCAGA CAAGCCCCCGGCAAGGAGAGAGGGCGTGGCTCACATCGACAGCGAC GGCTCCACAAGCTACGCCGATAGCGTGAAGGGAAGGTTCACAATCTCC AAGGACAACGCCAAGAACACTCTGTACCTCCAGATGAACTCTCTGAAG CCAGAGGACACTGCCATGTACTACTGTGCCGCCGATCCAATTCCCGGC CCCGGCTACTGCGATGGCGGCCCTAACAAGTACTGGGGCCAAGGCACA CAAGTGACTGTCTCGTCTGCTAGCCACCATCACCATCACCAC | 376 |
| 279 | CAAGTGCAGCTGCAAGAGAGCGGCGGAGGAAGCGTGCAAGCCGGAGGA TCTCTGAGACTGAGCTGCGCTGTGAGCGGCTACGCCTACTCCACATAC TGCATGGGCTGGTTTAGGCAAGCCCCCGGCAAAGAGAGAGAGGGCGTG GCTGCTATCGATAGCGGCGGCAGCACAAGCTACGCCGATAGCGTGAAG GGAAGGTTCACAATCAGCAAGGACAACGCCAAGAACACACTGTATCTG AGGATGAACTCTCTGAAGCCAGAGGACACAGCCATGTACTACTGTGCT GCTGTGCCTCCTCCTCCAGATGGCGGCAGCTGTCTGTTTCTGGGACCA GAGATCAAGGTCAGCAAGGCCGATTTTAGGTACTGGGGCCAAGGCACA CAAGTGACAGTCTCGAGCGGCGGAGGATCCCAAGTGCAGCTGCAAGAG TCCGGAGGAAGCGTGCAAGCCGGCGGATCTCTGAGACTGAGCTGT GCCGCCTCTAGGTACACTTACAACAGCTACTGCATGGGCTGGTTCAGA CAAGCCCCCGGCAAGGAAAGAGAGGGCGTGGCCACTATCGATAGCGAC GGCATGACTAGGTACGCTGATAGCGTCAAGGGAAGGTTCACAATCTCC AAGGACAATGCTAAGAACACTCTGTACCTCCAGATGAACTCTCTGAAG CCAGAGGACACAGCCATGTACTACTGCGCTGCCGATGCCGACTGCACT ATCGCCGCCATGACTACTAATCCTCTGGGCCAAGGCACACAAGTGACT GTCTCGTCTGCTAGCCACCATCACCATCACCAC | 377 |
| 280 | CAAGTGCAGCTGCAAGAGAGCGGCGGAGGAAGCGTGCAAGCCGGAGGA TCTCTGAGACTGAGCTGCGCTGTGAGCGGCTACGCCTACTCCACATAC TGCATGGGCTGGTTTAGGCAAGCCCCCGGCAAAGAGAGAGAGGGCGTG GCTGCTATCGATAGCGGCGGCAGCACAAGCTACGCCGATAGCGTGAAG GGAAGGTTCACAATCAGCAAGGACAACGCCAAGAACACACTGTATCTG AGGATGAACTCTCTGAAGCCAGAGGACACAGCCATGTACTACTGTGCT GCTGTGCCTCCTCCTCCAGATGGCGGCAGCTGTCTGTTTCTGGGACCA GAGATCAAGGTCAGCAAGGCCGATTTTAGGTACTGGGGCCAAGGCACA CAAGTGACAGTCTCGAGCGGCGGAGGATCCCAAGTGCAGCTGCAAGAG TCCGGCGGAGGCAGCGTCCAAGCCGGAGGATCTCTGAGGCTGAGCTGT ACAGTGAGCAGATACACTGCCAGCGTGAACTACATGGGCTGGTTCAGA CAAGCCCCCGGCAAAGAGAGAGGGCGTGGCCACAATCTTCACTGGC GCCGGCACAACATACTACGCCAACTCCGTCAAGGGAAGGTTCACAATC TCTAGGGACAACGCCAAGAACACTGCCTATCTGCAGATGAACTCCCTC | 378 |

TABLE 14-continued

IL10 Receptor Binding Molecules Nucleic Acids

| DNA ENCODING SEQ ID NO. | DNA Sequence | SEQ ID NO |
|---|---|---|
| | AAGCCAGAGGACACTGCCATCTACTACTGCGCCGTGGATTTCAGAGGC<br>GGACTGCTGTATAGGCCAGCCTACGAGTACACTTATAGGGGCCAAGGC<br>ACACAAGTGACAGTCTCGTCTGCTAGCCACCATCACCATCACCAC | |
| 281 | CAAGTGCAGCTGCAAGAGAGCGGCGGAGGAAGCGTGCAAGCCGGAGGA<br>TCTCTGAGACTGAGCTGCGCTGTGAGCGGCTACGCCTACTCCACATAC<br>TGCATGGGCTGGTTTAGGCAAGCCCCCGGCAAAGAGAGAGGGCGTG<br>GCTGCTATCGATAGCGGCGGCAGCACAAGCTACGCCGATAGCGTGAAG<br>GGAAGGTTCACAATCAGCAAGGACAACGCCAAGAACACACTGTATCTG<br>AGGATGAACTCTCTGAAGCCAGAGGACACAGCCATGTACTACTGTGCT<br>GCTGTGCCTCCTCCTCCAGATGGCGGCAGCTGTCTGTTTCTGGGACCA<br>GAGATCAAGGTCAGCAAGGCCGATTTTAGGTACTGGGGCCAAGGCACA<br>CAAGTGACAGTCTCGAGCGGCGGAGGATCCCAAGTGCAGCTGCAAGAG<br>AGCGGAGGAGGCAGCGTCGAAGCTGGAGGATCTCTGAGGCTGAGCTGT<br>GCTGCCAGCGGCTACACTCACAGCAGCTACTGTATGGGCTGGTTCAGA<br>CAAGCCCCCGGCAAGGAGAGGGAAGGCGTGGCTGCCATCGACGTGGAT<br>GGCAGCACTACTTACGCCGACAGCGTGAAGGGAAGGTTCACTATCAGC<br>AAGGACAACGCCAAGAACACACTCTATCTGCAGATGAACGCCTCAAG<br>CCAGAGGACACTGGCATGTACTACTGCGCCGCCGAGTTCGCCGATTGC<br>AGCAGCAACTACTTTCTGCCTCCCGGCGCCGTCAGATATTGGGGCCAA<br>GGCACTCAAGTGACAGTCTCGTCTGCTAGCCACCATCACCATCACCAC | 379 |
| 282 | CAAGTGCAGCTGCAAGAGAGCGGCGGAGGAAGCGTGCAAGCCGGAGGA<br>TCTCTGAGACTGAGCTGCGCTGTGAGCGGCTACGCCTACTCCACATAC<br>TGCATGGGCTGGTTTAGGCAAGCCCCCGGCAAAGAGAGAGAGGGCGTG<br>GCTGCTATCGATAGCGGCGGCAGCACAAGCTACGCCGATAGCGTGAAG<br>GGAAGGTTCACAATCAGCAAGGACAACGCCAAGAACACACTGTATCTG<br>AGGATGAACTCTCTGAAGCCAGAGGACACAGCCATGTACTACTGTGCT<br>GCTGTGCCTCCTCCTCCAGATGGCGGCAGCTGTCTGTTTCTGGGACCA<br>GAGATCAAGGTCAGCAAGGCCGATTTTAGGTACTGGGGCCAAGGCACA<br>CAAGTGACAGTCTCGAGCGGCGGAGGATCCCAAGTGCAGCTGCAAGAG<br>AGCGGAGGAGGAAGCGTCCAAGCCGGAGGATCTCTGAGACTGAGCTGC<br>GCCGCTAGTGGCTACTCCTACAGCAGCTACTGCATGGGCTGGTTTAGG<br>CAAGCCCCCGGCAAGGAGAGAGAAGGCGTGGCCACTATCGACAGCGAC<br>GGCATGACAAGGTACGCCGACAGCGTGAAGGGAAGGTTCACAATCAGC<br>AAGGACAACGCCAAGAACACACTGTATCTGCAGATGAACTCTCTGAAG<br>CCAGAGGACACTGCCATGTACTACTGTGCCGCTCCTCTGTACGACTGT<br>GATAGCGGCGCTGTGGGCAGAAATCCACCTTATTGGGGCCAAGGCACT<br>CAAGTGACAGTCTCGTCTGCTAGCCACCATCACCATCACCAC | 380 |
| 283 | CAAGTGCAGCTGCAAGAGAGCGGCGGAGGAAGCGTGCAAGCCGGAGGA<br>TCTCTGAGACTGAGCTGCGCTGTGAGCGGCTACGCCTACTCCACATAC<br>TGCATGGGCTGGTTTAGGCAAGCCCCCGGCAAAGAGAGAGAGGGCGTG<br>GCTGCTATCGATAGCGGCGGCAGCACAAGCTACGCCGATAGCGTGAAG<br>GGAAGGTTCACAATCAGCAAGGACAACGCCAAGAACACACTGTATCTG<br>AGGATGAACTCTCTGAAGCCAGAGGACACAGCCATGTACTACTGTGCT<br>GCTGTGCCTCCTCCTCCAGATGGCGGCAGCTGTCTGTTTCTGGGACCA<br>GAGATCAAGGTCAGCAAGGCCGATTTTAGGTACTGGGGCCAAGGCACA<br>CAAGTGACAGTCTCGAGCGGCGGAGGATCCCAAGTGCAGCTGCAAGAG<br>AGCGGAGGCGGCAGCGTGCAGACTGGAGGCTCTCTGAGACTGAGCTGT<br>GCTGCCAGCGGCTACACTTATCTGAGGGGCTGTATGGGCTGGTTTAGG<br>CAAGCCCCCGGCAAGGAGAGAGAGGGCGTGGCCGTCATGGATGTGGTG<br>GGCGATAGGAGAAGCTACATCGACAGCGTGAAGGGAAGGTTCACAATC<br>TCTAGGGACAATGCCGCCAACAGCGTCTATCTGCAGATGGACAATCTG<br>AAGCCAGAGGACACAGCCATGTACTACTGCACTGCCGGCCCTAACTGT<br>GTGGGCTGGAGAAGCGGACTGGATTACTGGGGCCAAGGCACACAAGTG<br>ACAGTCTCGTCTGCTAGCCACCATCACCATCACCAC | 381 |
| 284 | CAAGTGCAGCTGCAAGAGAGCGGAGGAGGAAGCGTGCAAGCCGGAGGC<br>TCTCTGAGGCTGAGCTGTACAGTGTCCGGCTACACTTACAGCTCCAAT<br>TGCATGGGCTGGTTTAGGCAAGCCCCCGGCAAGGAAAGAGAGGGCGTG<br>GCCACTATCTACACTGGCGGCGGCAACACATACTACGCCGATAGCGTG<br>AAGGGAAGGTTCACTATCAGCCAAGATAACGCCAAGAACACAGTGTAT<br>CTGCAGATGAACAATCTGAAGCCAGAGGACACTGCCATGTACTACTGT<br>GCTGCTGAGCCACTGTCTAGGGTGTACGCGGCAGCTGCCCAACTCCT<br>ACATTCGACTACTGGGGCCAAGGCACACAAGTGACTGTCTCGAGCGGC<br>GGAGGATCCCAAGTGCAGCTGCAAGAGAGCGGCGGAGGAAGCGTGCAA<br>GCTGGAGGCTCTCTGAGGCTGAGCTGTGCTGCCAGCGGCTACACTTAT<br>AGCAGCGGCTGTATGGGCTGGTTCAGACAAGCCCCCGGCAAGGAAAGG<br>GAAGCCGTGGCCGCCATCAATTCCGATGGCAGCACAAGCTACGCCGAC<br>AGCGTGAAGGGAAGGTTCACAATCAGCAAGGACAACGCCAAGAACACA<br>CTCTATCTGCAGATGAACTCTCTGAAGCCAGAGGACACAGCCATGTAC<br>TACTGCGCCGCTGAGCCTTACTGTAGCGGCGGCTACCCAAGATGGAGC | 382 |

TABLE 14-continued

IL10 Receptor Binding Molecules Nucleic Acids

| DNA ENCODING SEQ ID NO. | DNA Sequence | SEQ ID NO |
|---|---|---|
|  | GTCGCTGAGTTCGGCTACTGGGGCCAAGGCACACAAGTGACTGTCTCG TCTGCTAGCCACCATCACCATCACCAC |  |
| 285 | CAAGTGCAGCTGCAAGAGAGCGGAGGAGGAAGCGTGCAAGCCGGAGGC TCTCTGAGGCTGAGCTGTACAGTGTCCGGCTACACTTACAGCTCCAAT TGCATGGGCTGGTTTAGGCAAGCCCCCGGCAAGGAAAGAGAGGGCGTG GCCACTATCTACACTGGCGGCGGCAACACATACTACGCCGATAGCGTG AAGGGAAGGTTCACTATCAGCCAAGATAACGCCAAGAACACAGTGTAT CTGCAGATGAACAATCTGAAGCCAGAGGACACTGCCATGTACTACTGT GCTGCTGAGCCACTGTCTAGGGTGTACGGCGGCAGCTGCCCAACTCCT ACATTCGACTACTGGGGCCAAGGCACACAAGTGACTGTCTCGAGCGGC GGAGGATCCCAAGTGCAGCTGCAAGAGAGCGGAGGAGGCAGCGTCCAA GCCGGAGGCTCTCTGAGGCTGAGCTGTGCTGCCAGCGGCTACACTTAC AGCAGCTACTGCATGGGCTGGTTCAGACAAGCCCCCGGCAAGGAGAGA GAGGGCGTGGCTCACATCGACAGCGACGGCTCCACAAGCTACGCCGAT AGCGTGAAGGGAAGGTTCACAATCTCCAAGGACAACGCCAAGAACACT CTGTACCTCCAGATGAACTCTCTGAAGCCAGAGGACACTGCCATGTAC TACTGTGCCGCCGATCCAATTCCCGGCCCCGGCTACTGCGATGGCGGC CCTAACAAGTACTGGGGCCAAGGCACACAAGTGACTGTCTCGTCTGCT AGCCACCATCACCATCACCAC | 383 |
| 286 | CAAGTGCAGCTGCAAGAGAGCGGAGGAGGAAGCGTGCAAGCCGGAGGC TCTCTGAGGCTGAGCTGTACAGTGTCCGGCTACACTTACAGCTCCAAT TGCATGGGCTGGTTTAGGCAAGCCCCCGGCAAGGAAAGAGAGGGCGTG GCCACTATCTACACTGGCGGCGGCAACACATACTACGCCGATAGCGTG AAGGGAAGGTTCACTATCAGCCAAGATAACGCCAAGAACACAGTGTAT CTGCAGATGAACAATCTGAAGCCAGAGGACACTGCCATGTACTACTGT GCTGCTGAGCCACTGTCTAGGGTGTACGGCGGCAGCTGCCCAACTCCT ACATTCGACTACTGGGGCCAAGGCACACAAGTGACTGTCTCGAGCGGC GGAGGATCCCAAGTGCAGCTGCAAGAGTCCGAGGAGGAAGCGTGCAA GCCGGCGGATCTCTGAGACTGAGCTGTCCGCCTCTAGGTACACTTAC AACAGCTACTGCATGGGCTGGTTCAGACAAGCCCCCGGCAAGGAAAGA GAGGGCGTGGCCACTATCGATAGCGACGGCATGACTAGGTACGCTGAT AGCGTCAAGGGAAGGTTCACAATCTCCAAGGACAATGCTAAGAACACT CTGTACCTCCAGATGAACTCTCTGAAGCCAGAGGACACAGCCATGTAC TACTGCGCTGCCGATGCCGACTGCACTATCGCCGCCATGACTACTAAT CCTCTGGGCCAAGGCACACAAGTGACTGTCTCGTCTGCTAGCCACCAT CACCATCACCAC | 384 |
| 287 | CAAGTGCAGCTGCAAGAGAGCGGAGGAGGAAGCGTGCAAGCCGGAGGC TCTCTGAGGCTGAGCTGTACAGTGTCCGGCTACACTTACAGCTCCAAT TGCATGGGCTGGTTTAGGCAAGCCCCCGGCAAGGAAAGAGAGGGCGTG GCCACTATCTACACTGGCGGCGGCAACACATACTACGCCGATAGCGTG AAGGGAAGGTTCACTATCAGCCAAGATAACGCCAAGAACACAGTGTAT CTGCAGATGAACAATCTGAAGCCAGAGGACACTGCCATGTACTACTGT GCTGCTGAGCCACTGTCTAGGGTGTACGCGGCAGCTGCCCAACTCCT ACATTCGACTACTGGGGCCAAGGCACACAAGTGACTGTCTCGAGCGGC GGAGGATCCCAAGTGCAGCTGCAAGAGTCCGGCGGAGGCAGCGTCCAA GCCGGAGGATCTCTGAGGCTGAGCTGTACAGTGAGCAGATACACTGCC AGCGTGAACTACATGGGCTGGTTCAGACAAGCCCCCGGCAAAGAGAGA GAGGGCGTGGCCACAATCTTCACTGGCGCCGGCACAACATACTACGCC AACTCCGTCAAGGGAAGGTTCACAATCTCTAGGGACAACGCCAAGAAC ACTGCCTATCTGCAGATGAACTCCCTCAAGCCAGAGGACACTGCCATC TACTACTGCGCCGTGGATTTCAGAGGCGGACTGCTGTATAGGCCAGCC TACGAGTACACTTATAGGGGCCAAGGCACACAAGTGACAGTCTCGTCT GCTAGCCACCATCACCATCACCAC | 385 |
| 288 | CAAGTGCAGCTGCAAGAGAGCGGAGGAGGAAGCGTGCAAGCCGGAGGC TCTCTGAGGCTGAGCTGTACAGTGTCCGGCTACACTTACAGCTCCAAT TGCATGGGCTGGTTTAGGCAAGCCCCCGGCAAGGAAAGAGAGGGCGTG GCCACTATCTACACTGGCGGCGGCAACACATACTACGCCGATAGCGTG AAGGGAAGGTTCACTATCAGCCAAGATAACGCCAAGAACACAGTGTAT CTGCAGATGAACAATCTGAAGCCAGAGGACACTGCCATGTACTACTGT GCTGCTGAGCCACTGTCTAGGGTGTACGGCGGCAGCTGCCCAACTCCT ACATTCGACTACTGGGGCCAAGGCACACAAGTGACTGTCTCGAGCGGC GGAGGATCCCAAGTGCAGCTGCAAGAGCGGAGGAGGCAGCGTCGAA GCTGGAGGATCTCTGAGGCTGAGCTGTGCTGCCAGCGGCTACACTCAC AGCAGCTACTGTATGGGCTGGTTCAGACAAGCCCCCGGCAAGGAGAGG GAAGGCGTGGCTGCCATCGACTGGATGGCAGCACTACTTACGCCGAC AGCGTGAAGGGAAGGTTCACTATCAGCAAGGACAACGCCAAGAACACA CTCTATCTGCAGATGAACAGCCTCAAGCCAGAGGACACTGGCATGTAC | 386 |

TABLE 14-continued

IL10 Receptor Binding Molecules Nucleic Acids

| DNA ENCODING SEQ ID NO. | DNA Sequence | SEQ ID NO |
|---|---|---|
| | TACTGCGCCGCCGAGTTCGCCGATTGCAGCAGCAACTACTTTCTGCCT CCCGGCGCCGTCAGATATTGGGGCCAAGGCACTCAAGTGACAGTCTCG TCTGCTAGCCACCATCACCATCACCAC | |
| 289 | CAAGTGCAGCTGCAAGAGAGCGGAGGAGGAAGCGTGCAAGCCGGAGGC TCTCTGAGGCTGAGCTGTACAGTGTCCGGCTACACTTACAGCTCCAAT TGCATGGGCTGGTTTAGGCAAGCCCCCGGCAAGGAAAGAGAGGGCGTG GCCACTATCTACACTGGCGGCGGCAACACATACTACGCCGATAGCGTG AAGGGAAGGTTCACTATCAGCCAAGATAACGCCAAGAACACAGTGTAT CTGCAGATGAACAATCTGAAGCCAGAGGCACTGCCATGTACTACTGT GCTGCTGAGCCACTGTCTAGGGTGTACGCGGCAGCTGCCCAACTCCT ACATTCGACTACTGGGGCCAAGGCACACAAGTGACTGTCTCGAGCGGC GGAGGATCCCAAGTGCAGCTGCAAGAGAGCGGAGGAGGAAGCGTCCAA GCCGGAGGATCTCTGAGACTGAGCTGCGCCGCTAGTGGCTACTCCTAC AGCAGCTACTGCATGGGCTGGTTTAGGCAAGCCCCCGGCAAGGAGAGA GAAGGCGTGGCCACTATCGACAGCGACGGCATGACAAGGTACGCCGAC AGCGTGAAGGGAAGGTTCACAATCAGCAAGGACAACGCCAAGAACACA CTGTATCTGCAGATGAACTCTCTGAAGCCAGAGGACACTGCCATGTAC TACTGTGCCGCTCCTCTGTACGACTGTGATAGCGGCGCTGTGGGCAGA AATCCACCTTATTGGGGCCAAGGCACTCAAGTGACAGTCTCGTCTGCT AGCCACCATCACCATCACCAC | 387 |
| 290 | CAAGTGCAGCTGCAAGAGAGCGGAGGAGGAAGCGTGCAAGCCGGAGGC TCTCTGAGGCTGAGCTGTACAGTGTCCGGCTACACTTACAGCTCCAAT TGCATGGGCTGGTTTAGGCAAGCCCCCGGCAAGGAAAGAGAGGGCGTG GCCACTATCTACACTGGCGGCGGCAACACATACTACGCCGATAGCGTG AAGGGAAGGTTCACTATCAGCCAAGATAACGCCAAGAACACAGTGTAT CTGCAGATGAACAATCTGAAGCCAGAGGCACTGCCATGTACTACTGT GCTGCTGAGCCACTGTCTAGGGTGTACGGCGGCAGCTGCCCAACTCCT ACATTCGACTACTGGGGCCAAGGCACACAAGTGACTGTCTCGAGCGGC GGAGGATCCCAAGTGCAGCTGCAAGAGAGCGGAGGCGGCAGCGTGCAG ACTGGAGGCTCTCTGAGACTGAGCTGTGCTGCCAGCGGCTACACTTAT CTGAGGGGCTGTATGGGCTGGTTTAGGCAAGCCCCCGGCAAGGAGAGA GAGGGCGTGGCCGTCATGGATGTGGTGGGCGATAGGAGAAGCTACATC GACAGCGTGAAGGGAAGGTTCACAATCTCTAGGGACAATGCCGCCAAC AGCGTCTATCTGCAGATGGACAATCTGAAGCCAGAGGACACAGCCATG TACTACTGCACTGCCGGCCCTAACTGTGTGGGCTGGAGAAGCGGACTG GATTACTGGGGCCAAGGCACACAAGTGACAGTCTCGTCTGCTAGCCAC CATCACCATCACCAC | 388 |
| 291 | CAAGTGCAGCTGCAAGAGAGCGGAGGAGGAAGCGTCCAAGCCGGAGGC TCTCTGAGGCTGAGCTGTGGAGCCAGCGGCTACACTTACAGCAGCTAC TGTATGGGCTGGTTTAGGCAAGTGCCCGGCAAGGAGAGAGAGGGCGTG GCCGTGATCGATTCCGATGGCAGCACAAGCTACGCTGACAGCGTGAAG GGAAGGTTCACAATCAGCAAGGACAACGGCAAGAACACACTCTATCTG CAGATGAACAGCCTCAAGCCAGAGGACACAGCCATGTACTACTGCGCC GCTGATCTGGGCCACTATAGGCCTCCTTGTGGCGTGCTGTATCTGGGC ATGGATTACTGGGGCAAGGGCACACAAGTGACAGTCTCGAGCGGCGGA GGATCCCAAGTGCAGCTGCAAGAGAGCGGCGGAGGAAGCGTGCAAGCT GGAGGCTCTCTGAGGCTGAGCTGTGCTGCCAGCGGCTACACTTATAGC AGCGGCTGTATGGGCTGGTTCAGACAAGCCCCCGGCAAGGAAAGGGAA GCCGTGGCCGCCATCAATTCCGATGGCAGCACAAGCTACGCCGACAGC GTGAAGGGAAGGTTCACAATCAGCAAGGACAACGCCAAGAACACACTC TATCTGCAGATGAACTCTCTGAAGCCAGAGGACACAGCCATGTACTAC TGCGCCGCTGAGCCTTACTGTAGCGGCGGCTACCCAAGATGGAGCGTC GCTGAGTTCGGCTACTGGGGCCAAGGCACACAAGTGACTGTCTCGTCT GCTAGCCACCATCACCATCACCAC | 389 |
| 292 | CAAGTGCAGCTGCAAGAGAGCGGAGGAGGAAGCGTCCAAGCCGGAGGC TCTCTGAGGCTGAGCTGTGTGGAGCCAGCGGCTACACTTACAGCAGCTAC TGTATGGGCTGGTTAGGCAAGTGCCCGGCAAGGAGAGAGAGGGCGTG GCCGTGATCGATTCCGATGGCAGCACAAGCTACGCTGACAGCGTGAAG GGAAGGTTCACAATCAGCAAGGACAACGGCAAGAACACACTCTATCTG CAGATGAACAGCCTCAAGCCAGAGGACACAGCCATGTACTACTGCGCC GCTGATCTGGGCCACTATAGGCCTCCTTGTGGCGTGCTGTATCTGGGC ATGGATTACTGGGGCAAGGGCACACAAGTGACAGTCTCGAGCGGCGGA GGATCCCAAGTGCAGCTGCAAGAGAGCGGAGGAGGCAGCGTCCAAGCC GGAGGCTCTGAGGCTGAGCTGTGCTGCCAGCGGCTACACTTACAGC AGCTACTGCATGGGCTGGTTCAGACAAGCCCCCGGCAAGGAGAGAGAG GGCGTGGCTCACATCGACAGCGACGGCTCCACAAGCTACGCCGATAGC GTGAAGGGAAGGTTCACAATCTCCAAGGACAACGCCAAGAACACTCTG TACCTCCAGATGAACTCTCTGAAGCCAGAGGACACTGCCATGTACTAC TGTGCCGCCGATCCAATTCCCGGCCCCGGCTACTGCGATGGCGGCCCT | 390 |

TABLE 14-continued

IL10 Receptor Binding Molecules Nucleic Acids

| DNA ENCODING SEQ ID NO. | DNA Sequence | SEQ ID NO |
|---|---|---|
| | AACAAGTACTGGGGCCAAGGCACACAAGTGACTGTCTCGTCTGCTAGC CACCATCACCATCACCAC | |
| 293 | CAAGTGCAGCTGCAAGAGAGCGGAGGAGGAAGCGTCCAAGCCGGAGGC TCTCTGAGGCTGAGCTGTGGAGCCAGCGGCTACACTTACAGCAGCTAC TGTATGGGCTGGTTTAGGCAAGTGCCCGGCAAGGAGAGAGAGGGCGTG GCCGTGATCGATTCCGATGGCAGCACAAGCTACGCTGACAGCGTGAAG GGAAGGTTCACAATCAGCAAGGACAACGGCAAGAACACACTCTATCTG CAGATGAACAGCCTCAAGCCAGAGGACACAGCCATGTACTACTGCGCC GCTGATCTGGGCCACTATAGGCCTCCTTGTGGCGTGCTGTATCTGGGC ATGGATTACTGGGGCAAGGGCACACAAGTGACAGTCTCGAGCGGCGGA GGATCCCAAGTGCAGCTGCAAGAGTCCGGAGGAGGAAGCGTGCAAGCC GGCGGATCTCTGAGACTGAGCTGTGCCGCCTCTAGGTACACTTACAAC AGCTACTGCATGGGCTGGTTCAGACAAGCCCCCGGCAAGGAAAGAGAG GGCGTGGCCACTATCGATAGCGACGGCATGACTAGGTACGCTGATAGC GTCAAGGGAAGGTTCACAATCTCCAAGGACAATGCTAAGAACACTCTG TACCTCCAGATGAACTCTCTGAAGCCAGAGGACACAGCCATGTACTAC TGCGCTGCCGATGCCGACTGCACTATCGCCGCCATGACTACTAATCCT CTGGGCCAAGGCACACAAGTGACTGTCTCGTCTGCTAGCCACCATCAC CATCACCAC | 391 |
| 294 | CAAGTGCAGCTGCAAGAGAGCGGAGGAGGAAGCGTCCAAGCCGGAGGC TCTCTGAGGCTGAGCTGTGGAGCCAGCGGCTACACTTACAGCAGCTAC TGTATGGGCTGGTTTAGGCAAGTGCCCGGCAAGGAGAGAGAGGGCGTG GCCGTGATCGATTCCGATGGCAGCACAAGCTACGCTGACAGCGTGAAG GGAAGGTTCACAATCAGCAAGGACAACGGCAAGAACACACTCTATCTG CAGATGAACAGCCTCAAGCCAGAGGACACAGCCATGTACTACTGCGCC GCTGATCTGGGCCACTATAGGCCTCCTTGTGGCGTGCTGTATCTGGGC ATGGATTACTGGGGCAAGGGCACACAAGTGACAGTCTCGAGCGGCGGA GGATCCCAAGTGCAGCTGCAAGAGTCCGGCGGAGGCAGCGTCCAAGCC GGAGGATCTCTGAGGCTGAGCTGTACAGTGAGCAGATACACTGCCAGC GTGAACTACATGGGCTGGTTCAGACAAGCCCCCGGCAAAGAGAGAGAG GGCGTGGCCACAATCTTCACTGGCGCCGGCACAACATACTACGCCAAC TCCGTCAAGGGAAGGTTCACAATCTCTAGGGACAACGCCAAGAACACT GCCTATCTGCAGATGAACTCCCTCAAGCCAGAGGACACTGCCATCTAC TACTGCGCCGTGGATTTCAGAGGCGGACTGCTGTATAGGCCAGCCTAC GAGTACACTTATAGGGGCCAAGGCACACAAGTGACAGTCTCGTCTGCT AGCCACCATCACCATCACCAC | 392 |
| 295 | CAAGTGCAGCTGCAAGAGAGCGGAGGAGGAAGCGTCCAAGCCGGAGGC TCTCTGAGGCTGAGCTGTGGAGCCAGCGGCTACACTTACAGCAGCTAC TGTATGGGCTGGTTTAGGCAAGTGCCCGGCAAGGAGAGAGAGGGCGTG GCCGTGATCGATTCCGATGGCAGCACAAGCTACGCTGACAGCGTGAAG GGAAGGTTCACAATCAGCAAGGACAACGGCAAGAACACACTCTATCTG CAGATGAACAGCCTCAAGCCAGAGGACACAGCCATGTACTACTGCGCC GCTGATCTGGGCCACTATAGGCCTCCTTGTGGCGTGCTGTATCTGGGC ATGGATTACTGGGGCAAGGGCACACAAGTGACAGTCTCGAGCGGCGGA GGATCCCAAGTGCAGCTGCAAGAGAGCGGAGGAGGCAGCGTCGAAGCT GGAGGATCTCTGAGGCTGAGCTGTGCTGCCAGCGGCTACACTCACAGC AGCTACTGTATGGGCTGGTTCAGACAAGCCCCCGGCAAGGAGAGGGAA GGCGTGGCTGCCATCGACGTGGATGGCAGCACTACTTACGCCGACAGC GTGAAGGGAAGGTTCACTATCAGCAAGGACAACGCCAAGAACACACTC TATCTGCAGATGAACAGCCTCAAGCCAGAGGACACTGGCATGTACTAC TGCGCCGCCGAGTTCGCCGATTGCAGCAGCAACTACTTTCTGCCTCCC GGCGCCGTCAGATATTGGGGCCAAGGCACTCAAGTGACAGTCTCGTCT GCTAGCCACCATCACCATCACCAC | 393 |
| 296 | CAAGTGCAGCTGCAAGAGAGCGGAGGAGGAAGCGTCCAAGCCGGAGGC TCTCTGAGGCTGAGCTGTGGAGCCAGCGGCTACACTTACAGCAGCTAC TGTATGGGCTGGTTTAGGCAAGTGCCCGGCAAGGAGAGAGAGGGCGTG GCCGTGATCGATTCCGATGGCAGCACAAGCTACGCTGACAGCGTGAAG GGAAGGTTCACAATCAGCAAGGACAACGGCAAGAACACACTCTATCTG CAGATGAACAGCCTCAAGCCAGAGGACACAGCCATGTACTACTGCGCC GCTGATCTGGGCCACTATAGGCCTCCTTGTGGCGTGCTGTATCTGGGC ATGGATTACTGGGGCAAGGGCACACAAGTGACAGTCTCGAGCGGCGGA GGATCCCAAGTGCAGCTGCAAGAGAGCGGAGGAGGAAGCGTCCAAGCC GGAGGATCTCTGAGACTGAGCTGCGCCGCTAGTGGCTACTCCTACAGC AGCTACTGCATGGGCTGGTTAGGCAAGCCCCCGGCAAGGAGAGAGAA | 394 |

TABLE 14-continued

IL10 Receptor Binding Molecules Nucleic Acids

| DNA ENCODING SEQ ID NO. | DNA Sequence | SEQ ID NO |
|---|---|---|
|  | GGCGTGGCCACTATCGACAGCGACGGCATGACAAGGTACGCCGACAGC<br>GTGAAGGGAAGGTTCACAATCAGCAAGGACAACGCCAAGAACACACTG<br>TATCTGCAGATGAACTCTCTGAAGCCAGAGGACACTGCCATGTACTAC<br>TGTGCCGCTCCTCTGTACGACTGTGATAGCGGCGCTGTGGGCAGAAAT<br>CCACCTTATTGGGGCCAAGGCACTCAAGTGACAGTCTCGTCTGCTAGC<br>CACCATCACCATCACCAC |  |
| 297 | CAAGTGCAGCTGCAAGAGAGCGGAGGAGGAAGCGTCCAAGCCGGAGGC<br>TCTCTGAGGCTGAGCTGTGGAGCCAGCGGCTACACTTACAGCAGCTAC<br>TGTATGGGCTGGTTTAGGCAAGTGCCCGGCAAGGAGAGAGAGGGCGTG<br>GCCGTGATCGATTCCGATGGCAGCACAAGCTACGCTGACAGCGTGAAG<br>GGAAGGTTCACAATCAGCAAGGACAACGGCAAGAACACACTCTATCTG<br>CAGATGAACAGCCTCAAGCCAGAGGACACAGCCATGTACTACTGCGCC<br>GCTGATCTGGGCCACTATAGGCCTCCTTGTGGCGTGCTGTATCTGGGC<br>ATGGATTACTGGGGCAAGGGCACACAAGTGACAGTCTCGAGCGGCGGA<br>GGATCCCAAGTGCAGCTGCAAGAGAGCGGAGGCGGCAGCGTGCAGACT<br>GGAGGCTCTCTGAGACTGAGCTGTGCTGCCAGCGGCTACACTTATCTG<br>AGGGGCTGTATGGGCTGGTTTAGGCAAGCCCCCGGCAAGGAGAGAGAG<br>GGCGTGGCCGTCATGGATGTGGTGGGCGATAGGAGAAGCTACATCGAC<br>AGCGTGAAGGGAAGGTTCACAATCTCTAGGGACAATGCCGCCAACAGC<br>GTCTATCTGCAGATGGACAATCTGAAGCCAGAGGACACAGCCATGTAC<br>TACTGCACTGCCGGCCCTAACTGTGTGGGCTGGAGAAGCGGACTGGAT<br>TACTGGGGCCAAGGCACACAAGTGACAGTCTCGTCTGCTAGCCACCAT<br>CACCATCACCAC | 395 |
| 298 | CAAGTGCAGCTGCAAGAGAGCGGAGGAGGAAGCGTCCAAGCCGGAGGC<br>TCTCTGAGACTGAGCTGTGCCGCCAGCGGCTACTCCAACTGCAGCTAC<br>GACATGACTTGGTATAGGCAAGCCCCCGGCAAGGAGAGGGAGTTCGTG<br>TCCGCCATCCACAGCGACGGCAGCACTAGATACGCCGACAGCGTGAAG<br>GGAAGGTTCTTCATCAGCCAAGATAACGCCAAGAACACAGTGTATCTG<br>CAGATGAACTCCCTCAAGCCAGAGGACACTGCCATGTACTACTGCAAG<br>ACAGACCCACTGCACTGCAGAGCCCATGGCGGCAGCTGGTATAGCGTG<br>AGGGCCAACTACTGGGGCCAAGGCACACAAGTGACAGTCTCGAGCGGC<br>GGAGGATCCCAAGTGCAGCTGCAAGAGAGCGGCGGAGGAAGCGTGCAA<br>GCTGGAGGCTCTCTGAGGCTGAGCTGTGCTGCCAGCGGCTACACTTAT<br>AGCAGCGGCTGTATGGGCTGGTTCAGACAAGCCCCCGGCAAGGAAAGG<br>GAAGCCGTGGCCGCCATCAATTCCGATGGCAGCACAAGCTACGCCGAC<br>AGCGTGAAGGGAAGGTTCACAATCAGCAAGGACAACGCCAAGAACACA<br>CTCTATCTGCAGATGAACTCTCTGAAGCCAGAGGACACAGCCATGTAC<br>TACTGCGCCGCTGAGCCTTACTGTAGCGGCGGCTACCCAAGATGGAGC<br>GTCGCTGAGTTCGGCTACTGGGGCCAAGGCACACAAGTGACTGTCTCG<br>TCTGCTAGCCACCATCACCATCACCAC | 396 |
| 299 | CAAGTGCAGCTGCAAGAGAGCGGAGGAGGAAGCGTCCAAGCCGGAGGC<br>TCTCTGAGACTGAGCTGTGCCGCCAGCGGCTACTCCAACTGCAGCTAC<br>GACATGACTTGGTATAGGCAAGCCCCCGGCAAGGAGAGGGAGTTCGTG<br>TCCGCCATCCACAGCGACGGCAGCACTAGATACGCCGACAGCGTGAAG<br>GGAAGGTTCTTCATCAGCCAAGATAACGCCAAGAACACAGTGTATCTG<br>CAGATGAACTCCCTCAAGCCAGAGGACACTGCCATGTACTACTGCAAG<br>ACAGACCCACTGCACTGCAGAGCCCATGGCGGCAGCTGGTATAGCGTG<br>AGGGCCAACTACTGGGGCCAAGGCACACAAGTGACAGTCTCGAGCGGC<br>GGAGGATCCCAAGTGCAGCTGCAAGAGAGCGGAGGAGGCAGCGTCCAA<br>GCCGGAGGCTCTCTGAGGCTGAGCTGTGCTGCCAGCGGCTACACTTAC<br>AGCAGCTACTGCATGGGCTGGTTCAGACAAGCCCCCGGCAAGGAGAGA<br>GAGGGCGTGGCTCACATCGACAGCGACGGCTCCACAAGCTACGCCGAT<br>AGCGTGAAGGGAAGGTTCACAATCTCCAAGGACAACGCCAAGAACACT<br>CTGTACCTCCAGATGAACTCTCTGAAGCCAGAGGACACTGCCATGTAC<br>TACTGTGCCGCCGATCCAATTCCCGGCCCCGGCTACTGCGATGGCGGC<br>CCTAACAAGTACTGGGGCCAAGGCACACAAGTGACTGTCTCGTCTGCT<br>AGCCACCATCACCATCACCAC | 397 |
| 300 | CAAGTGCAGCTGCAAGAGAGCGGAGGAGGAAGCGTCCAAGCCGGAGGC<br>TCTCTGAGACTGAGCTGTGCCGCCAGCGGCTACTCCAACTGCAGCTAC<br>GACATGACTTGGTATAGGCAAGCCCCCGGCAAGGAGAGGGAGTTCGTG<br>TCCGCCATCCACAGCGACGGCAGCACTAGATACGCCGACAGCGTGAAG<br>GGAAGGTTCTTCATCAGCCAAGATAACGCCAAGAACACAGTGTATCTG<br>CAGATGAACTCCCTCAAGCCAGAGGACACTGCCATGTACTACTGCAAG<br>ACAGACCCACTGCACTGCAGAGCCCATGGCGGCAGCTGGTATAGCGTG<br>AGGGCCAACTACTGGGGCCAAGGCACACAAGTGACAGTCTCGAGCGGC<br>GGAGGATCCCAAGTGCAGCTGCAAGAGTCCGAGGAGGAAGCGTGCAA<br>GCCGGCGGATCTCTGAGACTGAGCTGTGCCGCCTCTAGGTACACTTAC<br>AACAGCTACTGCATGGGCTGGTTCAGACAAGCCCCCGGCAAGGAAAGA<br>GAGGGCGTGGCCACTATCGATAGCGACGGCATGACTAGGTACGCTGAT | 398 |

TABLE 14-continued

IL10 Receptor Binding Molecules Nucleic Acids

| DNA ENCODING SEQ ID NO. | DNA Sequence | SEQ ID NO |
|---|---|---|
| | AGCGTCAAGGGAAGGTTCACAATCTCCAAGGACAATGCTAAGAACACT CTGTACCTCCAGATGAACTCTCTGAAGCCAGAGGACACAGCCATGTAC TACTGCGCTGCCGATGCCGACTGCACTATCGCCGCCATGACTACTAAT CCTCTGGGCCAAGGCACACAAGTGACTGTCTCGTCTGCTAGCCACCAT CACCATCACCAC | |
| 301 | CAAGTGCAGCTGCAAGAGAGCGGAGGAGGAAGCGTCCAAGCCGGAGGC TCTCTGAGACTGAGCTGTGCCGCCAGCGGCTACTCCAACTGCAGCTAC GACATGACTTGGTATAGGCAAGCCCCCGGCAAGGAGAGGGAGTTCGTG TCCGCCATCCACAGCGACGGCAGCACTAGATACGCCGACAGCGTGAAG GGAAGGTTCTTCATCAGCCAAGATAACGCCAAGAACACAGTGTATCTG CAGATGAACTCCCTCAAGCCAGAGGACACTGCCATGTACTACTGCAAG ACAGACCCACTGCACTGCAGAGCCCATGGCGGCAGCTGGTATAGCGTG AGGGCCAACTACTGGGCCAAGGCACACAAGTGACAGTCTCGAGCGGC GGAGGATCCCAAGTGCAGCTGCAAGAGTCCGGCGGAGGCAGCGTCCAA GCCGGAGGATCTCTGAGGCTGAGCTGTACAGTGAGCAGATACACTGCC AGCGTGAACTACATGGGCTGGTTCAGACAAGCCCCCGGCAAAGAGAGA GAGGGCGTGGCCACAATCTTCACTGGCGCCGGCACAACATACTACGCC AACTCCGTCAAGGGAAGGTTCACAATCTCTAGGGACAACGCCAAGAAC ACTGCCTATCTGCAGATGAACTCCCTCAAGCCAGAGGACACTGCCATC TACTACTGCGCCGTGGATTTCAGAGGCGGACTGCTGTATAGGCCAGCC TACGAGTACACTTATAGGGGCCAAGGCACACAAGTGACAGTCTCGTCT GCTAGCCACCATCACCATCACCAC | 399 |
| 302 | CAAGTGCAGCTGCAAGAGAGCGGAGGAGGAAGCGTCCAAGCCGGAGGC TCTCTGAGACTGAGCTGTGCCGCCAGCGGCTACTCCAACTGCAGCTAC GACATGACTTGGTATAGGCAAGCCCCCGGCAAGGAGAGGGAGTTCGTG TCCGCCATCCACAGCGACGGCAGCACTAGATACGCCGACAGCGTGAAG GGAAGGTTCTTCATCAGCCAAGATAACGCCAAGAACACAGTGTATCTG CAGATGAACTCCCTCAAGCCAGAGGACACTGCCATGTACTACTGCAAG ACAGACCCACTGCACTGCAGAGCCCATGGCGGCAGCTGGTATAGCGTG AGGGCCAACTACTGGGCCAAGGCACACAAGTGACAGTCTCGAGCGGC GGAGGATCCCAAGTGCAGCTGCAAGAGAGCGGAGGAGGCAGCGTCGAA GCTGGAGGATCTCTGAGGCTGAGCTGTGCTGCCAGCGGCTACACTCAC AGCAGCTACTGTATGGGCTGGTTCAGACAAGCCCCCGGCAAGGAGAGG GAAGGCGTGGCTGCCATCGACGTGGATGGCAGCACTACTTACGCCGAC AGCGTGAAGGGAAGGTTCACTATCAGCAAGGACAACGCCAAGAACACA CTCTATCTGCAGATGAACAGCCTCAAGCCAGAGGACACTGGCATGTAC TACTGCGCCGCCGAGTTCGCCGATTGCAGCAGCAACTACTTTCTGCCT CCCGGCGCCGTCAGATATTGGGGCCAAGGCACTCAAGTGACAGTCTCG TCTGCTAGCCACCATCACCATCACCAC | 400 |
| 303 | CAAGTGCAGCTGCAAGAGAGCGGAGGAGGAAGCGTCCAAGCCGGAGGC TCTCTGAGACTGAGCTGTGCCGCCAGCGGCTACTCCAACTGCAGCTAC GACATGACTTGGTATAGGCAAGCCCCCGGCAAGGAGAGGGAGTTCGTG TCCGCCATCCACAGCGACGGCAGCACTAGATACGCCGACAGCGTGAAG GGAAGGTTCTTCATCAGCCAAGATAACGCCAAGAACACAGTGTATCTG CAGATGAACTCCCTCAAGCCAGAGGACACTGCCATGTACTACTGCAAG ACAGACCCACTGCACTGCAGAGCCCATGGCGGCAGCTGGTATAGCGTG AGGGCCAACTACTGGGCCAAGGCACACAAGTGACAGTCTCGAGCGGC GGAGGATCCCAAGTGCAGCTGCAAGAGAGCGGAGGAGGAAGCGTCCAA GCCGGAGGATCTCTGAGACTGAGCTGCGCCGCTAGTGGCTACTCCTAC AGCAGCTACTGCATGGGCTGGTTTAGGCAAGCCCCCGGCAAGGAGAGA GAAGGCGTGGCCACTATCGACAGCGACGGCATGACAAGGTACGCCGAC AGCGTGAAGGGAAGGTTCACAATCAGCAAGGACAACGCCAAGAACACA CTGTATCTGCAGATGAACTCTCTGAAGCCAGAGGACACTGCCATGTAC TACTGTGCCGCTCCTCGTACGACTGTGATAGCGGCGCTGTGGGCAGA AATCCACCTTATTGGGGCCAAGGCACTCAAGTGACAGTCTCGTCTGCT AGCCACCATCACCATCACCAC | 401 |
| 304 | CAAGTGCAGCTGCAAGAGAGCGGAGGAGGAAGCGTCCAAGCCGGAGGC TCTCTGAGACTGAGCTGTGCCGCCAGCGGCTACTCCAACTGCAGCTAC GACATGACTTGGTATAGGCAAGCCCCCGGCAAGGAGAGGGAGTTCGTG TCCGCCATCCACAGCGACGGCAGCACTAGATACGCCGACAGCGTGAAG GGAAGGTTCTTCATCAGCCAAGATAACGCCAAGAACACAGTGTATCTG CAGATGAACTCCCTCAAGCCAGAGGACACTGCCATGTACTACTGCAAG ACAGACCCACTGCACTGCAGAGCCCATGGCGGCAGCTGGTATAGCGTG AGGGCCAACTACTGGGCCAAGGCACACAAGTGACAGTCTCGAGCGGC GGAGGATCCCAAGTGCAGCTGCAAGAGAGCGGAGGCGGCAGCGTGCAG ACTGGAGGCTCTCTGAGACTGAGCTGTGCTGCCAGCGGCTACACTTAT CTGAGGGGCTGTATGGGCTGGTTTAGGCAAGCCCCCGGCAAGGAGAGA GAGGGCGTGGCCGTCATGGATGTGGTGGGCGATAGGAGAAGCTACATC GACAGCGTGAAGGGAAGGTTCACAATCTCTAGGGACAATGCCGCCAAC | 402 |

TABLE 14-continued

IL10 Receptor Binding Molecules Nucleic Acids

| DNA ENCODING SEQ ID NO. | DNA Sequence | SEQ ID NO |
|---|---|---|
| | AGCGTCTATCTGCAGATGGACAATCTGAAGCCAGAGGACACAGCCATG<br>TACTACTGCACTGCCGGCCCTAACTGTGTGGGCTGGAGAAGCGGACTG<br>GATTACTGGGGCCAAGGCACACAAGTGACAGTCTCGTCTGCTAGCCAC<br>CATCACCATCACCAC | |
| 305 | CAAGTGCAGCTGCAAGAGAGCGGCGGAGGAAGCGTGCAAGCTGGAGGC<br>TCTCTGAGGCTGAGCTGTGCTGCCAGCGGCTACACTTATAGCAGCGGC<br>TGTATGGGCTGGTTCAGACAAGCCCCCGGCAAGGAAAGGGAAGCCGTG<br>GCCGCCATCAATTCCGATGGCAGCACAAGCTACGCCGACAGCGTGAAG<br>GGAAGGTTCACAATCAGCAAGGACAACGCCAAGAACACACTCTATCTG<br>CAGATGAACTCTCTGAAGCCAGAGGACACAGCCATGTACTACTGCGCC<br>GCTGAGCCTTACTGTAGCGGCGGCTACCCAAGATGGAGCGTCGCTGAG<br>TTCGGCTACTGGGGCCAAGGCACACAAGTGACTGTCTCGAGCGGCGGA<br>GGATCCCAAGTGCAGCTGCAAGAGAGCGGAGGAGGAAGCGTGCAAGCC<br>GGAGGCTCTCTGAGACTGAGCTGTGCCGCCTCTAGGTATCTGTACAGC<br>ATCGACTACATGGCTTGGTTCAGACAGAGCCCCGGCAAGGAGAGGGAG<br>CCAGTGGCTGTCATCTACACTGCCTCCGGCGCCACATTCTATCCAGAT<br>AGCGTGAAGGGAAGGTTCACTATCAGCCAAGATAACGCCAAGATGACA<br>GTGTATCTGCAGATGAACTCTCTGAAGAGCGAGGACACTGCCATGTAC<br>TACTGTGCCGCCGTGAGGAAGACAGATAGCTACCTCTTCGACGCCCAG<br>AGCTTCACATACTGGGGCCAAGGCACACAAGTGACAGTCTCGTCTGCT<br>AGCCACCATCACCATCACCAC | 403 |
| 306 | CAAGTGCAGCTGCAAGAGAGCGGCGGAGGAAGCGTGCAAGCTGGAGGC<br>TCTCTGAGGCTGAGCTGTGCTGCCAGCGGCTACACTTATAGCAGCGGC<br>TGTATGGGCTGGTTCAGACAAGCCCCCGGCAAGGAAAGGGAAGCCGTG<br>GCCGCCATCAATTCCGATGGCAGCACAAGCTACGCCGACAGCGTGAAG<br>GGAAGGTTCACAATCAGCAAGGACAACGCCAAGAACACACTCTATCTG<br>CAGATGAACTCTCTGAAGCCAGAGGACACAGCCATGTACTACTGCGCC<br>GCTGAGCCTTACTGTAGCGGCGGCTACCCAAGATGGAGCGTCGCTGAG<br>TTCGGCTACTGGGGCCAAGGCACACAAGTGACTGTCTCGAGCGGCGGA<br>GGATCCCAAGTGCAGCTGCAAGAGAGCGGAGGAGGAAGCGTGCAAGCC<br>GGAGGCTCTCTGAGGCTGAGCTGTGCCGCCTCTAGGTTCACATACAGC<br>AGCTACTGCATGGGCTGGTTCAGACAAGCCCCGGCAAAGAGAGAGAA<br>GGCGTGGCCAGCATCGATAGCGATGGCTCCACTAGCTACACTGACAGC<br>GTGAAGGGAAGGTTCACTATCAGCAAGGACAACGCCAAGAACACTCTG<br>TATCTGCAGATGAACTCTCTGAAGCCAGAGGACACAGCCATGTACTAC<br>TGTGCCCTCGATCTGATGAGCACAGTGGTGCCCGGCTTCTGTGGCTTT<br>CTGCTGAGCGCTGGCATGGATTACTGGGGCAAGGGCACTCAAGTGACT<br>GTCTCGTCTGCTAGCCACCATCACCATCACCAC | 404 |
| 307 | CAAGTGCAGCTGCAAGAGAGCGGCGGAGGAAGCGTGCAAGCTGGAGGC<br>TCTCTGAGGCTGAGCTGTGCTGCCAGCGGCTACACTTATAGCAGCGGC<br>TGTATGGGCTGGTTCAGACAAGCCCCCGGCAAGGAAAGGGAAGCCGTG<br>GCCGCCATCAATTCCGATGGCAGCACAAGCTACGCCGACAGCGTGAAG<br>GGAAGGTTCACAATCAGCAAGGACAACGCCAAGAACACACTCTATCTG<br>CAGATGAACTCTCTGAAGCCAGAGGACACAGCCATGTACTACTGCGCC<br>GCTGAGCCTTACTGTAGCGGCGGCTACCCAAGATGGAGCGTCGCTGAG<br>TTCGGCTACTGGGGCCAAGGCACACAAGTGACTGTCTCGAGCGGCGGA<br>GGATCCCAAGTGCAGCTGCAAGAGTCCGGAGGAGGCAGCGTCCAAGCC<br>GGAGGCTCTCTGAGGCTGAGCTGTGCTGCCAGCGGCTACACTTACAGC<br>ATGTACTGCATGGGCTGGTTCAGACAAGCCCCCGGCAAGGAAAGAGAG<br>GGCGTGGCCCAGATCAATAGCGATGGCAGCACAAGCTACGCCGACAGC<br>GTGAAGGGAAGGTTCACTATCTCCAAGGACAACGCCAAGAACACTCTG<br>TATCTGCAGATGAACTCTCTGAAGCCAGAGGACACTGCCATGTACTAC<br>TGCGCTGCCGATTCTAGGGTGTACGGCGGCAGCTGGTATGAGAGGCTC<br>TGCGGCCCTTACACATACGAGTACAACTACTGGGGCAAGGCACACAA<br>GTGACTGTCTCGTCTGCTAGCCACCATCACCATCACCAC | 405 |
| 308 | CAAGTGCAGCTGCAAGAGAGCGGCGGAGGAAGCGTGCAAGCTGGAGGC<br>TCTCTGAGGCTGAGCTGTGCTGCCAGCGGCTACACTTATAGCAGCGGC<br>TGTATGGGCTGGTTCAGACAAGCCCCCGGCAAGGAAAGGGAAGCCGTG<br>GCCGCCATCAATTCCGATGGCAGCACAAGCTACGCCGACAGCGTGAAG<br>GGAAGGTTCACAATCAGCAAGGACAACGCCAAGAACACACTCTATCTG<br>CAGATGAACTCTCTGAAGCCAGAGGACACAGCCATGTACTACTGCGCC<br>GCTGAGCCTTACTGTAGCGGCGGCTACCCAAGATGGAGCGTCGCTGAG<br>TTCGGCTACTGGGGCCAAGGCACACAAGTGACTGTCTCGAGCGGCGGA<br>GGATCCCAAGTGCAGCTGCAAGAGAGCGGCGGAGGAAGCGTGCAAGCC<br>GGAGGATCTCTGAGACTGAGCTGCGCTGTGAGCGGCTACGCCTACTCC<br>ACATACTGCATGGGCTGGTTTAGGCAAGCCCCGGCAAAGAGAGAG<br>GGCGTGGCTGCTATCGATAGCGGCGGCAGCACAAGCTACGCCGATAGC<br>GTGAAGGGAAGGTTCACAATCAGCAAGGACAACGCCAAGAACACACTG<br>TATCTGAGGATGAACTCTCTGAAGCCAGAGGACACAGCCATGTACTAC | 406 |

TABLE 14-continued

IL10 Receptor Binding Molecules Nucleic Acids

| DNA ENCODING SEQ ID NO. | DNA Sequence | SEQ ID NO |
|---|---|---|
|  | TGTGCTGCTGTGCCTCCTCCTCCAGATGGCGGCAGCTGTCTGTTTCTG GGACCAGAGATCAAGGTCAGCAAGGCCGATTTTAGGTACTGGGGCCAA GGCACACAAGTGACAGTCTCGTCTGCTAGCCACCATCACCATCACCAC |  |
| 309 | CAAGTGCAGCTGCAAGAGAGCGGCGGAGGAAGCGTGCAAGCTGGAGGC TCTCTGAGGCTGAGCTGTGCTGCCAGCGGCTACACTTATAGCAGCGGC TGTATGGGCTGGTTCAGACAAGCCCCCGGCAAGGAAAGGGAAGCCGTG GCCGCCATCAATTCCGATGGCAGCACAAGCTACGCCGACAGCGTGAAG GGAAGGTTCACAATCAGCAAGGACAACGCCAAGAACACACTCTATCTG CAGATGAACTCTCTGAAGCCAGAGGACACAGCCATGTACTACTGCGCC GCTGAGCCTTACTGTAGCGGCGGCTACCCAAGATGGAGCGTCGCTGAG TTCGGCTACTGGGGCCAAGGCACACAAGTGACTGTCTCGAGCGGCGGA GGATCCCAAGTGCAGCTGCAAGAGAGCGGAGGAGGAAGCGTGCAAGCC GGAGGCTCTCTGAGGCTGAGCTGTACAGTGTCCGGCTACACTTACAGC TCCAATTGCATGGGCTGGTTTAGGCAAGCCCCCGGCAAGGAAAGAGAG GGCGTGGCCACTATCTACACTGGCGGCGGCAACATACTACGCCGAT AGCGTGAAGGGAAGGTTCACTATCAGCCAAGATAACGCCAAGAACACA GTGTATCTGCAGATGAACAATCTGAAGCCAGAGGACACTGCCATGTAC TACTGTGCTGCTGAGCCACTGTCTAGGGTGTACGGCGGCAGCTGCCCA ACTCCTACATTCGACTACTGGGGCCAAGGCACACAAGTGACTGTCTCG TCTGCTAGCCACCATCACCATCACCAC | 407 |
| 310 | CAAGTGCAGCTGCAAGAGAGCGGCGGAGGAAGCGTGCAAGCTGGAGGC TCTCTGAGGCTGAGCTGTGCTGCCAGCGGCTACACTTATAGCAGCGGC TGTATGGGCTGGTTCAGACAAGCCCCCGGCAAGGAAAGGGAAGCCGTG GCCGCCATCAATTCCGATGGCAGCACAAGCTACGCCGACAGCGTGAAG GGAAGGTTCACAATCAGCAAGGACAACGCCAAGAACACACTCTATCTG CAGATGAACTCTCTGAAGCCAGAGGACACAGCCATGTACTACTGCGCC GCTGAGCCTTACTGTAGCGGCGGCTACCCAAGATGGAGCGTCGCTGAG TTCGGCTACTGGGGCCAAGGCACACAAGTGACTGTCTCGAGCGGCGGA GGATCCCAAGTGCAGCTGCAAGAGAGCGGAGGAGGAAGCGTCCAAGCC GGAGGCTCTCTGAGGCTGAGCTGTGGAGCCAGCGGCTACACTTACAGC AGCTACTGTATGGGCTGGTTTAGGCAAGTGCCCGGCAAGGAGAGAGAG GGCGTGGCCGTGATCGATTCCGATGGCAGCACAAGCTACGCTGACAGC GTGAAGGGAAGGTTCACAATCAGCAAGGACAACGGCAAGAACACACTC TATCTGCAGATGAACAGCCTCAAGCCAGAGGACACAGCCATGTACTAC TGCGCCGCTGATCTGGGCCACTATAGGCCTCCTTGTGGCGTGCTGTAT CTGGGCATGGATTACTGGGGCAAGGGCACACAAGTGACAGTCTCGTCT GCTAGCCACCATCACCATCACCAC | 408 |
| 311 | CAAGTGCAGCTGCAAGAGAGCGGCGGAGGAAGCGTGCAAGCTGGAGGC TCTCTGAGGCTGAGCTGTGCTGCCAGCGGCTACACTTATAGCAGCGGC TGTATGGGCTGGTTCAGACAAGCCCCCGGCAAGGAAAGGGAAGCCGTG GCCGCCATCAATTCCGATGGCAGCACAAGCTACGCCGACAGCGTGAAG GGAAGGTTCACAATCAGCAAGGACAACGCCAAGAACACACTCTATCTG CAGATGAACTCTCTGAAGCCAGAGGACACAGCCATGTACTACTGCGCC GCTGAGCCTTACTGTAGCGGCGGCTACCCAAGATGGAGCGTCGCTGAG TTCGGCTACTGGGGCCAAGGCACACAAGTGACTGTCTCGAGCGGCGGA GGATCCCAAGTGCAGCTGCAAGAGAGCGGAGGAGGAAGCGTCCAAGCC GGAGGCTCTCTGAGACTGAGCTGTGCCGCCAGCGGCTACTCCAACTGC AGCTACGACATGACTTGGTATAGGCAAGCCCCCGGCAAGGAGAGGGAG TTCGTGTCCGCCATCCACAGCGACGGCAGCACTAGATACGCCGACAGC GTGAAGGGAAGGTTCTTCATCAGCCAAGATAACGCCAAGAACACAGTG TATCTGCAGATGAACTCCCTCAAGCCAGAGGACACTGCCATGTACTAC TGCAAGACAGACCCACTGCACTGCAGAGCCCATGGCGGCAGCTGGTAT AGCGTGAGGGCCAACTACTGGGGCCAAGGCACACAAGTGACAGTCTCG TCTGCTAGCCACCATCACCATCACCAC | 409 |
| 312 | CAAGTGCAGCTGCAAGAGAGCGGAGGAGGCAGCGTCCAAGCCGGAGGC TCTCTGAGGCTGAGCTGTGCTGCCAGCGGCTACACTTACAGCTAC TGCATGGGCTGGTTCAGACAAGCCCCCGGCAAGGAGAGAGAGGGCGTG GCTCACATCGACAGCGACGGCTCCACAAGCTACGCCGATAGCGTGAAG GGAAGGTTCACAATCTCCAAGGACAACGCCAAGAACACTCTGTACCTC CAGATGAACTCTCTGAAGCCAGAGGACACTGCCATGTACTACTGTGCC GCCGATCCAATTCCCGGCCCCGGCTACTGCGATGGCGGCCCTAACAAG TACTGGGGCCAAGGCACACAAGTGACTGTCTCGAGCGGCGGAGGATCC CAAGTGCAGCTGCAAGAGAGCGGAGGAGGAAGCGTGCAAGCCGGAGGC TCTCTGAGACTGAGCTGTGCCGCCTCTAGGTATCTGTACAGCATCGAC TACATGGCTTGGTTCAGACAGAGCCCCGGCAAGGAGAGGGAGCCAGTG GCTGTCATCTACACTGCCTCCGGCGCCACATTCTATCCAGATAGCGTG AAGGGAAGGTTCACTATCAGCCAAGATAACGCCAAGATGACAGTGTAT CTGCAGATGAACTCTCTGAAGAGCGAGGACACTGCCATGTACTACTGT GCCGCCGTGAGGAAGACAGATAGCTACCTCTTCGACGCCCAGAGCTTC | 410 |

TABLE 14-continued

IL10 Receptor Binding Molecules Nucleic Acids

| DNA ENCODING SEQ ID NO. | DNA Sequence | SEQ ID NO |
|---|---|---|
| | ACATACTGGGGCCAAGGCACACAAGTGACAGTCTCGTCTGCTAGCCAC CATCACCATCACCAC | |
| 313 | CAAGTGCAGCTGCAAGAGAGCGGAGGAGGCAGCGTCCAAGCCGGAGGC TCTCTGAGGCTGAGCTGTGCTGCCAGCGGCTACACTTACAGCAGCTAC TGCATGGGCTGGTTCAGACAAGCCCCCGGCAAGGAGAGAGAGGGCGTG GCTCACATCGACAGCGACGGCTCCACAAGCTACGCCGATAGCGTGAAG GGAAGGTTCACAATCTCCAAGGACAACGCCAAGAACACTCTGTACCTC CAGATGAACTCTCTGAAGCCAGAGGACACTGCCATGTACTACTGTGCC GCCGATCCAATTCCCGGCCCCGGCTACTGCGATGGCGGCCCTAACAAG TACTGGGGCCAAGGCACACAAGTGACTGTCTCGAGCGGCGGAGGATCC CAAGTGCAGCTGCAAGAGAGCGGAGGAGGAAGCGTGCAAGCCGGAGGC TCTCTGAGGCTGAGCTGTGCCGCCTCTAGGTTCACATACAGCAGCTAC TGCATGGGCTGGTTCAGACAAGCCCCCGGCAAAGAGAGAGAAGGCGTG GCCAGCATCGATAGCGATGGCTCCACTAGCTACACTGACAGCGTGAAG GGAAGGTTCACTATCAGCAAGGACAACGCCAAGAACACTCTGTATCTG CAGATGAACTCTCTGAAGCCAGAGGACACAGCCATGTACTACTGTGCC CTCGATCTGATGAGCACAGTGGTGCCCGGCTTCTGTGGCTTTCTGCTG AGCGCTGGCATGGATTACTGGGGCAAGGGCACTCAAGTGACTGTCTCG TCTGCTAGCCACCATCACCATCACCAC | 411 |
| 314 | CAAGTGCAGCTGCAAGAGAGCGGAGGAGGCAGCGTCCAAGCCGGAGGC TCTCTGAGGCTGAGCTGTGCTGCCAGCGGCTACACTTACAGCAGCTAC TGCATGGGCTGGTTCAGACAAGCCCCCGGCAAGGAGAGAGAGGGCGTG GCTCACATCGACAGCGACGGCTCCACAAGCTACGCCGATAGCGTGAAG GGAAGGTTCACAATCTCCAAGGACAACGCCAAGAACACTCTGTACCTC CAGATGAACTCTCTGAAGCCAGAGGACACTGCCATGTACTACTGTGCC GCCGATCCAATTCCCGCCCCGGCTACTGCGATGGCGGCCCTAACAAG TACTGGGGCCAAGGCACACAAGTGACTGTCTCGAGCGGCGGAGGATCC CAAGTGCAGCTGCAAGAGTCCGGAGGAGGCAGCGTCCAAGCCGGAGGC TCTCTGAGGCTGAGCTGTGCTGCCAGCGGCTACACTTACAGCATGTAC TGCATGGGCTGGTTCAGACAAGCCCCCGGCAAGGAAAGAGAGGGCGTG GCCCAGATCAATAGCGATGGCAGCACAAGCTACGCCGACAGCGTGAAG GGAAGGTTCACTATCTCCAAGGACAACGCCAAGAACACTCTGTATCTG CAGATGAACTCTCTGAAGCCAGAGGACACTGCCATGTACTACTGCGCT GCCGATTCTAGGGTGTACGGCGGCAGCTGGTATGAGAGGCTCTGCGGC CCTTACACATACGAGTACAACTACTGGGGCCAAGGCACACAAGTGACT GTCTCGTCTGCTAGCCACCATCACCATCACCAC | 412 |
| 315 | CAAGTGCAGCTGCAAGAGAGCGGAGGAGGCAGCGTCCAAGCCGGAGGC TCTCTGAGGCTGAGCTGTGCTGCCAGCGGCTACACTTACAGCAGCTAC TGCATGGGCTGGTTCAGACAAGCCCCCGGCAAGGAGAGAGAGGGCGTG GCTCACATCGACAGCGACGGCTCCACAAGCTACGCCGATAGCGTGAAG GGAAGGTTCACAATCTCCAAGGACAACGCCAAGAACACTCTGTACCTC CAGATGAACTCTCTGAAGCCAGAGGACACTGCCATGTACTACTGTGCC GCCGATCCAATTCCCGGCCCCGGCTACTGCGATGGCGGCCCTAACAAG TACTGGGGCCAAGGCACACAAGTGACTGTCTCGAGCGGCGGAGGATCC CAAGTGCAGCTGCAAGAGAGCGGCGGAGGAAGCGTGCAAGCCGGAGGA TCTCTGAGACTGAGCTGCGCTGTGAGCGGCTACGCCTACTCCACATAC TGCATGGGCTGGTTTAGGCAAGCCCCCGGCAAAGAGAGAGAGGGCGTG GCTGCTATCGATAGCGGCGGCAGCACAAGCTACGCCGATAGCGTGAAG GGAAGGTTCACAATCAGCAAGGACAACGCCAAGAACACACTGTATCTG AGGATGAACTCTCTGAAGCCAGAGGACACAGCCATGTACTACTGTGCT GCTGTGCCTCCTCCTCCAGATGGCGGCAGCTGTCGTTTCTGGGACCA GAGATCAAGGTCAGCAAGGCCGATTTTAGGTACTGGGGCCAAGGCACA CAAGTGACAGTCTCGTCTGCTAGCCACCATCACCATCACCAC | 413 |
| 316 | CAAGTGCAGCTGCAAGAGAGCGGAGGAGGCAGCGTCCAAGCCGGAGGC TCTCTGAGGCTGAGCTGTGCTGCCAGCGGCTACACTTACAGCAGCTAC TGCATGGGCTGGTTCAGACAAGCCCCCGGCAAGGAGAGAGAGGGCGTG GCTCACATCGACAGCGACGGCTCCACAAGCTACGCCGATAGCGTGAAG GGAAGGTTCACAATCTCCAAGGACAACGCCAAGAACACTCTGTACCTC CAGATGAACTCTCTGAAGCCAGAGGACACTGCCATGTACTACTGTGCC GCCGATCCAATTCCCGGCCCCGGCTACTGCGATGGCGGCCCTAACAAG TACTGGGGCCAAGGCACACAAGTGACTGTCTCGAGCGGCGGAGGATCC CAAGTGCAGCTGCAAGAGAGCGGAGGAGGAAGCGTGCAAGCCGGAGGC TCTCTGAGGCTGAGCTGTACAGTGTCCGGCTACACTTACAGCTCCAAT TGCATGGGCTGGTTTAGGCAAGCCCCCGGCAAGGAAAGAGAGGGCGTG | 414 |

TABLE 14-continued

IL10 Receptor Binding Molecules Nucleic Acids

| DNA ENCODING SEQ ID NO. | DNA Sequence | SEQ ID NO |
|---|---|---|
| | GCCACTATCTACACTGGCGGCGGCAACACATACTACGCCGATAGCGTG AAGGGAAGGTTCACTATCAGCCAAGATAACGCCAAGAACACAGTGTAT CTGCAGATGAACAATCTGAAGCCAGAGGACACTGCCATGTACTACTGT GCTGCTGAGCCACTGTCTAGGGTGTACGGCGGCAGCTGCCCAACTCCT ACATTCGACTACTGGGGCCAAGGCACACAAGTGACTGTCTCGTCTGCT AGCCACCATCACCATCACCAC | |
| 317 | CAAGTGCAGCTGCAAGAGAGCGGAGGAGGCAGCGTCCAAGCCGGAGGC TCTCTGAGGCTGAGCTGTGCTGCCAGCGGCTACACTTACAGCAGCTAC TGCATGGGCTGGTTCAGACAAGCCCCCGGCAAGGAGAGAGAGGGCGTG GCTCACATCGACAGCGACGGCTCCACAAGCTACGCCGATAGCGTGAAG GGAAGGTTCACAATCTCCAAGGACAACGCCAAGAACACTCTGTACCTC CAGATGAACTCTCTGAAGCCAGAGGACACTGCCATGTACTACTGTGCC GCCGATCCAATTCCCGGCCCCGGCTACTGCGATGGCGGCCCTAACAAG TACTGGGGCCAAGGCACACAAGTGACTGTCTCGAGCGGCGGAGGATCC CAAGTGCAGCTGCAAGAGAGCGGAGGAGGAAGCGTCCAAGCCGGAGGC TCTCTGAGGCTGAGCTGTGGAGCCAGCGGCTACACTTACAGCAGCTAC TGTATGGGCTGGTTTAGGCAAGTGCCCGGCAAGGAGAGAGAGGGCGTG GCCGTGATCGATTCCGATGGCAGCACAAGCTACGCTGACAGCGTGAAG GGAAGGTTCACAATCAGCAAGGACAACGGCAAGAACACACTCTATCTG CAGATGAACAGCCTCAAGCCAGAGGACACAGCCATGTACTACTGCGCC GCTGATCTGGGCCACTATAGGCCTCCTTGTGGCGTGCTGTATCTGGGC ATGGATTACTGGGGCAAGGGCACACAAGTGACAGTCTCGTCTGCTAGC CACCATCACCATCACCAC | 415 |
| 318 | CAAGTGCAGCTGCAAGAGAGCGGAGGAGGCAGCGTCCAAGCCGGAGGC TCTCTGAGGCTGAGCTGTGCTGCCAGCGGCTACACTTACAGCAGCTAC TGCATGGGCTGGTTCAGACAAGCCCCCGGCAAGGAGAGAGAGGGCGTG GCTCACATCGACAGCGACGGCTCCACAAGCTACGCCGATAGCGTGAAG GGAAGGTTCACAATCTCCAAGGACAACGCCAAGAACACTCTGTACCTC CAGATGAACTCTCTGAAGCCAGAGGACACTGCCATGTACTACTGTGCC GCCGATCCAATTCCCGGCCCCGGCTACTGCGATGGCGGCCCTAACAAG TACTGGGGCCAAGGCACACAAGTGACTGTCTCGAGCGGCGGAGGATCC CAAGTGCAGCTGCAAGAGAGCGGAGGAGGAAGCGTCCAAGCCGGAGGC TCTCTGAGACTGAGCTGTGCCGCCAGCGGCTACTCCAACTGCAGCTAC GACATGACTTGGTATAGGCAAGCCCCCGGCAAGGAGAGGGAGTTCGTG TCCGCCATCCACAGCGACGGCAGCACTAGATACGCCGACAGCGTGAAG GGAAGGTTCTTCATCAGCCAAGATAACGCCAAGAACACAGTGTATCTG CAGATGAACTCCCTCAAGCCAGAGGACACTGCCATGTACTACTGCAAG ACAGACCCACTGCACTGCAGAGCCCATGGCGGCAGCTGGTATAGCGTG AGGGCCAACTACTGGGGCCAAGGCACACAAGTGACAGTCTCGTCTGCT AGCCACCATCACCATCACCAC | 416 |
| 319 | CAAGTGCAGCTGCAAGAGTCCGGAGGAGGAAGCGTGCAAGCCGGCGGA TCTCTGAGACTGAGCTGTGCCGCCTCTAGGTACACTTACAACAGCTAC TGCATGGGCTGGTTCAGACAAGCCCCCGGCAAGGAAAGAGAGGGCGTG GCCACTATCGATAGCGACGGCATGACTAGGTACGCTGATAGCGTCAAG GGAAGGTTCACAATCTCCAAGGACAATGCTAAGAACACTCTGTACCTC CAGATGAACTCTCTGAAGCCAGAGGACACAGCCATGTACTACTGCGCT GCCGATGCCGACTGCACTATCGCCGCCATGACTACTAATCCTCTGGGC CAAGGCACACAAGTGACTGTCTCGAGCGGCGGAGGATCCCAAGTGCAG CTGCAAGAGAGCGGAGGAGGAAGCGTGCAAGCCGGAGGCTCTCTGAGA CTGAGCTGTGCCGCCTCTAGGTATCTGTACAGCATCGACTACATGGCT TGGTTCAGACAGAGCCCCGGCAAGGAGAGGGAGCCAGTGGCTGTCATC TACACTGCCTCCGGCGCCACATTCTATCCAGATAGCGTGAAGGGAAGG TTCACTATCAGCCAAGATAACGCCAAGATGACAGTGTATCTGCAGATG AACTCTCTGAAGAGCGAGGACACTGCCATGTACTACTGTGCCGCCGTG AGGAAGACAGATAGCTACCTCTTCGACGCCCAGAGCTTCACATACTGG GGCCAAGGCACACAAGTGACAGTCTCGTCTGCTAGCCACCATCACCAT CACCAC | 417 |
| 320 | CAAGTGCAGCTGCAAGAGTCCGGAGGAGGAAGCGTGCAAGCCGGCGGA TCTCTGAGACTGAGCTGTGCCGCCTCTAGGTACACTTACAACAGCTAC TGCATGGGCTGGTTCAGACAAGCCCCCGGCAAGGAAAGAGAGGGCGTG GCCACTATCGATAGCGACGGCATGACTAGGTACGCTGATAGCGTCAAG GGAAGGTTCACAATCTCCAAGGACAATGCTAAGAACACTCTGTACCTC CAGATGAACTCTCTGAAGCCAGAGGACACAGCCATGTACTACTGCGCT GCCGATGCCGACTGCACTATCGCCGCCATGACTACTAATCCTCTGGGC CAAGGCACACAAGTGACTGTCTCGAGCGGCGGAGGATCCCAAGTGCAG CTGCAAGAGAGCGGAGGAGGAAGCGTGCAAGCCGGAGGCTCTCTGAGG CTGAGCTGTGCCGCCTCTAGGTTCACATACAGCAGCTACTGCATGGGC TGGTTCAGACAAGCCCCCGGCAAAGAGAGAAGGCGTGGCCAGCATC GATAGCGATGGCTCCACTAGCTACACTGACAGCGTGAAGGGAAGGTTC | 418 |

TABLE 14-continued

IL10 Receptor Binding Molecules Nucleic Acids

| DNA ENCODING SEQ ID NO. | DNA Sequence | SEQ ID NO |
|---|---|---|
|  | ACTATCAGCAAGGACAACGCCAAGAACACTCTGTATCTGCAGATGAAC<br>TCTCTGAAGCCAGAGGACACAGCCATGTACTACTGTGCCCTCGATCTG<br>ATGAGCACAGTGGTGCCCGGCTTCTGTGGCTTTCTGCTGAGCGCTGGC<br>ATGGATTACTGGGGCAAGGGCACTCAAGTGACTGTCTCGTCTGCTAGC<br>CACCATCACCATCACCAC |  |
| 321 | CAAGTGCAGCTGCAAGAGTCCGGAGGAGGAAGCGTGCAAGCCGGCGGA<br>TCTCTGAGACTGAGCTGTGCCGCCTCTAGGTACACTTACAACAGCTAC<br>TGCATGGGCTGGTTCAGACAAGCCCCCGGCAAGGAAAGAGAGGGCGTG<br>GCCACTATCGATAGCGACGGCATGACTAGGTACGCTGATAGCGTCAAG<br>GGAAGGTTCACAATCTCCAAGGACAATGCTAAGAACACTCTGTACCTC<br>CAGATGAACTCTCTGAAGCCAGAGGACACAGCCATGTACTACTGCGCT<br>GCCGATGCCGACTGCACTATCGCCGCCATGACTACTAATCCTCTGGGC<br>CAAGGCACACAAGTGACTGTCTCGAGCGGCGGAGGATCCCAAGTGCAG<br>CTGCAAGAGTCCGGAGGAGGCAGCGTCCAAGCCGGAGGCTCTCTGAGG<br>CTGAGCTGTGCTGCCAGCGGCTACACTTACAGCATGTACTGCATGGGC<br>TGGTTCAGACAAGCCCCCGGCAAGGAAAGAGAGGGCGTGGCCCAGATC<br>AATAGCGATGGCACAAGCTACGCCGACAGCGTGAAGGGAAGGTTC<br>ACTATCTCCAAGGACAACGCCAAGAACACTCTGTATCTGCAGATGAAC<br>TCTCTGAAGCCAGAGGACACTGCCATGTACTACTGCGCTGCCGATTCT<br>AGGGTGTACGGCGGCAGCTGGTATGAGAGGCTCTGCGGCCCTTACACA<br>TACGAGTACAACTACTGGGGCCAAGGCACACAAGTGACTGTCTCGTCT<br>GCTAGCCACCATCACCATCACCAC | 419 |
| 322 | CAAGTGCAGCTGCAAGAGTCCGGAGGAGGAAGCGTGCAAGCCGGCGGA<br>TCTCTGAGACTGAGCTGTGCCGCCTCTAGGTACACTTACAACAGCTAC<br>TGCATGGGCTGGTTCAGACAAGCCCCCGGCAAGGAAAGAGAGGGCGTG<br>GCCACTATCGATAGCGACGGCATGACTAGGTACGCTGATAGCGTCAAG<br>GGAAGGTTCACAATCTCCAAGGACAATGCTAAGAACACTCTGTACCTC<br>CAGATGAACTCTCTGAAGCCAGAGGACACAGCCATGTACTACTGCGCT<br>GCCGATGCCGACTGCACTATCGCCGCCATGACTACTAATCCTCTGGGC<br>CAAGGCACACAAGTGACTGTCTCGAGCGGCGGAGGATCCCAAGTGCAG<br>CTGCAAGAGAGCGGCGAGGAAGCGTGCAAGCCGGAGGATCTCTGAGA<br>CTGAGCTGCGCTGTGAGCGGCTACGCCTACTCCACATACTGCATGGGC<br>TGGTTTAGGCAAGCCCCCGGCAAAGAGAGAGGGCGTGGCTGTATC<br>GATAGCGGCGGCAGCACAAGCTACGCCGATAGCGTGAAGGGAAGGTTC<br>ACAATCAGCAAGGACAACGCCAAGAACACACTGTATCTGAGGATGAAC<br>TCTCTGAAGCCAGAGGACACAGCCATGTACTACTGTGCTGCTGTGCCT<br>CCTCCTCCAGATGGCGGCAGCTGTCTGTTTCTGGGACCAGAGATCAAG<br>GTCAGCAAGGCCGATTTTAGGTACTGGGGCCAAGGCACACAAGTGACA<br>GTCTCGTCTGCTAGCCACCATCACCATCACCAC | 420 |
| 323 | CAAGTGCAGCTGCAAGAGTCCGGAGGAGGAAGCGTGCAAGCCGGCGGA<br>TCTCTGAGACTGAGCTGTGCCGCCTCTAGGTACACTTACAACAGCTAC<br>TGCATGGGCTGGTTCAGACAAGCCCCCGGCAAGGAAAGAGAGGGCGTG<br>GCCACTATCGATAGCGACGGCATGACTAGGTACGCTGATAGCGTCAAG<br>GGAAGGTTCACAATCTCCAAGGACAATGCTAAGAACACTCTGTACCTC<br>CAGATGAACTCTCTGAAGCCAGAGGACACAGCCATGTACTACTGCGCT<br>GCCGATGCCGACTGCACTATCGCCGCCATGACTACTAATCCTCTGGGC<br>CAAGGCACACAAGTGACTGTCTCGAGCGGCGGAGGATCCCAAGTGCAG<br>CTGCAAGAGAGCGGAGGAGGAAGCGTGCAAGCCGGAGGCTCTCTGAGG<br>CTGAGCTGTACAGTGTCCGGCTACACTTACAGCTCCAATTGCATGGGC<br>TGGTTTAGGCAAGCCCCCGGCAAGGAAAGAGAGGGCGTGGCCACTATC<br>TACACTGGCGGCGGCAACACATACTACGCCGATAGCGTGAAGGGAAGG<br>TTCACTATCAGCCAAGATAACGCCAAGAACACAGTGTATCTGCAGATG<br>AACAATCTGAAGCCAGAGGACACTGCCATGTACTACTGTGCTGCTGAG<br>CCACTGTCTAGGGTGTACGGCGGCAGCTGCCCAACTCCTACATTCGAC<br>TACTGGGGCCAAGGCACACAAGTGACTGTCTCGTCTGCTAGCCACCAT<br>CACCATCACCAC | 421 |
| 324 | CAAGTGCAGCTGCAAGAGTCCGGAGGAGGAAGCGTGCAAGCCGGCGGA<br>TCTCTGAGACTGAGCTGTGCCGCCTCTAGGTACACTTACAACAGCTAC<br>TGCATGGGCTGGTTCAGACAAGCCCCCGGCAAGGAAAGAGAGGGCGTG<br>GCCACTATCGATAGCGACGGCATGACTAGGTACGCTGATAGCGTCAAG<br>GGAAGGTTCACAATCTCCAAGGACAATGCTAAGAACACTCTGTACCTC<br>CAGATGAACTCTCTGAAGCCAGAGGACACAGCCATGTACTACTGCGCT<br>GCCGATGCCGACTGCACTATCGCCGCCATGACTACTAATCCTCTGGGC<br>CAAGGCACACAAGTGACTGTCTCGAGCGGCGGAGGATCCCAAGTGCAG<br>CTGCAAGAGAGCGGAGGAGGAAGCGTCCAAGCCGGAGGCTCTCTGAGG<br>CTGAGCTGTGGAGCCAGCGGCTACACTTACAGCAGCTACTGTATGGGC<br>TGGTTTAGGCAAGTGCCCGGCAAGGAGAGAGAGGGCGTGGCCGTGATC<br>GATTCCGATGGCAGCACAAGCTACGCTGACAGCGTGAAGGGAAGGTTC<br>ACAATCAGCAAGGACAACGGCAAGAACACACTCTATCTGCAGATGAAC | 422 |

TABLE 14-continued

IL10 Receptor Binding Molecules Nucleic Acids

| DNA ENCODING SEQ ID NO. | DNA Sequence | SEQ ID NO |
|---|---|---|
|  | AGCCTCAAGCCAGAGGACACAGCCATGTACTACTGCGCCGCTGATCTG GGCCACTATAGGCCTCCTTGTGGCGTGCTGTATCTGGGCATGGATTAC TGGGGCAAGGGCACACAAGTGACAGTCTCGTCTGCTAGCCACCATCAC CATCACCAC |  |
| 325 | CAAGTGCAGCTGCAAGAGTCCGGAGGAGGAAGCGTGCAAGCCGGCGGA TCTCTGAGACTGAGCTGTGCCGCCTCTAGGTACACTTACAACAGCTAC TGCATGGGCTGGTTCAGACAAGCCCCCGGCAAGGAAAGAGAGGGCGTG GCCACTATCGATAGCGACGGCATGACTAGGTACGCTGATAGCGTCAAG GGAAGGTTCACAATCTCCAAGGACAATGCTAAGAACACTCTGTACCTC CAGATGAACTCTCTGAAGCCAGAGGACACAGCCATGTACTACTGCGCT GCCGATGCCGACTGCACTATCGCCGCCATGACTACTAATCCTCTGGGC CAAGGCACACAAGTGACTGTCTCGAGCGGCGGAGGATCCCAAGTGCAG CTGCAAGAGAGCGGAGGAGGAAGCGTCCAAGCCGGAGGCTCTCTGAGA CTGAGCTGTGCCGCCAGCGGCTACTCCAACTGCAGCTACGACATGACT TGGTATAGGCAAGCCCCCGGCAAGGAGAGGGAGTTCGTGTCCGCCATC CACAGCGACGGCAGCACTAGATACGCCGACAGCGTGAAGGGAAGGTTC TTCATCAGCCAAGATAACGCCAAGAACACAGTGTATCTGCAGATGAAC TCCCTCAAGCCAGAGGACACTGCCATGTACTACTGCAAGACAGACCCA CTGCACTGCAGAGCCCATGGCGGCAGCTGGTATAGCGTGAGGGCCAAC TACTGGGGCCAAGGCACACAAGTGACAGTCTCGTCTGCTAGCCACCAT CACCATCACCAC | 423 |
| 326 | CAAGTGCAGCTGCAAGAGTCCGGCGGAGGCAGCGTCCAAGCCGGAGGA TCTCTGAGGCTGAGCTGTACAGTGAGCAGATACACTGCCAGCGTGAAC TACATGGGCTGGTTCAGACAAGCCCCCGGCAAAGAGAGAGAGGGCGTG GCCACAATCTTCACTGGCGCCGGCACAACATACTACGCCAACTCCGTC AAGGGAAGGTTCACAATCTCTAGGGACAACGCCAAGAACACTGCCTAT CTGCAGATGAACTCCCTCAAGCCAGAGGACACTGCCATCTACTACTGC GCCGTGGATTTCAGAGGCGGACTGCTGTATAGGCCAGCCTACGAGTAC ACTTATAGGGGCCAAGGCACACAAGTGACAGTCTCGAGCGGCGGAGGA TCCCAAGTGCAGCTGCAAGAGAGCGGAGGAGGAAGCGTGCAAGCCGGA GGCTCTCTGAGACTGAGCTGTGCCGCCTCTAGGTATCTGTACAGCATC GACTACATGGCTTGGTTCAGACAGAGCCCCGGCAAGGAGAGGGAGCCA GTGGCTGTCATCTACACTGCCTCCGGCGCCACATTCTATCCAGATAGC GTGAAGGGAAGGTTCACTATCAGCCAAGATAACGCCAAGATGACAGTG TATCTGCAGATGAACTCTCTGAAGAGCGAGGACACTGCCATGTACTAC TGTGCCGCCGTGAGGAAGACAGATAGCTACCTCTTCGACGCCCAGAGC TTCACATACTGGGGCCAAGGCACACAAGTGACAGTCTCGTCTGCTAGC CACCATCACCATCACCAC | 424 |
| 327 | CAAGTGCAGCTGCAAGAGTCCGGCGGAGGCAGCGTCCAAGCCGGAGGA TCTCTGAGGCTGAGCTGTACAGTGAGCAGATACACTGCCAGCGTGAAC TACATGGGCTGGTTCAGACAAGCCCCCGGCAAAGAGAGAGAGGGCGTG GCCACAATCTTCACTGGCGCCGGCACAACATACTACGCCAACTCCGTC AAGGGAAGGTTCACAATCTCTAGGGACAACGCCAAGAACACTGCCTAT CTGCAGATGAACTCCCTCAAGCCAGAGGACACTGCCATCTACTACTGC GCCGTGGATTTCAGAGGCGGACTGCTGTATAGGCCAGCCTACGAGTAC ACTTATAGGGGCCAAGGCACACAAGTGACAGTCTCGAGCGGCGGAGGA TCCCAAGTGCAGCTGCAAGAGAGCGGAGGAGGAAGCGTGCAAGCCGGA GGCTCTCTGAGGCTGAGCTGTGCCGCCTCTAGGTTCACATACAGCATG TACTGCATGGGCTGGTTCAGACAAGCCCCCGGCAAAGAGAGAGAAGGC GTGGCCAGCATCGATAGCGATGGCTCCACTAGCTACACTGACAGCGTG AAGGGAAGGTTCACTATCAGCAAGGACAACGCCAAGAACACTCTGTAT CTGCAGATGAACTCTCTGAAGCCAGAGGACACAGCCATGTACTACTGT GCCCTCGATCTGATGAGCACAGTGGTGCCCGGCTTCTGTGGCTTTCTG CTGAGCGCTGGCATGGATTACTGGGGCAAGGGCACTCAAGTGACTGTC TCGTCTGCTAGCCACCATCACCATCACCAC | 425 |
| 328 | CAAGTGCAGCTGCAAGAGTCCGGCGGAGGCAGCGTCCAAGCCGGAGGA TCTCTGAGGCTGAGCTGTACAGTGAGCAGATACACTGCCAGCGTGAAC TACATGGGCTGGTTCAGACAAGCCCCCGGCAAAGAGAGAGGGCGTG GCCACAATCTTCACTGGCGCCGGCACAACATACTACGCCAACTCCGTC AAGGGAAGGTTCACAATCTCTAGGGACAACGCCAAGAACACTGCCTAT CTGCAGATGAACTCCCTCAAGCCAGAGGACACTGCCATCTACTACTGC GCCGTGGATTTCAGAGGCGGACTGCTGTATAGGCCAGCCTACGAGTAC ACTTATAGGGGCCAAGGCACACAAGTGACAGTCTCGAGCGGCGGAGGA TCCCAAGTGCAGCTGCAAGAGTCCGGAGGAGGCAGCGTCCAAGCCGGA GGCTCTCTGAGGCTGAGCTGTGCTGCCAGCGGCTACACTTACAGCATG TACTGCATGGGCTGGTTCAGACAAGCCCCCGGCAAGGAAAGAGAGGGC GTGGCCCAGATCAATAGCGATGGCAGCACAAGCTACGCCGACAGCGTG AAGGGAAGGTTCACTATCTCCAAGGACAACGCCAAGAACACTCTGTAT CTGCAGATGAACTCTCTGAAGCCAGAGGACACTGCCATGTACTACTGC | 426 |

TABLE 14-continued

IL10 Receptor Binding Molecules Nucleic Acids

| DNA ENCODING SEQ ID NO. | DNA Sequence | SEQ ID NO |
|---|---|---|
| | GCTGCCGATTCTAGGGTGTACGGCGGCAGCTGGTATGAGAGGCTCTGC GGCCCTTACACATACGAGTACAACTACTGGGGCCAAGGCACACAAGTG ACTGTCTCGTCTGCTAGCCACCATCACCATCACCAC | |
| 329 | CAAGTGCAGCTGCAAGAGTCCGGCGGAGGCAGCGTCCAAGCCGGAGGA TCTCTGAGGCTGAGCTGTACAGTGAGCAGATACACTGCCAGCGTGAAC TACATGGGCTGGTTCAGACAAGCCCCCGGCAAAGAGAGAGAGGGCGTG GCCACAATCTTCACTGGCGCCGGCACAACATACTACGCCAACTCCGTC AAGGGAAGGTTCACAATCTCTAGGGACAACGCCAAGAACACTGCCTAT CTGCAGATGAACTCCCTCAAGCCAGAGGACACTGCCATCTACTACTGC GCCGTGGATTTCAGAGGCGGACTGCTGTATAGGCCAGCCTACGAGTAC ACTTATAGGGGCCAAGGCACACAAGTGACAGTCTCGAGCGGCGGAGGA TCCCAAGTGCAGCTGCAAGAGAGCGGCGGAGGAAGCGTGCAAGCCGGA GGATCTCTGAGACTGAGCTGCGCTGTGAGCGGCTACGCCTACTCCACA TACTGCATGGGCTGGTTTAGGCAAGCCCCCGGCAAAGAGAGAGAGGGC GTGGCTGCTATCGATAGCGGCGGCAGCACAAGCTACGCCGATAGCGTG AAGGGAAGGTTCACAATCAGCAAGGACAACGCCAAGAACACACTGTAT CTGAGGATGAACTCTCTGAAGCCAGAGGACACAGCCATGTACTACTGT GCTGCTGTGCCTCCTCCTCCAGATGGCGGCAGCTGTCTGTTTCTGGGA CCAGAGATCAAGGTCAGCAAGGCCGATTTTAGGTACTGGGGCCAAGGC ACACAAGTGACAGTCTCGTCTGCTAGCCACCATCACCATCACCAC | 427 |
| 330 | CAAGTGCAGCTGCAAGAGTCCGGCGGAGGCAGCGTCCAAGCCGGAGGA TCTCTGAGGCTGAGCTGTACAGTGAGCAGATACACTGCCAGCGTGAAC TACATGGGCTGGTTCAGACAAGCCCCCGGCAAAGAGAGAGAGGGCGTG GCCACAATCTTCACTGGCGCCGGCACAACATACTACGCCAACTCCGTC AAGGGAAGGTTCACAATCTCTAGGGACAACGCCAAGAACACTGCCTAT CTGCAGATGAACTCCCTCAAGCCAGAGGACACTGCCATCTACTACTGC GCCGTGGATTTCAGAGGCGGACTGCTGTATAGGCCAGCCTACGAGTAC ACTTATAGGGGCCAAGGCACACAAGTGACAGTCTCGAGCGGCGGAGGA TCCCAAGTGCAGCTGCAAGAGAGCGGCGGAGGAAGCGTGCAAGCCGGA GGCTCTCTGAGGCTGAGCTGTACAGTGTCCGGCTACACTTACAGCTCC AATTGCATGGGCTGGTTTAGGCAAGCCCCCGGCAAGGAAAGAGAGGGC GTGGCCACTATCTACACTGGCGGCGGCAACACATACTACGCCGATAGC GTGAAGGGAAGGTTCACTATCAGCCAAGATAACGCCAAGAACACAGTG TATCTGCAGATGAACAATCTGAAGCCAGAGGACACTGCCATGTACTAC TGTGCTGCTGAGCCACTGTCTAGGGTATACGGCGGCAGCTGCCCAACT CCTACATTCGACTACTGGGGCCAAGGCACACAAGTGACTGTCTCGTCT GCTAGCCACCATCACCATCACCAC | 428 |
| 331 | CAAGTGCAGCTGCAAGAGTCCGGCGGAGGCAGCGTCCAAGCCGGAGGA TCTCTGAGGCTGAGCTGTACAGTGAGCAGATACACTGCCAGCGTGAAC TACATGGGCTGGTTCAGACAAGCCCCCGGCAAAGAGAGAGAGGGCGTG GCCACAATCTTCACTGGCGCCGGCACAACATACTACGCCAACTCCGTC AAGGGAAGGTTCACAATCTCTAGGGACAACGCCAAGAACACTGCCTAT CTGCAGATGAACTCCCTCAAGCCAGAGGACACTGCCATCTACTACTGC GCCGTGGATTTCAGAGGCGGACTGCTGTATAGGCCAGCCTACGAGTAC ACTTATAGGGGCCAAGGCACACAAGTGACAGTCTCGAGCGGCGGAGGA TCCCAAGTGCAGCTGCAAGAGAGCGGCGGAGGAAGCGTCCAAGCCGGA GGCTCTCTGAGGCTGAGCTGTGGAGCCAGCGGCTACACTTACAGCAGC TACTGTATGGGCTGGTTTAGGCAAGTGCCCGGCAAGGAGAGAGAGGGC GTGGCCGTGATCGATTCCGATGGCAGCACAAGCTACGCTGACAGCGTG AAGGGAAGGTTCACAATCAGCAAGGACAACGGCAAGAACACACTCTAT CTGCAGATGAACAGCCTCAAGCCAGAGGACACAGCCATGTACTACTGC GCCGCTGATCTGGGCCACTATAGGCCTCCTTGTGGCGTGCTATATCTG GGCATGGATTACTGGGGCAAGGGCACACAAGTGACAGTCTCGTCTGCT AGCCACCATCACCATCACCAC | 429 |
| 332 | CAAGTGCAGCTGCAAGAGTCCGGCGGAGGCAGCGTCCAAGCCGGAGGA TCTCTGAGGCTGAGCTGTACAGTGAGCAGATACACTGCCAGCGTGAAC TACATGGGCTGGTTCAGACAAGCCCCCGGCAAAGAGAGAGAGGGCGTG GCCACAATCTTCACTGGCGCCGGCACAACATACTACGCCAACTCCGTC AAGGGAAGGTTCACAATCTCTAGGGACAACGCCAAGAACACTGCCTAT CTGCAGATGAACTCCCTCAAGCCAGAGGACACTGCCATCTACTACTGC GCCGTGGATTTCAGAGGCGGACTGCTGTATAGGCCAGCCTACGAGTAC ACTTATAGGGGCCAAGGCACACAAGTGACAGTCTCGAGCGGCGGAGGA TCCCAAGTGCAGCTGCAAGAGAGCGGCGGAGGAAGCGTCCAAGCCGGA GGCTCTCTGAGACTGAGCTGTGCCGCCAGCGGCTACTCCAACTGCAGC TACGACATGACTTGGTATAGGCAAGCCCCCGGCAAGGAGAGGGAGTTC GTGTCCGCCATCCACAGCGACGGCAGCACTAGATACGCCGACAGCGTG AAGGGAAGGTTCTTCATCAGCCAAGATAACGCCAAGAACACAGTGTAT CTGCAGATGAACTCCCTCAAGCCAGAGGACACTGCCATGTACTACTGC AAGACAGACCCCACTGCACTGCAGAGCCCATGGCGGCAGCTGGTATAGC | 430 |

TABLE 14-continued

IL10 Receptor Binding Molecules Nucleic Acids

| DNA ENCODING SEQ ID NO. | DNA Sequence | SEQ ID NO |
|---|---|---|
|  | GTGAGGGCCAACTACTGGGGCCAAGGCACACAAGTGACAGTCTCGTCT GCTAGCCACCATCACCATCACCAC |  |
| 333 | CAAGTGCAGCTGCAAGAGAGCGGAGGAGGCAGCGTCGAAGCTGGAGGA TCTCTGAGGCTGAGCTGTGCTGCCAGCGGCTACACTCACAGCAGCTAC TGTATGGGCTGGTTCAGACAAGCCCCCGGCAAGGAGAGGGAAGGCGTG GCTGCCATCGACGTGGATGGCAGCACTACTTACGCCGACAGCGTGAAG GGAAGGTTCACTATCAGCAAGGACAACGCCAAGAACACACTCTATCTG CAGATGAACAGCCTCAAGCCAGAGGACACTGGCATGTACTACTGCGCC GCCGAGTTCGCCGATTGCAGCAGCAACTACTTTCTGCCTCCCGGCGCC GTCAGATATTGGGGCCAAGGCACTCAAGTGACAGTCTCGAGCGGCGGA GGATCCCAAGTGCAGCTGCAAGAGAGCGGAGGAGGAAGCGTGCAAGCC GGAGGCTCTCTGAGACTGAGCTGTGCCGCCTCTAGGTATCTGTACAGC ATCGACTACATGGCTTGGTTCAGACAGAGCCCCGGCAAGGAGAGGGAG CCAGTGGCTGTCATCTACACTGCCTCCGGCGCCACATTCTATCCAGAT AGCGTGAAGGGAAGGTTCACTATCAGCCAAGATAACGCCAAGATGACA GTGTATCTGCAGATGAACTCTCTGAAGAGCGAGGACACTGCCATGTAC TACTGTGCCGCCGTGAGGAAGACAGATAGCTACCTCTTCGACGCCCAG AGCTTCACATACTGGGGCCAAGGCACACAAGTGACAGTCTCGTCTGCT AGCCACCATCACCATCACCAC | 431 |
| 334 | CAAGTGCAGCTGCAAGAGAGCGGAGGAGGCAGCGTCGAAGCTGGAGGA TCTCTGAGGCTGAGCTGTGCTGCCAGCGGCTACACTCACAGCAGCTAC TGTATGGGCTGGTTCAGACAAGCCCCCGGCAAGGAGAGGGAAGGCGTG GCTGCCATCGACGTGGATGGCAGCACTACTTACGCCGACAGCGTGAAG GGAAGGTTCACTATCAGCAAGGACAACGCCAAGAACACACTCTATCTG CAGATGAACAGCCTCAAGCCAGAGGACACTGGCATGTACTACTGCGCC GCCGAGTTCGCCGATTGCAGCAGCAACTACTTTCTGCCTCCCGGCGCC GTCAGATATTGGGGCCAAGGCACTCAAGTGACAGTCTCGAGCGGCGGA GGATCCCAAGTGCAGCTGCAAGAGAGCGGAGGAGGAAGCGTGCAAGCC GGAGGCTCTCTGAGGCTGAGCTGTGCCGCCTCTAGGTTCACATACAGC AGCTACTGCATGGGCTGGTTCAGACAAGCCCCCGGCAAAGAGAGAGAA GGCGTGGCCAGCATCGATAGCGATGGCTCCACTAGCTACACTGACAGC GTGAAGGGAAGGTTCACTATCAGCAAGGACAACGCCAAGAACACTCTG TATCTGCAGATGAACTCTCTGAAGCCAGAGGACACAGCCATGTACTAC TGTGCCCTCGATCTGATGAGCACAGTGGTGCCCGGCTTCTGTGGCTTT CTGCTGAGCGCTGGCATGGATTACTGGGGCAAGGGCACTCAAGTGACT GTCTCGTCTGCTAGCCACCATCACCATCACCAC | 432 |
| 335 | CAAGTGCAGCTGCAAGAGAGCGGAGGAGGCAGCGTCGAAGCTGGAGGA TCTCTGAGGCTGAGCTGTGCTGCCAGCGGCTACACTCACAGCAGCTAC TGTATGGGCTGGTTCAGACAAGCCCCCGGCAAGGAGAGGGAAGGCGTG GCTGCCATCGACGTGGATGGCAGCACTACTTACGCCGACAGCGTGAAG GGAAGGTTCACTATCAGCAAGGACAACGCCAAGAACACACTCTATCTG CAGATGAACAGCCTCAAGCCAGAGGACACTGGCATGTACTACTGCGCC GCCGAGTTCGCCGATTGCAGCAGCAACTACTTTCTGCCTCCCGGCGCC GTCAGATATTGGGGCCAAGGCACTCAAGTGACAGTCTCGAGCGGCGGA GGATCCCAAGTGCAGCTGCAAGAGTCCGGAGGAGGCAGCGTCCAAGCC GGAGGCTCTCTGAGGCTGAGCTGTGCTGCCAGCGGCTACACTTACAGC ATGTACTGCATGGGCTGGTTCAGACAAGCCCCCGGCAAGGAAAGAGAG GGCGTGGCCCAGATCAATAGCGATGGCAGCACAAGCTACGCCGACAGC GTGAAGGGAAGGTTCACTATCTCCAAGGACAACGCCAAGAACACTCTG TATCTGCAGATGAACTCTCTGAAGCCAGAGGACACTGCCATGTACTAC TGCGCTGCCGATTCTAGGGTGTACGGCGGCAGCTGGTATGAGAGGCTC TGCGGCCCTTACACATACGAGTACAACTACTGGGGCCAAGGCACACAA GTGACTGTCTCGTCTGCTAGCCACCATCACCATCACCAC | 433 |
| 336 | CAAGTGCAGCTGCAAGAGAGCGGAGGAGGCAGCGTCGAAGCTGGAGGA TCTCTGAGGCTGAGCTGTGCTGCCAGCGGCTACACTCACAGCAGCTAC TGTATGGGCTGGTTCAGACAAGCCCCCGGCAAGGAGAGGGAAGGCGTG GCTGCCATCGACGTGGATGGCAGCACTACTTACGCCGACAGCGTGAAG GGAAGGTTCACTATCAGCAAGGACAACGCCAAGAACACACTCTATCTG CAGATGAACAGCCTCAAGCCAGAGGACACTGGCATGTACTACTGCGCC GCCGAGTTCGCCGATTGCAGCAGCAACTACTTTCTGCCTCCCGGCGCC GTCAGATATTGGGGCCAAGGCACTCAAGTGACAGTCTCGAGCGGCGGA GGATCCCAAGTGCAGCTGCAAGAGAGCGGCGGAGGAAGCGTGCAAGCC GGAGGATCTCTGAGACTGAGCTGCGCTGTGAGCGGCTACGCCTACTCC ACATACTGCATGGGCTGGTTTAGGCAAGCCCCCGGCAAAGAGAGAGAG | 434 |

TABLE 14-continued

IL10 Receptor Binding Molecules Nucleic Acids

| DNA ENCODING SEQ ID NO. | DNA Sequence | SEQ ID NO |
|---|---|---|
| | GGCGTGGCTGCTATCGATAGCGGCGGCAGCACAAGCTACGCCGATAGC<br>GTGAAGGGAAGGTTCACAATCAGCAAGGACAACGCCAAGAACACACTG<br>TATCTGAGGATGAACTCTCTGAAGCCAGAGGACACAGCCATGTACTAC<br>TGTGCTGCTGTGCCTCCTCCTCCAGATGGCGGCAGCTGTCTGTTTCTG<br>GGACCAGAGATCAAGGTCAGCAAGGCCGATTTTAGGTACTGGGGCCAA<br>GGCACACAAGTGACAGTCTCGTCTGCTAGCCACCATCACCATCACCAC | |
| 337 | CAAGTGCAGCTGCAAGAGAGCGGAGGAGGCAGCGTCGAAGCTGGAGGA<br>TCTCTGAGGCTGAGCTGTGCTGCCAGCGGCTACACTCACAGCAGCTAC<br>TGTATGGGCTGGTTCAGACAAGCCCCCGGCAAGGAGAGGGAAGGCGTG<br>GCTGCCATCGACGTGGATGGCAGCACTACTTACGCCGACAGCGTGAAG<br>GGAAGGTTCACTATCAGCAAGGACAACGCCAAGAACACACTCTATCTG<br>CAGATGAACAGCCTCAAGCCAGAGGACACTGGCATGTACTACTGCGCC<br>GCCGAGTTCGCCGATTGCAGCAGCAACTACTTTCTGCCTCCCGGCGCC<br>GTCAGATATTGGGGCCAAGGCACTCAAGTGACAGTCTCGAGCGGCGGA<br>GGATCCCAAGTGCAGCTGCAAGAGAGCGGAGGAGGAAGCGTGCAAGCC<br>GGAGGCTCTCTGAGGCTGAGCTGTACAGTGTCCGGCTACACTTACAGC<br>TCCAATTGCATGGGCTGGTTTAGGCAAGCCCCCGGCAAGGAAAGAGAG<br>GGCGTGGCCACTATCTACACTGGCGGCGGCAACACATACTACGCCGAT<br>AGCGTGAAGGGAAGGTTCACTATCAGCCAAGATAACGCCAAGAACACA<br>GTGTATCTGCAGATGAACAATCTGAAGCCAGAGGACACTGCCATGTAC<br>TACTGTGCTGCTGAGCCACTGTCTAGGGTGTACGGCGGCAGCTGCCCA<br>ACTCCTACATTCGACTACTGGGGCCAAGGCACACAAGTGACTGTCTCG<br>TCTGCTAGCCACCATCACCATCACCAC | 435 |
| 338 | CAAGTGCAGCTGCAAGAGAGCGGAGGAGGCAGCGTCGAAGCTGGAGGA<br>TCTCTGAGGCTGAGCTGTGCTGCCAGCGGCTACACTCACAGCAGCTAC<br>TGTATGGGCTGGTTCAGACAAGCCCCCGGCAAGGAGAGGGAAGGCGTG<br>GCTGCCATCGACGTGGATGGCAGCACTACTTACGCCGACAGCGTGAAG<br>GGAAGGTTCACTATCAGCAAGGACAACGCCAAGAACACACTCTATCTG<br>CAGATGAACAGCCTCAAGCCAGAGGACACTGGCATGTACTACTGCGCC<br>GCCGAGTTCGCCGATTGCAGCAGCAACTACTTTCTGCCTCCCGGCGCC<br>GTCAGATATTGGGGCCAAGGCACTCAAGTGACAGTCTCGAGCGGCGGA<br>GGATCCCAAGTGCAGCTGCAAGAGAGCGGAGGAGGAAGCGTCCAAGCC<br>GGAGGCTCTCTGAGGCTGAGCTGTGGAGCCAGCGGCTACACTTACAGC<br>AGCTACTGTATGGGCTGGTTTAGGCAAGTGCCCGGCAAGGAGAGAGAG<br>GGCGTGGCCGTGATCGATTCCGATGGCAGCACAAGCTACGCTGACAGC<br>GTGAAGGGAAGGTTCACAATCAGCAAGGACAACGGCAAGAACACACTC<br>TATCTGCAGATGAACAGCCTCAAGCCAGAGGACACAGCTATGTACTAC<br>TGCGCCGCTGATCTGGGCCACTATAGGCCTCCTTGTGGCGTGCTGTAT<br>CTGGGCATGGATTACTGGGGCAAGGGCACACAAGTGACAGTCTCGTCT<br>GCTAGCCACCATCACCATCACCAC | 436 |
| 339 | CAAGTGCAGCTGCAAGAGAGCGGAGGAGGCAGCGTCGAAGCTGGAGGA<br>TCTCTGAGGCTGAGCTGTGCTGCCAGCGGCTACACTCACAGCAGCTAC<br>TGTATGGGCTGGTTCAGACAAGCCCCCGGCAAGGAGAGGGAAGGCGTG<br>GCTGCCATCGACGTGGATGGCAGCACTACTTACGCCGACAGCGTGAAG<br>GGAAGGTTCACTATCAGCAAGGACAACGCCAAGAACACACTCTATCTG<br>CAGATGAACAGCCTCAAGCCAGAGGACACTGGCATGTACTACTGCGCC<br>GCCGAGTTCGCCGATTGCAGCAGCAACTACTTTCTGCCTCCCGGCGCC<br>GTCAGATATTGGGGCCAAGGCACTCAAGTGACAGTCTCGAGCGGCGGA<br>GGATCCCAAGTGCAGCTGCAAGAGAGCGGAGGAGGAAGCGTCCAAGCC<br>GGAGGCTCTCTGAGACTGAGCTGTGCCGCCAGCGGCTACTCCAACTGC<br>AGCTACGACATGACTTGGTATAGGCAAGCCCCCGGCAAGGAGAGGGAG<br>TTCGTGTCCGCCATCCACAGCGACGGCAGCACTAGATACGCCGACAGC<br>GTGAAGGGAAGGTTCTTCATCAGCCAAGATAACGCCAAGAACACAGTG<br>TATCTGCAGATGAACTCCCTCAAGCCAGAGGACACTGCCATGTACTAC<br>TGCAAGACAGACCCACTGCACTGCAGAGCCCATGGCGGCAGCTGGTAT<br>AGCGTGAGGGCAACTACTGGGGCAAGGCACACAAGTGACAGTCTCG<br>TCTGCTAGCCACCATCACCATCACCAC | 437 |
| 340 | CAAGTGCAGCTGCAAGAGAGCGGAGGAGGAAGCGTCCAAGCCGGAGGA<br>TCTCTGAGACTGAGCTGCGCCGCTAGTGGCTACTCCTACAGCAGCTAC<br>TGCATGGGCTGGTTTAGGCAAGCCCCCGGCAAGGAGAGAGAAGGCGTG<br>GCCACTATCGACAGCGACGGCATGACAAGGTACGCCGACAGCGTGAAG<br>GGAAGGTTCACAATCAGCAAGGACAACGCCAAGAACACACTGTATCTG<br>CAGATGAACTCTCTGAAGCCAGAGGACACTGCCATGTACTACTGTGCC<br>GCTCCTCTGTACGACTGTGATAGCGGCGCTGTGGGCAGAAATCCACCT<br>TATTGGGGCCAAGGCACTCAAGTGACAGTCTCGAGCGGCGGAGGATCC<br>CAAGTGCAGCTGCAAGAGAGCGGAGGAGGAAGCGTGCAAGCCGGAGGC<br>TCTCTGAGACTGAGCTGTGCCGCCTCAGGTATCTGTACAGCATCGAC<br>TACATGGCTTGGTTCAGACAGAGCCCCGGCAAGGAGAGGGAGCCAGTG<br>GCTGTCATCTACACTGCCTCCGGCGCCACATTCTATCCAGATAGCGTG | 438 |

TABLE 14-continued

IL10 Receptor Binding Molecules Nucleic Acids

| DNA ENCODING SEQ ID NO. | DNA Sequence | SEQ ID NO |
|---|---|---|
|  | AAGGGAAGGTTCACTATCAGCCAAGATAACGCCAAGATGACAGTGTAT CTGCAGATGAACTCTCTGAAGAGCGAGGACACTGCCATGTACTACTGT GCCGCCGTGAGGAAGACAGATAGCTACCTCTTCGACGCCCAGAGCTTC ACATACTGGGGCCAAGGCACACAAGTGACAGTCTCGTCTGCTAGCCAC CATCACCATCACCAC |  |
| 341 | CAAGTGCAGCTGCAAGAGAGCGGAGGAGGAAGCGTCCAAGCCGGAGGA TCTCTGAGACTGAGCTGCGCCGCTAGTGGCTACTCCTACAGCAGCTAC TGCATGGGCTGGTTTAGGCAAGCCCCCGGCAAGGAGAGAGAAGGCGTG GCCACTATCGACAGCGACGGCATGACAAGGTACGCCGACAGCGTGAAG GGAAGGTTCACAATCAGCAAGGACAACGCCAAGAACACACTGTATCTG CAGATGAACTCTCTGAAGCCAGAGGACACTGCCATGTACTACTGTGCC GCTCCTCTGTACGACTGTGATAGCGGCGCTGTGGGCAGAAATCCACCT TATTGGGGCCAAGGCACTCAAGTGACAGTCTCGAGCGGCGGAGGATCC CAAGTGCAGCTGCAAGAGAGCGGAGGAGGAAGCGTGCAAGCCGGAGGC TCTCTGAGGCTGAGCTGTGCCGCCTCTAGGTTCACATACAGCAGCTAC TGCATGGGCTGGTTCAGACAAGCCCCCGGCAAAGAGAGAAGGCGTG GCCAGCATCGATAGCGATGGCTCCACTAGCTACACTGACAGCGTGAAG GGAAGGTTCACTATCAGCAAGGACAACGCCAAGAACACTCTGTATCTG CAGATGAACTCTCTGAAGCCAGAGGACACAGCCATGTACTACTGTGCC CTCGATCTGATGAGCACAGTGGTGCCCGGCTTCTGTGGCTTTCTGCTG AGCGCTGGCATGGATTACTGGGGCAAGGGCACTCAAGTGACTGTCTCG TCTGCTAGCCACCATCACCATCACCAC | 439 |
| 342 | CAAGTGCAGCTGCAAGAGAGCGGAGGAGGAAGCGTCCAAGCCGGAGGA TCTCTGAGACTGAGCTGCGCCGCTAGTGGCTACTCCTACAGCAGCTAC TGCATGGGCTGGTTTAGGCAAGCCCCCGGCAAGGAGAGAGAAGGCGTG GCCACTATCGACAGCGACGGCATGACAAGGTACGCCGACAGCGTGAAG GGAAGGTTCACAATCAGCAAGGACAACGCCAAGAACACACTGTATCTG CAGATGAACTCTCTGAAGCCAGAGGACACTGCCATGTACTACTGTGCC GCTCCTCTGTACGACTGTGATAGCGGCGCTGTGGGCAGAAATCCACCT TATTGGGGCCAAGGCACTCAAGTGACAGTCTCGAGCGGCGGAGGATCC CAAGTGCAGCTGCAAGAGTCCGGAGGAGGCAGCGTCCAAGCCGGAGGC TCTCTGAGGCTGAGCTGTGCTGCCAGCGGCTACACTTACAGCATGTAC TGCATGGGCTGGTTCAGACAAGCCCCCGGCAAGGAAAGAGAGGGCGTG GCCCAGATCAATAGCGATGGCAGCACAAGCTACGCCGACAGCGTGAAG GGAAGGTTCACTATCTCCAAGGACAACGCCAAGAACACTCTGTATCTG CAGATGAACTCTCTGAAGCCAGAGGACACTGCCATGTACTACTGCGCT GCCGATTCTAGGGTGTACGGCGGCAGCTGGTATGAGAGGCTCTGCGGC CCTTACACATACGAGTACAACTACTGGGGCCAAGGCACACAAGTGACT GTCTCGTCTGCTAGCCACCATCACCATCACCAC | 440 |
| 343 | CAAGTGCAGCTGCAAGAGAGCGGAGGAGGAAGCGTCCAAGCCGGAGGA TCTCTGAGACTGAGCTGCGCCGCTAGTGGCTACTCCTACAGCAGCTAC TGCATGGGCTGGTTTAGGCAAGCCCCCGGCAAGGAGAGAGAAGGCGTG GCCACTATCGACAGCGACGGCATGACAAGGTACGCCGACAGCGTGAAG GGAAGGTTCACAATCAGCAAGGACAACGCCAAGAACACACTGTATCTG CAGATGAACTCTCTGAAGCCAGAGGACACTGCCATGTACTACTGTGCC GCTCCTCTGTACGACTGTGATAGCGGCGCTGTGGGCAGAAATCCACCT TATTGGGGCCAAGGCACTCAAGTGACAGTCTCGAGCGGCGGAGGATCC CAAGTGCAGCTGCAAGAGAGCGGCGGAGGAAGCGTGCAAGCCGGAGGA TCTCTGAGACTGAGCTGCGCTGTGAGCGGCTACGCCTACTCCACATAC TGCATGGGCTGGTTTAGGCAAGCCCCCGGCAAAGAGAGAGGGCGTG GCTGCTATCGATAGCGGCGGCAGCACAAGCTACGCCGATAGCGTGAAG GGAAGGTTCACAATCAGCAAGGACAACGCCAAGAACACACTGTATCTG AGGATGAACTCTCTGAAGCCAGAGGACACAGCCATGTACTACTGTGCT GCTGTGCCTCCTCCTCCAGATGGCGGCAGCTGTCTGTTTCTGGGACCA GAGATCAAGGTCAGCAAGGCCGATTTTAGGTACTGGGGCCAAGGCACA CAAGTGACAGTCTCGTCTGCTAGCCACCATCACCATCACCAC | 441 |
| 344 | CAAGTGCAGCTGCAAGAGAGCGGAGGAGGAAGCGTCCAAGCCGGAGGA TCTCTGAGACTGAGCTGCGCCGCTAGTGGCTACTCCTACAGCAGCTAC TGCATGGGCTGGTTTAGGCAAGCCCCCGGCAAGGAGAGAGAAGGCGTG GCCACTATCGACAGCGACGGCATGACAAGGTACGCCGACAGCGTGAAG GGAAGGTTCACAATCAGCAAGGACAACGCCAAGAACACACTGTATCTG CAGATGAACTCTCTGAAGCCAGAGGACACTGCCATGTACTACTGTGCC GCTCCTCTGTACGACTGTGATAGCGGCGCTGTGGGCAGAAATCCACCT TATTGGGGCCAAGGCACTCAAGTGACAGTCTCGAGCGGCGGAGGATCC CAAGTGCAGCTGCAAGAGAGCGGAGGAGGAAGCGTGCAAGCCGGAGGC TCTCTGAGGCTGAGCTGTACAGTGTCCGGCTACACTTACAGCTCCAAT TGCATGGGCTGGTTTAGGCAAGCCCCCGGCAAGGAAAGAGAGGGCGTG GCCACTATCTACACTGGCGGCGGCAACACATACTACGCCGATAGCGTG AAGGGAAGGTTCACTATCAGCCAAGATAACGCCAAGAACACAGTGTAT | 442 |

TABLE 14-continued

IL10 Receptor Binding Molecules Nucleic Acids

| DNA ENCODING SEQ ID NO. | DNA Sequence | SEQ ID NO |
|---|---|---|
| | CTGCAGATGAACAATCTGAAGCCAGAGGACACTGCCATGTACTACTGT GCTGCTGAGCCACTGTCTAGGGTGTACGGCGGCAGCTGCCCAACTCCT ACATTCGACTACTGGGGCCAAGGCACACAAGTGACTGTCTCGTCTGCT AGCCACCATCACCATCACCAC | |
| 345 | CAAGTGCAGCTGCAAGAGAGCGGAGGAGGAAGCGTCCAAGCCGGAGGA TCTCTGAGACTGAGCTGCGCCGCTAGTGGCTACTCCTACAGCAGCTAC TGCATGGGCTGGTTTAGGCAAGCCCCCGGCAAGGAGAGAGAAGGCGTG GCCACTATCGACAGCGACGGCATGACAAGGTACGCCGACAGCGTGAAG GGAAGGTTCACAATCAGCAAGGACAACGCCAAGAACACACTGTATCTG CAGATGAACTCTCTGAAGCCAGAGGACACTGCCATGTACTACTGTGCC GCTCCTCTGTACGACTGTGATAGCGGCGCTGTGGGCAGAAATCCACCT TATTGGGGCCAAGGCACTCAAGTGACAGTCTCGAGCGGCGGAGGATCC CAAGTGCAGCTGCAAGAGAGCGGAGGAGGAAGCGTCCAAGCCGGAGGC TCTCTGAGGCTGAGCTGTGGAGCCAGCGGCTACACTTACAGCAGCTAC TGTATGGGCTGGTTTAGGCAAGTGCCCGGCAAGGAGAGAGAGGGCGTG GCCGTGATCGATTCCGATGGCAGCACAAGCTACGCTGACAGCGTGAAG GGAAGGTTCACAATCAGCAAGGACAACGGCAAGAACACACTCTATCTG CAGATGAACAGCCTCAAGCCAGAGGACACAGCCATGTACTACTGCGCC GCTGATCTGGGCCACTATAGGCCTCCTTGTGGCGTGCTGTATCTGGGC ATGGATTACTGGGGCAAGGGCACACAAGTGACAGTCTCGTCTGCTAGC CACCATCACCATCACCAC | 443 |
| 346 | CAAGTGCAGCTGCAAGAGAGCGGAGGAGGAAGCGTCCAAGCCGGAGGA TCTCTGAGACTGAGCTGCGCCGCTAGTGGCTACTCCTACAGCAGCTAC TGCATGGGCTGGTTTAGGCAAGCCCCCGGCAAGGAGAGAGAAGGCGTG GCCACTATCGACAGCGACGGCATGACAAGGTACGCCGACAGCGTGAAG GGAAGGTTCACAATCAGCAAGGACAACGCCAAGAACACACTGTATCTG CAGATGAACTCTCTGAAGCCAGAGGACACTGCCATGTACTACTGTGCC GCTCCTCTGTACGACTGTGATAGCGGCGCTGTGGGCAGAAATCCACCT TATTGGGGCCAAGGCACTCAAGTGACAGTCTCGAGCGGCGGAGGATCC CAAGTGCAGCTGCAAGAGAGCGGAGGAGGAAGCGTCCAAGCCGGAGGC TCTCTGAGACTGAGCTGTGCCGCCAGCGGCTACTCCAACTGCAGCTAC GACATGACTTGGTATAGGCAAGCCCCCGGCAAGGAGAGGGAGTTCGTG TCCGCCATCCACAGCGACGGCAGCACTAGATACGCCGACAGCGTGAAG GGAAGGTTCTTCATCAGCCAAGATAACGCCAAGAACACAGTGTATCTG CAGATGAACTCCCTCAAGCCAGAGGACACTGCCATGTACTACTGCAAG ACAGACCCACTGCACTGCAGAGCCCATGGCGGCAGCTGGTATAGCGTG AGGGCCAACTACTGGGGCCAAGGCACACAAGTGACAGTCTCGTCTGCT AGCCACCATCACCATCACCAC | 444 |
| 347 | CAAGTGCAGCTGCAAGAGAGCGGAGGCGGCAGCGTGCAGACTGGAGGC TCTCTGAGACTGAGCTGTGCTGCCAGCGGCTACACTTATCTGAGGGGC TGTATGGGCTGGTTTAGGCAAGCCCCCGGCAAGGAGAGAGAGGGCGTG GCCGTCATGGATGTGGTGGGCGATAGGAGAAGCTACATCGACAGCGTG AAGGGAAGGTTCACAATCTCTAGGGACAATGCCGCCAACAGCGTCTAT CTGCAGATGGACAATCTGAAGCCAGAGGACACAGCCATGTACTACTGC ACTGCCGGCCCTAACTGTGTGGGCTGGAGAAGCGGACTGGATTACTGG GGCCAAGGCACACAAGTGACAGTCTCGAGCGGCGGAGGATCCCAAGTG CAGCTGCAAGAGAGCGGAGGAGGAAGCGTGCAAGCCGGAGGCTCTCTG AGACTGAGCTGTGCCGCCTCTAGGTATCTGTACAGCATCGACTACATG GCTTGGTTCAGACAGAGCCCCGGCAAGGAGAGGGAGCCAGTGGCTGTC ATCTACACTGCCTCCGGCGCCACATTCTATCCAGATAGCGTGAAGGGA AGGTTCACTATCAGCCAAGATAACGCCAAGATGACAGTGTATCTGCAG ATGAACTCTCTGAAGAGCGAGGACACTGCCATGTACTACTGTGCCGCC GTGAGGAAGACAGATAGCTACCTCTTCGACGCCCAGAGCTTCACATAC TGGGGCCAAGGCACAAGTGACAGTCTCGTCTGCTAGCCACCATCAC CATCACCAC | 445 |
| 348 | CAAGTGCAGCTGCAAGAGAGCGGAGGCGGCAGCGTGCAGACTGGAGGC TCTCTGAGACTGAGCTGTGCTGCCAGCGGCTACACTTATCTGAGGGGC TGTATGGGCTGGTTTAGGCAAGCCCCCGGCAAGGAGAGAGAGGGCGTG GCCGTCATGGATGTGGTGGGCGATAGGAGAAGCTACATCGACAGCGTG AAGGGAAGGTTCACAATCTCTAGGGACAATGCCGCCAACAGCGTCTAT CTGCAGATGGACAATCTGAAGCCAGAGGACACAGCCATGTACTACTGC ACTGCCGGCCCTAACTGTGTGGGCTGGAGAAGCGGACTGGATTACTGG GGCCAAGGCACACAAGTGACAGTCTCGAGCGGCGGAGGATCCCAAGTG CAGCTGCAAGAGAGCGGAGGAGGAAGCGTGCAAGCCGGAGGCTCTCTG AGGCTGAGCTGTGCCGCCTCTAGGTTCACATACAGCAGCTACTGCATG GGCTGGTTCAGACAAGCCCCCGGCAAAGAGAGAAGGCGTGGCCAGC ATCGATAGCGATGGCTCCACTAGCTACACTGACAGCGTGAAGGGAAGG TTCACTATCAGCAAGGACAACGCCAAGAACACTCTGTATCTGCAGATG AACTCTCTGAAGCCAGAGGACACAGCCATGTACTACTGTGCCCTCGAT | 446 |

TABLE 14-continued

IL10 Receptor Binding Molecules Nucleic Acids

| DNA ENCODING SEQ ID NO. | DNA Sequence | SEQ ID NO |
|---|---|---|
|  | CTGATGAGCACAGTGGTGCCCGGCTTCTGTGGCTTTCTGCTGAGCGCT GGCATGGATTACTGGGGCAAGGGCACTCAAGTGACTGTCTCGTCTGCT AGCCACCATCACCATCACCAC |  |
| 349 | CAAGTGCAGCTGCAAGAGAGCGGAGGCGGCAGCGTGCAGACTGGAGGC TCTCTGAGACTGAGCTGTGCTGCCAGCGGCTACACTTATCTGAGGGGC TGTATGGGCTGGTTTAGGCAAGCCCCCGGCAAGGAGAGAGAGGGCGTG GCCGTCATGGATGTGGTGGGCGATAGGAGAAGCTACATCGACAGCGTG AAGGGAAGGTTCACAATCTCTAGGGACAATGCCGCCAACAGCGTCTAT CTGCAGATGGACAATCTGAAGCCAGAGGACACAGCCATGTACTACTGC ACTGCCGGCCCTAACTGTGTGGGCTGGAGAAGCGGACTGGATTACTGG GGCCAAGGCACACAAGTGACAGTCTCGAGCGGCGGAGGATCCCAAGTG CAGCTGCAAGAGTCCGGAGGAGGCAGCGTCCAAGCCGGAGGCTCTCTG AGGCTGAGCTGTGCTGCCAGCGGCTACACTTACAGCATGTACTGCATG GGCTGGTTCAGACAAGCCCCCGGCAAGGAAAGAGAGGGCGTGGCCCAG ATCAATAGCGATGGCAGCACAAGCTACGCCGACAGCGTGAAGGGAAGG TTCACTATCTCCAAGGACAACGCCAAGAACACTCTGTATCTGCAGATG AACTCTCTGAAGCCAGAGGACACTGCCATGTACTACTGCGCTGCCGAT TCTAGGGTGTACGGCGGCAGCTGGTATGAGAGGCTCTGCGGCCCTTAC ACATACGAGTACAACTACTGGGGCCAAGGCACACAAGTGACTGTCTCG TCTGCTAGCCACCATCACCATCACCAC | 447 |
| 350 | CAAGTGCAGCTGCAAGAGAGCGGAGGCGGCAGCGTGCAGACTGGAGGC TCTCTGAGACTGAGCTGTGCTGCCAGCGGCTACACTTATCTGAGGGGC TGTATGGGCTGGTTTAGGCAAGCCCCCGGCAAGGAGAGAGAGGGCGTG GCCGTCATGGATGTGGTGGGCGATAGGAGAAGCTACATCGACAGCGTG AAGGGAAGGTTCACAATCTCTAGGGACAATGCCGCCAACAGCGTCTAT CTGCAGATGGACAATCTGAAGCCAGAGGACACAGCCATGTACTACTGC ACTGCCGGCCCTAACTGTGTGGGCTGGAGAAGCGGACTGGATTACTGG GGCCAAGGCACACAAGTGACAGTCTCGAGCGGCGGAGGATCCCAAGTG CAGCTGCAAGAGAGCGGCGGAGGAAGCGTGCAAGCCGGAGGATCTCTG AGACTGAGCTGCGCTGTGAGCGGCTACGCCTACTCCACATACTGCATG GGCTGGTTTAGGCAAGCCCCCGGCAAAGAGAGAGGGCGTGGCTGCT ATCGATAGCGGCGGCAGCACAAGCTACGCCGATAGCGTGAAGGGAAGG TTCACAATCAGCAAGGACAACGCCAAGAACACACTGTATCTGAGGATG AACTCTCTGAAGCCAGAGGACACAGCCATGTACTACTGTGCTGCTGTG CCTCCTCCTCCAGATGGCGGCAGCTGTCTGTTTCTGGGACCAGAGATC AAGGTCAGCAAGGCCGATTTTAGGTACTGGGGCCAAGGCACACAAGTG ACAGTCTCGTCTGCTAGCCACCATCACCATCACCAC | 448 |
| 351 | CAAGTGCAGCTGCAAGAGAGCGGAGGCGGCAGCGTGCAGACTGGAGGC TCTCTGAGACTGAGCTGTGCTGCCAGCGGCTACACTTATCTGAGGGGC TGTATGGGCTGGTTTAGGCAAGCCCCCGGCAAGGAGAGAGAGGGCGTG GCCGTCATGGATGTGGTGGGCGATAGGAGAAGCTACATCGACAGCGTG AAGGGAAGGTTCACAATCTCTAGGGACAATGCCGCCAACAGCGTCTAT CTGCAGATGGACAATCTGAAGCCAGAGGACACAGCCATGTACTACTGC ACTGCCGGCCCTAACTGTGTGGGCTGGAGAAGCGGACTGGATTACTGG GGCCAAGGCACACAAGTGACAGTCTCGAGCGGCGGAGGATCCCAAGTG CAGCTGCAAGAGAGCGGAGGAGGAAGCGTGCAAGCCGGAGGCTCTCTG AGGCTGAGCTGTACAGTGTCCGGCTACACTTACAGCTCCAATTGCATG GGCTGGTTTAGGCAAGCCCCCGGCAAGGAAAGAGAGGGCGTGGCCACT ATCTACACTGGCGGCGGCAACACATACTACGCCGATAGCGTGAAGGGA AGGTTCACTATCAGCCAAGATAACGCCAAGAACACAGTATCTGCAG ATGAACAATCTGAAGCCAGAGGACACTGCCATGTACTACTGTGCTGCT GAGCCACTGTCTAGGGTGTACGGCGGCAGCTGCCCAACTCCTACATTC GACTACTGGGGCCAAGGCACACAAGTGACTGTCTCGTCTGCTAGCCAC CATCACCATCACCAC | 449 |
| 352 | CAAGTGCAGCTGCAAGAGAGCGGAGGCGGCAGCGTGCAGACTGGAGGC TCTCTGAGACTGAGCTGTGCTGCCAGCGGCTACACTTATCTGAGGGGC TGTATGGGCTGGTTTAGGCAAGCCCCCGGCAAGGAGAGAGAGGGCGTG GCCGTCATGGATGTGGTGGGCGATAGGAGAAGCTACATCGACAGCGTG AAGGGAAGGTTCACAATCTCTAGGGACAATGCCGCCAACAGCGTCTAT CTGCAGATGGACAATCTGAAGCCAGAGGACACAGCCATGTACTACTGC ACTGCCGGCCCTAACTGTGTGGGCTGGAGAAGCGGACTGGATTACTGG GGCCAAGGCACACAAGTGACAGTCTCGAGCGGCGGAGGATCCCAAGTG CAGCTGCAAGAGAGCGGAGGAGGAAGCGTCCAAGCCGGAGGCTCTCTG AGGCTGAGCTGTGGAGCCAGCGGCTACACTTACAGCAGCTACTGTATG GGCTGGTTTAGGCAAGTGCCCGGCAAGGAGAGAGAGGGCGTGGCCGTG ATCGATTCCGATGGCAGCACAAGCTACGCTGACAGCGTGAAGGGAAGG TTCACAATCAGCAAGGACAACGGCAAGAACACACTCTATCTGCAGATG AACAGCCTCAAGCCAGAGGACACAGCCATGTACTACTGCGCCGCTGAT CTGGGCCACTATAGGCCTCCTTGTGGCGTGCTGTATCTGGGCATGGAT | 450 |

TABLE 14-continued

IL10 Receptor Binding Molecules Nucleic Acids

| DNA ENCODING SEQ ID NO. | DNA Sequence | SEQ ID NO |
|---|---|---|
| | TACTGGGGCAAGGGCACACAAGTGACAGTCTCGTCTGCTAGCCACCAT CACCATCACCAC | |
| 353 | CAAGTGCAGCTGCAAGAGAGCGGAGGCGGCAGCGTGCAGACTGGAGGC TCTCTGAGACTGAGCTGTGCTGCCAGCGGCTACACTTATCTGAGGGGC TGTATGGGCTGGTTTAGGCAAGCCCCCGGCAAGGAGAGAGGGCGTG GCCGTCATGGATGTGGTGGGCGATAGGAGAAGCTACATCGACAGCGTG AAGGGAAGGTTCACAATCTCTAGGGACAATGCCGCCAACAGCGTCTAT CTGCAGATGGACAATCTGAAGCCAGAGGACACAGCCATGTACTACTGC ACTGCCGGCCCTAACTGTGTGGGCTGGAGAAGCGGACTGGATTACTGG GGCCAAGGCACACAAGTGACAGTCTCGAGCGGCGGAGGATCCCAAGTG CAGCTGCAAGAGAGCGGAGGAGGAAGCGTCCAAGCCGGAGGCTCTCTG AGACTGAGCTGTGCCGCCAGCGGCTACTCCAACTGCAGCTACGACATG ACTTGGTATAGGCAAGCCCCCGGCAAGGAGAGGGAGTTCGTGTCCGCC ATCCACAGCGACGGCAGCACTAGATACGCCGACAGCGTGAAGGGAAGG TTCTTCATCAGCCAAGATAACGCCAAGAACACAGTGTATCTGCAGATG AACTCCCTCAAGCCAGAGGACACTGCCATGTACTACTGCAAGACAGAC CCACTGCACTGCAGAGCCCATGGCGGCAGCTGGTATAGCGTGAGGGCC AACTACTGGGGCCAAGGCACACAAGTGACAGTCTCGTCTGCTAGCCAC CATCACCATCACCAC | 451 |

TABLE 15

IL10Ra and IL10Rb Receptor Subunits and IL10 Amino Acid Sequences

| Description | Amino Acid Sequence | SEQ ID NO |
|---|---|---|
| IL10RA Human PreProtein | MLPCLVVLLAALLSLRLGSDAHGTELPSPPSVWFEAEFFHHILH WTPIPNQSESTCYEVALLRYGIESWNSISNCSQTLSYDLTAVTL DLYHSNGYRARVRAVDGSRHSNWTVTNTRFSVDEVTLTVGSVNL EIHNGFILGKIQLPRPKMAPANDTYESIFSHFREYEIAIRKVPG NFTFTHKKVKHENFSLLTSGEVGEFCVQVKPSVASRSNKGMWSK EECISLTRQYFTVTNVIIFFAFVLLLSGALAYCLALQLYVRRRK KLPSVLLFKKPSPFIFISQRPSPETQDTIHPLDEEAFLKVSPEL KNLDLHGSTDSGFGSTKPSLQTEEPQFLLPDPHPQADRTLGNRE PPVLGDSCSSGSSNSTDSGICLQEPSLSPSTGPTWEQQVGSNSR GQDDSGIDLVQNSEGRAGDTQGGSALGHHSPPEPEVPGEEDPAA VAFQGYLROTRCAEEKATKTGCLEEESPLTDGLGPKFGRCLVDE AGLHPPALAKGYLKQDPLEMTLASSGAPTGOWNQPTEEWSLLAL SSCSDLGISDWSFAHDLAPLGCVAAPGGLLGSFNSDLVTLPLIS SLQSSE | 452 |
| IL10RA Human Extracellular Domain | HGTELPSPPSVWFEAEFFHHILHWTPIPNQSESTCYEVALLRYG IESWNSISNCSQTLSYDLTAVTLDLYHSNGYRARVRAVDGSRHS NWTVTNTRFSVDEVTLTVGSVNLEIHNGFILGKIQLPRPKMAPA NDTYESIFSHFREYEIAIRKVPGNFTFTHKKVKHENFSLLTSGE VGEFCVQVKPSVASRSNKGMWSKEECISLTRQYFTVTN | 453 |
| IL10RA Mouse Preprotein | MLSRLLPFLVTISSLSLEFIAYGTELPSPSYVWFEARFFQHILH WKPIPNQSESTYYEVALKQYGNSTWNDIHICRKAQALSCDLTTF TLDLYHRSYGYRARVRAVDNSQYSNWTTTETRFTVDEVILTVDS VTLKAMDGIIYGTIHPPRPTITPAGDEYEQVFKDLRVYKISIRK FSELKNATKRVKQETFTLTVPIGVRKFCVKVLPRLESRINKAEW SEEQCLLITTEQYFTVTNLSILVISMLLFCGILVCLVLQWYIRH PGKLPTVLVFKKPHDFFPANPLCPETPDAIHIVDLEVFPKVSLE LRDSVLHGSTDSGFGSGKPSLQTEESQFLLPGSHPQIQGTLGKE ESPGLQATCGDNTDSGICLQEPGLHSSMGPAWKQQLGYTHQDQD DSDVNLVQNSPGQPKYTQDASALGHVCLLEPKAPEEKDQVMVTF QGYQKQTRWKAEAAGPAECLDEEIPLTDAFDPELGVHLQDDLAW PPPALAAGYLKQESQGMASAPPGTPSRQWNQLTEEWSLLGVVSC EDLSIESWRFAHKLDPLDCGAAPGGLLDSLGSNLVTLPLISSLQ VEE | 454 |
| IL10RA ECD | LEFIAYGTELPSPSYVWFEARFFQHILHWKPIPNQSESTYYEVA LKQYGNSTWNDIHICRKAQALSCDLTTFTLDLYHRSYGYRARVR AVDNSQYSNWTTTETRFTVDEVILTVDSVTLKAMDGIIYGTIHP PRPTITPAGDEYEQVFKDLRVYKISIRKFSELKNATKRVKQETF | 455 |

TABLE 15-continued

IL10Ra and IL10Rb Receptor Subunits and IL10 Amino Acid Sequences

| Description | Amino Acid Sequence | SEQ ID NO |
|---|---|---|
| | TLTVPIGVRKFCVKVLPRLESRINKAEWSEEQCLLITTEQYFTV TNLSI | |
| IL10Rb Human Pre-protein | MAWSLGSWLGGCLLVSALGMVPPPENVRMNSVNFKNILQWESPA FAKGNLTFTAQYLSYRIFQDKCMNTTLTECDFSSLSKYGDHTLR VRAEFADEHSDWVNITFCPVDDTIIGPPGMQVEVLADSLHMRFL APKIENEYETWTMKNVYNSWTYNVQYWKNGTDEKFQITPQYDFE VLRNLEPWTTYCVQVRGFLPDRNKAGEWSEPVCEQTTHDETVPS WMVAVILMASVFMVCLALLGCFALLWCVYKKTKYAFSPRNSLPQ HLKEFLGHPHHNTLLFFSFPLSDENDVFDKLSVIAEDSESGKQN PGDSCSLGTPPGQGPQS | 456 |
| IL10Rb Human ECD | MVPPPENVRMNSVNFKNILQWESPAFAKGNLTFTAQYLSYRIFQ DKCMNTTLTECDFSSLSKYGDHTLRVRAEFADEHSDWVNITFCP VDDTIIGPPGMQVEVLADSLHMRFLAPKIENEYETWTMKNVYNS WTYNVQYWKNGTDEKFQITPQYDFEVLRNLEPWTTYCVQVRGFL PDRNKAGEWSEPVCEQTTHDETVPS | 457 |
| IL10Rb Murine Pre-Protein | MAPCVAGWLGGFLLVPALGIPPPEKVRMNSVNFKNILQWEVPAF PKTNLTFTAQYESYRSFQDHCKRTASTQCDFSHLSKYGDYTVRV RAELADEHSEWVNVTFCPVEDTIIGPPEMQIESLAESLHLRFSA PQIENEPETWTLKNIYDSWAYRVQYWKNGTNEKFQVVSPYDSEV LRNLEPWTTYCIQVQGFLLDQNRTGEWSEPICERTGNDEITPSW IVAIILIVSVLVVFLFLLGCFVVLWLIYKKTKHTFRSGTSLPQH LKEFLGHPHHSTFLLFSFPPPEEAEVFDKLSIISEESEGSKQSP EDNCASEPPSDPGPRELESKDEAPSPPHDDPKLLTSTSEV | 458 |
| IL10Rb Murine ECD | MIPPPEKVRMNSVNFKNILOWEVPAFPKTNLTFTAQYESYRSFQ DHCKRTASTOCDFSHLSKYGDYTVRVRAELADEHSEWVNVTFCP VEDTIIGPPEMQIESLAESLHLRFSAPQIENEPETWTLKNIYDS WAYRVQYWKNGTNEKFQVVSPYDSEVLRNLEPWTTYCIQVQGFL LDQNRTGEWSEPICERTGNDEITPS | 459 |
| IL10 Human Mature Protein | SPGQGTQSENSCTHFPGNLPNMLRDLRDAFSRVKTFFQMKDQLD NLLLKESLLEDFKGYLGCQALSEMIQFYLEEVMPQAENQDPDIK AHVNSLGENLKTLRLRLRRCHRFLPCENKSKAVEQVKNAFNKLQ EKGIYKAMSEFDIFINYIEAYMTMKIRN | 460 |
| IL10 Mouse Mature Protein | SRGQYSREDNNCTHFPVGQSHMLLELRTAFSQVKTFFQTKDQLD NILLTDSLMQDFKGYLGCQALSEMIQFYLVEVMPQAEKHGPEIK EHLNSLGEKLKTLRMRLRRCHRFLPCENKSKAVEQVKSDFNKLQ DQGVYKAMNEFDIFINCIEAYMMIKMKS | 461 |

TABLE 16

Exemplary Linkers

| Abbreviation | Amino Acid Sequence | SEQ ID NO |
|---|---|---|
| G4S | GGGGS | 462 |
| G5S | GGGGGS | 463 |
| GGSG | GGSG | 464 |
| SG3 | SGGG | 465 |
| GS$^2$ | GSGS | 466 |
| GS$^3$ | GSGSGS | 467 |
| GS$^4$ | GSGSGSGS | 468 |
| GS$^5$ | GSGSGSGSGS | 469 |
| 6X, GGS$^2$ | GGSGGS | 470 |
| GGS3 | GGSGGSGGS | 471 |
| 10x | GGSGGSGGSG | 472 |

TABLE 16-continued

Exemplary Linkers

| Abbreviation | Amino Acid Sequence | SEQ ID NO |
|---|---|---|
| GGSG$^2$ | GGSGGGSG | 473 |
| GGSG$^3$ | GGSGGGSGGGSG | 474 |
| GGSG$^4$ | GGSGGGSGGGSGGGSG | 475 |
| GGSG$^5$ | GGSGGGSGGGSGGGSGGGSG | 476 |
| G4S$^2$ | GGGGSGGGGS | 477 |
| 8X, GGGS | GGGSGGGS | 478 |
| GGSGG | GGSGG | 479 |
| GSGSG | GSGSG | 480 |
| GSGG | GSGG | 481 |
| GGGSG | GGGSG | 482 |
| GSSSG | GSSSG | 483 |
| 4X, G3S | GGGS | 484 |
| IgG4 Hinge | ASRVESKYGPPCPPCPAPEFLGGPSVFLFPPKPKDTLMIS RTPEVTCVVVDVSQEDPEVQFNWYVDGVEVHNAKTKPREE QFGSTYRVVSVLTVLHQDWLNGKEYKCKVSNKGLPSSIEK TISKAKGQPREPQVYTLPPSQEEMTKNQVSLTCLVKGFYP SDIAVEWESNGQPENNYKTTPPVLDSDGSFFLYSRLTVDK SRWQEGNVFSCSVMHEALHNHYTQKSLSLSLG | 485 |

TABLE 17

Exemplary IL10Ra/Rb Binding Molecules

| Name | Amino Acid Sequence | SEQ ID NO |
|---|---|---|
| DR838 | EVQLQESGGGSVQAGGSLRLSCAASGYSQCSYDMTWYRQAPGKER EFVSAIHSDGSTRYADSVKGRFFISQDNAKNTVYLQMNSLKPEDT AMYYCKTDPLHCRAHGGSWYSVRANYWGQGTQVTVSGGGSQVQLQ ESGGGGSVEAGGSLRLSCAASGYTHSSYCMGWFRQAPGKEREGVAA IDVDGSTTYADSVKGRFTISKDNAKNTLYLQMNSLKPEDTGMYYC AAEFADCSSNYFLPPGAVRYWGQGTQVTVSSASHHHHHH | 486 |
| DR839 | EVQLQESGGGSVQAGGSLRLSCAASGYSDCSYDMTWYRQAPGKER EFVSAIHSDGSTRYADSVKGRFFISQDNAKNTVYLQMNSLKPEDT AMYYCKTDPLHCRAHGGSWYSVRANYWGQGTQVTVSSGGGSQVQL QESGGGSVEAGGSLRLSCAASGYTHSSYCMGWFRQAPGKEREGVA AIDVDGSTTYADSVKGRFTISKDNAKNTLYLQMNSLKPEDTGMYY CAAEFADCSSNYFLPPGAVRYWGQGTQVTVSSASHHHHHH | 487 |
| DR841 | EVQLQESGGGSVQAGGSLRLSCAASGYSNCAYDMTWYRQAPGKER EFVSAIHSDGSTRYADSVKGRFFISQDNAKNTVYLQMNSLKPEDT AMYYCKTDPLHCRAHGGSWYSVRANYWGQGTQVTVSSGGGSQVQL QESGGGSVEAGGSLRLSCAASGYTHSSYCMGWFRQAPGKEREGVA AIDVDGSTTYADSVKGRFTISKDNAKNTLYLQMNSLKPEDTGMYY CAAEFADCSSNYFLPPGAVRYWGQGTQVTVSSASHHHHHH | 488 |
| DR890 | EVQLQESGGGSVQAGGSLRLSCAASGYSNCSYDMTWYRQAPGKER EFVSAIHSDGSTRYADSVKGRFFISQDNAKNTVYLQMNSLKPEDT AMYYCKTDPLHCRAHGGSWYSVRANYWGQGTQVTVSSQVQLQESG GGSVQAGGSLRLSCAASRYTYNSYCMGWFRQAPGKEREGVATIDS DGMTRYADSVKGRFTISKDNAKNTLYLQMNSLKPEDTAMYYCAAD ADCTIAAMTTNPLGQGTQVTVSSASHHHHHH | 489 |
| DR891 | EVQLQESGGGSVQAGGSLRLSCAASGYSNCSYDMTWYRQAPGKER EFVSAIHSDGSTRYADSVKGRFFISQDNAKNTVYLQMNSLKPEDT AMYYCKTDPLHCRAHGGSWYSVRANYWGQGTQVTVSSGSQVQLQE SGGGGSVQAGGSLRLSCAASRYTYNSYCMGWFRQAPGKEREGVATI DSDGMTRYADSVKGRFTISKDNAKNTLYLQMNSLKPEDTAMYYCA ADADCTIAAMTTNPLGQGTQVTVSSASHHHHHH | 490 |

TABLE 17-continued

Exemplary IL10Ra/Rb Binding Molecules

| Name | Amino Acid Sequence | SEQ ID NO |
|---|---|---|
| DR892 | EVQLQESGGGSVQAGGSLRLSCAASGYSNCSYDMTWYRQAPGKER EFVSAIHSDGSTRYADSVKGRFFISQDNAKNTVYLQMNSLKPEDT AMYYCKTDPLHCRAHGGSWYSVRANYWGQGTQVTVSSGGSGGSQV QLQESGGGSVQAGGSLRLSCAASRYTYNSYCMGWFRQAPGKEREG VATIDSDGMTRYADSVKGRFTISKDNAKNTLYLQMNSLKPEDTAM YYCAADADCTIAAMTTNPLGQGTQVTVSSASHHHHHH | 491 |
| DR893 | EVQLQESGGGSVQAGGSLRLSCAASGYSNCSYDMTWYRQAPGKER EFVSAIHSDGSTRYADSVKGRFFISQDNAKNTVYLQMNSLKPEDT AMYYCKTDPLHCRAHGGSWYSVRANYWGQGTQVTVSSGGGSGGGS QVQLQESGGGSVQAGGSLRLSCAASRYTYNSYCMGWFRQAPGKER EGVATIDSDGMTRYADSVKGRFTISKDNAKNTLYLQMNSLKPEDT AMYYCAADADCTIAAMTTNPLGQGTQVTVSSASHHHHHH | 492 |
| DR894 | EVQLQESGGGSVQAGGSLRLSCAASGYSNCSYDMTWYRQAPGKER EFVSAIHSDGSTRYADSVKGRFFISQDNAKNTVYLQMNSLKPEDT AMYYCKTDPLHCRAHGGSWYSVRANYWGQGTQVTVSSGGSGGSGG SGGQVQLQESGGGSVQAGGSLRLSCAASRYTYNSYCMGWFRQAPGK EREGVATIDSDGMTRYADSVKGRFTISKDNAKNTLYLQMNSLKPE DTAMYYCAADADCTIAAMTTNPLGQGTQVTVSSASHHHHHH | 493 |
| DR896 | QVQLQESGGGSVQAGGSLRLSCAASGYSNCSYDMTWYRQAPGKER EFVSAIHSDGSTRYADSVKGRFFISQDNAKNTVYLQMNSLKPEDT AMYYCKTDPLHCRAHGGSWYSVRANYWGQGTQVTVSSGSQVQLQE SGGGSVQAGGSLRLSCAASGYSYSSYCMGWFRQAPGKEREGVATI DSDGMTRYADSVKGRFTISKDNAKNTLYLQMNSLKPEDTAMYYCA APLYDCDSGAVGRNPPYWGQGTQVTVSSASHHHHHH | 494 |
| DR897 | QVQLQESGGGSVQAGGSLRLSCAASGYSNCSYDMTWYRQAPGKER EFVSAIHSDGSTRYADSVKGRFFISQDNAKNTVYLQMNSLKPEDT AMYYCKTDPLHCRAHGGSWYSVRANYWGQGTQVTVSSGGSGGSQV QLQESGGGSVQAGGSLRLSCAASGYSYSSYCMGWFRQAPGKEREG VATIDSDGMTRYADSVKGRFTISKDNAKNTLYLQMNSLKPEDTAM YYCAAPLYDCDSGAVGRNPPYWGQGTQVTVSSASHHHHHH | 495 |
| DR898 | QVQLQESGGGSVQAGGSLRLSCAASGYSNCSYDMTWYRQAPGKEREE AIHSDGSTRYADSVKGRFFISQDNAKNTVYLQMNSLKPEDTAMYYCK PLHCRAHGGSWYSVRANYWGQGTQVTVSSGGGSGGGSQVQLQESGGG QAGGSLRLSCAASGYSYSSYCMGWFRQAPGKEREGVATIDSDGMTRY SVKGRFTISKDNAKNTLYLQMNSLKPEDTAMYYCAAPLYDCDSGAVG PPYWGQGTQVTVSSASHHHHHH | 496 |
| DR899 | QVQLQESGGGSVQAGGSLRLSCAASGYSNCSYDMTWYRQAPGKEREE AIHSDGSTRYADSVKGRFFISQDNAKNTVYLQMNSLKPEDTAMYYCK PLHCRAHGGSWYSVRANYWGQGTQVTVSSGGSGGSGGSGQVQLQESG SVQAGGSLRLSCAASGYSYSSYCMGWFRQAPGKEREGVATIDSDGMT ADSVKGRFTISKDNAKNTLYLQMNSLKPEDTAMYYCAAPLYDCDSGA RNPPYWGQGTQVTVSSASHHHHHH | 497 |
| DR787 | QVQLQESGGGSVQAGGSLRLSCAASGYSNCSYDMTWYRQAPGKER EFVSAIHSDGSTRYADSVKGRFFISQDNAKNTVYLQMNSLKPEDT AMYYCKTDPLHCRAHGGSWYSVRANYWGQGTQVTVSSGSQVQLQE SGGGSVEAGGSLRLSCAASGYTHSSYCMGWFRQAPGKEREGVAAI DVDGSTTYADSVKGRFTISKDNAKNTLYLQMNSLKPEDTGMYYCA AEFADCSSNYFLPPGAVRYWGQGTQVTVSSASHHHHHH | 498 |

TABLE 18

IL10Ra/Rb Binding Protein Fc Fusions

| Name | Amino Acid Sequence | SEQ ID NO |
|---|---|---|
| DR900 | QVQLQESGGGSVQAGGSLRLSCAASGYSNCSYDMTWYRQAPGKER EFVSAIHSDGSTRYADSVKGRFFISQDNAKNTVYLQMNSLKPEDT AMYYCKTDPLHCRAHGGSWYSVRANYWGQGTQVTVSSGGGSQVQL QESGGGSVQAGGSLRLSCAASRYTYNSYCMGWFRQAPGKEREGVA TIDSDGMTRYADSVKGRFTISKDNAKNTLYLQMNSLKPEDTAMYY CAADADCTIAAMTTNPLGQGTQVTVSSASRVESKYGPPCPPCPAP EFLGGPSVFLFPPKPKDTLMISRTPEVTCVVVDVSQEDPEVQFNW YVDGVEVHNAKTKPREEQFGSTYRVVSVLTVLHQDWLNGKEYKCK | 499 |

TABLE 18-continued

IL10Ra/Rb Binding Protein Fc Fusions

| Name | Amino Acid Sequence | SEQ ID NO |
|---|---|---|
| | VSNKGLPSSIEKTISKAKGQPREPQVYTLPPSQEEMTKNQVSLTC LVKGFYPSDIAVEWESNGQPENNYKTTPPVLDSDGSFFLYSRLTV DKSRWQEGNVFSCSVMHEALHNHYTQKSLSLSLG | |
| DR901 | QVQLQESGGGSVQAGGSLRLSCAASGYSNCSYDMTWYRQAPGKER EFVSAIHSDGSTRYADSVKGRFFISQDNAKNTVYLQMNSLKPEDT AMYYCKTDPLHCRAHGGSWYSVRANYWGQGTQVTVSSGGGSQVQL QESGGGSVQAGGSLRLSCAASGYSYSSYCMGWFRQAPGKEREGVA TIDSDGMTRYADSVKGRFTISKDNAKNTLYLQMNSLKPEDTAMYY CAAPLYDCDSGAVGRNPPYWGQGTQVTVSSASRVESKYGPPCPPC PAPEFLGGPSVFLFPPKPKDTLMISRTPEVTCVVVDVSQEDPEVQ FNWYVDGVEVHNAKTKPREEQFGSTYRVVSVLTVLHQDWLNGKEY KCKVSNKGLPSSIEKTISKAKGQPREPQVYTLPPSQEEMTKNQVS LTCLVKGFYPSDIAVEWESNGQPENNYKTTPPVLDSDGSFFLYSR LTVDKSRWQEGNVFSCSVMHEALHNHYTQKSLSLSLG | 500 |
| DR902 | QVQLQESGGGSVQAGGSLRLSCAASGYSNCSYDMTWYRQAPGKER EFVSAIHSDGSTRYADSVKGRFFISQDNAKNTVYLQMNSLKPEDT AMYYCKTDPLHCRAHGGSWYSVRANYWGQGTQVTVSSGSQVQLQE SGGGSVEAGGSLRLSCAASGYTHSSYCMGWFRQAPGKEREGVAAI DVDGSTTYADSVKGRFTISKDNAKNTLYLQMNSLKPEDTGMYYCA AEFADCSSNYFLPPGAVRYWGQGTQVTVSSASRVESKYGPPCPPC PAPEFLGGPSVFLFPPKPKDTLMISRTPEVTCVVVDVSQEDPEVQ FNWYVDGVEVHNAKTKPREEQFGSTYRVVSVLTVLHQDWLNGKEY KCKVSNKGLPSSIEKTISKAKGQPREPQVYTLPPSQEEMTKNQVS LTCLVKGFYPSDIAVEWESNGQPENNYKTTPPVLDSDGSFFLYSR LTVDKSRWQEGNVFSCSVMHEALHNHYTQKSLSLSLG | 501 |
| Fc Monomer | RVESKYGPPCPPCPAPEFLGGPSVFLFPPKPKDTLMISRTPEVTC VVVDVSQEDPEVQFNWYVDGVEVHNAKTKPREEQFGSTYRVVSVL TVLHQDWLNGKEYKCKVSNKGLPSSIEKTISKAKGQPREPQVYTL PPSQEEMTKNQVSLTCLVKGFYPSDIAVEWESNGQPENNYKTTPP VLDSDGSFFLYSRLTVDKSRWQEGNVFSCSVMHEALHNHYTQKSL SLSLG | 502 |

TABLE 30

Nucleic Acid Sequences Encoding Humanized VHHS of Table 29

| VHH Encoded | DNA Sequence | SEQ ID |
|---|---|---|
| DR1223 | GAAGTGCAGTTGCTGGAGAGTGGTGGCGGACTTGTCCAACCCG GCGGTAGCCTGCGCCTCAGCTGCGCTGCCAGTGGCTATACACA GTGCAGTTATGACATGACCTGGGTCCGCCAAGCGCCCGGCAAG GGCCTGGAGTGGGTTTCCGCTATTCACTCCGATGGCAGCACCC GTTATGCAGACTCCGTTAAGGGCCGCTTCACCATCTCTCGCGA CAACTCCAAGAACACCCTGTATCTTCAGATGAACTCTCTCCGC GCTGAGGACACTGCTGTGTATTACTGTAAAACCGATCCACTGC ACTGTCGTGCGCACGGGGGCTCATGGTACTCTGTCAGAGCTAA CTATTGGGGGCAGGGCACCCTGGTGACTGTGTCCTCT | 546. |
| DR1224 | GAGGTGCAGCTTCTGGAGAGCGGTGGCGGTCTGGTACAACCCG GAGGTAGTCTGCGCCTGTCCTGTGCGGCTTCCGGCTACACCCA ATGTTCCTATGACATGACCTGGGTTCGCCAGGCCCCCGGTAAG GGCCTGGAATTTGTCAGCGCTATCCATAGTGATGGAAGCACCA GATATGCCGACAGTGTTAAGGGCCGCTTCACCATCAGCAGAGA TAATAGCAAGAACACCCTTTACCTCCAGATGAACTCTTTGCGT GCCGAGGATACCGCCGTCTATTACTGTAAGACCGATCCGCTGC ATTGCCGTGCACATGGCGGGTCCTGGTACAGTGTTCGCGCCAA CTATTGGGGGCCAGGGAACACTGGTGACTGTCAGCAGT | 547. |
| DR1225 | GAAGTGCAACTGGTGGAGAGCGGTGGAGGTTTGGTTCAGCCTG GAGGCTCCCTGCGCCTTTCCTGTGCTGCGAGCGGGTATACACA GTGCAGCTATGACATGACCTGGGTGAGGCAGGCACCGGGCAAA GGTTTGGAGTGGGTGTCAGCGATCCATTCTGATGGCAGCACAA GGTACGCGGATAGCGTTAAGGGCAGGTTTTTCATTTCCCGCGA CAACTCTAAGAACACACTCTATCTCCAGATGAACTCACTTCGC GCCGAGGATACCGCCGTGTATTACTGCAAGACAGACCCTCTGC ACTGTCGGGCTCACGGCGGTAGCTGGTATTCCGTCCGTGCTAA CTACTGGGGCCAGGGCACTCTCGTGACCGTGTCATCC | 548. |

TABLE 30-continued

Nucleic Acid Sequences Encoding Humanized
VHHS of Table 29

| VHH Encoded | DNA Sequence | SEQ ID |
|---|---|---|
| DR1226 | GAGGTGCAGCTGGTGGAGTCTGGGGGAGGCCTGGTACAGCCTG<br>GGGGCAGTCTGCGCCTGAGCTGCGCGGCCAGTGGCTATACTCA<br>GTGCTCCTACGACATGACTTGGGTAAGGCAGGCCCCCGGCAAA<br>GGTTTGGAGTTTGTTTCCGCAATTCATAGCGACGGCTCCACAC<br>GCTACGCCGATTCCGTCAAAGGTCGGTTTTTCATCTCCCGTGA<br>TAACAGCAAAAACACTCTGTACCTTCAGATGAACTCCCTCCGC<br>GCAGAGGATACCGCCGTTTATTACTGTAAAACTGACCCCCTCC<br>ACTGCCGCGCTCACGGCGGGAGCTGGTATAGTGTTCGCGCCAA<br>CTACTGGGGCCAGGGCACCTTGGTGACCGTCTCCAGT | 549. |
| DR1227 | GAGGTGCAGTTGCTGGAAAGCGGGGGTGGCCTGGTCCAGCCGG<br>GAGGTTCCCTGCGCCTTTCCTGCGCCGCTTCCGGCTACACCCA<br>TTCAAGTTACTGTATGGGCTGGGTTCGTCAGGCACCTGGCAAA<br>GGTCTCGAATGGGTGAGCGCTATCGACGTGGACGGAAGCACCA<br>CTTATGCTGATTCCGTGAAGGGTAGGTTCACCATTTCCCGCGA<br>CAACTCCAAGAACACTCTTTATCTGCAAATGAATAGCCTCCGC<br>GCTGAGGACACCGCCGTATATTACTGCGCTGCGGAGTTTGCCG<br>ACTGCTCTAGCAACTACTTTCTGCCCCCTGGGGCCGTAAGGTA<br>TTGGGGCCAGGGCACCTTGGTGACTGTGTCCTCC | 550. |
| DR1228 | GAGGTGCAGCTGCTCGAATCCGGGGGCGGACTGGTGCAGCCTG<br>GTGGCAGCCTGCGTCTGTCCTGTGCTGCCTCTGGTTATACCCA<br>TTCCAGCTACTGTATGGGTTGGGTGCGCCAAGCCCCTGGAAAG<br>GGGCTTGAAGGCGTCTCCGCCATTGATGTCGATGGCAGTACCA<br>CTTACGCTGACTCCGTGAAGGGACGCTTCACTATCAGCCGCGA<br>CAACTCCAAGAACACGCTCTATCTCCAGATGAACTCTCTCCGC<br>GCAGAAGACACCGCAGTGTACTATTGTGCCCGCAGAGTTTGCCG<br>ATTGCAGCTCAAACTACTTCCTGCCCCCAGGGGCAGTGCGTTA<br>TTGGGGCCAGGGAACACTTGTTACTGTTTCTTCT | 551. |
| DR1229 | GAGGTTCAGTTGGTGGAATCTGGCGGGGGCCTCGTGCAGCCCG<br>GAGGCTCCCTCAGGCTTTCCTGTGCTGCCTCTGGGTACACACA<br>CTCTAGTTATTGCATGGGCTGGGTGCGCCAAGCACCGGGCAAG<br>GGTCTGGAGTGGGTGAGCGCCATTGATGTGGACGGTTCTACTA<br>CCTATGCCGATAGCGTGAAGGGGCGTTTCACAATCAGCCGCGA<br>CAACTCCAAAAACACCCTGTATCTCCAGATGAATAGTCTTCGT<br>GCCGAAGACACCGCAGTGTACTATTGTGCGGCAGAGTTCGCGG<br>ACTGCTCTAGCAACTATTTTCTGCCCCCAGGAGCCGTCCGCTA<br>CTGGGGACAGGGCACCCTGGTCACCGTGTCTTCC | 552. |
| DR1230 | GAGGTCCAGCTGGTGGAGAGTGGGGGCGGACTGGTACAGCCAG<br>GTGGCAGTCTTCGCCTCTCTTGCGCTGCCTCCGGCTACACTCA<br>CAGCTCTTATTGCATGGGTTGGGTGAGACAGGCCCCCTGGTAAA<br>GGTCTTGAGGGCGTGAGTGCCATCGACGTGGATGGTTCCACTA<br>CCTACGCTGATAGTGTGAAGGGCCGCTTCACTATCTCACGTGA<br>TAACTCTAAGAATACTCTGTATCTTCAAATGAACAGCCTCCGC<br>GCAGAGGACACCGCAGTCTACTATTGTGCAGCCGAGTTTGCTG<br>ACTGTAGCTCCAACTACTTCCTTCCGCCCGGTGCAGTGCGCTA<br>TTGGGGGCAAGGCACTCTGGTGACAGTCTCCTCC | 553. |
| DR1308 | GAGGTGCAGCTGGTTGAATCCGGGGGTGGCCTCGTGCAGCCCG<br>GAGGCTCTCTGCGCCTGTCCTGCGCAGCCTCCGGCTATACCCA<br>GTGTTCCTATGATATGACGTGGGTCAGACAAGCTCCTGGCAAA<br>GGCCGCGAGTTTGTTTCCGCTATTCACTCTGACGGCTCCACCC<br>GGTACGCGGATAGCGTTAAGGGTCGCTTTTTCATCAGCCGGGA<br>TAACTCAAAGAACACTCTGTACTTGCAGATGAACTCTCTTCGC<br>GCTGAGGATACGGCGGTTTATTACTGCAAAACTGATCCTCTCC<br>ACTGTCGCGCCCACGGCGGATCTTGGTATAGCGTTCGCGCTAA<br>TTACTGGGGCAAGGAACTCTGGTGACTGTTTCCTCC | 554. |
| DR1309 | GAGGTGCAGTTGCAGGAGTCCGGCGGAGGGTCCGTCCAGGCCG<br>GAGGCAGTCTGCGCCTGTCCTGTGCCGCTTCCGGCTACTCCCA<br>ATGTTCTTACGACATGACTTGGTATCGCCAGGCTCCGGGCAAG<br>GAGCGCGAGTTCGTGAGCGCCATCCACTCAGACGGCTCCACCC<br>GTTACGCCGACTCAGTCAAGGGTCGCTTCTTTATCTCCCAGGA<br>CAACGCAAAGAACACCGTCTATCTCCAGATGAACTCCCTGAAG<br>CCAGAAGACACAGCTATGTATTACTGTAAAACCGACCCACTGC<br>ATTGCAGGGCTCATGGTGGCTCCTGGTACTCTGTACGCGCAAA<br>CTACTGGGGTCAGGGCACCCAGGTGACCGTGAGTTCC | 555. |

TABLE 31

Nucleic Acid Sequences Encoding Humanized IL10R

| VHH Encoded | DNA Sequence | SEQ ID |
|---|---|---|
| DR1328 | GAAGTCCAGCTTGTTGAATCTGGGGGAGGCCTGGTGCAGCCTG GGGGCTCCCTGCGCCTCTCCTGTGCTGCCAGCGGGTACACCCA ATGTTCCTATGATATGACCTGGGTCCGCCAGGCACCAGGCAAG GGATTGGAATTTGTGAGCGCAATCCATTCTGACGGCAGTACTC GTTACGCTGACTCCGTAAAGGGCAGATTCTTTATCTCTCGTGA CAACAGCAAAAACACTCTGTATCTGCAAATGAACTCTCTCCGC GCCGAAGACACTGCGGTCTATTACTGCAAGACCGATCCCCTCC ATTGTCGTGCCCACGGGGAAGTTGGTACTCAGTCCGCGCAAA TTATTGGGGCCAGGGCACTCTCGTGACCGTCTCCAGCGGGGGA GGTTCCGAGGTGCAGCTCGTGGAGAGCGGTGGGGGCCTGGTCC AGCCTGGCGGAAGCCTGCGCCTGTCATGCGCTGCGTCTGGTTA CACACACAGCTCCTATTGTATGGGATGGGTGCGGCAGGCCCCC GGTAAAGGACTGGAATGGGTTAGCGCCATCGACGTGGACGGCT CTACGACATACGCCGACTCCGTCAAGGGCCGCTTTACTATCAG CCGTGATAACAGCAAGAACACTCTGTACCTGCAAATGAACTCT CTCCGCGCCGAGGACACCGCTGTGTATTACTGTGCCGCAGAGT TCGCAGACTGCTCTTCCAATTATTTCCTGCCTCCCGGAGCCGT CCGTTATTGGGTCAGGGCACTCTGGTTACTGTGTCCTCTGCT TCCCATCACCATCATCACCAC | 556 |
| DR1329 | GAGGTGCAGCTGGTTGAGTCTGGCGGAGGTCTGGTGCAGCCCG GCGGTTCTCTGCGCCTGTCTTGCGCCGCGAGCGGCTACACGCA ATGCAGCTACGATATGACCTGGGTTCGTCAGGCCCCGGCAAG GGCTTGGAGTTCGTCAGCGCGATCCATAGCGACGGCTCCACAA GATATGCTGATAGCGTGAAGGGCCGCTTCTTTATTAGTAGAGA CAACTCTAAGAACACACTCTACCTCCAGATGAATAGTCTCCGC GCAGAGGACACGGCGGTGTACTATTGTAAGACCGATCCTCTGC ATTGCAGAGCCCACGGTGGCTCCTGGTACAGCGTGCGGGCTAA CTATTGGGGGCAAGGCACCCTGGTTACTGTCTCTAGCGGTGGA GGTAGCGAAGTCCAACTTGTCGAGTCCGGGGGAGGTCTGGTCC AGCCCGGTGGGTCTCTTAGGCTCTCCTGCGCTGCATCCGGCTA CACCCATAGCTCATATTGTATGGGCTGGGTCCGCCAAGCCCT GGGAAGGGGCTGGAAGGTGTCAGCGCCATTGATGTCGATGGCA GCACAACTTACGCTGATAGTGTGAAGGGTCGCTTCACTATCTC CAGAGACAATTCAAAGAACACCTTGTACCTCCAGATGAACTCT CTTCGCGCGGAAGACACCGCCGTCTATTACTGCGCCGCTGAGT TCGCGGACTGTAGCTCCAATTATTTCCTGCCACCCGGCGCTGT GCGGTATTGGGGCCAGGGTACTCTGGTGACTGTGTCTAGTGCC TCTCACCATCACCATCATCAC | 557 |
| DR1330 | GAGGTGCAGCTGGTGGAATCTGGAGGCGGTCTCGTCCAGCCAG GGGGCTCTCTGCGTCTGTCTTGCGCTGCGTCGGATATACCCA GTGCTCTTACGACATGACATGGTATCGGCAGGCTCCCGGCAAG GGACTTGAGTTCGTCTCTGCCATCCACAGCGATGGTTCCACAC GCTACGCAGATTCCGTGAAGGGACGTTTTTTCATCAGCCGTGA CAATAGCAAGAACACTCTGTATCTTCAAATGAACTCCCTCCGC GCGGAAGACACCGCCGTGTATTACTGTAAAACCGATCCTCTGC ACTGTAGGGCACATGGGGGCTCTTGGTATTCTGTTCGTGCTAA TTATTGGGGCCAGGGCACCCTGGTCACCGTTTCCAGCGGCGGA GGTAGTGAGGTCCAGCTCGTCGAATCCGGCGGTGGCCTCGTGC AGCCTGGCGGGTCCCTCCGCCTGTCCTGCGCTGCAAGCGGTTA TACGCACAGCTCCTATTGCATGGGCTGGGTGCGTCAAGCTCCT GGCAAAGGCCTGGAGTGGGTCAGCGCTATTGACGTGGACGGGA GTACTACCTACGCCGATTCAGTGAAGGGTAGATTCACCATCTC ACGTGACAACTCTAAGAACACACTGTACTTGCAGATGAATAGC CTGAGGGCTGAAGACACTGCTGTGTACTATTGCGCTGCCGAGT TCGCCGATTGTAGCTCCAACTACTTCCTGCCCCAGGAGCGGT CCGTTACTGGGGCCAAGGCACCCTCGTGACTGTCTCTTCAGCC AGTCATCACCATCATCACCAC | 558 |
| DR1331 | GAGGTCCAGCTGGTGGAGAGTGGGGGTGGGCTCGTTCAGCCTG GGGGCTCTCTGAGGCTGAGCTGTGCAGCCTCCGGCTATACCCA GTGTTCTTACGACATGACGTGGTATAGGCAGGCACCAGGCAAA GGACTGGAGTTTGTGAGTGCTATCCACTCCGACGGTTCCACCC GGTATGCTGACTCTGTTAAGGGCAGATTCTTTATTAGCCGGGA CAACAGCAAAAACACCCTTTACCTCCAGATGAACTCTCTGAGG GCAGAGGACACGCAGTGTATTACTGTAAAACAGACCCTCTTC ACTGCCGCGCACATGGAGGCTCTTGGTACAGTGTGAGGGCTAA TTATTGGGGTCAGGGCACCCTCGTCACAGTCTCTTCAGGGGGT GGATCTGAGGTGCAGTTGGTCGAGAGTGGGGGTGGCCTGGTGC AGCCTGGCGGTAGCCTGCGCCTGAGCTGCGCGGCCTCTGGGTA CACCCACTCCTCTTACTGTATGGGCTGGGTGAGGCAGGCTCCT GGAAAGGGGCTGGAGGGCGTGTCCGCTATTGACGTAGATGGCT CCACTACCTACGCCGACAGCGTAAAAGGTCGTTTCACAATCTC CCGCGACAACTCCAAGAACACCCTCTACTTGCAGATGAACTCC | 559 |

TABLE 31-continued

Nucleic Acid Sequences Encoding Humanized IL10R

| VHH Encoded | DNA Sequence | SEQ ID |
|---|---|---|
| | CTGCGGGCCGAAGACACAGCTGTTTATTACTGCGCCGCTGAGT | |
| | TCGCAGACTGTTCCAGTAATTACTTCCTGCCCCCTGGTGCCGT | |
| | GCGTTACTGGGGCCAGGGCACCCTCGTAACCGTCAGCTCCGCT | |
| | AGTCACCATCACCACCACCAT | |

EXAMPLES

Example 1—VbH Generation

Camels were acclimated at research facility for at least 7 days before immunization. Antigen was diluted with 1×PBS (antigen total about 1 mg). The quality of the antigen was assessed by SDS-PAGE to ensure purity (e.g., >80%). For the first time, 10 mL CFA (then followed 6 times using IFA) was added into mortar, then 10 mL antigen in 1×PBS was slowly added into the mortar with the pestle grinding. The antigen and CFA/IFA were ground until the component showed milky white color and appeared hard to disperse. Camels were injected with antigen emulsified in CFA subcutaneously at at least six sites on the body, injecting about 2 mL at each site (total of 10 mL per camel). A stronger immune response was generated by injecting more sites and in larger volumes. The immunization was conducted every week (7 days), for 7 times. The needle was inserted into the subcutaneous space for 10 to 15 seconds after each injection to avoid leakage of the emulsion. Alternatively, a light pull on the syringe plunger also prevented leakage. The blood sample was collected three days later after 7th immunization.

To generate VHHs against hIL10Ra, the immunogen employed was the extracellular domain (amino acids 22-235) of hIL10Ra (UNIPROT Ref. Q13651). To generate VHHs against hIL10Rb, the immunogen employed was the 201 amino acid extracellular domain of the hIL10Rb, amino acids 20-220 of the precursor and amino acids 1-201 of the mature protein (UNIPROT Reference No. Q08334). To generate VHHs against mIL10Rb, the immunogen employed was the 201 amino acid extracellular domain of the mIL10Rb, amino acids 20-220 of the precursor and amino acids 1-201 of the mature protein (UNIPROT Reference No. Q61190). With respect to each antigen, the following methodology was used to identify and isolate the VHHs.

After immunization, the library was constructed. Briefly, RNA was extracted from blood and transcribed to cDNA. The $V_HH$ regions were obtained via two-step PCR, which fragment about 400 bp. The PCR outcomes and the vector of pMECS phagemid were digested with Pst I and Not I, subsequently, ligated to pMECS/Nb recombinant. After ligation, the products were transformed into *Escherichia coli* (*E. coli*) TGT cells by electroporation. Then, the transformants were enriched in growth medium and planted on plates. Finally, the library size was estimated by counting the number of colonies. Library biopanning was conducted to screen candidates against the antigens after library construction. Phage display technology was applied in this procedure. Positive colonies were identified by PE-ELISA.

Example 2. Generation of anti-hIL10R VHHs

Camels were immunized with the extracellular domains of the human IL10R (amino acids 22-235, UniProtKB Q13651, hIL-10Raecd) and IL10RP (amino acids 20-220, UniProtKB Q08334, hIL-10Raecd) weekly for seven weeks and PBMCs harvested on day 52. Phage display libraries were constructed and biopanning conducted as described in Example 1 above. 50 VHH sequences were obtained after selection on hIL10-R1 and 47 VHH sequences were obtained after selection on hIL10-R2. Sequences were clonotyped using germline assignment and CDR3 sequence similarity.

Example 3. Synthesis of DNA Encoding Synthekines

Seven unique anti-hIL-10RC$\alpha_{ecd}$ sequences (SEQ ID Nos: 44-50) and seven unique anti-hIL-10R$\beta_{ecd}$ sequences (SEQ ID Nos: 51-57) were selected from each cohort and DNA was synthesized consisting of one IL-10R VHH encoding DNA and one IL-10RαVHH encoding DNA separated by a linker sequence by GGGS (SEQ ID NO: 484) encoding DNA. DNA was for each possible VHH combination and in both orientations for a total of 98 7×7×2=98 VHH dimers. An Ala-Ser ("AS") linker followed by His-6 (SEQ ID NO: 532) DNA (ASH6, SEQ ID NO: 560) was added at the 3' end of each DNA construct. The codon optimized DNA sequences encoding these constructs are provided as SEQ ID Nos: 290-237 and the orientation of components thereof are described in Table 2 of the specification above.

Example 4. Recombinant Production and Purification

Codon optimized DNA inserts (SEQ ID Nos: 290-237) and cloned into modified pcDNA3.4 (Genscript) for small scale expression in HEK293 cells in 24 well plates. Supernatants The cells The IL2R binding proteins were purified in substantial accordance with the following procedure. Using a Hamilton Star automated system, 96×4 ml of supernatants in 4×24-well blocks were re-arrayed into 4×96-well, 1 mL blocks. PhyNexus micropipette tips (Biotage, San Jose CA) holding 80 uL of Ni-Excel IMAC resin (Cytiva) are equilibrated wash buffer: PBS pH 7.4, 30 mM imidazole. PhyNexus tips were dipped and cycled through 14 cycles of 1 mL pipetting across all 4×96-well blocks. PhyNexus tips were washed in 2×1 mL blocks holding wash buffer. PhyNexus tips were eluted in 3×0.36 mL blocks holding elution buffer: PBS pH 7.4, 400 mM Imidazole. PhyNexus tips were regenerated in 3×1 mL blocks of 0.5 M sodium hydroxide.

The purified protein eluates were quantified using a Biacore® T200 as in substantial accordance with the following procedure. 10 uL of the first 96×0.36 mL eluates were transferred to a Biacore® 96-well microplate and diluted to 60 uL in HBS-EP+ buffer (10 mM Hepes pH 7.4, 150 mM NaCl, 1 mM EDTA, 0.05% Tween 20). Each of the 96 samples was injected on a CM5 series S chip previously functionalized with anti-histidine capture antibody (Cytiva): injection is performed for 18 seconds at 5 uL/min. Capture levels were recorded 60 seconds after buffer wash. A standard curve of known VHH concentrations (270, 90, 30, 10, 3.3, 1.1 µg/mL) was acquired in each of the 4 Biacore chip flow cells to eliminate cell-to-cell surface variability. The 96 captures were interpolated against the standard curve using a non-linear model including specific and unspecific, one-site binding. Concentrations in the first elution block varied from 12 to 452 µg/mL corresponding to a 4-149 µg. SDS-PAGE analysis of 5 randomly picked samples was performed to ensure molecular weight of eluates corresponded to expected values (~30 KDa).

The concentration of the proteins was normalized using the Hamilton Star automated system in substantial accordance with the following procedure. Concentration values are imported in an Excel spreadsheet where pipetting volumes were calculated to perform dilution to 50 µg/mL in 0.22 mL. The spreadsheet was imported in a Hamilton Star method dedicated to performing dilution pipetting using the first elution block and elution buffer as diluent. The final, normalized plate was sterile filtered using 0.22 µm filter plates (Corning) and the material used for the following in vitro assays.

Example 5. Evaluation of Binding Affinity Via Surface Plasmon Resonance

One representative example from each clonotype of IL10a generated in accordance with Examples 1-3 was selected for evaluation of binding via SPR as follows. Evaluation of binding affinity of the IL10Ra binding molecules for the ECD of hIL10Ra corresponding to SEQ ID NOS 159, 161, 162, 163, 165, 167 and 170 was conducted using surface plasmon resonance (SPR) in substantial accordance with the following procedure. All experiments were conducted in 10 mM Hepes, 150 mM NaCl, 0.05% (v/v) Polysorbate 20 (PS20) and 3 mM EDTA (HBS-EP+ buffer) on a Biacore T200 instrument equipped with a Protein A derivatized sensor chip (Cytiva). Mono-Fc VHH ligands were flowed at 5 µl/min for variable time ranging from 18 to 300 seconds, reaching the capture loads listed in the tables below. Following ligand capture, injections of a 2-fold dilution series of the extracellular domain of the IL2Rb-receptor modified to incorporate a C-terminal poly-His sequence, typically comprising at least five concentrations between 1 µM and 1 nM, were performed in either high performance or single cycle kinetics mode. Surface regeneration was achieved by flowing 10 mM glycine-HCl, pH 1.5 (60 seconds, 50 µL/min). Buffer-subtracted sensograms were processed with Biacore T200 Evaluation Software and globally fit with a 1:1 Langmuir binding model (bulk shift set to zero) to extract kinetics and affinity constants ($k_a$, $k_d$, $K_D$). $R_{MAX}$<100 RU indicates surface density compatible with kinetics analysis. Calculated $R_{max}$ values were generated using the equation: Rmax=Load (RU)×valency of ligand×(Molecular weight of analyte/Molecular weight of ligand). Surface activity was defined as the ratio of experimental/calculated Rmax. The results of these binding affinity experiments are provided in Tables 23, 24 and 25.

Example 6. IL10 Activity Assay

HEK-Blue™ IL-10 reporter cell line (Invivogen, San Diego CA) was used for screening the IL10R1/R2 VHHs. HEK-Blue™ IL-10 cells were generated by stable transfection of the human embryonic kidney HEK293 cell line with the genes encoding hIL-10R u and R chains, human STAT3, and the STAT3-inducible SEAP (secreted embryonic alkaline phosphatase) reporter. Binding of IL-10 to its receptor on the surface of HEK-Blue™ IL-10 cells triggers JAK1/STAT3 signaling and the subsequent production of SEAP. The signal was then detected by quantifying SEAP activity in the cell culture supernatant using a QUANTI-Blue™ development solution (Invivogen, San Diego CA) and the absorbance values were measured spectrophotometrically at 630 nm. Because STAT3 is also implicated in the signaling of cytokines such as IFN-α/β and IL-6, HEK-Blue™ IL-10 cells are knockout for the expression of hIFNAR2 and hIL-6R.

Example 7. Screening of SEQ ID NOs: 192-289

To screen the IL10R1/R2 VHHs, HEK-Blue™ IL-10 cells were seeded in a 96-well plate at 50,000 cells per well and treated with either 25 nM or 100 nM protein (in triplicates) for 24 hours. Recombinant Animal-Free Human IL-10 (Shenandoah Biotechnology, Inc. Warwick, PA Catalog No. 100-83AF) was used as a positive control and unstimulated cells were used as a negative control. 24 hours post treatment, 20 µl of the cell supernatant was transferred to a flat-bottom 96 well plate and the assay was developed by adding 180 µl of the QUANTI-Blue™ (Invivogen) for 2 hours. The absorbance values were measured at 630 nm on the Envision® (PerkinElmer, Waltham MA) multilabel plate reader. The results of this screening are presented in Table 3 of the specification.

Example 8. Evaluation of Binding Affinity of IL10Ra and IL10Rb Single Domain Antibodies Via Surface Plasmon Resonance One representative example from each clonotype generated in accordance with Examples 1-3 was selected for evaluation of binding via SPR as follows. Evaluation of binding affinity of the IL2Rb binding molecules for CD122 corresponding to SEQ ID NOS 21, 29, 33, 37, 45, 53 and 65 was conducted using surface plasmon resonance (SPR) in substantial accordance with the following procedure. All experiments were conducted in 10 mM Hepes, 150 mM NaCl, 0.05% (v/v) Polysorbate 20 (PS20) and 3 mM EDTA (HBS-EP+ buffer) on a Biacore T200 instrument equipped with a Protein A derivatized sensor chip (Cytiva). Mono-Fc VHH ligands were flowed at 5 µl/min for variable time ranging from 18 to 300 seconds, reaching the capture loads listed in the tables below. Following ligand capture, injections of a 2-fold dilution series of the extracellular domain of the IL2Rb-receptor modified to incorporate a C-terminal poly-His sequence, typically comprising at least five concentrations between 1 µM and 1 nM, were performed in either high performance or single cycle kinetics mode. Surface regeneration was achieved by flowing 10 mM glycine-HCl, pH 1.5 (60 seconds, 50 µL/min). Buffer-subtracted sensograms were processed with Biacore T200 Evaluation Software and globally fit with a 1:1 Langmuir binding model (bulk shift set to zero) to extract kinetics and affinity constants ($k_a$, $k_d$, $K_D$). $R_{MAX}$<100 RU indicates surface density compatible with kinetics analysis. Calculated $R_{max}$ values were generated using the equation: Rmax=Load (RU)×valency of ligand×(Molecular weight of analyte/Molecular weight of ligand). Surface activity was defined as the ratio of experimental/calculated Rmax. The results of these binding affinity experiments are provided in Table 4 below.

Example 9. Evaluation of Binding Affinity IL10R Binding Molecules Via Surface Plasmon Resonance All experiments were conducted in 10 mM Hepes, 150 mM NaCl, 0.05% (v/v) Polysorbate 20 (PS20) and 3 mM EDTA (HBS-EP+ buffer) on a Biacore T200 instrument equipped with Protein A or CAP biotin chips (Cytiva). For experiments on Protein A chips, Fc-fused ligands were flowed at 5 μl/min for variable time ranging from 18 to 300 seconds, reaching the capture loads listed in the tables below.

Following ligand capture, injections of a 2-fold dilution series of analyte typically comprising at least five concentrations between 1 μM and 1 nM were performed in either high performance or single cycle kinetics mode. Surface regeneration was achieved by flowing 10 mM glycine-HCl, pH 1.5 (60 seconds, 50 μL/min). Buffer-subtracted sensograms were processed with Biacore T200 Evaluation Software and globally fit with a 1:1 Langmuir binding model (bulk shift set to zero) to extract kinetics and affinity constants ($k_a$, $k_d$, $K_D$). $R_{MAX}$<100 RU indicates surface density compatible with kinetics analysis.

Experiments on CAP chips were performed as described above with an additional capture step of Biotin CAPture reagent (10 seconds, 40 uL/min) performed prior to capture of biotinylated ligands.

Calculated Rmax were generated using the equation Rmax=Load (RU)×valency of ligand×(Molecular weight of analyte/Molecular weight of ligand. Surface activity was defined as the ratio experimental/calculated Rmax. The configurations for samples evaluated and the results of these experiments are provided in Table s 22 and 23

Example 10: Evaluation of Binding Affinity of Humanized IL10RA Binding Molecules Via Surface Plasmon Resonance All experiments were conducted in 10 mM Hepes, 150 mM NaCl, 0.05% (v/v) Polysorbate 20 (PS20) and 3 mM EDTA (HBS-EP+ buffer) on a Biacore T200 instrument equipped with an anti-histidine capture chip (Cytiva). ~0.5 μg/mL hIL10Rb-his (Sino Biological cat #10945) was flowed at 5 μl/min for 120 seconds, reaching the capture loads listed in the table below. Following ligand capture, injections of a 2-fold dilution series (50, 25, 12.5, 6.25, 3.13 nM) of humanized, mono-Fc VHHs (see analyte in table) was performed in single cycle kinetics mode. Surface regeneration was achieved by flowing 10 mM glycine-HCl, pH 1.5 (60 seconds, 50 L/min). Buffer-subtracted sensograms were processed with Biacore T200 Evaluation Software and globally fit with a 1:1 Langmuir binding model (bulk shift set to zero) to extract kinetics and affinity constants ($k_a$, $k_d$, $K_D$). $R_{MAX}$<100 RU indicates surface density compatible with kinetics analysis. Calculated Rmax were generated using the equation Rmax=Load (RU)×valency of ligand× (Molecular weight of analyte/Molecular weight of ligand. Surface activity was defined as the ratio experimental/ calculated Rmax. See tables below for sample information and experimental results.

---

SEQUENCE LISTING

```
Sequence total quantity: 569
SEQ ID NO: 1            moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 1
YLYSIDYMA                                                                9

SEQ ID NO: 2            moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 2
VIYTASGATF YPDSVKG                                                      17

SEQ ID NO: 3            moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 3
VRKTDSYLFD AQSFTY                                                       16

SEQ ID NO: 4            moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 4
YLYSTNYMA                                                                9

SEQ ID NO: 5            moltype = AA  length = 17
```

-continued

```
FEATURE                 Location/Qualifiers
source                  1..17
                        mol_type = protein
                        organism = synthetic construct
                        note = Description of Artificial Sequence: Synthetic peptide
SEQUENCE: 5
VIYTASGATL YTDSVKG                                                        17

SEQ ID NO: 6            moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 6
VRKTDSYLFD AQSFTY                                                         16

SEQ ID NO: 7            moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 7
YLYSTNYMA                                                                 9

SEQ ID NO: 8            moltype = AA   length = 17
FEATURE                 Location/Qualifiers
source                  1..17
                        mol_type = protein
                        organism = synthetic construct
                        note = Description of Artificial Sequence: Synthetic peptide
SEQUENCE: 8
VIYTASGATL YTDSVKG                                                        17

SEQ ID NO: 9            moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 9
VRKTDSYLFD AQSFTY                                                         16

SEQ ID NO: 10           moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 10
YLYSIDYMA                                                                 9

SEQ ID NO: 11           moltype = AA   length = 17
FEATURE                 Location/Qualifiers
source                  1..17
                        mol_type = protein
                        organism = synthetic construct
                        note = Description of Artificial Sequence: Synthetic peptide
SEQUENCE: 11
VIYTASGATF YPDSVKG                                                        17

SEQ ID NO: 12           moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 12
VRKTDSYLFD AQSFTY                                                         16

SEQ ID NO: 13           moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 13
YLYSTNYMA                                                                 9
```

```
SEQ ID NO: 14            moltype = AA  length = 17
FEATURE                  Location/Qualifiers
source                   1..17
                         mol_type = protein
                         organism = synthetic construct
                         note = Description of Artificial Sequence: Synthetic peptide
SEQUENCE: 14
AIYTASGATL YSDSNKG                                                  17

SEQ ID NO: 15            moltype = AA  length = 16
FEATURE                  Location/Qualifiers
source                   1..16
                         mol_type = protein
                         organism = synthetic construct
                         note = Description of Artificial Sequence: Synthetic peptide
SEQUENCE: 15
VRKTGSYLFD AQSFTY                                                   16

SEQ ID NO: 16            moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 16
FTYSSYCMG                                                            9

SEQ ID NO: 17            moltype = AA  length = 16
FEATURE                  Location/Qualifiers
source                   1..16
                         mol_type = protein
                         organism = synthetic construct
                         note = Description of Artificial Sequence: Synthetic peptide
SEQUENCE: 17
SIDSDGSTSY TDSVKG                                                   16

SEQ ID NO: 18            moltype = AA  length = 21
FEATURE                  Location/Qualifiers
source                   1..21
                         mol_type = protein
                         organism = synthetic construct
                         note = Description of Artificial Sequence: Synthetic peptide
SEQUENCE: 18
DLMSTVVPGF CGFLLSAGMD Y                                             21

SEQ ID NO: 19            moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 19
YTFNSNCMG                                                            9

SEQ ID NO: 20            moltype = AA  length = 17
FEATURE                  Location/Qualifiers
source                   1..17
                         mol_type = protein
                         organism = synthetic construct
                         note = Description of Artificial Sequence: Synthetic peptide
SEQUENCE: 20
TIYTGVGSTY YADSVKG                                                  17

SEQ ID NO: 21            moltype = AA  length = 18
FEATURE                  Location/Qualifiers
source                   1..18
                         mol_type = protein
                         organism = synthetic construct
                         note = Description of Artificial Sequence: Synthetic peptide
SEQUENCE: 21
EPLSRVYGGS CPTPTFGY                                                 18

SEQ ID NO: 22            moltype = AA  length = 9
FEATURE                  Location/Qualifiers
source                   1..9
                         mol_type = protein
                         organism = synthetic construct
                         note = Description of Artificial Sequence: Synthetic peptide
```

```
SEQUENCE: 22
YTYSMYCMG                                                                        9

SEQ ID NO: 23           moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 23
QINSDGSTSY ADSVKG                                                               16

SEQ ID NO: 24           moltype = AA  length = 23
FEATURE                 Location/Qualifiers
source                  1..23
                        mol_type = protein
                        organism = synthetic construct
                        note = Description of Artificial Sequence: Synthetic peptide
SEQUENCE: 24
DSRVYGGSWY ERLCGPYTYE YNY                                                       23

SEQ ID NO: 25           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 25
YAYSTYCMG                                                                        9

SEQ ID NO: 26           moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 26
AIDSGGSTSY ADSVKG                                                               16

SEQ ID NO: 27           moltype = AA  length = 26
FEATURE                 Location/Qualifiers
source                  1..26
                        mol_type = protein
                        organism = synthetic construct
                        note = Description of Artificial Sequence: Synthetic peptide
SEQUENCE: 27
VPPPPDGGSC LFLGPEIKVS KADFRY                                                    26

SEQ ID NO: 28           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 28
YLYSIDYMA                                                                        9

SEQ ID NO: 29           moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 29
VIYTASGATF YPDSVKG                                                              17

SEQ ID NO: 30           moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 30
VRKTDSYLFD AQSFTY                                                               16

SEQ ID NO: 31           moltype = AA  length = 9
FEATURE                 Location/Qualifiers
source                  1..9
                        mol_type = protein
```

```
                        -continued organism = synthetic construct
                        note = Description of Artificial Sequence: Synthetic peptide
SEQUENCE: 31
YTYSSYCMG                                                                    9

SEQ ID NO: 32           moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 32
VIDSDGSTSY ADSVKG                                                           16

SEQ ID NO: 33           moltype = AA  length = 18
FEATURE                 Location/Qualifiers
source                  1..18
                        mol_type = protein
                        organism = synthetic construct
                        note = Description of Artificial Sequence: Synthetic peptide
SEQUENCE: 33
DLGHYRPPCG VLYLGMDY                                                         18

SEQ ID NO: 34           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 34
YTYSSNCMG                                                                    9

SEQ ID NO: 35           moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 35
TIYTGGGNTY YADSVKG                                                          17

SEQ ID NO: 36           moltype = AA  length = 18
FEATURE                 Location/Qualifiers
source                  1..18
                        mol_type = protein
                        organism = synthetic construct
                        note = Description of Artificial Sequence: Synthetic peptide
SEQUENCE: 36
EPLSRVYGGS CPTPTFDY                                                         18

SEQ ID NO: 37           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 37
YSYSSNCMG                                                                    9

SEQ ID NO: 38           moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 38
TIHTGGGSTY YADSVKG                                                          17

SEQ ID NO: 39           moltype = AA  length = 18
FEATURE                 Location/Qualifiers
source                  1..18
                        mol_type = protein
                        organism = synthetic construct
                        note = Description of Artificial Sequence: Synthetic peptide
SEQUENCE: 39
EPLSRLYGGS CPTPTFGY                                                         18

SEQ ID NO: 40           moltype = AA  length = 9
FEATURE                 Location/Qualifiers
```

```
source                      1..9
                            mol_type = protein
                            organism = synthetic construct
                            note = Description of Artificial Sequence: Synthetic peptide
SEQUENCE: 40
YTYSSYCMG                                                                              9

SEQ ID NO: 41               moltype = AA  length = 16
FEATURE                     Location/Qualifiers
source                      1..16
                            mol_type = protein
                            organism = synthetic construct
                            note = Description of Artificial Sequence: Synthetic peptide
SEQUENCE: 41
VIDSDGSTSY ADSVKG                                                                     16

SEQ ID NO: 42               moltype = AA  length = 18
FEATURE                     Location/Qualifiers
source                      1..18
                            mol_type = protein
                            organism = synthetic construct
                            note = Description of Artificial Sequence: Synthetic peptide
SEQUENCE: 42
DLGHYRPPCG VLYLGMDY                                                                   18

SEQ ID NO: 43               moltype = AA  length = 9
FEATURE                     Location/Qualifiers
source                      1..9
                            mol_type = protein
                            organism = synthetic construct
                            note = Description of Artificial Sequence: Synthetic peptide
SEQUENCE: 43
YTYSGYCMG                                                                              9

SEQ ID NO: 44               moltype = AA  length = 16
FEATURE                     Location/Qualifiers
source                      1..16
                            mol_type = protein
                            organism = synthetic construct
                            note = Description of Artificial Sequence: Synthetic peptide
SEQUENCE: 44
VIDSDGSTSY ADSVKG                                                                     16

SEQ ID NO: 45               moltype = AA  length = 18
FEATURE                     Location/Qualifiers
source                      1..18
                            mol_type = protein
                            organism = synthetic construct
                            note = Description of Artificial Sequence: Synthetic peptide
SEQUENCE: 45
DLGHYRPPCG VLYLGMDY                                                                   18

SEQ ID NO: 46               moltype = AA  length = 9
FEATURE                     Location/Qualifiers
source                      1..9
                            mol_type = protein
                            organism = synthetic construct
                            note = Description of Artificial Sequence: Synthetic peptide
SEQUENCE: 46
YTYSNYCMG                                                                              9

SEQ ID NO: 47               moltype = AA  length = 16
FEATURE                     Location/Qualifiers
source                      1..16
                            mol_type = protein
                            organism = synthetic construct
                            note = Description of Artificial Sequence: Synthetic peptide
SEQUENCE: 47
TIDSDGNTSY ADSVKG                                                                     16

SEQ ID NO: 48               moltype = AA  length = 18
FEATURE                     Location/Qualifiers
source                      1..18
                            mol_type = protein
                            organism = synthetic construct
                            note = Description of Artificial Sequence: Synthetic peptide
SEQUENCE: 48
DLGHYRPPCG AYYYGMDY                                                                   18
```

```
SEQ ID NO: 49              moltype = AA  length = 9
FEATURE                    Location/Qualifiers
source                     1..9
                           mol_type = protein
                           organism = synthetic construct
                           note = Description of Artificial Sequence: Synthetic peptide
SEQUENCE: 49
YSNCSYDMT                                                                    9

SEQ ID NO: 50              moltype = AA  length = 16
FEATURE                    Location/Qualifiers
source                     1..16
                           mol_type = protein
                           organism = synthetic construct
                           note = Description of Artificial Sequence: Synthetic peptide
SEQUENCE: 50
AIHSDGSTRY ADSVKG                                                           16

SEQ ID NO: 51              moltype = AA  length = 19
FEATURE                    Location/Qualifiers
source                     1..19
                           mol_type = protein
                           organism = synthetic construct
                           note = Description of Artificial Sequence: Synthetic peptide
SEQUENCE: 51
DPLHCRAHGG SWYSVRANY                                                        19

SEQ ID NO: 52              moltype = AA  length = 9
FEATURE                    Location/Qualifiers
source                     1..9
                           mol_type = protein
                           organism = synthetic construct
                           note = Description of Artificial Sequence: Synthetic peptide
SEQUENCE: 52
YTYNSNCMG                                                                    9

SEQ ID NO: 53              moltype = AA  length = 17
FEATURE                    Location/Qualifiers
source                     1..17
                           mol_type = protein
                           organism = synthetic construct
                           note = Description of Artificial Sequence: Synthetic peptide
SEQUENCE: 53
TIYTGVGSTY YADSVKG                                                          17

SEQ ID NO: 54              moltype = AA  length = 18
FEATURE                    Location/Qualifiers
source                     1..18
                           mol_type = protein
                           organism = synthetic construct
                           note = Description of Artificial Sequence: Synthetic peptide
SEQUENCE: 54
EPLSRVYGGS CPTPTFGY                                                         18

SEQ ID NO: 55              moltype = AA  length = 9
FEATURE                    Location/Qualifiers
source                     1..9
                           mol_type = protein
                           organism = synthetic construct
                           note = Description of Artificial Sequence: Synthetic peptide
SEQUENCE: 55
YTYSSGCMG                                                                    9

SEQ ID NO: 56              moltype = AA  length = 16
FEATURE                    Location/Qualifiers
source                     1..16
                           mol_type = protein
                           organism = synthetic construct
                           note = Description of Artificial Sequence: Synthetic peptide
SEQUENCE: 56
AINSDGSTSY ADSVKG                                                           16

SEQ ID NO: 57              moltype = AA  length = 18
FEATURE                    Location/Qualifiers
source                     1..18
                           mol_type = protein
                           organism = synthetic construct
                           note = Description of Artificial Sequence: Synthetic peptide
SEQUENCE: 57
```

```
EPYCSGGYPR WSVAEFGY                                                18

SEQ ID NO: 58           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 58
YTYSSYCMG                                                           9

SEQ ID NO: 59           moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 59
AIDSDGSTRY ADSVKG                                                  16

SEQ ID NO: 60           moltype = AA  length = 18
FEATURE                 Location/Qualifiers
source                  1..18
                        mol_type = protein
                        organism = synthetic construct
                        note = Description of Artificial Sequence: Synthetic peptide
SEQUENCE: 60
EPYCSGGYKR TMVAEFGY                                                18

SEQ ID NO: 61           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 61
YTYNSYCMG                                                           9

SEQ ID NO: 62           moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 62
TIDSDGMTRY ADSVKG                                                  16

SEQ ID NO: 63           moltype = AA  length = 13
FEATURE                 Location/Qualifiers
source                  1..13
                        mol_type = protein
                        organism = synthetic construct
                        note = Description of Artificial Sequence: Synthetic peptide
SEQUENCE: 63
DADCTIAAMT TNP                                                     13

SEQ ID NO: 64           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 64
YLYSIDYMA                                                           9

SEQ ID NO: 65           moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 65
VIYTASGATF YPDSVKG                                                 17

SEQ ID NO: 66           moltype = AA  length = 16
FEATURE                 Location/Qualifiers
source                  1..16
                        mol_type = protein
                        organism = synthetic construct
```

-continued

```
SEQUENCE: 66
VRKTDSYLFD AQSFTY                                                16

SEQ ID NO: 67           moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 67
YTYSSYCMG                                                        9

SEQ ID NO: 68           moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 68
HIDSDGSTTY ADSVKG                                                16

SEQ ID NO: 69           moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 69
DPIPGPGYCD GGPNKY                                                16

SEQ ID NO: 70           moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 70
DLYSTNYVA                                                        9

SEQ ID NO: 71           moltype = AA   length = 17
FEATURE                 Location/Qualifiers
source                  1..17
                        mol_type = protein
                        organism = synthetic construct
                        note = Description of Artificial Sequence: Synthetic peptide
SEQUENCE: 71
VIYTASGATL YSDSVKG                                               17

SEQ ID NO: 72           moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 72
VRKTGHYLFD AQSFTY                                                16

SEQ ID NO: 73           moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 73
YTYSSGCMG                                                        9

SEQ ID NO: 74           moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 74
TINSDGSTNY ADSVKG                                                16

SEQ ID NO: 75           moltype = AA   length = 18
FEATURE                 Location/Qualifiers
source                  1..18
```

```
                        mol_type = protein
                        organism = synthetic construct
                        note = Description of Artificial Sequence: Synthetic peptide
SEQUENCE: 75
EPYCSGGYPR WSVAEFGY                                                     18

SEQ ID NO: 76           moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 76
YSYSSYCMG                                                                9

SEQ ID NO: 77           moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 77
AIASDGSTSY ADSVKG                                                       16

SEQ ID NO: 78           moltype = AA   length = 18
FEATURE                 Location/Qualifiers
source                  1..18
                        mol_type = protein
                        organism = synthetic construct
                        note = Description of Artificial Sequence: Synthetic peptide
SEQUENCE: 78
EPWCTGGYSR LTPAEYGY                                                     18

SEQ ID NO: 79           moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 79
YTYSSGCMG                                                                9

SEQ ID NO: 80           moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 80
TINSDGSTNY ADSVKG                                                       16

SEQ ID NO: 81           moltype = AA   length = 18
FEATURE                 Location/Qualifiers
source                  1..18
                        mol_type = protein
                        organism = synthetic construct
                        note = Description of Artificial Sequence: Synthetic peptide
SEQUENCE: 81
EPYCSGGYPR WSVAEFGY                                                     18

SEQ ID NO: 82           moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 82
YTYSSYCMG                                                                9

SEQ ID NO: 83           moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 83
HIDSDGSTTY ADSVKG                                                       16

SEQ ID NO: 84           moltype = AA   length = 16
```

-continued

```
FEATURE                 Location/Qualifiers
source                  1..16
                        mol_type = protein
                        organism = synthetic construct
                        note = Description of Artificial Sequence: Synthetic peptide
SEQUENCE: 84
DPIPGPGYCD GGPNKY                                                           16

SEQ ID NO: 85           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 85
YTYSSYCMG                                                                    9

SEQ ID NO: 86           moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 86
AIDSDGSTRY ADSVKG                                                           16

SEQ ID NO: 87           moltype = AA  length = 18
FEATURE                 Location/Qualifiers
source                  1..18
                        mol_type = protein
                        organism = synthetic construct
                        note = Description of Artificial Sequence: Synthetic peptide
SEQUENCE: 87
EPYCSGGYKR TMVAEFGY                                                         18

SEQ ID NO: 88           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 88
YTYSSYCMG                                                                    9

SEQ ID NO: 89           moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 89
HIDSDGSTSY ADSVKG                                                           16

SEQ ID NO: 90           moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 90
DPIPGPGYCD GGPNKY                                                           16

SEQ ID NO: 91           moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 91
YTYSSYCMG                                                                    9

SEQ ID NO: 92           moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 92
HIDSDGSTSY ADSVKG                                                           16
```

```
SEQ ID NO: 93              moltype = AA  length = 16
FEATURE                    Location/Qualifiers
source                     1..16
                           mol_type = protein
                           organism = synthetic construct
                           note = Description of Artificial Sequence: Synthetic peptide
SEQUENCE: 93
DPIPGPGYCD GGPNNY                                                       16

SEQ ID NO: 94              moltype = AA  length = 9
FEATURE                    Location/Qualifiers
source                     1..9
                           mol_type = protein
                           organism = synthetic construct
                           note = Description of Artificial Sequence: Synthetic peptide
SEQUENCE: 94
YTYSSGCMG                                                                9

SEQ ID NO: 95              moltype = AA  length = 16
FEATURE                    Location/Qualifiers
source                     1..16
                           mol_type = protein
                           organism = synthetic construct
                           note = Description of Artificial Sequence: Synthetic peptide
SEQUENCE: 95
TINSDGSTNY ADSVKG                                                       16

SEQ ID NO: 96              moltype = AA  length = 18
FEATURE                    Location/Qualifiers
source                     1..18
                           mol_type = protein
                           organism = synthetic construct
                           note = Description of Artificial Sequence: Synthetic peptide
SEQUENCE: 96
EPYCSGGYPR WSVAEFGY                                                     18

SEQ ID NO: 97              moltype = AA  length = 9
FEATURE                    Location/Qualifiers
source                     1..9
                           mol_type = protein
                           organism = synthetic construct
                           note = Description of Artificial Sequence: Synthetic peptide
SEQUENCE: 97
YTASVNYMG                                                                9

SEQ ID NO: 98              moltype = AA  length = 17
FEATURE                    Location/Qualifiers
source                     1..17
                           mol_type = protein
                           organism = synthetic construct
                           note = Description of Artificial Sequence: Synthetic peptide
SEQUENCE: 98
TIFTGAGTTY YANSVKG                                                      17

SEQ ID NO: 99              moltype = AA  length = 16
FEATURE                    Location/Qualifiers
source                     1..16
                           mol_type = protein
                           organism = synthetic construct
                           note = Description of Artificial Sequence: Synthetic peptide
SEQUENCE: 99
DFRGGLLYRP AYEYTY                                                       16

SEQ ID NO: 100             moltype = AA  length = 9
FEATURE                    Location/Qualifiers
source                     1..9
                           mol_type = protein
                           organism = synthetic construct
                           note = Description of Artificial Sequence: Synthetic peptide
SEQUENCE: 100
YTHSSYCMG                                                                9

SEQ ID NO: 101             moltype = AA  length = 16
FEATURE                    Location/Qualifiers
source                     1..16
                           mol_type = protein
                           organism = synthetic construct
                           note = Description of Artificial Sequence: Synthetic peptide
```

```
SEQUENCE: 101
AIDVDGSTTY ADSVKG                                                            16

SEQ ID NO: 102          moltype = AA  length = 18
FEATURE                 Location/Qualifiers
source                  1..18
                        mol_type = protein
                        organism = synthetic construct
                        note = Description of Artificial Sequence: Synthetic peptide
SEQUENCE: 102
EFADCSSNYF LPPGAVRY                                                          18

SEQ ID NO: 103          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 103
YTASVNYMG                                                                     9

SEQ ID NO: 104          moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 104
TIFTGAGTTY YANSVKG                                                           17

SEQ ID NO: 105          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 105
DFRGGLLYRP AYEYTY                                                            16

SEQ ID NO: 106          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 106
DTYSSYCMG                                                                     9

SEQ ID NO: 107          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 107
FIDSDGSTRY ADSVEG                                                            16

SEQ ID NO: 108          moltype = AA  length = 18
FEATURE                 Location/Qualifiers
source                  1..18
                        mol_type = protein
                        organism = synthetic construct
                        note = Description of Artificial Sequence: Synthetic peptide
SEQUENCE: 108
EPYCSGGYHR KEMAEFGY                                                          18

SEQ ID NO: 109          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 109
YTYSSYCMG                                                                     9

SEQ ID NO: 110          moltype = AA  length = 16
FEATURE                 Location/Qualifiers
source                  1..16
                        mol_type = protein
```

```
                            organism = synthetic construct
                            note = Description of Artificial Sequence: Synthetic peptide
SEQUENCE: 110
HIDSDGSTSY ADSVKG                                                         16

SEQ ID NO: 111              moltype = AA   length = 16
FEATURE                     Location/Qualifiers
source                      1..16
                            mol_type = protein
                            organism = synthetic construct
                            note = Description of Artificial Sequence: Synthetic peptide
SEQUENCE: 111
DPIPGPGYCD GGPNKY                                                         16

SEQ ID NO: 112              moltype = AA   length = 9
FEATURE                     Location/Qualifiers
source                      1..9
                            mol_type = protein
                            organism = synthetic construct
                            note = Description of Artificial Sequence: Synthetic peptide
SEQUENCE: 112
YTYSSYCMG                                                                 9

SEQ ID NO: 113              moltype = AA   length = 16
FEATURE                     Location/Qualifiers
source                      1..16
                            mol_type = protein
                            organism = synthetic construct
                            note = Description of Artificial Sequence: Synthetic peptide
SEQUENCE: 113
HIDSDGSTTY ADSVKG                                                         16

SEQ ID NO: 114              moltype = AA   length = 16
FEATURE                     Location/Qualifiers
source                      1..16
                            mol_type = protein
                            organism = synthetic construct
                            note = Description of Artificial Sequence: Synthetic peptide
SEQUENCE: 114
DPIPGPGYCD GGPNKY                                                         16

SEQ ID NO: 115              moltype = AA   length = 9
FEATURE                     Location/Qualifiers
source                      1..9
                            mol_type = protein
                            organism = synthetic construct
                            note = Description of Artificial Sequence: Synthetic peptide
SEQUENCE: 115
YTASNNCMG                                                                 9

SEQ ID NO: 116              moltype = AA   length = 16
FEATURE                     Location/Qualifiers
source                      1..16
                            mol_type = protein
                            organism = synthetic construct
                            note = Description of Artificial Sequence: Synthetic peptide
SEQUENCE: 116
VIFTGAGTSY YDSSVG                                                         16

SEQ ID NO: 117              moltype = AA   length = 16
FEATURE                     Location/Qualifiers
source                      1..16
                            mol_type = protein
                            organism = synthetic construct
                            note = Description of Artificial Sequence: Synthetic peptide
SEQUENCE: 117
EDDCTLLLMT PNPDDQ                                                         16

SEQ ID NO: 118              moltype = AA   length = 9
FEATURE                     Location/Qualifiers
source                      1..9
                            mol_type = protein
                            organism = synthetic construct
                            note = Description of Artificial Sequence: Synthetic peptide
SEQUENCE: 118
YTDSRYCMG                                                                 9

SEQ ID NO: 119              moltype = AA   length = 16
FEATURE                     Location/Qualifiers
```

```
                        1..16
                        mol_type = protein
                        organism = synthetic construct
                        note = Description of Artificial Sequence: Synthetic peptide
SEQUENCE: 119
HIDSDGSTSY ADSVKG                                                       16

SEQ ID NO: 120          moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 120
DPIPGPGYCD GGPNKY                                                       16

SEQ ID NO: 121          moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 121
YTYSSYCMG                                                                9

SEQ ID NO: 122          moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 122
AIDSDGSTRY ADSVKG                                                       16

SEQ ID NO: 123          moltype = AA   length = 18
FEATURE                 Location/Qualifiers
source                  1..18
                        mol_type = protein
                        organism = synthetic construct
                        note = Description of Artificial Sequence: Synthetic peptide
SEQUENCE: 123
EPYCSGGYKR TMVAEFGF                                                     18

SEQ ID NO: 124          moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 124
YTYSSYCMG                                                                9

SEQ ID NO: 125          moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 125
HIDSDGSTTY ADSVKG                                                       16

SEQ ID NO: 126          moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 126
DPIPGPGYCD GGPNNY                                                       16

SEQ ID NO: 127          moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 127
YTYSSYCMG                                                                9
```

```
SEQ ID NO: 128           moltype = AA  length = 16
FEATURE                  Location/Qualifiers
source                   1..16
                         mol_type = protein
                         organism = synthetic construct
                         note = Description of Artificial Sequence: Synthetic peptide
SEQUENCE: 128
HIDSDGSTTY ADSVKG                                                         16

SEQ ID NO: 129           moltype = AA  length = 16
FEATURE                  Location/Qualifiers
source                   1..16
                         mol_type = protein
                         organism = synthetic construct
                         note = Description of Artificial Sequence: Synthetic peptide
SEQUENCE: 129
DPIPGPGYCD GGPNNY                                                         16

SEQ ID NO: 130           moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 130
YSYSSYCMG                                                                  9

SEQ ID NO: 131           moltype = AA  length = 16
FEATURE                  Location/Qualifiers
source                   1..16
                         mol_type = protein
                         organism = synthetic construct
                         note = Description of Artificial Sequence: Synthetic peptide
SEQUENCE: 131
TIDSDGMTRY ADSVKG                                                         16

SEQ ID NO: 132           moltype = AA  length = 16
FEATURE                  Location/Qualifiers
source                   1..16
                         mol_type = protein
                         organism = synthetic construct
                         note = Description of Artificial Sequence: Synthetic peptide
SEQUENCE: 132
PLYDCDSGAV GRNPPY                                                         16

SEQ ID NO: 133           moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 133
YTYLRGCMG                                                                  9

SEQ ID NO: 134           moltype = AA  length = 17
FEATURE                  Location/Qualifiers
source                   1..17
                         mol_type = protein
                         organism = synthetic construct
                         note = Description of Artificial Sequence: Synthetic peptide
SEQUENCE: 134
VMDVVGDRRS YIDSVKG                                                        17

SEQ ID NO: 135           moltype = AA  length = 13
FEATURE                  Location/Qualifiers
source                   1..13
                         mol_type = protein
                         organism = synthetic construct
                         note = Description of Artificial Sequence: Synthetic peptide
SEQUENCE: 135
GPNCVGWRSG LDY                                                            13

SEQ ID NO: 136           moltype = AA  length = 9
FEATURE                  Location/Qualifiers
source                   1..9
                         mol_type = protein
                         organism = synthetic construct
                         note = Description of Artificial Sequence: Synthetic peptide
SEQUENCE: 136
```

```
YTASSICMG                                                                 9

SEQ ID NO: 137          moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 137
VITTAASGTY YADSVNG                                                        17

SEQ ID NO: 138          moltype = AA  length = 18
FEATURE                 Location/Qualifiers
source                  1..18
                        mol_type = protein
                        organism = synthetic construct
                        note = Description of Artificial Sequence: Synthetic peptide
SEQUENCE: 138
TRRGGDCLDP LQTPAYNT                                                       18

SEQ ID NO: 139          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 139
DTYSRKYIA                                                                 9

SEQ ID NO: 140          moltype = AA  length = 17
FEATURE                 Location/Qualifiers
source                  1..17
                        mol_type = protein
                        organism = synthetic construct
                        note = Description of Artificial Sequence: Synthetic peptide
SEQUENCE: 140
VMYTPGSATY YTDTVMG                                                        17

SEQ ID NO: 141          moltype = AA  length = 14
FEATURE                 Location/Qualifiers
source                  1..14
                        mol_type = protein
                        organism = synthetic construct
                        note = Description of Artificial Sequence: Synthetic peptide
SEQUENCE: 141
KASGSMFNFR DYTY                                                           14

SEQ ID NO: 142          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 142
YASCSRAMR                                                                 9

SEQ ID NO: 143          moltype = AA  length = 16
FEATURE                 Location/Qualifiers
source                  1..16
                        mol_type = protein
                        organism = synthetic construct
                        note = Description of Artificial Sequence: Synthetic peptide
SEQUENCE: 143
YIDGVGSTGY ADSVKG                                                         16

SEQ ID NO: 144          moltype = AA  length = 13
FEATURE                 Location/Qualifiers
source                  1..13
                        mol_type = protein
                        organism = synthetic construct
                        note = Description of Artificial Sequence: Synthetic peptide
SEQUENCE: 144
GCRADGSNSL DNY                                                            13

SEQ ID NO: 145          moltype = AA  length = 9
FEATURE                 Location/Qualifiers
source                  1..9
                        mol_type = protein
                        organism = synthetic construct
```

```
                                note = Description of Artificial Sequence: Synthetic peptide
SEQUENCE: 145
YTYNRRFMG                                                                         9

SEQ ID NO: 146          moltype = AA   length = 17
FEATURE                 Location/Qualifiers
source                  1..17
                        mol_type = protein
                        organism = synthetic construct
                        note = Description of Artificial Sequence: Synthetic peptide
SEQUENCE: 146
IIYTPNSSTF YADSVTG                                                               17

SEQ ID NO: 147          moltype = AA   length = 16
FEATURE                 Location/Qualifiers
source                  1..16
                        mol_type = protein
                        organism = synthetic construct
                        note = Description of Artificial Sequence: Synthetic peptide
SEQUENCE: 147
ARIASMTELS VRDMDY                                                                16

SEQ ID NO: 148          moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 148
YIALNACMA                                                                         9

SEQ ID NO: 149          moltype = AA   length = 17
FEATURE                 Location/Qualifiers
source                  1..17
                        mol_type = protein
                        organism = synthetic construct
                        note = Description of Artificial Sequence: Synthetic peptide
SEQUENCE: 149
TIVTDGSRTY YADSVKG                                                               17

SEQ ID NO: 150          moltype = AA   length = 17
FEATURE                 Location/Qualifiers
source                  1..17
                        mol_type = protein
                        organism = synthetic construct
                        note = Description of Artificial Sequence: Synthetic peptide
SEQUENCE: 150
DRRCPVSRAP YEYELRY                                                               17

SEQ ID NO: 151          moltype = AA   length = 9
FEATURE                 Location/Qualifiers
source                  1..9
                        mol_type = protein
                        organism = synthetic construct
                        note = Description of Artificial Sequence: Synthetic peptide
SEQUENCE: 151
YTYNGKCMA                                                                         9

SEQ ID NO: 152          moltype = AA   length = 17
FEATURE                 Location/Qualifiers
source                  1..17
                        mol_type = protein
                        organism = synthetic construct
                        note = Description of Artificial Sequence: Synthetic peptide
SEQUENCE: 152
GIYTGGSSTY YADSVKG                                                               17

SEQ ID NO: 153          moltype = AA   length = 14
FEATURE                 Location/Qualifiers
source                  1..14
                        mol_type = protein
                        organism = synthetic construct
                        note = Description of Artificial Sequence: Synthetic peptide
SEQUENCE: 153
SRSCSDLRRR SIAY                                                                  14

SEQ ID NO: 154          moltype = AA   length = 125
FEATURE                 Location/Qualifiers
source                  1..125
```

```
                            mol_type = protein
                            organism = synthetic construct
                            note = Description of Artificial Sequence: Synthetic
                              polypeptide
SEQUENCE: 154
QVQLQESGGG SIQAGGSLRL SCAASRYLYS IDYMAWFRQS PGKEREPVAV IYTASGATFY   60
PDSVKGRFTI SQDNAKMTVY LQMNSLKSED TAMYYCAAVR KTDSYLFDAQ SFTYWGQGTQ  120
VTVSS                                                              125

SEQ ID NO: 155              moltype = AA  length = 125
FEATURE                     Location/Qualifiers
source                      1..125
                            mol_type = protein
                            organism = synthetic construct
                            note = Description of Artificial Sequence: Synthetic
                              polypeptide
SEQUENCE: 155
QVQLQESGGG SVQAGGSLRL SCVASRYLYS TNYMAWFRQS PGKEREAVAV IYTASGATLY   60
TDSVKGRFTI SQDNAKMTVY LQMNRLKSED TAMYYCAAVR KTDSYLFDAQ SFTYWGQGTQ  120
VTVSS                                                              125

SEQ ID NO: 156              moltype = AA  length = 125
FEATURE                     Location/Qualifiers
source                      1..125
                            mol_type = protein
                            organism = synthetic construct
                            note = Description of Artificial Sequence: Synthetic
                              polypeptide
SEQUENCE: 156
QVQLQESGGG SIQAGGSLRL SCVASRYLYS TNYMAWFRQS PGKEREAVAV IYTASGATLY   60
TDSVKGRFTI SQDNAKMTVY LQMNRLKSED TAMYYCAAVR KTDSYLFDAQ SFTYWGQGTQ  120
VTVSS                                                              125

SEQ ID NO: 157              moltype = AA  length = 125
FEATURE                     Location/Qualifiers
source                      1..125
                            mol_type = protein
                            organism = synthetic construct
                            note = Description of Artificial Sequence: Synthetic
                              polypeptide
SEQUENCE: 157
QVQLQESGGG SIQAGGSLRL SCAASRYLYS IDYMAWFRQS PGKEREPAAV IYTASGATFY   60
PDSVKGRFTI SQDNAKMTVY LQMNSLKSED TAMYYCAAVR KTDSYLFDAQ SFTYWGQGTQ  120
VTVSS                                                              125

SEQ ID NO: 158              moltype = AA  length = 125
FEATURE                     Location/Qualifiers
source                      1..125
                            mol_type = protein
                            organism = synthetic construct
                            note = Description of Artificial Sequence: Synthetic
                              polypeptide
SEQUENCE: 158
QVQLQESGGG SIQAGGSLRL SCVASKYLYS TNYMAWFRQS PGKEREAVAA IYTASGATLY   60
SDSNKGRFTI SQDNAKMTVY LQMNSLKSED TAMYYCAAVR KTGSYLFDAQ SFTYWGQGTQ  120
VTVSS                                                              125

SEQ ID NO: 159              moltype = AA  length = 129
FEATURE                     Location/Qualifiers
source                      1..129
                            mol_type = protein
                            organism = synthetic construct
                            note = Description of Artificial Sequence: Synthetic
                              polypeptide
SEQUENCE: 159
QVQLQESGGG SVQAGGSLRL SCAASRFTYS SYCMGWFRQA PGKEREGVAS IDSDGSTSYT   60
DSVKGRFTIS KDNAKNTLYL QMNSLKPEDT AMYYCALDLM STVVPGFCGF LLSAGMDYWG  120
KGTQVTVSS                                                          129

SEQ ID NO: 160              moltype = AA  length = 127
FEATURE                     Location/Qualifiers
source                      1..127
                            mol_type = protein
                            organism = synthetic construct
                            note = Description of Artificial Sequence: Synthetic
                              polypeptide
SEQUENCE: 160
QVQLQESGGG SVQAGGSLRL SCAVSGYTFN SNCMGWFRQA PGKEREGVAT IYTGVGSTYY   60
ADSVKGRFTI SQDNAKNTVY LQMNSLKPED TAMYYCAAEP LSRVYGGSCP TPTFGYWGQG  120
```

```
TQVTVSS                                                                           127

SEQ ID NO: 161            moltype = AA  length = 131
FEATURE                   Location/Qualifiers
source                    1..131
                          mol_type = protein
                          organism = synthetic construct
                          note = Description of Artificial Sequence: Synthetic
                             polypeptide
SEQUENCE: 161
QVQLQESGGG SVQAGGSLRL SCAASGYTYS MYCMGWFRQA PGKEREGVAQ INSDGSTSYA   60
DSVKGRFTIS KDNAKNTLYL QMNSLKPEDT AMYYCAADSR VYGGSWYERL CGPYTYEYNY  120
WGQGTQVTVS S                                                      131

SEQ ID NO: 162            moltype = AA  length = 134
FEATURE                   Location/Qualifiers
source                    1..134
                          mol_type = protein
                          organism = synthetic construct
                          note = Description of Artificial Sequence: Synthetic
                             polypeptide
SEQUENCE: 162
QVQLQESGGG SVQAGGSLRL SCAVSGYAYS TYCMGWFRQA PGKEREGVAA IDSGGSTSYA   60
DSVKGRFTIS KDNAKNTLYL RMNSLKPEDT AMYYCAAVPP PDGGSCLFL GPEIKVSKAD   120
FRYWGQGTQV TVSS                                                   134

SEQ ID NO: 163            moltype = AA  length = 125
FEATURE                   Location/Qualifiers
source                    1..125
                          mol_type = protein
                          organism = synthetic construct
                          note = Description of Artificial Sequence: Synthetic
                             polypeptide
SEQUENCE: 163
QVQLQESGGG SVQAGGSLRL SCAASRYLYS IDYMAWFRQS PGKEREPVAV IYTASGATFY   60
PDSVKGRFTI SQDNAKMTVY LQMNSLKSED TAMYYCAAVR KTDSYLFDAQ SFTYWGQGTQ  120
VTVSS                                                             125

SEQ ID NO: 164            moltype = AA  length = 126
FEATURE                   Location/Qualifiers
source                    1..126
                          mol_type = protein
                          organism = synthetic construct
                          note = Description of Artificial Sequence: Synthetic
                             polypeptide
SEQUENCE: 164
QVQLQESGGG SVQAGGSLRL SCGASRYTYS SYCMGWFRQA PGKEREGVAV IDSDGSTSYA   60
DSVKGRFTIS KDNGKNTLYL QMNSLKPEDT AMYYCAADLG HYRPPCGVLY LGMDYWGKGT  120
QVTVSS                                                            126

SEQ ID NO: 165            moltype = AA  length = 127
FEATURE                   Location/Qualifiers
source                    1..127
                          mol_type = protein
                          organism = synthetic construct
                          note = Description of Artificial Sequence: Synthetic
                             polypeptide
SEQUENCE: 165
QVQLQESGGG SVQAGGSLRL SCTVSGYTYS SNCMGWFRQA PGKEREGVAT IYTGGGNTYY   60
ADSVKGRFTI SQDNAKNTVY LQMNNLKPED TAMYYCAAEP LSRVYGGSCP TPTFDYWGQG  120
TQVTVSS                                                           127

SEQ ID NO: 166            moltype = AA  length = 127
FEATURE                   Location/Qualifiers
source                    1..127
                          mol_type = protein
                          organism = synthetic construct
                          note = Description of Artificial Sequence: Synthetic
                             polypeptide
SEQUENCE: 166
QVQLQESGGG SVQAGGSLRL SCAVSGYSYS SNCMGWFRQA PGKEREGVAT IHTGGGSTYY   60
ADSVKGRFTI SQDNAKNTVY LQMNSLKPED TAMYYCAAEP LSRLYGGSCP TPTFGYWGQG  120
TQVTVSS                                                           127

SEQ ID NO: 167            moltype = AA  length = 126
FEATURE                   Location/Qualifiers
source                    1..126
                          mol_type = protein
                          organism = synthetic construct
```

```
                    note = Description of Artificial Sequence: Synthetic
                          polypeptide
SEQUENCE: 167
QVQLQESGGG SVQAGGSLRL SCGASGYTYS SYCMGWFRQV PGKEREGVAV IDSDGSTSYA    60
DSVKGRFTIS KDNGKNTLYL QMNSLKPEDT AMYYCAADLG HYRPPCGVLY LGMDYWGKGT   120
QVTVSS                                                              126

SEQ ID NO: 168          moltype = AA  length = 126
FEATURE                 Location/Qualifiers
source                  1..126
                        mol_type = protein
                        organism = synthetic construct
                        note = Description of Artificial Sequence: Synthetic
                              polypeptide
SEQUENCE: 168
QVQLQESGGG SVQAGGSLRL SCGASGYTYS GYCMGWFRQA PGKEREGVAV IDSDGSTSYA    60
DSVKGRFTIS KDNGKNTLYL QMNSLKPEDT AMYYCAADLG HYRPPCGVLY LGMDYWGKGT   120
QVTVSS                                                              126

SEQ ID NO: 169          moltype = AA  length = 126
FEATURE                 Location/Qualifiers
source                  1..126
                        mol_type = protein
                        organism = synthetic construct
                        note = Description of Artificial Sequence: Synthetic
                              polypeptide
SEQUENCE: 169
QVQLQESGGG SVQAGGSLRL ACAASRYTYS NYCMGWFRQA PGKEREGVAT IDSDGNTSYA    60
DSVKGRFTIS RDNAKNTLYL QMNSLKPGDT AMYYCAADLG HYRPPCGAYY YGMDYWGKGT   120
QVTVSS                                                              126

SEQ ID NO: 170          moltype = AA  length = 127
FEATURE                 Location/Qualifiers
source                  1..127
                        mol_type = protein
                        organism = synthetic construct
                        note = Description of Artificial Sequence: Synthetic
                              polypeptide
SEQUENCE: 170
QVQLQESGGG SVQAGGSLRL SCAASGYSNC SYDMTWYRQA PGKEREFVSA IHSDGSTRYA    60
DSVKGRFFIS QDNAKNTVYL QMNSLKPEDT AMYYCKTDPL HCRAHGGSWY SVRANYWGQG   120
TQVTVSS                                                             127

SEQ ID NO: 171          moltype = AA  length = 127
FEATURE                 Location/Qualifiers
source                  1..127
                        mol_type = protein
                        organism = synthetic construct
                        note = Description of Artificial Sequence: Synthetic
                              polypeptide
SEQUENCE: 171
QVQLQESGGG SVQAGGSLRL SCAVSGYTYN SNCMGWFRQA PGKEREGVAT IYTGVGSTYY    60
ADSVKGRFTI SQDNAKNTVY LQMNSLKPED TAMYYCAAEP LSRVYGGSCP TPTFGYWGQG   120
TQVTVSS                                                             127

SEQ ID NO: 172          moltype = AA  length = 126
FEATURE                 Location/Qualifiers
source                  1..126
                        mol_type = protein
                        organism = synthetic construct
                        note = Description of Artificial Sequence: Synthetic
                              polypeptide
SEQUENCE: 172
QVQLQESGGG SVQAGGSLRL SCAASGYTYS SGCMGWFRQA PGKEREAVAA INSDGSTSYA    60
DSVKGRFTIS KDNAKNTLYL QMNSLKPEDT AMYYCAAEPY CSGGYPRWSV AEFGYWGQGT   120
QVTVSS                                                              126

SEQ ID NO: 173          moltype = AA  length = 126
FEATURE                 Location/Qualifiers
source                  1..126
                        mol_type = protein
                        organism = synthetic construct
                        note = Description of Artificial Sequence: Synthetic
                              polypeptide
SEQUENCE: 173
QVQLQESGGG SVQAGGSLRL SCAASGYTYS SYCMGWFRQA PGKEREGVAA IDSDGSTRYA    60
DSVKGRFTIS KDNAKNTLYL QMNSLKPEDT AMYYCAAEPY CSGGYKRTMV AEFGYWGQGT   120
QVTVSS                                                              126
```

```
SEQ ID NO: 174           moltype = AA  length = 121
FEATURE                  Location/Qualifiers
source                   1..121
                         mol_type = protein
                         organism = synthetic construct
                         note = Description of Artificial Sequence: Synthetic
                            polypeptide
SEQUENCE: 174
QVQLQESGGG SVQAGGSLRL SCAASRYTYN SYCMGWFRQA PGKEREGVAT IDSDGMTRYA    60
DSVKGRFTIS KDNAKNTLYL QMNSLKPEDT AMYYCAADAD CTIAAMTTNP LGQGTQVTVS   120
S                                                                  121

SEQ ID NO: 175           moltype = AA  length = 125
FEATURE                  Location/Qualifiers
source                   1..125
                         mol_type = protein
                         organism = synthetic construct
                         note = Description of Artificial Sequence: Synthetic
                            polypeptide
SEQUENCE: 175
QVQLQESGGG SIQAGGSLRL SCAASRYLYS IDYMAWFRQS PGKEREPVAV IYTASGATFY    60
PDSVKGRFTI SQDNAKMTVY LQMNSLKSED TAMYYCAAVR KTDSYLFDAQ SFTYWGQGTQ   120
VTVSS                                                              125

SEQ ID NO: 176           moltype = AA  length = 124
FEATURE                  Location/Qualifiers
source                   1..124
                         mol_type = protein
                         organism = synthetic construct
                         note = Description of Artificial Sequence: Synthetic
                            polypeptide
SEQUENCE: 176
QVQLQESGGG LVQPGGSLRL SCAASGYTYS SYCMGWFRQA PGKEREGVAH IDSDGSTTYA    60
DSVKGRFTIS KDNAKNTLYL QMNSLKPEDT AMYYCAADPI PGPGYCDGGP NKYWGQGTQV   120
TVSS                                                               124

SEQ ID NO: 177           moltype = AA  length = 125
FEATURE                  Location/Qualifiers
source                   1..125
                         mol_type = protein
                         organism = synthetic construct
                         note = Description of Artificial Sequence: Synthetic
                            polypeptide
SEQUENCE: 177
QVQLQESGGG SIQAGGSLTL SCAASRDLYS TNYVAWFRQS PGKEREAVAV IYTASGATLY    60
SDSVKGRFTI SQDNAKMTVY LQMNSLKSED TAMYYCAAVR KTGHYLFDAQ SFTYWGQGTQ   120
VTVSS                                                              125

SEQ ID NO: 178           moltype = AA  length = 126
FEATURE                  Location/Qualifiers
source                   1..126
                         mol_type = protein
                         organism = synthetic construct
                         note = Description of Artificial Sequence: Synthetic
                            polypeptide
SEQUENCE: 178
QVQLQESGGG SVQAGGSLRL SCAASGYTYS SGCMGWFRQA PGKEREGVAT INSDGSTNYA    60
DSVKGRFTIS KDNAKNTLYL QMNSLKPEDT AMYYCAAEPY CSGGYPRWSV AEFGYWGQGT   120
QVTVSS                                                             126

SEQ ID NO: 179           moltype = AA  length = 126
FEATURE                  Location/Qualifiers
source                   1..126
                         mol_type = protein
                         organism = synthetic construct
                         note = Description of Artificial Sequence: Synthetic
                            polypeptide
SEQUENCE: 179
QVQLQESGGG SVQAGGSLRL SCAASGYSYS SYCMGWFRQA PGKEREGVAA IASDGSTSYA    60
DSVKGRFAIS KDNAKNTLYL QMASLKPEDT AMYYCAAEPW CTGGYSRLTP AEYGYWGQGT   120
QVTVSS                                                             126

SEQ ID NO: 180           moltype = AA  length = 126
FEATURE                  Location/Qualifiers
source                   1..126
                         mol_type = protein
                         organism = synthetic construct
                         note = Description of Artificial Sequence: Synthetic
                            polypeptide
```

```
SEQUENCE: 180
QVQLQESGGG LVQPGGSLRL SCAASGYTYS SGCMGWFRQA PGKEREGVAT INSDGSTNYA    60
DSVKGRFTIS KDNAKNTLYL QMNSLKPEDT AMYYCAAEPY CSGGYPRWSV AEFGYWGQGT   120
QVTVSS                                                             126

SEQ ID NO: 181          moltype = AA  length = 124
FEATURE                 Location/Qualifiers
source                  1..124
                        mol_type = protein
                        organism = synthetic construct
                        note = Description of Artificial Sequence: Synthetic
                        polypeptide
SEQUENCE: 181
QVQLQESGGG LVQPGGSLRL SCAASGYTYS SYCMGWFRQA PGKEREGVAH IDSDGSTTYA    60
DSVKGRFAIS KDNAKNTLYL QMNSLKPEDT AMYYCAADPI PGPGYCDGGP NKYWGQGTQV   120
TVSS                                                               124

SEQ ID NO: 182          moltype = AA  length = 126
FEATURE                 Location/Qualifiers
source                  1..126
                        mol_type = protein
                        organism = synthetic construct
                        note = Description of Artificial Sequence: Synthetic
                        polypeptide
SEQUENCE: 182
QVQLQESGGG SVQAGGSLRL SCAASGYTYS SYCMGWFRQA PGKGREGVAA IDSDGSTRYA    60
DSVKGRFTIS KDNAKNTLYL QMNSLKPEDT AMYYCAAEPY CSGGYKRTMV AEFGYWGQGT   120
QVTVSS                                                             126

SEQ ID NO: 183          moltype = AA  length = 124
FEATURE                 Location/Qualifiers
source                  1..124
                        mol_type = protein
                        organism = synthetic construct
                        note = Description of Artificial Sequence: Synthetic
                        polypeptide
SEQUENCE: 183
QVQLQESGGG SVQAGGSLRL SCAASGYTYS SYCMGWFRQA PGKEREGVAH IDSDGSTSYA    60
DSVKGRFTIS KDNAKNTLYL QMNSLKPEDT AMYYCAADPI PGPGYCDGGP NKYWGQGTQV   120
TVSS                                                               124

SEQ ID NO: 184          moltype = AA  length = 124
FEATURE                 Location/Qualifiers
source                  1..124
                        mol_type = protein
                        organism = synthetic construct
                        note = Description of Artificial Sequence: Synthetic
                        polypeptide
SEQUENCE: 184
QVQLQESGGG SVQAGGSLRL SCAASGYTYS SYCMGWFRQA PGKEREGVAH IDSDGSTSYA    60
DSVKGRFTIS KDNAKNTLYL QMNSLKPEDT AMYYCAADPI PGPGYCDGGP NNYWGQGTQV   120
TVSS                                                               124

SEQ ID NO: 185          moltype = AA  length = 126
FEATURE                 Location/Qualifiers
source                  1..126
                        mol_type = protein
                        organism = synthetic construct
                        note = Description of Artificial Sequence: Synthetic
                        polypeptide
SEQUENCE: 185
QVQLQESGGG SVQAGGSLRL SCAASGYTYS SGCMGWFRQA PGKEREGVAT INSDGSTNYA    60
DSVKGRFTIS KDNAKNTLYL QMNSLKPEDT GMYYCAAEPY CSGGYPRWSV AEFGYWGQGT   120
QVTVSS                                                             126

SEQ ID NO: 186          moltype = AA  length = 125
FEATURE                 Location/Qualifiers
source                  1..125
                        mol_type = protein
                        organism = synthetic construct
                        note = Description of Artificial Sequence: Synthetic
                        polypeptide
SEQUENCE: 186
QVQLQESGGG SVQAGGSLRL SCTVSRYTAS VNYMGWFRQA PGKEREGVAT IFTGAGTTYY    60
ANSVKGRFTI SRDNAKNTAY LQMNSLKPED TAIYYCAVDF RGGLLYRPAY EYTYRGQGTQ   120
VTVSS                                                              125

SEQ ID NO: 187          moltype = AA  length = 126
FEATURE                 Location/Qualifiers
```

```
source                  1..126
                        mol_type = protein
                        organism = synthetic construct
                        note = Description of Artificial Sequence: Synthetic
                        polypeptide
SEQUENCE: 187
QVQLQESGGG SVEAGGSLRL SCAASGYTHS SYCMGWFRQA PGKEREGVAA IDVDGSTTYA    60
DSVKGRFTIS KDNAKNTLYL QMNSLKPEDT GMYYCAAEFA DCSSNYFLPP GAVRYWGQGT   120
QVTVSS                                                              126

SEQ ID NO: 188          moltype = AA   length = 125
FEATURE                 Location/Qualifiers
source                  1..125
                        mol_type = protein
                        organism = synthetic construct
                        note = Description of Artificial Sequence: Synthetic
                        polypeptide
SEQUENCE: 188
QVQLQESGGG SVQAGGSLRL SCTVSRYTAS VNYMGWFRQA PGKEREGVAT IFTGAGTTYY    60
ANSVKGRFTI SRDNAKNTAY LQMNSLKPED TAMYYCAVDF RGGLLYRPAY EYTYRGQGTQ   120
VTVSS                                                               125

SEQ ID NO: 189          moltype = AA   length = 126
FEATURE                 Location/Qualifiers
source                  1..126
                        mol_type = protein
                        organism = synthetic construct
                        note = Description of Artificial Sequence: Synthetic
                        polypeptide
SEQUENCE: 189
QVQLQESGGG SVQAGGSLRL SCAASGDTYS SYCMGWFRQA PGKEREGVAF IDSDGSTRYA    60
DSVEGRFTIS KDNAKNTLYL QMNSLKPEDT AMYYCAAEPY CSGGYHRKEM AEFGYWGQGT   120
QVTVSS                                                              126

SEQ ID NO: 190          moltype = AA   length = 124
FEATURE                 Location/Qualifiers
source                  1..124
                        mol_type = protein
                        organism = synthetic construct
                        note = Description of Artificial Sequence: Synthetic
                        polypeptide
SEQUENCE: 190
QVQLQESGGG SVQAGGSLRL SCAASGYTYS SYCMGWFRQA PGKEREGVAH IDSDGSTSYA    60
DSVKGRFTIS KDNAKNTLYL QMNSLKPEDT AMYYCAADPI PGPGYCDGGP NKYRGQGTQV   120
TVSS                                                                124

SEQ ID NO: 191          moltype = AA   length = 124
FEATURE                 Location/Qualifiers
source                  1..124
                        mol_type = protein
                        organism = synthetic construct
                        note = Description of Artificial Sequence: Synthetic
                        polypeptide
SEQUENCE: 191
QVQLQESGGG SVQAGGSLRL SCAASGYTYS SYCMGWFRQA PGKEREGVAH IDSDGSTTYA    60
DSVKGRFAIS KDNAKNTLYL QMNSLKPEDT AMYYCAADPI PGPGYCDGGP NKYWGQGTQV   120
TVSS                                                                124

SEQ ID NO: 192          moltype = AA   length = 121
FEATURE                 Location/Qualifiers
source                  1..121
                        mol_type = protein
                        organism = synthetic construct
                        note = Description of Artificial Sequence: Synthetic
                        polypeptide
SEQUENCE: 192
QVQLQESGGG SVQAGGSLRL SCTGSGYTAS NNCMGWFRQA PGKEREGVAV IFTGAGTSYY    60
DSSVGRLFIS SQDAASTLDQ LLMSLLPDDT AVMYCGAEDD CTLLLMTPNP DDQWSRLSVS   120
S                                                                   121

SEQ ID NO: 193          moltype = AA   length = 124
FEATURE                 Location/Qualifiers
source                  1..124
                        mol_type = protein
                        organism = synthetic construct
                        note = Description of Artificial Sequence: Synthetic
                        polypeptide
SEQUENCE: 193
QVQLQESGGG SVQAGGSLRL SCAASGYTDS RYCMGWFRKA PGKEREGVAH IDSDGSTSYA    60
```

```
DSVKGRFTIS KDNAKNTLYL QMNSLKPEDT AMYYCAADPI PGPGYCDGGP NKYWGQGTQV    120
TVSS                                                               124

SEQ ID NO: 194          moltype = AA  length = 126
FEATURE                 Location/Qualifiers
source                  1..126
                        mol_type = protein
                        organism = synthetic construct
                        note = Description of Artificial Sequence: Synthetic
                          polypeptide
SEQUENCE: 194
QVQLQESGGG SVQAGGSLRL SCAASGYTYS SYCMGWFRQA PGKEREGVAA IDSDGSTRYA    60
DSVKGRFTIS KDNAKKILYL QMNSLKVEDT AMYYCAAEPY CSGGYKRTMV AEFGFWGQGT    120
QVTVSS                                                              126

SEQ ID NO: 195          moltype = AA  length = 124
FEATURE                 Location/Qualifiers
source                  1..124
                        mol_type = protein
                        organism = synthetic construct
                        note = Description of Artificial Sequence: Synthetic
                          polypeptide
SEQUENCE: 195
QVQLQESGGG SVQAGGSLKL SCAASGYTYS SYCMGWFRQA PGKEREGVAH IDSDGSTTYA    60
DSVKGRFTIS KDNAKNTLYL QMNSLKPEDT AMYYCAADPI PGPGYCDGGP NNYWGQGTQV    120
TVSS                                                                124

SEQ ID NO: 196          moltype = AA  length = 124
FEATURE                 Location/Qualifiers
source                  1..124
                        mol_type = protein
                        organism = synthetic construct
                        note = Description of Artificial Sequence: Synthetic
                          polypeptide
SEQUENCE: 196
QVQLQESGGG SVQAGGSLRL SCAASGYTYS SYCMGWFRQA PGKEREGIAH IDSDGSTTYA    60
DSVKGRFTIS KDNAKNTLYL QMNSLKPEDT AMYYCAADPI PGPGYCDGGP NNYWGQGTQV    120
TVSS                                                                124

SEQ ID NO: 197          moltype = AA  length = 124
FEATURE                 Location/Qualifiers
source                  1..124
                        mol_type = protein
                        organism = synthetic construct
                        note = Description of Artificial Sequence: Synthetic
                          polypeptide
SEQUENCE: 197
QVQLQESGGG SVQAGGSLRL SCAASGYSYS SYCMGWFRQA PGKEREGVAT IDSDGMTRYA    60
DSVKGRFTIS KDNAKNTLYL QMNSLKPEDT AMYYCAAPLY DCDSGAVGRN PPYWGQGTQV    120
TVSS                                                                124

SEQ ID NO: 198          moltype = AA  length = 122
FEATURE                 Location/Qualifiers
source                  1..122
                        mol_type = protein
                        organism = synthetic construct
                        note = Description of Artificial Sequence: Synthetic
                          polypeptide
SEQUENCE: 198
QVQLQESGGG SVQTGGSLRL SCAASGYTYL RGCMGWFRQA PGKEREGVAV MDVVGDRRSY    60
IDSVKGRFTI SRDNAANSVY LQMDNLKPED TAMYYCTAGP NCVGWRSGLD YWGQGTQVTV    120
SS                                                                  122

SEQ ID NO: 199          moltype = AA  length = 127
FEATURE                 Location/Qualifiers
source                  1..127
                        mol_type = protein
                        organism = synthetic construct
                        note = Description of Artificial Sequence: Synthetic
                          polypeptide
SEQUENCE: 199
QVQLQESGGG SVQAGGALRL SCTASGYTAS SICMGWFRQA PGKERERVAV ITTAASGTYY    60
ADSVNGRFSI SQNNAKNTVY LQMNSLKPDD TAMYYCAATR RGGDCLDPLQ TPAYNTWGQG    120
TQVTVSS                                                             127

SEQ ID NO: 200          moltype = AA  length = 123
FEATURE                 Location/Qualifiers
source                  1..123
                        mol_type = protein
```

```
                        organism = synthetic construct
                        note = Description of Artificial Sequence: Synthetic
                           polypeptide
SEQUENCE: 200
QVQLQESGGG SVQAGGSLRL SCVASGDTYS RKYIAWVRQV PGKEREGVAV MYTPGSATYY    60
TDTVMGRFTI SQDNAKNTVY LQMNSLKPED TAMYFCAAKA SGSMFNFRDY TYWGQGTQVT   120
VSS                                                                 123

SEQ ID NO: 201          moltype = AA   length = 121
FEATURE                 Location/Qualifiers
source                  1..121
                        mol_type = protein
                        organism = synthetic construct
                        note = Description of Artificial Sequence: Synthetic
                           polypeptide
SEQUENCE: 201
QVQLQESGGG SVQAGGSLRL SCATSGYASC SRAMRWYRQA PGKEREFVAY IDGVGSTGYA    60
DSVKGRFTIS QDNAKYTAYL QMNSLKPEDT AMYYCNRGCR ADGSNSLDNY WGQGTQVTVS   120
S                                                                   121

SEQ ID NO: 202          moltype = AA   length = 125
FEATURE                 Location/Qualifiers
source                  1..125
                        mol_type = protein
                        organism = synthetic construct
                        note = Description of Artificial Sequence: Synthetic
                           polypeptide
SEQUENCE: 202
QVQLQESGGG SVQAGGSLRL SCAASGYTYN RRFMGWFRQA PGKEREGLAI IYTPNSSTFY    60
ADSVTGRFTI SQDSARNTVY LQMNSLKPED TAMYYCAAAR IASMTELSVR DMDYWGKGTQ   120
VTVSS                                                               125

SEQ ID NO: 203          moltype = AA   length = 126
FEATURE                 Location/Qualifiers
source                  1..126
                        mol_type = protein
                        organism = synthetic construct
                        note = Description of Artificial Sequence: Synthetic
                           polypeptide
SEQUENCE: 203
QVQLQESGGG SVQAGGSLRL SCTASRYIAL NACMAWIRQA PGSEREVVAT IVTDGSRTYY    60
ADSVKGRFTI SQDNAKNTMY LQMNGLKPED TAMYYCAADR RCPVSRAPYE YELRYWGQGT   120
QVTVSS                                                              126

SEQ ID NO: 204          moltype = AA   length = 123
FEATURE                 Location/Qualifiers
source                  1..123
                        mol_type = protein
                        organism = synthetic construct
                        note = Description of Artificial Sequence: Synthetic
                           polypeptide
SEQUENCE: 204
QVQLQESGGG SVQAGGSLRL SCAASGYTYN GKCMAWFRQA PGKEREVVAG IYTGGSSTYY    60
ADSVKGRFTI SQDNAKNTVY LQMDSLKPED TAMYYCATSR SCSDLRRRSI AYWGQGTQVT   120
VSS                                                                 123

SEQ ID NO: 205          moltype = DNA   length = 375
FEATURE                 Location/Qualifiers
source                  1..375
                        mol_type = other DNA
                        organism = synthetic construct
                        note = Description of Artificial Sequence: Synthetic
                           polynucleotide
SEQUENCE: 205
caggttcagc ttcaggagtc cggtggaggc tccatccagg ccgggggctc tctccgcctg    60
tcttgcgccg cttccagata cctctacagt atcgactaca tggcttggtt tcgtcagagc   120
ccaggaaaag agcgggaacc cgtggcagta atctacactg cctcaggtgc acatttttac   180
cccgactctg tcaagggcag gttcaccatc tctcaggata tgccaagat gacagtgtac    240
ttgcagatga actccctgaa atctgaggat accgctatgt attactgtgc cgcagtcgc    300
aagaccgatt cttacctgtt cgacgctcag agttttacct actggggcca gggcactcag   360
gtcaccgtca gcagc                                                    375

SEQ ID NO: 206          moltype = DNA   length = 375
FEATURE                 Location/Qualifiers
source                  1..375
                        mol_type = other DNA
                        organism = synthetic construct
                        note = Description of Artificial Sequence: Synthetic
                           polynucleotide
```

```
SEQUENCE: 206
caggtgcagt tgcaggagtc cggcggggt tccgtgcaag caggcggatc tctgcgcctg    60
tcctgcgtgg cctctcgtta tttgtatagc accaactaca tggcttggtt ccgtcagtcc   120
ccaggcaaag agcgcgaagc cgtagccgta atctatacgg cctctgggc aacactctat   180
accgactcag tgaagggacg cttcacgatt tcccaagaca atgcaaagat gaccgtgtac   240
ttgcagatga accgcctgaa gagcgaggac acggctatgt attactgcgc agccgtgcgc   300
aagaccgact cctacttgtt tgacgctcag tccttcactt attggggcca gggtacacag   360
gtcaccgtga gcagt                                                     375

SEQ ID NO: 207          moltype = DNA  length = 375
FEATURE                 Location/Qualifiers
source                  1..375
                        mol_type = other DNA
                        organism = synthetic construct
                        note = Description of Artificial Sequence: Synthetic
                            polynucleotide
SEQUENCE: 207
caagtacagc tccaggagag cggcggtgga tctatccaag cagggggtag ccttaggttg    60
tcctgtgtgg cgtccagata cctgtatagc acgaactaca tggcatggtt cagacagtcc   120
ccaggcaagg aacgcgaggc agtcgccgtt atttacactg catctgggc caccctctat   180
acggacagct gaaggaag gtttacaatc tcccaggaca acgcgaagat gaccgtgtac    240
cttcagatga accgcctgaa gtccgaggac accgccatgt attactgtgc agcggtgcgc   300
aagaccgaca gctatctgtt cgacgcgcag tcattcactt attggggcca aggaacccaa   360
gtgaccgtca gctca                                                     375

SEQ ID NO: 208          moltype = DNA  length = 375
FEATURE                 Location/Qualifiers
source                  1..375
                        mol_type = other DNA
                        organism = synthetic construct
                        note = Description of Artificial Sequence: Synthetic
                            polynucleotide
SEQUENCE: 208
caggtgcagc tccaagagtc cggggagggc tctatccagg cgggaggcag tctgcgcttg    60
tcctgcgccg caagtcgtta tctgtactcc attgattaca tggcatggtt ccgccagtcc   120
ccaggtaagg aacgtgaacc tgccgctgtg atctacaccg cttctggagc aaccttttat   180
cctgatagcg ttaagggtcg cttcaccatc tctcaggata acgccaaaat gacagtgtac   240
ctccagatga acagcctgaa gtctgaggac actgccatgt actattgtgc ggctgtgcgc   300
aagaccgact cctatctgtt tgatgcacag agctttacct attgggtca gggcacccag   360
gtgactgtgt ctagc                                                     375

SEQ ID NO: 209          moltype = DNA  length = 375
FEATURE                 Location/Qualifiers
source                  1..375
                        mol_type = other DNA
                        organism = synthetic construct
                        note = Description of Artificial Sequence: Synthetic
                            polynucleotide
SEQUENCE: 209
caggtccagt tgcaggagtc cggtggaggt tccatccagg cgggtgggtc ccttcgtctc    60
tcctgcgtgg cctctaagta cctgtattca accaactaca tggcatggtt cagacagtct   120
cccggcaaag agcgtgaggc agtgccgcg atctatacag cttctgggc caccctgtac    180
tctgattcca ataagggaag gttcactatc tcacaggata acgccaaaat gaccgtgtac   240
cttcagatga acagcctcaa gtctgaagac acggcaatgt attactgtgc agccgtgcgc   300
aaaactggga gctacctgtt tgacgctcag tctttcactt attggggcca gggtacgcag   360
gtgacagtct cttct                                                     375

SEQ ID NO: 210          moltype = DNA  length = 387
FEATURE                 Location/Qualifiers
source                  1..387
                        mol_type = other DNA
                        organism = synthetic construct
                        note = Description of Artificial Sequence: Synthetic
                            polynucleotide
SEQUENCE: 210
caggtgcaac tccaggagag cggaggcggt tctgttcagg caggaggttc cctgagactg    60
tcctgtgccg cgtctcgctt tacgtattca tcctactgca tgggatggtt cagacaagcg   120
ccggggaaag aaagggaagg cgtggcctcc attgactccg acggctcaac ttcatacact   180
gatagcgtga aaggccggtt caccatctct aaggacaacg cgaagaacgc cgtctatctc   240
cagatgaaca gcctcaagcc tgaggatact gccatgtact attgcgcact cgacctgatg   300
tctactgtgg tccaggcttt ctgcgggttc ctgctctctg ctggcatgga ctactggggg   360
aagggcactc aggtaacggt tagctcc                                        387

SEQ ID NO: 211          moltype = DNA  length = 381
FEATURE                 Location/Qualifiers
source                  1..381
                        mol_type = other DNA
                        organism = synthetic construct
                        note = Description of Artificial Sequence: Synthetic
```

```
                        polynucleotide
SEQUENCE: 211
caggtgcagc ttcaggaatc tggcggggc tccgtgcagg ccgggggctc cctcagactt   60
tcctgtgccg tctccggtta cacatttaac agtaactgta tgggctggtt ccgccaggca  120
ccaggcaagg agagggaagg tgtggccaca atctatatcg gtgttgggag tacgtactat  180
gctgattccg tgaaaggtcg cttcacaatt tcccaggaca acgcgaagaa cactgtgtac  240
ttgcagatga atagcctgaa gcctgaagat accgcaatgt attactgcgc tgccgagcca  300
ctctcccgcg tatatggtgg aagttgcccc accccacttt cggttactg gggccagggc   360
actcaagtga ccgtgtcctc t                                             381

SEQ ID NO: 212          moltype = DNA   length = 393
FEATURE                 Location/Qualifiers
source                  1..393
                        mol_type = other DNA
                        organism = synthetic construct
                        note = Description of Artificial Sequence: Synthetic
                        polynucleotide
SEQUENCE: 212
caggttcagc ttcaggagtc tgggggcggt tcagtgcagg ctggcggttc tctccgcctg   60
tcctgcgctg ccagcggcta tacttacagc atgtactgca tgggctggtt ccggcaagcc  120
cccggcaaag agcgtgaggg cgtcgctcaa atcaacagcg acgggtcaac cagctacgcc  180
gattctgtca agggcagatt tactatcagc aaggacaacg ccaaaaacac attgtacctc  240
cagatgaact ctttgaagcc tgaggacacc gcgatgtatt actgcgcgc tgacagccgc  300
gtgtacggtg gcagctggta tgagaggctg tgcggcccgt acacctacga gtacaactat  360
tggggacagg gcacgcaggt gacagttagc tcc                                393

SEQ ID NO: 213          moltype = DNA   length = 402
FEATURE                 Location/Qualifiers
source                  1..402
                        mol_type = other DNA
                        organism = synthetic construct
                        note = Description of Artificial Sequence: Synthetic
                        polynucleotide
SEQUENCE: 213
caggtgcaac tgcaagagag tggcggaggc tccgtccagg ctggaggttc cctgcgctg   60
tcttgcgccg tcagcggcta cgcatattcc acttactgta tgggttggtt ccgccaggcc  120
cctgaaaggg aacgcgaggg tgttgccgct attgatagcg gaggtccac atcctatgcg  180
gactccgtga aaggtcgttt caccatctcc aaggataacg ccaagaacac tctgtacctg  240
cgcatgaact ctctgaagcc tgaggacact gccatgtatt actgcgccgc tgtgccccct  300
ccacccgacg ggggctcttg tctgtttctt ggcccggaga tcaaggtgtc caaggctgat  360
ttccgttatt ggggccaggg aactcaagtc accgtgtctt cc                     402

SEQ ID NO: 214          moltype = DNA   length = 375
FEATURE                 Location/Qualifiers
source                  1..375
                        mol_type = other DNA
                        organism = synthetic construct
                        note = Description of Artificial Sequence: Synthetic
                        polynucleotide
SEQUENCE: 214
caggtccagc tccaggagtc cggtggaggc tccgttcagg ccggtggcag cttgcgtctg   60
agctgcgcgg cttcaagata cctgtactcc attgattaca tggcatggtt ccgtcagtct  120
cctggcaagg agcgcgagcc cgtcgctgtg atctataccg ccagcggagc cacgttctac  180
cctgattccg tcaagggccg cttcaccatt agccaagaca acgctaagat gacggtgtac  240
ctccaaatga atagcctgaa aagcgaggac acagcgatgt attactgcgc cgctgttagg  300
aaaactgata gttacctgtt cgatgcacag tctttcactt actgggggca gggcacccaa  360
gttaccgtct cctct                                                    375

SEQ ID NO: 215          moltype = DNA   length = 378
FEATURE                 Location/Qualifiers
source                  1..378
                        mol_type = other DNA
                        organism = synthetic construct
                        note = Description of Artificial Sequence: Synthetic
                        polynucleotide
SEQUENCE: 215
caggtgcagc tccaggaatc tggagggggc agtgtgcagg ccgggggctc cctgcgcttg   60
agctgtggag ccagccgcta cacgtattcc agttactgta gggctggtt cagacaagct  120
ccgggtaagg agagagaggg agttgccgta attgattctg aaggctccac tagctatgcg  180
gattcagtca agggccggtt caccatcagc aaggacaatg gtaagaacac actgtacctg  240
caaatgaaca gcctgaagcc cgaggacacc gccatgtact attgtgccgc tgatctcgga  300
cattaccgcc ctccctgcgg tgtgctctat ctcgggatgg actattgggg taagggcacc  360
caggtgaccg tgtcctct                                                 378

SEQ ID NO: 216          moltype = DNA   length = 381
FEATURE                 Location/Qualifiers
source                  1..381
                        mol_type = other DNA
                        organism = synthetic construct
```

```
                        note = Description of Artificial Sequence: Synthetic
                        polynucleotide
SEQUENCE: 216
caggtgcagc tccaggaaag cggcgggggt agcgttcaag caggtgggtc cctgcgcttg   60
agctgtactg tgtccggcta cacctactca agcaactgca tgggatggtt ccgtcaggcc  120
cctggcaagg aacgcgaagg cgtggctact atctacaccg gcgtggcaa  cacttattac  180
gccgactccg ttaaggggcg tttcactatc agccaagaca acgccaagaa caccgtgtat  240
ctgcaaatga ataacctgaa gcctgaagac accgccatgt attactgtgc tgccgagccc  300
ctttcccgcg tttacggcgg ttcttgtcct acccctacct ttgactactg gggtcaggga  360
acacaggtga cagtgtccag t                                            381

SEQ ID NO: 217          moltype = DNA    length = 381
FEATURE                 Location/Qualifiers
source                  1..381
                        mol_type = other DNA
                        organism = synthetic construct
                        note = Description of Artificial Sequence: Synthetic
                        polynucleotide
SEQUENCE: 217
caagtccaac tccaggaatc tgggggaggc tccgtacagg ctggcggttc ccttcgtctg   60
tcctgtgctg tgtcagggta ctcctactcc agtaactgta tgggctggtt ccggcaagcc  120
cccggaaagg agcgcgaggg cgtggctacc atccacacag acggcggttc cacatattac  180
gccgatagtg tcaagggccg cttcaccatt agtcaggaca acgccaagaa taccgtttac  240
cttcaaatga actctttgaa acctgaggac actgcgatgt attactgtgc ggcagagcct  300
ttgtcccgcc tgtacggggg atcttgtccg accccgactt tcgggtactg gggacagggc  360
acccaggtga cagtgtcctc c                                            381

SEQ ID NO: 218          moltype = DNA    length = 378
FEATURE                 Location/Qualifiers
source                  1..378
                        mol_type = other DNA
                        organism = synthetic construct
                        note = Description of Artificial Sequence: Synthetic
                        polynucleotide
SEQUENCE: 218
caggtgcagt tgcaggaaag cggggtggc  agcgtccaag ccggtggcag cctgcgtctg   60
tcctgcggtg cctccggcta tacttactcc agctattgca tgggttggtt ccgccaagtg  120
ccaggaaagg agcgtgaggg ggtggctgta attgattcag atgggtcaac aagctacgct  180
gacagcgtta aaggtcgctt caccatcagt aaggacaacg gcaagaacac cctctacctg  240
caaatgaact ccctgaagcc ggaggatacc gcaatgtatt actgtgccgc tgacttggga  300
cactaccgcc ctccgtgcgg tgtgctttat ctgggcatgg attactgggg taagggaacc  360
caagtgacgg tgtcttct                                                378

SEQ ID NO: 219          moltype = DNA    length = 378
FEATURE                 Location/Qualifiers
source                  1..378
                        mol_type = other DNA
                        organism = synthetic construct
                        note = Description of Artificial Sequence: Synthetic
                        polynucleotide
SEQUENCE: 219
caggtacaac tccaggagtc tggcggtggg tccgtgcagg caggtggcag ccttcgcctc   60
tcctgcgggg cctccgggta cacctatagt ggctactgca tggggtggtt caggcaagcc  120
cccggtaagg aacgtgaggg agttgctgtg attgattcag atgggtccac gagttacgct  180
gactccgtga aagtaggtt  cacaatctcc aaagataatg gcaagaacac cctctacctt  240
cagatgaata gcctgaagcc agaagacacc gccatgtatt actgtgctgc cgacctggga  300
cactatcgcc ctccgtgcgg ggtcctgtac ttgggcatgg actattgggg caaggggacc  360
caggtgactg tgtcctct                                                378

SEQ ID NO: 220          moltype = DNA    length = 378
FEATURE                 Location/Qualifiers
source                  1..378
                        mol_type = other DNA
                        organism = synthetic construct
                        note = Description of Artificial Sequence: Synthetic
                        polynucleotide
SEQUENCE: 220
caggtgcagt tgcaggaatc cggtggaggc tctgttcagg ccgggggctc tctccgcctg   60
gcctgcgcag cctccaggta tacttacagc aactactgca tgggggtggtt tcgccaggct  120
ccgggcaaag agcgtgaggg agtggctact attgattccg atggaaacac cagctacgcc  180
gatagcgtga agggcagatt tactatcagc agagataacg ctaaaaacac gttgtacctc  240
cagatgaact cactcaagcc gggggacaca gctatgtatt actgcgcagc cgatctggtt  300
cactaccgcc cgccctgcgg cgcatattac tatggcatgg actactgggg caagggcacc  360
caggtgaccg tgtccagt                                                378

SEQ ID NO: 221          moltype = DNA    length = 381
FEATURE                 Location/Qualifiers
source                  1..381
                        mol_type = other DNA
```

```
                            organism = synthetic construct
                            note = Description of Artificial Sequence: Synthetic
                                polynucleotide
SEQUENCE: 221
caggtgcagc tccaagagtc tggcgggggt tccgtgcaag ccggtggctc actcaggttg    60
agttgcgcag ccagcggcta tagcaactgt tcctatgaca tgacttggta tcgccaggcc   120
cctggcaaag agcgtgagtt cgtgtcagct attcactccg acggctccac tcgttatgcg   180
gactctgtga agggccggtt tttcatctcc caggacaacg ctaaaaacac tgtctatttg   240
cagatgaact ctctgaaacc cgaagatacc gccatgtact attgcaaaac cgatcctctg   300
cattgtcgcg cccacggcgg gagttggtac tctgtgcggg ccaactattg gggccagggc   360
acccaggtca ccgtgtcctc a                                             381

SEQ ID NO: 222              moltype = DNA  length = 381
FEATURE                     Location/Qualifiers
source                      1..381
                            mol_type = other DNA
                            organism = synthetic construct
                            note = Description of Artificial Sequence: Synthetic
                                polynucleotide
SEQUENCE: 222
caggtacaac tccaggagtc tggcggtggc agcgtgcagg caggcggaag cctgaggctg    60
tcctgcgctg tatctggcta cacttataat tccaactgtg tgggttggtt tcggcaggct   120
ccaggtaagg agcgcgaggg cgtcgccacc atttatacag gtgttggcag cacatattac   180
gccgacagcg tgaagggaag gttcaccatc tcccaagaca atgcgaaaaa cacagtgtat   240
ctccagatga atagcctgaa gcccgaggac acggctatgt attactgcgc tgccgagcca   300
ctgagcagag tgtatggggg cagctgtcct acacccactt tcggctattg gggtcaaggc   360
acccaggtta cagtcagctc c                                             381

SEQ ID NO: 223              moltype = DNA  length = 378
FEATURE                     Location/Qualifiers
source                      1..378
                            mol_type = other DNA
                            organism = synthetic construct
                            note = Description of Artificial Sequence: Synthetic
                                polynucleotide
SEQUENCE: 223
caggtgcagc ttcaggaatc aggcggaggc agcgtgcagg caggggtag cctgcgtctg     60
tcttgcgcag ccagcgggta cacctacagc tctggctgta tgggctggtt tcgccaagcc   120
ccaggaaaag aacgggaagc cgtggcggct atcaataccg acggctccac ctcctatgct   180
gactccgtca aaggacgctt caccattagt aaagataacg ccaagaacac cttgtacctt   240
cagatgaact ccttgaaacc ggaggacacc gcaatgtatt actgtgcggc tgagccctac   300
tgctcaggag gctacccacg gtggtcagtg gccgagtttg gttattgggg cagggcacc    360
caagtgactg tgtcctcc                                                 378

SEQ ID NO: 224              moltype = DNA  length = 378
FEATURE                     Location/Qualifiers
source                      1..378
                            mol_type = other DNA
                            organism = synthetic construct
                            note = Description of Artificial Sequence: Synthetic
                                polynucleotide
SEQUENCE: 224
caggtgcaac tccaggagtc aggggggaggt tccgtgcagg ctggcggttc tctcaggttg    60
tcttgcgcgg ccagcggcta tacgtacagt agctactgca tgggctggtt ccggcaagcc   120
cccgcaagg agcgcgaagg cgtggctgcc attgattccg atggatctac taggtatgct    180
gatagtgtaa agggccgctt cacaatctcc aaggacaatg ccaagaacac actgtatttg   240
caaatgaact ccctcaagcc cgaggatacc gctatgtact attgcgctgc cgaaccctac   300
tgttccggtg gctataagcg cactatggtg gccgagttcg gatactgggg tcaaggcaca   360
caggtcacag tgtcctct                                                 378

SEQ ID NO: 225              moltype = DNA  length = 363
FEATURE                     Location/Qualifiers
source                      1..363
                            mol_type = other DNA
                            organism = synthetic construct
                            note = Description of Artificial Sequence: Synthetic
                                polynucleotide
SEQUENCE: 225
caggtgcagt tgcaggagtc cgggggcggt agcgttcagg ctggagggtc cctgcgtctg    60
agttgtgcgg catctcggta tacttataac agttactgta tgggttggtt ccgccaggca   120
cctggaaagg agcgggaggg ggtggcgact attgatagcg acggaatgac cagatatgcc   180
gactctgtga agggaagatt tactatctca aaagataatg ccaagaacac actctatttg   240
cagatgaaca gcctcaagcc agaggatacc gctatgtatt actgtgctgc cgacgctgat   300
tgcaccatcg ctgccatgac gaccaaccc ttgggccagg aacccaagt aaccgtctct     360
agc                                                                 363

SEQ ID NO: 226              moltype = DNA  length = 375
FEATURE                     Location/Qualifiers
source                      1..375
```

```
                        mol_type = other DNA
                        organism = synthetic construct
                        note = Description of Artificial Sequence: Synthetic
                            polynucleotide
SEQUENCE: 226
caggtccagc tccaggaatc tggtggcggg tctatccagg cgggtggcag cctgcggctg    60
agttgcgccg cttcccgcta cctgtatagt attgattata tggcctggtt caggcagtca   120
ccgggcaaag agcgcgaacc cgtcgctgtg atttacacag cctctggtgc caccttctat   180
cccgatagtg tgaagggccg gttcactatc tctcaagaca acgcgaagat gactgtctat   240
cttcagatga actctctgaa gtccgaggac actgccatgt attactgtgc cgctgtgcgc   300
aagacggact cttatctgtt cgatgcccag agtttcactt actggggtca gggtactcag   360
gtgaccgtat cctcc                                                    375

SEQ ID NO: 227          moltype = DNA  length = 372
FEATURE                 Location/Qualifiers
source                  1..372
                        mol_type = other DNA
                        organism = synthetic construct
                        note = Description of Artificial Sequence: Synthetic
                            polynucleotide
SEQUENCE: 227
caggtgcagc tccaggagtc tggtggcggg ctggttcagc ctggggttc actccgttg     60
tcctgcgctg cgtctggtta tacctactcc agctactgta tgggttggtt ccgccaggca   120
ccggggaagg agagggaggg cgtggctcac attgattctg atggctctac gacctacgct   180
gatagcgtta aggggcgctt cactatctcc aaggataacg ccaagaacac cctgtatctg   240
caaatgaaca gcctgaagcc agaagacact gccatgtact attgcgctgc cgatcctatt   300
cccggtcctg gctattgtga cggcggtcct aacaagtact ggggccaagg cacacaggtg   360
actgtcagtt cc                                                       372

SEQ ID NO: 228          moltype = DNA  length = 375
FEATURE                 Location/Qualifiers
source                  1..375
                        mol_type = other DNA
                        organism = synthetic construct
                        note = Description of Artificial Sequence: Synthetic
                            polynucleotide
SEQUENCE: 228
caggttcaac tccaggaatc cggcggtgga agcattcagg cgggcggttc tttgactctg    60
agctgtgcgg catctcggga cctttacagc actaactatg ttgcctggtt ccggcagtca   120
cccggcaagg aacgcgaagc tgtggccgtg atttatacag ccagcggcgc aaccctgtat   180
agcgattcag tcaaaggccg gttcaccatc tcccaggaca acgcgaagat gaccgtgtac   240
ctgcaaatga acagcctgaa gtctgaggac actgccatgt attactgcgc agctgtgaga   300
aagaccggac attacctctt cgacgcccaa tctttcacct actggggcca gggaacccag   360
gtcaccgtct cctct                                                    375

SEQ ID NO: 229          moltype = DNA  length = 378
FEATURE                 Location/Qualifiers
source                  1..378
                        mol_type = other DNA
                        organism = synthetic construct
                        note = Description of Artificial Sequence: Synthetic
                            polynucleotide
SEQUENCE: 229
caggtgcaac tccaggagtc aggcggtggg tccgtccagg ccggtggctc cctgaggctg    60
agttgcgccg cttccggcta tacttactcc agcggttgca tggggtggtt ccgccaagcc   120
cccggtaaag aacgcgaggg agtggctaca attaactccg atggaagcac taactacgcc   180
gactctgtga agggacgctt caccattagc aaagacaatg ctaagaacac cctttacctt   240
caaatgaaca gcctgaagcc tgaggatacc gctatgtatt actgtgccgc agaaccgtat   300
tgtagcggtg gctaccctcg ctggtccgtc gccgagttcg gttattgggg ccaggggacc   360
caagtgactg tttctagc                                                 378

SEQ ID NO: 230          moltype = DNA  length = 378
FEATURE                 Location/Qualifiers
source                  1..378
                        mol_type = other DNA
                        organism = synthetic construct
                        note = Description of Artificial Sequence: Synthetic
                            polynucleotide
SEQUENCE: 230
caggtgcaac tcaggagag cggcggggc tctgtgcaag ctggtggctc cctgcggctc      60
agctgtgctg cctctgggta ttcttacagt agctactgta tgggctggtt cagacaggca   120
ccaggcaagg agcgcgaggg tgtggcggcc atcgcttccg acgggagtac cagctacgcc   180
gacagcgtta aaggtaggtt tgccatctct aaggataatg cgaagaatac actctacctt   240
cagatggcta gtctgaagcc agaggatacc gccatgtatt actgcgcggc agagccctgg   300
tgcacgggag ggtattcacg cctgaccccg gctgagtatg gatactgggg gcagggcacc   360
caggtgaccg ttagctcc                                                 378

SEQ ID NO: 231          moltype = DNA  length = 378
FEATURE                 Location/Qualifiers
```

```
source                  1..378
                        mol_type = other DNA
                        organism = synthetic construct
                        note = Description of Artificial Sequence: Synthetic
                          polynucleotide
SEQUENCE: 231
caggtccagt tgcaggaaag cggagggggc ctggtgcagc caggaggttc tctgagactg    60
agctgtgccg cttctggtta cacatattct agcgggtgca tgggctggtt ccgccaggct   120
cccgcaagg aacgtgaggg tgtggcaact atcaattccg acggctctac aaactacgcc   180
gattctgtta aaggccgctt cacaatctct aaggacaacg ccaaaaacac tctgtacttg   240
cagatgaata gcctgaagcc tgaagcacct gccatgtact attgcgcagc tgagccctac   300
tgttctggag gctaccccg ctggtctgtg gccgagttcg gttactgggg acaaggaacc   360
caggtcacag tgtccagt                                                 378

SEQ ID NO: 232          moltype = DNA  length = 372
FEATURE                 Location/Qualifiers
source                  1..372
                        mol_type = other DNA
                        organism = synthetic construct
                        note = Description of Artificial Sequence: Synthetic
                          polynucleotide
SEQUENCE: 232
caggttcagc tccaggagtc aggcgggggt cttgtccagc ctggtggctc cctgcgcctg    60
tcctgtgctg cctccggtta cacctactcc agctattgca tgggatggtt cagacaagcg   120
ccaggcaagg aacgtgaggg ggtcgcccac attgactccg acgttccac tacctacgcc    180
gacagcgtca aaggccgctt cgcgatttct aaggataacg ctaagaatac tctgtacttg   240
cagatgaact cactgaagcc agaggacacg gccatgtatt actgcgcagc cgatccgatc   300
cccgccccg gctattgtga cggtggcccg aacaagtact ggggacaggg cacccaagtg    360
acggtgtcct ct                                                       372

SEQ ID NO: 233          moltype = DNA  length = 378
FEATURE                 Location/Qualifiers
source                  1..378
                        mol_type = other DNA
                        organism = synthetic construct
                        note = Description of Artificial Sequence: Synthetic
                          polynucleotide
SEQUENCE: 233
caggtacagt tgcaggagag cggaggcggt tccgtgcagg caggtggctc tcttagactg    60
tcctgcgccg cgagcgggta cacctacagt agctattgta tgggctggtt ccgccaggct   120
cctggtaagg gtcgcgaggg cgtcgctgcc atcgactccg atggctctac tcgctacgca   180
gattctgtca aggggcgctt cacaatttcc aaggacaacg ccaagaacac gctttacttg   240
cagatgaact cactgaagcc ggaggacacc gctatgtatt actgcgctgc cgagccctac   300
tgttctgggg gctacaagcg cactatggtg gccgagttcg gatattgggg ccagggtaca   360
caggtgaccg tcagttct                                                 378

SEQ ID NO: 234          moltype = DNA  length = 372
FEATURE                 Location/Qualifiers
source                  1..372
                        mol_type = other DNA
                        organism = synthetic construct
                        note = Description of Artificial Sequence: Synthetic
                          polynucleotide
SEQUENCE: 234
caggtgcagt tgcaggagtc tggcggtggc tctgtgcagg ctgggggctc tctgcgcctg    60
agttgcgctg ccagcggtta cacctactcc agctattgta tgggatggtt ccgccaggct   120
ccggggaagg agagggaggg cgtggcccat atcgactctg atggctccac atcctacgcc   180
gacagcgtga agggacgttt caccattagc aaggacaatg cgaagaatac cctctacttg   240
cagatgaact ccctgaagcc ggaggatact gccatgtatt actgcgccgc tgatcccatc   300
ccaggcctg ggtactgtga cggaggcccg aacaagtatt ggggacaagg aacgcaggtc    360
acagtgtcat ct                                                       372

SEQ ID NO: 235          moltype = DNA  length = 372
FEATURE                 Location/Qualifiers
source                  1..372
                        mol_type = other DNA
                        organism = synthetic construct
                        note = Description of Artificial Sequence: Synthetic
                          polynucleotide
SEQUENCE: 235
caggtacaac tccaggagag tggtggaggc tccgttcaag ccgggggctc cctgcggctg    60
tcctgtgcgg ccagcggtta cacctattca tcttactgta tgggctggtt ccggcaggcc   120
cctggtaagg aaagagaggg tgtcgctcac attgattccg acgtagtac ctcttacgca    180
gactca agggcaggtt caccatctct aaggacaacg ccaagaacac cttgtacctc       240
cagatgaact ctctgaagcc cgaggacact gcaatgtact attgtgcggc tgacccatt    300
cccgccctg atattgcga cggcggacct aacaattact ggggacaggg cacccaggtc     360
accgtcagct cc                                                       372

SEQ ID NO: 236          moltype = DNA  length = 378
```

```
FEATURE              Location/Qualifiers
source               1..378
                     mol_type = other DNA
                     organism = synthetic construct
                     note = Description of Artificial Sequence: Synthetic
                       polynucleotide
SEQUENCE: 236
caggttcagc tccaagaatc cggcgggggc tctgtgcagg cgggcggaag tctgcgtctg    60
tcatgcgctg ccagcgggta cacttactct tccggttgta tgggctggtt taggcaggct   120
ccgggaaagg aaagggaggg cgtcgcaact atcaacagcg acggctctac gaactacgct   180
gactctgtga aaggccgctt caccatcagc aaagacaacg ccaaaaatac actgtatctc   240
cagatgaata gcttgaaacc cgaggacacc ggaatgtatt actgcgcggc agagccatac   300
tgttcaggcg gttacccaag atggtccgtg gctgagttcg gttattgggg gcagggcact   360
caggttactg tgtcttcc                                                 378

SEQ ID NO: 237       moltype = DNA   length = 375
FEATURE              Location/Qualifiers
source               1..375
                     mol_type = other DNA
                     organism = synthetic construct
                     note = Description of Artificial Sequence: Synthetic
                       polynucleotide
SEQUENCE: 237
caggtgcagc tccaggaatc cggggggcggt tctgtgcagg ctggtggctc tctgcgcctg   60
tcttgcactg tttccaggta cactgcctct gtaaactata tgggctggtt tagacaagct   120
ccgggcaagg aacgcgaagg cgtcgctacc atctttacag gtgcaggtac gacctattac   180
gccaatagcg ttaaagggag gttcaccatc tccagggaca atgccaaaaa cacagcctat   240
ctccagatga actccctcaa acctgaagac acagccatct actattgcgc ggttgacttc   300
cgtggtggcc tgctctatag accggcgtat gagtacacct accgtggaca aggcacccaa   360
gtcacagtga gcagc                                                    375

SEQ ID NO: 238       moltype = DNA   length = 378
FEATURE              Location/Qualifiers
source               1..378
                     mol_type = other DNA
                     organism = synthetic construct
                     note = Description of Artificial Sequence: Synthetic
                       polynucleotide
SEQUENCE: 238
caggtgcagc tccaagagtc cggcggaggg agtgtagagg ctggcgggtc cctgcgcctt    60
agctgcgcgg ccagcggcta tacacacagt tcttattgta tgggttggtt ccgccaagct   120
ccgggaaagg agcgtgaggg cgtggctgcc atcgacgtgg atggctccac aacctacgcc   180
gacagcgtga agggcaggtt tacgatctct aaggataacg ctaagaatac tctctatttg   240
cagatgaact ccctcaaacc cgaggataca ggaatgtact attgcgctgc cgagttcgcc   300
gactgctcaa gcaattattt cctgcctcca ggagccgtta ggtactgggg ccaggggact   360
caggtcacag taagcagc                                                 378

SEQ ID NO: 239       moltype = DNA   length = 375
FEATURE              Location/Qualifiers
source               1..375
                     mol_type = other DNA
                     organism = synthetic construct
                     note = Description of Artificial Sequence: Synthetic
                       polynucleotide
SEQUENCE: 239
caggtgcagc tccaggagag cggtggcgga tcagtgcagg ctggaggctc cctcagactg    60
tcctgcaccg tgagccgcta taccgcctcc gtcaactata tgggatggtt taggcaggct   120
ccgggcaagg agcgcgaggg ggtcgcgact atcttcaccg gagccggtac tacctattac   180
gctaattctg ttaaaggccg ctttaccatt agtcgcgaca acgtaagaa cacagcttac    240
ctccagatga actctctgaa gccagaggat accgccatgt attactgcgc cgtggacttc   300
cggggcggtt tgctctaccg cccggcctac gaatacacct atcgcggcca gggcacgcag   360
gtcacggtgt cctca                                                    375

SEQ ID NO: 240       moltype = DNA   length = 378
FEATURE              Location/Qualifiers
source               1..378
                     mol_type = other DNA
                     organism = synthetic construct
                     note = Description of Artificial Sequence: Synthetic
                       polynucleotide
SEQUENCE: 240
caggtgcagc tccaagagtc cggtggaggc agcgtccagg ccggggggtag tcttaggctc    60
agctgtgctg ccagtggaga cacctactct tcctattgca tgggatggtt cagacaggcc   120
cccggcaaag agcgtgaggg cgttgcattc atcgactccg acggctccac tcgctacgcc   180
gatagcgtgg agggccgttt taccatctcc aaggacaacg cgaagaacac tctgtatctg   240
caaatgaact ccctgaagcc cgaagacacc gccatgtact attgcgcggc tgagccatac   300
tgtagtggcg gatatcatcg taaggaaatg gcagagttcg gctattgggg ccagggcacc   360
caggtcactg tgagttcc                                                 378
```

```
SEQ ID NO: 241          moltype = DNA  length = 372
FEATURE                 Location/Qualifiers
source                  1..372
                        mol_type = other DNA
                        organism = synthetic construct
                        note = Description of Artificial Sequence: Synthetic
                          polynucleotide
SEQUENCE: 241
caggtgcagt tgcaggaatc cggcggaggc tctgtgcagg cgggcggttc cctccgcctg   60
agttgtgccg cgtctggcta tacttactct tcctattgta tgggatggtt ccggcaagcg  120
cccggcaaag agcgggaggg cgttgcgcat atcgacagtg atggtagcac cagttacgct  180
gatagcgtga aaggcagatt cactatctca aaggataacg cgaagaacac tctttacctc  240
cagatgaact cccttaaacc tgaggatacc gcgatgtatt actgtgctgc cgaccccatt  300
cccggccctg gatactgtga cggaggccct aacaagtacc gtgggcaagg aacacaggtc  360
acagtgtcca gc                                                      372

SEQ ID NO: 242          moltype = DNA  length = 372
FEATURE                 Location/Qualifiers
source                  1..372
                        mol_type = other DNA
                        organism = synthetic construct
                        note = Description of Artificial Sequence: Synthetic
                          polynucleotide
SEQUENCE: 242
caggtgcaac tccaggagtc tggcgggggc agcgtccagg caggtggaag tctccgtctc   60
tcatgtgctg ccagcggcta tacatactcc agctactgta tgggatggtt tagacaggca  120
cccggcaagg agcgcgaagg ggtgcccat atcgactccg atggcagcac aacctatgcc  180
gactctgtga aagggcggtt cgccatctcc aaggacaacg ctaagaatac cctgtacctc  240
cagatgaact ctctgaagcc tgaggacacc gccatgtatt actgcgctgc cgacccaatc  300
cctggcccag gttactgcga tgggggacca aacaaatatt ggggacaggg cacgcaggtt  360
acagtctcca gc                                                      372

SEQ ID NO: 243          moltype = DNA  length = 363
FEATURE                 Location/Qualifiers
source                  1..363
                        mol_type = other DNA
                        organism = synthetic construct
                        note = Description of Artificial Sequence: Synthetic
                          polynucleotide
SEQUENCE: 243
caggtccaac tccaggaaag tggaggtggc tctgttcagg ccgggggcag cctgaggctg   60
agctgcaccg gctcaggcta tacagccagt aataactgca tgggctggtt ccgtcaagcg  120
cccggcaaag agcgtgaagg tgtggccgta attttaccg gcgctaacgc cagctattac  180
gacagttccg tgggccgtct gttcatcagc tcacaggacg ccgcttccac cctcgatcag  240
ttgctgatga gccttctgcc cgatgacacc gcagtaatgt actgtggagc cgaagatgac  300
tgcacactgc tcctgatgac gccaaacccc gatgaccaat ggtcccgcct gagtgtgtcc  360
tcc                                                                363

SEQ ID NO: 244          moltype = DNA  length = 372
FEATURE                 Location/Qualifiers
source                  1..372
                        mol_type = other DNA
                        organism = synthetic construct
                        note = Description of Artificial Sequence: Synthetic
                          polynucleotide
SEQUENCE: 244
caggtgcagc tccaggagag cgggggcggt tctgttcagg cgggaggcag cctgcgtctg   60
tcctgtgcag cctctggtta cacagacagt cgttactgca tgggctggtt ccgcaaggca  120
cctggaaagg agcgcgaggg tgttgcgcac atcgactccg acgggagcac tagctatgct  180
gacagcgtga aggggcgctt cactatcagc aaggataacg cgaaaaacac cttgtaccttt  240
cagatgaact ccctcaaacc cgaagacaca gcgatgtact attgtgccgc tgatccgatc  300
ccagggcctg gctactgtga tggtggacct aataagtact ggggcaggg aactcaggtg  360
accgtgtcat ca                                                      372

SEQ ID NO: 245          moltype = DNA  length = 378
FEATURE                 Location/Qualifiers
source                  1..378
                        mol_type = other DNA
                        organism = synthetic construct
                        note = Description of Artificial Sequence: Synthetic
                          polynucleotide
SEQUENCE: 245
caggtccagt tgcaggaatc tggaggcggt tccgtgcaag caggggctc actcagactg   60
tcctgcgctg ccagcggcta cacttactct tcatattgca tgggctggtt cgccaggca  120
ccgggcaagg agcgggaagg cgtgccgct attgatagcg atggctctac gcgctacgca  180
gatagcgtga aaggcaggtt cacgatctcc aaagataatg ccaagaaaat tctgtatctc  240
cagatgaact ctctgaaggt cgaggacacc gccatgtact attgtgcagc gaaccctac  300
tgttctggtg gctacaagag gactatggtg gccgagttcg gcttctgggg ccaggggacc  360
caagtgactg tcagtagc                                                378
```

```
SEQ ID NO: 246           moltype = DNA  length = 372
FEATURE                  Location/Qualifiers
source                   1..372
                         mol_type = other DNA
                         organism = synthetic construct
                         note = Description of Artificial Sequence: Synthetic
                             polynucleotide
SEQUENCE: 246
caggtgcaac ttcaggagag cggtggcgga tctgtgcagg ctggagggtc tctgaagctg   60
tcctgcgcgg ccagcggtta cacatacagt agctactgca tgggatggtt tcgtcaggcc  120
ccaggcaagg agcgcgaagg agtggcgcac atcgactccg atgggtccac cacatacgcc  180
gactccgtga agggccgttt cacaatcagc aaggataacg cgaagaacac gctgtacttg  240
cagatgaact ctctcaaacc agaggacact gcaatgtact attgcgcggc tgaccccatc  300
cctggccctg gttactgtga cggtggcccc aacaattact gggggcaagg gacccaagtc  360
accgtgtcct cc                                                      372

SEQ ID NO: 247           moltype = DNA  length = 372
FEATURE                  Location/Qualifiers
source                   1..372
                         mol_type = other DNA
                         organism = synthetic construct
                         note = Description of Artificial Sequence: Synthetic
                             polynucleotide
SEQUENCE: 247
caggtccagc tccaggagtc cggcggggc tccgtccagg caggggggctc cctgcgtctg   60
tcatgcgccg cttctgggta tacctacagt tcctattgta tgggttggtt tcgccaagca  120
cccggtaagg agcgcgaagg tattgcgcac attgatagcg atggctccac aacctatgct  180
gacagtgtga aaggacgctt cactatttcc aaggataacg ctaagaacac actctacctt  240
cagatgaaca gcctgaagcc ggaagacacc gcaatgtact attgtgcagc tgaccccatt  300
cctggacccg gttactgtga tggaggtcct aataactatt ggggacaggg cactcaagtg  360
accgtctcaa gc                                                      372

SEQ ID NO: 248           moltype = DNA  length = 372
FEATURE                  Location/Qualifiers
source                   1..372
                         mol_type = other DNA
                         organism = synthetic construct
                         note = Description of Artificial Sequence: Synthetic
                             polynucleotide
SEQUENCE: 248
caggtgcagt tgcaggagag cgggggtggc tctgtgcagg ccgggggctc cctgaggctg   60
agctgcgcgg ccagcgggta cagctactct agctattgcg tgggttggtt cgccaggcc  120
cctggcaagg agcgcgaggg agtggccacg attgactcag atggcatgac ccgttatgcg  180
gattccgtca agggcgcctt caccatcagc aaagataacg ccaaaaatac cctgtacttg  240
cagatgaact cactgaaacc tgaggataca gccatgtatt actgcgcagc tccgctctat  300
gactgtgact ctggtgccgt gggtagaaac ccaccttact gggggcaggg aacccaggtg  360
accgtgtcct ca                                                      372

SEQ ID NO: 249           moltype = DNA  length = 366
FEATURE                  Location/Qualifiers
source                   1..366
                         mol_type = other DNA
                         organism = synthetic construct
                         note = Description of Artificial Sequence: Synthetic
                             polynucleotide
SEQUENCE: 249
caggtccagc tccaggaaag cggtgggggc agcgtccaaa caggggtag cctgcgcctc    60
tcttgcgcag ccagcggcta cacatatctg cgcggatgta tgggctggtt ccgccaggcc  120
cctggtaagg aaagagaggg ggtggccgtg atggacgtgg ttggagacag acgttcctac  180
attgattccg tgaagggccg ctttactatc tcacgcgata acgcggctaa ctctgtgtat  240
ttgcagatgg ataacctgaa gcccgaggac accgctatgt actattgcac agctggtccc  300
aactgtgtcg gttggcgctc cggcctggac tattggggtc agggaaccca ggttacagtt  360
agcagt                                                             366

SEQ ID NO: 250           moltype = DNA  length = 381
FEATURE                  Location/Qualifiers
source                   1..381
                         mol_type = other DNA
                         organism = synthetic construct
                         note = Description of Artificial Sequence: Synthetic
                             polynucleotide
SEQUENCE: 250
caggtgcagc tccaggagag tggtggcggt tctgtccaag ctggcggagc cctgcgcctg   60
tcctgcacag caagcggcta caccgcctct agcatttgca tgggatggtt ccgtcaggcc  120
ccaggcaagg agagggagg agtggctgtg attaccacgg cagcctccgg tacttactat  180
gccgactctg tgaatggccg cttctcaatc tctcagaata cgccaaaaaa tactgtgtac  240
ctccagatga actccctgaa acctgacgat accgcgatgt attactgcgc agccaccagg  300
cgcggcggtg actgcctgga cccattgcag accccagcct ataatacctg gggccaggga  360
```
acccaggtca ccgtctcttc t                                                   381

SEQ ID NO: 251          moltype = DNA   length = 369
FEATURE                 Location/Qualifiers
source                  1..369
                        mol_type = other DNA
                        organism = synthetic construct
                        note = Description of Artificial Sequence: Synthetic
                            polynucleotide
SEQUENCE: 251
caggtgcagc tccaggaaag cggcggtggc tccgtccagg ccgtggctc cctgaggctg          60
agctgtgtgg cttccggcga tacttattct cgcaagtaca tcgcatgggt gcgtcaggtg        120
cccggtaaag aacgtgaggg agtggcagtg atgtataccc aggctccgc tacttactat         180
acagacacag tgatgggtcg tttcaccatc tcccaggaca acgccaagaa cactgtgtac        240
cttcaaatga acagcctcaa acctgaagac accgccatgt acttttgcgc ggccaaggcc        300
agcggctcca tgtttaactt ccgcgattac acttattggg acagggcac tcaggtgacc         360
gtaagctct                                                                369

SEQ ID NO: 252          moltype = DNA   length = 363
FEATURE                 Location/Qualifiers
source                  1..363
                        mol_type = other DNA
                        organism = synthetic construct
                        note = Description of Artificial Sequence: Synthetic
                            polynucleotide
SEQUENCE: 252
caggtgcagc tgcaagaaag cggaggtggc tctgtccagg caggaggctc cctccggctt        60
agctgcgcta ccagcgggta tgcttcctgt tcccgcgcca tgaggtggta caggcaggca       120
ccgggcaagg agcgcgaatt tgtggcgtac atcgacgggg tgggcagtac tggttatgcg        180
gacagcgtta aaggccggtt taccatctcc caagataatg caaagtacac ggcttacttg        240
cagatgaact ccctcaagcc tgaggatacc gcgatgtatt actgtaatcg gggctgtaga        300
gccgatggta gcaatagtct ggacaactac tggggccagg gcacacaggt gactgtctct        360
tca                                                                      363

SEQ ID NO: 253          moltype = DNA   length = 375
FEATURE                 Location/Qualifiers
source                  1..375
                        mol_type = other DNA
                        organism = synthetic construct
                        note = Description of Artificial Sequence: Synthetic
                            polynucleotide
SEQUENCE: 253
caggtgcagt tgcaggagtc cggcggtggc agcgttcagg cgggcggtag cctgcgtctg        60
agctgcgccg cgtccggcta cacctataac cgtcgcttca tgggttggtt ccgtcaagcg       120
cccggcaagg agagagaggg cctcgccatt atctacaccc caacagctc cacctctac          180
gccgactctg tgacgggccg ctttacaatc tcacaggatt ctgcccgcaa caccgtctat        240
ttgcagatga actccctgaa acctgaggac accgctatgt actattgtgc agccgctcgc        300
atcgcttcta tgactgagct ttcagtgaga gatatggact attggggcaa gggcacccag        360
gtgaccgttt cctcc                                                         375

SEQ ID NO: 254          moltype = DNA   length = 378
FEATURE                 Location/Qualifiers
source                  1..378
                        mol_type = other DNA
                        organism = synthetic construct
                        note = Description of Artificial Sequence: Synthetic
                            polynucleotide
SEQUENCE: 254
caggtacaac tccaggagag cggggggaggt agcgtacagg ctggcgggtc cttgcgtctg       60
agctgcactg catctcgtta catcgctctt aatgcgtgta tggcttggat tcggcaggcc       120
cccggctccg aaagggaggt cgtggccaca atcgtgactg atggctccag aacctattac       180
gcagactctg tcaagggccg gtttactatc tctcaagaca acgccaagaa caccatgtac       240
ctccagatga acgtttgaa acccgaagac accgccatgt attactgtgc agccgacagg         300
cgctgcccccg tgtccagagc cccatacgaa tacgaactgc gctactgggg tcagggcacc     360
caggtgactg tcagcagc                                                      378

SEQ ID NO: 255          moltype = DNA   length = 369
FEATURE                 Location/Qualifiers
source                  1..369
                        mol_type = other DNA
                        organism = synthetic construct
                        note = Description of Artificial Sequence: Synthetic
                            polynucleotide
SEQUENCE: 255
caagtccagc ttcaagaaag cggaggggggc tctgttcagg caggcgggtc cctccggctg       60
tcctgcgctg cctccggcta cacatacaac ggaaagtgca tggcttggtt ccgccaggct       120
cccggcaagg agcgcgaagt cgtgctggc atttacaccg ggggctccag cacatattac        180
gccgatagtg tgaaggacg ctttacgatt tcccaagaca tgctaaaaa tacagtctat         240
ctccagatgg acagcctgaa gcccgaagac actgccatgt attactgcgc caccagcaga       300

-continued

```
agctgtagcg  acctgcgcag  acgctccatc  gcctactggg  gacagggggac  tcaggtcacc    360
gtcagctct                                                                  369
```

SEQ ID NO: 256        moltype = AA  length = 263
FEATURE               Location/Qualifiers
source                1..263
                      mol_type = protein
                      organism = synthetic construct
                      note = Description of Artificial Sequence: Synthetic
                         polypeptide
SEQUENCE: 256
QVQLQESGGG SVQAGGSLRL SCAASRYLYS IDYMAWFRQS PGKEREPVAV IYTASGATFY    60
PDSVKGRFTI SQDNAKMTVY LQMNSLKSED TAMYYCAAVR KTDSYLFDAQ SFTYWGQGTQ   120
VTVSSGGGSQ VQLQESGGGS VQAGGSLRLS CAASGYTYSS GCMGWFRQAP GKEREAVAAI   180
NSDGSTSYAD SVKGRFTISK DNAKNTLYLQ MNSLKPEDTA MYYCAAEPYC SGGYPRWSVA   240
EFGYWGQGTQ VTVSSASHHH HHH                                           263

SEQ ID NO: 257        moltype = AA  length = 261
FEATURE               Location/Qualifiers
source                1..261
                      mol_type = protein
                      organism = synthetic construct
                      note = Description of Artificial Sequence: Synthetic
                         polypeptide
SEQUENCE: 257
QVQLQESGGG SVQAGGSLRL SCAASRYLYS IDYMAWFRQS PGKEREPVAV IYTASGATFY    60
PDSVKGRFTI SQDNAKMTVY LQMNSLKSED TAMYYCAAVR KTDSYLFDAQ SFTYWGQGTQ   120
VTVSSGGGSQ VQLQESGGGS VQAGGSLRLS CAASGYTYSS YCMGWFRQAP GKEREGVAHI   180
DSDGSTSYAD SVKGRFTISK DNAKNTLYLQ MNSLKPEDTA MYYCAADPIP GPGYCDGGPN   240
KYWGQGTQVT VSSASHHHHH H                                             261

SEQ ID NO: 258        moltype = AA  length = 258
FEATURE               Location/Qualifiers
source                1..258
                      mol_type = protein
                      organism = synthetic construct
                      note = Description of Artificial Sequence: Synthetic
                         polypeptide
SEQUENCE: 258
QVQLQESGGG SVQAGGSLRL SCAASRYLYS IDYMAWFRQS PGKEREPVAV IYTASGATFY    60
PDSVKGRFTI SQDNAKMTVY LQMNSLKSED TAMYYCAAVR KTDSYLFDAQ SFTYWGQGTQ   120
VTVSSGGGSQ VQLQESGGGS VQAGGSLRLS CAASRYTYNS YCMGWFRQAP GKEREGVATI   180
DSDGMTRYAD SVKGRFTISK DNAKNTLYLQ MNSLKPEDTA MYYCAADADC TIAAMTTNPL   240
GQGTQVTVSS ASHHHHHH                                                 258

SEQ ID NO: 259        moltype = AA  length = 262
FEATURE               Location/Qualifiers
source                1..262
                      mol_type = protein
                      organism = synthetic construct
                      note = Description of Artificial Sequence: Synthetic
                         polypeptide
SEQUENCE: 259
QVQLQESGGG SVQAGGSLRL SCAASRYLYS IDYMAWFRQS PGKEREPVAV IYTASGATFY    60
PDSVKGRFTI SQDNAKMTVY LQMNSLKSED TAMYYCAAVR KTDSYLFDAQ SFTYWGQGTQ   120
VTVSSGGGSQ VQLQESGGGS VQAGGSLRLS CTVSRYTASV NYMGWFRQAP GKEREGVATI   180
FTGAGTTYYA NSVKGRFTIS RDNAKNTAYL QMNSLKPEDT AIYYCAVDFR GGLLYRPAYE   240
YTYRGQGTQV TVSSASHHHH HH                                            262

SEQ ID NO: 260        moltype = AA  length = 263
FEATURE               Location/Qualifiers
source                1..263
                      mol_type = protein
                      organism = synthetic construct
                      note = Description of Artificial Sequence: Synthetic
                         polypeptide
SEQUENCE: 260
QVQLQESGGG SVQAGGSLRL SCAASRYLYS IDYMAWFRQS PGKEREPVAV IYTASGATFY    60
PDSVKGRFTI SQDNAKMTVY LQMNSLKSED TAMYYCAAVR KTDSYLFDAQ SFTYWGQGTQ   120
VTVSSGGGSQ VQLQESGGGS VEAGGSLRLS CAASGYTHSS YCMGWFRQAP GKEREGVAAI   180
DVDGSTTYAD SVKGRFTISK DNAKNTLYLQ MNSLKPEDTG MYYCAAEFAD CSSNYFLPPG   240
AVRYWGQGTQ VTVSSASHHH HHH                                           263

SEQ ID NO: 261        moltype = AA  length = 261
FEATURE               Location/Qualifiers
source                1..261
                      mol_type = protein
                      organism = synthetic construct
                      note = Description of Artificial Sequence: Synthetic

```
                            polypeptide
SEQUENCE: 261
QVQLQESGGG SVQAGGSLRL SCAASRYLYS IDYMAWFRQS PGKEREPVAV IYTASGATFY   60
PDSVKGRFTI SQDNAKMTVY LQMNSLKSED TAMYYCAAVR KTDSYLFDAQ SFTYWGQGTQ  120
VTVSSGGGSQ VQLQESGGGS VQAGGSLRLS CAASGYSYSS YCMGWFRQAP GKEREGVATI  180
DSDGMTRYAD SVKGRFTISK DNAKNTLYLQ MNSLKPEDTA MYYCAAPLYD CDSGAVGRNP  240
PYWGQGTQVT VSSASHHHHH H                                           261

SEQ ID NO: 262          moltype = AA  length = 259
FEATURE                 Location/Qualifiers
source                  1..259
                        mol_type = protein
                        organism = synthetic construct
                        note = Description of Artificial Sequence: Synthetic
                            polypeptide
SEQUENCE: 262
QVQLQESGGG SVQAGGSLRL SCAASRYLYS IDYMAWFRQS PGKEREPVAV IYTASGATFY   60
PDSVKGRFTI SQDNAKMTVY LQMNSLKSED TAMYYCAAVR KTDSYLFDAQ SFTYWGQGTQ  120
VTVSSGGGSQ VQLQESGGGS VQTGGSLRLS CAASGYTYLR GCMGWFRQAP GKEREGVAVM  180
DVVGDRRSYI DSVKGRFTIS RDNAANSVYL QMDNLKPEDT AMYYCTAGPN CVGWRSGLDY  240
WGQGTQVTVS SASHHHHHH                                              259

SEQ ID NO: 263          moltype = AA  length = 267
FEATURE                 Location/Qualifiers
source                  1..267
                        mol_type = protein
                        organism = synthetic construct
                        note = Description of Artificial Sequence: Synthetic
                            polypeptide
SEQUENCE: 263
QVQLQESGGG SVQAGGSLRL SCAASRFTYS SYCMGWFRQA PGKEREGVAS IDSDGSTSYT   60
DSVKGRFTIS KDNAKNTLYL QMNSLKPEDT AMYYCALDLM STVVPGFCGF LLSAGMDYWG  120
KGTQVTVSSG GGSVQLQES GGGSVQAGGS LRLSCAASGY TYSSGCMGWF RQAPGKEREA  180
VAAINSDGST SYADSVKGRF TISKDNAKNT LYLQMNSLKP EDTAMYYCAA EPYCSGGYPR  240
WSVAEFGYWG QGTQVTVSSA SHHHHHH                                     267

SEQ ID NO: 264          moltype = AA  length = 265
FEATURE                 Location/Qualifiers
source                  1..265
                        mol_type = protein
                        organism = synthetic construct
                        note = Description of Artificial Sequence: Synthetic
                            polypeptide
SEQUENCE: 264
QVQLQESGGG SVQAGGSLRL SCAASRFTYS SYCMGWFRQA PGKEREGVAS IDSDGSTSYT   60
DSVKGRFTIS KDNAKNTLYL QMNSLKPEDT AMYYCALDLM STVVPGFCGF LLSAGMDYWG  120
KGTQVTVSSG GGSVQLQES GGGSVQAGGS LRLSCAASGY TYSSYCMGWF RQAPGKEREG  180
VAHIDSDGST SYADSVKGRF TISKDNAKNT LYLQMNSLKP EDTAMYYCAA DPIPGPGYCD  240
GGPNKYWGQG TQVTVSSASH HHHH                                        265

SEQ ID NO: 265          moltype = AA  length = 262
FEATURE                 Location/Qualifiers
source                  1..262
                        mol_type = protein
                        organism = synthetic construct
                        note = Description of Artificial Sequence: Synthetic
                            polypeptide
SEQUENCE: 265
QVQLQESGGG SVQAGGSLRL SCAASRFTYS SYCMGWFRQA PGKEREGVAS IDSDGSTSYT   60
DSVKGRFTIS KDNAKNTLYL QMNSLKPEDT AMYYCALDLM STVVPGFCGF LLSAGMDYWG  120
KGTQVTVSSG GGSVQLQES GGGSVQAGGS LRLSCAASRY TYNSYCMGWF RQAPGKEREG  180
VATIDSDGMT RYADSVKGRF TISKDNAKNT LYLQMNSLKP EDTAMYYCAA DADCTIAAMT  240
TNPLGQGTQV TVSSASHHHH HH                                          262

SEQ ID NO: 266          moltype = AA  length = 266
FEATURE                 Location/Qualifiers
source                  1..266
                        mol_type = protein
                        organism = synthetic construct
                        note = Description of Artificial Sequence: Synthetic
                            polypeptide
SEQUENCE: 266
QVQLQESGGG SVQAGGSLRL SCAASRFTYS SYCMGWFRQA PGKEREGVAS IDSDGSTSYT   60
DSVKGRFTIS KDNAKNTLYL QMNSLKPEDT AMYYCALDLM STVVPGFCGF LLSAGMDYWG  120
KGTQVTVSSG GGSVQLQES GGGSVQAGGS LRLSCTVSRY TASVNYMGWF RQAPGKEREG  180
VATIFTGAGT TYYANSVKGR FTISRDNAKN TAYLQMNSLK PEDTAIYYCA VDFRGGLLYR  240
PAYEYTYRGQ GTQVTVSSAS HHHHHH                                      266

SEQ ID NO: 267          moltype = AA  length = 267
```

```
FEATURE                 Location/Qualifiers
source                  1..267
                        mol_type = protein
                        organism = synthetic construct
                        note = Description of Artificial Sequence: Synthetic
                          polypeptide
SEQUENCE: 267
QVQLQESGGG SVQAGGSLRL SCAASRFTYS SYCMGWFRQA PGKEREGVAS IDSDGSTSYT      60
DSVKGRFTIS KDNAKNTLYL QMNSLKPEDT AMYYCALDLM STVVPGFCGF LLSAGMDYWG     120
KGTQVTVSSG GGSQVQLQES GGGSVEAGGS LRLSCAASGY THSSYCMGWF RQAPGKEREG     180
VAAAIDVDGST TYADSVKGRF TISKDNAKNT LYLQMNSLKP EDTGMYYCAA EFADCSSNYF    240
LPPGAVRYWG QGTQVTVSSA SHHHHHH                                        267

SEQ ID NO: 268          moltype = AA   length = 265
FEATURE                 Location/Qualifiers
source                  1..265
                        mol_type = protein
                        organism = synthetic construct
                        note = Description of Artificial Sequence: Synthetic
                          polypeptide
SEQUENCE: 268
QVQLQESGGG SVQAGGSLRL SCAASRFTYS SYCMGWFRQA PGKEREGVAS IDSDGSTSYT      60
DSVKGRFTIS KDNAKNTLYL QMNSLKPEDT AMYYCALDLM STVVPGFCGF LLSAGMDYWG     120
KGTQVTVSSG GGSQVQLQES GGGSVQAGGS LRLSCAASGY SYSSYCMGWF RQAPGKEREG     180
VATIDSDGMT RYADSVKGRF TISKDNAKNT LYLQMNSLKP EDTAMYYCAA PLYDCDSGAV     240
GRNPPYWGQG TQVTVSSASH HHHHH                                          265

SEQ ID NO: 269          moltype = AA   length = 263
FEATURE                 Location/Qualifiers
source                  1..263
                        mol_type = protein
                        organism = synthetic construct
                        note = Description of Artificial Sequence: Synthetic
                          polypeptide
SEQUENCE: 269
QVQLQESGGG SVQAGGSLRL SCAASRFTYS SYCMGWFRQA PGKEREGVAS IDSDGSTSYT      60
DSVKGRFTIS KDNAKNTLYL QMNSLKPEDT AMYYCALDLM STVVPGFCGF LLSAGMDYWG     120
KGTQVTVSSG GGSQVQLQES GGGSVQTGGS LRLSCAASGY TYLRGCMGWF RQAPGKEREG     180
VAVMDVVGDR RSYIDSVKGR FTISRDNAAN SVYLQMDNLK PEDTAMYYCT AGPNCVGWRS     240
GLDYWGQGTQ VTVSSASHHH HHH                                            263

SEQ ID NO: 270          moltype = AA   length = 269
FEATURE                 Location/Qualifiers
source                  1..269
                        mol_type = protein
                        organism = synthetic construct
                        note = Description of Artificial Sequence: Synthetic
                          polypeptide
SEQUENCE: 270
QVQLQESGGG SVQAGGSLRL SCAASGYTYS MYCMGWFRQA PGKEREGVAQ INSDGSTSYA      60
DSVKGRFTIS KDNAKNTLYL QMNSLKPEDT AMYYCAADSR VYGGSWYERL CGPYTYEYNY     120
WGQGTQVTVS SGGGSQVQLQ ESGGGSVQAG GSLRLSCAAS GYTYSSGCMG WFRQAPGKER     180
EAVAAINSDG STSYADSVKG RFTISKDNAK NTLYLQMNSL KPEDTAMYYC AAEPYCSGGY     240
PRWSVAEFGY WGQGTQVTVS SASHHHHHH                                      269

SEQ ID NO: 271          moltype = AA   length = 267
FEATURE                 Location/Qualifiers
source                  1..267
                        mol_type = protein
                        organism = synthetic construct
                        note = Description of Artificial Sequence: Synthetic
                          polypeptide
SEQUENCE: 271
QVQLQESGGG SVQAGGSLRL SCAASGYTYS MYCMGWFRQA PGKEREGVAQ INSDGSTSYA      60
DSVKGRFTIS KDNAKNTLYL QMNSLKPEDT AMYYCAADSR VYGGSWYERL CGPYTYEYNY     120
WGQGTQVTVS SGGGSQVQLQ ESGGGSVQAG GSLRLSCAAS GYTYSSYCMG WFRQAPGKER     180
EGVAHIDSDG STSYADSVKG RFTISKDNAK NTLYLQMNSL KPEDTAMYYC AADPIPGPGY     240
CDGGPNKYWG QGTQVTVSSA SHHHHHH                                        267

SEQ ID NO: 272          moltype = AA   length = 264
FEATURE                 Location/Qualifiers
source                  1..264
                        mol_type = protein
                        organism = synthetic construct
                        note = Description of Artificial Sequence: Synthetic
                          polypeptide
SEQUENCE: 272
QVQLQESGGG SVQAGGSLRL SCAASGYTYS MYCMGWFRQA PGKEREGVAQ INSDGSTSYA      60
DSVKGRFTIS KDNAKNTLYL QMNSLKPEDT AMYYCAADSR VYGGSWYERL CGPYTYEYNY     120
```

```
WGQGTQVTVS SGGGSQVQLQ ESGGGSVQAG GSLRLSCAAS RYTYNSYCMG WFRQAPGKER   180
EGVATIDSDG MTRYADSVKG RFTISKDNAK NTLYLQMNSL KPEDTAMYYC AADADCTIAA   240
MTTNPLGQGT QVTVSSASHH HHHH                                         264

SEQ ID NO: 273           moltype = AA  length = 268
FEATURE                  Location/Qualifiers
source                   1..268
                         mol_type = protein
                         organism = synthetic construct
                         note = Description of Artificial Sequence: Synthetic
                         polypeptide
SEQUENCE: 273
QVQLQESGGG SVQAGGSLRL SCAASGYTYS MYCMGWFRQA PGKEREGVAQ INSDGSTSYA   60
DSVKGRFTIS KDNAKNTLYL QMNSLKPEDT AMYYCAADSR VYGGSWYERL CGPYTYEYNY   120
WGQGTQVTVS SGGGSQVQLQ ESGGGSVQAG GSLRLSCTVS RYTASVNYMG WFRQAPGKER   180
EGVATIFTGA GTTYYANSVK GRFTISRDNA KNTAYLQMNS LKPEDTAIYY CAVDFRGGLL   240
YRPAYEYTYR GQGTQVTVSS ASHHHHHH                                     268

SEQ ID NO: 274           moltype = AA  length = 269
FEATURE                  Location/Qualifiers
source                   1..269
                         mol_type = protein
                         organism = synthetic construct
                         note = Description of Artificial Sequence: Synthetic
                         polypeptide
SEQUENCE: 274
QVQLQESGGG SVQAGGSLRL SCAASGYTYS MYCMGWFRQA PGKEREGVAQ INSDGSTSYA   60
DSVKGRFTIS KDNAKNTLYL QMNSLKPEDT AMYYCAADSR VYGGSWYERL CGPYTYEYNY   120
WGQGTQVTVS SGGGSQVQLQ ESGGGSVEAG GSLRLSCAAS GYTHSSYCMG WFRQAPGKER   180
EGVAAIDVDG STTYADSVKG RFTISKDNAK NTLYLQMNSL KPEDTGMYYC AAEFADCSSN   240
YFLPPGAVRY WGQGTQVTVS SASHHHHHH                                    269

SEQ ID NO: 275           moltype = AA  length = 267
FEATURE                  Location/Qualifiers
source                   1..267
                         mol_type = protein
                         organism = synthetic construct
                         note = Description of Artificial Sequence: Synthetic
                         polypeptide
SEQUENCE: 275
QVQLQESGGG SVQAGGSLRL SCAASGYTYS MYCMGWFRQA PGKEREGVAQ INSDGSTSYA   60
DSVKGRFTIS KDNAKNTLYL QMNSLKPEDT AMYYCAADSR VYGGSWYERL CGPYTYEYNY   120
WGQGTQVTVS SGGGSQVQLQ ESGGGSVQAG GSLRLSCAAS GYSYSSYCMG WFRQAPGKER   180
EGVATIDSDG MTRYADSVKG RFTISKDNAK NTLYLQMNSL KPEDTAMYYC AAPLYDCDSG   240
AVGRNPPYWG QGTQVTVSSA SHHHHHH                                      267

SEQ ID NO: 276           moltype = AA  length = 265
FEATURE                  Location/Qualifiers
source                   1..265
                         mol_type = protein
                         organism = synthetic construct
                         note = Description of Artificial Sequence: Synthetic
                         polypeptide
SEQUENCE: 276
QVQLQESGGG SVQAGGSLRL SCAASGYTYS MYCMGWFRQA PGKEREGVAQ INSDGSTSYA   60
DSVKGRFTIS KDNAKNTLYL QMNSLKPEDT AMYYCAADSR VYGGSWYERL CGPYTYEYNY   120
WGQGTQVTVS SGGGSQVQLQ ESGGGSVQTG GSLRLSCAAS GYTYLRGCMG WFRQAPGKER   180
EGVAVMDVVG DRRSYIDSVK GRFTISRDNA ANSVYLQMDN LKPEDTAMYY CTAGPNCVGW   240
RSGLDYWGQG TQVTVSSASH HHHH                                         265

SEQ ID NO: 277           moltype = AA  length = 272
FEATURE                  Location/Qualifiers
source                   1..272
                         mol_type = protein
                         organism = synthetic construct
                         note = Description of Artificial Sequence: Synthetic
                         polypeptide
SEQUENCE: 277
QVQLQESGGG SVQAGGSLRL SCAVSGYAYS TYCMGWFRQA PGKEREGVAA IDSGGSTSYA   60
DSVKGRFTIS KDNAKNTLYL RMNSLKPEDT AMYYCAAVPP PDDGGSCLFL GPEIKVSKAD   120
FRYWGQGTQV TVSSGGGSQV QLQESGGGSV QAGGSLRLSC AASGYTYSSG CMGWFRQAPG   180
KEREAVAAIN SDGSTSYADS VKGRFTISKD NAKNTLYLQM NSLKPEDTAM YYCAAEPYCS   240
GGYPRWSVAE FGYWGQGTQV TVSSASHHHH HH                                272

SEQ ID NO: 278           moltype = AA  length = 270
FEATURE                  Location/Qualifiers
source                   1..270
                         mol_type = protein
                         organism = synthetic construct
```

```
                        note = Description of Artificial Sequence: Synthetic
                              polypeptide
SEQUENCE: 278
QVQLQESGGG SVQAGGSLRL SCAVSGYAYS TYCMGWFRQA PGKEREGVAA IDSGGSTSYA    60
DSVKGRFTIS KDNAKNTLYL RMNSLKPEDT AMYYCAAVPP PPDGGSCLFL GPEIKVSKAD   120
FRYWGQGTQV TVSSGGGSQV QLQESGGGSV QAGGSLRLSC AASGYTYSSY CMGWFRQAPG   180
KEREGVAHID SDGSTSYADS VKGRFTISKD NAKNTLYLQM NSLKPEDTAM YYCAADPIPG   240
PGYCDGGPNK YWGQGTQVTV SSASHHHHHH                                   270

SEQ ID NO: 279          moltype = AA  length = 267
FEATURE                 Location/Qualifiers
source                  1..267
                        mol_type = protein
                        organism = synthetic construct
                        note = Description of Artificial Sequence: Synthetic
                              polypeptide
SEQUENCE: 279
QVQLQESGGG SVQAGGSLRL SCAVSGYAYS TYCMGWFRQA PGKEREGVAA IDSGGSTSYA    60
DSVKGRFTIS KDNAKNTLYL RMNSLKPEDT AMYYCAAVPP PPDGGSCLFL GPEIKVSKAD   120
FRYWGQGTQV TVSSGGGSQV QLQESGGGSV QAGGSLRLSC AASRYTYNSY CMGWFRQAPG   180
KEREGVATID SDGMTRYADS VKGRFTISKD NAKNTLYLQM NSLKPEDTAM YYCAADADCT   240
IAAMTTNPLG QGTQVTVSSA SHHHHHH                                      267

SEQ ID NO: 280          moltype = AA  length = 271
FEATURE                 Location/Qualifiers
source                  1..271
                        mol_type = protein
                        organism = synthetic construct
                        note = Description of Artificial Sequence: Synthetic
                              polypeptide
SEQUENCE: 280
QVQLQESGGG SVQAGGSLRL SCAVSGYAYS TYCMGWFRQA PGKEREGVAA IDSGGSTSYA    60
DSVKGRFTIS KDNAKNTLYL RMNSLKPEDT AMYYCAAVPP PPDGGSCLFL GPEIKVSKAD   120
FRYWGQGTQV TVSSGGGSQV QLQESGGGSV QAGGSLRLSC TVSRYTASVN YMGWFRQAPG   180
KEREGVATIF TGAGTTYYAN SVKGRFTISR DNAKNTAYLM NSLKPEDTA IYYCAVDFRG    240
GLLYRPAYEY TYRGQGTQVT VSSASHHHHH H                                 271

SEQ ID NO: 281          moltype = AA  length = 272
FEATURE                 Location/Qualifiers
source                  1..272
                        mol_type = protein
                        organism = synthetic construct
                        note = Description of Artificial Sequence: Synthetic
                              polypeptide
SEQUENCE: 281
QVQLQESGGG SVQAGGSLRL SCAVSGYAYS TYCMGWFRQA PGKEREGVAA IDSGGSTSYA    60
DSVKGRFTIS KDNAKNTLYL RMNSLKPEDT AMYYCAAVPP PPDGGSCLFL GPEIKVSKAD   120
FRYWGQGTQV TVSSGGGSQV QLQESGGGSV EAGGSLRLSC AASGYTHSSY CMGWFRQAPG   180
KEREGVAAID VDGSTTYADS VKGRFTISKD NAKNTLYLQM NSLKPEDTGM YYCAAEFADC   240
SSNYFLPPGA VRYWGQGTQV TVSSASHHHH HH                                272

SEQ ID NO: 282          moltype = AA  length = 270
FEATURE                 Location/Qualifiers
source                  1..270
                        mol_type = protein
                        organism = synthetic construct
                        note = Description of Artificial Sequence: Synthetic
                              polypeptide
SEQUENCE: 282
QVQLQESGGG SVQAGGSLRL SCAVSGYAYS TYCMGWFRQA PGKEREGVAA IDSGGSTSYA    60
DSVKGRFTIS KDNAKNTLYL RMNSLKPEDT AMYYCAAVPP PPDGGSCLFL GPEIKVSKAD   120
FRYWGQGTQV TVSSGGGSQV QLQESGGGSV QAGGSLRLSC AASGYSYSSY CMGWFRQAPG   180
KEREGVATID SDGMTRYADS VKGRFTISKD NAKNTLYLQM NSLKPEDTAM YYCAAPLYDC   240
DSGAVGRNPP YWGQGTQVTV SSASHHHHHH                                   270

SEQ ID NO: 283          moltype = AA  length = 268
FEATURE                 Location/Qualifiers
source                  1..268
                        mol_type = protein
                        organism = synthetic construct
                        note = Description of Artificial Sequence: Synthetic
                              polypeptide
SEQUENCE: 283
QVQLQESGGG SVQAGGSLRL SCAVSGYAYS TYCMGWFRQA PGKEREGVAA IDSGGSTSYA    60
DSVKGRFTIS KDNAKNTLYL RMNSLKPEDT AMYYCAAVPP PPDGGSCLFL GPEIKVSKAD   120
FRYWGQGTQV TVSSGGGSQV QLQESGGGSV QTGGSLRLSC AASGYTYLRG CMGWFRQAPG   180
KEREGVAVMD VVGDRRSYID SVKGRFTISR DNAANSVYLQ MDNLKPEDTA MYYCTAGPNC   240
VGWRSGLDYW GQGTQVTVSS ASHHHHHH                                     268
```

```
SEQ ID NO: 284           moltype = AA  length = 265
FEATURE                  Location/Qualifiers
source                   1..265
                         mol_type = protein
                         organism = synthetic construct
                         note = Description of Artificial Sequence: Synthetic
                         polypeptide
SEQUENCE: 284
QVQLQESGGG SVQAGGSLRL SCTVSGYTYS SNCMGWFRQA PGKEREGVAT IYTGGGNTYY    60
ADSVKGRFTI SQDNAKNTVY LQMNNLKPED TAMYYCAAEP LSRVYGGSCP TPTFDYWGQG   120
TQVTVSSGGG SQVQLQESGG GSVQAGGSLR LSCAASGYTY SSGCMGWFRQ APGKEREAVA   180
AINSDGSTSY ADSVKGRFTI SKDNAKNTLY LQMNSLKPED TAMYYCAAEP YCSGGYPRWS   240
VAEFGYWGQG TQVTVSSASH HHHHH                                        265

SEQ ID NO: 285           moltype = AA  length = 263
FEATURE                  Location/Qualifiers
source                   1..263
                         mol_type = protein
                         organism = synthetic construct
                         note = Description of Artificial Sequence: Synthetic
                         polypeptide
SEQUENCE: 285
QVQLQESGGG SVQAGGSLRL SCTVSGYTYS SNCMGWFRQA PGKEREGVAT IYTGGGNTYY    60
ADSVKGRFTI SQDNAKNTVY LQMNNLKPED TAMYYCAAEP LSRVYGGSCP TPTFDYWGQG   120
TQVTVSSGGG SQVQLQESGG GSVQAGGSLR LSCAASGYTY SSYCMGWFRQ APGKEREGVA   180
HIDSDGSTSY ADSVKGRFTI SKDNAKNTLY LQMNSLKPED TAMYYCAADP IPGPGYCDGG   240
PNKYWGQGTQ VTVSSASHHH HHH                                          263

SEQ ID NO: 286           moltype = AA  length = 260
FEATURE                  Location/Qualifiers
source                   1..260
                         mol_type = protein
                         organism = synthetic construct
                         note = Description of Artificial Sequence: Synthetic
                         polypeptide
SEQUENCE: 286
QVQLQESGGG SVQAGGSLRL SCTVSGYTYS SNCMGWFRQA PGKEREGVAT IYTGGGNTYY    60
ADSVKGRFTI SQDNAKNTVY LQMNNLKPED TAMYYCAAEP LSRVYGGSCP TPTFDYWGQG   120
TQVTVSSGGG SQVQLQESGG GSVQAGGSLR LSCAASRYTY NSYCMGWFRQ APGKEREGVA   180
TIDSDGMTRY ADSVKGRFTI SKDNAKNTLY LQMNSLKPED TAMYYCAADA DCTIAAMTTN   240
PLGQGTQVTV SSASHHHHHH                                              260

SEQ ID NO: 287           moltype = AA  length = 264
FEATURE                  Location/Qualifiers
source                   1..264
                         mol_type = protein
                         organism = synthetic construct
                         note = Description of Artificial Sequence: Synthetic
                         polypeptide
SEQUENCE: 287
QVQLQESGGG SVQAGGSLRL SCTVSGYTYS SNCMGWFRQA PGKEREGVAT IYTGGGNTYY    60
ADSVKGRFTI SQDNAKNTVY LQMNNLKPED TAMYYCAAEP LSRVYGGSCP TPTFDYWGQG   120
TQVTVSSGGG SQVQLQESGG GSVQAGGSLR LSCTVSRYTA SVNYMGWFRQ APGKEREGVA   180
TIFTGAGTTY YANSVKGRFT ISRDNAKNTA YLQMNSLKPE DTAIYYCAVD FRGGLLYRPA   240
YEYTYRGQGT QVTVSSASHH HHHH                                         264

SEQ ID NO: 288           moltype = AA  length = 265
FEATURE                  Location/Qualifiers
source                   1..265
                         mol_type = protein
                         organism = synthetic construct
                         note = Description of Artificial Sequence: Synthetic
                         polypeptide
SEQUENCE: 288
QVQLQESGGG SVQAGGSLRL SCTVSGYTYS SNCMGWFRQA PGKEREGVAT IYTGGGNTYY    60
ADSVKGRFTI SQDNAKNTVY LQMNNLKPED TAMYYCAAEP LSRVYGGSCP TPTFDYWGQG   120
TQVTVSSGGG SQVQLQESGG GSVEAGGSLR LSCAASGYTH SSYCMGWFRQ APGKEREGVA   180
AIDVDGSTTY ADSVKGRFTI SKDNAKNTLY LQMNSLKPED TGMYYCAAEF ADCSSNYFLP   240
PGAVRYWGQG TQVTVSSASH HHHH                                         265

SEQ ID NO: 289           moltype = AA  length = 263
FEATURE                  Location/Qualifiers
source                   1..263
                         mol_type = protein
                         organism = synthetic construct
                         note = Description of Artificial Sequence: Synthetic
                         polypeptide
SEQUENCE: 289
QVQLQESGGG SVQAGGSLRL SCTVSGYTYS SNCMGWFRQA PGKEREGVAT IYTGGGNTYY    60
```

```
ADSVKGRFTI SQDNAKNTVY LQMNNLKPED TAMYYCAAEP LSRVYGGSCP TPTFDYWGQG    120
TQVTVSSGGG SQVQLQESGG GSVQAGGSLR LSCAASGYSY SSYCMGWFRQ APGKEREGVA    180
TIDSDGMTRY ADSVKGRFTI SKDNAKNTLY LQMNSLKPED TAMYYCAAPL YDCDSGAVGR    240
NPPYWGQGTQ VTVSSASHHH HHH                                           263

SEQ ID NO: 290         moltype = AA  length = 261
FEATURE                Location/Qualifiers
source                 1..261
                       mol_type = protein
                       organism = synthetic construct
                       note = Description of Artificial Sequence: Synthetic
                         polypeptide
SEQUENCE: 290
QVQLQESGGG SVQAGGSLRL SCTVSGYTYS SNCMGWFRQA PGKEREGVAT IYTGGGNTYY    60
ADSVKGRFTI SQDNAKNTVY LQMNNLKPED TAMYYCAAEP LSRVYGGSCP TPTFDYWGQG    120
TQVTVSSGGG SQVQLQESGG GSVQTGGSLR LSCAASGYTY LRGCMGWFRQ APGKEREGVA    180
VMDVVGDRRS YIDSVKGRFT ISRDNAANSV YLQMDNLKPE DTAMYYCTAG PNCVGWRSGL    240
DYWGQGTQVT VSSASHHHHH H                                             261

SEQ ID NO: 291         moltype = AA  length = 264
FEATURE                Location/Qualifiers
source                 1..264
                       mol_type = protein
                       organism = synthetic construct
                       note = Description of Artificial Sequence: Synthetic
                         polypeptide
SEQUENCE: 291
QVQLQESGGG SVQAGGSLRL SCGASGYTYS SYCMGWFRQV PGKEREGVAV IDSDGSTSYA    60
DSVKGRFTIS KDNGKNTLYL QMNSLKPEDT AMYYCAADLG HYRPPCGVLY LGMDYWGKGT    120
QVTVSSGGGS QVQLQESGGG SVQAGGSLRL SCAASGYTYS SGCMGWFRQA PGKEREAVAA    180
INSDGSTSYA DSVKGRFTIS KDNAKNTLYL QMNSLKPEDT AMYYCAAEPY CSGGYPRWSV    240
AEFGYWGQGT QVTVSSASHH HHHH                                          264

SEQ ID NO: 292         moltype = AA  length = 262
FEATURE                Location/Qualifiers
source                 1..262
                       mol_type = protein
                       organism = synthetic construct
                       note = Description of Artificial Sequence: Synthetic
                         polypeptide
SEQUENCE: 292
QVQLQESGGG SVQAGGSLRL SCGASGYTYS SYCMGWFRQV PGKEREGVAV IDSDGSTSYA    60
DSVKGRFTIS KDNGKNTLYL QMNSLKPEDT AMYYCAADLG HYRPPCGVLY LGMDYWGKGT    120
QVTVSSGGGS QVQLQESGGG SVQAGGSLRL SCAASGYTYS SYCMGWFRQA PGKEREGVAH    180
IDSDGSTSYA DSVKGRFTIS KDNAKNTLYL QMNSLKPEDT AMYYCAADPI PGPGYCDGGP    240
NKYWGQGTQV TVSSASHHHH HH                                            262

SEQ ID NO: 293         moltype = AA  length = 259
FEATURE                Location/Qualifiers
source                 1..259
                       mol_type = protein
                       organism = synthetic construct
                       note = Description of Artificial Sequence: Synthetic
                         polypeptide
SEQUENCE: 293
QVQLQESGGG SVQAGGSLRL SCGASGYTYS SYCMGWFRQV PGKEREGVAV IDSDGSTSYA    60
DSVKGRFTIS KDNGKNTLYL QMNSLKPEDT AMYYCAADLG HYRPPCGVLY LGMDYWGKGT    120
QVTVSSGGGS QVQLQESGGG SVQAGGSLRL SCAASRYTYN SYCMGWFRQA PGKEREGVAT    180
IDSDGMTRYA DSVKGRFTIS KDNAKNTLYL QMNSLKPEDT AMYYCAADAD CTIAAMTTNP    240
LGQGTQVTVS SASHHHHHH                                                259

SEQ ID NO: 294         moltype = AA  length = 263
FEATURE                Location/Qualifiers
source                 1..263
                       mol_type = protein
                       organism = synthetic construct
                       note = Description of Artificial Sequence: Synthetic
                         polypeptide
SEQUENCE: 294
QVQLQESGGG SVQAGGSLRL SCGASGYTYS SYCMGWFRQV PGKEREGVAV IDSDGSTSYA    60
DSVKGRFTIS KDNGKNTLYL QMNSLKPEDT AMYYCAADLG HYRPPCGVLY LGMDYWGKGT    120
QVTVSSGGGS QVQLQESGGG SVQAGGSLRL SCTVSRYTAS VNYMGWFRQA PGKEREGVAT    180
IFTGAGTTYY ANSVKGRFTI SRDNAKNTAY LQMNSLKPED TAIYYCAVDF RGGLLYRPAY    240
EYTYRGQGTQ VTVSSASHHH HHH                                           263

SEQ ID NO: 295         moltype = AA  length = 264
FEATURE                Location/Qualifiers
source                 1..264
                       mol_type = protein
```

```
                        organism = synthetic construct
                        note = Description of Artificial Sequence: Synthetic
                          polypeptide
SEQUENCE: 295
QVQLQESGGG SVQAGGSLRL SCGASGYTYS SYCMGWFRQV PGKEREGVAV IDSDGSTSYA    60
DSVKGRFTIS KDNGKNTLYL QMNSLKPEDT AMYYCAADLG HYRPPCGVLY LGMDYWGKGT   120
QVTVSSGGGS QVQLQESGGG SVEAGGSLRL SCAASGYTHS SYCMGWFRQA PGKEREGVAA   180
IDVDGSTTYA DSVKGRFTIS KDNAKNTLYL QMNSLKPEDT GMYYCAAEFA DCSSNYFLPP   240
GAVRYWGQGT QVTVSSASHH HHHH                                         264

SEQ ID NO: 296          moltype = AA  length = 262
FEATURE                 Location/Qualifiers
source                  1..262
                        mol_type = protein
                        organism = synthetic construct
                        note = Description of Artificial Sequence: Synthetic
                          polypeptide
SEQUENCE: 296
QVQLQESGGG SVQAGGSLRL SCGASGYTYS SYCMGWFRQV PGKEREGVAV IDSDGSTSYA    60
DSVKGRFTIS KDNGKNTLYL QMNSLKPEDT AMYYCAADLG HYRPPCGVLY LGMDYWGKGT   120
QVTVSSGGGS QVQLQESGGG SVQAGGSLRL SCAASGYSYS SYCMGWFRQA PGKEREGVAT   180
IDSDGMTRYA DSVKGRFTIS KDNAKNTLYL QMNSLKPEDT AMYYCAAPLY DCDSGAVGRN   240
PPYWGQGTQV TVSSASHHHH HH                                           262

SEQ ID NO: 297          moltype = AA  length = 260
FEATURE                 Location/Qualifiers
source                  1..260
                        mol_type = protein
                        organism = synthetic construct
                        note = Description of Artificial Sequence: Synthetic
                          polypeptide
SEQUENCE: 297
QVQLQESGGG SVQAGGSLRL SCGASGYTYS SYCMGWFRQV PGKEREGVAV IDSDGSTSYA    60
DSVKGRFTIS KDNGKNTLYL QMNSLKPEDT AMYYCAADLG HYRPPCGVLY LGMDYWGKGT   120
QVTVSSGGGS QVQLQESGGG SVQTGGSLRL SCAASGYTYL RGCMGWFRQA PGKEREGVAV   180
MDVVGDRRSY IDSVKGRFTI SRDNAANSVY LQMDNLKPED TAMYYCTAGP NCVGWRSGLD   240
YWGQGTQVTV SSASHHHHHH                                              260

SEQ ID NO: 298          moltype = AA  length = 265
FEATURE                 Location/Qualifiers
source                  1..265
                        mol_type = protein
                        organism = synthetic construct
                        note = Description of Artificial Sequence: Synthetic
                          polypeptide
SEQUENCE: 298
QVQLQESGGG SVQAGGSLRL SCAASGYSNC SYDMTWYRQA PGKEREFVSA IHSDGSTRYA    60
DSVKGRFFIS QDNAKNTVYL QMNSLKPEDT AMYYCKTDPL HCRAHGGSWY SVRANYWGQG   120
TQVTVSSGGG SQVQLQESGG GSVQAGGSLR LSCAASGYTY SSGCMGWFRQ APGKEREAVA   180
AINSDGSTSY ADSVKGRFTI SKDNAKNTLY LQMNSLKPED TAMYYCAAEP YCSGGYPRWS   240
VAEFGYWGQG TQVTVSSASH HHHH                                         265

SEQ ID NO: 299          moltype = AA  length = 263
FEATURE                 Location/Qualifiers
source                  1..263
                        mol_type = protein
                        organism = synthetic construct
                        note = Description of Artificial Sequence: Synthetic
                          polypeptide
SEQUENCE: 299
QVQLQESGGG SVQAGGSLRL SCAASGYSNC SYDMTWYRQA PGKEREFVSA IHSDGSTRYA    60
DSVKGRFFIS QDNAKNTVYL QMNSLKPEDT AMYYCKTDPL HCRAHGGSWY SVRANYWGQG   120
TQVTVSSGGG SQVQLQESGG GSVQAGGSLR LSCAASGYTY SSYCMGWFRQ APGKEREGVA   180
HIDSDGSTSY ADSVKGRFTI SKDNAKNTLY LQMNSLKPED TAMYYCAADP IPGPGYCDGG   240
PNKYWGQGTQ VTVSSASHHH HHH                                          263

SEQ ID NO: 300          moltype = AA  length = 260
FEATURE                 Location/Qualifiers
source                  1..260
                        mol_type = protein
                        organism = synthetic construct
                        note = Description of Artificial Sequence: Synthetic
                          polypeptide
SEQUENCE: 300
QVQLQESGGG SVQAGGSLRL SCAASGYSNC SYDMTWYRQA PGKEREFVSA IHSDGSTRYA    60
DSVKGRFFIS QDNAKNTVYL QMNSLKPEDT AMYYCKTDPL HCRAHGGSWY SVRANYWGQG   120
TQVTVSSGGG SQVQLQESGG GSVQAGGSLR LSCAASRYTY NSYCMGWFRQ APGKEREGVA   180
TIDSDGMTRY ADSVKGRFTI SKDNAKNTLY LQMNSLKPED TAMYYCAADA DCTIAAMTTN   240
PLGQGTQVTV SSASHHHHHH                                              260
```

```
SEQ ID NO: 301          moltype = AA  length = 264
FEATURE                 Location/Qualifiers
source                  1..264
                        mol_type = protein
                        organism = synthetic construct
                        note = Description of Artificial Sequence: Synthetic
                        polypeptide
SEQUENCE: 301
QVQLQESGGG SVQAGGSLRL SCAASGYSNC SYDMTWYRQA PGKEREFVSA IHSDGSTRYA    60
DSVKGRFFIS QDNAKNTVYL QMNSLKPEDT AMYYCKTDPL HCRAHGGSWY SVRANYWGQG   120
TQVTVSSGGG SQVQLQESGG GSVQAGGSLR LSCTVSRYTA SVNYMGWFRQ APGKEREGVA   180
TIFTGAGTTY YANSVKGRFT ISRDNAKNTA YLQMNSLKPE DTAIYYCAVD FRGGLLYRPA   240
YEYTYRGQGT QVTVSSASHH HHHH                                         264

SEQ ID NO: 302          moltype = AA  length = 265
FEATURE                 Location/Qualifiers
source                  1..265
                        mol_type = protein
                        organism = synthetic construct
                        note = Description of Artificial Sequence: Synthetic
                        polypeptide
SEQUENCE: 302
QVQLQESGGG SVQAGGSLRL SCAASGYSNC SYDMTWYRQA PGKEREFVSA IHSDGSTRYA    60
DSVKGRFFIS QDNAKNTVYL QMNSLKPEDT AMYYCKTDPL HCRAHGGSWY SVRANYWGQG   120
TQVTVSSGGG SQVQLQESGG GSVEAGGSLR LSCAASGYTH SSYCMGWFRQ APGKEREGVA   180
AIDVDGSTTY ADSVKGRFTI SKDNAKNTLY LQMNSLKPED TGMYYCAAEF ADCSSNYFLP   240
PGAVRYWGQG TQVTVSSASH HHHHH                                        265

SEQ ID NO: 303          moltype = AA  length = 263
FEATURE                 Location/Qualifiers
source                  1..263
                        mol_type = protein
                        organism = synthetic construct
                        note = Description of Artificial Sequence: Synthetic
                        polypeptide
SEQUENCE: 303
QVQLQESGGG SVQAGGSLRL SCAASGYSNC SYDMTWYRQA PGKEREFVSA IHSDGSTRYA    60
DSVKGRFFIS QDNAKNTVYL QMNSLKPEDT AMYYCKTDPL HCRAHGGSWY SVRANYWGQG   120
TQVTVSSGGG SQVQLQESGG GSVQAGGSLR LSCAASGYSY SSYCMGWFRQ APGKEREGVA   180
TIDSDGMTRY ADSVKGRFTI SKDNAKNTLY LQMNSLKPED TAMYYCAAPL YDCDSGAVGR   240
NPPYWGQGTQ VTVSSASHHH HHH                                          263

SEQ ID NO: 304          moltype = AA  length = 261
FEATURE                 Location/Qualifiers
source                  1..261
                        mol_type = protein
                        organism = synthetic construct
                        note = Description of Artificial Sequence: Synthetic
                        polypeptide
SEQUENCE: 304
QVQLQESGGG SVQAGGSLRL SCAASGYSNC SYDMTWYRQA PGKEREFVSA IHSDGSTRYA    60
DSVKGRFFIS QDNAKNTVYL QMNSLKPEDT AMYYCKTDPL HCRAHGGSWY SVRANYWGQG   120
TQVTVSSGGG SQVQLQESGG GSVQTGGSLR LSCAASGYTY LRGCMGWFRQ APGKEREGVA   180
VMDVVGDRRS YIDSVKGRFT ISRDNAANSV YLQMDNLKPE DTAMYYCTAG PNCVGWRSGL   240
DYWGQGTQVT VSSASHHHHH H                                            261

SEQ ID NO: 305          moltype = AA  length = 263
FEATURE                 Location/Qualifiers
source                  1..263
                        mol_type = protein
                        organism = synthetic construct
                        note = Description of Artificial Sequence: Synthetic
                        polypeptide
SEQUENCE: 305
QVQLQESGGG SVQAGGSLRL SCAASGYTYS SGCMGWFRQA PGKEREAVAA INSDGSTSYA    60
DSVKGRFTIS KDNAKNTLYL QMNSLKPEDT AMYYCAAEPY CSGGYPRWSV AEFGYWGQGT   120
QVTVSSGGGS QVQLQESGGG SVQAGGSLRL SCAASRYLYS IDYMAWFRQS PGKEREPVAV   180
IYTASGATFY PDSVKGRFTI SQDNAKMTVY LQMNSLKSED TAMYYCAAVR KTDSYLFDAQ   240
SFTYWGQGTQ VTVSSASHHH HHH                                          263

SEQ ID NO: 306          moltype = AA  length = 267
FEATURE                 Location/Qualifiers
source                  1..267
                        mol_type = protein
                        organism = synthetic construct
                        note = Description of Artificial Sequence: Synthetic
                        polypeptide
SEQUENCE: 306
```

```
QVQLQESGGG SVQAGGSLRL SCAASGYTYS SGCMGWFRQA PGKEREAVAA INSDGSTSYA    60
DSVKGRFTIS KDNAKNTLYL QMNSLKPEDT AMYYCAAEPY CSGGYPRWSV AEFGYWGQGT   120
QVTVSSGGGS QVQLQESGGG SVQAGGSLRL SCAASRFTYS SYCMGWFRQA PGKEREGVAS   180
IDSDGSTSYT DSVKGRFTIS KDNAKNTLYL QMNSLKPEDT AMYYCALDLM STVVPGFCGF   240
LLSAGMDYWG KGTQVTVSSA SHHHHHH                                      267

SEQ ID NO: 307          moltype = AA   length = 269
FEATURE                 Location/Qualifiers
source                  1..269
                        mol_type = protein
                        organism = synthetic construct
                        note = Description of Artificial Sequence: Synthetic
                        polypeptide
SEQUENCE: 307
QVQLQESGGG SVQAGGSLRL SCAASGYTYS SGCMGWFRQA PGKEREAVAA INSDGSTSYA    60
DSVKGRFTIS KDNAKNTLYL QMNSLKPEDT AMYYCAAEPY CSGGYPRWSV AEFGYWGQGT   120
QVTVSSGGGS QVQLQESGGG SVQAGGSLRL SCAASGYTYS MYCMGWFRQA PGKEREGVAQ   180
INSDGSTSYA DSVKGRFTIS KDNAKNTLYL QMNSLKPEDT AMYYCAADSR VYGGSWYERL   240
CGPYTYEYNY WGQGTQVTVS SASHHHHHH                                    269

SEQ ID NO: 308          moltype = AA   length = 272
FEATURE                 Location/Qualifiers
source                  1..272
                        mol_type = protein
                        organism = synthetic construct
                        note = Description of Artificial Sequence: Synthetic
                        polypeptide
SEQUENCE: 308
QVQLQESGGG SVQAGGSLRL SCAASGYTYS SGCMGWFRQA PGKEREAVAA INSDGSTSYA    60
DSVKGRFTIS KDNAKNTLYL QMNSLKPEDT AMYYCAAEPY CSGGYPRWSV AEFGYWGQGT   120
QVTVSSGGGS QVQLQESGGG SVQAGGSLRL SCAVSGYAYS TYCMGWFRQA PGKEREGVAA   180
IDSGGSTSYA DSVKGRFTIS KDNAKNTLYL RMNSLKPEDT AMYYCAAVPP PDDGGSCLFL   240
GPEIKVSKAD FRYWGQGTQV TVSSASHHHH HH                                272

SEQ ID NO: 309          moltype = AA   length = 265
FEATURE                 Location/Qualifiers
source                  1..265
                        mol_type = protein
                        organism = synthetic construct
                        note = Description of Artificial Sequence: Synthetic
                        polypeptide
SEQUENCE: 309
QVQLQESGGG SVQAGGSLRL SCAASGYTYS SGCMGWFRQA PGKEREAVAA INSDGSTSYA    60
DSVKGRFTIS KDNAKNTLYL QMNSLKPEDT AMYYCAAEPY CSGGYPRWSV AEFGYWGQGT   120
QVTVSSGGGS QVQLQESGGG SVQAGGSLRL SCTVSGYTYS SNCMGWFRQA PGKEREGVAT   180
IYTGGGNTYY ADSVKGRFTI SQDNAKNTVY LQMNNLKPED TAMYYCAAEP LSRVYGGSCP   240
TPTFDYWGQG TQVTVSSASH HHHH                                         265

SEQ ID NO: 310          moltype = AA   length = 264
FEATURE                 Location/Qualifiers
source                  1..264
                        mol_type = protein
                        organism = synthetic construct
                        note = Description of Artificial Sequence: Synthetic
                        polypeptide
SEQUENCE: 310
QVQLQESGGG SVQAGGSLRL SCAASGYTYS SGCMGWFRQA PGKEREAVAA INSDGSTSYA    60
DSVKGRFTIS KDNAKNTLYL QMNSLKPEDT AMYYCAAEPY CSGGYPRWSV AEFGYWGQGT   120
QVTVSSGGGS QVQLQESGGG SVQAGGSLRL SCGASGYTYS SMCMGWFRQA PGKEREGVAV   180
IDSDGSTSYA DSVKGRFTIS KDNGKNTLYL QMNSLKPEDT AMYYCAADLG HYRPPCGVLY   240
LGMDYWGKGT QVTVSSASHH HHHH                                         264

SEQ ID NO: 311          moltype = AA   length = 265
FEATURE                 Location/Qualifiers
source                  1..265
                        mol_type = protein
                        organism = synthetic construct
                        note = Description of Artificial Sequence: Synthetic
                        polypeptide
SEQUENCE: 311
QVQLQESGGG SVQAGGSLRL SCAASGYTYS SGCMGWFRQA PGKEREAVAA INSDGSTSYA    60
DSVKGRFTIS KDNAKNTLYL QMNSLKPEDT AMYYCAAEPY CSGGYPRWSV AEFGYWGQGT   120
QVTVSSGGGS QVQLQESGGG SVQAGGSLRL SCAASGYSNC SYDMTWYRQA PGKEREFVSA   180
IHSDGSTRYA DSVKGRFFIS QDNAKNTVYL QMNSLKPEDT AMYYCKTDPL HCRAHGGSWY   240
SVRANYWGQG TQVTVSSASH HHHH                                         265

SEQ ID NO: 312          moltype = AA   length = 261
FEATURE                 Location/Qualifiers
source                  1..261
```

```
                        mol_type = protein
                        organism = synthetic construct
                        note = Description of Artificial Sequence: Synthetic
                            polypeptide
SEQUENCE: 312
QVQLQESGGG SVQAGGSLRL SCAASGYTYS SYCMGWFRQA PGKEREGVAH IDSDGSTSYA    60
DSVKGRFTIS KDNAKNTLYL QMNSLKPEDT AMYYCAADPI PGPGYCDGGP NKYWGQGTQV   120
TVSSGGGSQV QLQESGGGSV QAGGSLRLSC AASRYLYSID YMAWFRQSPG KEREPVAVIY   180
TASGATFYPD SVKGRFTISQ DNAKMTVYLQ MNSLKSEDTA MYYCAAVRKT DSYLFDAQSF   240
TYWGQGTQVT VSSASHHHHH H                                             261

SEQ ID NO: 313          moltype = AA  length = 265
FEATURE                 Location/Qualifiers
source                  1..265
                        mol_type = protein
                        organism = synthetic construct
                        note = Description of Artificial Sequence: Synthetic
                            polypeptide
SEQUENCE: 313
QVQLQESGGG SVQAGGSLRL SCAASGYTYS SYCMGWFRQA PGKEREGVAH IDSDGSTSYA    60
DSVKGRFTIS KDNAKNTLYL QMNSLKPEDT AMYYCAADPI PGPGYCDGGP NKYWGQGTQV   120
TVSSGGGSQV QLQESGGGSV QAGGSLRLSC AASRFTYSSY CMGWFRQAPG KEREGVASID   180
SDGSTSYTDS VKGRFTISKD NAKNTLYLQM NSLKPEDTAM YYCALDLMST VVPGFCGFLL   240
SAGMDYWGKG TQVTVSSASH HHHHH                                         265

SEQ ID NO: 314          moltype = AA  length = 267
FEATURE                 Location/Qualifiers
source                  1..267
                        mol_type = protein
                        organism = synthetic construct
                        note = Description of Artificial Sequence: Synthetic
                            polypeptide
SEQUENCE: 314
QVQLQESGGG SVQAGGSLRL SCAASGYTYS SYCMGWFRQA PGKEREGVAH IDSDGSTSYA    60
DSVKGRFTIS KDNAKNTLYL QMNSLKPEDT AMYYCAADPI PGPGYCDGGP NKYWGQGTQV   120
TVSSGGGSQV QLQESGGGSV QAGGSLRLSC AASGYTYSMY CMGWFRQAPG KEREGVAQIN   180
SDGSTSYADS VKGRFTISKD NAKNTLYLQM NSLKPEDTAM YYCAADSRVY GGSWYERLCG   240
PYTYEYNYWG QGTQVTVSSA SHHHHHH                                       267

SEQ ID NO: 315          moltype = AA  length = 270
FEATURE                 Location/Qualifiers
source                  1..270
                        mol_type = protein
                        organism = synthetic construct
                        note = Description of Artificial Sequence: Synthetic
                            polypeptide
SEQUENCE: 315
QVQLQESGGG SVQAGGSLRL SCAASGYTYS SYCMGWFRQA PGKEREGVAH IDSDGSTSYA    60
DSVKGRFTIS KDNAKNTLYL QMNSLKPEDT AMYYCAADPI PGPGYCDGGP NKYWGQGTQV   120
TVSSGGGSQV QLQESGGGSV QAGGSLRLSC AVSGYAYSTY CMGWFRQAPG KEREGVAAID   180
SGGSTSYADS VKGRFTISKD NAKNTLYLRM NSLKPEDTAM YYCAAVPPPP DGGSCLFLGP   240
EIKVSKADFR YWGQGTQVTV SSASHHHHHH                                    270

SEQ ID NO: 316          moltype = AA  length = 263
FEATURE                 Location/Qualifiers
source                  1..263
                        mol_type = protein
                        organism = synthetic construct
                        note = Description of Artificial Sequence: Synthetic
                            polypeptide
SEQUENCE: 316
QVQLQESGGG SVQAGGSLRL SCAASGYTYS SYCMGWFRQA PGKEREGVAH IDSDGSTSYA    60
DSVKGRFTIS KDNAKNTLYL QMNSLKPEDT AMYYCAADPI PGPGYCDGGP NKYWGQGTQV   120
TVSSGGGSQV QLQESGGGSV QAGGSLRLSC TVSGYTYSSN CMGWFRQAPG KEREGVATIY   180
TGGGNTYYAD SVKGRFTISQ DNAKNTVYLQ MNNLKPEDTA MYYCAAEPLS RVYGGSCPTP   240
TFDYWGQGTQ VTVSSASHHH HHH                                           263

SEQ ID NO: 317          moltype = AA  length = 262
FEATURE                 Location/Qualifiers
source                  1..262
                        mol_type = protein
                        organism = synthetic construct
                        note = Description of Artificial Sequence: Synthetic
                            polypeptide
SEQUENCE: 317
QVQLQESGGG SVQAGGSLRL SCAASGYTYS SYCMGWFRQA PGKEREGVAH IDSDGSTSYA    60
DSVKGRFTIS KDNAKNTLYL QMNSLKPEDT AMYYCAADPI PGPGYCDGGP NKYWGQGTQV   120
TVSSGGGSQV QLQESGGGSV QAGGSLRLSC GASGYTYSSY CMGWFRQVPG KEREGVAID   180
SDGSTSYADS VKGRFTISKD NGKNTLYLQM NSLKPEDTAM YYCAADLGHY RPPCGVLYLG   240
```

```
MDYWGKGTQV TVSSASHHHH HH                                                   262

SEQ ID NO: 318           moltype = AA  length = 263
FEATURE                  Location/Qualifiers
source                   1..263
                         mol_type = protein
                         organism = synthetic construct
                         note = Description of Artificial Sequence: Synthetic
                           polypeptide
SEQUENCE: 318
QVQLQESGGG SVQAGGSLRL SCAASGYTYS SYCMGWFRQA PGKEREGVAH IDSDGSTSYA            60
DSVKGRFTIS KDNAKNTLYL QMNSLKPEDT AMYYCAADPI PGPGYCDGGP NKYWGQGTQV           120
TVSSGGGSQV QLQESGGGSV QAGGSLRLSC AASGYSNCSY DMTWYRQAPG KEREFVSAIH           180
SDGSTRYADS VKGRFFISQD NAKNTVYLQM NSLKPEDTAM YYCKTDPLHC RAHGGSWYSV           240
RANYWGQGTQ VTVSSASHHH HHH                                                  263

SEQ ID NO: 319           moltype = AA  length = 258
FEATURE                  Location/Qualifiers
source                   1..258
                         mol_type = protein
                         organism = synthetic construct
                         note = Description of Artificial Sequence: Synthetic
                           polypeptide
SEQUENCE: 319
QVQLQESGGG SVQAGGSLRL SCAASRYTYN SYCMGWFRQA PGKEREGVAT IDSDGMTRYA            60
DSVKGRFTIS KDNAKNTLYL QMNSLKPEDT AMYYCAADAD CTIAAMTTNP LGQGTQVTVS           120
SGGGSQVQLQ ESGGGSVQAG GSLRLSCAAS RYLYSIDYMA WFRQSPGKER EPVAVIYTAS           180
GATFYPDSVK GRFTISQDNA KMTVYLQMNS LKSEDTAMYY CAAVRKTDSY LFDAQSFTYW           240
GQGTQVTVSS ASHHHHHH                                                        258

SEQ ID NO: 320           moltype = AA  length = 262
FEATURE                  Location/Qualifiers
source                   1..262
                         mol_type = protein
                         organism = synthetic construct
                         note = Description of Artificial Sequence: Synthetic
                           polypeptide
SEQUENCE: 320
QVQLQESGGG SVQAGGSLRL SCAASRYTYN SYCMGWFRQA PGKEREGVAT IDSDGMTRYA            60
DSVKGRFTIS KDNAKNTLYL QMNSLKPEDT AMYYCAADAD CTIAAMTTNP LGQGTQVTVS           120
SGGGSQVQLQ ESGGGSVQAG GSLRLSCAAS RFTYSSYCMG WFRQAPGKER EGVASIDSDG           180
STSYTDSVKG RFTISKDNAK NTLYLQMNSL KPEDTAMYYC ALDLMSTVVP GFCGFLLSAG           240
MDYWGKGTQV TVSSASHHHH HH                                                   262

SEQ ID NO: 321           moltype = AA  length = 264
FEATURE                  Location/Qualifiers
source                   1..264
                         mol_type = protein
                         organism = synthetic construct
                         note = Description of Artificial Sequence: Synthetic
                           polypeptide
SEQUENCE: 321
QVQLQESGGG SVQAGGSLRL SCAASRYTYN SYCMGWFRQA PGKEREGVAT IDSDGMTRYA            60
DSVKGRFTIS KDNAKNTLYL QMNSLKPEDT AMYYCAADAD CTIAAMTTNP LGQGTQVTVS           120
SGGGSQVQLQ ESGGGSVQAG GSLRLSCAAS GYTYSMYCMG WFRQAPGKER EGVAQINSDG           180
STSYADSVKG RFTISKDNAK NTLYLQMNSL KPEDTAMYYC AADSRVYGGS WYERLCGPYT           240
YEYNYWGQGT QVTVSSASHH HHHH                                                 264

SEQ ID NO: 322           moltype = AA  length = 267
FEATURE                  Location/Qualifiers
source                   1..267
                         mol_type = protein
                         organism = synthetic construct
                         note = Description of Artificial Sequence: Synthetic
                           polypeptide
SEQUENCE: 322
QVQLQESGGG SVQAGGSLRL SCAASRYTYN SYCMGWFRQA PGKEREGVAT IDSDGMTRYA            60
DSVKGRFTIS KDNAKNTLYL QMNSLKPEDT AMYYCAADAD CTIAAMTTNP LGQGTQVTVS           120
SGGGSQVQLQ ESGGGSVQAG GSLRLSCAVS GYAYSTYCMG WFRQAPGKER EGVAAIDSGG           180
STSYADSVKG RFTISKDNAK NTLYLRMNSL KPEDTAMYYC AAVPPPPDGG SCLFLGPEIK           240
VSKADFRYWG QGTQVTVSSA SHHHHHH                                              267

SEQ ID NO: 323           moltype = AA  length = 260
FEATURE                  Location/Qualifiers
source                   1..260
                         mol_type = protein
                         organism = synthetic construct
                         note = Description of Artificial Sequence: Synthetic
                           polypeptide
```

```
SEQUENCE: 323
QVQLQESGGG SVQAGGSLRL SCAASRYTYN SYCMGWFRQA PGKEREGVAT IDSDGMTRYA    60
DSVKGRFTIS KDNAKNTLYL QMNSLKPEDT AMYYCAADAD CTIAAMTTNP LGQGTQVTVS   120
SGGGSQVQLQ ESGGGSVQAG GSLRLSCTVS GYTYSSNCMG WFRQAPGKER EGVATIYTGG   180
GNTYYADSVK GRFTISQDNA KNTVYLQMNN LKPEDTAMYY CAAEPLSRVY GGSCPTPTFD   240
YWGQGTQVTV SSASHHHHHH                                               260

SEQ ID NO: 324          moltype = AA  length = 259
FEATURE                 Location/Qualifiers
source                  1..259
                        mol_type = protein
                        organism = synthetic construct
                        note = Description of Artificial Sequence: Synthetic
                           polypeptide
SEQUENCE: 324
QVQLQESGGG SVQAGGSLRL SCAASRYTYN SYCMGWFRQA PGKEREGVAT IDSDGMTRYA    60
DSVKGRFTIS KDNAKNTLYL QMNSLKPEDT AMYYCAADAD CTIAAMTTNP LGQGTQVTVS   120
SGGGSQVQLQ ESGGGSVQAG GSLRLSCGAS GYTYSSYCMG WFRQVPGKER EGVAVIDSDG   180
STSYADSVKG RFTISKDNGK NTLYLQMNSL KPEDTAMYYC AADLGHYRPP CGVLYLGMDY   240
WGKGTQVTVS SASHHHHHH                                                259

SEQ ID NO: 325          moltype = AA  length = 260
FEATURE                 Location/Qualifiers
source                  1..260
                        mol_type = protein
                        organism = synthetic construct
                        note = Description of Artificial Sequence: Synthetic
                           polypeptide
SEQUENCE: 325
QVQLQESGGG SVQAGGSLRL SCAASRYTYN SYCMGWFRQA PGKEREGVAT IDSDGMTRYA    60
DSVKGRFTIS KDNAKNTLYL QMNSLKPEDT AMYYCAADAD CTIAAMTTNP LGQGTQVTVS   120
SGGGSQVQLQ ESGGGSVQAG GSLRLSCAAS GYSNCSYDMT WYRQAPGKER EFVSAIHSDG   180
STRYADSVKG RFFISQDNAK NTVYLQMNSL KPEDTAMYYC KTDPLHCRAH GGSWYSVRAN   240
YWGQGTQVTV SSASHHHHHH                                               260

SEQ ID NO: 326          moltype = AA  length = 262
FEATURE                 Location/Qualifiers
source                  1..262
                        mol_type = protein
                        organism = synthetic construct
                        note = Description of Artificial Sequence: Synthetic
                           polypeptide
SEQUENCE: 326
QVQLQESGGG SVQAGGSLRL SCTVSRYTAS VNYMGWFRQA PGKEREGVAT IFTGAGTTYY    60
ANSVKGRFTI SRDNAKNTAY LQMNSLKPED TAIYYCAVDF RGGLLYRPAY EYTYRGQGTQ   120
VTVSSGGGSQ VQLQESGGGS VQAGGSLRLS CAASRYLYSI DYMAWFRQSP GKEREPVAVI   180
YTASGATFYP DSVKGRFTIS QDNAKMTVYL QMNSLKSEDT AMYYCAAVRK TDSYLFDAQS   240
FTYWGQGTQV TVSSASHHHH HH                                            262

SEQ ID NO: 327          moltype = AA  length = 266
FEATURE                 Location/Qualifiers
source                  1..266
                        mol_type = protein
                        organism = synthetic construct
                        note = Description of Artificial Sequence: Synthetic
                           polypeptide
SEQUENCE: 327
QVQLQESGGG SVQAGGSLRL SCTVSRYTAS VNYMGWFRQA PGKEREGVAT IFTGAGTTYY    60
ANSVKGRFTI SRDNAKNTAY LQMNSLKPED TAIYYCAVDF RGGLLYRPAY EYTYRGQGTQ   120
VTVSSGGGSQ VQLQESGGGS VQAGGSLRLS CAASRFTYSS YCMGWFRQAP GKEREGVASI   180
DSDGSTSYTD SVKGRFTISK DNAKNTLYLQ MNSLKPEDTA MYYCALDLMS TVVPGFCGFL   240
LSAGMDYWGK GTQVTVSSAS HHHHHH                                        266

SEQ ID NO: 328          moltype = AA  length = 268
FEATURE                 Location/Qualifiers
source                  1..268
                        mol_type = protein
                        organism = synthetic construct
                        note = Description of Artificial Sequence: Synthetic
                           polypeptide
SEQUENCE: 328
QVQLQESGGG SVQAGGSLRL SCTVSRYTAS VNYMGWFRQA PGKEREGVAT IFTGAGTTYY    60
ANSVKGRFTI SRDNAKNTAY LQMNSLKPED TAIYYCAVDF RGGLLYRPAY EYTYRGQGTQ   120
VTVSSGGGSQ VQLQESGGGS VQAGGSLRLS CAASGYTYSM YCMGWFRQAP GKEREGVAQI   180
NSDGSTSYAD SVKGRFTISK DNAKNTLYLQ MNSLKPEDTA MYYCAADSRV YGGSWYERLC   240
GPYTYEYNYW GQGTQVTVSS ASHHHHHH                                      268

SEQ ID NO: 329          moltype = AA  length = 271
FEATURE                 Location/Qualifiers
```

```
source                  1..271
                        mol_type = protein
                        organism = synthetic construct
                        note = Description of Artificial Sequence: Synthetic
                        polypeptide
SEQUENCE: 329
QVQLQESGGG SVQAGGSLRL SCTVSRYTAS VNYMGWFRQA PGKEREGVAT IFTGAGTTYY      60
ANSVKGRFTI SRDNAKNTAY LQMNSLKPED TAIYYCAVDF RGGLLYRPAY EYTYRGQGTQ    120
VTVSSGGGSQ VQLQESGGGS VQAGGSLRLS CAVSGYAYST YCMGWFRQAP GKEREGVAAI    180
DSGGSTSYAD SVKGRFTISK DNAKNTLYLR MNSLKPEDTA MYYCAAVPPP PDGGSCLFLG    240
PEIKVSKADF RYWGQGTQVT VSSASHHHHH H                                   271

SEQ ID NO: 330          moltype = AA  length = 264
FEATURE                 Location/Qualifiers
source                  1..264
                        mol_type = protein
                        organism = synthetic construct
                        note = Description of Artificial Sequence: Synthetic
                        polypeptide
SEQUENCE: 330
QVQLQESGGG SVQAGGSLRL SCTVSRYTAS VNYMGWFRQA PGKEREGVAT IFTGAGTTYY      60
ANSVKGRFTI SRDNAKNTAY LQMNSLKPED TAIYYCAVDF RGGLLYRPAY EYTYRGQGTQ    120
VTVSSGGGSQ VQLQESGGGS VQAGGSLRLS CTVSGYTYSS NCMGWFRQAP GKEREGVATI    180
YTGGGNTYYA DSVKGRFTIS QDNAKNTVYL QMNNLKPEDT AMYYCAAEPL SRVYGGSCPT    240
PTFDYWGQGT QVTVSSASHH HHHH                                           264

SEQ ID NO: 331          moltype = AA  length = 263
FEATURE                 Location/Qualifiers
source                  1..263
                        mol_type = protein
                        organism = synthetic construct
                        note = Description of Artificial Sequence: Synthetic
                        polypeptide
SEQUENCE: 331
QVQLQESGGG SVQAGGSLRL SCTVSRYTAS VNYMGWFRQA PGKEREGVAT IFTGAGTTYY      60
ANSVKGRFTI SRDNAKNTAY LQMNSLKPED TAIYYCAVDF RGGLLYRPAY EYTYRGQGTQ    120
VTVSSGGGSQ VQLQESGGGS VQAGGSLRLS CGASGYTYSS YCMGWFRQVP GKEREGVAVI    180
DSDGSTSYAD SVKGRFTISK DNGKNTLYLQ MNSLKPEDTA MYYCAADLGH YRPPCGVLYL    240
GMDYWGKGTQ VTVSSASHHH HHH                                            263

SEQ ID NO: 332          moltype = AA  length = 264
FEATURE                 Location/Qualifiers
source                  1..264
                        mol_type = protein
                        organism = synthetic construct
                        note = Description of Artificial Sequence: Synthetic
                        polypeptide
SEQUENCE: 332
QVQLQESGGG SVQAGGSLRL SCTVSRYTAS VNYMGWFRQA PGKEREGVAT IFTGAGTTYY      60
ANSVKGRFTI SRDNAKNTAY LQMNSLKPED TAIYYCAVDF RGGLLYRPAY EYTYRGQGTQ    120
VTVSSGGGSQ VQLQESGGGS VQAGGSLRLS CAASGYSNCS YDMTWYRQAP GKEREFVSAI    180
HSDGSTRYAD SVKGRFFISQ DNAKNTVYLQ MNSLKPEDTA MYYCKTDPLH CRAHGGSWYS    240
VRANYWGQGT QVTVSSASHH HHHH                                           264

SEQ ID NO: 333          moltype = AA  length = 263
FEATURE                 Location/Qualifiers
source                  1..263
                        mol_type = protein
                        organism = synthetic construct
                        note = Description of Artificial Sequence: Synthetic
                        polypeptide
SEQUENCE: 333
QVQLQESGGG SVEAGGSLRL SCAASGYTHS SYCMGWFRQA PGKEREGVAA IDVDGSTTYA      60
DSVKGRFTIS KDNAKNTLYL QMNSLKPEDT GMYYCAAEFA DCSSNYFLPP GAVRYWGQGT    120
QVTVSSGGGS QVQLQESGGG SVQAGGSLRL SCAASRYLYS IDYMAWFRQS PGKEREPVAV    180
IYTASGATFY PDSVKGRFTI SQDNAKMTVY LQMNSLKSED TAMYYCAAVR KTDSYLFDAQ    240
SFTYWGQGTQ VTVSSASHHH HHH                                            263

SEQ ID NO: 334          moltype = AA  length = 267
FEATURE                 Location/Qualifiers
source                  1..267
                        mol_type = protein
                        organism = synthetic construct
                        note = Description of Artificial Sequence: Synthetic
                        polypeptide
SEQUENCE: 334
QVQLQESGGG SVEAGGSLRL SCAASGYTHS SYCMGWFRQA PGKEREGVAA IDVDGSTTYA      60
DSVKGRFTIS KDNAKNTLYL QMNSLKPEDT GMYYCAAEFA DCSSNYFLPP GAVRYWGQGT    120
QVTVSSGGGS QVQLQESGGG SVQAGGSLRL SCAASRFTYS SYCMGWFRQA PGKEREGVAS    180
```

```
IDSDGSTSYT DSVKGRFTIS KDNAKNTLYL QMNSLKPEDT AMYYCALDLM STVVPGFCGF    240
LLSAGMDYWG KGTQVTVSSA SHHHHHH                                        267

SEQ ID NO: 335          moltype = AA  length = 269
FEATURE                 Location/Qualifiers
source                  1..269
                        mol_type = protein
                        organism = synthetic construct
                        note = Description of Artificial Sequence: Synthetic
                           polypeptide
SEQUENCE: 335
QVQLQESGGG SVEAGGSLRL SCAASGYTHS SYCMGWFRQA PGKEREGVAA IDVDGSTTYA    60
DSVKGRFTIS KDNAKNTLYL QMNSLKPEDT GMYYCAAEFA DCSSNYFLPP GAVRYWGQGT    120
QVTVSSGGGS QVQLQESGGG SVQAGGSLRL SCAASGYTYS MYCMGWFRQA PGKEREGVAQ    180
INSDGSTSYA DSVKGRFTIS KDNAKNTLYL QMNSLKPEDT AMYYCAADSR VYGGSWYERL    240
CGPYTYEYNY WGQGTQVTVS SASHHHHHH                                      269

SEQ ID NO: 336          moltype = AA  length = 272
FEATURE                 Location/Qualifiers
source                  1..272
                        mol_type = protein
                        organism = synthetic construct
                        note = Description of Artificial Sequence: Synthetic
                           polypeptide
SEQUENCE: 336
QVQLQESGGG SVEAGGSLRL SCAASGYTHS SYCMGWFRQA PGKEREGVAA IDVDGSTTYA    60
DSVKGRFTIS KDNAKNTLYL QMNSLKPEDT GMYYCAAEFA DCSSNYFLPP GAVRYWGQGT    120
QVTVSSGGGS QVQLQESGGG SVQAGGSLRL SCAVSGYAYS TYCMGWFRQA PGKEREGVAA    180
IDSGGSTSYA DSVKGRFTIS KDNAKNTLYL RMNSLKPEDT AMYYCAAVPP PPDGGSCLFL    240
GPEIKVSKAD FRYWGQGTQV TVSSASHHHH HH                                  272

SEQ ID NO: 337          moltype = AA  length = 265
FEATURE                 Location/Qualifiers
source                  1..265
                        mol_type = protein
                        organism = synthetic construct
                        note = Description of Artificial Sequence: Synthetic
                           polypeptide
SEQUENCE: 337
QVQLQESGGG SVEAGGSLRL SCAASGYTHS SYCMGWFRQA PGKEREGVAA IDVDGSTTYA    60
DSVKGRFTIS KDNAKNTLYL QMNSLKPEDT GMYYCAAEFA DCSSNYFLPP GAVRYWGQGT    120
QVTVSSGGGS QVQLQESGGG SVQAGGSLRL SCTVSGYTYS SNCMGWFRQA PGKEREGVAT    180
IYTGGGNTYY ADSVKGRFTI SQDNAKNTVY LQMNNLKPED TAMYYCAAEP LSRVYGGSCP    240
TPTFDYWGQG TQVTVSSASH HHHH                                           265

SEQ ID NO: 338          moltype = AA  length = 264
FEATURE                 Location/Qualifiers
source                  1..264
                        mol_type = protein
                        organism = synthetic construct
                        note = Description of Artificial Sequence: Synthetic
                           polypeptide
SEQUENCE: 338
QVQLQESGGG SVEAGGSLRL SCAASGYTHS SYCMGWFRQA PGKEREGVAA IDVDGSTTYA    60
DSVKGRFTIS KDNAKNTLYL QMNSLKPEDT GMYYCAAEFA DCSSNYFLPP GAVRYWGQGT    120
QVTVSSGGGS QVQLQESGGG SVQAGGSLRL SCGASGYTYS SYCMGWFRQV PGKEREGVAV    180
IDSDGSTSYA DSVKGRFTIS KDNGKNTLYL QMNSLKPEDT AMYYCAADLG HYRPPCGVLY    240
LGMDYWGKGT QVTVSSASHH HHHH                                           264

SEQ ID NO: 339          moltype = AA  length = 265
FEATURE                 Location/Qualifiers
source                  1..265
                        mol_type = protein
                        organism = synthetic construct
                        note = Description of Artificial Sequence: Synthetic
                           polypeptide
SEQUENCE: 339
QVQLQESGGG SVEAGGSLRL SCAASGYTHS SYCMGWFRQA PGKEREGVAA IDVDGSTTYA    60
DSVKGRFTIS KDNAKNTLYL QMNSLKPEDT GMYYCAAEFA DCSSNYFLPP GAVRYWGQGT    120
QVTVSSGGGS QVQLQESGGG SVQAGGSLRL SCAASGYSNC SYDMTWYRQA PGKEREFVSA    180
IHSDGSTRYA DSVKGRFFIS QDNAKNTVYL QMNSLKPEDT AMYYCKTDPL HCRAHGGSWY    240
SVRANYWGQG TQVTVSSASH HHHH                                           265

SEQ ID NO: 340          moltype = AA  length = 261
FEATURE                 Location/Qualifiers
source                  1..261
                        mol_type = protein
                        organism = synthetic construct
                        note = Description of Artificial Sequence: Synthetic
```

```
                        polypeptide
SEQUENCE: 340
QVQLQESGGG SVQAGGSLRL SCAASGYSYS SYCMGWFRQA PGKEREGVAT IDSDGMTRYA    60
DSVKGRFTIS KDNAKNTLYL QMNSLKPEDT AMYYCAAPLY DCDSGAVGRN PPYWGQGTQV   120
TVSSGGGSQV QLQESGGGSV QAGGSLRLSC AASRYLYSID YMAWFRQSPG KEREPVAVIY   180
TASGATFYPD SVKGRFTISQ DNAKMTVYLQ MNSLKSEDTA MYYCAAVRKT DSYLFDAQSF   240
TYWGQGTQVT VSSASHHHHH H                                             261

SEQ ID NO: 341          moltype = AA  length = 265
FEATURE                 Location/Qualifiers
source                  1..265
                        mol_type = protein
                        organism = synthetic construct
                        note = Description of Artificial Sequence: Synthetic
                        polypeptide
SEQUENCE: 341
QVQLQESGGG SVQAGGSLRL SCAASGYSYS SYCMGWFRQA PGKEREGVAT IDSDGMTRYA    60
DSVKGRFTIS KDNAKNTLYL QMNSLKPEDT AMYYCAAPLY DCDSGAVGRN PPYWGQGTQV   120
TVSSGGGSQV QLQESGGGSV QAGGSLRLSC AASRFTYSSY CMGWFRQAPG KEREGVASID   180
SDGSTSYTDS VKGRFTISKD NAKNTLYLQM NSLKPEDTAM YYCALDLMST VVPGFCGFLL   240
SAGMDYWGKG TQVTVSSASH HHHHH                                         265

SEQ ID NO: 342          moltype = AA  length = 267
FEATURE                 Location/Qualifiers
source                  1..267
                        mol_type = protein
                        organism = synthetic construct
                        note = Description of Artificial Sequence: Synthetic
                        polypeptide
SEQUENCE: 342
QVQLQESGGG SVQAGGSLRL SCAASGYSYS SYCMGWFRQA PGKEREGVAT IDSDGMTRYA    60
DSVKGRFTIS KDNAKNTLYL QMNSLKPEDT AMYYCAAPLY DCDSGAVGRN PPYWGQGTQV   120
TVSSGGGSQV QLQESGGGSV QAGGSLRLSC AASGYTYSMY CMGWFRQAPG KEREGVAQIN   180
SDGSTSYADS VKGRFTISKD NAKNTLYLQM NSLKPEDTAM YYCAADSRVY GGSWYERLCG   240
PYTYEYNYWG QGTQVTVSSA SHHHHHH                                       267

SEQ ID NO: 343          moltype = AA  length = 270
FEATURE                 Location/Qualifiers
source                  1..270
                        mol_type = protein
                        organism = synthetic construct
                        note = Description of Artificial Sequence: Synthetic
                        polypeptide
SEQUENCE: 343
QVQLQESGGG SVQAGGSLRL SCAASGYSYS SYCMGWFRQA PGKEREGVAT IDSDGMTRYA    60
DSVKGRFTIS KDNAKNTLYL QMNSLKPEDT AMYYCAAPLY DCDSGAVGRN PPYWGQGTQV   120
TVSSGGGSQV QLQESGGGSV QAGGSLRLSC AVSGYAYSTY CMGWFRQAPG KEREGVAAID   180
SGGSTSYADS VKGRFTISKD NAKNTLYLRM NSLKPEDTAM YYCAAVPPPP DGGSCLFLGP   240
EIKVSKADFR YWGQGTQVTV SSASHHHHHH                                    270

SEQ ID NO: 344          moltype = AA  length = 263
FEATURE                 Location/Qualifiers
source                  1..263
                        mol_type = protein
                        organism = synthetic construct
                        note = Description of Artificial Sequence: Synthetic
                        polypeptide
SEQUENCE: 344
QVQLQESGGG SVQAGGSLRL SCAASGYSYS SYCMGWFRQA PGKEREGVAT IDSDGMTRYA    60
DSVKGRFTIS KDNAKNTLYL QMNSLKPEDT AMYYCAAPLY DCDSGAVGRN PPYWGQGTQV   120
TVSSGGGSQV QLQESGGGSV QAGGSLRLSC TVSGYTYSSN CMGWFRQAPG KEREGVATIY   180
TGGGNTYYAD SVKGRFTISQ DNAKNTVYLQ MNNLKPEDTA MYYCAAEPLS RVYGGSCPTP   240
TFDYWGQGTQ VTVSSASHHH HHH                                           263

SEQ ID NO: 345          moltype = AA  length = 262
FEATURE                 Location/Qualifiers
source                  1..262
                        mol_type = protein
                        organism = synthetic construct
                        note = Description of Artificial Sequence: Synthetic
                        polypeptide
SEQUENCE: 345
QVQLQESGGG SVQAGGSLRL SCAASGYSYS SYCMGWFRQA PGKEREGVAT IDSDGMTRYA    60
DSVKGRFTIS KDNAKNTLYL QMNSLKPEDT AMYYCAAPLY DCDSGAVGRN PPYWGQGTQV   120
TVSSGGGSQV QLQESGGGSV QAGGSLRLSC GASGYTYSSY CMGWFRQVPG KEREGVAVID   180
SDGSTSYADS VKGRFTISKD NGKNTLYLQM NSLKPEDTAM YYCAADLGHY RPPCGVLYLG   240
MDYWGKGTQV TVSSASHHHH HH                                            262

SEQ ID NO: 346          moltype = AA  length = 263
```

| FEATURE | Location/Qualifiers |
|---|---|
| source | 1..263<br>mol_type = protein<br>organism = synthetic construct<br>note = Description of Artificial Sequence: Synthetic polypeptide |

SEQUENCE: 346
```
QVQLQESGGG SVQAGGSLRL SCAASGYSYS SYCMGWFRQA PGKEREGVAT IDSDGMTRYA   60
DSVKGRFTIS KDNAKNTLYL QMNSLKPEDT AMYYCAAPLY DCDSGAVGRN PPYWGQGTQV  120
TVSSGGGSQV QLQESGGGSV QAGGSLRLSC AASGYSNCSY DMTWYRQAPG KEREFVSAIH  180
SDGSTRYADS VKGRFFISQD NAKNTVYLQM NSLKPEDTAM YYCKTDPLHC RAHGGSWYSV  240
RANYWGQGTQ VTVSSASHHH HHH                                         263
```

| SEQ ID NO: 347 | moltype = AA length = 259 |
|---|---|
| FEATURE | Location/Qualifiers |
| source | 1..259<br>mol_type = protein<br>organism = synthetic construct<br>note = Description of Artificial Sequence: Synthetic polypeptide |

SEQUENCE: 347
```
QVQLQESGGG SVQTGGSLRL SCAASGYTYL RGCMGWFRQA PGKEREGVAV MDVVGDRRSY   60
IDSVKGRFTI SRDNAANSVY LQMDNLKPED TAMYYCTAGP NCVGWRSGLD YWGQGTQVTV  120
SSGGGSQVQL QESGGGSVQA GGSLRLSCAA SRYLYSIDYM AWFRQSPGKE REPVAVIYTA  180
SGATFYPDSV KGRFTISQDN AKMTVYLQMN SLKSEDTAMY YCAAVRKTDS YLFDAQSFTY  240
WGQGTQVTVS SASHHHHHH                                              259
```

| SEQ ID NO: 348 | moltype = AA length = 263 |
|---|---|
| FEATURE | Location/Qualifiers |
| source | 1..263<br>mol_type = protein<br>organism = synthetic construct<br>note = Description of Artificial Sequence: Synthetic polypeptide |

SEQUENCE: 348
```
QVQLQESGGG SVQTGGSLRL SCAASGYTYL RGCMGWFRQA PGKEREGVAV MDVVGDRRSY   60
IDSVKGRFTI SRDNAANSVY LQMDNLKPED TAMYYCTAGP NCVGWRSGLD YWGQGTQVTV  120
SSGGGSQVQL QESGGGSVQA GGSLRLSCAA SRFTYSSYCM GWFRQAPGKE REGVASIDSD  180
GSTSYTDSVK GRFTISKDNA KNTLYLQMNS LKPEDTAMYY CALDLMSTVV PGFCGFLLSA  240
GMDYWGKGTQ VTVSSASHHH HHH                                         263
```

| SEQ ID NO: 349 | moltype = AA length = 265 |
|---|---|
| FEATURE | Location/Qualifiers |
| source | 1..265<br>mol_type = protein<br>organism = synthetic construct<br>note = Description of Artificial Sequence: Synthetic polypeptide |

SEQUENCE: 349
```
QVQLQESGGG SVQTGGSLRL SCAASGYTYL RGCMGWFRQA PGKEREGVAV MDVVGDRRSY   60
IDSVKGRFTI SRDNAANSVY LQMDNLKPED TAMYYCTAGP NCVGWRSGLD YWGQGTQVTV  120
SSGGGSQVQL QESGGGSVQA GGSLRLSCAA SGYTYSMYCM GWFRQAPGKE REGVAQINSD  180
GSTSYADSVK GRFTISKDNA KNTLYLQMNS LKPEDTAMYY CAADSRVYGG SWYERLCGPY  240
TYEYNYWGQG TQVTVSSASH HHHH                                        265
```

| SEQ ID NO: 350 | moltype = AA length = 268 |
|---|---|
| FEATURE | Location/Qualifiers |
| source | 1..268<br>mol_type = protein<br>organism = synthetic construct<br>note = Description of Artificial Sequence: Synthetic polypeptide |

SEQUENCE: 350
```
QVQLQESGGG SVQTGGSLRL SCAASGYTYL RGCMGWFRQA PGKEREGVAV MDVVGDRRSY   60
IDSVKGRFTI SRDNAANSVY LQMDNLKPED TAMYYCTAGP NCVGWRSGLD YWGQGTQVTV  120
SSGGGSQVQL QESGGGSVQA GGSLRLSCAV SGYAYSTYCM GWFRQAPGKE REGVAAIDSG  180
GSTSYADSVK GRFTISKDNA KNTLYLRMNS LKPEDTAMYY CAAVPPPPDG GSCLFLGPEI  240
KVSKADFRYW GQGTQVTVSS ASHHHHHH                                    268
```

| SEQ ID NO: 351 | moltype = AA length = 261 |
|---|---|
| FEATURE | Location/Qualifiers |
| source | 1..261<br>mol_type = protein<br>organism = synthetic construct<br>note = Description of Artificial Sequence: Synthetic polypeptide |

SEQUENCE: 351
```
QVQLQESGGG SVQTGGSLRL SCAASGYTYL RGCMGWFRQA PGKEREGVAV MDVVGDRRSY   60
IDSVKGRFTI SRDNAANSVY LQMDNLKPED TAMYYCTAGP NCVGWRSGLD YWGQGTQVTV  120
```

```
SSGGGSQVQL QESGGGSVQA GGSLRLSCTV SGYTYSSNCM GWFRQAPGKE REGVATIYTG    180
GGNTYYADSV KGRFTISQDN AKNTVYLQMN NLKPEDTAMY YCAAEPLSRV YGGSCPTPTF    240
DYWGQGTQVT VSSASHHHHH H                                              261

SEQ ID NO: 352          moltype = AA   length = 260
FEATURE                 Location/Qualifiers
source                  1..260
                        mol_type = protein
                        organism = synthetic construct
                        note = Description of Artificial Sequence: Synthetic
                          polypeptide
SEQUENCE: 352
QVQLQESGGG SVQTGGSLRL SCAASGYTYL RGCMGWFRQA PGKEREGVAV MDVVGDRRSY     60
IDSVKGRFTI SRDNAANSVY LQMDNLKPED TAMYYCTAGP NCVGWRSGLD YWGQGTQVTV    120
SSGGGSQVQL QESGGGSVQA GGSLRLSCGA SGYTYSSYCM GWFRQVPGKE REGVAVIDSD    180
GSTSYADSVK GRFTISKDNG KNTLYLQMNS LKPEDTAMYY CAADLGHYRP PCGVLYLGMD    240
YWGKGTQVTV SSASHHHHHH                                                260

SEQ ID NO: 353          moltype = AA   length = 261
FEATURE                 Location/Qualifiers
source                  1..261
                        mol_type = protein
                        organism = synthetic construct
                        note = Description of Artificial Sequence: Synthetic
                          polypeptide
SEQUENCE: 353
QVQLQESGGG SVQTGGSLRL SCAASGYTYL RGCMGWFRQA PGKEREGVAV MDVVGDRRSY     60
IDSVKGRFTI SRDNAANSVY LQMDNLKPED TAMYYCTAGP NCVGWRSGLD YWGQGTQVTV    120
SSGGGSQVQL QESGGGSVQA GGSLRLSCAA SGYSNCSYDM TWYRQAPGKE REFVSAIHSD    180
GSTRYADSVK GRFFISQDNA KNTVYLQMNS LKPEDTAMYY CKTDPLHCRA HGGSWYSVRA    240
NYWGQGTQVT VSSASHHHHH H                                              261

SEQ ID NO: 354          moltype = DNA   length = 789
FEATURE                 Location/Qualifiers
source                  1..789
                        mol_type = other DNA
                        organism = synthetic construct
                        note = Description of Artificial Sequence: Synthetic
                          polynucleotide
SEQUENCE: 354
caagtgcagc tgcaagagag cggaggagga agcgtgcaag ccggaggctc tctgagactg     60
agctgtgccg cctctaggta tctgtacagc atcgactaca tggcttggtt cagacagagc    120
cccggcaagg agagggagcc agtggctgtc atctacactg cctccggcgc cacattctat    180
ccagatagcg tgaagggaag gttcactatc agccaagata cgccaagat gacagtgtat     240
ctgcagatga actctctgaa gagcgaggac actgccatgt actactgtgc cgccgtgagg    300
aagacagata gctacctctt cgacgcccag agcttcacat actggggcca aggcacacaa    360
gtgacagtct cgagcggcgg aggatcccaa gtgcagctgc aagagagcgg aggaagc       420
gtgcaagctg gaggctctct gaggctgagc tgtgctgcca gcggctacac ttatagcagc    480
ggctgtatgg gctggttcag acaagccccc ggcaaggaaa gggaagccgt ggccgccatc    540
aattccgatg gcagcacaag ctacgccgac agcgtgaagg gaaggttcac aatcagcaag    600
gacaacgcca agaacacact ctatctgcag atgaactctc tgaagccaga ggacacagcc    660
atgtactact gcgccgctga gccttactgt agcggcggct acccaagatg gagcgtcgct    720
gagttcggct actggggcca aggcacacaa gtgactgtct cgtctgctag ccaccatcac    780
catcaccac                                                            789

SEQ ID NO: 355          moltype = DNA   length = 783
FEATURE                 Location/Qualifiers
source                  1..783
                        mol_type = other DNA
                        organism = synthetic construct
                        note = Description of Artificial Sequence: Synthetic
                          polynucleotide
SEQUENCE: 355
caagtgcagc tgcaagagag cggaggagga agcgtgcaag ccggaggctc tctgagactg     60
agctgtgccg cctctaggta tctgtacagc atcgactaca tggcttggtt cagacagagc    120
cccggcaagg agagggagcc agtggctgtc atctacactg cctccggcgc cacattctat    180
ccagatagcg tgaagggaag gttcactatc agccaagata cgccaagat gacagtgtat     240
ctgcagatga actctctgaa gagcgaggac actgccatgt actactgtgc cgccgtgagg    300
aagacagata gctacctctt cgacgcccag agcttcacat actggggcca aggcacacaa    360
gtgacagtct cgagcggcgg aggatcccaa gtgcagctgc aagagagcgg aggaggcagc    420
gtccaagccg gaggctctct gaggctgagc tgtgctgcca gcggctacac ttacagcagc    480
tactgcatgg gctggttcag acaagccccc ggcaaggaga gagggcgt ggctcacatc      540
gacagcgacg gctccacaag ctacgccgat agcgtgaagg gaaggttcac aatctccaag    600
gacaacgcca agaacacact gtacctccag atgaactctc tgaagccaga ggacacagcc    660
atgtactact gtgccgccga tccaattccc ggccccggct actgcgatgg cggccctaac    720
aagtactggg gccaaggcac acaagtgact gtctcgtctg ctagccacca tcaccatcac    780
cac                                                                  783

SEQ ID NO: 356          moltype = DNA   length = 774
```

```
FEATURE            Location/Qualifiers
source             1..774
                   mol_type = other DNA
                   organism = synthetic construct
                   note = Description of Artificial Sequence: Synthetic
                   polynucleotide
SEQUENCE: 356
caagtgcagc tgcaagagag cggaggagga agcgtgcaag ccggaggctc tctgagactg    60
agctgtgccg cctctaggta tctgtacagc atcgactaca tggcttggtt cagacagagc   120
cccggcaagg agagggagcc agtggctgtc atctacactg cctccggcgc cacattctat   180
ccagatagcg tgaagggaag gttcactatc agccaagata cgccaagat gacagtgtat    240
ctgcagatga actctctgaa gagcgaggac actgccatgt actactgtgc cgccgtgagg   300
aagacagata gctacctctt cgacgcccag agcttcacat actggggcca aggcacacaa   360
gtgacagtct cgagcggcgg aggatcccaa gtgcagctgc aagagtccgg aggaggaagc   420
gtgcaagccg gcggatctct gagactgagc tgtgccgcct ctaggtacac ttacaacagc   480
tactgcatgg gctggttcag acaagccccc ggcaaggaaa gagagggcgt ggccactatc   540
gatagcgacg gcatgactag gtacgctgat agcgtcaagg gaaggttcac aatctccaag   600
gacaatgcta agaacactct gtacctccag atgaactctc tgaagccaga ggacacagcc   660
atgtactact cgcgctgccga tgccgactgc actatcgccg ccatgactac taatcctctg   720
ggccaaggca cacaagtgac tgtctcgtct gctagccacc atcaccatca ccac          774

SEQ ID NO: 357       moltype = DNA   length = 786
FEATURE              Location/Qualifiers
source               1..786
                     mol_type = other DNA
                     organism = synthetic construct
                     note = Description of Artificial Sequence: Synthetic
                     polynucleotide
SEQUENCE: 357
caagtgcagc tgcaagagag cggaggagga agcgtgcaag ccggaggctc tctgagactg    60
agctgtgccg cctctaggta tctgtacagc atcgactaca tggcttggtt cagacagagc   120
cccggcaagg agagggagcc agtggctgtc atctacactg cctccggcgc cacattctat   180
ccagatagcg tgaagggaag gttcactatc agccaagata cgccaagat gacagtgtat    240
ctgcagatga actctctgaa gagcgaggac actgccatgt actactgtgc cgccgtgagg   300
aagacagata gctacctctt cgacgcccag agcttcacat actggggcca aggcacacaa   360
gtgacagtct cgagcggcgg aggatcccaa gtgcagctgc aagagtccgg cggaggcagc   420
gtccaagccg gaggatctct gaggctgagc tgtacagtga gcagatacac tgccagcgtg   480
aactacatgg gctggttcag acaagccccc ggcaaagaga gagggcgt ggccacaatc    540
ttcactggcg ccggcacaac atactacgcc aactccgtca agggaaggtt cacaatctct   600
agggacaacg ccaagaacac tgcctatctg cagatgaact ccctcaagcc agaggacact   660
gccatctact actgcgccgt ggatttcaga ggcggactgc tgtataggcc agcctacgag   720
tacacttata ggggccaagg cacacaagtg acagtctcgt ctgctagcca ccatcaccat   780
caccac                                                             786

SEQ ID NO: 358       moltype = DNA   length = 789
FEATURE              Location/Qualifiers
source               1..789
                     mol_type = other DNA
                     organism = synthetic construct
                     note = Description of Artificial Sequence: Synthetic
                     polynucleotide
SEQUENCE: 358
caagtgcagc tgcaagagag cggaggagga agcgtgcaag ccggaggctc tctgagactg    60
agctgtgccg cctctaggta tctgtacagc atcgactaca tggcttggtt cagacagagc   120
cccggcaagg agagggagcc agtggctgtc atctacactg cctccggcgc cacattctat   180
ccagatagcg tgaagggaag gttcactatc agccaagata cgccaagat gacagtgtat    240
ctgcagatga actctctgaa gagcgaggac actgccatgt actactgtgc cgccgtgagg   300
aagacagata gctacctctt cgacgcccag agcttcacat actggggcca aggcacacaa   360
gtgacagtct cgagcggcgg aggatcccaa gtgcagctgc aagagtccgg cggctcacag   420
gtcgaagctg gaggatctct gaggctgagc tgtgctgcca gcgggctacac tcacagcgc   480
tactgtatgg gctggttcag acaagccccc ggcaaggaga gggaaggcgt ggctgccatc   540
gacgtggatg gcagcactac ttacgccgac agcgtgaagg gaaggttcac tatcagcaag   600
gacaacgcca agaacacact ctatctgcag atgaacagcc tcaagccaga ggacactggc   660
atgtactact cgcgccgccga gttcgccgat tgcagcagca actactttct gcctcccggc   720
gccgtcagat attgggggcca aggcactcaa gtgacagtct cgtctgctag ccaccatcac   780
catcaccac                                                           789

SEQ ID NO: 359       moltype = DNA   length = 783
FEATURE              Location/Qualifiers
source               1..783
                     mol_type = other DNA
                     organism = synthetic construct
                     note = Description of Artificial Sequence: Synthetic
                     polynucleotide
SEQUENCE: 359
caagtgcagc tgcaagagag cggaggagga agcgtgcaag ccggaggctc tctgagactg    60
agctgtgccg cctctaggta tctgtacagc atcgactaca tggcttggtt cagacagagc   120
cccggcaagg agagggagcc agtggctgtc atctacactg cctccggcgc cacattctat   180
ccagatagcg tgaagggaag gttcactatc agccaagata cgccaagat gacagtgtat    240
```

```
ctgcagatga actctctgaa gagcgaggac actgccatgt actactgtgc cgccgtgagg    300
aagacagata gctacctctt cgacgcccag agcttcacat actggggcca aggcacacaa    360
gtgacagtct cgagcggcgg aggatcccaa gtgcagctgc aagagagcgg aggaggaagc    420
gtccaagccg gaggatctct gagactgagc tgcgccgcta gtggctactc ctacagcagc    480
tactgcatgg gctggtttag gcaagccccc ggcaaggaga gagaaggcgt ggccactatc    540
gacagcgacg gcatgacaag gtacgccgac agcgtgaagg gaaggttcac aatcagcaag    600
gacaacgcca agaacacact gtatctgcag atgaactctc tgaagccaga ggacactgcc    660
atgtactact gtgccgctcc tctgtacgac tgtgatagcg cgctgtggg cagaaatcca     720
ccttattggg gccaaggcac tcaagtgaca gtctcgtctg ctagccacca tcaccatcac    780
cac                                                                  783
```

SEQ ID NO: 360          moltype = DNA   length = 777
FEATURE                 Location/Qualifiers
source                  1..777
                        mol_type = other DNA
                        organism = synthetic construct
                        note = Description of Artificial Sequence: Synthetic
                            polynucleotide SEQUENCE: 360
```
caagtgcagc tgcaagagag cggaggagga agcgtgcaag ccggaggctc tctgagactg    60
agctgtgccg cctctaggta tctgtacagc atcgactaca tggcttggtt cagacagagc    120
cccggcaagg agagggagcc agtggctgtc atctcacactg cctccggcgc cacattctat    180
ccagatagcg tgaagggaag gttcactatc agccaagata cgccaagat gacagtgtat     240
ctgcagatga actctctgaa gagcgaggac actgccatgt actactgtgc cgccgtgagg    300
aagacagata gctacctctt cgacgcccag agcttcacat actggggcca aggcacacaa    360
gtgacagtct cgagcggcgg aggatcccaa gtgcagctgc aagagagcgg aggaggcagc    420
gtgcagactg gaggctctct gagactgagc tgtgctgcca gcggctacac ttatctgagg    480
ggctgtatgg gctggtttag gcaagccccc ggcaaggaga gagagggcgt ggccgtcatg    540
gatgtggtgg gcgataggag aagctacatc gacagcgtga agggaaggtt cacaatctct    600
agggacaatg ccgccaacag cgtctatctg cagatgaaca tctgaagcc agaggacaca    660
gccatgtact actgcactgc cggccctaac tgtgtgggct ggagaagcgg actggattac    720
tggggccaag gcacacaagt gacagtctcg tctgctagcc accatcacca tcaccac       777
```

SEQ ID NO: 361          moltype = DNA   length = 801
FEATURE                 Location/Qualifiers
source                  1..801
                        mol_type = other DNA
                        organism = synthetic construct
                        note = Description of Artificial Sequence: Synthetic
                            polynucleotide SEQUENCE: 361
```
caagtgcagc tgcaagagag cggaggagga agcgtgcaag ccggaggctc tctgaggctg    60
agctgtgccg cctctaggtt cacatacagc agctactgca tgggctgtt cagacaagcc     120
cccggcaaag agagagaagg cgtggccagc atcgatagcg atggctccac tagctacact    180
gacagcgtga agggaaggtt cactatcagc aaggacaacg ccaagaacac tctgtatctg    240
cagatgaact ctctgaagcc agaggacaca gccatgtact actgtgccct cgatctgatg    300
agcacagtgg tgcccggctt ctgtggcttt ctgctgagcg ctggcatgga ttactggggc    360
aagggcactc aagtgactgt ctcgagcggc ggaggatccc aagtgcagct gcaagagagc    420
ggcggaggaa gcgtgcaagc tggaggctct gaggctga gctgtgctgc cagcggctac    480
acttatagca gcggctgtat gggctggttc agacaagccc ccggcaagga aagggaagcc    540
gtggccgcca tcaattccga tggcagcaca agctacgccg acagcgtgaa gggaaggttc    600
acaatcagca aggacaacgc caagaacaca ctctatctgc agatgaactc tctgaagcca    660
gaggacacag ccatgtacta ctgcgccgct gagccttact gtagcggcgg ctacccaaga    720
tggagcgtcg ctgagttcgg ctactggggc caaggcacac aagtgactgt ctcgtctgct    780
agccaccatc accatcacca c                                              801
```

SEQ ID NO: 362          moltype = DNA   length = 795
FEATURE                 Location/Qualifiers
source                  1..795
                        mol_type = other DNA
                        organism = synthetic construct
                        note = Description of Artificial Sequence: Synthetic
                            polynucleotide SEQUENCE: 362
```
caagtgcagc tgcaagagag cggaggagga agcgtgcaag ccggaggctc tctgaggctg    60
agctgtgccg cctctaggtt cacatacagc agctactgca tgggctgtt cagacaagcc     120
cccggcaaag agagagaagg cgtggccagc atcgatagcg atggctccac tagctacact    180
gacagcgtga agggaaggtt cactatcagc aaggacaacg ccaagaacac tctgtatctg    240
cagatgaact ctctgaagcc agaggacaca gccatgtact actgtgccct cgatctgatg    300
agcacagtgg tgcccggctt ctgtggcttt ctgctgagcg ctggcatgga ttactggggc    360
aagggcactc aagtgactgt ctcgagcggc ggaggatccc aagtgcagct gcaagagagc    420
ggaggaggca gcgtccaagc cggaggctct ctgaggctga gctgtgctgc cagcggctac    480
acttacagca gctactgcat gggctggttc agacaagccc ccggcaagga gagagggc     540
gtggctcaca tcgacagcga cggctccaca agctacgccg atagcgtgaa gggaaggttc    600
acaatctcca aggacaacgc caagaacact ctgtacctcc agatgaactc tctgaagcca    660
gaggacactg ccatgtacta ctgtgccgcc gatccaattc ccggcccgg ctactgcgat     720
ggcggcccta acagtactg gggccaaggc acaagtga ctgtctcgtc tgctagccac      780
catcaccatc accac                                                     795
```

| SEQ ID NO: 363 | moltype = DNA length = 786 |
| --- | --- |
| FEATURE | Location/Qualifiers |
| source | 1..786 |
| | mol_type = other DNA |
| | organism = synthetic construct |
| | note = Description of Artificial Sequence: Synthetic polynucleotide |

SEQUENCE: 363

```
caagtgcagc tgcaagagag cggaggagga agcgtgcaag ccggaggctc tctgaggctg   60
agctgtgccg cctctaggtt cacatacagc agctactgca tgggctggtt cagacaagcc  120
cccggcaaag agagagaagg cgtggccagc atcgatagcg atggctccac tagctacact  180
gacagcgtga agggaaggtt cactatcagc aaggacaacg ccaagaacac tctgtatctg  240
cagatgaact ctctgaagcc agaggacaca gccatgtact actgtgccct cgatctgatg  300
agcacagtgg tgcccggctt ctgtggcttt ctgctgagcg ctggcatgga ttactggggc  360
aagggcactc aagtgactgt ctcgagcggc ggaggatccc aagtgcagct gcaagagtcc  420
ggaggaggaa gcgtgcaagc cggcggatcc ctgagactga gctgtgccgc ctctaggtac  480
acttacaaca gctactgcat gggctggttc agacaagccc ccgcaagga aagagagggc  540
gtggccacta tcgatagcga cggcatgact aggtacgctg atagcgtcaa gggaaggttc  600
acaatctcca aggacaatgc taagaacact ctgtacctcc agatgaactc tctgaagcca  660
gaggacacag ccatgtacta ctgcgctgcc gatgccgact gcactatcgc cgccatgact  720
actaatcctc tgggccaagg cacacaagtg actgtctcgt ctgctagcca ccatcaccat  780
caccac                                                             786
```

| SEQ ID NO: 364 | moltype = DNA length = 798 |
| --- | --- |
| FEATURE | Location/Qualifiers |
| source | 1..798 |
| | mol_type = other DNA |
| | organism = synthetic construct |
| | note = Description of Artificial Sequence: Synthetic polynucleotide |

SEQUENCE: 364

```
caagtgcagc tgcaagagag cggaggagga agcgtgcaag ccggaggctc tctgaggctg   60
agctgtgccg cctctaggtt cacatacagc agctactgca tgggctggtt cagacaagcc  120
cccggcaaag agagagaagg cgtggccagc atcgatagcg atggctccac tagctacact  180
gacagcgtga agggaaggtt cactatcagc aaggacaacg ccaagaacac tctgtatctg  240
cagatgaact ctctgaagcc agaggacaca gccatgtact actgtgccct cgatctgatg  300
agcacagtgg tgcccggctt ctgtggcttt ctgctgagcg ctggcatgga ttactggggc  360
aagggcactc aagtgactgt ctcgagcggc ggaggatccc aagtgcagct gcaagagtcc  420
ggcggaggca gcgtccaagc cggaggatcc ctgaggctga gctgtacagt gagcagatac  480
actgccagcg tgaactacat gggctggttc agacaagccc ccgcaaaga gagagaggc  540
gtggccacaa tcttcactgg cgccggcaca acatactacg ccaactccgt caagggaagg  600
ttcacaatct ctagggacaa cgccaagaac actgccatct gcagatgaa ctcccctcaag  660
ccagaggaca ctgccatcta ctactgcgcc gtggatttca gaggcggact gctgtatagg  720
ccagcctacg agtacactta tagggccaa ggcacacaag tgacagtctc gtctgctagc  780
caccatcacc atcaccac                                                798
```

| SEQ ID NO: 365 | moltype = DNA length = 801 |
| --- | --- |
| FEATURE | Location/Qualifiers |
| source | 1..801 |
| | mol_type = other DNA |
| | organism = synthetic construct |
| | note = Description of Artificial Sequence: Synthetic polynucleotide |

SEQUENCE: 365

```
caagtgcagc tgcaagagag cggaggagga agcgtgcaag ccggaggctc tctgaggctg   60
agctgtgccg cctctaggtt cacatacagc agctactgca tgggctggtt cagacaagcc  120
cccggcaaag agagagaagg cgtggccagc atcgatagcg atggctccac tagctacact  180
gacagcgtga agggaaggtt cactatcagc aaggacaacg ccaagaacac tctgtatctg  240
cagatgaact ctctgaagcc agaggacaca gccatgtact actgtgccct cgatctgatg  300
agcacagtgg tgcccggctt ctgtggcttt ctgctgagcg ctggcatgga ttactggggc  360
aagggcactc aagtgactgt ctcgagcggc ggaggatccc aagtgcagct gcaagagagc  420
ggaggaggca gcgtcgaagc tggaggatct ctgaggctga gctgtgctgc cagcggctac  480
actcacagca gctactgtat gggctggttc agacaagccc ccgcaagga gagggaaggc  540
gtggctgcca tcgacgtgga tggcagcact acttacgccg acagcgtgaa gggaaggttc  600
actatcagca aggacaacgc caagaacaca ctctatctgc agatgaacag cctcaagcca  660
gaggacactg catgtacta ctgcgccgcc gagtcgccg attgcagcag caactacttt  720
ctgcctccg cgccgtcag atattgggc caaggcactc aagtgacagt ctcgtctgct  780
agccaccatc accatcacca c                                            801
```

| SEQ ID NO: 366 | moltype = DNA length = 795 |
| --- | --- |
| FEATURE | Location/Qualifiers |
| source | 1..795 |
| | mol_type = other DNA |
| | organism = synthetic construct |
| | note = Description of Artificial Sequence: Synthetic polynucleotide |

SEQUENCE: 366

```
caagtgcagc tgcaagagag cggaggagga agcgtgcaag ccggaggctc tctgaggctg   60
agctgtgccg cctctaggtt cacatacagc agctactgca tgggctggtt cagacaagcc  120
```

```
cccggcaaag agagagaagg cgtggccagc atcgatagcg atggctccac tagctacact  180
gacagcgtga agggaaggtt cactatcagc aaggacaacg ccaagaacac tctgtatctg  240
cagatgaact ctctgaagcc agaggacaca gccatgtact actgtgccct cgatctgatg  300
agcacagtgg tgcccggctt ctgtggcttt ctgctgagcg ctggcatgga ttactggggc  360
aagggcactc aagtgactgt ctcgagcggg ggaggatccc aagtgcagct gcaagagagc  420
ggaggaggaa gcgtccaagc cggaggatct ctgagactga gctgcgccgc tagtggctac  480
tcctacagca gctactgcat gggctggttt aggcaagccc ccgcaagga gagaaaggc  540
gtggccacta tcgacagcga cggcatgaca aggtacgccg acagcgtgaa gggaaggttc  600
acaatcagca aggacaacgc caagaacaca ctgtatctgc agatgaactc tctgaagcca  660
gaggacactg ccatgtacta ctgtgccgct cctctgtacg actgtgatag cggcgctgtg  720
ggcagaaatc caccttattg gggccaaggc actcaagtga cagtctcgtc tgctagccac  780
catcaccatc accac                                                 795

SEQ ID NO: 367        moltype = DNA   length = 789
FEATURE               Location/Qualifiers
source                1..789
                      mol_type = other DNA
                      organism = synthetic construct
                      note = Description of Artificial Sequence: Synthetic
                      polynucleotide
SEQUENCE: 367
caagtgcagc tgcaagagag cggaggagga agcgtgcaag ccggaggctc tctgaggctg   60
agctgtgccg cctctaggtt cacatacagc agctactgca tgggctggtt cagacaagcc  120
cccggcaaag agagagaagg cgtggccagc atcgatagcg atggctccac tagctacact  180
gacagcgtga agggaaggtt cactatcagc aaggacaacg ccaagaacac tctgtatctg  240
cagatgaact ctctgaagcc agaggacaca gccatgtact actgtgccct cgatctgatg  300
agcacagtgg tgcccggctt ctgtggcttt ctgctgagcg ctggcatgga ttactggggc  360
aagggcactc aagtgactgt ctcgagcggg ggaggatccc aagtgcagct gcaagagagc  420
ggaggcggca gcgtgcagac tggaggctct ctgagactga gctgtgctgc cagcggctac  480
acttatctga ggggctgtat gggctggttt aggcaagccc ccggcaagga gagagaggcc  540
gtggccgtca tggatgtggt gggcgatagg agaagctaca tcgacagcgt gaagggaagg  600
ttcacaatct ctaggacaa tgccgccaac agcgtctatc tgcagatgga caatctgaag  660
ccagaggaca cagccatgta ctactgcact gccggcccta actgtgtggg ctggagaagc  720
ggactggatt actggggcca aggcacacaa gtgacagtc cgtctgctag ccaccatcac  780
catcaccac                                                        789

SEQ ID NO: 368        moltype = DNA   length = 807
FEATURE               Location/Qualifiers
source                1..807
                      mol_type = other DNA
                      organism = synthetic construct
                      note = Description of Artificial Sequence: Synthetic
                      polynucleotide
SEQUENCE: 368
caagtgcagc tgcaagagtc cggaggaggc agcgtccaag ccggaggctc tctgaggctg   60
agctgtgctg ccagcggcta cacttacagc atgtactgca tgggctggtt cagacaagcc  120
cccggcaagg aaagagaggg cgtggcccag atcaatagcg atggcagcac aagctacgcc  180
gacagcgtga agggaaggtt cactatctcc aaggacaacg ccaagaacac tctgtatctg  240
cagatgaact ctctgaagcc agaggacact gccatgtact actgcgctgc cgattctagg  300
gtgtacggcg gcagctggta tgagaggctc tgcggccctt acacatacga gtacaactac  360
tggggccaag gcacacaagt gactgtctcg agcggcgtga gatccagtgc agctgcaa  420
gagagcggcg gaggaagcgt gcaagctgga ggctctctga ggctgagctg tgctgccagc  480
ggctacactt atagcagcgg ctgtatgggc tggttcagac aagcccccgg caaggaaagg  540
gaagccgtgg ccgccatcaa ttccgatggc agcacaagct acgccgacag cgtgaaggga  600
aggttcacaa tcagcaagga caacgccaag aacacactct atctgcagat gaactctctg  660
aagccagagg acacagccat gtactactgc gccgctgagc cttactgtag cggcggctac  720
ccaagatgga gcgtcgctga gttcggctac tggggccaag gcacacaagt gactgtctcg  780
tctgctagcc accatcacca tcaccac                                    807

SEQ ID NO: 369        moltype = DNA   length = 801
FEATURE               Location/Qualifiers
source                1..801
                      mol_type = other DNA
                      organism = synthetic construct
                      note = Description of Artificial Sequence: Synthetic
                      polynucleotide
SEQUENCE: 369
caagtgcagc tgcaagagtc cggaggaggc agcgtccaag ccggaggctc tctgaggctg   60
agctgtgctg ccagcggcta cacttacagc atgtactgca tgggctggtt cagacaagcc  120
cccggcaagg aaagagaggg cgtggcccag atcaatagcg atggcagcac aagctacgcc  180
gacagcgtga agggaaggtt cactatctcc aaggacaacg ccaagaacac tctgtatctg  240
cagatgaact ctctgaagcc agaggacact gccatgtact actgcgctgc cgattctagg  300
gtgtacggcg gcagctggta tgagaggctc tgcggccctt acacatacga gtacaactac  360
tggggccaag gcacacaagt gactgtctcg agcggcgcaa gatccagtgc agctgcaa  420
gagagcggag gaggcagcgt ccaagccgga ggctctctga ggctgagctg tgctgccagc  480
ggctacactt acagcagcta ctgcatgggc tggttcagac aagcccccgg caaggagaga  540
gagggcgtgg ctcacatcga cagcgacggc tccacaagct acgccgatag cgtgaaggga  600
aggttcacaa tctccaagga caacgccaag aacactctgt acctccagat gaactctctg  660
aagccagagg acactgccat gtactactgt gccgccgatc caattcccgg ccccggctac  720
```

```
tgcgatggcg gccctaacaa gtactggggc caaggcacac aagtgactgt ctcgtctgct  780
agccaccatc accatcacca c                                            801
```

| SEQ ID NO: 370 | moltype = DNA  length = 792 |
|---|---|
| FEATURE | Location/Qualifiers |
| source | 1..792 |
| | mol_type = other DNA |
| | organism = synthetic construct |
| | note = Description of Artificial Sequence: Synthetic polynucleotide |

SEQUENCE: 370
```
caagtgcagc tgcaagagtc cggaggaggc agcgtccaag ccggaggctc tctgaggctg  60
agctgtgctg ccagcggcta cacttacagc atgtactgca tgggctggtt cagacaagcc  120
cccggcaagg aaagagaggg cgtggcccag atcaatagcg atggcagcac aagctacgcc  180
gacagcgtga agggaaggtt cactatctcc aaggacaacg ccaagaacac tctgtatctg  240
cagatgaact ctctgaagcc agaggacact gccatgtact actgcgctgc cgattctagg  300
gtgtacggcg gcagctggta tgagaggctc tgcggccctt acacatacga gtacaactac  360
tggggccaag gcacacaagt gactgtctcg agcggcggag gatccaagt gcagctgcaa  420
gagtccggag gaggaagcgt gcaagccggc ggatctctga gactgagctg tgccgcctct  480
aggtacactt acaacagcta ctgcatgggc tggttcagac aagcccccgg caaggaaaga  540
gagggcgtgg ccactatcga tagcgacggc atgactaggt acgctgatag cgtcaaggga  600
aggttcacaa tctccaagga caatgctaag aacactctg acctccagat gaactctctg  660
aagccagagg acacagccat gtactactgc gctgccgatg ccgactgcac tatcgccgcc  720
atgactacta atcctctggg ccaaggcaca caagtgactg tctcgtctgc tagccaccat  780
caccatcacc ac                                                       792
```

| SEQ ID NO: 371 | moltype = DNA  length = 804 |
|---|---|
| FEATURE | Location/Qualifiers |
| source | 1..804 |
| | mol_type = other DNA |
| | organism = synthetic construct |
| | note = Description of Artificial Sequence: Synthetic polynucleotide |

SEQUENCE: 371
```
caagtgcagc tgcaagagtc cggaggaggc agcgtccaag ccggaggctc tctgaggctg  60
agctgtgctg ccagcggcta cacttacagc atgtactgca tgggctggtt cagacaagcc  120
cccggcaagg aaagagaggg cgtggcccag atcaatagcg atggcagcac aagctacgcc  180
gacagcgtga agggaaggtt cactatctcc aaggacaacg ccaagaacac tctgtatctg  240
cagatgaact ctctgaagcc agaggacact gccatgtact actgcgctgc cgattctagg  300
gtgtacggcg gcagctggta tgagaggctc tgcggccctt acacatacga gtacaactac  360
tggggccaag gcacacaagt gactgtctcg agcggcggag gatccaagt gcagctgcaa  420
gagtccggcg gaggcagcgt ccaagccgga ggatctctga gctgagctg tacagtgagc  480
agatacactg ccagcgtgaa ctacatgggc tggttcagac aagcccccgg caaagagaga  540
gagggcgtgg ccacaatctt cactggcgcc ggcacaacat actacgccaa ctccgtcaag  600
ggaaggttca atctctag ggacaacgcc aagaacactg cctatctgca gatgaactcc  660
ctcaagccag aggacactgc catctactac tgcgccgtgg atttcagagg cggactgctg  720
tataggccag cctacgagta cacttatagg ggccaaggca cacaagtgac agtctcgtct  780
gctagccacc atcaccatca ccac                                          804
```

| SEQ ID NO: 372 | moltype = DNA  length = 807 |
|---|---|
| FEATURE | Location/Qualifiers |
| source | 1..807 |
| | mol_type = other DNA |
| | organism = synthetic construct |
| | note = Description of Artificial Sequence: Synthetic polynucleotide |

SEQUENCE: 372
```
caagtgcagc tgcaagagtc cggaggaggc agcgtccaag ccggaggctc tctgaggctg  60
agctgtgctg ccagcggcta cacttacagc atgtactgca tgggctggtt cagacaagcc  120
cccggcaagg aaagagaggg cgtggcccag atcaatagcg atggcagcac aagctacgcc  180
gacagcgtga agggaaggtt cactatctcc aaggacaacg ccaagaacac tctgtatctg  240
cagatgaact ctctgaagcc agaggacact gccatgtact actgcgctgc cgattctagg  300
gtgtacggcg gcagctggta tgagaggctc tgcggccctt acacatacga gtacaactac  360
tggggccaag gcacacaagt gactgtctcg agcggcggag gatccaagt gcagctgcaa  420
gagagcggag gaggcagcgt cgaagctgga ggatctctga gctgagctg tgctgccagc  480
ggctacactc acagcagcta ctgtatgggc tggttcagac aagcccccgg caaggagagg  540
gaaggcgtgg ctgccatcga cgtggatggc agcactactt acgccgacag cgtgaaggga  600
aggttcacta tcagcaagga caacgccaag aacactctat ctgcagat gaacagctc  660
aagccagagg acactggcat gtactactgc gccgccgagt cgccgattg cagcagcaac  720
tactttctgc ctcccggcgc cgtcagatat tggggccaag gcactcaagt gacagtctcg  780
tctgctagcc accatcacca tcaccac                                      807
```

| SEQ ID NO: 373 | moltype = DNA  length = 801 |
|---|---|
| FEATURE | Location/Qualifiers |
| source | 1..801 |
| | mol_type = other DNA |
| | organism = synthetic construct |
| | note = Description of Artificial Sequence: Synthetic polynucleotide |

```
SEQUENCE: 373
caagtgcagc tgcaagagtc cggaggaggc agcgtccaag ccggaggctc tctgaggctg    60
agctgtgctg ccagcggcta cacttacagc atgtactgca tgggctggtt cagacaagcc   120
cccggcaagg aaagagaggg cgtggcccag atcaatagcg atggcagcac aagctacgcc   180
gacagcgtga agggaaggtt cactatctcc aaggacaacg ccaagaacac tctgtatctg   240
cagatgaact ctctgaagcc agaggacact gccatgtact actgcgctgc cgattctagg   300
gtgtacggcg gcagctggta tgagaggctc tgccggccct tacacatacga gtacaactac   360
tggggccaag gcacacaagt gactgtctcg agcggcggag gatcccaagt gcagctgcaa   420
gagagcggag gaggaagcgt ccaagccgga ggatctctga gactgagctg cgccgctagt   480
ggctactcct acagcagcta ctgcatgggc tggtttaggc aagccccccgg caaggagaga   540
gaaggcgtgg ccactatcga cagcgacggc atgacaaggt acgccgacag cgtgaaggga   600
aggttcacaa tcagcaagga caacgccaag aacacactgt atctgcagat gaactctctg   660
aagccagagg acactgccat gtactactgt gccgctcctc tgtacgactg tgatagcggc   720
gctgtgggca gaaatccacc ttattgggc caaggcactc aagtgacagt ctcgtctgct   780
agccaccatc accatcacca c                                              801

SEQ ID NO: 374           moltype = DNA   length = 795
FEATURE                  Location/Qualifiers
source                   1..795
                         mol_type = other DNA
                         organism = synthetic construct
                         note = Description of Artificial Sequence: Synthetic
                             polynucleotide
SEQUENCE: 374
caagtgcagc tgcaagagtc cggaggaggc agcgtccaag ccggaggctc tctgaggctg    60
agctgtgctg ccagcggcta cacttacagc atgtactgca tgggctggtt cagacaagcc   120
cccggcaagg aaagagaggg cgtggcccag atcaatagcg atggcagcac aagctacgcc   180
gacagcgtga agggaaggtt cactatctcc aaggacaacg ccaagaacac tctgtatctg   240
cagatgaact ctctgaagcc agaggacact gccatgtact actgcgctgc cgattctagg   300
gtgtacggcg gcagctggta tgagaggctc tgccggccct tacacatacga gtacaactac   360
tggggccaag gcacacaagt gactgtctcg agcggcggag gatcccaagt gcagctgcaa   420
gagagcggag gcggcagcgt gcagactgga ggctctctga gactgagctg tgctgccagc   480
ggctacactt atctgagggg ctgtatgggc tggtttaggc aagcccccgg caaggagaga   540
gagggcgtgg ccgtcatgga tgtggtgggc gataggagaa gctacatcga cagcgtgaag   600
ggaaggttca caatctctag ggacaatgcc gccaacagcg tctatctgca gatggacaat   660
ctgaagccag aggacacagc catgtactac tgcactgccg gcctaactg tgtgggctgg   720
agaagcggac tggattactg gggccaaggc acacaagtga cagtctcgtc tgctagccac   780
catcaccatc accac                                                     795

SEQ ID NO: 375           moltype = DNA   length = 816
FEATURE                  Location/Qualifiers
source                   1..816
                         mol_type = other DNA
                         organism = synthetic construct
                         note = Description of Artificial Sequence: Synthetic
                             polynucleotide
SEQUENCE: 375
caagtgcagc tgcaagagag cggcggagga agcgtgcaag ccggaggatc tctgagactg    60
agctgcgctg tgagcggcta cgcctactcc acatactgca tgggctggtt taggcaagcc   120
cccggcaaag agagagaggg cgtggctgct atcgatagcg cggcagcac aagctacgcc   180
gatagcgtga agggaaggtt cacaatcagc aaggacaacg ccaagaacac actgtatctg   240
aggatgaact ctctgaagcc agaggacaca gccatgtact actgtgctgc tgtgcctcct   300
cctccagatg cgcgcagctg tctgtttctg ggaccagaga tcaaggtcag caaggccgat   360
tttaggtact ggggccaagg cacacaagtg acagtctcga gcggcggagg atcccaagtg   420
cagctgcaag agagcggcgg aggaagcgtg caagccggag gctctctgag gctgagctgt   480
gctgccagcg gctacactta tagcagcggc tgtatgggct ggttcagaca agcccccggc   540
aaggaagggg aagccgtggc cgccatcaat tccgatggca gcacaagcta cgccgacagc   600
gtgaagggaa ggttcacaat cagcaaggac aacgccaaga acacactcta tctgcagatg   660
aactctctga agccagagga cacagccatg tactactgcg ccgctgagcc ttactgtagc   720
ggcggctacc aagatggagc gtcgctgag ttcggctact ggggccaagg cacacaagtg   780
actgtctcgt ctgctagcca ccatcaccat caccac                              816

SEQ ID NO: 376           moltype = DNA   length = 810
FEATURE                  Location/Qualifiers
source                   1..810
                         mol_type = other DNA
                         organism = synthetic construct
                         note = Description of Artificial Sequence: Synthetic
                             polynucleotide
SEQUENCE: 376
caagtgcagc tgcaagagag cggcggagga agcgtgcaag ccggaggatc tctgagactg    60
agctgcgctg tgagcggcta cgcctactcc acatactgca tgggctggtt taggcaagcc   120
cccggcaaag agagagaggg cgtggctgct atcgatagcg cggcagcac aagctacgcc   180
gatagcgtga agggaaggtt cacaatcagc aaggacaacg ccaagaacac actgtatctg   240
aggatgaact ctctgaagcc agaggacaca gccatgtact actgtgctgc tgtgcctcct   300
cctccagatg cgcgcagctg tctgtttctg ggaccagaga tcaaggtcag caaggccgat   360
tttaggtact ggggccaagg cacacaagtg acagtctcga gcggcggagg atcccaagtg   420
cagctgcaag agagcggagg aggcagcgtc aagccggag gctctctgag gctgagctgt   480
gctgccagcg gctacactta cagcagctac tgcatgggct ggttcagaca agcccccggc   540
```

```
aaggagagag agggcgtggc tcacatcgac agcgacggct ccacaagcta cgccgatagc   600
gtgaagggaa ggttcacaat ctccaaggac aacgccaaga acactctgta cctccagatg   660
aactctctga agccagagga cactgccatg tactactgtg ccgccgatcc aattcccggc   720
cccggctact gcgatggcgg ccctaacaag tactggggcc aaggcacaca agtgactgtc   780
tcgtctgcta gccaccatca ccatcaccac                                    810
```

| SEQ ID NO: 377 | moltype = DNA length = 801 |
|---|---|
| FEATURE | Location/Qualifiers |
| source | 1..801 |
| | mol_type = other DNA |
| | organism = synthetic construct |
| | note = Description of Artificial Sequence: Synthetic polynucleotide |

SEQUENCE: 377
```
caagtgcagc tgcaagagag cggcggagga agcgtgcaag ccggaggatc tctgagactg    60
agctgcgctg tgagcggcta cgcctactcc acatactgca tgggctggtt taggcaagcc   120
cccggcaaag agagagaggg cgtggctgct atcgatagcg cggcagcac aagctacgcc    180
gatagcgtga agggaaggtt cacaatcagc aaggacaacg ccaagaacac actgtatctg   240
aggatgaact ctctgaagcc agaggacaca gccatgtact actgtgctgc tgtgcctcct   300
cctccagatg gcggcagctg tctgtttctg ggaccagaga tcaaggtcag caaggccgat   360
tttaggtact ggggccaagg cacacaagtg acagtctcga gcggcggagg atcccaagtg   420
cagctgcaag agtccggagg aggaagcgtg caagccggag gatctctgag actgagctgt   480
gccgcctcta ggtacactta caacagctac tgcatgggct ggttcagaca agcccccggc   540
aaggaaagag agggcgtggc cactatcgat agcgacggca tgactaggta cgctgatagc   600
gtcaaggaa ggttcacaat ctccaaggac aatgctaaga acactctgta cctccagatg    660
aactctctga agccagagga cacagccatg tactactgcg ctgccgatgc cgactgcact   720
atcgccgcca tgactactaa tcctctgggc caaggcacac aagtgactgt ctcgtctgct   780
agccaccatc accatcacca c                                             801
```

| SEQ ID NO: 378 | moltype = DNA length = 813 |
|---|---|
| FEATURE | Location/Qualifiers |
| source | 1..813 |
| | mol_type = other DNA |
| | organism = synthetic construct |
| | note = Description of Artificial Sequence: Synthetic polynucleotide |

SEQUENCE: 378
```
caagtgcagc tgcaagagag cggcggagga agcgtgcaag ccggaggatc tctgagactg    60
agctgcgctg tgagcggcta cgcctactcc acatactgca tgggctggtt taggcaagcc   120
cccggcaaag agagagaggg cgtggctgct atcgatagcg cggcagcac aagctacgcc    180
gatagcgtga agggaaggtt cacaatcagc aaggacaacg ccaagaacac actgtatctg   240
aggatgaact ctctgaagcc agaggacaca gccatgtact actgtgctgc tgtgcctcct   300
cctccagatg gcggcagctg tctgtttctg ggaccagaga tcaaggtcag caaggccgat   360
tttaggtact ggggccaagg cacacaagtg acagtctcga gcggcggagg atcccaagtg   420
cagctgcaag agtccggcgg aggcagcgtc aagccggag gatctctgag gctgagctgt    480
acagtgagca gatacactgc cagcgtgaac tacatgggct ggttcagaca agcccccggc   540
aaagagagag agggcgtggc cacaatcttc actggcgtgg gcacaaacata ctacgccaac   600
tccgtcaagg gaaggttcac aatctctagg gacaacgcca agaacactgc ctatctgcag   660
atgaactccc tcaagccaga ggacactgcc atctactact gcgccgtgga tttcagaggc   720
ggactgctgt ataggccagc ctacgagtac acttataggg gccaaggcac acaagtgaca   780
gtctcgtctg ctagccacca tcaccatcac cac                                813
```

| SEQ ID NO: 379 | moltype = DNA length = 816 |
|---|---|
| FEATURE | Location/Qualifiers |
| source | 1..816 |
| | mol_type = other DNA |
| | organism = synthetic construct |
| | note = Description of Artificial Sequence: Synthetic polynucleotide |

SEQUENCE: 379
```
caagtgcagc tgcaagagag cggcggagga agcgtgcaag ccggaggatc tctgagactg    60
agctgcgctg tgagcggcta cgcctactcc acatactgca tgggctggtt taggcaagcc   120
cccggcaaag agagagaggg cgtggctgct atcgatagcg cggcagcac aagctacgcc    180
gatagcgtga agggaaggtt cacaatcagc aaggacaacg ccaagaacac actgtatctg   240
aggatgaact ctctgaagcc agaggacaca gccatgtact actgtgctgc tgtgcctcct   300
cctccagatg gcggcagctg tctgtttctg ggaccagaga tcaaggtcag caaggccgat   360
tttaggtact ggggccaagg cacacaagtg acagtctcga gcggcggagg atcccaagtg   420
cagctgcaag agagcggagg aggcagcgtc gaagctggag gatctctgag gctgagctgt   480
gctgccagcg gctacactca cagcagctac tgtatgggct ggttcagaca agcccccggc   540
aaggagaggg aaggcgtggc tgccatcgac gtgatgcga gcactactta cgccgacagc    600
gtgaagggaa ggttcactat cagcaaggac aacgccaaga acacactcta tctgcagatg   660
aacagcctca gccagagga cactggcatg tactactgcg ccgccgagtt cgccgattgc    720
agcagcaact actttctgcc tcccggcgcc gtcagatatt ggggccaagg cactcaagtg   780
acagtctcgt ctgctagcca ccatcaccat caccac                             816
```

| SEQ ID NO: 380 | moltype = DNA length = 810 |
|---|---|
| FEATURE | Location/Qualifiers |
| source | 1..810 |
| | mol_type = other DNA |

```
                        organism = synthetic construct
                        note = Description of Artificial Sequence: Synthetic
                           polynucleotide
SEQUENCE: 380
caagtgcagc tgcaagagag cggcggagga agcgtgcaag ccggaggatc tctgagactg    60
agctgcgctg tgagcggcta cgcctactcc acatactgca tgggctggtt taggcaagcc   120
cccggcaaag agagagaggg cgtggctgct atcgatagcg gcggcagcac aagctacgcc   180
gatagcgtga agggaaggtt cacaatcagc aaggacaacg ccaagaacac actgtatctg   240
aggatgaact ctctgaagcc agaggacaca gccatgtact actgtgctgc tgtgcctcct   300
cctccagatg gcggcagctg tctgtttctg ggaccagaga tcaaggtcag caaggccgat   360
tttaggtact ggggccaagg cacacaagtg acagtctcga gcggcggagg atcccaagtg   420
cagctgcaag agagcggagg aggaagcgtc aagccggaga atctctgag actgagctgc    480
gccgctagtg gctactccta cagcagctac tgcatgggct ggtttaggca agcccccggc   540
aaggagagag aaggcgtggc cactatcgac agcgacggca tgacaaggta cgccgacagc   600
gtgaagggaa ggttcacaat cagcaaggac aacgccaaga acacactgta tctgcagatg   660
aactctctga agccagagga cactgccatg tactactgtg ccgctcctct gtacgactgt   720
gatagcggcg ctgtgggcag aaatccacct tattggggcc aaggcactca agtgacagtc   780
tcgtctgcta gccaccatca ccatcaccac                                   810

SEQ ID NO: 381           moltype = DNA  length = 804
FEATURE                  Location/Qualifiers
source                   1..804
                        mol_type = other DNA
                        organism = synthetic construct
                        note = Description of Artificial Sequence: Synthetic
                           polynucleotide
SEQUENCE: 381
caagtgcagc tgcaagagag cggcggagga agcgtgcaag ccggaggatc tctgagactg    60
agctgcgctg tgagcggcta cgcctactcc acatactgca tgggctggtt taggcaagcc   120
cccggcaaag agagagaggg cgtggctgct atcgatagcg gcggcagcac aagctacgcc   180
gatagcgtga agggaaggtt cacaatcagc aaggacaacg ccaagaacac actgtatctg   240
aggatgaact ctctgaagcc agaggacaca gccatgtact actgtgctgc tgtgcctcct   300
cctccagatg gcggcagctg tctgtttctg ggaccagaga tcaaggtcag caaggccgat   360
tttaggtact ggggccaagg cacacaagtg acagtctcga gcggcggagg atcccaagtg   420
cagctgcaag agagcggagg cggcagcgtg cagactgag gctctctgag actgagctgc    480
gctgccagcg gctacactta tctgagggc tgtatgggct ggtttaggca agcccccggc    540
aaggagagag agggcgtggc cgtcatggat gtggtgggcg ataggagaag ctacatcgac   600
agcgtgaagg gaaggttcac aatctctagg gacaatgccg ccaacagcgt ctatctgcag   660
atggaaatc tgaagccaga ggacacagcc atgtactact gcactgccgg ccctaactgt    720
gtgggctgga aagcggact ggattactgg ggccaaggca cacaagtgac agtctcgtct   780
gctagccacc atcaccatca ccac                                         804

SEQ ID NO: 382           moltype = DNA  length = 795
FEATURE                  Location/Qualifiers
source                   1..795
                        mol_type = other DNA
                        organism = synthetic construct
                        note = Description of Artificial Sequence: Synthetic
                           polynucleotide
SEQUENCE: 382
caagtgcagc tgcaagagag cggaggagga agcgtgcaag ccggaggctc tctgaggctg    60
agctgtacag tgtccggcta cacttacagc tccaattgca tgggctggtt taggcaagcc   120
cccggcaagg aaagagaggg cgtggccact atctacactg gcggcggcaa cacatactac   180
gccgatagcg tgaagggaag gttcactatc agcaagata cgccaagaa cacagtgtat     240
ctgcagatga acaatctgaa gccagaggac actgccatgt actactgtgc tgctgagcca   300
ctgtctaggg tgtacggcgg cagctgccca actcctacat cgactactg gggccaaggc    360
acacaagtga ctgtctcgag cggcggagga tcccaagtgc agctgcaaga gagcggcgga   420
ggaagcgtgc aagctggagg ctctctgagg ctgagctgtg ctgccagcgg ctacacttat   480
agcagcggct gtatgggctg gttcagacaa gcccccggca aggaaaggaa agccgtggcc   540
gccatcaatt ccgatgcag cacaagctac gccgacagcg tgaagggaag gttcacaatc    600
agcaaggaca acgccaagaa cacactctat ctgcagatga actctctgaa gccagaggac   660
acagccatgt actactgcgc cgctgagcct tactgtagcg gcggctaccc aagatggagc   720
gtcgctgagt tcggctactg gggccaaggc acacaagtga ctgtctcgtc tgctagccac   780
catcaccatc accac                                                   795

SEQ ID NO: 383           moltype = DNA  length = 789
FEATURE                  Location/Qualifiers
source                   1..789
                        mol_type = other DNA
                        organism = synthetic construct
                        note = Description of Artificial Sequence: Synthetic
                           polynucleotide
SEQUENCE: 383
caagtgcagc tgcaagagag cggaggagga agcgtgcaag ccggaggctc tctgaggctg    60
agctgtacag tgtccggcta cacttacagc tccaattgca tgggctggtt taggcaagcc   120
cccggcaagg aaagagaggg cgtggccact atctacactg gcggcggcaa cacatactac   180
gccgatagcg tgaagggaag gttcactatc agcaagata cgccaagaa cacagtgtat     240
ctgcagatga acaatctgaa gccagaggac actgccatgt actactgtgc tgctgagcca   300
ctgtctaggg tgtacggcgg cagctgccca actcctacat cgactactg gggccaaggc    360
```

```
acacaagtga ctgtctcgag cggcggagga tcccaagtgc agctgcaaga gagcggagga    420
ggcagcgtcc aagccggagg ctctctgagg ctgagctgtg ctgccagcgg ctacacttac    480
agcagctact gcatgggctg gttcagacaa gcccccggca aggagagaga gggcgtggct    540
cacatcgaca gcgacggctc cacaagctac gccgatagcg tgaagggaag gttcacaatc    600
tccaaggaca acgccaagaa cactctgtac ctccagatga actctctgaa gccagaggac    660
actgccatgt actactgtgc cgccgatcca attcccggcc ccggctactg cgatggcggc    720
cctaacaagt actggggcca aggcacacaa gtgactgtct cgtctgctag ccaccatcac    780
catcaccac                                                            789

SEQ ID NO: 384          moltype = DNA  length = 780
FEATURE                 Location/Qualifiers
source                  1..780
                        mol_type = other DNA
                        organism = synthetic construct
                        note = Description of Artificial Sequence: Synthetic
                        polynucleotide
SEQUENCE: 384
caagtgcagc tgcaagagag cggaggagga agcgtgcaag ccggaggctc tctgaggctg    60
agctgtacag tgtccggcta cacttacagc tccaattgca tgggctggtt taggcaagcc    120
cccggcaagg aaagagaggg cgtggccact atctacactg cggcggcaa cacatactac    180
gccgatagcg tgaagggaag gttcactatc agccaagata cgccaagaa cacagtgtat    240
ctgcagatga acaatctgaa gccagaggac actgccatgt actactgtgc tgctgagcca    300
ctgtctaggg tgtacggcgg cagctgccca actcctacat tcgactactg ggccaaggc    360
acacaagtga ctgtctcgag cggcggagga tcccaagtgc agctgcaaga gtccggagga    420
ggaagcgtgc aagccggcgg atctctgaga ctgagctgtg ccgcctctag gtacacttac    480
aacagctact gcatgggctg gttcagacaa gcccccggca aggaaagaga gggcgtggcc    540
actatcgata gcgacggcat gactaggtac gctgatagcg tcaagggaag gttcacaatc    600
tccaaggaca atgctaagaa cactctgtac ctccagatga actctctgaa gccagaggac    660
acagccatgt actactgcgc tgccgatgcc gactgcacta tcgccgccat gactactaat    720
cctctgggcc aaggcacaca agtgactgtc tcgtctgcta gccaccatca ccatcaccac    780

SEQ ID NO: 385          moltype = DNA  length = 792
FEATURE                 Location/Qualifiers
source                  1..792
                        mol_type = other DNA
                        organism = synthetic construct
                        note = Description of Artificial Sequence: Synthetic
                        polynucleotide
SEQUENCE: 385
caagtgcagc tgcaagagag cggaggagga agcgtgcaag ccggaggctc tctgaggctg    60
agctgtacag tgtccggcta cacttacagc tccaattgca tgggctggtt taggcaagcc    120
cccggcaagg aaagagaggg cgtggccact atctacactg cggcggcaa cacatactac    180
gccgatagcg tgaagggaag gttcactatc agccaagata cgccaagaa cacagtgtat    240
ctgcagatga acaatctgaa gccagaggac actgccatgt actactgtgc tgctgagcca    300
ctgtctaggg tgtacggcgg cagctgccca actcctacat tcgactactg ggccaaggc    360
acacaagtga ctgtctcgag cggcggagga tcccaagtgc agctgcaaga gtccggcgga    420
ggcagcgtcc aagccggagg atctctgagg ctgagctgtc cagtgacagc atacactgct    480
agcgtgaact acatgggctg gttcagacaa gcccccggca aagagagaga gggcgtggcc    540
acaatcttca ctggcgccgg cacaacatac tacgccaact ccgtcaaggg aaggttcaca    600
atctctaggg acaacgccaa gaacactgcc tatctgcaga tgaactccct caagccagag    660
gacactgcca tctactactg cgccgtggat ttcagaggcg gactgctgta taggccagcc    720
tacgagtaca cttatagggg ccaaggcaca caagtgcagg tctcgtctgc tagccaccat    780
caccatcacc ac                                                        792

SEQ ID NO: 386          moltype = DNA  length = 795
FEATURE                 Location/Qualifiers
source                  1..795
                        mol_type = other DNA
                        organism = synthetic construct
                        note = Description of Artificial Sequence: Synthetic
                        polynucleotide
SEQUENCE: 386
caagtgcagc tgcaagagag cggaggagga agcgtgcaag ccggaggctc tctgaggctg    60
agctgtacag tgtccggcta cacttacagc tccaattgca tgggctggtt taggcaagcc    120
cccggcaagg aaagagaggg cgtggccact atctacactg cggcggcaa cacatactac    180
gccgatagcg tgaagggaag gttcactatc agccaagata cgccaagaa cacagtgtat    240
ctgcagatga acaatctgaa gccagaggac actgccatgt actactgtgc tgctgagcca    300
ctgtctaggg tgtacggcgg cagctgccca actcctacat tcgactactg ggccaaggc    360
acacaagtga ctgtctcgag cggcggagga tcccaagtgc agctgcaaga gagcggagga    420
ggcagcgtcg aagctggagg atctctgagg ctgagctgtg ctgccagcgg ctacactcac    480
agcagctact gtatgggctg gttcagacaa gcccccggca aggagaggga aggcgtggct    540
gccatcgacg tggatggcag cactacttac gccgacagct gaagggaag gttcactatc    600
agcaaggaca acgccaagaa cacactctat ctgcagatga acagcctcaa gccagaggac    660
actggcatgt actactgcgc cgccgagttc gccgattgca gcaactact cttctgcct    720
cccggcgccg tcagatattg gggccaaggc actcaagtga cagtctcgtc tgctagccac    780
catcaccatc accac                                                    795

SEQ ID NO: 387          moltype = DNA  length = 789
FEATURE                 Location/Qualifiers
```

| source | 1..789 |
| --- | --- |
| | mol_type = other DNA |
| | organism = synthetic construct |
| | note = Description of Artificial Sequence: Synthetic polynucleotide |

SEQUENCE: 387

```
caagtgcagc tgcaagagag cggaggagga agcgtgcaag ccggaggctc tctgaggctg    60
agctgtacag tgtccggcta cacttacagc tccaattgca tgggctggtt taggcaagcc   120
cccggcaagg aaagagaggg cgtggccact atctcactg gcgcggcaa cacatactac    180
gccgatagcg tgaagggaag gttcactatc agccaagata acgccaagaa cacagtgtat   240
ctgcagatga acaatctgaa gccagaggac actgccatgt actactgtgc tgctgagcca   300
ctgtctaggg tgtacggcgg cagctgccca actcctacat tcgactactg gggccaaggc   360
acacaagtga ctgtctcgag cggcggagga tcccaagtgc agctgcaaga gagcggagga   420
ggaagcgtcc aagccggagg atctctgaga ctgagctgcg ccgctagtgg ctactcctac   480
agcagctact gcatgggctg gtttaggcaa gcccccggca aggagagaga aggcgtggcc   540
actatcgaca gcgacggcat gacaaggtac gccgacagcg tgaagggaag gttcacaatc   600
agcaaggaca acgccaagaa cacactgtat ctgcagatga actctctgaa gccagaggac   660
actgccatgt actactgtgc cgctcctctg tacgactgtg atagcggcgc tgtgggcaga   720
aatccaccct ttattgggcca aggcactcaa gtgacagtct cgtctgctag ccaccatcac   780
catcaccac                                                           789
```

| SEQ ID NO: 388 | moltype = DNA length = 783 |
| --- | --- |
| FEATURE | Location/Qualifiers |
| source | 1..783 |
| | mol_type = other DNA |
| | organism = synthetic construct |
| | note = Description of Artificial Sequence: Synthetic polynucleotide |

SEQUENCE: 388

```
caagtgcagc tgcaagagag cggaggagga agcgtgcaag ccggaggctc tctgaggctg    60
agctgtacag tgtccggcta cacttacagc tccaattgca tgggctggtt taggcaagcc   120
cccggcaagg aaagagaggg cgtggccact atctcactg gcgcggcaa cacatactac    180
gccgatagcg tgaagggaag gttcactatc agccaagata acgccaagaa cacagtgtat   240
ctgcagatga acaatctgaa gccagaggac actgccatgt actactgtgc tgctgagcca   300
ctgtctaggg tgtacggcgg cagctgccca actcctacat tcgactactg gggccaaggc   360
acacaagtga ctgtctcgag cggcggagga tcccaagtgc agctgcaaga gagcggaggc   420
ggcagcgtgc agactggagg ctctctgaga ctgagctgtg ctgccagcgg ctacacttat   480
ctgagggct gtatgggctg gtttaggcaa gcccccggca aggagagaga gggcgtggcc   540
gtcatggatg tggtgggcga taggagaagc tacatcgaca gcgtgaaggg aaggttcaca   600
atctctaggg acaatgccgc caacagcgtc tatctgcaga tggacaatct gaagccagag   660
gacacagcca tgtactactg cactgccggc cctaactgtg tgggctggag aagcggactg   720
gattactggg gccaaggcac acaagtgaca gtctcgtctg ctagccacca tcaccatcac   780
cac                                                                 783
```

| SEQ ID NO: 389 | moltype = DNA length = 792 |
| --- | --- |
| FEATURE | Location/Qualifiers |
| source | 1..792 |
| | mol_type = other DNA |
| | organism = synthetic construct |
| | note = Description of Artificial Sequence: Synthetic polynucleotide |

SEQUENCE: 389

```
caagtgcagc tgcaagagag cggaggagga agcgtccaag ccggaggctc tctgaggctg    60
agctgtggag ccagcggcta cacttacagc agctactgta tgggctggtt taggcaagtg   120
cccggcaagg agagagaggg cgtggccgtg atcgattccg atggcagcac aagctacgct   180
gacagcgtga agggaaggtt cacaatcagc aaggacaacg gcaagaacac actctatctg   240
cagatgaaca gcctcaagcc agaggacaca gccatgtact actgcgccgc tgatctgggc   300
cactataggc ctccttgtgg cgtgctgtat ctgggcatgg attactgggg caagggcaca   360
caagtgacag tctcgagcgg cggaggatcc caagtgcagc tgcaagagag cggcggagga   420
agcgtgcaag ctggaggctc tctgaggctg agctgtctg ccagcggcta cacttatagc    480
agcggctgta tgggctggtt cagacaagcc cccggcaagg aaagggaagc cgtgccgcc    540
atcaattccg atggcagcac aagctacgcc gacagcgtga agggaaggtt cacaatcagc   600
aaggacaacg ccaagaacac actctatctg cagatgaact ctctgaagcc agaggacaca   660
gccatgtact actgcgccgc tgagccttac tgtagcggcg gctacccaag atggagcgtc   720
gctgagttcg gctactgggg ccaaggcaca caagtgactg tctcgtctgc tagccaccat   780
caccatcacc ac                                                       792
```

| SEQ ID NO: 390 | moltype = DNA length = 786 |
| --- | --- |
| FEATURE | Location/Qualifiers |
| source | 1..786 |
| | mol_type = other DNA |
| | organism = synthetic construct |
| | note = Description of Artificial Sequence: Synthetic polynucleotide |

SEQUENCE: 390

```
caagtgcagc tgcaagagag cggaggagga agcgtccaag ccggaggctc tctgaggctg    60
agctgtggag ccagcggcta cacttacagc agctactgta tgggctggtt taggcaagtg   120
cccggcaagg agagagaggg cgtggccgtg atcgattccg atggcagcac aagctacgct   180
gacagcgtga agggaaggtt cacaatcagc aaggacaacg gcaagaacac actctatctg   240
```

```
cagatgaaca gcctcaagcc agaggacaca gccatgtact actgcgccgc tgatctgggc  300
cactataggc ctccttgtgg cgtgctgtat ctgggcatgg attactgggg caagggcaca  360
caagtgacag tctcgagcgg cggaggatcc caagtgcagc tgcaagagag cggaggaggc  420
agcgtccaag ccggaggctc tctgaggctg agctgtgctg ccagcggcta cacttacagc  480
agctactgca tgggctggtt cagacaagcc cccggcaagg agagagaggg cgtggctcac  540
atcgacagcg acggctccac aagctacgcg gatagcgtga agggaaggtt cacaatctcc  600
aaggacaacg ccaagaacac tctgtacctc cagatgaact ctctgaagcc agaggacact  660
gccatgtact actgtgccgc cgatccaatt cccggccccg gctactgcga tggcggccct  720
aacaagtact ggggccaagg cacacaagtg actgtctcgt ctgctagcca ccatcaccat  780
caccac                                                             786
```

| SEQ ID NO: 391<br>FEATURE<br>source | moltype = DNA   length = 777<br>Location/Qualifiers<br>1..777<br>mol_type = other DNA<br>organism = synthetic construct<br>note = Description of Artificial Sequence: Synthetic<br>  polynucleotide |
|---|---|

```
SEQUENCE: 391
caagtgcagc tgcaagagag cggaggagga agcgtccaag ccggaggctc tctgaggctg   60
agctgtggag ccagcggcta cacttacagc agctactgta tgggctggtt taggcaagtg  120
cccggcaagg agagagaggg cgtggccgtg atcgattccg atggcagcac aagctacgct  180
gacagcgtga agggaaggtt cacaatcagc aaggacaacg caagaacac actctatctg  240
cagatgaaca gcctcaagcc agaggacaca gccatgtact actgcgccgc tgatctgggc  300
cactataggc ctccttgtgg cgtgctgtat ctgggcatgg attactgggg caagggcaca  360
caagtgacag tctcgagcgg cggaggatcc caagtgcagc tgcaagagtc cggaggagga  420
agcgtgcaag ccggcggatc tctgagactg agctgtgccg cctctaggta cacttacaac  480
agctactgca tgggctggtt cagacaagcc cccggcaagg aaagagaggg cgtggccact  540
atcgatagcg acggcatgac taggtacgct gatagcgtca agggaaggtt cacaatctcc  600
aaggacaatg ctaagaacac tctgtacctc cagatgaact ctctgaagcc agaggacaca  660
gccatgtact actgcgctgc cgatgccgac tgcactatcg ccgccatgac tactaatcct  720
ctgggccaag gcacacaagt gactgtctcg tctgctagcc accatcacca tcaccac     777
```

| SEQ ID NO: 392<br>FEATURE<br>source | moltype = DNA   length = 789<br>Location/Qualifiers<br>1..789<br>mol_type = other DNA<br>organism = synthetic construct<br>note = Description of Artificial Sequence: Synthetic<br>  polynucleotide |
|---|---|

```
SEQUENCE: 392
caagtgcagc tgcaagagag cggaggagga agcgtccaag ccggaggctc tctgaggctg   60
agctgtggag ccagcggcta cacttacagc agctactgta tgggctggtt taggcaagtg  120
cccggcaagg agagagaggg cgtggccgtg atcgattccg atggcagcac aagctacgct  180
gacagcgtga agggaaggtt cacaatcagc aaggacaacg caagaacac actctatctg  240
cagatgaaca gcctcaagcc agaggacaca gccatgtact actgcgccgc tgatctgggc  300
cactataggc ctccttgtgg cgtgctgtat ctgggcatgg attactgggg caagggcaca  360
caagtgacag tctcgagcgg cggaggatcc caagtgcagc tgcaagagtc cggcggaggc  420
agcgtccaag ccggaggatc tctgaggctg agctgtacag tgagcagata cactgccagc  480
gtgaactaca tgggctggtt cagacaagcc cccggcaaag agagagaggg cgtggccaca  540
atcttcactg gcgccggcac aacatactac gccaactcct caagggaag gttcacaatc  600
tctagggaca cgccaagaa cactgcctat ctgcagatga actccctcaa gccagaggac  660
actgccatct actactgcgc cgtggatttc agaggcggac tgctgtatag gccagcctac  720
gagtacactt ataggggcca aggcacacaa gtgacagtct cgtctgctag ccaccatcac  780
catcaccac                                                          789
```

| SEQ ID NO: 393<br>FEATURE<br>source | moltype = DNA   length = 792<br>Location/Qualifiers<br>1..792<br>mol_type = other DNA<br>organism = synthetic construct<br>note = Description of Artificial Sequence: Synthetic<br>  polynucleotide |
|---|---|

```
SEQUENCE: 393
caagtgcagc tgcaagagag cggaggagga agcgtccaag ccggaggctc tctgaggctg   60
agctgtggag ccagcggcta cacttacagc agctactgta tgggctggtt taggcaagtg  120
cccggcaagg agagagaggg cgtggccgtg atcgattccg atggcagcac aagctacgct  180
gacagcgtga agggaaggtt cacaatcagc aaggacaacg caagaacac actctatctg  240
cagatgaaca gcctcaagcc agaggacaca gccatgtact actgcgccgc tgatctgggc  300
cactataggc ctccttgtgg cgtgctgtat ctgggcatgg attactgggg caagggcaca  360
caagtgacag tctcgagcgg cggaggatcc caagtgcagc tgcaagagag cggaggaggc  420
agcgtcgaag ctggaggatc tctgaggctg agctgtgctg ccagcggcta cactcacagc  480
agctactgta tgggctggtt cagacaagcc cccggcaagg agagggaagg cgtggctgcc  540
atcgacgtga atggcagcac tacttacgcc gacagcgtga agggaaggtt cactatcagc  600
aaggacaacg ccaagaacac actctatctg cagatgaaca gcctcaagcc agaggacact  660
gccatgtact actgcgccgc cgagttcgcg gattgcagca gcaactactt tctgcctccc  720
ggcgccgtca gatattgggg ccaaggcact caagtgacag tctcgtctgc tagccaccat  780
caccatcacc ac                                                      792
```

| SEQ ID NO: 394 | moltype = DNA length = 786 |
| --- | --- |
| FEATURE | Location/Qualifiers |
| source | 1..786 |
| | mol_type = other DNA |
| | organism = synthetic construct |
| | note = Description of Artificial Sequence: Synthetic polynucleotide |

SEQUENCE: 394

```
caagtgcagc tgcaagagag cggaggagga agcgtccaag ccggaggctc tctgaggctg   60
agctgtggag ccagcggcta cacttacagc agctactgta tgggctggtt taggcaagtg  120
cccggcaagg agagagaggg cgtggccgtg atcgattccg atggcagcac aagctacgct  180
gacagcgtga agggaaggtt cacaatcagc aaggacaacg gcaagaacac actctatctg  240
cagatgaaca gcctcaagcc agaggacaca gccatgtact actgcgccgc tgatctgggc  300
cactataggc ctccttgtgg cgtgctgtat ctgggcatgg attactgggg caagggcaca  360
caagtgacag tctcgagcgg cggaggatcc caagtgcagc tgcaagagag cggaggagga  420
agcgtccaag ccggaggatc tctgagactg agctgcgccg ctagtggcta ctcctacagc  480
agctactgca tgggctggtt taggcaagcc cccggcaagg agagagaagg cgtggccact  540
atcgacagcg acggcatgac aaggtacgcc gacagcgtga agggaaggtt cacaatcagc  600
aaggacaacg ccaagaacac actgtatctg cagatgaact ctctgaagcc agaggacact  660
gccatgtact actgtgccgc tcctctgtac gactgtgata gcggcgctgt gggcagaaat  720
ccaccttatt ggggccaagg cactcaagtg acagtctcgt ctgctagcca ccatcaccat  780
caccac                                                              786
```

| SEQ ID NO: 395 | moltype = DNA length = 780 |
| --- | --- |
| FEATURE | Location/Qualifiers |
| source | 1..780 |
| | mol_type = other DNA |
| | organism = synthetic construct |
| | note = Description of Artificial Sequence: Synthetic polynucleotide |

SEQUENCE: 395

```
caagtgcagc tgcaagagag cggaggagga agcgtccaag ccggaggctc tctgaggctg   60
agctgtggag ccagcggcta cacttacagc agctactgta tgggctggtt taggcaagtg  120
cccggcaagg agagagaggg cgtggccgtg atcgattccg atggcagcac aagctacgct  180
gacagcgtga agggaaggtt cacaatcagc aaggacaacg gcaagaacac actctatctg  240
cagatgaaca gcctcaagcc agaggacaca gccatgtact actgcgccgc tgatctgggc  300
cactataggc ctccttgtgg cgtgctgtat ctgggcatgg attactgggg caagggcaca  360
caagtgacag tctcgagcgg cggaggatcc caagtgcagc tgcaagagag cggaggcggc  420
agcgtgcaga ctggaggctc tctgagactg agctgtgccg ccagcggcta cacttatctg  480
aggggctgta tgggctggtt taggcaagcc cccggcaagg agagagaggg cgtggccgtc  540
atggatgtgg tgggcgatag agaaagctac atcgacagcg tgaagggaag gttcacaatc  600
tctagggaca atgccgccaa cagcgtctat ctgcagatgc acaatctgaa gccagaggac  660
acagccatgt actactgcac tgccggcccct aactgtgtgg gctggagaag cggactggat  720
tactggggcc aaggcacaca agtgacagtc tcgtctgcta gccaccatca ccatcaccac  780
```

| SEQ ID NO: 396 | moltype = DNA length = 795 |
| --- | --- |
| FEATURE | Location/Qualifiers |
| source | 1..795 |
| | mol_type = other DNA |
| | organism = synthetic construct |
| | note = Description of Artificial Sequence: Synthetic polynucleotide |

SEQUENCE: 396

```
caagtgcagc tgcaagagag cggaggagga agcgtccaag ccggaggctc tctgagactg   60
agctgtgccg ccagcggcta ctccaactgc agctacgaca tgacttggta taggcaagcc  120
cccggcaagg agagggagtt cgtgtccgcc atccacagcg acggcagcac tagatacgcc  180
gacagcgtga agggaaggtt cttcatcagc caagataacg ccaagaacac agtgtatctg  240
cagatgaact ccctcaagcc agaggacact gccatgtact actgcaagac agacccactg  300
cactgcagag cccatggcgg cagctggtat agcgtgaggg ccaactactg gggccaaggc  360
acacaagtga cagtctcgag cggcggagga tcccaagtgc agctgcaaga gagcggcggc  420
ggaagcgtgc aagctggagg ctctctgagg ctgagctgtg ctgccagcgg ctacacttat  480
agcagcggct gtatgggctg gttcagacaa gccccccggca aggaaaggga agccgtggcc  540
gccatcaatt ccgatggcag cacaagctac gccgacagcg tgaaggaaag gttcacaatc  600
agcaaggaca acgccaagaa cacactctat ctgcagatga actctctgaa gccagaggac  660
acagccatgt actactgcgc cgctgagcct tactgtagcg cgggctaccc aagatggagc  720
gtcgctgagt tcggctactg gggccaaggc acacaagtga ctgtctcgtc tgctagccac  780
catcaccatc accac                                                    795
```

| SEQ ID NO: 397 | moltype = DNA length = 789 |
| --- | --- |
| FEATURE | Location/Qualifiers |
| source | 1..789 |
| | mol_type = other DNA |
| | organism = synthetic construct |
| | note = Description of Artificial Sequence: Synthetic polynucleotide |

SEQUENCE: 397

```
caagtgcagc tgcaagagag cggaggagga agcgtccaag ccggaggctc tctgagactg   60
agctgtgccg ccagcggcta ctccaactgc agctacgaca tgacttggta taggcaagcc  120
cccggcaagg agagggagtt cgtgtccgcc atccacagcg acggcagcac tagatacgcc  180
```

```
gacagcgtga agggaaggtt cttcatcagc caagataacg ccaagaacac agtgtatctg    240
cagatgaact ccctcaagcc agaggacact gccatgtact actgcaagac agacccactg    300
cactgcagag cccatggcgg cagctggtat agcgtgaggg ccaactactg gggccaaggc    360
acacaagtga cagtctcgag cggcggagga tcccaagtgc agctgcaaga gagcggagga    420
ggcagcgtcc aagccggagg ctctctgagg ctgagctgtg ctgccagcgg ctacacttac    480
agcagctact gcatgggctg gttcagacaa gccccccggca aggagagaga gggcgtggcc    540
cacatcgaca gcgacggctc cacaagctac gccgatagcg tgaaggaaag gttcacaatc    600
tccaaggaca acgccaagaa cactctgtac ctccagatga actctctgaa gccagaggac    660
actgccatgt actactgtgc cgccgatcca attcccggcc ccggctactg cgatggcggc    720
cctaacaagt actggggcca aggcacacaa gtgactgtct cgtctgctag ccaccatcac    780
catcaccac                                                            789

SEQ ID NO: 398         moltype = DNA   length = 780
FEATURE                Location/Qualifiers
source                 1..780
                       mol_type = other DNA
                       organism = synthetic construct
                       note = Description of Artificial Sequence: Synthetic
                         polynucleotide
SEQUENCE: 398
caagtgcagc tgcaagagag cggaggagga agcgtccaag ccggaggctc tctgagactg     60
agctgtgccg ccagcggcta ctccaactgc agctacgaca tgacttggta taggcaagcc    120
cccggcaagg agagggagtt cgtgtccgcc atccacagcg acggcagcac tagatacgcc    180
gacagcgtga agggaaggtt cttcatcagc caagataacg ccaagaacac agtgtatctg    240
cagatgaact ccctcaagcc agaggacact gccatgtact actgcaagac agacccactg    300
cactgcagag cccatggcgg cagctggtat agcgtgaggg ccaactactg gggccaaggc    360
acacaagtga cagtctcgag cggcggagga tcccaagtgc agctgcaaga gtccggagga    420
ggaagcgtgc aagccggcgg atctctgaga ctgagctgtg ccgcctctag gtacacttac    480
aacagctact gcatgggctg gttcagacaa gccccccggca aggaaagaga gggcgtggcc    540
actatcgata gcgacggcat gactaggtac gctgatagcg tcaagggaag gttcacaatc    600
tccaaggaca atgctaagaa cactctgtac ctccagatga actctctgaa gccagaggac    660
acagccatgt actactgcgc tgccgatgcc gactgcacta tcgccgccat gactactaat    720
cctctgggcc aaggcacaca agtgactgtc tcgtctgcta gccaccatca ccatcaccac    780

SEQ ID NO: 399         moltype = DNA   length = 792
FEATURE                Location/Qualifiers
source                 1..792
                       mol_type = other DNA
                       organism = synthetic construct
                       note = Description of Artificial Sequence: Synthetic
                         polynucleotide
SEQUENCE: 399
caagtgcagc tgcaagagag cggaggagga agcgtccaag ccggaggctc tctgagactg     60
agctgtgccg ccagcggcta ctccaactgc agctacgaca tgacttggta taggcaagcc    120
cccggcaagg agagggagtt cgtgtccgcc atccacagcg acggcagcac tagatacgcc    180
gacagcgtga agggaaggtt cttcatcagc caagataacg ccaagaacac agtgtatctg    240
cagatgaact ccctcaagcc agaggacact gccatgtact actgcaagac agacccactg    300
cactgcagag cccatggcgg cagctggtat agcgtgaggg ccaactactg gggccaaggc    360
acacaagtga cagtctcgag cggcggagga tcccaagtgc agctgcaaga gtccggcgga    420
ggcagcgtcc aagccggagg atctctgagg ctgagctgta cagtgagcag atacactgcc    480
agcgtgaact acatgggctg gttcagacaa gccccccgga aagagagaga gggcgtggcc    540
acaatcttca ctggcgccgg cacaacatac tacgccaact ccgtcaaggg aaggttcaca    600
atctctaggg acaacgccaa gaacactgcc tatctgcaga tgaactccct caagccagag    660
gacactgcca tctactactg cgccgtggat ttcagaggcg gactgctgta taggccagcc    720
tacgagtaca cttataggg ccaaggcaca caagtgacag tctcgtctgc tagccaccat    780
caccatcacc ac                                                        792

SEQ ID NO: 400         moltype = DNA   length = 795
FEATURE                Location/Qualifiers
source                 1..795
                       mol_type = other DNA
                       organism = synthetic construct
                       note = Description of Artificial Sequence: Synthetic
                         polynucleotide
SEQUENCE: 400
caagtgcagc tgcaagagag cggaggagga agcgtccaag ccggaggctc tctgagactg     60
agctgtgccg ccagcggcta ctccaactgc agctacgaca tgacttggta taggcaagcc    120
cccggcaagg agagggagtt cgtgtccgcc atccacagcg acggcagcac tagatacgcc    180
gacagcgtga agggaaggtt cttcatcagc caagataacg ccaagaacac agtgtatctg    240
cagatgaact ccctcaagcc agaggacact gccatgtact actgcaagac agacccactg    300
cactgcagag cccatggcgg cagctggtat agcgtgaggg ccaactactg gggccaaggc    360
acacaagtga cagtctcgag cggcggagga tcccaagtgc agctgcaaga gagcggagga    420
ggcagcgtcg aagctggagg atctctgagg ctgagctgtg ctgccagcgg ctacactcac    480
agcagctact gtatgggctg gttcagacaa gccccccgga aggagagaga gggcgtggct    540
gccatcgacg tggatggcag cactacttac gccgacagcg tgaagggaag gttcactatc    600
agcaaggaca cgccaagaa cacactctat ctgcagatga acagcctcaa gccagaggac    660
actggcatgt actactgcgc cgccgagttc gccgattgca gcagcaacta ctttctgcct    720
cccggcgccg tcagatattg gggccaaggc actcaagtga cagtctcgtc tgctagccac    780
catcaccatc accac                                                    795
```

```
SEQ ID NO: 401          moltype = DNA  length = 789
FEATURE                 Location/Qualifiers
source                  1..789
                        mol_type = other DNA
                        organism = synthetic construct
                        note = Description of Artificial Sequence: Synthetic
                        polynucleotide
SEQUENCE: 401
caagtgcagc tgcaagagag cggaggagga agcgtccaag ccggaggctc tctgagactg    60
agctgtgccg ccagcggcta ctccaactgc agctacgaca tgacttggta taggcaagcc   120
cccggcaagg agagggagtt cgtgtccgcc atccacagcg acggcagcac tagatacgcc   180
gacagcgtga agggaaggtt cttcatcagc caagataacg ccaagaacac agtgtatctg   240
cagatgaact ccctcaagcc agaggacact gccatgtact actgcaagac agacccactg   300
cactgcagag cccatggcgg cagctggtat agcgtgaggg ccaactactg gggccaaggc   360
acacaagtga cagtctcgag cggcggagga tcccaagtgc agctgcaaga gagcggagga   420
ggaagcgtcc aagccggagg atctctgaga ctgagctgcg ccgctagtgg ctactcctac   480
agcagctact gcatgggctg gtttaggcaa gcccccggca aggagagaga gggcgtggcc   540
actatcgaca gcgacggcat gacaaggtac gccgacagcg tgaagggaag gttcacaatc   600
agcaaggaca acgccaagaa cacactgtat ctgcagatga actctctgaa gccagaggac   660
actgccatgt actactgtgc cgctcctctg tacgactgta tagcggcgc tgtgggcaga    720
aatccacctt attggggcca aggcactcaa gtgacagtc cgtctgctag ccaccatcac   780
catcaccac                                                           789

SEQ ID NO: 402          moltype = DNA  length = 783
FEATURE                 Location/Qualifiers
source                  1..783
                        mol_type = other DNA
                        organism = synthetic construct
                        note = Description of Artificial Sequence: Synthetic
                        polynucleotide
SEQUENCE: 402
caagtgcagc tgcaagagag cggaggagga agcgtccaag ccggaggctc tctgagactg    60
agctgtgccg ccagcggcta ctccaactgc agctacgaca tgacttggta taggcaagcc   120
cccggcaagg agagggagtt cgtgtccgcc atccacagcg acggcagcac tagatacgcc   180
gacagcgtga agggaaggtt cttcatcagc caagataacg ccaagaacac agtgtatctg   240
cagatgaact ccctcaagcc agaggacact gccatgtact actgcaagac agacccactg   300
cactgcagag cccatggcgg cagctggtat agcgtgaggg ccaactactg gggccaaggc   360
acacaagtga cagtctcgag cggcggagga tcccaagtgc agctgcaaga gagcggagga   420
ggcagcgtgc agactggagg ctctctgaga ctgagctgtg ctgccagcgg ctacacttat   480
ctgaggggct gtatgggctg gtttaggcaa gccccccggca aggagagaga gggcgtggcc   540
gtcatggatg tggtgggcga taggagaagc tacatcgaca gcgtgaaggg aaggttcaca   600
atctctaggg acaatgccgc caacagcgtc tatctgcaga tggacaatct gaagccagag   660
gacacagcca tgtactactg cactgccggc cctaactgtg tgggctggag aagcggactg   720
gattactggg gccaaggcac acaagtgaca gtctcgtctg ctagccacca tcaccatcac   780
cac                                                                 783

SEQ ID NO: 403          moltype = DNA  length = 789
FEATURE                 Location/Qualifiers
source                  1..789
                        mol_type = other DNA
                        organism = synthetic construct
                        note = Description of Artificial Sequence: Synthetic
                        polynucleotide
SEQUENCE: 403
caagtgcagc tgcaagagag cggcggagga agcgtgcaag ctggaggctc tctgaggctg    60
agctgtgctg ccagcggcta cacttatagc agcggctgta tgggctggtt cagacaagcc   120
cccggcaagg aaagggaagc cgtggccgcc atcaattccg atggcagcac aagctacgcc   180
gacagcgtga agggaaggtt cacaatcagc aaggacaacg ccaagaacac actctatctg   240
cagatgaact ctctgaagcc agaggacaca gccatgtact actgcgccgc tgagccttac   300
tgtagcggcg gctacccaag atggagcgtc gctgagttcg gctactgggg ccaaggcaca   360
caagtgactg tctcgagcgg cggaggatcc caagtgcagc tgcaagagag cggaggagga   420
agcgtgcaag ccggaggctc tctgagactg agctgtgccg cctctaggta tctgtacagc   480
atcgactaca tggcttggtt cagacagagc cccggcaagg agagggaagt ggcgtgtcc   540
atctacactg cctccggcgc cacattctat ccagatagcg tgaagggaag gttcactatc   600
agccaagata cgccaagat gacagtgtat ctgcagatga actctctgaa gagcgaggac   660
actgccatgt actactgtgc cgccgtgagg aagacagata gctacctctt cgacgcccag   720
agcttcacat actgggggcca aggcacacaa gtgacagtc cgtctgctag ccaccatcac   780
catcaccac                                                           789

SEQ ID NO: 404          moltype = DNA  length = 801
FEATURE                 Location/Qualifiers
source                  1..801
                        mol_type = other DNA
                        organism = synthetic construct
                        note = Description of Artificial Sequence: Synthetic
                        polynucleotide
SEQUENCE: 404
caagtgcagc tgcaagagag cggcggagga agcgtgcaag ctggaggctc tctgaggctg    60
```

```
agctgtgctg ccagcggcta cacttatagc agcggctgta tgggctggtt cagacaagcc   120
cccggcaagg aaagggaagc cgtggccgcc atcaattccg atggcagcac aagctacgcc   180
gacagcgtga agggaaggtt cacaatcagc aaggacaacg ccaagaacac actctatctg   240
cagatgaact ctctgaagcc agaggacaca gccatgtact actgcgccgc tgagccttac   300
tgtagcggcg gctacccaag atggagcgtc gctgagttcg gctactgggg ccaaggcaca   360
caagtgactg tctcgagcgg cggaggatcc caagtgcagc tgcaagagag cggaggagga   420
agcgtgcaag ccggaggctc tctgaggctg agctgtgccg cctctaggtt cacatacagc   480
agctactgca tgggctggtt cagacaagcc cccggcaagg agagagaagg cgtggccagc   540
atcgatagcg atggctccac tagctacact gacagcgtga agggaaggtt cactatcagc   600
aaggacaacg ccaagaacac tctgtatctg cagatgaact ctctgaagcc agaggacaca   660
gccatgtact actgtgccct cgatctgatg agcacagtgg tgcccggctt ctgtggcttt   720
ctgctgagcg ctggcatgga ttactggggc aagggcactc aagtgactgt ctcgtctgct   780
agccaccatc accatcacca c                                             801
```

```
SEQ ID NO: 405          moltype = DNA  length = 807
FEATURE                 Location/Qualifiers
source                  1..807
                        mol_type = other DNA
                        organism = synthetic construct
                        note = Description of Artificial Sequence: Synthetic
                        polynucleotide
SEQUENCE: 405
caagtgcagc tgcaagagag cggcggagga agcgtgcaag ctggaggctc tctgaggctg    60
agctgtgctg ccagcggcta cacttatagc agcggctgta tgggctggtt cagacaagcc   120
cccggcaagg aaagggaagc cgtggccgcc atcaattccg atggcagcac aagctacgcc   180
gacagcgtga agggaaggtt cacaatcagc aaggacaacg ccaagaacac actctatctg   240
cagatgaact ctctgaagcc agaggacaca gccatgtact actgcgccgc tgagccttac   300
tgtagcggcg gctacccaag atggagcgtc gctgagttcg gctactgggg ccaaggcaca   360
caagtgactg tctcgagcgg cggaggatcc caagtgcagc tgcaagagtc cggaggaggc   420
agcgtccaag ccggaggctc tctgaggctg agctgtctg cagcggcta cacttacagc    480
atgtactgca tgggctggtt cagacaagcc cccggcaagg aaagagaggg cgtggcccga   540
atcaatagcg atggcagcac aagctacgcc gacagcgtga agggaaggtt cactatctcc   600
aaggacaacg ccaagaacac tctgtatctg cagatgaact ctctgaagcc agaggacact   660
gccatgtact actgcgctgc cgattctagg gtgtacggcg gcagctggta tgagaggctc   720
tgcggcccctt acacatacga gtacaactac tggggccaag gcacacaagt gactgtctcg   780
tctgctagcc accatcacca tcaccac                                       807
```

```
SEQ ID NO: 406          moltype = DNA  length = 816
FEATURE                 Location/Qualifiers
source                  1..816
                        mol_type = other DNA
                        organism = synthetic construct
                        note = Description of Artificial Sequence: Synthetic
                        polynucleotide
SEQUENCE: 406
caagtgcagc tgcaagagag cggcggagga agcgtgcaag ctggaggctc tctgaggctg    60
agctgtgctg ccagcggcta cacttatagc agcggctgta tgggctggtt cagacaagcc   120
cccggcaagg aaagggaagc cgtggccgcc atcaattccg atggcagcac aagctacgcc   180
gacagcgtga agggaaggtt cacaatcagc aaggacaacg ccaagaacac actctatctg   240
cagatgaact ctctgaagcc agaggacaca gccatgtact actgcgccgc tgagccttac   300
tgtagcggcg gctacccaag atggagcgtc gctgagttcg gctactgggg ccaaggcaca   360
caagtgactg tctcgagcgg cggaggatcc caagtgcagc tgcaagagag cggcggagga   420
agcgtgcaag ccggaggatc tctgagactg agctgcgctg tgagcggcta cgcctactcc   480
acatactgca tgggctggtt taggcaagcc cccggcaaag agagagggg cgtggctgct    540
atcgatagcg gcggcagcac aagctacgcc gatagcgtga agggaaggtt cacaatcagc   600
aaggacaacg ccaagaacac actgtatctg aggatgaact ctctgaagcc agaggacaca   660
gccatgtact actgtgctgc tgtgcctcct cctccagatg gcggcagctg tctgtttctg   720
ggaccagaga tcaaggtcag caaggccgat tttaggtact ggggccaagg cacacaagtg   780
acagtctcgt ctgctagcca ccatcaccat caccac                             816
```

```
SEQ ID NO: 407          moltype = DNA  length = 795
FEATURE                 Location/Qualifiers
source                  1..795
                        mol_type = other DNA
                        organism = synthetic construct
                        note = Description of Artificial Sequence: Synthetic
                        polynucleotide
SEQUENCE: 407
caagtgcagc tgcaagagag cggcggagga agcgtgcaag ctggaggctc tctgaggctg    60
agctgtgctg ccagcggcta cacttatagc agcggctgta tgggctggtt cagacaagcc   120
cccggcaagg aaagggaagc cgtggccgcc atcaattccg atggcagcac aagctacgcc   180
gacagcgtga agggaaggtt cacaatcagc aaggacaacg ccaagaacac actctatctg   240
cagatgaact ctctgaagcc agaggacaca gccatgtact actgcgccgc tgagccttac   300
tgtagcggcg gctacccaag atggagcgtc gctgagttcg gctactgggg ccaaggcaca   360
caagtgactg tctcgagcgg cggaggatcc caagtgcagc tgcaagagag cggaggagga   420
agcgtgcaag ccggaggctc tctgaggctg agctgtacag tgtccggcta cacttacagc   480
tccaattgca tgggctggtt taggcaagcc cccggcaagg aaagagaggg cgtggccact   540
atctacactg gcggcggcaa cacatactac gccgatagcg tgaaggggaag gttcactatc   600
agccaagata cgccaagaa cacagtgtat ctgcagatga caatctgaa gccagaggac    660
```

```
actgccatgt actactgtgc tgctgagcca ctgtctaggg tgtacggcgg cagctgccca    720
actcctacat tcgactactg gggccaaggc acacaagtga ctgtctcgtc tgctagccac    780
catcaccatc accac                                                     795

SEQ ID NO: 408          moltype = DNA  length = 792
FEATURE                 Location/Qualifiers
source                  1..792
                        mol_type = other DNA
                        organism = synthetic construct
                        note = Description of Artificial Sequence: Synthetic
                          polynucleotide
SEQUENCE: 408
caagtgcagc tgcaagagag cggcggagga agcgtgcaag ctggaggctc tctgaggctg     60
agctgtgctg ccagcggcta cacttatagc agcggctgta tgggctggtt cagacaagcc    120
cccggcaagg aaagggaagc cgtggccgcc atcaattccg atggcagcac aagctacgcc    180
gacagcgtga agggaaggtt cacaatcagc aaggacaacg ccaagaacac actctatctg    240
cagatgaact ctctgaagcc agaggacaca gccatgtact actgcgccgc tgagccttac    300
tgtagcggcg gctacccaag atggagcgtc gctgagttcg gctactgggg ccaaggcaca    360
caagtgactg tctcgagcgg cggaggatcc caagtgcagc tgcaagagag cggaggagga    420
agcgtccaag ccggaggctc tctgaggctg agctgtggag ccagcggcta cacttacagc    480
agctactgta tgggctggtt taggcaagtg cccggcaagg agagagggg  cgtggccgtg    540
atcgattccg atggcagcac aagctacgct gacagcgtgcg agggaaggtt cacaatcagc    600
aaggacaacg gcaagaacac actctatctg cagatgaaca gcctcaagcc agaggacaca    660
gccatgtact actgcgccgc tgatctgggc cactataggc ctccttgtgg cgtgctgtat    720
ctgggcatgg attactgggg caagggcaca caagtgacac tctcgtctgc tagccaccat    780
caccatcacc ac                                                        792

SEQ ID NO: 409          moltype = DNA  length = 795
FEATURE                 Location/Qualifiers
source                  1..795
                        mol_type = other DNA
                        organism = synthetic construct
                        note = Description of Artificial Sequence: Synthetic
                          polynucleotide
SEQUENCE: 409
caagtgcagc tgcaagagag cggcggagga agcgtgcaag ctggaggctc tctgaggctg     60
agctgtgctg ccagcggcta cacttatagc agcggctgta tgggctggtt cagacaagcc    120
cccggcaagg aaagggaagc cgtggccgcc atcaattccg atggcagcac aagctacgcc    180
gacagcgtga agggaaggtt cacaatcagc aaggacaacg ccaagaacac actctatctg    240
cagatgaact ctctgaagcc agaggacaca gccatgtact actgcgccgc tgagccttac    300
tgtagcggcg gctacccaag atggagcgtc gctgagttcg gctactgggg ccaaggcaca    360
caagtgactg tctcgagcgg cggaggatcc caagtgcagc tgcaagagag cggaggagga    420
agcgtccaag ccggaggctc tctgagactg agctgtgccg gcagcggcta ctccaactgg    480
agctacgaca tgacttggta taggcaagcc cccggcaagg agagggagtt cgtgtccgcc    540
atccacagcg acggcagcac tagatacgcc gacagcgtga agggaaggtt cttcatcagc    600
caagataacg ccaagaacac agtgtatctg cagatgaact ccctcaagcc agaggacact    660
gccatgtact actgcaagac agacccactg cactgcagag cccatggcgg cagctggtat    720
agcgtgaggg ccaactactg gggccaaggc acacaagtga cagtctcgtc tgctagccac    780
catcaccatc accac                                                     795

SEQ ID NO: 410          moltype = DNA  length = 783
FEATURE                 Location/Qualifiers
source                  1..783
                        mol_type = other DNA
                        organism = synthetic construct
                        note = Description of Artificial Sequence: Synthetic
                          polynucleotide
SEQUENCE: 410
caagtgcagc tgcaagagag cggaggaggc agcgtccaag ccggaggctc tctgaggctg     60
agctgtgctg ccagcggcta cacttacagc agctactgca tgggctggtt cagacaagcc    120
cccggcaagg agagagaggg cgtggctcac atcgacagcg acggctccac aagctacgcc    180
gatagcgtga agggaaggtt cacaatctcc aaggacaacg ccaagaacac tctgtacctc    240
cagatgaact ctctgaagcc agaggacact gccatgtact actgtgccgc cgatccaatt    300
cccggcccccg gctactgcga tggcggccct aacaagtgac ggggcaaggg cacacaagtg    360
actgtctcga gcggcggagg atcccaagtg cagctgcaag agagcggagg aggaagcgtg    420
caagccggag gctctctgag actgagctgt ccgcctcta ggtatctgta cagcatcgac    480
tacatggctt ggttcagaca gagccccggc aaggagaggg agccagtggc tgtcatctac    540
actgcctccg gcgccacatt ctatccagat agcgtgaagg gaaggttcac tatcagcaa    600
gataacgcca agatgacagt gtatctgcag atgaactctg taagagcga ggacactgc    660
atgtactact gtgccgccgt gaggaagaca gatagctacc tcttcgacgc ccagagcttc    720
acatactggg gccaaggcac acaagtgaca gtctcgtctg ctagccacca tcaccatcac    780
cac                                                                  783

SEQ ID NO: 411          moltype = DNA  length = 795
FEATURE                 Location/Qualifiers
source                  1..795
                        mol_type = other DNA
                        organism = synthetic construct
                        note = Description of Artificial Sequence: Synthetic
```

```
                                polynucleotide
SEQUENCE: 411
caagtgcagc tgcaagagag cggaggaggc agcgtccaag ccggaggctc tctgaggctg    60
agctgtgctg ccagcggcta cacttacagc agctactgca tgggctggtt cagacaagcc   120
cccggcaagg agagagaggg cgtggctcac atcgacagcg acggctccac aagctacgcc   180
gatagcgtga agggaaggtt cacaatctcc aaggacaacg ccaagaacac tctgtacctc   240
cagatgaact ctctgaagcc agaggacact gccatgtact actgtgccgc cgatccaatt   300
cccggccccg gctactgcga tggcggccct aacaagtact ggggccaagg cacacaagtg   360
actgtctcga gcggcggagg atcccaagtg cagctgcaag agagcggagg aggaagcgtg   420
caagccggag gctctctgag gctgagctgt gccgcctcta ggttcacata cagcagctac   480
tgcatgggct ggttcagaca agcccccggc aaagagagag aaggcgtggc cagcatcgat   540
agcgatggct ccactagcta cactgacagc gtgaagggaa ggttcactat cagcaaggac   600
aacgccaaga acactctgta tctgcagatg aactctctga gccagagga cacagccatg   660
tactactgtg ccctcgatct gatgagcaca gtggtgcccg gcttctgtgg ctttctgctg   720
agcgctggca tggattactg gggcaaggc actcaagtga ctgtctcgtc tgctagccac   780
catcaccatc accac                                                    795

SEQ ID NO: 412           moltype = DNA  length = 801
FEATURE                  Location/Qualifiers
source                   1..801
                         mol_type = other DNA
                         organism = synthetic construct
                         note = Description of Artificial Sequence: Synthetic
                                polynucleotide
SEQUENCE: 412
caagtgcagc tgcaagagag cggaggaggc agcgtccaag ccggaggctc tctgaggctg    60
agctgtgctg ccagcggcta cacttacagc agctactgca tgggctggtt cagacaagcc   120
cccggcaagg agagagaggg cgtggctcac atcgacagcg acggctccac aagctacgcc   180
gatagcgtga agggaaggtt cacaatctcc aaggacaacg ccaagaacac tctgtacctc   240
cagatgaact ctctgaagcc agaggacact gccatgtact actgtgccgc cgatccaatt   300
cccggccccg gctactgcga tggcggccct aacaagtact ggggccaagg cacacaagtg   360
actgtctcga gcggcggagg atcccaagtg cagctgcaag agtccggagg aggcagcgtc   420
caagccggag gctctctgag gctgagctgt gctgccagcg gctacactta cagcatgtac   480
tgcatgggct ggttcagaca agcccccggc aaggaaagag agggcgtggc cagatcaat   540
agcgatggca gcacaagcta cgccgacagc gtgaaggaa ggttcactat ctccaaggac   600
aacgccaaga acactctgta tctgcagatg aactctctga gccagagga cactgccatg   660
tactactgcg ctgccgattc tagggtgtac ggcggcagct ggtatgagag gctctgcggc   720
ccttacacat acgagtacaa ctactggggc caaggcacac aagtgactgt ctcgtctgct   780
agccaccatc accatcacca c                                             801

SEQ ID NO: 413           moltype = DNA  length = 810
FEATURE                  Location/Qualifiers
source                   1..810
                         mol_type = other DNA
                         organism = synthetic construct
                         note = Description of Artificial Sequence: Synthetic
                                polynucleotide
SEQUENCE: 413
caagtgcagc tgcaagagag cggaggaggc agcgtccaag ccggaggctc tctgaggctg    60
agctgtgctg ccagcggcta cacttacagc agctactgca tgggctggtt cagacaagcc   120
cccggcaagg agagagaggg cgtggctcac atcgacagcg acggctccac aagctacgcc   180
gatagcgtga agggaaggtt cacaatctcc aaggacaacg ccaagaacac tctgtacctc   240
cagatgaact ctctgaagcc agaggacact gccatgtact actgtgccgc cgatccaatt   300
cccggccccg gctactgcga tggcggccct aacaagtact ggggccaagg cacacaagtg   360
actgtctcga gcggcggagg atcccaagtg cagctgcaag agagcggagg aggaagcgtg   420
caagccggag gatctctgag actgagctgc gctgtgagcg gctacgccta ctccacatac   480
tgcatgggct ggtttaggca agcccccggc aaagagagag aaggcgtggc tgctatcgat   540
agcggcggca gcacaagcta cgccgatagc gtgaagggaa ggttcacaat cagcaaggac   600
aacgccaaga acacactgta tctgaggatg aactctctga gccagagga cacagccatg   660
tactactgtg ctgctgtgcc tcctcctcca gatgcggca gctgtctgtt tctgggacca   720
gagatcaagg tcagcaaggc cgattttagg tactggggcc aaggcacaca agtgacagtc   780
tcgtctgcta gccaccatca ccatcaccac                                    810

SEQ ID NO: 414           moltype = DNA  length = 789
FEATURE                  Location/Qualifiers
source                   1..789
                         mol_type = other DNA
                         organism = synthetic construct
                         note = Description of Artificial Sequence: Synthetic
                                polynucleotide
SEQUENCE: 414
caagtgcagc tgcaagagag cggaggaggc agcgtccaag ccggaggctc tctgaggctg    60
agctgtgctg ccagcggcta cacttacagc agctactgca tgggctggtt cagacaagcc   120
cccggcaagg agagagaggg cgtggctcac atcgacagcg acggctccac aagctacgcc   180
gatagcgtga agggaaggtt cacaatctcc aaggacaacg ccaagaacac tctgtacctc   240
cagatgaact ctctgaagcc agaggacact gccatgtact actgtgccgc cgatccaatt   300
cccggccccg gctactgcga tggcggccct aacaagtact ggggccaagg cacacaagtg   360
actgtctcga gcggcggagg atcccaagtg cagctgcaag agagcggagg aggaagcgtg   420
caagccggag gctctctgag gctgagctgt acagtgtccg gctacactta cagctccaat   480
```

```
tgcatgggct ggtttaggca agcccccggc aaggaaagag agggcgtggc cactatctac    540
actggcggcg gcaacacata ctacgccgat agcgtgaagg gaaggttcac tatcagccaa    600
gataacgcca agaacacagt gtatctgcag atgaacaatc tgaagccaga ggacactgcc    660
atgtactact gtgctgctga gccactgtct agggtgtacg gcggcagctg cccaactcct    720
acattcgact actggggcca aggcacacaa gtgactgtct cgtctgctag ccaccatcac    780
catcaccac                                                            789

SEQ ID NO: 415        moltype = DNA  length = 786
FEATURE               Location/Qualifiers
source                1..786
                      mol_type = other DNA
                      organism = synthetic construct
                      note = Description of Artificial Sequence: Synthetic
                      polynucleotide
SEQUENCE: 415
caagtgcagc tgcaagagag cggaggaggc agcgtccaag ccggaggctc tctgaggctg    60
agctgtgctg ccagcggcta cacttacagc agctactgca tgggctggtt cagacaagcc    120
cccggcaagg agagagggc cgtggctcac atcgacacgc acggctccac aagctacgcc    180
gatagcgtga agggaaggtt cacaatctcc aaggacaacg ccaagaacac tctgtacctc    240
cagatgaact ctctgaagcc agaggacact gccatgtact actgtgccgc cgatccaatt    300
cccggccccg gctactgcga tggcggccct aacaagtact ggggccaagg cacacaagtg    360
actgtctcga gcggcggagg atcccaagtg cagctgcaag agagcggagg aggaagcgtc    420
caagccggag gctctctgag gctgagctgt ggagccagcg gctacactta cagcagctac    480
tgtatgggct ggtttaggca agtgcccggc aaggagagag agggcgtggc cgtgatcgat    540
tccgatggca gcacaagcta cgctgacagc gtgaagggaa ggttcacaat cagcaaggac    600
aacgccaaga acacactcta tctgcagatg aacagcctca agccagagga cacagccatg    660
tactactgcg ccgctgatct gggccactat aggcctcctt gtggcgtgct gtatctgggc    720
atggattact ggggcaaggg cacacaagtg acagtctcgt ctgctagcca ccatcaccat    780
caccac                                                              786

SEQ ID NO: 416        moltype = DNA  length = 789
FEATURE               Location/Qualifiers
source                1..789
                      mol_type = other DNA
                      organism = synthetic construct
                      note = Description of Artificial Sequence: Synthetic
                      polynucleotide
SEQUENCE: 416
caagtgcagc tgcaagagag cggaggaggc agcgtccaag ccggaggctc tctgaggctg    60
agctgtgctg ccagcggcta cacttacagc agctactgca tgggctggtt cagacaagcc    120
cccggcaagg agagagggc cgtggctcac atcgacagcg acggctccac aagctacgcc    180
gatagcgtga agggaaggtt cacaatctcc aaggacaacg ccaagaacac tctgtacctc    240
cagatgaact ctctgaagcc agaggacact gccatgtact actgtgccgc cgatccaatt    300
cccggccccg gctactgcga tggcggccct aacaagtact ggggccaagg cacacaagtg    360
actgtctcga gcggcggagg atcccaagtg cagctgcaag agagcggagg aggaagcgtc    420
caagccggag gctctctgag actgagctgt ccgccagcg gctactccaa ctgcagctac    480
gacatgactt ggtataggca agccccccggc aaggagagag agttcgtgtc cgccatccac    540
agcgacggca gcactagata cgccgacagc gtgaagggaa ggttcttcat cagccaagat    600
aacgccaaga acacagtgta tctgcagatg aactccctca agccagagga cactgccatg    660
tactactgca agacagaccc actgcactgc agagcccatg cggcagctg gtatagcgtg    720
agggccaact actggggcca aggcacacaa gtgacagtct cgtctgctag ccaccatcac    780
catcaccac                                                            789

SEQ ID NO: 417        moltype = DNA  length = 774
FEATURE               Location/Qualifiers
source                1..774
                      mol_type = other DNA
                      organism = synthetic construct
                      note = Description of Artificial Sequence: Synthetic
                      polynucleotide
SEQUENCE: 417
caagtgcagc tgcaagagtc cggaggagga agcgtgcaag ccggcggatc tctgagactg    60
agctgtgccg cctctaggta cacttacaac agctactgca tgggctggtt cagacaagcc    120
cccggcaagg aaagagaggg cgtggccact atcgataggc acggcatgac taggtacgct    180
gatagcgtca agggaaggtt cacaatctcc aaggacaatg ctaagaacac tctgtacctc    240
cagatgaact ctctgaagcc agaggacaca gccatgtact actgcgctgc cgatgccgac    300
tgcactatcc ccgccatgac tactaatcct ctgggccaag gcacacaagt gactgtctcg    360
agcggcggag gatcccaagt gcagctgcaa gagagcggag gaggaagcgt gcaagccgga    420
ggctctctga gactgagctg tgccgcctct aggtatctgt acagcatcga ctacatgcgt    480
tggttcagac agagccccgg caaggagagg gagccagtgg ctgtcatcta cactgcctcc    540
ggcgccacat tctatccaga tagcgtgaag ggaaggttca ctatcagcca agataacgcc    600
aagatgacag tgtatctgca gatgaactct ctgaagagcg aggacactgc catgtactac    660
tgtgccgccg tgaggaagac agatagctac ctcttcgacg cccagagctt cacatactgg    720
ggccaaggca cacaagtgac agtctcgtct gctagccacc atcaccatca ccac          774

SEQ ID NO: 418        moltype = DNA  length = 786
FEATURE               Location/Qualifiers
source                1..786
                      mol_type = other DNA
```

```
                        organism = synthetic construct
                        note = Description of Artificial Sequence: Synthetic
                            polynucleotide
SEQUENCE: 418
caagtgcagc tgcaagagtc cggaggagga agcgtgcaag ccggcggatc tctgagactg    60
agctgtgccg cctctaggta cacttacaac agctactgca tgggctggtt cagacaagcc   120
cccggcaagg aaagagaggg cgtggccact atcgatagcg acggcatgac taggtacgct   180
gatagcgtca agggaaggtt cacaatctcc aaggacaatg ctaagaacac tctgtacctc   240
cagatgaact ctctgaagcc agaggacaca gccatgtact actgcgctgc cgatgccgac   300
tgcactatcg ccgccatgac tactaatcct ctgggccaag gcacacaagt gactgtctcg   360
agcggcggag gatcccaagt gcagctgcaa gagagcggag gaggaagcgt gcaagccgga   420
ggctctctga ggctgagctg tgccgcctct aggttcacat acagcagcta ctgcatgggc   480
tggttcagac aagcccccgg caagagagag aaggcgtgg ccagcatcga tagcgatggc   540
tccactagct acactgacag cgtgaaggga aggttcacta tcagcaagga caacgccaag   600
aacactctgt atctgcagat gaactctctg aagccagagg acacagccat gtactactgt   660
gccctcgatc tgatgagcac agtggtgccc ggcttctgtg gctttctgct gagcgctggc   720
atggattact ggggcaaggg cactcaagtg actgtctcgt ctgctagcca ccatcaccat   780
caccac                                                              786

SEQ ID NO: 419          moltype = DNA   length = 792
FEATURE                 Location/Qualifiers
source                  1..792
                        mol_type = other DNA
                        organism = synthetic construct
                        note = Description of Artificial Sequence: Synthetic
                            polynucleotide
SEQUENCE: 419
caagtgcagc tgcaagagtc cggaggagga agcgtgcaag ccggcggatc tctgagactg    60
agctgtgccg cctctaggta cacttacaac agctactgca tgggctggtt cagacaagcc   120
cccggcaagg aaagagaggg cgtggccact atcgatagcg acggcatgac taggtacgct   180
gatagcgtca agggaaggtt cacaatctcc aaggacaatg ctaagaacac tctgtacctc   240
cagatgaact ctctgaagcc agaggacaca gccatgtact actgcgctgc cgatgccgac   300
tgcactatcg ccgccatgac tactaatcct ctgggccaag gcacacaagt gactgtctcg   360
agcggcggag gatcccaagt gcagctgcaa gagtccggag gaggcagcgt ccaagccgga   420
ggctctctga ggctgagctg tgctgccagc ggctacactt acagcagcta ctgcatgggc   480
tggttcagac aagcccccgg caaggaaaga gagggcgtgg cccagatcaa tagcgatggc   540
agcacaagct acgccgacag cgtgaaggga aggttcacta tctccaagga caacgccaag   600
aacactctgt atctgcagat gaactctctg aagccagagg acactgccat gtactactgc   660
gctgccgatt ctagggtgta cggcggcagc tggtatgaga ggctctgcgg cccttacaca   720
tacgagtaca actactgggg ccaaggcaca caagtgactg tctcgtctgc tagccaccat   780
caccatcacc ac                                                       792

SEQ ID NO: 420          moltype = DNA   length = 801
FEATURE                 Location/Qualifiers
source                  1..801
                        mol_type = other DNA
                        organism = synthetic construct
                        note = Description of Artificial Sequence: Synthetic
                            polynucleotide
SEQUENCE: 420
caagtgcagc tgcaagagtc cggaggagga agcgtgcaag ccggcggatc tctgagactg    60
agctgtgccg cctctaggta cacttacaac agctactgca tgggctggtt cagacaagcc   120
cccggcaagg aaagagaggg cgtggccact atcgatagcg acggcatgac taggtacgct   180
gatagcgtca agggaaggtt cacaatctcc aaggacaatg ctaagaacac tctgtacctc   240
cagatgaact ctctgaagcc agaggacaca gccatgtact actgcgctgc cgatgccgac   300
tgcactatcg ccgccatgac tactaatcct ctgggccaag gcacacaagt gactgtctcg   360
agcggcggag gatcccaagt gcagctgcaa gagagcggcg gaggaagcgt gcaagccgga   420
ggatctctga gactgagctg cgctgtgagc ggctacgcct actccacata ctgcatgggc   480
tggtttaggc aagcccccgg caaagagaga gagggcgtgg ctgctatcga tagcggcggc   540
agcacaagct acgccgatag cgtgaaggga aggttcacaa tcagcaagga caacgccaag   600
aacacactgt atctgaggat gaactctctg aagccagagg acacagccat gtactactgt   660
gctgctgtgc ctcctcctcc agatggcggc agctgtctgt ttctgggacc agagatcaag   720
gtcagcaagg ccgattttag gtactggggc aaggcacac aagtgacagt ctcgtctgct   780
agccaccatc accatcacca c                                             801

SEQ ID NO: 421          moltype = DNA   length = 780
FEATURE                 Location/Qualifiers
source                  1..780
                        mol_type = other DNA
                        organism = synthetic construct
                        note = Description of Artificial Sequence: Synthetic
                            polynucleotide
SEQUENCE: 421
caagtgcagc tgcaagagtc cggaggagga agcgtgcaag ccggcggatc tctgagactg    60
agctgtgccg cctctaggta cacttacaac agctactgca tgggctggtt cagacaagcc   120
cccggcaagg aaagagaggg cgtggccact atcgatagcg acggcatgac taggtacgct   180
gatagcgtca agggaaggtt cacaatctcc aaggacaatg ctaagaacac tctgtacctc   240
cagatgaact ctctgaagcc agaggacaca gccatgtact actgcgctgc cgatgccgac   300
tgcactatcg ccgccatgac tactaatcct ctgggccaag gcacacaagt gactgtctcg   360
```

```
agcggcggag gatcccaagt gcagctgcaa gagagcggag gaggaagcgt gcaagccgga    420
ggctctctga ggctgagctg tacagtgtcc ggctacactt acagctccaa ttgcatgggc    480
tggtttaggc aagcccccgg caaggaaaga gagggcgtgg ccactatcta cactggcggc    540
ggcaacacat actacgccga tagcgtgaag ggaaggttca ctatcagcca agataacgcc    600
aagaacacag tgtatctgca gatgaacaat ctgaagccag aggacactgc catgtactac    660
tgtgctgctg agccactgtc tagggtgtac ggcggcagct gcccaactcc tacattcgac    720
tactggggcc aaggcacaca agtgactgtc tcgtctgcta gccaccatca ccatcaccac    780

SEQ ID NO: 422           moltype = DNA  length = 777
FEATURE                  Location/Qualifiers
source                   1..777
                         mol_type = other DNA
                         organism = synthetic construct
                         note = Description of Artificial Sequence: Synthetic
                             polynucleotide
SEQUENCE: 422
caagtgcagc tgcaagagtc cggaggagga agcgtgcaag ccggcggatc tctgagactg    60
agctgtgccg cctctaggta cacttacaac agctactgca tgggctggtt cagacaagcc    120
cccggcaagg aaagagaggg cgtggccact atcgatagcg acggcatgac taggtacgct    180
gatagcgtca agggaaggtt cacaatctcc aaggacaatg ctaagaacac tctgtacctc    240
cagatgaact ctctgaagcc agaggacaca gccatgtact actgcgctgc cgatgccgac    300
tgcactatcg ccgccatgac tactaatcct ctgggccaag gcacacaagt gactgtctcg    360
agcggcggag gatcccaagt gcagctgcaa gagagcggag gaggaagcgt ccaagccgga    420
ggctctctga ggctgagctg tggagccagc ggctacactt acagcagcta ctgtatgggc    480
tggtttaggc aagtgcccgg caaggagaga gagggcgtgg ccgtgatcga ttccgatggc    540
agcacaagct acgctgacag cgtgaaggga aggttcacaa tctcaaggac aacgccaag    600
aacacactct atctgcagat gaacagcctc aagccagagg acacagccat gtactactgc    660
gccgctgatc tgggccacta taggcctcct tgtggcgtgc tgtatctggg catggattac    720
tggggcaagg cacacaagt gacagtctcg tctgctagcc accatcacca tcaccac        777

SEQ ID NO: 423           moltype = DNA  length = 780
FEATURE                  Location/Qualifiers
source                   1..780
                         mol_type = other DNA
                         organism = synthetic construct
                         note = Description of Artificial Sequence: Synthetic
                             polynucleotide
SEQUENCE: 423
caagtgcagc tgcaagagtc cggaggagga agcgtgcaag ccggcggatc tctgagactg    60
agctgtgccg cctctaggta cacttacaac agctactgca tgggctggtt cagacaagcc    120
cccggcaagg aaagagaggg cgtggccact atcgatagcg acggcatgac taggtacgct    180
gatagcgtca agggaaggtt cacaatctcc aaggacaatg ctaagaacac tctgtacctc    240
cagatgaact ctctgaagcc agaggacaca gccatgtact actgcgctgc cgatgccgac    300
tgcactatcg ccgccatgac tactaatcct ctgggccaag gcacacaagt gactgtctcg    360
agcggcggag gatcccaagt gcagctgcaa gagagcggag gaggaagcgt ccaagccgga    420
ggctctctga gactgagctg tgccgccagc ggctactcca actgcagcta cgacatgact    480
tggtataggc aagcccccgg caaggagagg gagttcgtgg cgccatcca cagcgacggc    540
agcactagat acgccgacag cgtgaaggga aggttcttca tcagccaaga taacgccaag    600
aacacagtgt atctgcagat gaactccctc aagccagagg acactgccat gtactactgc    660
aagacagacc cactgcactg cagagcccat ggcggcagct ggtatagcgt gagggccaac    720
tactggggcc aaggcacaca agtgacagtc tcgtctgcta gccaccatca ccatcaccac    780

SEQ ID NO: 424           moltype = DNA  length = 786
FEATURE                  Location/Qualifiers
source                   1..786
                         mol_type = other DNA
                         organism = synthetic construct
                         note = Description of Artificial Sequence: Synthetic
                             polynucleotide
SEQUENCE: 424
caagtgcagc tgcaagagtc cggcggaggc agcgtccaag ccggaggatc tctgaggctg    60
agctgtacag tgagcagata cactgccagc gtgaactaca tgggctggtt cagacaagcc    120
cccggcaaag agagagaggg cgtggccaca atcttcactg cgccggcac aacatactac    180
gccaactccg tcaagggaag gttcacaatc tctagggaca ccaagaa cactgcctat    240
ctgcagatga actccctcaa gccagaggac actgccatct actactgcgc cgtggatttc    300
agaggcggac tgctgtatag gccagcctac gagtacactt ataggggcca aggcacacaa    360
gtgacagtct cgagcggcgg aggatcccaa gtgcagctgc aagagagcgg aggaggaagc    420
gtgcaagccg gaggctctct gagactgagc tgtgccgcct ctaggtatct gtacagcgtc    480
gactcatgg cttggttcag acagagcccc ggcaaggcag gtgctgtcatc    540
tacactgcct ccggcgccac attctatcca gatagcgtga agggaaggtt cactatcagc    600
caagataacg ccaagatgac agtgtatctg cagatgaact ctctgaagag cgaggacact    660
gccatgtact actgtgccgc cgtgaggaag acagatagcc acctcttcga cgcccagagc    720
ttcacatact ggggccaagg cacacaagtg acagtctcgt ctgctagcca ccatcaccat    780
caccac                                                               786

SEQ ID NO: 425           moltype = DNA  length = 798
FEATURE                  Location/Qualifiers
source                   1..798
                         mol_type = other DNA
```

```
                        organism = synthetic construct
                        note = Description of Artificial Sequence: Synthetic
                           polynucleotide
SEQUENCE: 425
caagtgcagc tgcaagagtc cggcggaggc agcgtccaag ccggaggatc tctgaggctg    60
agctgtacag tgagcagata cactgccagc gtgaactaca tgggctggtt cagacaagcc   120
cccggcaaag agagagaggg cgtggccaca atcttcactg cgccggcac aacatactac    180
gccaactccg tcaagggaag gttcacaatc tctagggaca cgccaagaa cactgcctat    240
ctgcagatga actccctcaa gccagaggac actgccatct actactgcgc cgtggatttc    300
agaggcggac tgctgtatag gccagcctac gagtacactt ataggggcca aggcacacaa    360
gtgacagtct cgagcggcgg aggatcccaa gtgcagctgc aagagagcgg aggaggaagc    420
gtgcaagccg gaggctctct gaggctgagc tgtgccgcct ctaggttcac atacagcagc    480
tactgcatgg gctggttcag acaagccccc ggcaaagaga gagaaggcgt ggccagcatc    540
gatagcgatg gctccactag ctacactgac agcgtgaagg gaaggttcac tatcagcaag    600
gacaacgcca agaacactct gtatctgcag atgaactctc tgaagccaga ggacacagcc    660
atgtactact gtgccctcga tctgatgagc acagtggtgc ccggcttctg tggctttctg    720
ctgagcgctg gcatggatta ctggggcaag ggcactcaag tgactgtctc gtctgctagc    780
caccatcacc atcaccac                                                  798

SEQ ID NO: 426          moltype = DNA   length = 804
FEATURE                 Location/Qualifiers
source                  1..804
                        mol_type = other DNA
                        organism = synthetic construct
                        note = Description of Artificial Sequence: Synthetic
                           polynucleotide
SEQUENCE: 426
caagtgcagc tgcaagagtc cggcggaggc agcgtccaag ccggaggatc tctgaggctg    60
agctgtacag tgagcagata cactgccagc gtgaactaca tgggctggtt cagacaagcc   120
cccggcaaag agagagaggg cgtggccaca atcttcactg cgccggcac aacatactac    180
gccaactccg tcaagggaag gttcacaatc tctagggaca cgccaagaa cactgcctat    240
ctgcagatga actccctcaa gccagaggac actgccatct actactgcgc cgtggatttc    300
agaggcggac tgctgtatag gccagcctac gagtacactt ataggggcca aggcacacaa    360
gtgacagtct cgagcggcgg aggatcccaa gtgcagctgc aagagtccgg aggaggcagc    420
gtccaagccg gaggctctct gaggctgagc tgtgctgcca ttacagcagc               480
tactgcatgg gctggttcag acaagccccc ggcaaggaaa gagagggcgt ggcccagatc    540
aatagcgatg gcagcacaag ctacgccgac agcgtgaagg gaaggttcac tatctccaag    600
gacaacgcca agaacactct gtatctgcag atgaactctc tgaagccaga ggacactgcc    660
atgtactact gcgctgccga ttctaggggtg tacggcggca gctggtatga gagctctgc    720
ggcccttaca catacgagta caactactgg ggccaaggca cacaagtgac tgtctcgtct    780
gctagccacc atcaccatca ccac                                            804

SEQ ID NO: 427          moltype = DNA   length = 813
FEATURE                 Location/Qualifiers
source                  1..813
                        mol_type = other DNA
                        organism = synthetic construct
                        note = Description of Artificial Sequence: Synthetic
                           polynucleotide
SEQUENCE: 427
caagtgcagc tgcaagagtc cggcggaggc agcgtccaag ccggaggatc tctgaggctg    60
agctgtacag tgagcagata cactgccagc gtgaactaca tgggctggtt cagacaagcc   120
cccggcaaag agagagaggg cgtggccaca atcttcactg cgccggcac aacatactac    180
gccaactccg tcaagggaag gttcacaatc tctagggaca cgccaagaa cactgcctat    240
ctgcagatga actccctcaa gccagaggac actgccatct actactgcgc cgtggatttc    300
agaggcggac tgctgtatag gccagcctac gagtacactt ataggggcca aggcacacaa    360
gtgacagtct cgagcggcgg aggatcccaa gtgcagctgc aagagagcgg cggaggaagc    420
gtgcaagccg gaggatctct gagactgagc tgcgctgtga cggcggctacgc ctactccaca    480
tactgcatgg gctggtttag gcaagccccc ggcaaagaga gagggcgt ggctgctatc      540
gatagcggcg gcagcacaag ctacgccgat agcgtgaagg gaaggttcac aatcagcaag    600
gacaacgcca agaacacact gtatctgagg atgaactctc tgaagccaga ggacacagcc    660
atgtactact gtgctgctgt gcctcctcct ccagatggcg gcagctgtct gtttctggga    720
ccagagatca aggtcagcaa ggccgatttt aggtactggg gccaaggcac acaagtgaca    780
gtctcgtctg ctagccacca tcaccatcac cac                                  813

SEQ ID NO: 428          moltype = DNA   length = 792
FEATURE                 Location/Qualifiers
source                  1..792
                        mol_type = other DNA
                        organism = synthetic construct
                        note = Description of Artificial Sequence: Synthetic
                           polynucleotide
SEQUENCE: 428
caagtgcagc tgcaagagtc cggcggaggc agcgtccaag ccggaggatc tctgaggctg    60
agctgtacag tgagcagata cactgccagc gtgaactaca tgggctggtt cagacaagcc   120
cccggcaaag agagagaggg cgtggccaca atcttcactg cgccggcac aacatactac    180
gccaactccg tcaagggaag gttcacaatc tctagggaca cgccaagaa cactgcctat    240
ctgcagatga actccctcaa gccagaggac actgccatct actactgcgc cgtggatttc    300
agaggcggac tgctgtatag gccagcctac gagtacactt ataggggcca aggcacacaa    360
```

```
gtgacagtct cgagcggcgg aggatcccaa gtgcagctgc aagagagcgg aggaggaagc    420
gtgcaagccg gaggctctct gaggctgagc tgtacagtgt ccggctacac ttacagctcc    480
aattgcatgg gctggtttag gcaagccccc ggcaaggaaa gagagggcgt ggccactatc    540
tacactggcg gcggcaacac atactacgcc gatagcgtga agggaaggtt cactatcagc    600
caagataacg ccaagaacac agtgtatctg cagatgaaca atctgaagcc agaggacact    660
gccatgtact actgtgctgc tgagccactg tctagggtgt acggcggcag ctgcccaact    720
cctacattcg actactgggg ccaaggcaca caagtgactg tctcgtctgc tagccaccat    780
caccatcacc ac                                                        792

SEQ ID NO: 429          moltype = DNA    length = 789
FEATURE                 Location/Qualifiers
source                  1..789
                        mol_type = other DNA
                        organism = synthetic construct
                        note = Description of Artificial Sequence: Synthetic
                        polynucleotide
SEQUENCE: 429
caagtgcagc tgcaagagtc cggcggaggc agcgtccaag ccggaggatc tctgaggctg     60
agctgtacag tgagcagata cactgccagc gtgaactaca tgggctggtt cagacaagcc    120
cccggcaaag agagagaggg cgtggccaca atcttcactg gcgccggcac aacatactac    180
gccaactccg tcaagggaag gttcacaatc tctaggaca acgccaagaa cactgcctat    240
ctgcagatga actccctcaa gccagaggac actgccatct actactgcgc cgtggatttc    300
agaggcggac tgctgtatag gccagcctac gagtacactt ataggggcca aggcacacaa    360
gtgacagtct cgagcggcgg aggatcccaa gtgcagctgc aagagagcgg aggaggaagc    420
gtccaagccg gaggctctct gaggctgagc tgtggagcca cgggctacac ttacagcagc    480
tactgtatgg gctggtttag gcaagtgccc ggcaaggaga gagggggct ggccgtgatc    540
gattccgatg gcagcacaag ctacgctgac agcgtgaagg gaaggttcac aatcagcaag    600
gacaacggca agaacacact ctatctgcag atgaacagcc tcaagccaga ggacacagcc    660
atgtactact gcgccgctga tctgggccac tataggcctc cttgtggcgt gctgtatctg    720
ggcatggatt actgggcaa gggcacacaa gtgacagtct cgtctgctag ccaccatcac    780
catcaccac                                                            789

SEQ ID NO: 430          moltype = DNA    length = 792
FEATURE                 Location/Qualifiers
source                  1..792
                        mol_type = other DNA
                        organism = synthetic construct
                        note = Description of Artificial Sequence: Synthetic
                        polynucleotide
SEQUENCE: 430
caagtgcagc tgcaagagtc cggcggaggc agcgtccaag ccggaggatc tctgaggctg     60
agctgtacag tgagcagata cactgccagc gtgaactaca tgggctggtt cagacaagcc    120
cccggcaaag agagagaggg cgtggccaca atcttcactg gcgccggcac aacatactac    180
gccaactccg tcaagggaag gttcacaatc tctaggaca acgccaagaa cactgcctat    240
ctgcagatga actccctcaa gccagaggac actgccatct actactgcgc cgtggatttc    300
agaggcggac tgctgtatag gccagcctac gagtacactt ataggggcca aggcacacaa    360
gtgacagtct cgagcggcgg aggatcccaa gtgcagctgc aagagagcgg aggaggaagc    420
gtccaagccg gaggctctct gagactgagc tgtgccgcca cgggctactc caactgcagc    480
tacgacatga cttggtatag gcaagccccc ggcaaggaga gggagttcgt gtccgccatc    540
cacagcgacg gcagcactag atacgccgac agcgtgaagg gaaggttctt catcagccaa    600
gataacacagt gtatctgcag atgaactccc tcaagccaga ggacactgcc    660
atgtactact gcaagacaga cccactgcac tgcagagccc atggcggcag ctggtatagc    720
gtgagggcca actactgggg ccaaggcaca caagtgacag tctcgtctgc tagccaccat    780
caccatcacc ac                                                        792

SEQ ID NO: 431          moltype = DNA    length = 789
FEATURE                 Location/Qualifiers
source                  1..789
                        mol_type = other DNA
                        organism = synthetic construct
                        note = Description of Artificial Sequence: Synthetic
                        polynucleotide
SEQUENCE: 431
caagtgcagc tgcaagagag cggaggaggc agcgtcgaag ctggaggatc tctgaggctg     60
agctgtgctg ccagcggcta cactcacagc agctactgta tgggctggtt cagacaagcc    120
cccggcaagg agagggaagg cgtggctgcc atcgacgtgg atggcagcac tacttacgcc    180
gacagcgtga agggaaggtt cactatcagc aaggacaacg ccaagaacac actctatctg    240
cagatgaaca gcctcaagcc agaggacact ggcatgtact actgcgccgc cgagttcgcc    300
gattcagca gcaactactt tctgcctccc ggcgccgtca gatattgggg ccaaggcact    360
caagtgacag tctcgagcgg cggaggatcc caagtgcagc tgcaagagag cggaggagga    420
agcgtgcaag ccggaggctc tctgagactg agctgtgccg cctctaggta tctgtacagc    480
atcgactaca tggcttggtt cagacagagc cccggcaagg agagggagcc agtggctgtc    540
atctacactg cctccggcgc cacattctat ccagatagcg tgaaggaag gttcactatc    600
agcaagata acgccaagat gacagtgtat ctgcagatga actctgaa gagcgaggac    660
actgccatgt actactgtgc cgccgtgagg aagacagata gctacctctt cgacgccagc    720
agcttcacat actggggcca aggcacacaa gtgacagtct cgtctgctag ccaccatcac    780
catcaccac                                                            789

SEQ ID NO: 432          moltype = DNA    length = 801
```

```
FEATURE              Location/Qualifiers
source               1..801
                     mol_type = other DNA
                     organism = synthetic construct
                     note = Description of Artificial Sequence: Synthetic
                     polynucleotide
SEQUENCE: 432
caagtgcagc tgcaagagag cggaggaggc agcgtcgaag ctggaggatc tctgaggctg    60
agctgtgctg ccagcggcta cactcacagc agctactgta tgggctggtt cagacaagcc   120
cccggcaagg agagggaagg cgtggctgcc atcgacgtgg atggcagcac tacttacgcc   180
gacagcgtga agggaaggtt cactatcagc aaggacaacg ccaagaacac actctatctg   240
cagatgaaca gcctcaagcc agaggacact ggcatgtact actgcgccgc cgagttcgcc   300
gattgcagca gcaactactt tctgcctccc ggcgccgtca gatattgggg ccaaggcact   360
caagtgacag tctcgagcgg cggaggatcc caagtgcagc tgcaagagag cggaggagga   420
agcgtgcaag ccggaggctc tctgaggctg agctgtgccg cctctaggtt cacatacagc   480
agctactgca tgggctggtt cagacaagcc cccggcaaag agagaaagg cgtggccagc   540
atcgatagcg atggctccac tagctacact gacagcgtga agggaaggtt cactatcagc   600
aaggacaacg ccaagaacac tctgtatctg cagatgaact ctctgaagcc agaggacaca   660
gccatgtact actgtgccct cgatctgatg agcacagtgg tgcccggctt ctgtggcttt   720
ctgctgagcg ctggcatgga ttactgggc aagggcactc aagtgactgt ctcgtctgct   780
agccaccatc accatcacca c                                              801

SEQ ID NO: 433       moltype = DNA   length = 807
FEATURE              Location/Qualifiers
source               1..807
                     mol_type = other DNA
                     organism = synthetic construct
                     note = Description of Artificial Sequence: Synthetic
                     polynucleotide
SEQUENCE: 433
caagtgcagc tgcaagagag cggaggaggc agcgtcgaag ctggaggatc tctgaggctg    60
agctgtgctg ccagcggcta cactcacagc agctactgta tgggctggtt cagacaagcc   120
cccggcaagg agagggaagg cgtggctgcc atcgacgtgg atggcagcac tacttacgcc   180
gacagcgtga agggaaggtt cactatcagc aaggacaacg ccaagaacac actctatctg   240
cagatgaaca gcctcaagcc agaggacact ggcatgtact actgcgccgc cgagttcgcc   300
gattgcagca gcaactactt tctgcctccc ggcgccgtca gatattgggg ccaaggcact   360
caagtgacag tctcgagcgg cggaggatcc caagtgcagc tgcaagagtc cggaggaggc   420
agcgtccaag ccggaggctc tctgaggctg agctgtgctg ccagcggcta cacttacagc   480
atgtactgca tgggctggtt cagacaagcc cccggcaaag aaagagaggg cgtggcccag   540
atcaatagcg atggcagcac aagctacgcc gacagcgtga agggaaggtt cactatctcc   600
aaggacaacg ccaagaacac tctgtatctg cagatgaact ctctgaagcc agaggacact   660
gccatgtact actgcgctgc cgattctagg gtgtacggcg gcagctggta tgagaggctc   720
tgcggccctt acacatacga gtacaactac tggggccaag gcacacaagt gactgtctcg   780
tctgctagcc accatcacca tcaccac                                        807

SEQ ID NO: 434       moltype = DNA   length = 816
FEATURE              Location/Qualifiers
source               1..816
                     mol_type = other DNA
                     organism = synthetic construct
                     note = Description of Artificial Sequence: Synthetic
                     polynucleotide
SEQUENCE: 434
caagtgcagc tgcaagagag cggaggaggc agcgtcgaag ctggaggatc tctgaggctg    60
agctgtgctg ccagcggcta cactcacagc agctactgta tgggctggtt cagacaagcc   120
cccggcaagg agagggaagg cgtggctgcc atcgacgtgg atggcagcac tacttacgcc   180
gacagcgtga agggaaggtt cactatcagc aaggacaacg ccaagaacac actctatctg   240
cagatgaaca gcctcaagcc agaggacact ggcatgtact actgcgccgc cgagttcgcc   300
gattgcagca gcaactactt tctgcctccc ggcgccgtca gatattgggg ccaaggcact   360
caagtgacag tctcgagcgg cggaggatcc caagtgcagc tgcaagagag cggcggagga   420
agcgtgcaag ccggaggatc tctgagactg agctgcgctg tgagcggcta cgcctactcc   480
acatactgca tgggctggtt taggcaagcc cccggcaaag agagagggg cgtggctgct   540
atcgatagcg cggcagcac aagctacgcc gatagcgtga agggaaggtt cacaatcagc   600
aaggacaacg ccaagaacac actgtatctg aggatgaact ctctgaagcc agaggacaca   660
gccatgtact actgtgctgc tgtgcctcct cctccagatg gcggcagctg tctgtttctg   720
ggaccagaga tcaaggtcag caaggccgat tttaggtact ggggccaagg cacacaagtg   780
acagtctcgt ctgctagcca ccatcaccat caccac                              816

SEQ ID NO: 435       moltype = DNA   length = 795
FEATURE              Location/Qualifiers
source               1..795
                     mol_type = other DNA
                     organism = synthetic construct
                     note = Description of Artificial Sequence: Synthetic
                     polynucleotide
SEQUENCE: 435
caagtgcagc tgcaagagag cggaggaggc agcgtcgaag ctggaggatc tctgaggctg    60
agctgtgctg ccagcggcta cactcacagc agctactgta tgggctggtt cagacaagcc   120
cccggcaagg agagggaagg cgtggctgcc atcgacgtgg atggcagcac tacttacgcc   180
```

```
gacagcgtga agggaaggtt cactatcagc aaggacaacg ccaagaacac actctatctg    240
cagatgaaca gcctcaagcc agaggacact ggcatgtact actgcgccgc cgagttcgcc    300
gattgcagca gcaactactt tctgcctccc ggcgccgtca gatattgggg ccaaggcact    360
caagtgcacag tctcgagcgg cggaggatcc caagtgcagc tgcaagagag cggaggagga   420
agcgtgcaag ccggaggctc tctgaggctg agctgtacag tgtccggcta cacttacagc    480
tccaattgca tgggctggtt taggcaagcc cccggcaagg aaagagaggg cgtggccact    540
atctacactg gcggcggcaa cacatactac gccgatagcg tgaagggaag gttcactatc    600
agccaagata acgccaagaa cacagtgtat ctgcagatga acaatctgaa gccagaggac    660
actgccatgt actactgtgc tgctgagcca ctgtctaggg tgtacggcgg cagctgccca    720
actcctacat tcgactactg gggccaaggc acacaagtga ctgtctcgtc tgctagccac    780
catcaccatc accac                                                    795

SEQ ID NO: 436         moltype = DNA   length = 792
FEATURE                Location/Qualifiers
source                 1..792
                       mol_type = other DNA
                       organism = synthetic construct
                       note = Description of Artificial Sequence: Synthetic
                       polynucleotide
SEQUENCE: 436
caagtgcagc tgcaagagag cggaggaggc agcgtcgaag ctggaggatc tctgaggctg     60
agctgtgctg ccagcggcta cactcacagc agctactgta tgggctggtt cagacaagcc    120
cccggcaagg agagggaagg cgtggctgcc atcgacgtgg atggcagcac tacttacgcc    180
gacagcgtga agggaaggtt cactatcagc aaggacaacg ccaagaacac actctatctg    240
cagatgaaca gcctcaagcc agaggacact ggcatgtact actgcgccgc cgagttcgcc    300
gattgcagca gcaactactt tctgcctccc ggcgccgtca gatattgggg ccaaggcact    360
caagtgacag tctcgagcgg cggaggatcc caagtgcagc tgcaagagag cggaggagga    420
agcgtccaag ccggaggctc tctgaggctg agctgtggag ccagcggcta cacttacagc    480
agctactgta tgggctggtt taggcaagtg cccggcaagg agagagaggg cgtggccgtg    540
atcgattccg atggcagcac aagctacgct gacagcgtga agggaaggtt cacaatcagc    600
aaggacaacg gcaagaacac actctatctg cagatgaaca gcctcaagcc agaggacaca    660
gccatgtact actgcgccgc tgatctgggc cactataggc ctccttgtgg cgtgctgtat    720
ctgggcatgg attactgggg caagggcaca caagtgacag tctcgtctgc tagccaccat    780
caccatcacc ac                                                       792

SEQ ID NO: 437         moltype = DNA   length = 795
FEATURE                Location/Qualifiers
source                 1..795
                       mol_type = other DNA
                       organism = synthetic construct
                       note = Description of Artificial Sequence: Synthetic
                       polynucleotide
SEQUENCE: 437
caagtgcagc tgcaagagag cggaggaggc agcgtcgaag ctggaggatc tctgaggctg     60
agctgtgctg ccagcggcta cactcacagc agctactgta tgggctggtt cagacaagcc    120
cccggcaagg agagggaagg cgtggctgcc atcgacgtgg atggcagcac tacttacgcc    180
gacagcgtga agggaaggtt cactatcagc aaggacaacg ccaagaacac actctatctg    240
cagatgaaca gcctcaagcc agaggacact ggcatgtact actgcgccgc cgagttcgcc    300
gattgcagca gcaactactt tctgcctccc ggcgccgtca gatattgggg ccaaggcact    360
caagtgacag tctcgagcgg cggaggatcc caagtgcagc tgcaagagag cggaggagga    420
agcgtccaag ccggaggctc tctgagactg agctgtgcg cggcggcta ctccaactgc      480
agctacgaca tgacttggta taggcaagcc cccggcaagg agagggagtt cgtgtccgcc    540
atccacagcg acggcagcac tagatacgcc gacagcgtga agggaaggtt cttcatcagc    600
caagataacg ccaagaacac agtgtatctg cagatgaact ccctcaagcc agaggacact    660
gccatgtact actgcaagac agacccactg cactgcagag cccatggcgg cagctggtat    720
agcgtgaggg ccaactactg gggccaaggc acacaagtga cagtctcgtc tgctagccac    780
catcaccatc accac                                                    795

SEQ ID NO: 438         moltype = DNA   length = 783
FEATURE                Location/Qualifiers
source                 1..783
                       mol_type = other DNA
                       organism = synthetic construct
                       note = Description of Artificial Sequence: Synthetic
                       polynucleotide
SEQUENCE: 438
caagtgcagc tgcaagagag cggaggagga agcgtccaag ccggaggatc tctgagactg     60
agctgcgccg ctagtggcta ctcctacagc agctactgca tgggctggtt taggcaagcc    120
cccggcaagg agagagaagg cgtggccact atcgacacgc acggcatgaa aaggtacgcc    180
gacagcgtga agggaaggtt cacaatcagc aaggacaacg ccaagaacac actgtatctg    240
cagatgaact ctctgaagcc agaggacact gccatgtact actgtgccgc tcctctgtac    300
gactgtgata gcgcgctgt gggcagaaat ccaccttatt ggggccaagg cactcaagtg    360
acagtctcga gcggcggagg atcccaagtg cagctgcaag agcggagg aggaagcgtg     420
caagccggag gctctctgag actgagctgt gccgcctcta ggtatctgta cagcatcgac    480
tacatggctt ggttcagaca gagccccggc aaggagaggg agccagtggc tgtcatctac    540
actgcctccg gcgccacatt ctatccagat agcgtgaagg gaaggttcac tatcagccaa    600
gataacgcca agatgacagt gtatctgcag atgaactctc tgaagagcga ggacactgcc    660
atgtactact gtgccgccgt gaggaagaca gatagctacc tcttcgacgc ccagagcttc    720
acatactggg gccaaggcac acaagtgaca gtctcgtctg ctagccacca tcaccatcac    780
```

```
cac                                                                        783

SEQ ID NO: 439          moltype = DNA  length = 795
FEATURE                 Location/Qualifiers
source                  1..795
                        mol_type = other DNA
                        organism = synthetic construct
                        note = Description of Artificial Sequence: Synthetic
                            polynucleotide
SEQUENCE: 439
caagtgcagc tgcaagagag cggaggagga agcgtccaag ccggaggatc tctgagactg    60
agctgcgccg ctagtggcta ctcctacagc agctactgca tgggctggtt taggcaagcc   120
cccggcaagg agagagaagg cgtggccact atcgacagcg acggcatgac aaggtacgcc   180
gacagcgtga agggaaggtt cacaatcagc aaggacaacg ccaagaacac actgtatctg   240
cagatgaact ctctgaagcc agaggacact gccatgtact actgtgccgc tcctctgtac   300
gactgtgata gcggcgctgt gggcagaaat ccaccttatt ggggccaagg cactcaagtg   360
acagtctcga gcggcggagg atcccaagtg cagctgcaag agagcggagg aggaagcgtg   420
caagccggag gctctctgag gctgagctgt gccgcctcta ggttcacata cagcagctac   480
tgcatgggct ggttcagaca agcccccggc aaagagagag aaggcgtggc cagcatcgat   540
agcgatggct ccactagcta cactgacagc gtgaagggaa ggttcactat cagcaaggac   600
aacgccaaga acactctgta tctgcagatg aactctctga agccagagga cacagccatg   660
tactactgtg ccctcgatct gatgagcaca gtggtgcccg gcttctgtgg ctttctgctg   720
agcgctggca tggattactg gggcaagggc actcaagtga ctgtctcgtc tgctagccac   780
catcaccatc accac                                                    795

SEQ ID NO: 440          moltype = DNA  length = 801
FEATURE                 Location/Qualifiers
source                  1..801
                        mol_type = other DNA
                        organism = synthetic construct
                        note = Description of Artificial Sequence: Synthetic
                            polynucleotide
SEQUENCE: 440
caagtgcagc tgcaagagag cggaggagga agcgtccaag ccggaggatc tctgagactg    60
agctgcgccg ctagtggcta ctcctacagc agctactgca tgggctggtt taggcaagcc   120
cccggcaagg agagagaagg cgtggccact atcgacagcg acggcatgac aaggtacgcc   180
gacagcgtga agggaaggtt cacaatcagc aaggacaacg ccaagaacac actgtatctg   240
cagatgaact ctctgaagcc agaggacact gccatgtact actgtgccgc tcctctgtac   300
gactgtgata gcggcgctgt gggcagaaat ccaccttatt ggggccaagg cactcaagtg   360
acagtctcga gcggcggagg atcccaagtg cagctgcaag agtccggagg aggcagcgtc   420
caagccggag gctctctgag gctgagctgt gctgccagcg gctacactta cagcatgtac   480
tgcatgggct ggttcagaca agcccccggc aaggaaagag agggcgtggc ccagatcaat   540
agcgatggca gcacaagcta cgccgacagc gtgaagggaa ggttcactat ctccaaggac   600
aacgccaaga acactctgta tctgcagatg aactctctga agccagagga cactgccatg   660
tactactgcg ctgccgattc tagggtgtac ggcggcagct ggtatgagag gctctgcggc   720
ccttacacat acgagtacaa ctactggggc caaggcacac aagtgactgt ctcgtctgct   780
agccaccatc accatcacca c                                             801

SEQ ID NO: 441          moltype = DNA  length = 810
FEATURE                 Location/Qualifiers
source                  1..810
                        mol_type = other DNA
                        organism = synthetic construct
                        note = Description of Artificial Sequence: Synthetic
                            polynucleotide
SEQUENCE: 441
caagtgcagc tgcaagagag cggaggagga agcgtccaag ccggaggatc tctgagactg    60
agctgcgccg ctagtggcta ctcctacagc agctactgca tgggctggtt taggcaagcc   120
cccggcaagg agagagaagg cgtggccact atcgacagcg acggcatgac aaggtacgcc   180
gacagcgtga agggaaggtt cacaatcagc aaggacaacg ccaagaacac actgtatctg   240
cagatgaact ctctgaagcc agaggacact gccatgtact actgtgccgc tcctctgtac   300
gactgtgata gcggcgctgt gggcagaaat ccaccttatt ggggccaagg cactcaagtg   360
acagtctcga gcggcggagg atcccaagtg cagctgcaag agagcggcgg aggaagcgtg   420
caagccggag gatctctgag actgagctgc gctgtgagcg gctacgccta ctccacatac   480
tgcatgggct ggtttaggca agcccccggc aaagagagag agggcgtggc tgctatcgat   540
agcggcggca gcacaagcta cgccgatagc gtgaagggaa ggttcacaat cagcaaggac   600
aacgccaaga acacactgta tctgaggatg aactctctga agccagagga cacagccatg   660
tactactgtg ctgctgtgcc tcctcctcca gatggcggca gctgtctgtt tctgggacca   720
gagatcaagg tcagcaaggc cgattttagg tactgggggc aaggcacaca agtgacagtc   780
tcgtctgcta gccaccatca ccatcaccac                                    810

SEQ ID NO: 442          moltype = DNA  length = 789
FEATURE                 Location/Qualifiers
source                  1..789
                        mol_type = other DNA
                        organism = synthetic construct
                        note = Description of Artificial Sequence: Synthetic
                            polynucleotide
SEQUENCE: 442
```

```
caagtgcagc tgcaagagag cggaggagga agcgtccaag ccggaggatc tctgagactg    60
agctgcgccg ctagtggcta ctcctacagc agctactgca tgggctggtt taggcaagcc   120
cccggcaagg agagagaagg cgtggccact atcgacagcg acggcatgac aaggtacgcc   180
gacagcgtga agggaaggtt cacaatcagc aaggacaacg ccaagaacac actgtatctg   240
cagatgaact ctctgaagcc agaggacact gccatgtact actgtgccgc tcctctgtac   300
gactgtgata gcggcgctgt gggcagaaat ccaccttatt ggggccaagg cactcaagtg   360
acagtctcga gcggcggagg atcccaagtg cagctgcaag agagcggagg aggaagcgtg   420
caagccggag gctctctgag gctgagctgt acagtgtccg gctacactta cagctccaat   480
tgcatgggct ggtttaggca agcccccggc aaggaaagag agggcgtggc cactatctac   540
actggcggcg gcaacacata ctacgccgat agcgtgaagg gaaggttcac tatcagccaa   600
gataacgcca agaacacagt gtatctgcag atgaacaatc tgaagccaga ggacactgcc   660
atgtactact gtgctgctga gccactgtct gggtgtacga gcggcagctg cccaactcct   720
acattcgact actggggcca aggcacacaa gtgactgtct cgtctgctag ccaccatcac   780
catcaccac                                                          789

SEQ ID NO: 443        moltype = DNA  length = 786
FEATURE               Location/Qualifiers
source                1..786
                      mol_type = other DNA
                      organism = synthetic construct
                      note = Description of Artificial Sequence: Synthetic
                      polynucleotide
SEQUENCE: 443
caagtgcagc tgcaagagag cggaggagga agcgtccaag ccggaggatc tctgagactg    60
agctgcgccg ctagtggcta ctcctacagc agctactgca tgggctggtt taggcaagcc   120
cccggcaagg agagagaagg cgtggccact atcgacagcg acggcatgac aaggtacgcc   180
gacagcgtga agggaaggtt cacaatcagc aaggacaacg ccaagaacac actgtatctg   240
cagatgaact ctctgaagcc agaggacact gccatgtact actgtgccgc tcctctgtac   300
gactgtgata gcggcgctgt gggcagaaat ccaccttatt ggggccaagg cactcaagtg   360
acagtctcga gcggcggagg atcccaagtg cagctgcaag agagcggagg aggaagcgtc   420
caagccggag gctctctgag gctgagctgt ggagccagcg gctacactta cagcagctac   480
tgtatgggct ggtttaggca agtgcccggc aaggagagag agggcgtggc cgtgatcgat   540
tccgatggca gcacaagcta cgctgacagc gtgaagggaa ggttcacaat cagcaaggac   600
aacggcaaga acacactcta tctgcagatg aacagcctca gccagagga cacagccatg   660
tactactgcg ccgctgatct gggccactat aggcctcctt gtggcgtgct gtatctgggc   720
atggattact ggggcaaggg cacacaagtg acagtctcgt ctgctagcca ccatcaccat   780
caccac                                                             786

SEQ ID NO: 444        moltype = DNA  length = 789
FEATURE               Location/Qualifiers
source                1..789
                      mol_type = other DNA
                      organism = synthetic construct
                      note = Description of Artificial Sequence: Synthetic
                      polynucleotide
SEQUENCE: 444
caagtgcagc tgcaagagag cggaggagga agcgtccaag ccggaggatc tctgagactg    60
agctgcgccg ctagtggcta ctcctacagc agctactgca tgggctggtt taggcaagcc   120
cccggcaagg agagagaagg cgtggccact atcgacagcg acggcatgac aaggtacgcc   180
gacagcgtga agggaaggtt cacaatcagc aaggacaacg ccaagaacac actgtatctg   240
cagatgaact ctctgaagcc agaggacact gccatgtact actgtgccgc tcctctgtac   300
gactgtgata gcggcgctgt gggcagaaat ccaccttatt ggggccaagg cactcaagtg   360
acagtctcga gcggcggagg atcccaagtg cagctgcaag agagcggagg aggaagcgtc   420
caagccggag gctctctgag actgagctgt gccgccagcg gctactccaa ctgcagctac   480
gacatgactt ggtataggca agcccccggc aaggagagag agttcgtgtc cgccatccat   540
agcgacggca gcactagata cgccgacagc gtgaagggaa ggttcttcat cagccaagat   600
aacgccaaga acacagtgta tctgcagatg aactccctca gccagagga cactgccatg   660
tactactgca agacagaccc actgcactgc agagcccatg cggcagctg gtatagcgtg   720
agggccaact actggggcca aggcacacaa gtgacagtcg tctgctag ccaccatcac   780
catcaccac                                                          789

SEQ ID NO: 445        moltype = DNA  length = 777
FEATURE               Location/Qualifiers
source                1..777
                      mol_type = other DNA
                      organism = synthetic construct
                      note = Description of Artificial Sequence: Synthetic
                      polynucleotide
SEQUENCE: 445
caagtgcagc tgcaagagag cggaggcggc agcgtgcaga ctggaggctc tctgagactg    60
agctgtgctg ccagcggcta cacttatctg aggggctgta tgggctggtt taggcaagcc   120
cccggcaagg agagagaggg cgtggccgtc atggatgtgg tgggcgatag agaagctac   180
atcgacagcg tgaagggaag gttcacaatc tctagggaca tgccgccaa cagcgtctat   240
ctgcagatgg acaatctgaa gccagaggac acagccatgt actactgcac tgccggccct   300
aactgtgtgg gctgagaag cggactggat tactggggcc aaggcacaca agtgacagtc   360
tcgagcggcg gaggatccca agtgcagctg aagagagcg gaggaggaag cgtgcaagcc   420
ggaggctctc tgagactgag ctgtgccgcc tctaggtatc tgtacagcat cgactacatg   480
gcttggttca cagagcccc cggcaaggag agggagccag tggctgtcat ctacactgcc   540
tccggcgcca cattctatcc agatagcgtg aagggaaggt tcactatcag ccaagataac   600
```

```
gccaagatga cagtgtatct gcagatgaac tctctgaaga gcgaggacac tgccatgtac  660
tactgtgccg ccgtgaggaa gacagatagc tacctcttcg acgcccagag cttcacatac  720
tggggccaag gcacacaagt gacagtctcg tctgctagcc accatcacca tcaccac     777
```

SEQ ID NO: 446                 moltype = DNA   length = 789
FEATURE                        Location/Qualifiers
source                         1..789
                               mol_type = other DNA
                               organism = synthetic construct
                               note = Description of Artificial Sequence: Synthetic
                                polynucleotide
SEQUENCE: 446
```
caagtgcagc tgcaagagag cggaggcggc agcgtgcaga ctggaggctc tctgagactg  60
agctgtgctg ccagcggcta cacttatctg aggggctgta tgggctggtt taggcaagcc  120
cccggcaagg agagagaggg cgtggccgtc atggatgtgg tgggcgatag gagaagctac  180
atcgacagcg tgaagggaag gttcacaatc tctaggaca atgccgccaa cagcgtctat  240
ctgcagatgg acaatctgaa gccagaggac acagccatgt actactgcac tgccggccct  300
aactgtgtgg gctggagaag cggactggat tactggggcc aaggcacaca agtgacagtc  360
tcgagcggcg gaggatccca agtgcagctg caagagagcg gaggaggaag cgtgcaagcc  420
ggaggctctc tgaggctgag ctgtgccgcc tctaggttca catacagcag ctactgcatg  480
ggctggttca gacaagcccc cggcaaagag agagaaggcg tggccagcat cgatagcgat  540
ggctccacta gctacactga cagcgtgaag ggaaggttca ctatcagcag ggacaacgcc  600
aagaacactc tgtatctgca gatgaactct ctgaagccag aggacacagc catgtactac  660
tgtgccctcg atctgatgag cacagtggtg cccggcttct gtggctttct gctgagcgct  720
ggcatggatt actggggcaa gggcactcaa gtgactgtct cgtctgctag ccaccatcac  780
catcaccac                                                          789
```

SEQ ID NO: 447                 moltype = DNA   length = 795
FEATURE                        Location/Qualifiers
source                         1..795
                               mol_type = other DNA
                               organism = synthetic construct
                               note = Description of Artificial Sequence: Synthetic
                                polynucleotide
SEQUENCE: 447
```
caagtgcagc tgcaagagag cggaggcggc agcgtgcaga ctggaggctc tctgagactg  60
agctgtgctg ccagcggcta cacttatctg aggggctgta tgggctggtt taggcaagcc  120
cccggcaagg agagagaggg cgtggccgtc atggatgtgg tgggcgatag gagaagctac  180
atcgacagcg tgaagggaag gttcacaatc tctaggaca atgccgccaa cagcgtctat  240
ctgcagatgg acaatctgaa gccagaggac acagccatgt actactgcac tgccggccct  300
aactgtgtgg gctggagaag cggactggat tactggggcc aaggcacaca agtgacagtc  360
tcgagcggcg gaggatccca agtgcagctg caagagtccg gaggaggcag cgtccaagcc  420
ggaggctctc tgaggctgag ctgtgctgcc agcggctaca cttacagcat gtactgcatg  480
ggctggttca gacaagcccc cggcaaggaa agagagggcg tgcccagat caatagcgat  540
ggcagcacaa gctacgccga cagcgtgaag ggaaggttca ctatctccaa ggacaacgcc  600
aagaacactc tgtatctgca gatgaactct ctgaagccag aggacactgc catgtactac  660
tgcgctgccg attctagggt gtacggcggc agctggtatg agaggctctg cggcccttac  720
acatacgagt acaactactg gggccaaggc acacaagtga ctgtctcgtc tgctagccac  780
catcaccatc accac                                                   795
```

SEQ ID NO: 448                 moltype = DNA   length = 804
FEATURE                        Location/Qualifiers
source                         1..804
                               mol_type = other DNA
                               organism = synthetic construct
                               note = Description of Artificial Sequence: Synthetic
                                polynucleotide
SEQUENCE: 448
```
caagtgcagc tgcaagagag cggaggcggc agcgtgcaga ctggaggctc tctgagactg  60
agctgtgctg ccagcggcta cacttatctg aggggctgta tgggctggtt taggcaagcc  120
cccggcaagg agagagaggg cgtggccgtc atggatgtgg tgggcgatag gagaagctac  180
atcgacagcg tgaagggaag gttcacaatc tctaggaca atgccgccaa cagcgtctat  240
ctgcagatgg acaatctgaa gccagaggac acagccatgt actactgcac tgccggccct  300
aactgtgtgg gctggagaag cggactggat tactggggcc aaggcacaca agtgacagtc  360
tcgagcggcg gaggatccca agtgcagctg caagagagcg gcggaggaag cgtgcaagcc  420
ggaggatctc tgagactgag ctgcgctgtg gccggctacg cctactccac atactgcatg  480
ggctggttta ggcaagcccc cggcaaagag agagagggcg tggctgctat cgatagcggc  540
ggcagcacaa gctacgccga tagcgtgaag ggaaggttca caatcagcag ggacaacgcc  600
aagaacacac tgtatctgag gatgaactct ctgaagccag aggacacagc catgtactac  660
tgtgctgctg tgcctcctcc tccagatggc ggcagctgtc tgtttctggg accagagatc  720
aaggtcagca aggccgattt taggtactgg ggccaaggca cacaagtgac agtctcgtct  780
gctagccacc atcaccatca ccac                                         804
```

SEQ ID NO: 449                 moltype = DNA   length = 783
FEATURE                        Location/Qualifiers
source                         1..783
                               mol_type = other DNA
                               organism = synthetic construct
                               note = Description of Artificial Sequence: Synthetic -continued

```
                        polynucleotide
SEQUENCE: 449
caagtgcagc tgcaagagag cggaggcggc agcgtgcaga ctggaggctc tctgagactg    60
agctgtgctg ccagcggcta cacttatctg aggggctgta tgggctggtt taggcaagcc   120
cccggcaagg agagagaggg cgtggccgtc atggatgtgg tgggcgatag agaagctac    180
atcgacagcg tgaagggaag gttcacaatc tctagggaca atgccgccaa cagcgtctat   240
ctgcagatgg acaatctgaa gccagaggac acagccatgt actactgcac tgccggccct   300
aactgtgtgg gctggagaag cggactggat tactggggcc aaggcacaca agtgacagtc   360
tcgagcggcg gaggatccca agtgcagctg caagagagcg gaggaggaag cgtccaagcc   420
ggaggctctc tgaggctgag ctgtacagtg tccggctaca cttacagctc caattgcatg   480
ggctggttta ggcaagcccc cggcaaggaa agagagggcg tggccactat ctacactggc   540
ggcggcaaca catactacgc cgatagcgtg aagggaaggt tcactatcag ccaagataac   600
gccaagaaca cagtgtatct gcagatgaac aatctgaagc cagaggacac tgccatgtac   660
tactgtgctc tgagccact  gtcaggggtg tacgcggca gctgcccaac tcctacattc   720
gactactggg gccaaggcac acaagtgact gtctcgtctg ctagccacca tcaccatcac   780
cac                                                                 783

SEQ ID NO: 450       moltype = DNA  length = 780
FEATURE              Location/Qualifiers
source               1..780
                     mol_type = other DNA
                     organism = synthetic construct
                     note = Description of Artificial Sequence: Synthetic
                        polynucleotide
SEQUENCE: 450
caagtgcagc tgcaagagag cggaggcggc agcgtgcaga ctggaggctc tctgagactg    60
agctgtgctg ccagcggcta cacttatctg aggggctgta tgggctggtt taggcaagcc   120
cccggcaagg agagagaggg cgtggccgtc atggatgtgg tgggcgatag agaagctac    180
atcgacagcg tgaagggaag gttcacaatc tctagggaca atgccgccaa cagcgtctat   240
ctgcagatgg acaatctgaa gccagaggac acagccatgt actactgcac tgccggccct   300
aactgtgtgg gctggagaag cggactggat tactggggcc aaggcacaca agtgacagtc   360
tcgagcggcg gaggatccca agtgcagctg caagagagcg gaggaggaag cgtccaagcc   420
ggaggctctc tgaggctgag ctgtggagcc agcggctaca cttacagcag ctactgtatg   480
ggctggttta ggcaagtgcc cggcaaggag agagagggcg tggccgtgat cgattccgat   540
ggcagcacaa gctacgctga cagcgtgaag ggaaggttca atcagcaa ggacaacggc     600
aagaacacac tctatctgca gatgaacagc ctcaagccag aggacacagc catgtactac   660
tgcgccgctg atctgggcca ctataggcct ccttgtggcg tgctgtatct gggcatggat   720
tactgggca agggcacaca agtgacagtc tcgtctgcta gccaccatca ccatcaccac   780

SEQ ID NO: 451       moltype = DNA  length = 783
FEATURE              Location/Qualifiers
source               1..783
                     mol_type = other DNA
                     organism = synthetic construct
                     note = Description of Artificial Sequence: Synthetic
                        polynucleotide
SEQUENCE: 451
caagtgcagc tgcaagagag cggaggcggc agcgtgcaga ctggaggctc tctgagactg    60
agctgtgctg ccagcggcta cacttatctg aggggctgta tgggctggtt taggcaagcc   120
cccggcaagg agagagaggg cgtggccgtc atggatgtgg tgggcgatag agaagctac    180
atcgacagcg tgaagggaag gttcacaatc tctagggaca atgccgccaa cagcgtctat   240
ctgcagatgg acaatctgaa gccagaggac acagccatgt actactgcac tgccggccct   300
aactgtgtgg gctggagaag cggactggat tactggggcc aaggcacaca agtgacagtc   360
tcgagcggcg gaggatccca agtgcagctg caagagagcg gaggaggaag cgtccaagcc   420
ggaggctctc tgagactgag ctgtgccgcc agcggctaca ccaactggga ctacgacatg   480
acttggtata ggcaagcccc cggcaaggag agggagttcg tgtccgccat ccacagcgac   540
ggcagcacta gatacgccga cagcgtgaag ggaaggttct tcatcagcca agataacgcc   600
aagaacacag tgtatctgca gatgaactcc ctcaagccag aggacactgc catgtactac   660
tgcaagacag acccactgca ctgcagagcc atggcggca gctggtatag cgtgagggcc   720
aactactggg gccaaggcac acaagtgaca gtctcgtctg ctagccacca tcaccatcac   780
cac                                                                 783

SEQ ID NO: 452       moltype = AA  length = 578
FEATURE              Location/Qualifiers
source               1..578
                     mol_type = protein
                     organism = Homo sapiens
SEQUENCE: 452
MLPCLVVLLA ALLSLRLGSD AHGTELPSPP SVWFEAEFFH HILHWTPIPN QSESTCYEVA    60
LLRYGIESWN SISNCSQTLS YDLTAVTLDL YHSNGYRARV RAVDGSRHSN WTVTNTRFSV   120
DEVTLTVGSV NLEIHNGFIL GKIQLPRPKM APANDTYESI FSHFREYEIA IRKVPGNFTF   180
THKKVKHENF SLLTSGEVGE FCVQVKPSVA SRSNKGMWSK EECISLTRQY FTVTNVIIFF   240
AFVLLLSGAL AYCLALQLYV RRRKKLPSVL LFKKPSPFIF ISQRPSPETQ DTIHPLDEEA   300
FLKVSPELKN LDLHGSTDSG FGSTKPSLQT EEPQFLLDP HPQADRTLGN REPPVLGDSC    360
SSGSSNSTDS GICLQEPSLS PSTGPTWEQQ VGSNSRGQDD SGIDLVQNSE GRAGDTQGGS   420
ALGHHSPPEP EVPGEEDPAA VAFQGYLRQT RCAEEKATKT GCLEEESPLT DGLGPKFGRC   480
LVDEAGLHPP ALAKGYLKQD PLEMTLASSG APTGQWNQPT EEWSLLALSS CSDLGISDWS   540
FAHDLAPLGC VAAPGLLGS FNSDLVTLPL ISSLQSSE                            578
```

```
SEQ ID NO: 453              moltype = AA   length = 214
FEATURE                     Location/Qualifiers
source                      1..214
                            mol_type = protein
                            organism = Homo sapiens
SEQUENCE: 453
HGTELPSPPS  VWFEAEFFHH  ILHWTPIPNQ  SESTCYEVAL  LRYGIESWNS  ISNCSQTLSY   60
DLTAVTLDLY  HSNGYRARVR  AVDGSRHSNW  TVTNTRFSVD  EVTLTVGSVN  LEIHNGFILG  120
KIQLPRPKMA  PANDTYESIF  SHFREYEIAI  RKVPGNFTFT  HKKVKHENFS  LLTSGEVGEF  180
CVQVKPSVAS  RSNKGMWSKE  ECISLTRQYF  TVTN                                214

SEQ ID NO: 454              moltype = AA   length = 575
FEATURE                     Location/Qualifiers
source                      1..575
                            mol_type = protein
                            organism = Mus musculus
SEQUENCE: 454
MLSRLLPFLV  TISSLSLEFI  AYGTELPSPS  YVWFEARFFQ  HILHWKPIPN  QSESTYYEVA   60
LKQYGNSTWN  DIHICRKAQA  LSCDLTTFTL  DLYHRSYGYR  ARVRAVDNSQ  YSNWTTTETR  120
FTVDEVILTV  DSVTLKAMDG  IIYGTIHPPR  PTITPAGDEY  EQVFKDLRVY  KISIRKFSEL  180
KNATKRVKQE  TFTLTVPIGV  RKFCVKVLPR  LESRINKAEW  SEEQCLLITT  EQYFTVTNLS  240
ILVISMLLFC  GILVCLVLQW  YIRHPGKLPT  VLVFKKPHDF  FPANPLCPET  PDAIHIVDLE  300
VFPKVSLELR  DSVLHGSTDS  GFGSGKPSLQ  TEESQFLLPG  SHPQIQGTLG  KEESPGLQAT  360
CGDNTDSGIC  LQEPGLHSSM  GPAWQQLGY   THQDQDDSDV  NLVQNSPGQP  KYTQDASALG  420
HVCLLEPKAP  EEKDQVMVTF  QGYQKQTRWK  AEAAGPAECL  DEEIPLTDAF  DPELGVHLQD  480
DLAWPPPALA  AGYLKQESQG  MASAPPGTPS  RQWNQLTEEW  SLLGVVSCED  LSIESWRFAH  540
KLDPLDCGAA  PGGLLDSLGS  NLVTLPLISS  LQVEE                               575

SEQ ID NO: 455              moltype = AA   length = 225
FEATURE                     Location/Qualifiers
source                      1..225
                            mol_type = protein
                            organism = Mus musculus
SEQUENCE: 455
LEFIAYGTEL  PSPSYVWFEA  RFFQHILHWK  PIPNQSESTY  YEVALKQYGN  STWNDIHICR   60
KAQALSCDLT  TFTLDLYHRS  YGYRARVRAV  DNSQYSNWTT  TETRFTVDEV  ILTVDSVTLK  120
AMDGIIYGTI  HPPRPTITPA  GDEYEQVFKD  LRVYKISIRK  FSELKNATKR  VKQETFTLTV  180
PIGVRKFCVK  VLPRLESRIN  KAEWSEEQCL  LITTEQYFTV  TNLSI                   225

SEQ ID NO: 456              moltype = AA   length = 325
FEATURE                     Location/Qualifiers
source                      1..325
                            mol_type = protein
                            organism = Homo sapiens
SEQUENCE: 456
MAWSLGSWLG  GCLLVSALGM  VPPPENVRMN  SVNFKNILQW  ESPAFAKGNL  TFTAQYLSYR   60
IFQDKCMNTT  LTECDFSSLS  KYGDHTLRVR  AEFADEHSDW  VNITFCPVDD  TIIGPPGMQV  120
EVLADSLHMR  FLAPKIENEY  ETWTMKNVYN  SWTYNVQYWK  NGTDEKFQIT  PQYDFEVLRN  180
LEPWTTYCVQ  VRGFLPDRNK  AGEWSEPVCE  QTTHDETVPS  WMVAVILMAS  VFMVCLALLG  240
CFALLWCVYK  KTKYAFSPRN  SLPQHLKEFL  GHPHHNTLLF  FSFPPLSDEND  VFDKLSVIAE 300
DSESGKQNPG  DSCSLGTPPG  QGPQS                                           325

SEQ ID NO: 457              moltype = AA   length = 201
FEATURE                     Location/Qualifiers
source                      1..201
                            mol_type = protein
                            organism = Homo sapiens
SEQUENCE: 457
MVPPPENVRM  NSVNFKNILQ  WESPAFAKGN  LTFTAQYLSY  RIFQDKCMNT  TLTECDFSSL   60
SKYGDHTLRV  RAEFADEHSD  WVNITFCPVD  DTIIGPPGMQ  VEVLADSLHM  RFLAPKIENE  120
YETWTMKNVY  NSWTYNVQYW  KNGTDEKFQI  TPQYDFEVLR  NLEPWTTYCV  QVRGFLPDRN  180
KAGEWSEPVC  EQTTHDETVP  S                                               201

SEQ ID NO: 458              moltype = AA   length = 348
FEATURE                     Location/Qualifiers
source                      1..348
                            mol_type = protein
                            organism = Mus musculus
SEQUENCE: 458
MAPCVAGWLG  GFLLVPALGI  PPPEKVRMNS  VNFKNILQWE  VPAFPKTNLT  FTAQYESYRS   60
FQDHCKRTAS  TQCDFSHLSK  YGDYTVRVRA  ELADEHSEWV  NVTFCPVEDT  IIGPPEMQIE  120
SLAESLHLRF  SAPQIENEPE  TWTLKNIYDS  WAYRVQYWKN  GTNEKFQVVS  PYDSEVLRNL  180
EPWTTYCIQV  QGFLLDQNRT  GEWSEPICER  TGNDEITPSW  IVAIILIVSV  LVVFLFLLGC  240
FVVLWLIYKK  TKHTFRSGTS  LPQHLKEFLG  HPHHSTFLLF  SFPPPEEAEV  FDKLSIISEE  300
SEGSKQSPED  NCASEPPSDP  GPRELESKDE  APSPPHDDPK  LLTSTSEV                348

SEQ ID NO: 459              moltype = AA   length = 201
FEATURE                     Location/Qualifiers
source                      1..201
```

```
                        mol_type = protein
                        organism = Mus musculus
SEQUENCE: 459
MIPPPEKVRM NSVNFKNILQ WEVPAFPKTN LTFTAQYESY RSFQDHCKRT ASTQCDFSHL    60
SKYGDYTVRV RAELADEHSE WVNVTFCPVE DTIIGPPEMQ IESLAESLHL RFSAPQIENE   120
PETWTLKNIY DSWAYRVQYW KNGTNEKFQV VSPYDSEVLR NLEPWTTYCI QVQGFLLDQN   180
RTGEWSEPIC ERTGNDEITP S                                            201

SEQ ID NO: 460          moltype = AA  length = 160
FEATURE                 Location/Qualifiers
source                  1..160
                        mol_type = protein
                        organism = Homo sapiens
SEQUENCE: 460
SPGQGTQSEN SCTHFPGNLP NMLRDLRDAF SRVKTFFQMK DQLDNLLLKE SLLEDFKGYL    60
GCQALSEMIQ FYLEEVMPQA ENQDPDIKAH VNSLGENLKT LRLRLRRCHR FLPCENKSKA   120
VEQVKNAFNK LQEKGIYKAM SEFDIFINYI EAYMTMKIRN                        160

SEQ ID NO: 461          moltype = AA  length = 160
FEATURE                 Location/Qualifiers
source                  1..160
                        mol_type = protein
                        organism = Mus musculus
SEQUENCE: 461
SRGQYSREDN NCTHFPVGQS HMLLELRTAF SQVKTFFQTK DQLDNILLTD SLMQDFKGYL    60
GCQALSEMIQ FYLVEVMPQA EKHGPEIKEH LNSLGEKLKT LRMRLRRCHR FLPCENKSKA   120
VEQVKSDFNK LQDQGVYKAM NEFDIFINCI EAYMMIKMKS                        160

SEQ ID NO: 462          moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 462
GGGGS                                                                5

SEQ ID NO: 463          moltype = AA  length = 6
FEATURE                 Location/Qualifiers
source                  1..6
                        mol_type = protein
                        organism = synthetic construct
                        note = Description of Artificial Sequence: Synthetic peptide
SEQUENCE: 463
GGGGGS                                                               6

SEQ ID NO: 464          moltype = AA  length = 4
FEATURE                 Location/Qualifiers
source                  1..4
                        mol_type = protein
                        organism = synthetic construct
                        note = Description of Artificial Sequence: Synthetic peptide
SEQUENCE: 464
GGSG                                                                 4

SEQ ID NO: 465          moltype = AA  length = 4
FEATURE                 Location/Qualifiers
source                  1..4
                        mol_type = protein
                        organism = synthetic construct
                        note = Description of Artificial Sequence: Synthetic peptide
SEQUENCE: 465
SGGG                                                                 4

SEQ ID NO: 466          moltype = AA  length = 4
FEATURE                 Location/Qualifiers
source                  1..4
                        mol_type = protein
                        organism = synthetic construct
                        note = Description of Artificial Sequence: Synthetic peptide
SEQUENCE: 466
GSGS                                                                 4

SEQ ID NO: 467          moltype = AA  length = 6
FEATURE                 Location/Qualifiers
source                  1..6
                        mol_type = protein
                        organism = synthetic construct
                        note = Description of Artificial Sequence: Synthetic peptide
```

-continued

```
SEQUENCE: 467
GSGSGS                                                                         6

SEQ ID NO: 468         moltype = AA   length = 10
FEATURE                Location/Qualifiers
source                 1..10
                       mol_type = protein
                       organism = synthetic construct
                       note = Description of Artificial Sequence: Synthetic peptide
SEQUENCE: 468
GSGSGSGSGS                                                                    10

SEQ ID NO: 469         moltype = AA   length = 12
FEATURE                Location/Qualifiers
source                 1..12
                       mol_type = protein
                       organism = synthetic construct
                       note = Description of Artificial Sequence: Synthetic peptide
SEQUENCE: 469
GSGSGSGSGS GS                                                                 12

SEQ ID NO: 470         moltype = AA   length = 6
FEATURE                Location/Qualifiers
source                 1..6
                       mol_type = protein
                       organism = synthetic construct
                       note = Description of Artificial Sequence: Synthetic peptide
SEQUENCE: 470
GGSGGS                                                                         6

SEQ ID NO: 471         moltype = AA   length = 9
FEATURE                Location/Qualifiers
source                 1..9
                       mol_type = protein
                       organism = synthetic construct
                       note = Description of Artificial Sequence: Synthetic peptide
SEQUENCE: 471
GGSGGSGGS                                                                      9

SEQ ID NO: 472         moltype = AA   length = 10
FEATURE                Location/Qualifiers
source                 1..10
                       mol_type = protein
                       organism = synthetic construct
                       note = Description of Artificial Sequence: Synthetic peptide
SEQUENCE: 472
GGSGGSGGSG                                                                    10

SEQ ID NO: 473         moltype = AA   length = 8
FEATURE                Location/Qualifiers
source                 1..8
                       mol_type = protein
                       organism = synthetic construct
                       note = Description of Artificial Sequence: Synthetic peptide
SEQUENCE: 473
GGSGGGSG                                                                       8

SEQ ID NO: 474         moltype = AA   length = 12
FEATURE                Location/Qualifiers
source                 1..12
                       mol_type = protein
                       organism = synthetic construct
                       note = Description of Artificial Sequence: Synthetic peptide
SEQUENCE: 474
GGSGGGSGGG SG                                                                 12

SEQ ID NO: 475         moltype = AA   length = 16
FEATURE                Location/Qualifiers
source                 1..16
                       mol_type = protein
                       organism = synthetic construct
                       note = Description of Artificial Sequence: Synthetic peptide
SEQUENCE: 475
GGSGGGSGGG SGGGSG                                                             16

SEQ ID NO: 476         moltype = AA   length = 20
FEATURE                Location/Qualifiers
source                 1..20
                       mol_type = protein
```

```
                                    organism = synthetic construct
                                    note = Description of Artificial Sequence: Synthetic peptide
SEQUENCE: 476
GGSGGGSGGG SGGGSGGGSG                                                    20

SEQ ID NO: 477          moltype = AA  length = 10
FEATURE                 Location/Qualifiers
source                  1..10
                        mol_type = protein
                        organism = synthetic construct
                        note = Description of Artificial Sequence: Synthetic peptide
SEQUENCE: 477
GGGGSGGGGS                                                               10

SEQ ID NO: 478          moltype = AA  length = 8
FEATURE                 Location/Qualifiers
source                  1..8
                        mol_type = protein
                        organism = synthetic construct
                        note = Description of Artificial Sequence: Synthetic peptide
SEQUENCE: 478
GGGSGGGS                                                                  8

SEQ ID NO: 479          moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 479
GGSGG                                                                     5

SEQ ID NO: 480          moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 480
GSGSG                                                                     5

SEQ ID NO: 481          moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 481
GSGGG                                                                     5

SEQ ID NO: 482          moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 482
GGGSG                                                                     5

SEQ ID NO: 483          moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 483
GSSSG                                                                     5

SEQ ID NO: 484          moltype = AA  length = 4
FEATURE                 Location/Qualifiers
source                  1..4
                        mol_type = protein
                        organism = synthetic construct
                        note = Description of Artificial Sequence: Synthetic peptide
SEQUENCE: 484
GGGS                                                                      4

SEQ ID NO: 485          moltype = AA  length = 232
FEATURE                 Location/Qualifiers
```

```
source                  1..232
                        mol_type = protein
                        organism = synthetic construct
                        note = Description of Artificial Sequence: Synthetic
                            polypeptide
SEQUENCE: 485
ASRVESKYGP PCPPCPAPEF LGGPSVFLFP PKPKDTLMIS RTPEVTCVVV DVSQEDPEVQ      60
FNWYVDGVEV HNAKTKPREE QFGSTYRVVS VLTVLHQDWL NGKEYKCKVS NKGLPSSIEK     120
TISKAKGQPR EPQVYTLPPS QEEMTKNQVS LTCLVKGFYP SDIAVEWESN GQPENNYKTT     180
PPVLDSDGSF FLYSRLTVDK SRWQEGNVFS CSVMHEALHN HYTQKSLSLS LG             232

SEQ ID NO: 486          moltype = AA  length = 264
FEATURE                 Location/Qualifiers
source                  1..264
                        mol_type = protein
                        organism = synthetic construct
                        note = Description of Artificial Sequence: Synthetic
                            polypeptide
SEQUENCE: 486
EVQLQESGGG SVQAGGSLRL SCAASGYSQC SYDMTWYRQA PGKEREFVSA IHSDGSTRYA      60
DSVKGRFFIS QDNAKNTVYL QMNSLKPEDT AMYYCKTDPL HCRAHGGSWY SVRANYWGQG     120
TQVTVSGGGS QVQLQESGGG SVEAGGSLRL SCAASGYTHS SYCMGWFRQA PGKEREGVAA     180
IDVDGSTTYA DSVKGRFTIS KDNAKNTLYL QMNSLKPEDT GMYYCAAEFA DCSSNYFLPP     240
GAVRYWGQGT QVTVSSASHH HHHH                                            264

SEQ ID NO: 487          moltype = AA  length = 265
FEATURE                 Location/Qualifiers
source                  1..265
                        mol_type = protein
                        organism = synthetic construct
                        note = Description of Artificial Sequence: Synthetic
                            polypeptide
SEQUENCE: 487
EVQLQESGGG SVQAGGSLRL SCAASGYSDC SYDMTWYRQA PGKEREFVSA IHSDGSTRYA      60
DSVKGRFFIS QDNAKNTVYL QMNSLKPEDT AMYYCKTDPL HCRAHGGSWY SVRANYWGQG     120
TQVTVSSGGG SQVQLQESGG GSVEAGGSLR LSCAASGYTH SSYCMGWFRQ APGKEREGVA     180
AIDVDGSTTY ADSVKGRFTI SKDNAKNTLY LQMNSLKPED TGMYYCAAEF ADCSSNYFLP     240
PGAVRYWGQG TQVTVSSASH HHHHH                                           265

SEQ ID NO: 488          moltype = AA  length = 265
FEATURE                 Location/Qualifiers
source                  1..265
                        mol_type = protein
                        organism = synthetic construct
                        note = Description of Artificial Sequence: Synthetic
                            polypeptide
SEQUENCE: 488
EVQLQESGGG SVQAGGSLRL SCAASGYSNC AYDMTWYRQA PGKEREFVSA IHSDGSTRYA      60
DSVKGRFFIS QDNAKNTVYL QMNSLKPEDT AMYYCKTDPL HCRAHGGSWY SVRANYWGQG     120
TQVTVSSGGG SQVQLQESGG GSVEAGGSLR LSCAASGYTH SSYCMGWFRQ APGKEREGVA     180
AIDVDGSTTY ADSVKGRFTI SKDNAKNTLY LQMNSLKPED TGMYYCAAEF ADCSSNYFLP     240
PGAVRYWGQG TQVTVSSASH HHHH                                            265

SEQ ID NO: 489          moltype = AA  length = 256
FEATURE                 Location/Qualifiers
source                  1..256
                        mol_type = protein
                        organism = synthetic construct
                        note = Description of Artificial Sequence: Synthetic
                            polypeptide
SEQUENCE: 489
EVQLQESGGG SVQAGGSLRL SCAASGYSNC SYDMTWYRQA PGKEREFVSA IHSDGSTRYA      60
DSVKGRFFIS QDNAKNTVYL QMNSLKPEDT AMYYCKTDPL HCRAHGGSWY SVRANYWGQG     120
TQVTVSSQVQ LQESGGGSVQ AGGSLRLSCA ASRYTNSYC MGWFRQAPGK EREGVATIDS      180
DGMTRYADSV KGRFTISKDN AKNTLYLQMN SLKPEDTAMY YCAADADCTI AAMTTNPLGQ     240
GTQVTVSSAS HHHHHH                                                     256

SEQ ID NO: 490          moltype = AA  length = 258
FEATURE                 Location/Qualifiers
source                  1..258
                        mol_type = protein
                        organism = synthetic construct
                        note = Description of Artificial Sequence: Synthetic
                            polypeptide
SEQUENCE: 490
EVQLQESGGG SVQAGGSLRL SCAASGYSNC SYDMTWYRQA PGKEREFVSA IHSDGSTRYA      60
DSVKGRFFIS QDNAKNTVYL QMNSLKPEDT AMYYCKTDPL HCRAHGGSWY SVRANYWGQG     120
TQVTVSSGSQ VQLQESGGGS VQAGGSLRLS CAASRYTYNS YCMGWFRQAP GKEREGVATI     180
DSDGMTRYAD SVKGRFTISK DNAKNTLYLQ MNSLKPEDTA MYYCAADADC TIAAMTTNPL     240
```

```
GQGTQVTVSS ASHHHHHH                                                      258

SEQ ID NO: 491           moltype = AA  length = 262
FEATURE                  Location/Qualifiers
source                   1..262
                         mol_type = protein
                         organism = synthetic construct
                         note = Description of Artificial Sequence: Synthetic
                           polypeptide
SEQUENCE: 491
EVQLQESGGG SVQAGGSLRL SCAASGYSNC SYDMTWYRQA PGKEREFVSA IHSDGSTRYA          60
DSVKGRFFIS QDNAKNTVYL QMNSLKPEDT AMYYCKTDPL HCRAHGGSWY SVRANYWGQG         120
TQVTVSSGGS GGGSVQVLQES GGGSVQAGGS LRLSCAASRY TYNSYCMGWF RQAPGKEREG        180
VATIDSDGMT RYADSVKGRF TISKDNAKNT LYLQMNSLKP EDTAMYYCAA DADCTIAAMT         240
TNPLGQGTQV TVSSASHHHH HH                                                 262

SEQ ID NO: 492           moltype = AA  length = 264
FEATURE                  Location/Qualifiers
source                   1..264
                         mol_type = protein
                         organism = synthetic construct
                         note = Description of Artificial Sequence: Synthetic
                           polypeptide
SEQUENCE: 492
EVQLQESGGG SVQAGGSLRL SCAASGYSNC SYDMTWYRQA PGKEREFVSA IHSDGSTRYA          60
DSVKGRFFIS QDNAKNTVYL QMNSLKPEDT AMYYCKTDPL HCRAHGGSWY SVRANYWGQG         120
TQVTVSSGGG SGGGSQVQLQ ESGGGSVQAG GSLRLSCAAS RYTYNSYCMG WFRQAPGKER         180
EGVATIDSDG MTRYADSVKG RFTISKDNAK NTLYLQMNSL KPEDTAMYYC AADADCTIAA         240
MTTNPLGQGT QVTVSSASHH HHHH                                               264

SEQ ID NO: 493           moltype = AA  length = 266
FEATURE                  Location/Qualifiers
source                   1..266
                         mol_type = protein
                         organism = synthetic construct
                         note = Description of Artificial Sequence: Synthetic
                           polypeptide
SEQUENCE: 493
EVQLQESGGG SVQAGGSLRL SCAASGYSNC SYDMTWYRQA PGKEREFVSA IHSDGSTRYA          60
DSVKGRFFIS QDNAKNTVYL QMNSLKPEDT AMYYCKTDPL HCRAHGGSWY SVRANYWGQG         120
TQVTVSSGGS GGGSGGQVQ LQESGGGSVQ AGGSLRLSCA ASRYTYNSYC MGWFRQAPGK          180
EREGVATIDS DGMTRYADSV KGRFTISKDN AKNTLYLQMN SLKPEDTAMY YCAADADCTI         240
AAMTTNPLGQ GTQVTVSSAS HHHHHH                                             266

SEQ ID NO: 494           moltype = AA  length = 261
FEATURE                  Location/Qualifiers
source                   1..261
                         mol_type = protein
                         organism = synthetic construct
                         note = Description of Artificial Sequence: Synthetic
                           polypeptide
SEQUENCE: 494
QVQLQESGGG SVQAGGSLRL SCAASGYSNC SYDMTWYRQA PGKEREFVSA IHSDGSTRYA          60
DSVKGRFFIS QDNAKNTVYL QMNSLKPEDT AMYYCKTDPL HCRAHGGSWY SVRANYWGQG         120
TQVTVSSGSQ VQLQESGGGS VQAGGSLRLS CAASGYSYSS YCMGWFRQAP GKEREGVATI         180
DSDGMTRYAD SVKGRFTISK DNAKNTLYLQ MNSLKPEDTA MYYCAAPLYD CDSGAVGRNP         240
PYWGQGTQVT VSSASHHHHH H                                                  261

SEQ ID NO: 495           moltype = AA  length = 265
FEATURE                  Location/Qualifiers
source                   1..265
                         mol_type = protein
                         organism = synthetic construct
                         note = Description of Artificial Sequence: Synthetic
                           polypeptide
SEQUENCE: 495
QVQLQESGGG SVQAGGSLRL SCAASGYSNC SYDMTWYRQA PGKEREFVSA IHSDGSTRYA          60
DSVKGRFFIS QDNAKNTVYL QMNSLKPEDT AMYYCKTDPL HCRAHGGSWY SVRANYWGQG         120
TQVTVSSGGS GGSQVQLQES GGGSVQAGGS LRLSCAASGY SYSSYCMGWF RQAPGKEREG         180
VATIDSDGMT RYADSVKGRF TISKDNAKNT LYLQMNSLKP EDTAMYYCAA PLYDCDSGAV         240
GRNPPYWGQG TQVTVSSASH HHHH                                               265

SEQ ID NO: 496           moltype = AA  length = 267
FEATURE                  Location/Qualifiers
source                   1..267
                         mol_type = protein
                         organism = synthetic construct
                         note = Description of Artificial Sequence: Synthetic
                           polypeptide
```

-continued

```
SEQUENCE: 496
QVQLQESGGG SVQAGGSLRL SCAASGYSNC SYDMTWYRQA PGKEREFVSA IHSDGSTRYA    60
DSVKGRFFIS QDNAKNTVYL QMNSLKPEDT AMYYCKTDPL HCRAHGGSWY SVRANYWGQG   120
TQVTVSSGGG SGGGSQVQLQ ESGGGSVQAG GSLRLSCAAS GYSYSSYCMG WFRQAPGKER   180
EGVATIDSDG MTRYADSVKG RFTISKDNAK NTLYLQMNSL KPEDTAMYYC AAPLYDCDSG   240
AVGRNPPYWG QGTQVTVSSA SHHHHHH                                       267

SEQ ID NO: 497          moltype = AA  length = 269
FEATURE                 Location/Qualifiers
source                  1..269
                        mol_type = protein
                        organism = synthetic construct
                        note = Description of Artificial Sequence: Synthetic
                          polypeptide
SEQUENCE: 497
QVQLQESGGG SVQAGGSLRL SCAASGYSNC SYDMTWYRQA PGKEREFVSA IHSDGSTRYA    60
DSVKGRFFIS QDNAKNTVYL QMNSLKPEDT AMYYCKTDPL HCRAHGGSWY SVRANYWGQG   120
TQVTVSSGGG GGGGSGQVQ LQESGGGSVQ AGGSLRLSCA ASGYSYSSYC MGWFRQAPGK   180
EREGVATIDS DGMTRYADSV KGRFTISKDN AKNTLYLQMN SLKPEDTAMY YCAAPLYDCD   240
SGAVGRNPPY WGQGTQVTVS SASHHHHHH                                     269

SEQ ID NO: 498          moltype = AA  length = 263
FEATURE                 Location/Qualifiers
source                  1..263
                        mol_type = protein
                        organism = synthetic construct
                        note = Description of Artificial Sequence: Synthetic
                          polypeptide
SEQUENCE: 498
QVQLQESGGG SVQAGGSLRL SCAASGYSNC SYDMTWYRQA PGKEREFVSA IHSDGSTRYA    60
DSVKGRFFIS QDNAKNTVYL QMNSLKPEDT AMYYCKTDPL HCRAHGGSWY SVRANYWGQG   120
TQVTVSSGSQ VQLQESGGGS VEAGGSLRLS CAASGYTHSS YCMGWFRQAP GKEREGVAAI   180
DVDGSTTYAD SVKGRFTISK DNAKNTLYLQ MNSLKPEDTG MYYCAAEFAD CSSNYFLPPG   240
AVRYWGQGTQ VTVSSASHHH HHH                                           263

SEQ ID NO: 499          moltype = AA  length = 484
FEATURE                 Location/Qualifiers
source                  1..484
                        mol_type = protein
                        organism = synthetic construct
                        note = Description of Artificial Sequence: Synthetic
                          polypeptide
SEQUENCE: 499
QVQLQESGGG SVQAGGSLRL SCAASGYSNC SYDMTWYRQA PGKEREFVSA IHSDGSTRYA    60
DSVKGRFFIS QDNAKNTVYL QMNSLKPEDT AMYYCKTDPL HCRAHGGSWY SVRANYWGQG   120
TQVTVSSGGG SQVQLQESGG GSVQAGGSLR LSCAASRYTY NSYCMGWFRQ APGKEREGVA   180
TIDSDGMTRY ADSVKGRFTI SKDNAKNTLY LQMNSLKPED TAMYYCAADA DCTIAAMTTN   240
PLGQGTQVTV SSASRVESKY GPPCPPCPAP EFLGGPSVFL FPPKPKDTLM ISRTPEVTCV   300
VVDVSQEDPE VQFNWYVDGV EVHNAKTKPR EEQFGSTYRV VSVLTVLHQD WLNGKEYKCK   360
VSNKGLPSSI EKTISKAKGQ PREPQVYTLP PSQEEMTKNQ VSLTCLVKGF YPSDIAVEWE   420
SNGQPENNYK TTPPVLDSDG SFFLYSRLTV DKSRWQEGNV FSCSVMHEAL HNHYTQKSLS   480
LSLG                                                                484

SEQ ID NO: 500          moltype = AA  length = 487
FEATURE                 Location/Qualifiers
source                  1..487
                        mol_type = protein
                        organism = synthetic construct
                        note = Description of Artificial Sequence: Synthetic
                          polypeptide
SEQUENCE: 500
QVQLQESGGG SVQAGGSLRL SCAASGYSNC SYDMTWYRQA PGKEREFVSA IHSDGSTRYA    60
DSVKGRFFIS QDNAKNTVYL QMNSLKPEDT AMYYCKTDPL HCRAHGGSWY SVRANYWGQG   120
TQVTVSSGGG SQVQLQESGG GSVQAGGSLR LSCAASGYSY SSYCMGWFRQ APGKEREGVA   180
TIDSDGMTRY ADSVKGRFTI SKDNAKNTLY LQMNSLKPED TAMYYCAAPL YDCDSGAVGR   240
NPPYWGQGTQ VTVSSASRVE SKYGPPCPPC PAPEFLGGPS VFLFPPKPKD TLMISRTPEV   300
TCVVVDVSQE DPEVQFNWYV DGVEVHNAKT KPREEQFGST YRVVSVLTVL HQDWLNGKEY   360
KCKVSNKGLP SSIEKTISKA KGQPREPQVY TLPPSQEEMT KNQVSLTCLV KGFYPSDIAV   420
EWESNGQPEN NYKTTPPVLD SDGSFFLYSR LTVDKSRWQE GNVFSCSVMH EALHNHYTQK   480
SLSLSLG                                                             487

SEQ ID NO: 501          moltype = AA  length = 487
FEATURE                 Location/Qualifiers
source                  1..487
                        mol_type = protein
                        organism = synthetic construct
                        note = Description of Artificial Sequence: Synthetic
                          polypeptide
SEQUENCE: 501
```

```
QVQLQESGGG SVQAGGSLRL SCAASGYSNC SYDMTWYRQA PGKEREFVSA IHSDGSTRYA   60
DSVKGRFFIS QDNAKNTVYL QMNSLKPEDT AMYYCKTDPL HCRAHGGSWY SVRANYWGQG  120
TQVTVSSGSQ VQLQESGGGS VEAGGSLRLS CAASGYTHSS YCMGWFRQAP GKEREGVAAI  180
DVDGSTTYAD SVKGRFTISK DNAKNTLYLQ MNSLKPEDTG MYYCAAEFAD CSSNYFLPPG  240
AVRYWGQGTQ VTVSSASRVE SKYGPPCPPC PAPEFLGGPS VFLFPPKPKD TLMISRTPEV  300
TCVVVDVSQE DPEVQFNWYV DGVEVHNAKT KPREEQFGST YRVVSVLTVL HQDWLNGKEY  360
KCKVSNKGLP SSIEKTISKA KGQPREPQVY TLPPSQEEMT KNQVSLTCLV KGFYPSDIAV  420
EWESNGQPEN NYKTTPPVLD SDGSFFLYSR LTVDKSRWQE GNVFSCSVMH EALHNHYTQK  480
SLSLSLG                                                           487

SEQ ID NO: 502           moltype = AA  length = 230
FEATURE                  Location/Qualifiers
source                   1..230
                         mol_type = protein
                         organism = synthetic construct
                         note = Description of Artificial Sequence: Synthetic
                           polypeptide
SEQUENCE: 502
RVESKYGPPC PPCPAPEFLG GPSVFLFPPK PKDTLMISRT PEVTCVVVDV SQEDPEVQFN   60
WYVDGVEVHN AKTKPREEQF GSTYRVVSVL TVLHQDWLNG KEYKCKVSNK GLPSSIEKTI  120
SKAKGQPREP QVYTLPPSQE EMTKNQVSLT CLVKGFYPSD IAVEWESNGQ PENNYKTTPP  180
VLDSDGSFFL YSRLTVDKSR WQEGNVFSCS VMHEALHNHY TQKSLSLSLG             230

SEQ ID NO: 503           moltype = AA  length = 127
FEATURE                  Location/Qualifiers
source                   1..127
                         mol_type = protein
                         organism = synthetic construct
                         note = Description of Artificial Sequence: Synthetic
                           polypeptide
SEQUENCE: 503
EVQLLESGGG LVQPGGSLRL SCAASGYTQC SYDMTWVRQA PGKGLEWVSA IHSDGSTRYA   60
DSVKGRFTIS RDNSKNTLYL QMNSLRAEDT AVYYCKTDPL HCRAHGGSWY SVRANYWGQG  120
TLVTVSS                                                           127

SEQ ID NO: 504           moltype = AA  length = 127
FEATURE                  Location/Qualifiers
source                   1..127
                         mol_type = protein
                         organism = synthetic construct
                         note = Description of Artificial Sequence: Synthetic
                           polypeptide
SEQUENCE: 504
EVQLLESGGG LVQPGGSLRL SCAASGYTQC SYDMTWVRQA PGKGLEFVSA IHSDGSTRYA   60
DSVKGRFTIS RDNSKNTLYL QMNSLRAEDT AVYYCKTDPL HCRAHGGSWY SVRANYWGQG  120
TLVTVSS                                                           127

SEQ ID NO: 505           moltype = AA  length = 127
FEATURE                  Location/Qualifiers
source                   1..127
                         mol_type = protein
                         organism = synthetic construct
                         note = Description of Artificial Sequence: Synthetic
                           polypeptide
SEQUENCE: 505
EVQLVESGGG LVQPGGSLRL SCAASGYTQC SYDMTWVRQA PGKGLEWVSA IHSDGSTRYA   60
DSVKGRFFIS RDNSKNTLYL QMNSLRAEDT AVYYCKTDPL HCRAHGGSWY SVRANYWGQG  120
TLVTVSS                                                           127

SEQ ID NO: 506           moltype = AA  length = 127
FEATURE                  Location/Qualifiers
source                   1..127
                         mol_type = protein
                         organism = synthetic construct
                         note = Description of Artificial Sequence: Synthetic
                           polypeptide
SEQUENCE: 506
EVQLVESGGG LVQPGGSLRL SCAASGYTQC SYDMTWVRQA PGKGLEFVSA IHSDGSTRYA   60
DSVKGRFFIS RDNSKNTLYL QMNSLRAEDT AVYYCKTDPL HCRAHGGSWY SVRANYWGQG  120
TLVTVSS                                                           127

SEQ ID NO: 507           moltype = AA  length = 126
FEATURE                  Location/Qualifiers
source                   1..126
                         mol_type = protein
                         organism = synthetic construct
                         note = Description of Artificial Sequence: Synthetic
                           polypeptide
SEQUENCE: 507
```

```
EVQLLESGGG LVQPGGSLRL SCAASGYTHS SYCMGWVRQA PGKGLEWVSA IDVDGSTTYA   60
DSVKGRFTIS RDNSKNTLYL QMNSLRAEDT AVYYCAAEFA DCSSNYFLPP GAVRYWGQGT  120
LVTVSS                                                            126

SEQ ID NO: 508            moltype = AA  length = 126
FEATURE                   Location/Qualifiers
source                    1..126
                          mol_type = protein
                          organism = synthetic construct
                          note = Description of Artificial Sequence: Synthetic
                             polypeptide
SEQUENCE: 508
EVQLLESGGG LVQPGGSLRL SCAASGYTHS SYCMGWVRQA PGKGLEWVSA IDVDGSTTYA   60
DSVKGRFTIS RDNSKNTLYL QMNSLRAEDT AVYYCAAEFA DCSSNYFLPP GAVRYWGQGT  120
LVTVSS                                                            126

SEQ ID NO: 509            moltype = AA  length = 126
FEATURE                   Location/Qualifiers
source                    1..126
                          mol_type = protein
                          organism = synthetic construct
                          note = Description of Artificial Sequence: Synthetic
                             polypeptide
SEQUENCE: 509
EVQLVESGGG LVQPGGSLRL SCAASGYTHS SYCMGWVRQA PGKGLEWVSA IDVDGSTTYA   60
DSVKGRFTIS RDNSKNTLYL QMNSLRAEDT AVYYCAAEFA DCSSNYFLPP GAVRYWGQGT  120
LVTVSS                                                            126

SEQ ID NO: 510            moltype = AA  length = 126
FEATURE                   Location/Qualifiers
source                    1..126
                          mol_type = protein
                          organism = synthetic construct
                          note = Description of Artificial Sequence: Synthetic
                             polypeptide
SEQUENCE: 510
EVQLVESGGG LVQPGGSLRL SCAASGYTHS SYCMGWVRQA PGKGLEGVSA IDVDGSTTYA   60
DSVKGRFTIS RDNSKNTLYL QMNSLRAEDT AVYYCAAEFA DCSSNYFLPP GAVRYWGQGT  120
LVTVSS                                                            126

SEQ ID NO: 511            moltype = AA  length = 127
FEATURE                   Location/Qualifiers
source                    1..127
                          mol_type = protein
                          organism = synthetic construct
                          note = Description of Artificial Sequence: Synthetic
                             polypeptide
SEQUENCE: 511
EVQLVESGGG LVQPGGSLRL SCAASGYTQC SYDMTWVRQA PGKGREFVSA IHSDGSTRYA   60
DSVKGRFFIS RDNSKNTLYL QMNSLRAEDT AVYYCKTDPL HCRAHGGSWY SVRANYWGQG  120
TLVTVSS                                                           127

SEQ ID NO: 512            moltype = AA  length = 127
FEATURE                   Location/Qualifiers
source                    1..127
                          mol_type = protein
                          organism = synthetic construct
                          note = Description of Artificial Sequence: Synthetic
                             polypeptide
SEQUENCE: 512
EVQLQESGGG SVQAGGSLRL SCAASGYSQC SYDMTWYRQA PGKEREFVSA IHSDGSTRYA   60
DSVKGRFFIS QDNAKNTVYL QMNSLKPEDT AMYYCKTDPL HCRAHGGSWY SVRANYWGQG  120
TQVTVSS                                                           127

SEQ ID NO: 513            moltype = AA  length = 265
FEATURE                   Location/Qualifiers
source                    1..265
                          mol_type = protein
                          organism = synthetic construct
                          note = Description of Artificial Sequence: Synthetic
                             polypeptide
SEQUENCE: 513
EVQLVESGGG LVKPGGSLRL SCAASGYSNC AYDMTWYRQA PGKGLEWVSA IHSDGSTRYA   60
DSVKGRFFIS RDNAKNSLYL QMNSLRAEDT AVYYCKTDPL HCRAHGGSWY SVRANYWGQG  120
TLVTVSSGGG SEVQLVESGG GLVQPGGSLR LSCAASGYTH SSYCMGWVRQ APGKGLEGVS  180
AIDVDGSTTY ADSVKGRFTI SRDNSKNTLY LQMNSLRAED TAVYYCAAEF ADCSSNYFLP  240
PGAVRYWGQG TLVTVSSASH HHHHH                                       265

SEQ ID NO: 514            moltype = AA  length = 265
```

```
FEATURE                 Location/Qualifiers
source                  1..265
                        mol_type = protein
                        organism = synthetic construct
                        note = Description of Artificial Sequence: Synthetic
                          polypeptide
SEQUENCE: 514
EVQLVESGGG LVQPGGSLRL SCAASGYSNC AYDMTWYRQA PGKGLEWVSA IHSDGSTRYA    60
DSVKGRFFIS RDNSKNTLYL QMNSLRAEDT AVYYCKTDPL HCRAHGGSWY SVRANYWGQG   120
TLVTVSSGGG SEVQLVESGG GLVQPGGSLR LSCAASGYTH SSYCMGWVRQ APGKGLEGVS   180
AIDVDGSTTY ADSVKGRFTI SRDNSKNTLY LQMNSLRAED TAVYYCAAEF ADCSSNYFLP   240
PGAVRYWGQG TLVTVSSASH HHHHH                                         265

SEQ ID NO: 515          moltype = AA   length = 265
FEATURE                 Location/Qualifiers
source                  1..265
                        mol_type = protein
                        organism = synthetic construct
                        note = Description of Artificial Sequence: Synthetic
                          polypeptide
SEQUENCE: 515
EVQLLESGGG LVQPGGSLRL SCAASGYSNC AYDMTWYRQA PGKGLEWVSA IHSDGSTRYA    60
DSVKGRFFIS RDNSKNTLYL QMNSLRAEDT AVYYCKTDPL HCRAHGGSWY SVRANYWGQG   120
TLVTVSSGGG SEVQLVESGG GLVQPGGSLR LSCAASGYTH SSYCMGWVRQ APGKGLEGVS   180
AIDVDGSTTY ADSVKGRFTI SRDNSKNTLY LQMNSLRAED TAVYYCAAEF ADCSSNYFLP   240
PGAVRYWGQG TLVTVSSASH HHHHH                                         265

SEQ ID NO: 516          moltype = AA   length = 265
FEATURE                 Location/Qualifiers
source                  1..265
                        mol_type = protein
                        organism = synthetic construct
                        note = Description of Artificial Sequence: Synthetic
                          polypeptide
SEQUENCE: 516
EVQLVESGGG LVKPGGSLRL SCAASGYSNC AYDMTWYRQA PGKGLEFVSA IHSDGSTRYA    60
DSVKGRFFIS RDNAKNSLYL QMNSLRAEDT AVYYCKTDPL HCRAHGGSWY SVRANYWGQG   120
TLVTVSSGGG SEVQLVESGG GLVQPGGSLR LSCAASGYTH SSYCMGWVRQ APGKGLEGVS   180
AIDVDGSTTY ADSVKGRFTI SRDNSKNTLY LQMNSLRAED TAVYYCAAEF ADCSSNYFLP   240
PGAVRYWGQG TLVTVSSASH HHHHH                                         265

SEQ ID NO: 517          moltype = AA   length = 265
FEATURE                 Location/Qualifiers
source                  1..265
                        mol_type = protein
                        organism = synthetic construct
                        note = Description of Artificial Sequence: Synthetic
                          polypeptide
SEQUENCE: 517
EVQLVESGGG LVQPGGSLRL SCAASGYSNC AYDMTWYRQA PGKGLEFVSA IHSDGSTRYA    60
DSVKGRFFIS RDNSKNTLYL QMNSLRAEDT AVYYCKTDPL HCRAHGGSWY SVRANYWGQG   120
TLVTVSSGGG SEVQLVESGG GLVQPGGSLR LSCAASGYTH SSYCMGWVRQ APGKGLEGVS   180
AIDVDGSTTY ADSVKGRFTI SRDNSKNTLY LQMNSLRAED TAVYYCAAEF ADCSSNYFLP   240
PGAVRYWGQG TLVTVSSASH HHHHH                                         265

SEQ ID NO: 518          moltype = AA   length = 265
FEATURE                 Location/Qualifiers
source                  1..265
                        mol_type = protein
                        organism = synthetic construct
                        note = Description of Artificial Sequence: Synthetic
                          polypeptide
SEQUENCE: 518
EVQLLESGGG LVQPGGSLRL SCAASGYSNC AYDMTWYRQA PGKGLEFVSA IHSDGSTRYA    60
DSVKGRFFIS RDNSKNTLYL QMNSLRAEDT AVYYCKTDPL HCRAHGGSWY SVRANYWGQG   120
TLVTVSSGGG SEVQLVESGG GLVQPGGSLR LSCAASGYTH SSYCMGWVRQ APGKGLEGVS   180
AIDVDGSTTY ADSVKGRFTI SRDNSKNTLY LQMNSLRAED TAVYYCAAEF ADCSSNYFLP   240
PGAVRYWGQG TLVTVSSASH HHHHH                                         265

SEQ ID NO: 519          moltype = AA   length = 265
FEATURE                 Location/Qualifiers
source                  1..265
                        mol_type = protein
                        organism = synthetic construct
                        note = Description of Artificial Sequence: Synthetic
                          polypeptide
SEQUENCE: 519
EVQLVESGGG LVKPGGSLRL SCAASGYSNC AYDMTWYRQA PGKGREWVSA IHSDGSTRYA    60
DSVKGRFFIS RDNAKNSLYL QMNSLRAEDT AVYYCKTDPL HCRAHGGSWY SVRANYWGQG   120
```

```
TLVTVSSGGG SEVQLVESGG GLVQPGGSLR LSCAASGYTH SSYCMGWVRQ APGKGLEGVS    180
AIDVDGSTTY ADSVKGRFTI SRDNSKNTLY LQMNSLRAED TAVYYCAAEF ADCSSNYFLP    240
PGAVRYWGQG TLVTVSSASH HHHHH                                          265

SEQ ID NO: 520         moltype = AA  length = 265
FEATURE                Location/Qualifiers
source                 1..265
                       mol_type = protein
                       organism = synthetic construct
                       note = Description of Artificial Sequence: Synthetic
                         polypeptide
SEQUENCE: 520
EVQLVESGGG LVQPGGSLRL SCAASGYSNC AYDMTWYRQA PGKGREWVSA IHSDGSTRYA    60
DSVKGRFFIS RDNSKNTLYL QMNSLRAEDT AVYYCKTDPL HCRAHGGSWY SVRANYWGQG    120
TLVTVSSGGG SEVQLVESGG GLVQPGGSLR LSCAASGYTH SSYCMGWVRQ APGKGLEGVS    180
AIDVDGSTTY ADSVKGRFTI SRDNSKNTLY LQMNSLRAED TAVYYCAAEF ADCSSNYFLP    240
PGAVRYWGQG TLVTVSSASH HHHHH                                          265

SEQ ID NO: 521         moltype = AA  length = 265
FEATURE                Location/Qualifiers
source                 1..265
                       mol_type = protein
                       organism = synthetic construct
                       note = Description of Artificial Sequence: Synthetic
                         polypeptide
SEQUENCE: 521
EVQLLESGGG LVQPGGSLRL SCAASGYSNC AYDMTWYRQA PGKGREWVSA IHSDGSTRYA    60
DSVKGRFFIS RDNSKNTLYL QMNSLRAEDT AVYYCKTDPL HCRAHGGSWY SVRANYWGQG    120
TLVTVSSGGG SEVQLVESGG GLVQPGGSLR LSCAASGYTH SSYCMGWVRQ APGKGLEGVS    180
AIDVDGSTTY ADSVKGRFTI SRDNSKNTLY LQMNSLRAED TAVYYCAAEF ADCSSNYFLP    240
PGAVRYWGQG TLVTVSSASH HHHHH                                          265

SEQ ID NO: 522         moltype = AA  length = 265
FEATURE                Location/Qualifiers
source                 1..265
                       mol_type = protein
                       organism = synthetic construct
                       note = Description of Artificial Sequence: Synthetic
                         polypeptide
SEQUENCE: 522
EVQLVESGGG LVKPGGSLRL SCAASGYSNC AYDMTWYRQA PGKELEWVSA IHSDGSTRYA    60
DSVKGRFFIS RDNAKNSLYL QMNSLRAEDT AVYYCKTDPL HCRAHGGSWY SVRANYWGQG    120
TLVTVSSGGG SEVQLVESGG GLVQPGGSLR LSCAASGYTH SSYCMGWVRQ APGKGLEGVS    180
AIDVDGSTTY ADSVKGRFTI SRDNSKNTLY LQMNSLRAED TAVYYCAAEF ADCSSNYFLP    240
PGAVRYWGQG TLVTVSSASH HHHHH                                          265

SEQ ID NO: 523         moltype = AA  length = 265
FEATURE                Location/Qualifiers
source                 1..265
                       mol_type = protein
                       organism = synthetic construct
                       note = Description of Artificial Sequence: Synthetic
                         polypeptide
SEQUENCE: 523
EVQLVESGGG LVQPGGSLRL SCAASGYSNC AYDMTWYRQA PGKELEWVSA IHSDGSTRYA    60
DSVKGRFFIS RDNSKNTLYL QMNSLRAEDT AVYYCKTDPL HCRAHGGSWY SVRANYWGQG    120
TLVTVSSGGG SEVQLVESGG GLVQPGGSLR LSCAASGYTH SSYCMGWVRQ APGKGLEGVS    180
AIDVDGSTTY ADSVKGRFTI SRDNSKNTLY LQMNSLRAED TAVYYCAAEF ADCSSNYFLP    240
PGAVRYWGQG TLVTVSSASH HHHHH                                          265

SEQ ID NO: 524         moltype = AA  length = 265
FEATURE                Location/Qualifiers
source                 1..265
                       mol_type = protein
                       organism = synthetic construct
                       note = Description of Artificial Sequence: Synthetic
                         polypeptide
SEQUENCE: 524
EVQLVESGGG LVKPGGSLRL SCAASGYSNC AYDMTWYRQA PGKEREFVSA IHSDGSTRYA    60
DSVKGRFFIS RDNAKNSLYL QMNSLRAEDT AVYYCKTDPL HCRAHGGSWY SVRANYWGQG    120
TLVTVSSGGG SEVQLVESGG GLVQPGGSLR LSCAASGYTH SSYCMGWVRQ APGKGLEGVS    180
AIDVDGSTTY ADSVKGRFTI SRDNSKNTLY LQMNSLRAED TAVYYCAAEF ADCSSNYFLP    240
PGAVRYWGQG TLVTVSSASH HHHHH                                          265

SEQ ID NO: 525         moltype = AA  length = 265
FEATURE                Location/Qualifiers
source                 1..265
                       mol_type = protein
                       organism = synthetic construct
```

-continued

```
                        note = Description of Artificial Sequence: Synthetic
                        polypeptide
SEQUENCE: 525
EVQLVESGGG LVQPGGSLRL SCAASGYSNC AYDMTWYRQA PGKEREFVSA IHSDGSTRYA      60
DSVKGRFFIS RDNSKNTLYL QMNSLRAEDT AVYYCKTDPL HCRAHGGSWY SVRANYWGQG     120
TLVTVSSGGG SEVQLVESGG GLVQPGGSLR LSCAASGYTH SSYCMGWVRQ APGKGLEGVS     180
AIDVDGSTTY ADSVKGRFTI SRDNSKNTLY LQMNSLRAED TAVYYCAAEF ADCSSNYFLP     240
PGAVRYWGQG TLVTVSSASH HHHHH                                          265

SEQ ID NO: 526          moltype = AA  length = 265
FEATURE                 Location/Qualifiers
source                  1..265
                        mol_type = protein
                        organism = synthetic construct
                        note = Description of Artificial Sequence: Synthetic
                        polypeptide
SEQUENCE: 526
EVQLLESGGG LVQPGGSLRL SCAASGYSNC AYDMTWYRQA PGKEREFVSA IHSDGSTRYA      60
DSVKGRFFIS RDNSKNTLYL QMNSLRAEDT AVYYCKTDPL HCRAHGGSWY SVRANYWGQG     120
TLVTVSSGGG SEVQLVESGG GLVQPGGSLR LSCAASGYTH SSYCMGWVRQ APGKGLEGVS     180
AIDVDGSTTY ADSVKGRFTI SRDNSKNTLY LQMNSLRAED TAVYYCAAEF ADCSSNYFLP     240
PGAVRYWGQG TLVTVSSASH HHHHH                                          265

SEQ ID NO: 527          moltype = AA  length = 265
FEATURE                 Location/Qualifiers
source                  1..265
                        mol_type = protein
                        organism = synthetic construct
                        note = Description of Artificial Sequence: Synthetic
                        polypeptide
SEQUENCE: 527
EVQLVESGGG LVQPGGSLRL SCAASGYTQC SYDMTWVRQA PGKGLEFVSA IHSDGSTRYA      60
DSVKGRFFIS RDNSKNTLYL QMNSLRAEDT AVYYCKTDPL HCRAHGGSWY SVRANYWGQG     120
TLVTVSSGGG SEVQLVESGG GLVQPGGSLR LSCAASGYTH SSYCMGWVRQ APGKGLEWVS     180
AIDVDGSTTY ADSVKGRFTI SRDNSKNTLY LQMNSLRAED TAVYYCAAEF ADCSSNYFLP     240
PGAVRYWGQG TLVTVSSASH HHHHH                                          265

SEQ ID NO: 528          moltype = AA  length = 265
FEATURE                 Location/Qualifiers
source                  1..265
                        mol_type = protein
                        organism = synthetic construct
                        note = Description of Artificial Sequence: Synthetic
                        polypeptide
SEQUENCE: 528
EVQLVESGGG LVQPGGSLRL SCAASGYTQC SYDMTWVRQA PGKGLEFVSA IHSDGSTRYA      60
DSVKGRFFIS RDNSKNTLYL QMNSLRAEDT AVYYCKTDPL HCRAHGGSWY SVRANYWGQG     120
TLVTVSSGGG SEVQLVESGG GLVQPGGSLR LSCAASGYTH SSYCMGWVRQ APGKGLEGVS     180
AIDVDGSTTY ADSVKGRFTI SRDNSKNTLY LQMNSLRAED TAVYYCAAEF ADCSSNYFLP     240
PGAVRYWGQG TLVTVSSASH HHHHH                                          265

SEQ ID NO: 529          moltype = AA  length = 265
FEATURE                 Location/Qualifiers
source                  1..265
                        mol_type = protein
                        organism = synthetic construct
                        note = Description of Artificial Sequence: Synthetic
                        polypeptide
SEQUENCE: 529
EVQLVESGGG LVQPGGSLRL SCAASGYTQC SYDMTWYRQA PGKGLEFVSA IHSDGSTRYA      60
DSVKGRFFIS RDNSKNTLYL QMNSLRAEDT AVYYCKTDPL HCRAHGGSWY SVRANYWGQG     120
TLVTVSSGGG SEVQLVESGG GLVQPGGSLR LSCAASGYTH SSYCMGWVRQ APGKGLEWVS     180
AIDVDGSTTY ADSVKGRFTI SRDNSKNTLY LQMNSLRAED TAVYYCAAEF ADCSSNYFLP     240
PGAVRYWGQG TLVTVSSASH HHHHH                                          265

SEQ ID NO: 530          moltype = AA  length = 265
FEATURE                 Location/Qualifiers
source                  1..265
                        mol_type = protein
                        organism = synthetic construct
                        note = Description of Artificial Sequence: Synthetic
                        polypeptide
SEQUENCE: 530
EVQLVESGGG LVQPGGSLRL SCAASGYTQC SYDMTWYRQA PGKGLEFVSA IHSDGSTRYA      60
DSVKGRFFIS RDNSKNTLYL QMNSLRAEDT AVYYCKTDPL HCRAHGGSWY SVRANYWGQG     120
TLVTVSSGGG SEVQLVESGG GLVQPGGSLR LSCAASGYTH SSYCMGWVRQ APGKGLEGVS     180
AIDVDGSTTY ADSVKGRFTI SRDNSKNTLY LQMNSLRAED TAVYYCAAEF ADCSSNYFLP     240
PGAVRYWGQG TLVTVSSASH HHHHH                                          265
```

| | | |
|---|---|---|
| SEQ ID NO: 531<br>FEATURE<br>source | moltype = AA  length = 5<br>Location/Qualifiers<br>1..5<br>mol_type = protein<br>organism = synthetic construct<br>note = Description of Artificial Sequence: Synthetic 5xHis<br>   tag | |
| SEQUENCE: 531<br>HHHHH | | 5 |
| SEQ ID NO: 532<br>FEATURE<br>source | moltype = AA  length = 6<br>Location/Qualifiers<br>1..6<br>mol_type = protein<br>organism = synthetic construct<br>note = Description of Artificial Sequence: Synthetic 6xHis<br>   tag | |
| SEQUENCE: 532<br>HHHHHH | | 6 |
| SEQ ID NO: 533<br>FEATURE<br>source | moltype = AA  length = 7<br>Location/Qualifiers<br>1..7<br>mol_type = protein<br>organism = synthetic construct<br>note = Description of Artificial Sequence: Synthetic 7xHis<br>   tag | |
| SEQUENCE: 533<br>HHHHHHH | | 7 |
| SEQ ID NO: 534<br>FEATURE<br>source | moltype = AA  length = 8<br>Location/Qualifiers<br>1..8<br>mol_type = protein<br>organism = synthetic construct<br>note = Description of Artificial Sequence: Synthetic 8xHis<br>   tag | |
| SEQUENCE: 534<br>HHHHHHHH | | 8 |
| SEQ ID NO: 535<br>FEATURE<br>source | moltype = AA  length = 9<br>Location/Qualifiers<br>1..9<br>mol_type = protein<br>organism = synthetic construct<br>note = Description of Artificial Sequence: Synthetic 9xHis<br>   tag | |
| SEQUENCE: 535<br>HHHHHHHHH | | 9 |
| SEQ ID NO: 536<br>FEATURE<br>source | moltype = AA  length = 5<br>Location/Qualifiers<br>1..5<br>mol_type = protein<br>organism = synthetic construct<br>note = Description of Artificial Sequence: Synthetic peptide | |
| SEQUENCE: 536<br>HWHMY | | 5 |
| SEQ ID NO: 537<br>FEATURE<br>source | moltype = AA  length = 5<br>Location/Qualifiers<br>1..5<br>mol_type = protein<br>organism = synthetic construct<br>note = Description of Artificial Sequence: Synthetic peptide | |
| SEQUENCE: 537<br>HHHMY | | 5 |
| SEQ ID NO: 538<br>FEATURE<br>source | moltype = AA  length = 5<br>Location/Qualifiers<br>1..5<br>mol_type = protein<br>organism = synthetic construct<br>note = Description of Artificial Sequence: Synthetic peptide | |
| SEQUENCE: 538<br>HHHHY | | 5 |
| SEQ ID NO: 539<br>FEATURE | moltype = AA  length = 5<br>Location/Qualifiers | |

-continued

```
source                  1..5
                        mol_type = protein
                        organism = synthetic construct
                        note = Description of Artificial Sequence: Synthetic peptide
SEQUENCE: 539
HWHWH                                                                               5

SEQ ID NO: 540          moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 540
HWHHH                                                                               5

SEQ ID NO: 541          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 541
HHHHYMHHH                                                                           9

SEQ ID NO: 542          moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 542
HHHHH                                                                               5

SEQ ID NO: 543          moltype = AA  length = 5
FEATURE                 Location/Qualifiers
source                  1..5
                        mol_type = protein
                        organism = synthetic construct
                        note = Description of Artificial Sequence: Synthetic peptide
SEQUENCE: 543
HWHHH                                                                               5

SEQ ID NO: 544          moltype = AA  length = 9
FEATURE                 Location/Qualifiers
source                  1..9
                        mol_type = protein
                        organism = synthetic construct
                        note = Description of Artificial Sequence: Synthetic peptide
SEQUENCE: 544
HGHGGHGH                                                                            9

SEQ ID NO: 545          moltype = AA  length = 12
FEATURE                 Location/Qualifiers
source                  1..12
                        mol_type = protein
                        organism = synthetic construct
                        note = Description of Artificial Sequence: Synthetic peptide
SEQUENCE: 545
HGHGGGGGGH GH                                                                      12

SEQ ID NO: 546          moltype = DNA  length = 381
FEATURE                 Location/Qualifiers
source                  1..381
                        mol_type = other DNA
                        organism = synthetic construct
                        note = Description of Artificial Sequence: Synthetic
                        polynucleotide
SEQUENCE: 546
gaagtgcagt tgctggagag tggtggcgga cttgtccaac ccggcggtag cctgcgcctc    60
agctgcgctg ccagtggcta tacacagtgc agttatgaca tgacctgggt ccgccaagcg   120
cccggcaagg gcctggagtg ggtttccgct attcactccg atggcagcac ccgttatgca   180
gactccgtta agggccgctt caccatctct cgcgacaact ccaagaacac cctgtatctt   240
cagatgaact ctctccgcgc tgaggacact gctgtgtatt actgtaaaac cgatccactg   300
cactgtcgtg cgcacggggg ctcatggtac tctgtcagag ctaactattg ggggcagggc   360
accctggtga ctgtgtcctc t                                             381

SEQ ID NO: 547          moltype = DNA  length = 381
FEATURE                 Location/Qualifiers
```

| | | |
|---|---|---|
| source | 1..381 | |
| | mol_type = other DNA | |
| | organism = synthetic construct | |
| | note = Description of Artificial Sequence: Synthetic polynucleotide | |

SEQUENCE: 547
```
gaggtgcagc ttctggagag cggtggcggt ctggtacaac ccggaggtag tctgcgcctg   60
tcctgtgcgg cttccggcta cacccaatgt tcctatgaca tgacctgggt tcgccaggcc  120
cccggtaagg gcctggaatt tgtcagcgct atccatagtg atggaagcac cagatatgcc  180
gacagtgtta agggccgctt caccatcagc agagataata gcaagaacac cctttacctc  240
cagatgaact ctttgcgtgc cgaggatacc gccgtctatt actgtaagac cgatccgctg  300
cattgccgtg cacatggcgg gtcctggtac agtgttcgcg ccaactattg gggccaggga  360
acactggtga ctgtcagcag t                                            381
```

| SEQ ID NO: 548 | moltype = DNA length = 381 | |
|---|---|---|
| FEATURE | Location/Qualifiers | |
| source | 1..381 | |
| | mol_type = other DNA | |
| | organism = synthetic construct | |
| | note = Description of Artificial Sequence: Synthetic polynucleotide | |

SEQUENCE: 548
```
gaagtgcaac tggtggagag cggtggaggt ttggttcagc ctggaggctc cctgcgcctt   60
tcctgtgctg cgagcgggta tacacagtgc agctatgaca tgacctgggt gaggcaggca  120
ccgggcaaag gtttggagtg ggtgtcagcg atccattctg atggcagcac aaggtacgcg  180
gatagcgtta agggcaggtt tttcatttcc cgcgacaact ctaagaacac actctatctc  240
cagatgaact cacttcgcgc cgaggatacc gccgtgtatt actgcaagac agaccctctg  300
cactgtcggg ctcacggcgg tagctggtat tccgtccgtg ctaactactg gggccagggc  360
actctcgtga ccgtgtcatc c                                            381
```

| SEQ ID NO: 549 | moltype = DNA length = 381 | |
|---|---|---|
| FEATURE | Location/Qualifiers | |
| source | 1..381 | |
| | mol_type = other DNA | |
| | organism = synthetic construct | |
| | note = Description of Artificial Sequence: Synthetic polynucleotide | |

SEQUENCE: 549
```
gaggtgcagc tggtggagtc tgggggaggc ctggtacagc ctgggggcag tctgcgcctg   60
agctgcgcgg ccagtggcta tactcagtgc tcctacgaca tgacttgggt aaggcaggcc  120
cccggcaaag gtttggagtt tgtttccgca attcatagcg acggctccac acgctacgcc  180
gattccgtca aaggtcggtt tttcatctcc cgtgataaca gcaaaaacac tctgtacctt  240
cagatgaact ccctccgcgc agaggatacc gccgtttatt actgtaaaac tgaccccctc  300
cactgccgcg ctcacggcgg gagctggtat agtgttcgcg ccaactactg gggccagggc  360
accttggtga ccgtctccag t                                            381
```

| SEQ ID NO: 550 | moltype = DNA length = 378 | |
|---|---|---|
| FEATURE | Location/Qualifiers | |
| source | 1..378 | |
| | mol_type = other DNA | |
| | organism = synthetic construct | |
| | note = Description of Artificial Sequence: Synthetic polynucleotide | |

SEQUENCE: 550
```
gaggtgcagt tgctggaaag cggggtggc ctggtccagc cgggaggttc cctgcgcctt    60
tcctgcgccg cttccggcta cacccattca agttactgta tgggctgggt tcgtcaggca  120
cctggcaaag gtctcgaatg ggtgagcgct atcgacgtgg acggaagcac cacttatgct  180
gattccgtga agggtaggtt caccatttcc cgcgacaact ccaagaacac tctttatctg  240
caaatgaata gcctccgcgc tgaggacacc gccgtatatt actgcgctgc ggagtttgcc  300
gactgctcta gcaactactt tctgccccct ggggccgtaa ggtattgggg ccagggcacc  360
ttggtgactg tgtcctcc                                                378
```

| SEQ ID NO: 551 | moltype = DNA length = 378 | |
|---|---|---|
| FEATURE | Location/Qualifiers | |
| source | 1..378 | |
| | mol_type = other DNA | |
| | organism = synthetic construct | |
| | note = Description of Artificial Sequence: Synthetic polynucleotide | |

SEQUENCE: 551
```
gaggtgcagc tgctcgaatc cggggcgga ctggtgcagc ctggtggcag cctgcgtctg     60
tcctgtgctc cctctggtta tacccattcc agctactgta tgggttgggt gcgccaagcc  120
cctgaaaagg ggcttgaagg cgtctccgcc attgatgtcg atggcagtac cacttacgct  180
gactccgtga agggacgctt cactatcagc cgcgacaact ccaagaacac gctctatctc  240
cagatgaact ctccgcgc agaagacacc gcagtgtact attgtgccgc agagtttgcc   300
gattgcagct caaactactt cctgccccca ggggcagtgc gttattgggg ccagggaaca  360
cttgttactg tttcttct                                                378
```

SEQ ID NO: 552   moltype = DNA length = 378

```
FEATURE              Location/Qualifiers
source               1..378
                     mol_type = other DNA
                     organism = synthetic construct
                     note = Description of Artificial Sequence: Synthetic
                     polynucleotide
SEQUENCE: 552
gaggttcagt tggtggaatc tggcgggggc ctcgtgcagc ccggaggctc cctcaggctt   60
tcctgtgctg cctctgggta cacacactct agttattgca tgggctgggt gcgccaagca  120
ccgggcaagg gtctggagtg ggtgagcgcc attgatgtgg acggttctac tacctatgcc  180
gatagcgtga aggggcgttt cacaatcagc cgcgacaact ccaaaaacac cctgtatctc  240
cagatgaata gtcttcgtgc cgaagacacc gcagtgtact attgtgcggc agagttcgcg  300
gactgctcta gcaactattt tctgcccccca ggagccgtcc gctactgggg acagggcacc  360
ctggtcaccg tgtcttcc                                                378

SEQ ID NO: 553       moltype = DNA  length = 378
FEATURE              Location/Qualifiers
source               1..378
                     mol_type = other DNA
                     organism = synthetic construct
                     note = Description of Artificial Sequence: Synthetic
                     polynucleotide
SEQUENCE: 553
gaggtccagc tggtggagag tgggggcgga ctggtacagc caggtggcag tcttcgcctc   60
tcttgcgctg cctccggcta cactcacagc tcttattgca tgggttgggt gagacaggcc  120
cctggtaaag gtcttgaggg cgtgagtgcc atcgacgtgg atggttccac tacctacgct  180
gatagtgtga agggccgctt cactatctca cgtgataact ctaagaatac tctgtatctt  240
caaatgaaca gcctccgcgc agaggacacc gcagtctact attgtgcagc cgagtttgct  300
gactgtagct ccaactactt ccttccgccc ggtgcagtgc gctattgggg gcaaggcact  360
ctggtgacag tctcctcc                                                378

SEQ ID NO: 554       moltype = DNA  length = 381
FEATURE              Location/Qualifiers
source               1..381
                     mol_type = other DNA
                     organism = synthetic construct
                     note = Description of Artificial Sequence: Synthetic
                     polynucleotide
SEQUENCE: 554
gaggtgcagc tggttgaatc cggggggtggc ctcgtgcagc ccggaggctc tctgcgcctg   60
tcctgcgcag cctccggcta tacccagtgt tcctatgata tgacgtgggt cagacaagct  120
cctggcaaag gccgcgagtt tgtttccgct attcactctg acggtccac ccggtacgcg  180
gatagcgtta aggggtcgct tttcatcagc cgggataact caaagaacac tctgtacttg  240
cagatgaact ctcttcgcgc tgaggatacg gcggtttatt actgcaaaac tgatcctctc  300
cactgtcgcg cccacggcgg atcttggtat agcgttcgcg ctaattactg ggggcaagga  360
actctggtga ctgtttcctc c                                            381

SEQ ID NO: 555       moltype = DNA  length = 381
FEATURE              Location/Qualifiers
source               1..381
                     mol_type = other DNA
                     organism = synthetic construct
                     note = Description of Artificial Sequence: Synthetic
                     polynucleotide
SEQUENCE: 555
gaggtgcagt tgcaggagtc cggcggaggg tccgtccagg ccggaggcag tctgcgcctg   60
tcctgtgccg cttccggcta ctcccaatgt tcttacgaca tgacttggta tcgccaggct  120
ccgggcaagg agcgcgagtt cgtgagcgcc atccactcag acggctccac ccgttacgcc  180
gactcagtca agggtcgctt ctttatctcc caggacacg caaagaacac cgtctatctc  240
cagatgaact ccctgaagcc agaagacaca gctatgtatt actgtaaaac cgacccactg  300
cattgcaggg ctcatggtgg ctcctggtac tctgtacgcg caaactactg ggtcagggc  360
acccaggtga ccgtgagttc c                                            381

SEQ ID NO: 556       moltype = DNA  length = 795
FEATURE              Location/Qualifiers
source               1..795
                     mol_type = other DNA
                     organism = synthetic construct
                     note = Description of Artificial Sequence: Synthetic
                     polynucleotide
SEQUENCE: 556
gaagtccagc ttgttgaatc tggggggaggc ctggtgcagc ctgggggctc cctgcgcctc   60
tcctgtgctg ccagcgggta cacccaatgt tcctatgata tgacctgggt ccgccaggca  120
ccaggcaagg gattggaatt tgtgagcgca atccattctg acggcagtac tcgttacgct  180
gactccgtaa agggcagatt ctttatctct cgtgacaaca gcaaaaacac tctgtatctg  240
caaatgaact ctctccgcgc cgaagacact gcggtctatt actgcaagac cgatccctc  300
cattgtcgtg cccacggggg aagttggtac tcagtccgcg caaattattg ggccagggc  360
actctcgtga ccgtctccag cggggaggt tcgaggtgc agctcgtgga gagcggtggg  420
ggcctggtcc agcctggcgg aagcctgcgc ctgtcatgcg ctgcgtctgg ttacacacac  480
```

```
agctcctatt gtatgggatg ggtgcggcag gcccccggta aaggactgga atgggttagc    540
gccatcgacg tggacggctc tacgacatac gccgactccg tcaagggccg ctttactatc    600
agccgtgata acagcaagaa cactctgtac ctgcaaatga actctctccg cgccgaggac    660
accgctgtgt attactgtgc cgcagagttc gcagactgct cttccaatta tttcctgcct    720
cccggagccg tccgttattg gggtcagggc actctggtta ctgtgtcctc tgcttcccat    780
caccatcatc accac                                                     795

SEQ ID NO: 557          moltype = DNA  length = 795
FEATURE                 Location/Qualifiers
source                  1..795
                        mol_type = other DNA
                        organism = synthetic construct
                        note = Description of Artificial Sequence: Synthetic
                        polynucleotide
SEQUENCE: 557
gaggtgcagc tggttgagtc tggcggaggt ctggtgcagc ccggcggttc tctgcgcctg    60
tcttgcgccg cgagcggcta cacgcaatgc agctacgata tgacctgggt tcgtcaggcc    120
cccggcaagg gcttggagtt cgtcagcgcg atccatagcg acggtccac aagatatgct    180
gatagcgtga agggccgctt ctttattagt agagacaact ctaagaacac actctacctc    240
cagatgaata gtctccgcgc agaggacacg gcggtgtact attgtaagac cgatcctctg    300
cattgcgagg cccacggtgg ctcctggtac agcgtgcggg ctaactattg ggggcaaggc    360
accctggtta ctgtctctag cggtggaggt agcgaagtgc aacttgtcga gtccggggga    420
ggtctggtcc agcccggtgg gtctcttagg ctctcctgcg ctgcatccgg ctacacccat    480
agctcatatt gtatgggctg ggtccgccaa gcccctggga aggggctgga aggtgtcagc    540
gccattgatg tcgatggcag cacaacttac gctgatagtg tgaagggtcg cttcactatc    600
tccagagaca attcaaagaa caccttgtac tccagatga atctctcttg cgccgaagac    660
accgccgtct attactgcgc cgctgagttc gcggactgta gctccaatta tttcctgcca    720
cccggcgctg tgcggtattg gggccagggt actctggtga ctgtgtctag tgcctctcac    780
catcaccatc atcac                                                     795

SEQ ID NO: 558          moltype = DNA  length = 795
FEATURE                 Location/Qualifiers
source                  1..795
                        mol_type = other DNA
                        organism = synthetic construct
                        note = Description of Artificial Sequence: Synthetic
                        polynucleotide
SEQUENCE: 558
gaggtgcagc tggtggaatc tggaggcggt ctcgtccagc caggggggctc tctgcgtctg    60
tcttgcgctg cgtctggata tacccagtgc tcttacgaca tgacatggta tcggcaggct    120
cccggcaagg gacttgagtt cgtctctgcc atccacagcg atggttccac acgctacgca    180
gattccgtga agggacgttt tttcatcagc cgtgacaata gcaagaacac tctgtatctt    240
caaatgaact ccctccgcgc ggaagacacc gccgtgtatt actgtaaaac cgatcctctg    300
cactgtaggg cacatggggg ctcttggtat tctgttcgtg ctaattattg gggccagggc    360
accctggtca ccgtttccag cggcggaggt agtgaggtcc agctcgtcga atccggcggt    420
ggcctcgtgc agcctggcgg gtccctccgc ctgtcctgcg ctgcaagcgg ttatacgcac    480
agctcctatt gcatgggctg ggtgcgtcaa gctcctggca agggggctgga gtgggtcagc    540
gctattgacg tggacgggag tactacctac gccgattcag tgaagggtag attcaccatc    600
tcacgtgaca actctaagaa cacactgtac ttgcagatga atagcctgag ggctgaagac    660
actgctgtgt actattgcgc tgccgagttc gccgattgta gctccaacta cttcctgccc    720
ccaggagcgg tccgttactg gggccaaggc accctcgtga ctgtctcttc agccagtcat    780
caccatcatc accac                                                     795

SEQ ID NO: 559          moltype = DNA  length = 795
FEATURE                 Location/Qualifiers
source                  1..795
                        mol_type = other DNA
                        organism = synthetic construct
                        note = Description of Artificial Sequence: Synthetic
                        polynucleotide
SEQUENCE: 559
gaggtccagc tggtggagag tgggggtggg ctcgttcagc ctgggggctc tctgaggctg    60
agctgtgcag cctccggcta tacccagtgt tcttacgaca tgacgtggta taggcaggca    120
ccaggcaaag gactggagtt tgtgagtgct atccactccg acggttccac ccggtatgct    180
gactctgtta agggcagatt ctttattagc cggacaacaa gcaaaaacac cctttacctc    240
cagatgaact ctctgagggc agaggacacg gcagtgtatt actgtaaaac agaccctctt    300
cactgccgcg cacatggagg ctcttggtac agtgtgaggg ctaattattg gggtcaggc   360
accctcgtca cagtctcttc aggggggtgga tctgaggtgc agttggtcga gagtggggt   420
ggcctggtgc agcctggcgg tagcctgcgc ctgagctgcg cggcctctgg gtacacccac   480
tcctcttact gtatgggctg ggtgaggcag gctcctggaa aggggctgga gggcgtgtcc   540
gctattgacg tagatggctc cactacctac gccgacagcg taaaggtcg tttcacaatc   600
tcccgcgaca actccaagaa cacctctac ttgcagatga actccctgcg ggccgaagac   660
acagctgttt attactgcgc cgctgagttc gcagactgtt ccagtaatta cttcctgccc   720
cctggtgccg tgcgttactg gggccagggc accctcgtaa ccgtcagctc cgctagtcac   780
catcaccacc accat                                                    795

SEQ ID NO: 560          moltype = AA   length = 8
FEATURE                 Location/Qualifiers
source                  1..8
```

```
                        mol_type = protein
                        organism = synthetic construct
                        note = Description of Artificial Sequence: Synthetic peptide
SEQUENCE: 560
ASHHHHHH                                                                8

SEQ ID NO: 561          moltype = AA  length = 265
FEATURE                 Location/Qualifiers
source                  1..265
                        mol_type = protein
                        organism = synthetic construct
                        note = Description of Artificial Sequence: Synthetic
                         polypeptide
SEQUENCE: 561
EVQLLESGGG LVQPGGSLRL SCAASGYSNC AYDMTWYRQA PGKELEWVSA IHSDGSTRYA    60
DSVKGRFFIS RDNSKNTLYL QMNSLRAEDT AVYYCKTDPL HCRAHGGSWY SVRANYWGQG   120
TLVTVSSGGG SEVQLVESGG GLVQPGGSLR LSCAASGYTH SSYCMGWVRQ APGKGLEGVS   180
AIDVDGSTTY ADSVKGRFTI SRDNSKNTLY LQMNSLRAED TAVYYCAAEF ADCSSNYFLP   240
PGAVRYWGQG TLVTVSSASH HHHHH                                         265

SEQ ID NO: 562          moltype = AA  length = 800
FEATURE                 Location/Qualifiers
source                  1..800
                        mol_type = protein
                        organism = synthetic construct
                        note = Description of Artificial Sequence: Synthetic
                         polypeptide
VARIANT                 1..20
                        note = SITE - This region may encompass 1-20 residues
VARIANT                 21..40
                        note = SITE - This region may encompass 1-20 residues
VARIANT                 41..60
                        note = SITE - This region may encompass 1-20 residues
VARIANT                 61..80
                        note = SITE - This region may encompass 1-20 residues
VARIANT                 81..100
                        note = SITE - This region may encompass 1-20 residues
VARIANT                 101..120
                        note = SITE - This region may encompass 1-20 residues
VARIANT                 121..140
                        note = SITE - This region may encompass 1-20 residues
VARIANT                 141..160
                        note = SITE - This region may encompass 1-20 residues
VARIANT                 161..180
                        note = SITE - This region may encompass 1-20 residues
VARIANT                 181..200
                        note = SITE - This region may encompass 1-20 residues
VARIANT                 201..220
                        note = SITE - This region may encompass 1-20 residues
VARIANT                 221..240
                        note = SITE - This region may encompass 1-20 residues
VARIANT                 241..260
                        note = SITE - This region may encompass 1-20 residues
VARIANT                 261..280
                        note = SITE - This region may encompass 1-20 residues
VARIANT                 281..300
                        note = SITE - This region may encompass 1-20 residues
VARIANT                 301..320
                        note = SITE - This region may encompass 1-20 residues
VARIANT                 321..340
                        note = SITE - This region may encompass 1-20 residues
VARIANT                 341..360
                        note = SITE - This region may encompass 1-20 residues
VARIANT                 361..380
                        note = SITE - This region may encompass 1-20 residues
VARIANT                 381..400
                        note = SITE - This region may encompass 1-20 residues
VARIANT                 401..420
                        note = SITE - This region may encompass 1-20 residues
VARIANT                 421..440
                        note = SITE - This region may encompass 1-20 residues
VARIANT                 441..460
                        note = SITE - This region may encompass 1-20 residues
VARIANT                 461..480
                        note = SITE - This region may encompass 1-20 residues
VARIANT                 481..500
                        note = SITE - This region may encompass 1-20 residues
VARIANT                 501..520
                        note = SITE - This region may encompass 1-20 residues
```

```
VARIANT           521..540
                  note = SITE - This region may encompass 1-20 residues
VARIANT           541..560
                  note = SITE - This region may encompass 1-20 residues
VARIANT           561..580
                  note = SITE - This region may encompass 1-20 residues
VARIANT           581..600
                  note = SITE - This region may encompass 1-20 residues
VARIANT           601..620
                  note = SITE - This region may encompass 1-20 residues
VARIANT           621..640
                  note = SITE - This region may encompass 1-20 residues
VARIANT           641..660
                  note = SITE - This region may encompass 1-20 residues
VARIANT           661..680
                  note = SITE - This region may encompass 1-20 residues
VARIANT           681..700
                  note = SITE - This region may encompass 1-20 residues
VARIANT           701..720
                  note = SITE - This region may encompass 1-20 residues
VARIANT           721..740
                  note = SITE - This region may encompass 1-20 residues
VARIANT           741..760
                  note = SITE - This region may encompass 1-20 residues
VARIANT           761..780
                  note = SITE - This region may encompass 1-20 residues
VARIANT           781..800
                  note = SITE - This region may encompass 1-20 residues
VARIANT           1..800
                  note = SITE - This sequence may encompass 1-20 (Gly)m(Ser)o
                     repeating units, wherein m = 1 to 20, o = 1 to 20
REGION            1..800
                  note = See specification as filed for detailed description
                     of substitutions and preferred embodiments
SEQUENCE: 562
GGGGGGGGGG GGGGGGGGGG SSSSSSSSSS SSSSSSSSSS GGGGGGGGGG GGGGGGGGGG    60
SSSSSSSSSS SSSSSSSSSS GGGGGGGGGG GGGGGGGGGG SSSSSSSSSS SSSSSSSSSS   120
GGGGGGGGGG GGGGGGGGGG SSSSSSSSSS SSSSSSSSSS GGGGGGGGGG GGGGGGGGGG   180
SSSSSSSSSS SSSSSSSSSS GGGGGGGGGG GGGGGGGGGG SSSSSSSSSS SSSSSSSSSS   240
GGGGGGGGGG GGGGGGGGGG SSSSSSSSSS SSSSSSSSSS GGGGGGGGGG GGGGGGGGGG   300
SSSSSSSSSS SSSSSSSSSS GGGGGGGGGG GGGGGGGGGG SSSSSSSSSS SSSSSSSSSS   360
GGGGGGGGGG GGGGGGGGGG SSSSSSSSSS SSSSSSSSSS GGGGGGGGGG GGGGGGGGGG   420
SSSSSSSSSS SSSSSSSSSS GGGGGGGGGG GGGGGGGGGG SSSSSSSSSS SSSSSSSSSS   480
GGGGGGGGGG GGGGGGGGGG SSSSSSSSSS SSSSSSSSSS GGGGGGGGGG GGGGGGGGGG   540
SSSSSSSSSS SSSSSSSSSS GGGGGGGGGG GGGGGGGGGG SSSSSSSSSS SSSSSSSSSS   600
GGGGGGGGGG GGGGGGGGGG SSSSSSSSSS SSSSSSSSSS GGGGGGGGGG GGGGGGGGGG   660
SSSSSSSSSS SSSSSSSSSS GGGGGGGGGG GGGGGGGGGG SSSSSSSSSS SSSSSSSSSS   720
GGGGGGGGGG GGGGGGGGGG SSSSSSSSSS SSSSSSSSSS GGGGGGGGGG GGGGGGGGGG   780
SSSSSSSSSS SSSSSSSSSS                                               800

SEQ ID NO: 563     moltype = AA  length = 100
FEATURE            Location/Qualifiers
source             1..100
                   mol_type = protein
                   organism = synthetic construct
                   note = Description of Artificial Sequence: Synthetic
                      polypeptide
VARIANT            1..100
                   note = SITE - This sequence may encompass 1-20 Gly Ser Gly
                      Gly Ser repeating units
REGION             1..100
                   note = See specification as filed for detailed description
                      of substitutions and preferred embodiments
SEQUENCE: 563
GSGGSGSGGS GSGGSGSGGS GSGGSGSGGS GSGGSGSGGS GSGGSGSGGS GSGGSGSGGS    60
GSGGSGSGGS GSGGSGSGGS GSGGSGSGGS GSGGSGSGGS                         100

SEQ ID NO: 564     moltype = AA  length = 1200
FEATURE            Location/Qualifiers
source             1..1200
                   mol_type = protein
                   organism = synthetic construct
                   note = Description of Artificial Sequence: Synthetic
                      polypeptide
VARIANT            1..20
                   note = SITE - This region may encompass 1-20 residues
VARIANT            21..40
                   note = SITE - This region may encompass 1-20 residues
VARIANT            41..60
```

| | | |
|---|---|---|
| VARIANT | 61..80 | note = SITE - This region may encompass 1-20 residues |
| VARIANT | 81..100 | note = SITE - This region may encompass 1-20 residues |
| VARIANT | 101..120 | note = SITE - This region may encompass 1-20 residues |
| VARIANT | 121..140 | note = SITE - This region may encompass 1-20 residues |
| VARIANT | 141..160 | note = SITE - This region may encompass 1-20 residues |
| VARIANT | 161..180 | note = SITE - This region may encompass 1-20 residues |
| VARIANT | 181..200 | note = SITE - This region may encompass 1-20 residues |
| VARIANT | 201..220 | note = SITE - This region may encompass 1-20 residues |
| VARIANT | 221..240 | note = SITE - This region may encompass 1-20 residues |
| VARIANT | 241..260 | note = SITE - This region may encompass 1-20 residues |
| VARIANT | 261..280 | note = SITE - This region may encompass 1-20 residues |
| VARIANT | 281..300 | note = SITE - This region may encompass 1-20 residues |
| VARIANT | 301..320 | note = SITE - This region may encompass 1-20 residues |
| VARIANT | 321..340 | note = SITE - This region may encompass 1-20 residues |
| VARIANT | 341..360 | note = SITE - This region may encompass 1-20 residues |
| VARIANT | 361..380 | note = SITE - This region may encompass 1-20 residues |
| VARIANT | 381..400 | note = SITE - This region may encompass 1-20 residues |
| VARIANT | 401..420 | note = SITE - This region may encompass 1-20 residues |
| VARIANT | 421..440 | note = SITE - This region may encompass 1-20 residues |
| VARIANT | 441..460 | note = SITE - This region may encompass 1-20 residues |
| VARIANT | 461..480 | note = SITE - This region may encompass 1-20 residues |
| VARIANT | 481..500 | note = SITE - This region may encompass 1-20 residues |
| VARIANT | 501..520 | note = SITE - This region may encompass 1-20 residues |
| VARIANT | 521..540 | note = SITE - This region may encompass 1-20 residues |
| VARIANT | 541..560 | note = SITE - This region may encompass 1-20 residues |
| VARIANT | 561..580 | note = SITE - This region may encompass 1-20 residues |
| VARIANT | 581..600 | note = SITE - This region may encompass 1-20 residues |
| VARIANT | 601..620 | note = SITE - This region may encompass 1-20 residues |
| VARIANT | 621..640 | note = SITE - This region may encompass 1-20 residues |
| VARIANT | 641..660 | note = SITE - This region may encompass 1-20 residues |
| VARIANT | 661..680 | note = SITE - This region may encompass 1-20 residues |
| VARIANT | 681..700 | note = SITE - This region may encompass 1-20 residues |
| VARIANT | 701..720 | note = SITE - This region may encompass 1-20 residues |
| VARIANT | 721..740 | note = SITE - This region may encompass 1-20 residues |
| VARIANT | 741..760 | note = SITE - This region may encompass 1-20 residues |
| VARIANT | 761..780 | note = SITE - This region may encompass 1-20 residues |
| VARIANT | 781..800 | note = SITE - This region may encompass 1-20 residues |
| VARIANT | 801..820 | note = SITE - This region may encompass 1-20 residues |
| VARIANT | 821..840 | note = SITE - This region may encompass 1-20 residues |

```
VARIANT          841..860
                 note = SITE - This region may encompass 1-20 residues
VARIANT          861..880
                 note = SITE - This region may encompass 1-20 residues
VARIANT          881..900
                 note = SITE - This region may encompass 1-20 residues
VARIANT          901..920
                 note = SITE - This region may encompass 1-20 residues
VARIANT          921..940
                 note = SITE - This region may encompass 1-20 residues
VARIANT          941..960
                 note = SITE - This region may encompass 1-20 residues
VARIANT          961..980
                 note = SITE - This region may encompass 1-20 residues
VARIANT          981..1000
                 note = SITE - This region may encompass 1-20 residues
VARIANT          1001..1020
                 note = SITE - This region may encompass 1-20 residues
VARIANT          1021..1040
                 note = SITE - This region may encompass 1-20 residues
VARIANT          1041..1060
                 note = SITE - This region may encompass 1-20 residues
VARIANT          1061..1080
                 note = SITE - This region may encompass 1-20 residues
VARIANT          1081..1100
                 note = SITE - This region may encompass 1-20 residues
VARIANT          1101..1120
                 note = SITE - This region may encompass 1-20 residues
VARIANT          1121..1140
                 note = SITE - This region may encompass 1-20 residues
VARIANT          1141..1160
                 note = SITE - This region may encompass 1-20 residues
VARIANT          1161..1180
                 note = SITE - This region may encompass 1-20 residues
VARIANT          1181..1200
                 note = SITE - This region may encompass 1-20 residues
VARIANT          1..1200
                 note = SITE - This sequence may encompass 1-20
                 (Gly)m(Ser)o(Gly)m repeating units, wherein m = 1 to 20, o
                 = 1 to 20
REGION           1..1200
                 note = See specification as filed for detailed description
                 of substitutions and preferred embodiments
SEQUENCE: 564
GGGGGGGGGG GGGGGGGGGG SSSSSSSSSS SSSSSSSSSS GGGGGGGGGG GGGGGGGGGG    60
GGGGGGGGGG GGGGGGGGGG SSSSSSSSSS SSSSSSSSSS GGGGGGGGGG GGGGGGGGGG   120
GGGGGGGGGG GGGGGGGGGG SSSSSSSSSS SSSSSSSSSS GGGGGGGGGG GGGGGGGGGG   180
GGGGGGGGGG GGGGGGGGGG SSSSSSSSSS SSSSSSSSSS GGGGGGGGGG GGGGGGGGGG   240
GGGGGGGGGG GGGGGGGGGG SSSSSSSSSS SSSSSSSSSS GGGGGGGGGG GGGGGGGGGG   300
GGGGGGGGGG GGGGGGGGGG SSSSSSSSSS SSSSSSSSSS GGGGGGGGGG GGGGGGGGGG   360
GGGGGGGGGG GGGGGGGGGG SSSSSSSSSS SSSSSSSSSS GGGGGGGGGG GGGGGGGGGG   420
GGGGGGGGGG GGGGGGGGGG SSSSSSSSSS SSSSSSSSSS GGGGGGGGGG GGGGGGGGGG   480
GGGGGGGGGG GGGGGGGGGG SSSSSSSSSS SSSSSSSSSS GGGGGGGGGG GGGGGGGGGG   540
GGGGGGGGGG GGGGGGGGGG SSSSSSSSSS SSSSSSSSSS GGGGGGGGGG GGGGGGGGGG   600
GGGGGGGGGG GGGGGGGGGG SSSSSSSSSS SSSSSSSSSS GGGGGGGGGG GGGGGGGGGG   660
GGGGGGGGGG GGGGGGGGGG SSSSSSSSSS SSSSSSSSSS GGGGGGGGGG GGGGGGGGGG   720
GGGGGGGGGG GGGGGGGGGG SSSSSSSSSS SSSSSSSSSS GGGGGGGGGG GGGGGGGGGG   780
GGGGGGGGGG GGGGGGGGGG SSSSSSSSSS SSSSSSSSSS GGGGGGGGGG GGGGGGGGGG   840
GGGGGGGGGG GGGGGGGGGG SSSSSSSSSS SSSSSSSSSS GGGGGGGGGG GGGGGGGGGG   900
GGGGGGGGGG GGGGGGGGGG SSSSSSSSSS SSSSSSSSSS GGGGGGGGGG GGGGGGGGGG   960
GGGGGGGGGG GGGGGGGGGG SSSSSSSSSS SSSSSSSSSS GGGGGGGGGG GGGGGGGGGG  1020
GGGGGGGGGG GGGGGGGGGG SSSSSSSSSS SSSSSSSSSS GGGGGGGGGG GGGGGGGGGG  1080
GGGGGGGGGG GGGGGGGGGG SSSSSSSSSS SSSSSSSSSS GGGGGGGGGG GGGGGGGGGG  1140
GGGGGGGGGG GGGGGGGGGG SSSSSSSSSS SSSSSSSSSS GGGGGGGGGG GGGGGGGGGG  1200

SEQ ID NO: 565          moltype = AA  length = 2000
FEATURE                 Location/Qualifiers
source                  1..2000
                        mol_type = protein
                        organism = synthetic construct
                        note = Description of Artificial Sequence: Synthetic
                        polypeptide
VARIANT                 1..20
                        note = SITE - This region may encompass 1-20 residues
VARIANT                 21..40
                        note = SITE - This region may encompass 1-20 residues
VARIANT                 41..60
                        note = SITE - This region may encompass 1-20 residues
VARIANT                 61..80
```

```
                     note = SITE - This region may encompass 1-20 residues
VARIANT              81..100
                     note = SITE - This region may encompass 1-20 residues
VARIANT              101..120
                     note = SITE - This region may encompass 1-20 residues
VARIANT              121..140
                     note = SITE - This region may encompass 1-20 residues
VARIANT              141..160
                     note = SITE - This region may encompass 1-20 residues
VARIANT              161..180
                     note = SITE - This region may encompass 1-20 residues
VARIANT              181..200
                     note = SITE - This region may encompass 1-20 residues
VARIANT              201..220
                     note = SITE - This region may encompass 1-20 residues
VARIANT              221..240
                     note = SITE - This region may encompass 1-20 residues
VARIANT              241..260
                     note = SITE - This region may encompass 1-20 residues
VARIANT              261..280
                     note = SITE - This region may encompass 1-20 residues
VARIANT              281..300
                     note = SITE - This region may encompass 1-20 residues
VARIANT              301..320
                     note = SITE - This region may encompass 1-20 residues
VARIANT              321..340
                     note = SITE - This region may encompass 1-20 residues
VARIANT              341..360
                     note = SITE - This region may encompass 1-20 residues
VARIANT              361..380
                     note = SITE - This region may encompass 1-20 residues
VARIANT              381..400
                     note = SITE - This region may encompass 1-20 residues
VARIANT              401..420
                     note = SITE - This region may encompass 1-20 residues
VARIANT              421..440
                     note = SITE - This region may encompass 1-20 residues
VARIANT              441..460
                     note = SITE - This region may encompass 1-20 residues
VARIANT              461..480
                     note = SITE - This region may encompass 1-20 residues
VARIANT              481..500
                     note = SITE - This region may encompass 1-20 residues
VARIANT              501..520
                     note = SITE - This region may encompass 1-20 residues
VARIANT              521..540
                     note = SITE - This region may encompass 1-20 residues
VARIANT              541..560
                     note = SITE - This region may encompass 1-20 residues
VARIANT              561..580
                     note = SITE - This region may encompass 1-20 residues
VARIANT              581..600
                     note = SITE - This region may encompass 1-20 residues
VARIANT              601..620
                     note = SITE - This region may encompass 1-20 residues
VARIANT              621..640
                     note = SITE - This region may encompass 1-20 residues
VARIANT              641..660
                     note = SITE - This region may encompass 1-20 residues
VARIANT              661..680
                     note = SITE - This region may encompass 1-20 residues
VARIANT              681..700
                     note = SITE - This region may encompass 1-20 residues
VARIANT              701..720
                     note = SITE - This region may encompass 1-20 residues
VARIANT              721..740
                     note = SITE - This region may encompass 1-20 residues
VARIANT              741..760
                     note = SITE - This region may encompass 1-20 residues
VARIANT              761..780
                     note = SITE - This region may encompass 1-20 residues
VARIANT              781..800
                     note = SITE - This region may encompass 1-20 residues
VARIANT              801..820
                     note = SITE - This region may encompass 1-20 residues
VARIANT              821..840
                     note = SITE - This region may encompass 1-20 residues
VARIANT              841..860
                     note = SITE - This region may encompass 1-20 residues
```

| | |
|---|---|
| VARIANT | 861..880 |
| | note = SITE - This region may encompass 1-20 residues |
| VARIANT | 881..900 |
| | note = SITE - This region may encompass 1-20 residues |
| VARIANT | 901..920 |
| | note = SITE - This region may encompass 1-20 residues |
| VARIANT | 921..940 |
| | note = SITE - This region may encompass 1-20 residues |
| VARIANT | 941..960 |
| | note = SITE - This region may encompass 1-20 residues |
| VARIANT | 961..980 |
| | note = SITE - This region may encompass 1-20 residues |
| VARIANT | 981..1000 |
| | note = SITE - This region may encompass 1-20 residues |
| VARIANT | 1001..1020 |
| | note = SITE - This region may encompass 1-20 residues |
| VARIANT | 1021..1040 |
| | note = SITE - This region may encompass 1-20 residues |
| VARIANT | 1041..1060 |
| | note = SITE - This region may encompass 1-20 residues |
| VARIANT | 1061..1080 |
| | note = SITE - This region may encompass 1-20 residues |
| VARIANT | 1081..1100 |
| | note = SITE - This region may encompass 1-20 residues |
| VARIANT | 1101..1120 |
| | note = SITE - This region may encompass 1-20 residues |
| VARIANT | 1121..1140 |
| | note = SITE - This region may encompass 1-20 residues |
| VARIANT | 1141..1160 |
| | note = SITE - This region may encompass 1-20 residues |
| VARIANT | 1161..1180 |
| | note = SITE - This region may encompass 1-20 residues |
| VARIANT | 1181..1200 |
| | note = SITE - This region may encompass 1-20 residues |
| VARIANT | 1201..1220 |
| | note = SITE - This region may encompass 1-20 residues |
| VARIANT | 1221..1240 |
| | note = SITE - This region may encompass 1-20 residues |
| VARIANT | 1241..1260 |
| | note = SITE - This region may encompass 1-20 residues |
| VARIANT | 1261..1280 |
| | note = SITE - This region may encompass 1-20 residues |
| VARIANT | 1281..1300 |
| | note = SITE - This region may encompass 1-20 residues |
| VARIANT | 1301..1320 |
| | note = SITE - This region may encompass 1-20 residues |
| VARIANT | 1321..1340 |
| | note = SITE - This region may encompass 1-20 residues |
| VARIANT | 1341..1360 |
| | note = SITE - This region may encompass 1-20 residues |
| VARIANT | 1361..1380 |
| | note = SITE - This region may encompass 1-20 residues |
| VARIANT | 1381..1400 |
| | note = SITE - This region may encompass 1-20 residues |
| VARIANT | 1401..1420 |
| | note = SITE - This region may encompass 1-20 residues |
| VARIANT | 1421..1440 |
| | note = SITE - This region may encompass 1-20 residues |
| VARIANT | 1441..1460 |
| | note = SITE - This region may encompass 1-20 residues |
| VARIANT | 1461..1480 |
| | note = SITE - This region may encompass 1-20 residues |
| VARIANT | 1481..1500 |
| | note = SITE - This region may encompass 1-20 residues |
| VARIANT | 1501..1520 |
| | note = SITE - This region may encompass 1-20 residues |
| VARIANT | 1521..1540 |
| | note = SITE - This region may encompass 1-20 residues |
| VARIANT | 1541..1560 |
| | note = SITE - This region may encompass 1-20 residues |
| VARIANT | 1561..1580 |
| | note = SITE - This region may encompass 1-20 residues |
| VARIANT | 1581..1600 |
| | note = SITE - This region may encompass 1-20 residues |
| VARIANT | 1601..1620 |
| | note = SITE - This region may encompass 1-20 residues |
| VARIANT | 1621..1640 |
| | note = SITE - This region may encompass 1-20 residues |
| VARIANT | 1641..1660 |

```
VARIANT         1661..1680
                note = SITE - This region may encompass 1-20 residues
VARIANT         1681..1700
                note = SITE - This region may encompass 1-20 residues
VARIANT         1701..1720
                note = SITE - This region may encompass 1-20 residues
VARIANT         1721..1740
                note = SITE - This region may encompass 1-20 residues
VARIANT         1741..1760
                note = SITE - This region may encompass 1-20 residues
VARIANT         1761..1780
                note = SITE - This region may encompass 1-20 residues
VARIANT         1781..1800
                note = SITE - This region may encompass 1-20 residues
VARIANT         1801..1820
                note = SITE - This region may encompass 1-20 residues
VARIANT         1821..1840
                note = SITE - This region may encompass 1-20 residues
VARIANT         1841..1860
                note = SITE - This region may encompass 1-20 residues
VARIANT         1861..1880
                note = SITE - This region may encompass 1-20 residues
VARIANT         1881..1900
                note = SITE - This region may encompass 1-20 residues
VARIANT         1901..1920
                note = SITE - This region may encompass 1-20 residues
VARIANT         1921..1940
                note = SITE - This region may encompass 1-20 residues
VARIANT         1941..1960
                note = SITE - This region may encompass 1-20 residues
VARIANT         1961..1980
                note = SITE - This region may encompass 1-20 residues
VARIANT         1981..2000
                note = SITE - This region may encompass 1-20 residues
VARIANT         1..2000
                note = SITE - This sequence may encompass 1-20
                (Gly)m(Ser)o(Gly)m(Ser)o(Gly)m repeating units, wherein m
                = 1 to 20, o = 1 to 20
REGION          1..2000
                note = See specification as filed for detailed description
                of substitutions and preferred embodiments
SEQUENCE: 565
GGGGGGGGGG GGGGGGGGGG SSSSSSSSSS SSSSSSSSSS GGGGGGGGGG GGGGGGGGGG    60
SSSSSSSSSS SSSSSSSSSS GGGGGGGGGG GGGGGGGGGG GGGGGGGGGG GGGGGGGGGG   120
SSSSSSSSSS SSSSSSSSSS SSSSSSSSSS SSSSSSSSSS GGGGGGGGGG GGGGGGGGGG   180
GGGGGGGGGG GGGGGGGGGG GGGGGGGGGG GGGGGGGGGG SSSSSSSSSS SSSSSSSSSS   240
GGGGGGGGGG GGGGGGGGGG SSSSSSSSSS SSSSSSSSSS GGGGGGGGGG GGGGGGGGGG   300
GGGGGGGGGG GGGGGGGGGG SSSSSSSSSS SSSSSSSSSS GGGGGGGGGG GGGGGGGGGG   360
SSSSSSSSSS SSSSSSSSSS GGGGGGGGGG GGGGGGGGGG GGGGGGGGGG GGGGGGGGGG   420
SSSSSSSSSS SSSSSSSSSS GGGGGGGGGG GGGGGGGGGG SSSSSSSSSS SSSSSSSSSS   480
GGGGGGGGGG GGGGGGGGGG GGGGGGGGGG GGGGGGGGGG SSSSSSSSSS SSSSSSSSSS   540
GGGGGGGGGG GGGGGGGGGG SSSSSSSSSS SSSSSSSSSS GGGGGGGGGG GGGGGGGGGG   600
GGGGGGGGGG GGGGGGGGGG SSSSSSSSSS SSSSSSSSSS GGGGGGGGGG GGGGGGGGGG   660
SSSSSSSSSS SSSSSSSSSS GGGGGGGGGG GGGGGGGGGG SSSSSSSSSS SSSSSSSSSS   720
SSSSSSSSSS SSSSSSSSSS GGGGGGGGGG GGGGGGGGGG SSSSSSSSSS SSSSSSSSSS   780
GGGGGGGGGG GGGGGGGGGG GGGGGGGGGG GGGGGGGGGG SSSSSSSSSS SSSSSSSSSS   840
GGGGGGGGGG GGGGGGGGGG GGGGGGGGGG GGGGGGGGGG GGGGGGGGGG GGGGGGGGGG   900
GGGGGGGGGG GGGGGGGGGG SSSSSSSSSS SSSSSSSSSS GGGGGGGGGG GGGGGGGGGG   960
SSSSSSSSSS SSSSSSSSSS GGGGGGGGGG GGGGGGGGGG GGGGGGGGGG GGGGGGGGGG  1020
SSSSSSSSSS SSSSSSSSSS GGGGGGGGGG GGGGGGGGGG SSSSSSSSSS SSSSSSSSSS  1080
GGGGGGGGGG GGGGGGGGGG GGGGGGGGGG GGGGGGGGGG SSSSSSSSSS SSSSSSSSSS  1140
GGGGGGGGGG GGGGGGGGGG SSSSSSSSSS SSSSSSSSSS GGGGGGGGGG GGGGGGGGGG  1200
GGGGGGGGGG GGGGGGGGGG SSSSSSSSSS SSSSSSSSSS GGGGGGGGGG GGGGGGGGGG  1260
SSSSSSSSSS SSSSSSSSSS GGGGGGGGGG GGGGGGGGGG GGGGGGGGGG GGGGGGGGGG  1320
SSSSSSSSSS SSSSSSSSSS GGGGGGGGGG GGGGGGGGGG SSSSSSSSSS SSSSSSSSSS  1380
GGGGGGGGGG GGGGGGGGGG GGGGGGGGGG GGGGGGGGGG SSSSSSSSSS SSSSSSSSSS  1440
GGGGGGGGGG GGGGGGGGGG SSSSSSSSSS SSSSSSSSSS GGGGGGGGGG GGGGGGGGGG  1500
GGGGGGGGGG GGGGGGGGGG SSSSSSSSSS SSSSSSSSSS GGGGGGGGGG GGGGGGGGGG  1560
SSSSSSSSSS SSSSSSSSSS GGGGGGGGGG GGGGGGGGGG GGGGGGGGGG GGGGGGGGGG  1620
SSSSSSSSSS SSSSSSSSSS GGGGGGGGGG GGGGGGGGGG SSSSSSSSSS SSSSSSSSSS  1680
GGGGGGGGGG GGGGGGGGGG GGGGGGGGGG GGGGGGGGGG SSSSSSSSSS SSSSSSSSSS  1740
GGGGGGGGGG GGGGGGGGGG SSSSSSSSSS SSSSSSSSSS GGGGGGGGGG GGGGGGGGGG  1800
GGGGGGGGGG GGGGGGGGGG SSSSSSSSSS SSSSSSSSSS GGGGGGGGGG GGGGGGGGGG  1860
SSSSSSSSSS SSSSSSSSSS GGGGGGGGGG GGGGGGGGGG GGGGGGGGGG GGGGGGGGGG  1920
SSSSSSSSSS SSSSSSSSSS GGGGGGGGGG GGGGGGGGGG SSSSSSSSSS SSSSSSSSSS  1980
GGGGGGGGGG GGGGGGGGGG                                              2000

SEQ ID NO: 566          moltype = AA  length = 480
```

```
FEATURE            Location/Qualifiers
source             1..480
                   mol_type = protein
                   organism = synthetic construct
                   note = Description of Artificial Sequence: Synthetic
                    polypeptide
VARIANT            5..24
                   note = SITE - This region may encompass 1-20 residues
VARIANT            29..48
                   note = SITE - This region may encompass 1-20 residues
VARIANT            53..72
                   note = SITE - This region may encompass 1-20 residues
VARIANT            77..96
                   note = SITE - This region may encompass 1-20 residues
VARIANT            101..120
                   note = SITE - This region may encompass 1-20 residues
VARIANT            125..144
                   note = SITE - This region may encompass 1-20 residues
VARIANT            149..168
                   note = SITE - This region may encompass 1-20 residues
VARIANT            173..192
                   note = SITE - This region may encompass 1-20 residues
VARIANT            197..216
                   note = SITE - This region may encompass 1-20 residues
VARIANT            221..240
                   note = SITE - This region may encompass 1-20 residues
VARIANT            245..264
                   note = SITE - This region may encompass 1-20 residues
VARIANT            269..288
                   note = SITE - This region may encompass 1-20 residues
VARIANT            293..312
                   note = SITE - This region may encompass 1-20 residues
VARIANT            317..336
                   note = SITE - This region may encompass 1-20 residues
VARIANT            341..360
                   note = SITE - This region may encompass 1-20 residues
VARIANT            365..384
                   note = SITE - This region may encompass 1-20 residues
VARIANT            389..408
                   note = SITE - This region may encompass 1-20 residues
VARIANT            413..432
                   note = SITE - This region may encompass 1-20 residues
VARIANT            437..456
                   note = SITE - This region may encompass 1-20 residues
VARIANT            461..480
                   note = SITE - This region may encompass 1-20 residues
VARIANT            1..480
                   note = SITE - This sequence may encompass 1-20
                    (Gly)(Ser)(Gly)(Gly)(Ser)m repeating units, wherein m = 1
                    to 20
REGION             1..480
                   note = See specification as filed for detailed description
                    of substitutions and preferred embodiments
SEQUENCE: 566
GSGGSSSSSS SSSSSSSSSS SSSSGSGGSS SSSSSSSSSS SSSSSSSSGS GGSSSSSSSS    60
SSSSSSSSSS SSGSGGSSSS SSSSSSSSSS SSSSSSGSGG SSSSSSSSSS SSSSSSSSSS   120
GSGGSSSSSS SSSSSSSSSS SSSSGSGGSS SSSSSSSSSS SSSSSSSSGS GGSSSSSSSS   180
SSSSSSSSSS SSGSGGSSSS SSSSSSSSSS SSSSSSGSGG SSSSSSSSSS SSSSSSSSSS   240
GSGGSSSSSS SSSSSSSSSS SSSSGSGGSS SSSSSSSSSS SSSSSSSSGS GGSSSSSSSS   300
SSSSSSSSSS SSGSGGSSSS SSSSSSSSSS SSSSSSGSGG SSSSSSSSSS SSSSSSSSSS   360
GSGGSSSSSS SSSSSSSSSS SSSSGSGGSS SSSSSSSSSS SSSSSSSSGS GGSSSSSSSS   420
SSSSSSSSSS SSGSGGSSSS SSSSSSSSSS SSSSSSGSGG SSSSSSSSSS SSSSSSSSSS   480

SEQ ID NO: 567     moltype = AA   length = 480
FEATURE            Location/Qualifiers
source             1..480
                   mol_type = protein
                   organism = synthetic construct
                   note = Description of Artificial Sequence: Synthetic
                    polypeptide
VARIANT            4..23
                   note = SITE - This region may encompass 1-20 residues
VARIANT            28..47
                   note = SITE - This region may encompass 1-20 residues
VARIANT            52..71
                   note = SITE - This region may encompass 1-20 residues
VARIANT            76..95
                   note = SITE - This region may encompass 1-20 residues
VARIANT            100..119
```

```
                        note = SITE - This region may encompass 1-20 residues
VARIANT                 124..143
                        note = SITE - This region may encompass 1-20 residues
VARIANT                 148..167
                        note = SITE - This region may encompass 1-20 residues
VARIANT                 172..191
                        note = SITE - This region may encompass 1-20 residues
VARIANT                 196..215
                        note = SITE - This region may encompass 1-20 residues
VARIANT                 220..239
                        note = SITE - This region may encompass 1-20 residues
VARIANT                 244..263
                        note = SITE - This region may encompass 1-20 residues
VARIANT                 268..287
                        note = SITE - This region may encompass 1-20 residues
VARIANT                 292..311
                        note = SITE - This region may encompass 1-20 residues
VARIANT                 316..335
                        note = SITE - This region may encompass 1-20 residues
VARIANT                 340..359
                        note = SITE - This region may encompass 1-20 residues
VARIANT                 364..383
                        note = SITE - This region may encompass 1-20 residues
VARIANT                 388..407
                        note = SITE - This region may encompass 1-20 residues
VARIANT                 412..431
                        note = SITE - This region may encompass 1-20 residues
VARIANT                 436..455
                        note = SITE - This region may encompass 1-20 residues
VARIANT                 460..479
                        note = SITE - This region may encompass 1-20 residues
VARIANT                 1..480
                        note = SITE - This sequence may encompass 1-20
                          (Gly)(Ser)(Gly)(Ser)m(Gly) repeating units, wherein m = 1
                          to 20
REGION                  1..480
                        note = See specification as filed for detailed description
                          of substitutions and preferred embodiments
SEQUENCE: 567
GSGSSSSSSS SSSSSSSSSS SSSGGSGSSS SSSSSSSSSS SSSSSSSGGS GSSSSSSSSS    60
SSSSSSSSSS SGGSGSSSSS SSSSSSSSSS SSSSSGGSGS SSSSSSSSSS SSSSSSSSSG   120
GSGSSSSSSS SSSSSSSSSS SSSGGSGSSS SSSSSSSSSS SSSSSSSGGS GSSSSSSSSS   180
SSSSSSSSSS SGGSGSSSSS SSSSSSSSSS SSSSSGGSGS SSSSSSSSSS SSSSSSSSSG   240
GSGSSSSSSS SSSSSSSSSS SSSGGSGSSS SSSSSSSSSS SSSSSSSGGS GSSSSSSSSS   300
SSSSSSSSSS SGGSGSSSSS SSSSSSSSSS SSSSSGGSGS SSSSSSSSSS SSSSSSSSSG   360
GSGSSSSSSS SSSSSSSSSS SSSGGSGSSS SSSSSSSSSS SSSSSSSGGS GSSSSSSSSS   420
SSSSSSSSSS SGGSGSSSSS SSSSSSSSSS SSSSSGGSGS SSSSSSSSSS SSSSSSSSSG   480

SEQ ID NO: 568          moltype = AA  length = 460
FEATURE                 Location/Qualifiers
source                  1..460
                        mol_type = protein
                        organism = synthetic construct
                        note = Description of Artificial Sequence: Synthetic
                          polypeptide
VARIANT                 4..23
                        note = SITE - This region may encompass 1-20 residues
VARIANT                 27..46
                        note = SITE - This region may encompass 1-20 residues
VARIANT                 50..69
                        note = SITE - This region may encompass 1-20 residues
VARIANT                 73..92
                        note = SITE - This region may encompass 1-20 residues
VARIANT                 96..115
                        note = SITE - This region may encompass 1-20 residues
VARIANT                 119..138
                        note = SITE - This region may encompass 1-20 residues
VARIANT                 142..161
                        note = SITE - This region may encompass 1-20 residues
VARIANT                 165..184
                        note = SITE - This region may encompass 1-20 residues
VARIANT                 188..207
                        note = SITE - This region may encompass 1-20 residues
VARIANT                 211..230
                        note = SITE - This region may encompass 1-20 residues
VARIANT                 234..253
                        note = SITE - This region may encompass 1-20 residues
VARIANT                 257..276
                        note = SITE - This region may encompass 1-20 residues
```

```
VARIANT             280..299
                    note = SITE - This region may encompass 1-20 residues
VARIANT             303..322
                    note = SITE - This region may encompass 1-20 residues
VARIANT             326..345
                    note = SITE - This region may encompass 1-20 residues
VARIANT             349..368
                    note = SITE - This region may encompass 1-20 residues
VARIANT             372..391
                    note = SITE - This region may encompass 1-20 residues
VARIANT             395..414
                    note = SITE - This region may encompass 1-20 residues
VARIANT             418..437
                    note = SITE - This region may encompass 1-20 residues
VARIANT             441..460
                    note = SITE - This region may encompass 1-20 residues
VARIANT             1..460
                    note = SITE - This sequence may encompass 1-20
                    (Gly)(Gly)(Gly)(Ser)m repeating units, wherein m = 1 to 20
REGION              1..460
                    note = See specification as filed for detailed description
                    of substitutions and preferred embodiments
SEQUENCE: 568
GGGSSSSSSS SSSSSSSSSS SSSGGGSSSS SSSSSSSSSS SSSSSGGGS SSSSSSSSSS    60
SSSSSSSSSG GGSSSSSSSS SSSSSSSSSS SSGGGSSSSS SSSSSSSSSS SSSSSGGGSS  120
SSSSSSSSSS SSSSSSSSGG GSSSSSSSSS SSSSSSSSSS SGGGSSSSSS SSSSSSSSSS  180
SSSSGGGSSS SSSSSSSSSS SSSSSSSGGG SSSSSSSSSS SSSSSSSSSS GGGSSSSSSS  240
SSSSSSSSSS SSSGGGSSSS SSSSSSSSSS SSSSSSGGGS SSSSSSSSSS SSSSSSSSSG  300
GGSSSSSSSS SSSSSSSSSS SSGGGSSSSS SSSSSSSSSS SSSSSGGGSS SSSSSSSSS  360
SSSSSSSSGG GSSSSSSSSS SSSSSSSSSS SGGGSSSSSS SSSSSSSSSS SSSSGGGSSS  420
SSSSSSSSSS SSSSSSSGGG SSSSSSSSSS SSSSSSSSS                         460

SEQ ID NO: 569      moltype = AA  length = 6
FEATURE             Location/Qualifiers
source              1..6
                    mol_type = protein
                    organism = synthetic construct
                    note = Description of Artificial Sequence: Synthetic His tag
VARIANT             1..6
                    note = SITE - This sequence may encompass 3-6 residues
SEQUENCE: 569
HHHHHH                                                                6
```

What is claimed is:

1. An IL10 receptor (IL10R) binding molecule comprising:
   (a) a first single domain antibody that specifically binds to the extracellular domain of IL10Rα (IL10Rα sdAb), wherein the IL10Rα sdAb comprises a CDR1 comprising (i) SEQ ID NO: 49 or (ii) SEQ ID NO:49 having an amino acid substitution in an Asn-Cys-Ser motif thereof to eliminate an N-linked glycosylation site, wherein the amino acid substitution is a conservative amino acid substitution of the Asn (N) residue of the N-linked glycosylation motif, a CDR2 comprising SEQ ID NO: 50, and a CDR3 comprising SEQ ID NO: 51; and
   (b) a second single domain antibody that specifically binds to the extracellular domain of an IL10Rβ (IL10Rβ sdAb), wherein the IL10Rβ sdAb comprises a CDR1 comprising SEQ ID NO: 100, a CDR2 comprising SEQ ID NO: 101, and a CDR3 comprising SEQ ID NO: 102;
   wherein:
   the IL10Rα sdAb and IL10Rβ sdAb are in stable association.

2. The IL10R binding molecule of claim 1 wherein the IL10Rα sdAb and the IL10Rβ sdAb are covalently linked.

3. The IL10R binding molecule of claim 1, wherein the IL10Rα sdAb is a sdAb having least 90% sequence identity to SEQ ID NO: 170.

4. The IL10R binding molecule of claim 1, wherein the IL10Rβ sdAb is a sdAb having least 90% sequence identity to SEQ ID NO: 187.

5. The IL10R binding molecule of claim 1, having at least 90% sequence identity to SEQ ID NO: 302 or SEQ ID NO: 339.

6. The IL10R binding molecule of claim 1, wherein the IL10R binding molecule is PEGylated.

7. A pharmaceutically acceptable formulation of an IL10R binding molecule of claim 1.

8. The IL10R binding molecule of claim 1, wherein the IL10Rα sdAb comprises SEQ ID NO: 170.

9. The IL10R binding molecule of claim 1, wherein the IL10Rβ sdAb comprises SEQ ID NO: 187.

10. The IL10R binding molecule of claim 1, wherein the IL10Rα sdAb comprises SEQ ID NO: 170; and the IL10Rβ sdAb comprises SEQ ID NO: 187.

11. The IL10R binding molecule of claim 1, wherein the IL10R binding molecule is conjugated to a targeting domain that selectively binds to a cell surface molecule on a cell or tissue.

12. The IL10R binding molecule of claim 11, wherein the targeting domain is an antibody or an antigen-binding portion thereof.

13. The IL10R binding molecule of claim 1, wherein the IL10Rα sdAb CDR1 comprises SEQ ID NO: 49.

14. The IL10R binding molecule of claim 1, wherein the IL10Rα sdAb CDR1 comprises the conservative amino acid substitution of the Asn (N) residue of the N-linked glycosylation motif.

15. The IL10R binding molecule of claim 1, wherein the substitution is an asparagine-to-glutamine substitution in the Asn-Cys-Ser motif in SEQ ID NO:49.

* * * * *